(12) United States Patent
Mao et al.

(10) Patent No.: US 11,753,373 B2
(45) Date of Patent: Sep. 12, 2023

(54) PROTEASE INHIBITORS AS ANTIVIRALS

(71) Applicant: ACEA Therapeutics, Inc., San Diego, CA (US)

(72) Inventors: Long Mao, San Diego, CA (US); Xiao Xu, San Diego, CA (US); Namir Shaabani, San Diego, CA (US); Can Jin, San Diego, CA (US)

(73) Assignee: ACEA Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/830,185

(22) Filed: Jun. 1, 2022

(65) Prior Publication Data
US 2023/0026438 A1 Jan. 26, 2023

Related U.S. Application Data

(60) Provisional application No. 63/275,113, filed on Nov. 3, 2021, provisional application No. 63/195,930, filed on Jun. 2, 2021.

(51) Int. Cl.
| | |
|---|---|
| *C07D 401/12* | (2006.01) |
| *C07D 403/12* | (2006.01) |
| *C07D 207/26* | (2006.01) |
| *C07D 207/416* | (2006.01) |
| *C07D 401/14* | (2006.01) |
| *C07D 403/14* | (2006.01) |
| *C07D 413/14* | (2006.01) |

(52) U.S. Cl.
CPC ....... *C07D 207/26* (2013.01); *C07D 207/416* (2013.01); *C07D 401/12* (2013.01); *C07D 401/14* (2013.01); *C07D 403/12* (2013.01); *C07D 403/14* (2013.01); *C07D 413/14* (2013.01)

(58) Field of Classification Search
CPC ............... C07D 401/12; C07D 403/12
See application file for complete search history.

(56) References Cited

U.S. PATENT DOCUMENTS

| | | | |
|---|---|---|---|
| 11,124,497 B1 * | 9/2021 | Arnold .................. | C07D 207/26 |
| 2022/0112177 A1 | 4/2022 | Liu et al. | |

FOREIGN PATENT DOCUMENTS

| | | | | |
|---|---|---|---|---|
| WO | WO-2005113580 A1 * | 12/2005 | ............. | A61K 38/21 |
| WO | 2006061714 A2 | 6/2006 | | |
| WO | 2020/030143 A1 | 2/2020 | | |
| WO | 2020/247665 A1 | 12/2020 | | |
| WO | 2021205296 A1 | 10/2021 | | |
| WO | 2021250648 A1 | 12/2021 | | |
| WO | 2021252644 A1 | 12/2021 | | |
| WO | WO-2022036018 A1 * | 2/2022 | ............. | A61P 31/14 |

OTHER PUBLICATIONS

Vuong et al. European J. of Med. Chem., vol. 222, May 2021, pp. 1-11.*
Thanigaimalai et al. European J. Of Med. Chem., 2013, vol. 68, pp. 372-384.*
Halford, B., "Pfizer unveils its oral SARS-CoV-2 inhibitor," Chem. Eng. News, vol. 99, Issue 13, Apr. 7, 2021.
Hoffman et al., "Discovery of Ketone-Based Covalent Inhibitors of Coronavirus 3CL Proteases for the Potential Therapeutic Treatment of COVID-19," J. Med. Chem. 2020, 63, 12725-12747.

(Continued)

*Primary Examiner* — Samira J Jean-Louis
(74) *Attorney, Agent, or Firm* — McNeill Baur PLLC

(57) ABSTRACT

Provided herein, inter alia, are compounds, pharmaceutical compositions and methods related to the treatment of viral infections caused by coronavirus or enterovirus. Provided herein are compounds of Formula (I), (II) and (III)

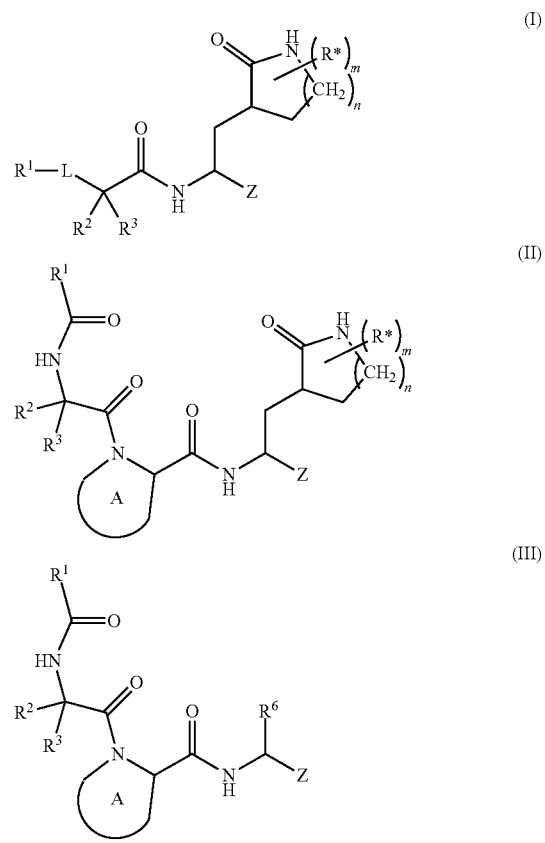

and methods of using the compounds for therapy. These compounds are peptidomimetics that inhibit protease 3CL of a coronavirus, and are useful for treating conditions caused by viral infections, including COVID-19.

18 Claims, No Drawings

(56) References Cited

OTHER PUBLICATIONS

Qiao et al., "SARS-CoV-2 Mpro inhibitors with antiviral activity in a transgenic mouse model," Science, 371, 1374-1378 (2021).
Citarella A et al, "SARS-CoV-2 Mpro: A Potential Target for Peptidomimetics and Small-Molecule Inhibitors" Biomolecules, vol. 11(4), 607 (2021).
International Search Report and Written Opinion, International Application No. PCT/US2022/031815, dated Nov. 3, 2020, 21 pages.
Thanigaimalai P et al, "Design, synthesis, and biological evaluation of novel dipeptide-type SARS-CoV 3CL protease inhibitors: structure-activity relationship study" Eur J Med Chem, vol. 65, pp. 436-447 (2013).
Tiew et al, "Design, synthesis, and evaluation of inhibitors of Norwalk virus 3C protease" Bioorg Med Chem Lett, vol. 21(18), pp. 5315-5319 (2011).
Dai Wenhao et al, "Structure-Based, Design, Synthesis and Biological, Evaluation of Peptidomimetic Aldehydes as a Novel Series of Antiviral Drug Candidates Targeting the SARS-CoV-2 Main Protease", bioRxiv, Mar. 28, 2020 (Mar. 28, 2020), pp. 1-17.

\* cited by examiner

PROTEASE INHIBITORS AS ANTIVIRALS

CROSS-REFERENCE TO RELATED APPLICATIONS

This application claims priority to U.S. provisional application No. 63/195,930, filed on Jun. 2, 2021, and U.S. provisional application No. 63/275,113, filed on Nov. 3, 2021, the disclosures of both of which are incorporated herein by reference in their entireties.

TECHNICAL FIELD

The field of this invention is pharmaceutical compounds, compositions, and methods, for preventing, treating, and/or curing viral diseases, including Coronavirus infections and Enterovirus infections. More specifically, the invention provides specifically designed peptido mimetics that are believed to act by inhibition of proteases, as well as pharmaceutically acceptable salts and other derivatives thereof, and also provides methods to administer these compounds and compositions for the treatment of viral infections.

BACKGROUND

Coronaviruses (CoVs) are a group of related RNA viruses that cause diseases in a wide range of vertebrates, including humans and domestic animals. COVID-19 is a relatively new and potentially fatal respiratory infection caused by severe acute respiratory syndrome coronavirus 2 (SARS-CoV-2), which poses a serious threat to global public health. It is believed that the main protease ($M^{pro}$, which is also called the 3CL protease) of SARS-CoV-2 plays a central role in viral replication. The compounds described herein are new inhibitors of $M^{pro}$ (or 3CL), which can be used for the treatment of COVID-19 disease.

There are a number of reports of inhibitors of the 3CL protease that exhibit antiviral activity against the COVID-19 virus. Pfizer has described two different peptidomimetic compounds, PF-07321332 (*Chem. Eng. News*, Apr. 12, 2021) and PF-00835231 (*J. Med. Chem.* July 2020 (pp. A-W)), that appear to form reversible covalent attachments to a cysteine residue of 3CL, and thus achieve tight binding and potent inhibition. Researchers in China reported another inhibitor of 3CL protease (*Science*, vol. 371, 1374-8, 26 Mar. 2021) that acts similarly, using an aldehyde group to attach to the cysteine residue. See also WO2020/030143 and WO2020/2475665. While these reports demonstrate that small-molecule peptidomimetic inhibitors can provide antiviral activity for treating COVID-19, there remains a need for alternative compounds with suitable medicinal chemistry properties to help control the COVID-19 pandemic. The invention provides such compounds as well as methods of making and using them for treating viral infections such as COVID-19.

BRIEF SUMMARY OF THE INVENTION

In one aspect, the present disclosure provides heterocyclic compounds having a structure according to Formula I:

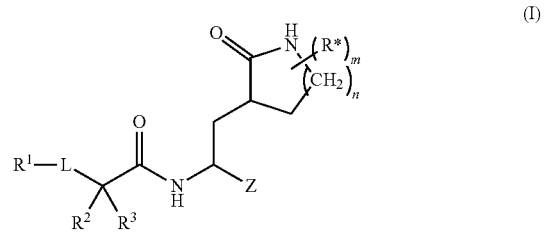

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

Z is selected from —CHO, —CN, —CH$_2$CN, —C(=O)—CH=CH$_2$, —NH—C(=O)—CH=CH$_2$, —CH$_2$—C(=O)—CH=CH$_2$, —C(=O)CH$_2$OH,

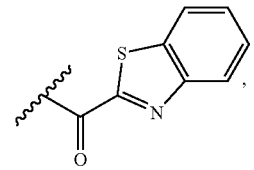 [SMILES: *C(=O)c1nc2ccccc2s1]

—CH(OH)SO$_3^-$ (and an associated cation, such as Na$^+$), —CO$_2$—C$_{1-3}$alkyl, —CH$_2$OH, —C(=O)OH, —CH(OCH$_3$)$_2$, and —C(=O)—C$_{1-3}$haloalkyl;

L is selected from a bond, —(CR$_2$)$_{1-2}$—, —(CR$_2$)$_{0-2}$—NR—, —NR—(CR$_2$)$_{0-2}$, —(CR$_2$)$_{0-2}$—O—, —O—(CR$_2$)$_{0-2}$, —(CR$_2$)$_{0-2}$—C(=O)—NR—, —NR—C(=O)—(CR$_2$)$_{0-2}$—, —NR—C(=O)—CHR$_2$—NR—C(=O)—(CR$_2$)$_{0-2}$—, —NR—C(=O)—CHR$^2$—NR—C(=O)—O—(CR$_2$)$_{0-2}$—, —(CR$_2$)$_{0-2}$—C(=O)—NR—CHR$^2$—C(=O)—NR—, —(CR$_2$)$_{0-2}$—O—C(=O)—NR—CHR$^2$—C(=O)—NR—, —NR—C(=O)—O—(CR$_2$)$_{0-2}$—, and —(CR$_2$)$_{0-2}$—O—C(=O)—NR—;

R$^1$ is selected from —CF$_3$, —CHF$_2$, —CH$_2$F, phenyl, naphthyl, and 5-10 membered heteroaryl containing one or two heteroatoms selected from N, O and S as ring members, and wherein each phenyl, naphthyl, and 5-10 membered heteroaryl is optionally substituted with one to three groups independently selected from halo, CN, C$_{1-3}$ alkyl, C$_{1-3}$ alkoxy, C$_{1-3}$ haloalkyl, and C$_{1-3}$ haloalkoxy;

each R$^2$ is selected from C$_{1-6}$ alkyl, 3-7 membered cycloalkyl, C$_{1-3}$ alkyl-(3-7 membered cycloalkyl), and (3-7 membered cycloalkyl)-C$_{1-3}$ alkyl, each of which is optionally substituted with up to three groups selected from halo, CN, C$_{1-3}$ alkyl, C$_{1-6}$alkoxy, C$_{1-3}$ haloalkyl, and C$_{1-3}$ haloalkoxy;

R$^3$ is H or C$_{1-4}$ alkyl;

Each R* is independently selected from C$_{1-3}$ alkyl, C$_{1-3}$ alkoxy, C$_{1-3}$ haloalkyl, CN, halo, and —OH;

m is an integer from 0 to 2;

n is an integer from 0 to 4; and each R is independently selected from H and C$_{1-4}$alkyl.

In another aspect, the invention provides a compound of Formula (II):

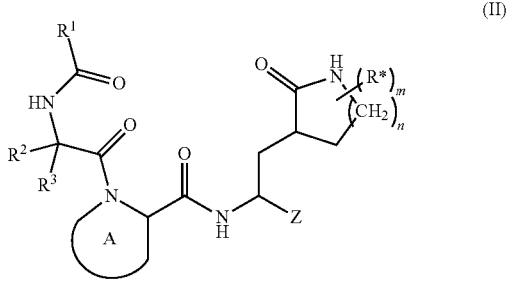

(II)

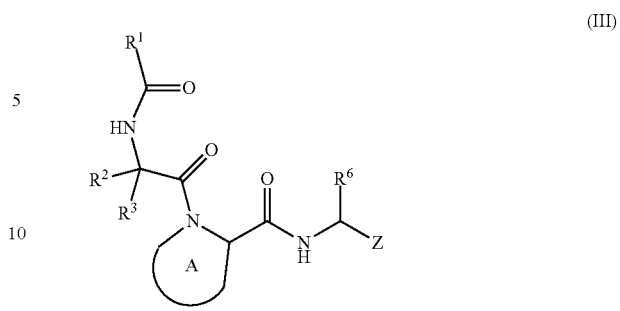

(III)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

Ring A is a 5-9 atom cycloalkyl that is optionally substituted with up to three groups selected from $C_{1-3}$ alkyl, $C_{1-6}$ alkoxy, $C_{1-3}$ haloalkyl, and $C_{1-3}$ haloalkoxy;

Z is selected from $-CO_2-C_{1-3}$alkyl, $-CHO$, $-CH_2CN$, $-C(=O)-CH=CH_2$, $-CH_2-C(=O)-CH=CH_2$, $-C(=O)-C_{1-3}$ haloalkyl, $-NH-C(=O)-CH=CH_2$, $-C(=O)CH_2OH$,

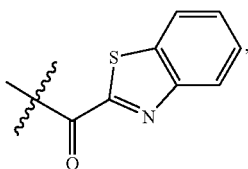 [SMILES: *C(=O)c1nc2ccccc2s1]

and $-CH(OH)SO_3^-$ (and an associated cation, such as $Na^+$);

or Z can be $-CN$ provided $R^2$ is not t-butyl when n is 1;

$R^1$ is H, 3-7 membered cycloalkyl, $C_{1-4}$alkoxy, or $C_{1-4}$ alkyl, wherein the 3-7 membered cycloalkyl, $C_{1-4}$alkoxy and $C_{1-4}$ alkyl are optionally substituted with one to three groups independently selected from halo, CN, $C_{3-6}$ cycloalkyl, $C_{1-3}$ alkoxy, $C_{1-3}$ haloalkyl, and $C_{1-3}$haloalkoxy; or $R^1$ is 5-10 membered heteroaryl containing one or two heteroatoms selected from N, O and S as ring members, and wherein the 5-10 membered heteroaryl is optionally substituted with one to three groups independently selected from halo, CN, $C_{1-3}$ alkyl, $C_{1-3}$ alkoxy, $C_{1-3}$ haloalkyl, and $C_{1-3}$ haloalkoxy;

$R^2$ is selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy;

$R^3$ is H or $C_{1-4}$ alkyl;

each $R^*$ is independently selected from $C_{1-3}$ alkyl, $C_{1-3}$ alkoxy, $C_{1-3}$ haloalkyl, CN, halo, and $-OH$;

m is an integer from 0 to 2; and n is an integer from 0 to 4.

In yet another aspect, the invention provides a compound of Formula (III):

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

Ring A is a 5-9 atom cycloalkyl that is optionally substituted with up to three groups selected from $C_{1-3}$ alkyl, $C_{1-6}$ alkoxy, $C_{1-3}$ haloalkyl, and $C_{1-3}$ haloalkoxy;

Z is selected from $-CO_2-C_{1-3}$alkyl, $-CHO$, $-CN$, $-CH_2CN$, $-C(=O)-CH=CH_2$, $-CH_2-C(=O)-CH=CH_2$, $-C(=O)-C_{1-3}$ haloalkyl, $-NH-C(=O)-CH=CH_2$, $-C(=O)CH_2OH$,

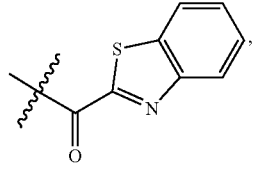 [SMILES: *C(=O)c1nc2ccccc2s1]

and $-CH(OH)SO_3^-$ (and an associated cation, such as $Na^+$);

$R^1$ is H, 3-7 membered cycloalkyl, $C_{1-4}$alkoxy, $C_{1-4}$ alkyl optionally substituted with one to three groups independently selected from halo, CN, $C_{3-6}$ cycloalkyl, $C_{1-3}$ alkoxy, $C_{1-3}$ haloalkyl, and $C_{1-3}$ haloalkoxy, or 5-10 membered heteroaryl containing one or two heteroatoms selected from N, O and S as ring members, and wherein the 5-10 membered heteroaryl is optionally substituted with one to three groups independently selected from halo, CN, $C_{1-3}$ alkyl, $C_{1-3}$ alkoxy, $C_{1-3}$ haloalkyl, and $C_{1-3}$ haloalkoxy;

$R^2$ is selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy;

$R^3$ is H or $C_{1-4}$ alkyl; and $R^6$ is hydrogen, halo, $C_{1-6}$ alkyl, $C_{1-6}$ alkoxy, $C_{1-3}$ haloalkyl, or $C_{1-3}$ haloalkoxy.

The compounds described herein can be used for any suitable purpose. In some embodiments, the compounds described above can be used in therapy, typically for treating a viral infection such as COVID-19.

In another aspect, the invention provides pharmaceutical compositions comprising a compound of Formula I, Formula II, or Formula III.

In another aspect, the invention provides methods of using the compounds and compositions for treating a viral infection, in particular COVID-19.

In still another aspect, the present disclosure provides a pharmaceutical composition comprising a compound described above admixed with at least one pharmaceutically acceptable carrier or excipient.

In yet another aspect, the present disclosure provides for a method for treating and/or preventing a viral infection, which comprises administering to a subject in need thereof an effective amount of a compound described herein or a pharmaceutical composition comprising such compound(s). The compounds and compositions are useful for treatment or prevention of coronavirus and enterovirus infections, including COVID-19.

In yet another aspect, the present disclosure provides for a use of a compound described herein for the manufacture of a medicament, especially for a medicament useful for treatment or prevention of coronavirus and enterovirus infections, including COVID-19.

In yet another aspect, the present disclosure provides a combination for treating and/or preventing a coronavirus or enterovirus infection, including COVID-19 infection, which combination comprises an effective amount of a compound of Formula I, Formula II, or Formula III, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and an effective amount of a second prophylactic or therapeutic agent for treating and/or preventing a viral infection in a subject.

In yet another aspect, the present disclosure provides a method for treating and/or preventing a viral infection in a subject, which methods comprises administering to a subject in need thereof an effective amount of the combination described above.

In yet another aspect, the present disclosure provides a method for inhibiting an activity of a viral protease in a cell or subject, which methods comprises contacting the cell or administering to a subject in need thereof an effective amount of a compound described herein, or a pharmaceutical composition comprising such compound, or a combination comprising such compounds of Formula (I), (II), or (III).

DETAILED DESCRIPTION OF THE INVENTION

General Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight or branched, configuration or a combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, etc.

Alkyl groups can be unsubstituted, or they can be substituted to the extent that such substitution makes sense chemically. Typical substituents include, but are not limited to, halo, =O, =N—CN, =N—OR$^a$, =NR$^a$, —OR$^a$, —NR$^a{}_2$, —SR$^a$, —SO$_2$R$^a$, —SO$_2$NR$^a{}_2$, —NR$^a$SO$_2$R$^a$, —NR$^a$CONR$^a{}_2$, —NR$^a$COOR$^a$, —NR$^a$COR$^a$, —CN, —COOR$^a$, —CONR$^a{}_2$, —OOCR$^a$, —COR$^a$, and —NO$_2$, wherein each R$^a$ is independently H, C$_1$-C$_8$ alkyl, C$_2$-C$_8$ heteroalkyl, C$_3$-C$_8$ heterocyclyl, C$_4$-C$_{10}$ heterocyclylalkyl, C$_1$-C$_8$ acyl, C$_2$-C$_8$ heteroacyl, C$_2$-C$_8$ alkenyl, C$_2$-C$_8$ heteroalkenyl, C$_2$-C$_8$ alkynyl, C$_2$-C$_8$ heteroalkynyl, C$_6$-C$_{10}$ aryl, or C$_5$-C$_{10}$ heteroaryl, and each R$^a$ is optionally substituted with halo, =O, =N—CN, =N—OR$^b$, =NR$^b$, OR$^b$, NR$^b{}_2$, SR$^b$, SO$_2$R$^b$, SO$_2$NR$^b{}_2$, NR$^b$SO$_2$R$^b$, NR$^b$CONR$^b{}_2$, NR$^b$COOR$^b$, NR$^b$COR$^b$, CN, COOR$^b$, CONR$^b{}_2$, OOCR$^b$, COR$^b$, and NO$_2$, wherein each R$^b$ is independently H, C$_1$-C$_8$ alkyl, C$_2$-C$_8$ heteroalkyl, C$_3$-C$_8$ heterocyclyl, C$_4$-C$_{10}$ heterocyclylalkyl, C$_1$-C$_8$ acyl, C$_2$-C$_8$ heteroacyl, C$_6$-C$_{10}$ aryl or C$_5$-C$_{10}$ heteroaryl. Alkyl, alkenyl and alkynyl groups can also be substituted by C$_1$-C$_8$ acyl, C$_2$-C$_8$ heteroacyl, C$_6$-C$_{10}$ aryl or C$_5$-C$_{10}$ heteroaryl, each of which can be substituted by the substituents that are appropriate for the particular group. Where a substituent group contains two R$^a$ or R$^b$ groups on the same or adjacent atoms (e.g., —NR$^b$2, or —NR$^b$—C(O)R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein.

Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings.

In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring.

In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl.

In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl.

In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic $C_5$-$C_6$ aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically, these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —$OR^a$, —$NR^a_2$, —$SR^a$, —$SO_2R^a$, —$SO_2NR^a_2$, —$NR^aSO_2R^a$, —$NR^aCONR^a_2$, —$NR^aCOOR^a$, —$NR^a$-$COR^a$, —CN, —$COOR^a$, —$CONR^a_2$, —$OOCR^a$, —$COR^a$, and —$NO_2$, wherein each $R^a$ is independently H, $C_1$-$C_8$ alkyl, $C_2$-$C_8$ heteroalkyl, $C_3$-$C_8$ heterocyclyl, $C_4$-$C_{10}$ heterocyclylalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each $R^a$ is optionally substituted with halo, =O, =N—CN, =N—$OR^b$, =$NR^b$, $OR^b$, $NR^b_2$, $SR^b$, $SO_2R^b$, $SO_2NR^b_2$, $NR^bSO_2R^b$, $NR^b$-$CONR^b_2$, $NR^bCOOR^b$, $NR^bCOR^b$, CN, $COOR^b$, $CONR^b_2$, $OOCR^b$, $COR^b$, and $NO_2$, wherein each $R^b$ is independently H, $C_1$-$C_8$ alkyl, $C_2$-$C_8$ heteroalkyl, $C_3$-$C_8$heterocyclyl, $C_4$-$C_{10}$ heterocyclylalkyl, $C_1$-$C_8$ acyl, $C_2$-$C_8$ heteroacyl, $C_6$-$C_{10}$ aryl or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group. Where a substituent group contains two $R^a$ or $R^b$ groups on the same or adjacent atoms (e.g., —$NR^{b2}$, or —$NR^b$—C(O) $R^b$), the two $R^a$ or $R^b$ groups can optionally be taken together with the atoms in the substituent group to which both are attached to form a ring having 5-8 ring members, which can be substituted as allowed for the $R^a$ or $R^b$ itself, and can contain an additional heteroatom (N, O or S) as a ring member.

The term "alkoxy" as used herein refers to a hydrocarbon group connected through an oxygen atom, e.g., —O—Hc, wherein the hydrocarbon portion He may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S—He, wherein the hydrocarbon portion He is as described for alkoxy groups. For example, contemplated alkylthio groups include methylthio, ethylthio, isopropylthio, methoxyethylthio, benzylthio, allylthio, and the like.

The term 'amino' as used herein refers to the group —$NH_2$. The term "alkylamino" refers to amino groups where one or both hydrogen atoms are replaced by a hydrocarbon group He as described above, wherein the amino nitrogen "N" can be substituted by one or two He groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group He as described above, wherein the amino nitrogen "N" can be substituted by one or two He groups as set forth for alkoxy groups described above.

The term 'acyl' as used herein refers to a group of the formula —C(=O)—D, where D represents an alkyl, alkenyl, alkynyl, cycloalkyl, aryl, heteroaryl, or heterocycle as described above. Typical examples are groups wherein D is a $C_1$-$C_{10}$ alkyl, $C_2$-$C_{10}$ alkenyl or alkynyl, or phenyl, each of which is optionally substituted. In some embodiments, D can be H, Me, Et, isopropyl, propyl, butyl, $C_1$-$C_4$ alkyl substituted with —OH, —OMe, or $NH_2$, phenyl, halophenyl, alkylphenyl, and the like.

The term "aryloxy" as used herein refers to an aryl group connecting to an oxygen atom, wherein the aryl group may be further substituted. For example suitable aryloxy groups include phenyloxy, etc. Similarly, the term "arylthio" as used herein refers to an aryl group connecting to a sulfur atom, wherein the aryl group may be further substituted. For example suitable arylthio groups include phenylthio, etc.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group alkyl-O— wherein one or more hydrogen atoms on the alkyl group have been substituted with a halo group and include, by way of examples, groups such as trifluoromethoxy, and the like.

The term "lactam" as used herein refers to a cyclic amide, typically a saturated ring, having 4-8 ring atoms.

The term "sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein each alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

The term "sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein The term "aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

The term "acylamino" refers to the groups —$NR^{20}C(O)$alkyl, —$NR^{20}C(O)$substituted alkyl, —$NR^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR20C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "aminocarbonylamino" refers to the group —$NR^{20}C(O)NR^{21}R^{22}$, wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

It should further be recognized that all of the above-defined groups may further be substituted with one or more substituents, which may in turn be substituted with hydroxy, amino, cyano, $C_1$-$C_4$ alkyl, halo, or $C_1$-$C_4$ haloalkyl. For example, a hydrogen atom in an alkyl or aryl can be replaced by an amino, halo or $C_{1-4}$ haloalkyl or alkyl group.

The term "substituted" as used herein refers to a replacement of a hydrogen atom of the unsubstituted group with a functional group, and particularly contemplated functional groups include nucleophilic groups (e.g., —$NH_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —$NH_3^+$), and halogens (e.g., —F, —Cl), NHCOR, $NHCONH_2$, $OCH_2COOH$, $OCH_2CONH_2$, $OCH_2CONHR$, $NHCH_2COOH$, $NHCH_2CONH_2$, $NHSO_2R$, $OCH_2$-heterocycles, $PO_3H$, $SO_3H$, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, a tautomer, a mixture of two or more tautomers, or isotopic variant thereof; or a pharmaceutically acceptable salt, solvate, hydrate, or prodrug thereof" has the same meaning as the phrase "an enantiomer, a mixture of enantiomers, a mixture of two or more diastereomers, a tautomer, a mixture of two or more tautomers, or isotopic variant of the compound referenced therein; or a pharmaceutically acceptable salt, solvate, hydrate, or prodrug of the compound referenced therein, or a pharmaceutically acceptable salt, solvate, hydrate, or prodrug of an enantiomer, a mixture of enantiomers, a mixture of two or more diastereomers, a tautomer, a mixture of two or more tautomers, or isotopic variant of the compound referenced therein."

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

The terms "effective amount", "therapeutically effective amount" or "effective dose" or related terms may be used interchangeably and refer to an amount of the therapeutic agent that when administered to a subject, is sufficient to affect a measurable improvement or prevention of a disease or disorder associated with coronavirus infection. For example, administering an effective dose sufficient to inhibit the proliferation and/or replication of the coronavirus, and/or the development of the viral infection within the subject. Therapeutically effective amounts of the therapeutic agents provided herein, when used alone or in combination with an antiviral agent, will vary depending upon the relative activity of the therapeutic agent, and depending upon the subject and disease condition being treated, the weight and age and sex of the subject, the severity of the disease condition in the subject, the manner of administration and the like, which can readily be determined by one of ordinary skill in the art. In one embodiment, a therapeutically effective amount will depend on certain aspects of the subject to be treated and the disorder to be treated and may be ascertained by one skilled in the art using known techniques. In addition, as is known in the art, adjustments for age as well as the body weight, general health, sex, diet, time of administration, drug interaction, and the severity of the disease may be necessary.

The terms "subject" and "patient" as used herein refer to human and non-human animals, including vertebrates, mammals and non-mammals. In one embodiment, the subject can be human, non-human primates, simian, ape, murine (e.g., mice and rats), bovine, porcine, equine, canine, feline, caprine, lupine, ranine or piscine.

The term "administering", "administered" and grammatical variants refers to the physical introduction of a therapeutic agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In one embodiment, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

"Treating" is to be understood broadly and encompasses any beneficial effect, including, e.g., delaying, slowing, or arresting the worsening of symptoms associated with pulmonary inflammatory disease or remedying such symptoms, at least in part. Treating also encompasses bringing about any form of improved patient function, as discussed in detail below. In some embodiments, treatment also means prolonging survival as compared to expected survival if not receiving treatment. Those in need of treatment include those who already have the disease or disorder, as well as those who tend to have the disease or disorder or who should prevent the disease or disorder.

The term "synergistic effect" refers to a situation where the combination of two or more agents produces a greater effect than the sum of the effects of each of the individual agents. The term encompasses not only a reduction in symptoms of the disorder to be treated, but also an improved side effect profile, improved tolerability, improved patient compliance, improved efficacy, or any other improved clinical outcome.

The term a "sub-therapeutic amount" of an agent or therapy is an amount less than the effective amount for that agent or therapy as a single agent, but when combined with an effective or sub-therapeutic amount of another agent or therapy can produce a result desired by the physician, due to, for example, synergy in the resulting efficacious effects, or reduced side effects.

Combination therapy or "in combination with" refer to the use of more than one therapeutic agent to treat a particular disorder or condition. By "in combination with," it is not intended to imply that the therapeutic agents must be administered at the same time and/or formulated for delivery together, although these methods of delivery are within the scope of this disclosure. A therapeutic agent can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other additional agents. The therapeutic agents in a combination therapy can also be administered on an alternating dosing schedule, with or without a resting period (e.g., no therapeutic agent is administered on certain days of the schedule). The administration of a therapeutic agent "in combination with" another therapeutic agent includes, but is not limited to, sequential administration and concomitant administration of the two agents. In general, each therapeutic agent is administered at a dose and/or on a time schedule determined for that particular agent.

The compounds and compositions described herein can be administered to a subject in need of treatment for a viral infection. The subject is typically a mammal diagnosed as being in need of treatment for at least one coronavirus infection or enterovirus infection. The methods comprise administering an effective amount of at least one compound of the invention; optionally the compound may be administered in combination with one or more additional therapeutic agents, particularly therapeutic agents known to be useful for treating the symptoms afflicting the particular subject or an additional antiviral.

Compounds

In an aspect, provided herein is a compound of Formula (I):

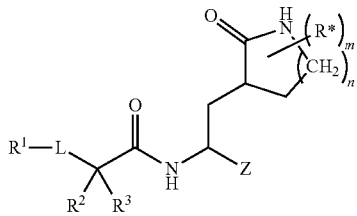
(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

Z is selected from —CHO, —CN, —CH$_2$CN, —C(=O)—CH=CH$_2$, —NH—C(=O)—CH=CH$_2$, —CH$_2$—C(=O)—CH=CH$_2$, —C(=O)CH$_2$OH,

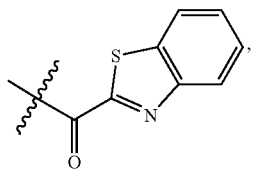 [SMILES: *C(=O)c1nc2ccccc2s1]

—CH(OH)SO$_3^-$ (and an associated cation, such as Na$^+$), —CO$_2$-C$_{1-3}$alkyl, —CH$_2$OH, —C(=O)OH, —CH(OCH$_3$)$_2$, and —C(=O)—C$_{1-3}$haloalkyl;

L is selected from a bond, —(CR$_2$)$_{1-2}$—, —(CR$_2$)$_{0-2}$—NR—, —NR—(CR$_2$)$_{0-2}$—, —(CR$_2$)$_{0-2}$—O—, —O—(CR$_2$)$_{0-2}$—, —(CR$_2$)$_{0-2}$—C(=O)—NR—, —NR—C(=O)—(CR$_2$)$_{0-2}$—, —NR—C(=O)—CHR$^2$—NR—C(=O)—(CR$_2$)$_{0-2}$—, —NR—C(=O)—CHR$^2$—NR—C(=O)—O—(CR$_2$)$_{0-2}$—, —(CR$_2$)$_{0-2}$—C(=O)—NR—CHR$^2$—C(=O)—NR—, —(CR$_2$)$_{0-2}$—O—C(=O)—NR—CHR$^2$—C(=O)—NR—, —NR—C(=O)—O—(CR$_2$)$_{0-2}$—, and —(CR$_2$)$_{0-2}$—O—C(=O)—NR—;

R$^1$ is selected from —CF$_3$, —CHF$_2$, —CH$_2$F, phenyl, naphthyl, and 5-10 membered heteroaryl containing one or two heteroatoms selected from N, O and S as ring members, and wherein each phenyl, naphthyl, and 5-10 membered heteroaryl is optionally substituted with one to three groups independently selected from halo, CN, C$_{1-3}$ alkyl, C$_{1-3}$ alkoxy, C$_{1-3}$ haloalkyl, and C$_{1-3}$ haloalkoxy;

each R$^2$ is selected from C$_{1-6}$ alkyl, 3-7 membered cycloalkyl, C$_{1-3}$ alkyl-(3-7 membered cycloalkyl), and (3-7 membered cycloalkyl)-C$_{1-3}$ alkyl, each of which is optionally substituted with up to three groups selected from halo, CN, C$_{1-3}$ alkyl, C$_{1-6}$ alkoxy, C$_{1-3}$ haloalkyl, and C$_{1-3}$ haloalkoxy;

R$^3$ is H or C$_{1-4}$ alkyl;

each R* is independently selected from C$_{1-3}$ alkyl, C$_{1-3}$ alkoxy, C$_{1-3}$ haloalkyl, CN, halo, and —OH;

m is an integer from 0 to 2;

n is an integer from 0 to 4; and each R is independently selected from H and C$_{1-4}$alkyl.

In embodiments, R$^1$ is —CF$_3$, —CHF$_2$, —CH$_2$F, phenyl, naphthyl or indolyl, wherein each phenyl, naphthyl, and 5-10 membered heteroaryl is optionally substituted with one or two groups selected from halo, CN, C$_{1-3}$ alkyl, C$_{1-3}$ alkoxy, C$_{1-3}$ haloalkyl, and C$_{1-3}$ haloalkoxy. In embodiments, R$^1$ is —CF$_3$. In embodiments, R$^1$ is —CHF$_2$. In embodiments, R$^1$ is —CH$_2$F. In embodiments, R$^1$ is unsubstituted phenyl. In embodiments, R$^1$ is unsubstituted naphthyl. In embodiments, R$^1$ is unsubstituted indolyl. In embodiments, R$^1$ is phenyl substituted with one group selected from halo, CN, C$_{1-3}$ alkyl, C$_{1-3}$ alkoxy, C$_{1-3}$ haloalkyl, and C$_{1-3}$ haloalkoxy. In embodiments, R$^1$ is naphthyl substituted with one group selected from halo, CN, C$_{1-3}$ alkyl, C$_{1-3}$ alkoxy, C$_{1-3}$ haloalkyl, and C$_{1-3}$ haloalkoxy. In embodiments, R$^1$ is indolyl substituted with one group selected from halo, CN, C$_{1-3}$ alkyl, C$_{1-3}$ alkoxy, C$_{1-3}$ haloalkyl, and C$_{1-3}$ haloalkoxy. In embodiments, R$^1$ is phenyl substituted with two groups independently selected from halo, CN, C$_{1-3}$ alkyl, C$_{1-3}$ alkoxy, C$_{1-3}$ haloalkyl, and C$_{1-3}$ haloalkoxy. In embodiments, R$^1$ is naphthyl substituted with two groups independently selected from halo, CN, C$_{1-3}$ alkyl, C$_{1-3}$ alkoxy, C$_{1-3}$ haloalkyl, and C$_{1-3}$ haloalkoxy. In embodiments, R$^1$ is indolyl substituted with two groups independently selected from halo, CN, C$_{1-3}$ alkyl, C$_{1-3}$ alkoxy, C$_{1-3}$ haloalkyl, and C$_{1-3}$ haloalkoxy. In embodiments, R$^1$ is phenyl substituted with three groups independently selected from halo, CN, C$_{1-3}$ alkyl, C$_{1-3}$ alkoxy, C$_{1-3}$ haloalkyl, and C$_{1-3}$ haloalkoxy. In embodiments, R$^1$ is naphthyl substituted with three groups independently selected from halo, CN, C$_{1-3}$ alkyl, C$_{1-3}$ alkoxy, C$_{1-3}$ haloalkyl, and C$_{1-3}$ haloalkoxy. In embodiments, R$^1$ is indolyl substituted with three groups independently selected from halo, CN, C$_{1-3}$ alkyl, C$_{1-3}$ alkoxy, C$_{1-3}$ haloalkyl, and C$_{1-3}$ haloalkoxy. In embodiments, R$^1$ is phenyl substituted with one group selected from halo, C$_{1-3}$ alkyl, and C$_{1-3}$ alkoxy. In embodiments, R$^1$ is naphthyl substituted with one group selected from halo, C$_{1-3}$ alkyl, and C$_{1-3}$ alkoxy. In embodiments, R$^1$ is indolyl substituted with one group selected from halo, C$_{1-3}$ alkyl, and C$_{1-3}$ alkoxy. In embodiments, R$^1$ is phenyl substituted with two groups independently selected from halo, C$_{1-3}$ alkyl, and C$_{1-3}$ alkoxy. In embodiments, R$^1$ is naphthyl substituted with two groups independently selected from halo, C$_{1-3}$ alkyl, and C$_{1-3}$ alkoxy. In embodiments, R$^1$ is indolyl substituted with two groups independently selected from halo, C$_{1-3}$ alkyl, and C$_{1-3}$ alkoxy. In embodiments, R$^1$ is phenyl substituted with three groups independently selected from halo, C$_{1-3}$ alkyl, and C$_{1-3}$ alkoxy. In embodiments, R$^1$ is naphthyl substituted with three groups independently selected from halo, C$_{1-3}$ alkyl, and C$_{1-3}$ alkoxy. In embodiments, R$^1$ is indolyl substituted with three groups independently selected from halo, C$_{1-3}$ alkyl, and C$_{1-3}$ alkoxy. In embodiments, R$^1$ is phenyl substituted with one group selected from fluoro, methyl, and methoxy. In embodiments, R$^1$ is naphthyl substituted with one group selected from fluoro, methyl, and methoxy. In embodiments, R$^1$ is indolyl substituted with one group selected from fluoro, methyl, and methoxy. In embodiments, R$^1$ is phenyl substituted with two groups independently selected from fluoro, methyl, and methoxy. In embodiments, R$^1$ is naphthyl substituted with two groups independently selected from fluoro, methyl, and methoxy. In embodiments, R$^1$ is indolyl substituted with two groups independently selected from fluoro, methyl, and methoxy. In embodiments, R$^1$ is phenyl substituted with three groups independently selected from fluoro, methyl, and methoxy. In embodiments, R$^1$ is naphthyl substituted with three groups independently selected from fluoro, methyl, and methoxy. In embodiments, R$^1$ is indolyl substituted with three groups independently selected from fluoro, methyl, and methoxy.

In embodiments, R$^1$ is phenyl or 5-10 membered heteroaryl containing one or two heteroatoms selected from N, O and S as ring members, where each phenyl or 5-10 membered heteroaryl is optionally substituted with one, two or three groups independently selected from halo, CN, $C_{1-3}$ alkyl, $C_{1-3}$ alkoxy, $C_{1-3}$ haloalkyl, and $C_{1-3}$ haloalkoxy.

In embodiments, $R^1$ is unsubstituted phenyl or 5-10 membered heteroaryl containing one or two heteroatoms selected from N, O and S as ring members. In embodiments, $R^1$ is unsubstituted phenyl. In embodiments, $R^1$ is unsubstituted 5-10 membered heteroaryl containing one or two heteroatoms selected from N, O and S as ring members. In embodiments, $R^1$ is unsubstituted 5-10 membered heteroaryl containing one heteroatom selected from N, O and S as ring member. In embodiments, $R^1$ is unsubstituted 5-10 membered heteroaryl containing two heteroatoms selected from N, O and S as ring members. In embodiments, $R^1$ is unsubstituted 5-10 membered heteroaryl containing one heteroatom N as ring member. In embodiments, $R^1$ is unsubstituted 5-10 membered heteroaryl containing one heteroatom O as ring member. In embodiments, $R^1$ is unsubstituted 5-10 membered heteroaryl containing one heteroatom S as ring member.

In embodiments, $R^1$ is a phenyl substituted with one, two, or three groups independently selected from halo, CN, $C_{1-3}$ alkyl, $C_{1-3}$ alkoxy, or $C_{1-3}$ haloalkyl. In embodiments, $R^1$ is a phenyl substituted with one group independently selected from halo, CN, $C_{1-3}$ alkyl, $C_{1-3}$ alkoxy, or $C_{1-3}$ haloalkyl. In embodiments, $R^1$ is a phenyl substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one or two heteroatoms selected from N, O and S as ring members, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one or two heteroatoms selected from N, O and S as ring members, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one or two heteroatoms selected from N, O and S as ring members, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom selected from N, O and S as ring member, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, O and S as ring member, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, O and S as ring member, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom N, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom N, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom O, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom O, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from O, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom S, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom S, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from S, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is phenyl or indolyl, each of which is substituted with one group selected from halo, $C_{1-3}$ alkyl, and $C_{1-3}$ alkoxy. In embodiments, $R^1$ is —$CF_3$, —$CHF_2$, phenyl or indolyl, wherein phenyl and indolyl are optionally substituted with one group selected from halo, $C_{1-3}$ alkyl, and $C_{1-3}$ alkoxy. In embodiments, $R^1$ is —$CF_3$, —$CHF_2$, phenyl or indolyl, wherein phenyl and indolyl are optionally substituted with one group selected from fluoro, methyl, and methoxy.

In embodiments, L is selected from —NHC(=O)—, —C(=O)NH—, —NH(C=O)—O—CH$_2$—, —CH$_2$—O—C(=O)NH—, —NHC(=O)—CHR$^2$—NHC(=O)—, —C(=O)NH—CHR$^2$—C(=O)NH—, —CH$_2$—O—C(=O)NH—CHR$^2$—C(=O)NH—, and —NHC(=O)—CHR$^2$—NHC(=O)—O—CH$_2$—. In embodiments, L is —NHC(=O)—, —C(=O)NH—, —NHC(=O)—CHR$^2$—NHC(=O)—, or —C(=O)NH—CHR$^2$—C(=O)NH—. In embodiments, L is —NHC(=O)— or —C(=O)NH—.

In embodiments, L is —NHC(=O)—. In embodiments, L is —C(=O)NH—. In embodiments, L is —NH(C=O)—O—CH$_2$—. In embodiments, L is —CH$_2$—O—C(=O)NH—. In embodiments, L is —NHC(=O)—CHR$^2$—NHC(=O)—. In embodiments, L is —C(=O)NH—CHR$^2$—C(=O)NH—. In embodiments, L is —CH$_2$—O—C(=O)NH—CHR$^2$—C(=O)NH—. In embodiments, L is —NHC(=O)—CHR$^2$—NHC(=O)—O—CH$_2$—.

In embodiments, $R^2$ is a $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with one, two or three groups selected from halo, CN, $C_{1-3}$ alkyl, $C_{1-6}$ alkoxy, and $C_{1-3}$ haloalkyl. In embodiments, $R^2$ is $C_{1-4}$ alkyl, 3-7 membered cycloalkyl, $C_{1-2}$ alkyl-($C_{3-6}$ cycloalkyl), or ($C_{3-6}$ cycloalkyl)$C_{1-2}$alkyl each of which is optionally substituted with $C_{1-6}$ alkoxy. In embodiments, $R^2$ is an unsubstituted branched $C_{1-6}$ alkyl. In embodiments, $R^2$ is an unsubstituted straight $C_{1-6}$ alkyl. In embodiments, $R^2$ is an unsubstituted 3-7 membered cycloalkyl. In embodiments, $R^2$ is an unsubstituted $C_{1-3}$ alkyl-(3-7 membered cycloalkyl). In embodiments, $R^2$ is an unsubstituted (3-7 membered cycloalkyl)-$C_{1-3}$ alkyl.

In embodiments, $R^2$ is methyl, ethyl, propyl, butyl, isopropyl, isobutyl, t-butyl, or isopentyl. In embodiments, $R^2$ is isopropylmethyl, isobutylmethyl, isobutylethyl, or isopentylmethyl. In embodiments, $R^2$ is cyclopropyl, cyclobutyl, cyclopentyl, cyclohexyl, or cycloheptyl. In embodiments, $R^2$ is cyclopropylmethyl, cyclopropylethyl, cyclohexylmethyl, or cyclohexylethyl. In embodiments, $R^2$ is methyl. In embodiments, $R^2$ is ethyl. In embodiments, $R^2$ is propyl. In embodiments, $R^2$ is butyl. In embodiments, $R^2$ is isopropyl. In embodiments, $R^2$ is isobutyl. In embodiments, $R^2$ is t-butyl. In embodiments, $R^2$ is isopentyl. In embodiments, $R^2$ is isopropylmethyl. In embodiments, $R^2$ is isobutylmethyl. In embodiments, $R^2$ is isobutylethyl. In embodiments, $R^2$ is isopentylmethyl. In embodiments, $R^2$ is cyclopropyl. In embodiments, $R^2$ is cyclobutyl. In embodiments, $R^2$ is cyclopentyl. In embodiments, $R^2$ is cyclohexyl. In embodiments, $R^2$ is cycloheptyl. In embodiments, $R^2$ is cyclopropylmethyl. In embodiments, $R^2$ is cyclopropylethyl. In embodiments, $R^2$ is cyclohexylmethyl. In embodiments, $R^2$ is cyclohexylethyl.

In embodiments, $R^2$ is methyl, ethyl, propyl, butyl, isopropyl, isobutyl, t-butyl, or isopentyl substituted with one, two or three groups selected from halo, CN, $C_{1-3}$ alkyl, and $C_{1-6}$ alkoxy. In embodiments, $R^2$ is trifluoromethyl, difluoromethyl, fluoromethyl, trifluoroethyl, trifluorobutyl, fluoroethyl, fluorobutyl, fluoro-t-butyl, fluoroisopentyl, methoxyethyl, ethoxyethyl, propoxyethyl, butoxyethyl, t-butoxyethyl or 1-methyl-t-butoxyethyl. In embodiments, $R^2$ is 1-methyl-t-butoxyethyl.

In embodiments, $R^2$ is cyclopropyl, cyclobutyl, cyclopentyl, cyclohexyl, or cycloheptyl substituted with one, two or three groups selected from halo, CN, $C_{1-3}$ alkyl, and $C_{1-6}$ alkoxy. In embodiments, $R^2$ is cyclopropyl, cyclobutyl, cyclopentyl, cyclohexyl, or cycloheptyl substituted with one group selected from halo, CN, $C_{1-3}$ alkyl, and $C_{1-6}$ alkoxy. In embodiments, $R^2$ is cyclopropyl, cyclobutyl, cyclopentyl, cyclohexyl, or cycloheptyl substituted with two groups selected from halo, CN, $C_{1-3}$ alkyl, and $C_{1-6}$ alkoxy. In embodiments, $R^2$ is cyclopropyl, cyclobutyl, cyclopentyl, cyclohexyl, or cycloheptyl substituted with three groups selected from halo, CN, $C_{1-3}$ alkyl, and $C_{1-6}$ alkoxy. In embodiments, $R^2$ is cyclopropyl, cyclobutyl, cyclopentyl, cyclohexyl, or cycloheptyl substituted with one two or three groups selected from fluoro, CN, methyl, ethyl, propyl, methoxy, ethoxy or propoxy. In embodiments, $R^2$ is cyclopropyl, cyclobutyl, cyclopentyl, cyclohexyl, or cycloheptyl substituted with one group selected from fluoro, CN, methyl, ethyl, propyl, methoxy, ethoxy or propoxy.

In embodiments, $R^2$ is methyl, ethyl, propyl, isopropyl, t-butyl, isobutyl, isopropylmethyl, 1-methyl-t-butoxyethyl, cyclopropyl, cyclohexyl, cyclopropylmethyl, or cyclohexylmethyl. In embodiments, $R^2$ is ethyl, propyl, t-butyl, isobutyl, isopropylmethyl, cyclopropyl, cyclohexyl, 1-methyl-t-butoxyethyl, cyclopropylmethyl, or cyclohexylmethyl. In embodiments, $R^2$ is t-butyl, isopropylmethyl, cyclohexylmethyl or 1-methyl-t-butoxyethyl.

In embodiments, $R^3$ is H, methyl, ethyl, propyl, isopropyl, butyl, isobutyl or t-butyl. In embodiments, $R^3$ is H. In embodiments, $R^3$ is methyl. In embodiments, $R^3$ is ethyl. In embodiments, $R^3$ is propyl. In embodiments, $R^3$ is isopropyl. In embodiments, $R^3$ is butyl. In embodiments, $R^3$ is isobutyl. In embodiments, $R^3$ is t-butyl.

In embodiments, Z is selected from —CHO, —CN, —CH$_2$CN, —C(=O)CH=CH$_2$, —C(=O)CH$_2$Cl, —C(=O)CH$_2$F, —C(=O)CH$_2$Br, —C(=O)CH$_2$I, —NHC(=O)CH=CH$_2$, —C(=O)CH$_2$OH,

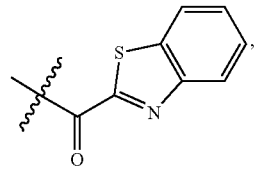 [SMILES: *C(=O)c1nc2ccccc2s1]

—CO$_2$CH$_3$, —CH$_2$OH, —C(=O)OH, —CH(OCH$_3$)$_2$, and —CH(OH)SO$_3$— (and an associated cation, such as Na$^+$). In embodiments, Z is —CN, —CO$_2$CH$_3$, —CH$_2$OH, —C(=O)OH, —NHC(=O)CH=CH$_2$, —C(=O)CH=CH$_2$, —C(=O)CH$_2$OH, —CH(OCH$_3$)$_2$, —CHO, —CH(OH)SO$_3$— (and an associated cation, such as Na$^+$), or —C(=O)—CH$_2$X, where X is F, Cl, Br, or I.

In embodiments Z is —CHO. In embodiments, Z is —CN. In embodiments, Z is —CH$_2$CN. In embodiments, Z is —C(=O)CH=CH$_2$. In embodiments, Z is —C(=O)CH$_2$Cl. In embodiments, Z is —C(=O)CH$_2$F. In embodiments, Z is —C(=O)CH$_2$Br. In embodiments, Z is —C(=O)CH$_2$I. In embodiments, Z is —NHC(=O)CH=CH$_2$. In embodiments, Z is —C(=O)CH$_2$OH. In embodiments, Z is

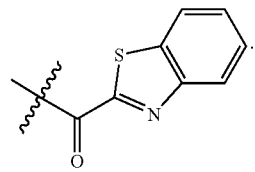 [SMILES: *C(=O)c1nc2ccccc2s1]

In embodiments, Z is —CO$_2$CH$_3$. In embodiments, Z is —CH$_2$OH. In embodiments, Z is —C(=O)OH. In embodiments, Z is —CH(OCH$_3$)$_2$. In embodiments, Z is —CH(OH)SO$_3^-$ (and an associated cation, such as Na$^+$).

In embodiments, R* is independently selected from chloro, fluoro, bromo, iodo, methyl, ethyl, propyl, methoxy, ethoxy, propoxy, CN, —OH, trifluoromethyl, difluoromethyl, fluoromethyl, trifluoroethyl, difluoroethyl, fluoroethyl, trichloromethyl, dichloromethyl, chloromethyl, trichloroethyl, dichloroethyl, and chloroethyl. In embodiments, R* is independently chloro. In embodiments, R* is independently fluoro. In embodiments, R* is independently bromo. In embodiments, R* is independently iodo. In embodiments, R* is independently methyl. In embodiments, R* is independently ethyl. In embodiments, R* is independently propyl. In embodiments, R* is independently methoxy. In embodiments, R* is independently ethoxy. In embodiments, R* is independently propoxy. In embodiments, R* is independently CN. In embodiments, R* is independently —OH. In embodiments, R* is independently trifluoromethyl. In embodiments, R* is independently trifluoroethyl. In embodiments, R* is independently difluoromethyl. In embodiments, R* is independently difluoroethyl. In embodiments, R* is independently fluoromethyl. In embodiments, R* is independently fluoroethyl. In embodiments, R* is independently trichloromethyl. In embodiments, R* is independently trichloroethyl. In embodiments, R* is independently dichloromethyl. In embodiments, R* is independently dichloroethyl. In embodiments, R* is independently chloromethyl. In embodiments, R* is independently chloroethyl.

In embodiments, m is 0, 1, or 2. In embodiments, m is 0. In embodiments, m is 1. In embodiments, m is 2.

In embodiments, n is 0, 1, 2, 3, or 4. In embodiments, n is 1, 2, or 3. In embodiments, n is 0. In embodiments, n is 1. In embodiments, n is 2. In embodiments, n is 3. In embodiments, n is 4.

In embodiments, provided herein is a compound of Formula (IA):

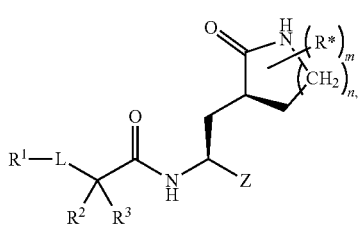

(IA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, L, $R^2$, $R^3$, Z, R*, m, and n are as described herein, including in embodiments.

In embodiments, provided herein is a compound of Formula (IB):

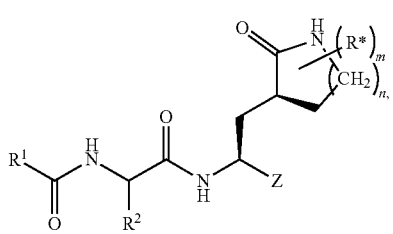

(IB)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, R*, m, and n are as described herein, including in embodiments.

In embodiments, provided herein is a compound of Formula (IC):

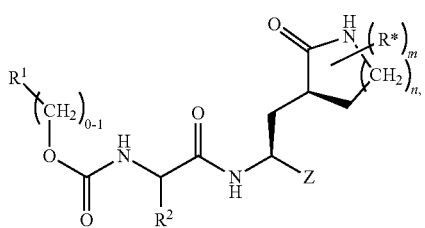

(IC)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, R*, m, and n are as described herein, including in embodiments.

In embodiments, provided herein is a compound of Formula (IC1):

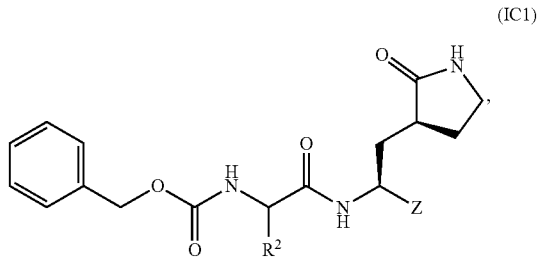

(IC1)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IC1A):

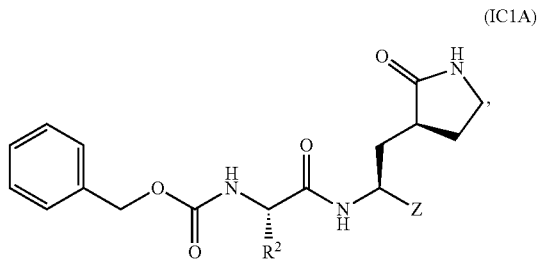

(IC1A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (ID):

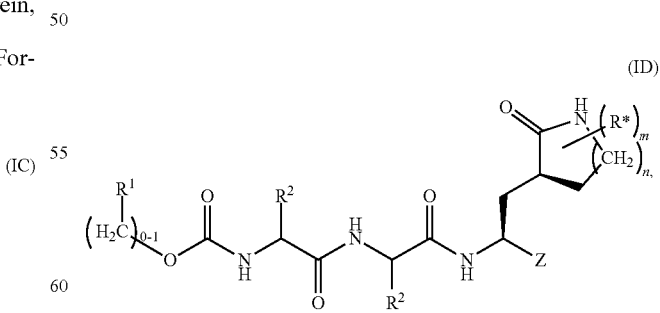

(ID)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, R*, m, and n are as described herein, including in embodiments. In embodiments, each $R^2$ is independently selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy. In embodiments, each $R^2$ is independently as described herein, including in embodiments.

In embodiments, provided herein is a compound of Formula (ID1):

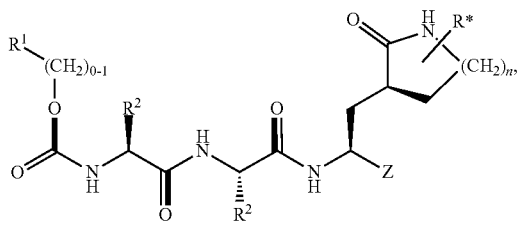

(ID1)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, $R^*$, and n are as described herein, including in embodiments. In embodiments, each $R^2$ is independently selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy. In embodiments, each $R^2$ is independently as described herein, including in embodiments.

In embodiments, provided herein is a compound of Formula (IE):

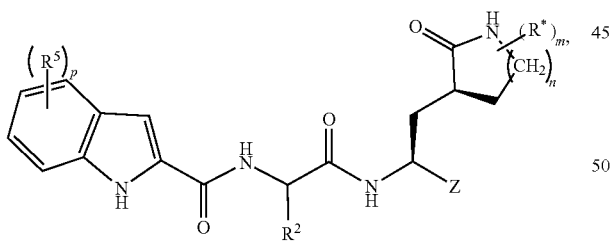

(IE)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^5$ is independently selected from hydrogen, halo, —CN, $C_{1-3}$ alkyl, $C_{1-3}$ alkoxy, $C_{1-3}$ haloalkyl, and $C_{1-3}$ haloalkoxy; p is an integer from 0 to 4; and $R^2$, Z, $R^*$, m, and n are as described herein, including in embodiments.

In embodiments, $R^5$ is independently selected from hydrogen, halo, $C_{1-3}$ alkyl, and $C_{1-3}$ alkoxy. In embodiments, $R^5$ is independently selected from hydrogen, halo, —CN, methyl, ethyl, propyl, methoxy, ethoxy, propoxy, trifluoromethyl, trichloromethyl, tribromomethyl, triiodomethyl, difluoromethyl, dichloromethyl, dibromomethyl, diiodomethyl, fluoromethyl, chloromethyl, bromomethyl, iodomethyl, trifluoethyl, trifluoropropyl, trichloroethyl, and tribromoethyl. In embodiments, $R^5$ is independently selected from hydrogen, —CN, fluoro, chloro, bromo, iodo, methyl, ethyl, propyl, methoxy, ethoxy, propoxy, trifluoromethyl, trichloromethyl, tribromomethyl, trifluoroethyl, trichloroethyl, and tribromoethyl. In embodiments, $R^5$ is independently selected from hydrogen, fluoro, methyl and methoxy. In embodiments, $R^5$ is hydrogen. In embodiments, $R^5$ is methyl. In embodiments, $R^5$ is methoxy.

In embodiments, p is 0. In embodiments, p is 1. In embodiments, p is 2. In embodiments, p is 3. In embodiments, p is 4.

In embodiments, provided herein is a compound of Formula (IF):

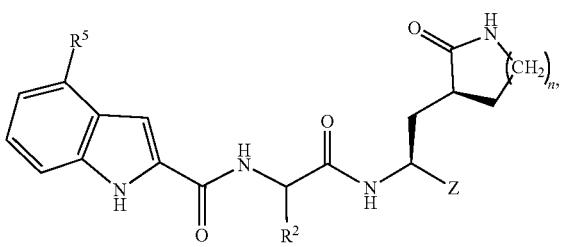

(IF)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, $R^5$, Z, and n are as described herein, including in embodiments.

In embodiments, provided herein is a compound of Formula (IG):

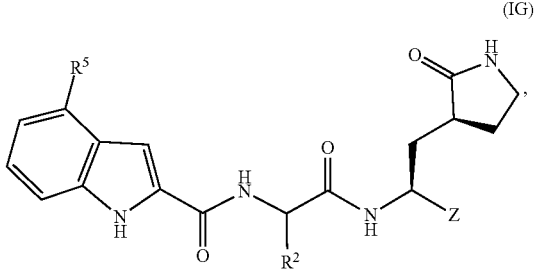

(IG)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, $R^5$, and Z are as described herein, including in embodiments.

In embodiments, provided herein is a compound of Formula (IG1):

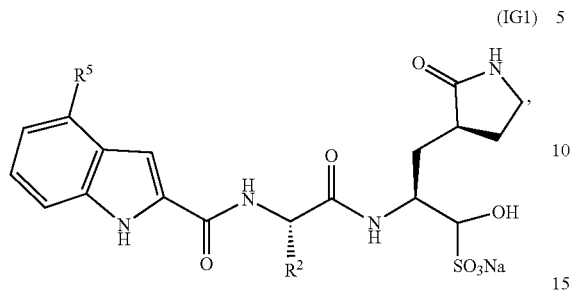

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and $R^5$ are as described herein, including in embodiments.

In embodiments, provided herein is a compound of Formula (IG2):

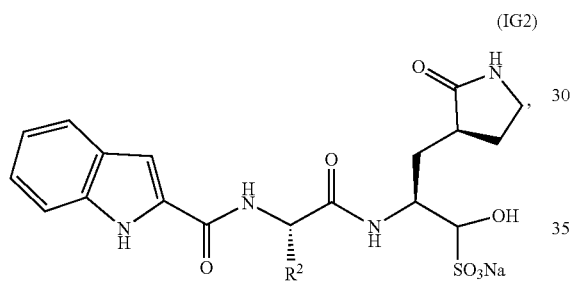

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ is as described herein, including in embodiments.

In embodiments, provided herein is a compound of Formula (IH):

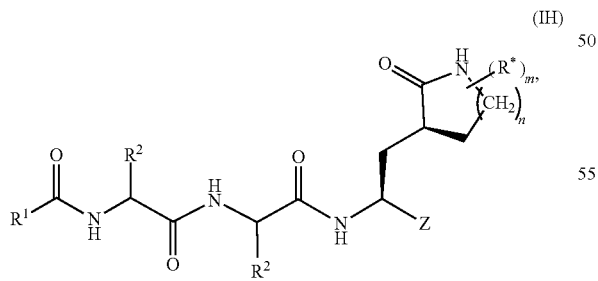

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, $R^*$, m, and n are as described herein, including in embodiments. In embodiments, each $R^2$ is independently selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy. In embodiments, each $R^2$ is independently as described herein, including in embodiments.

In embodiments, provided herein are compounds selected from:

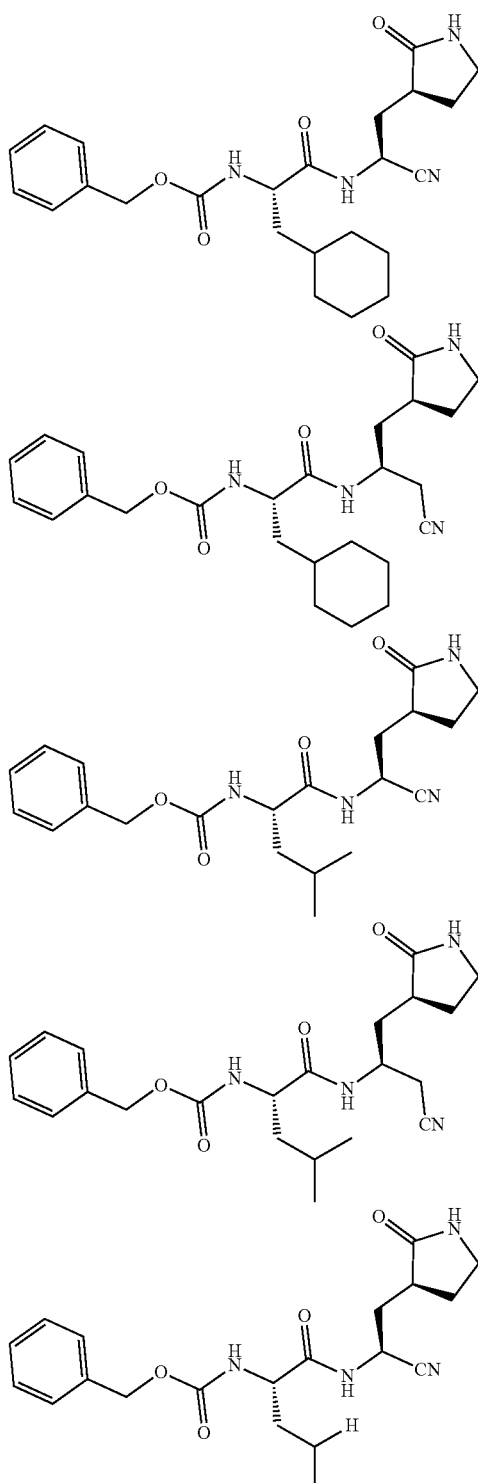

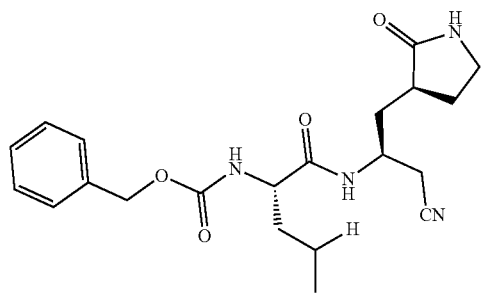
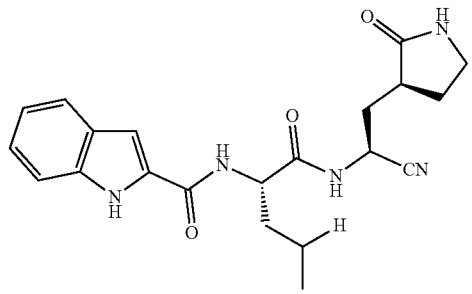
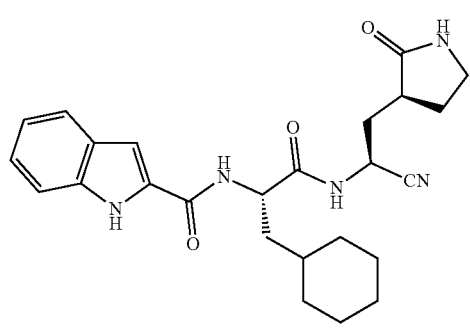
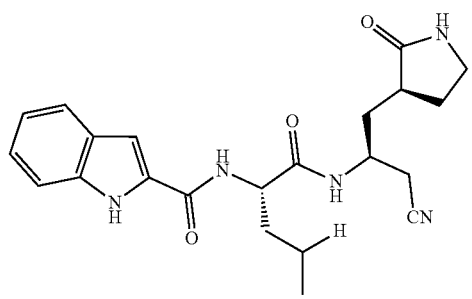
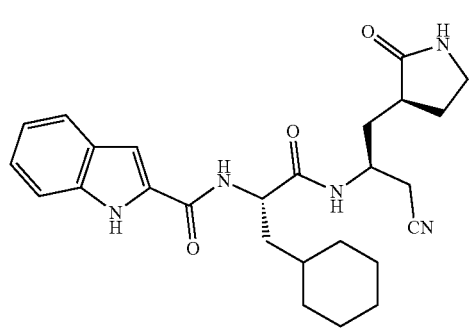
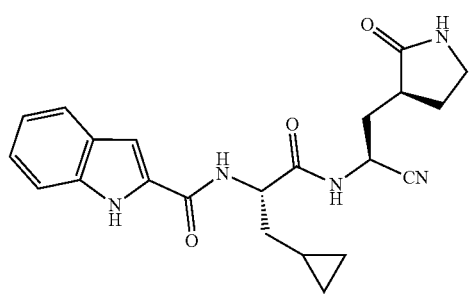
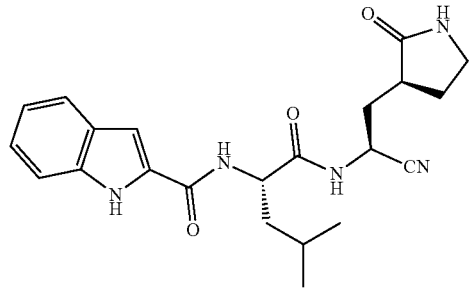
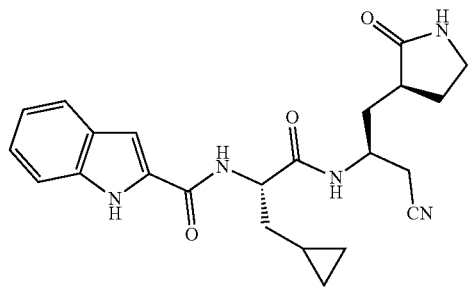
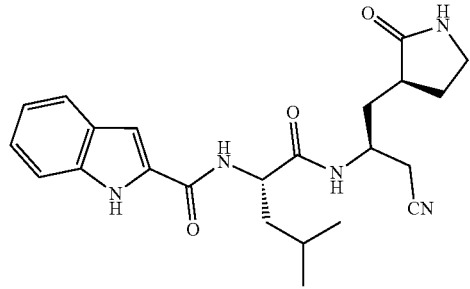
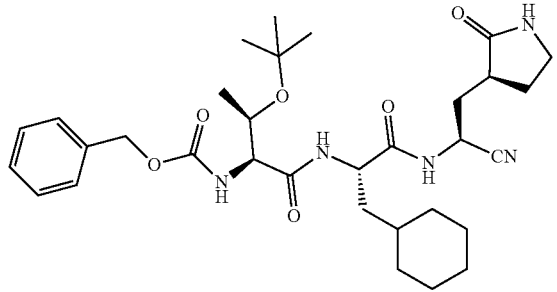

31
-continued
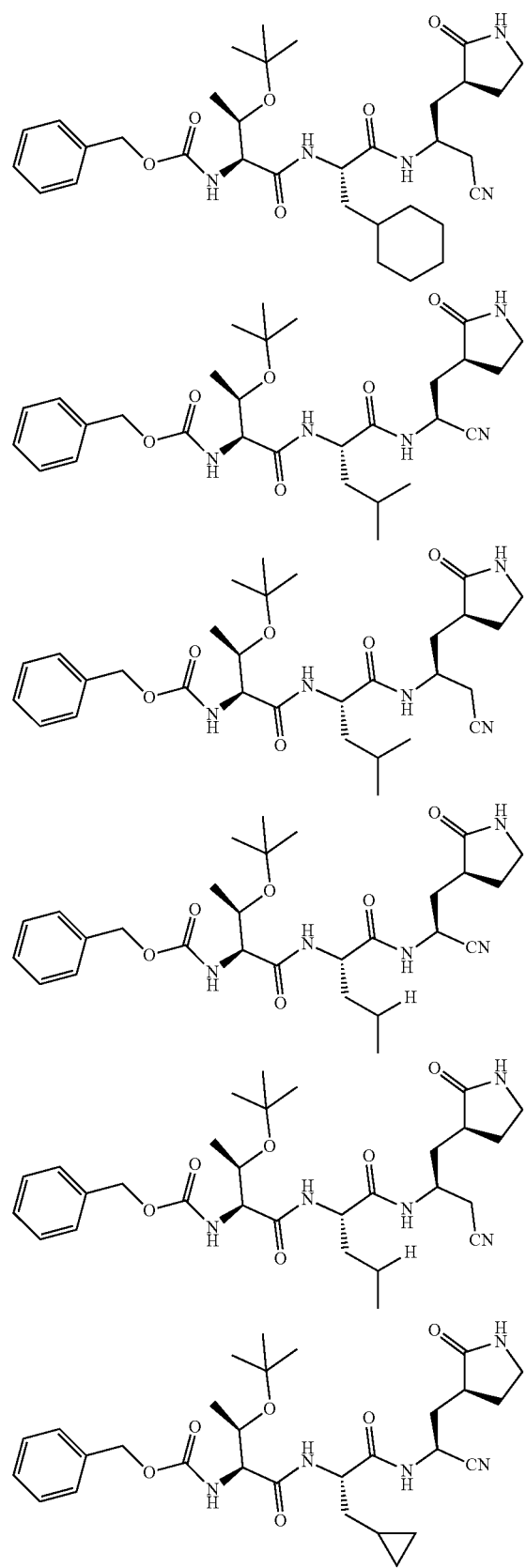
32
-continued
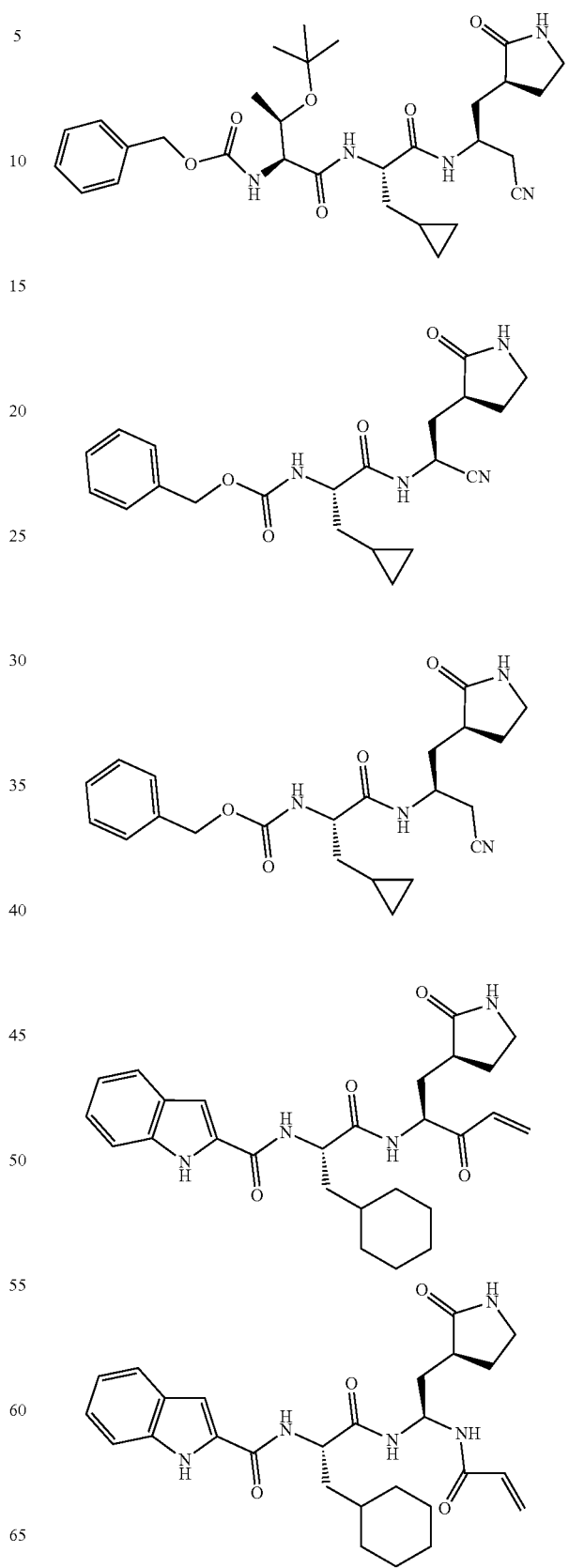

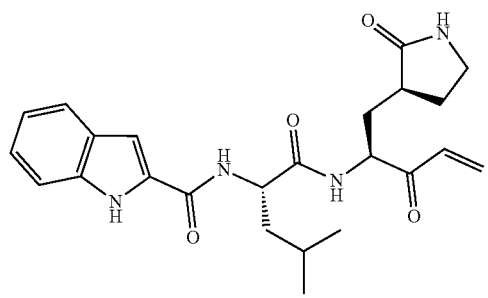
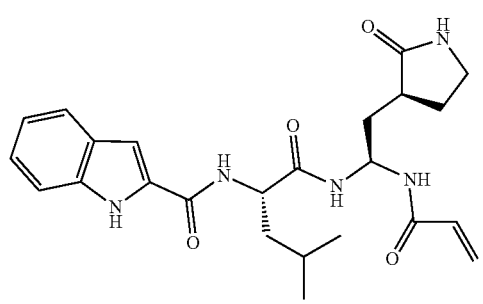
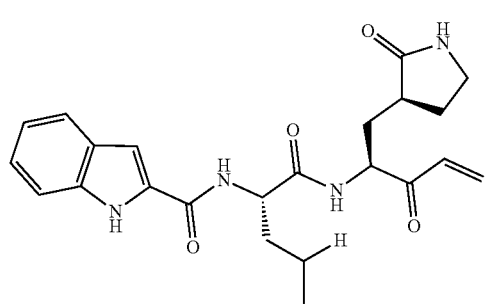
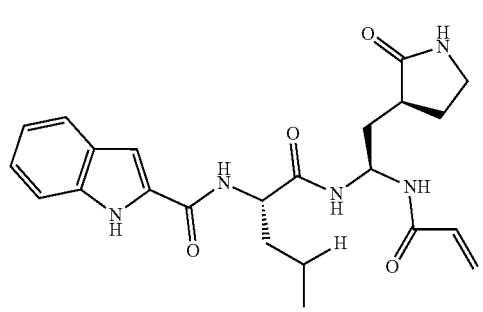
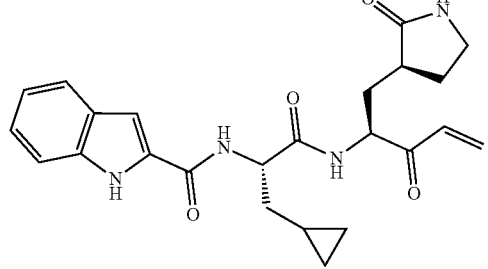
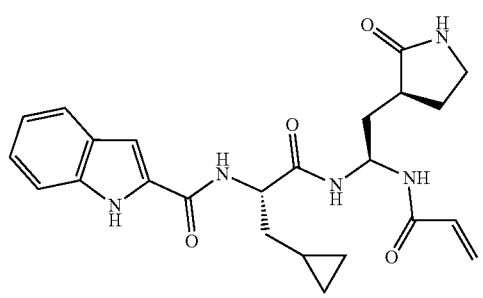
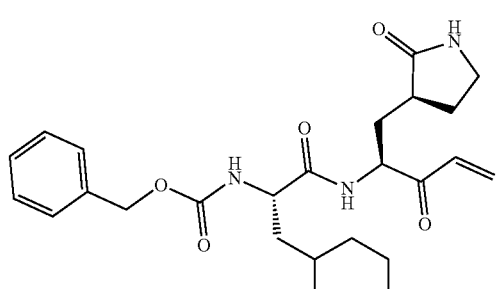
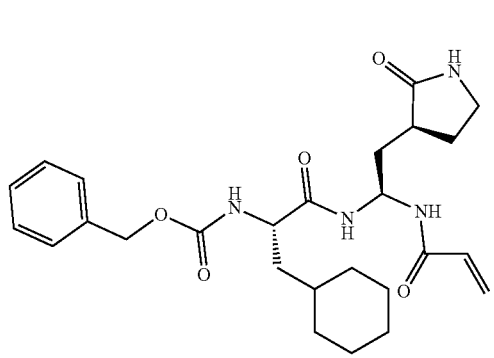
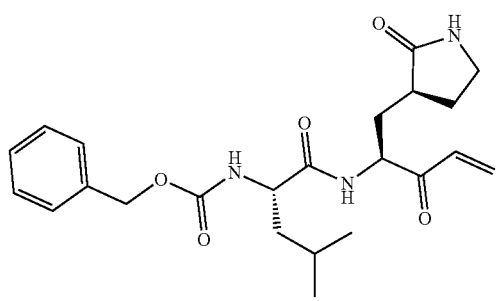
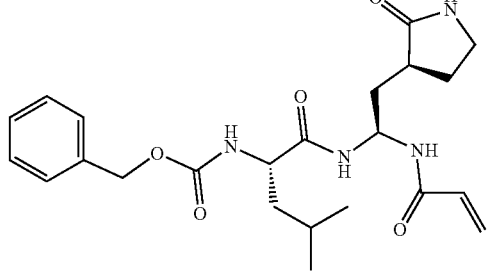

35
-continued
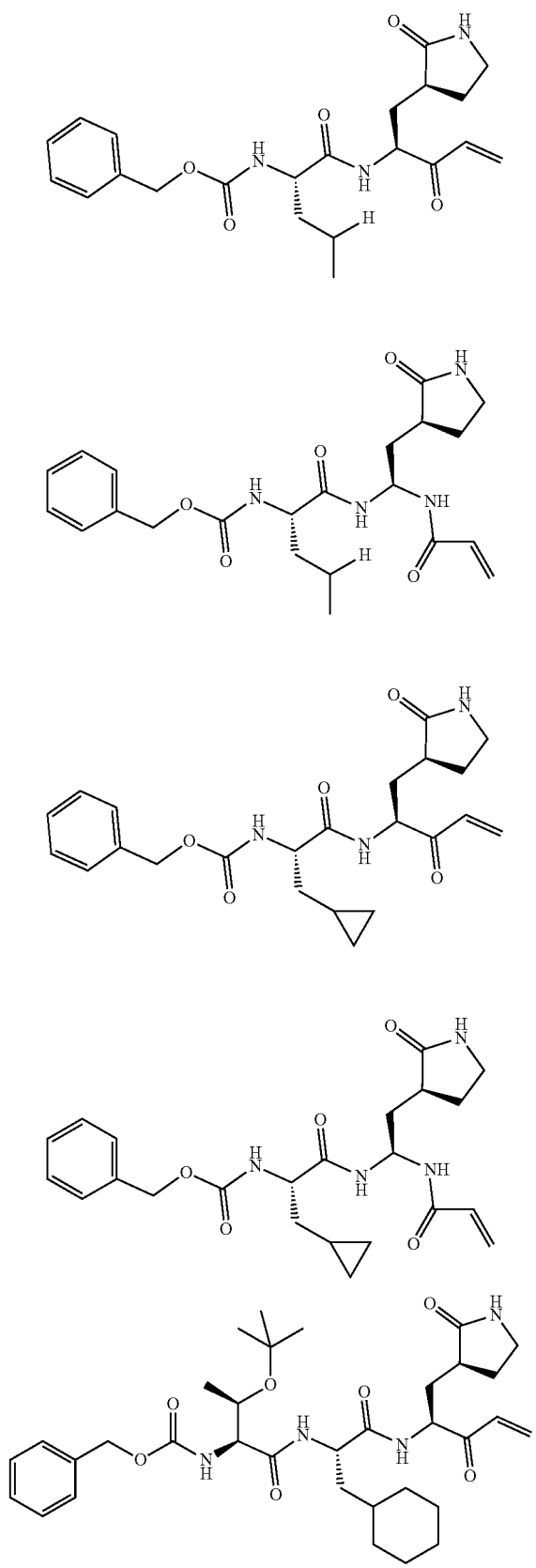
36
-continued
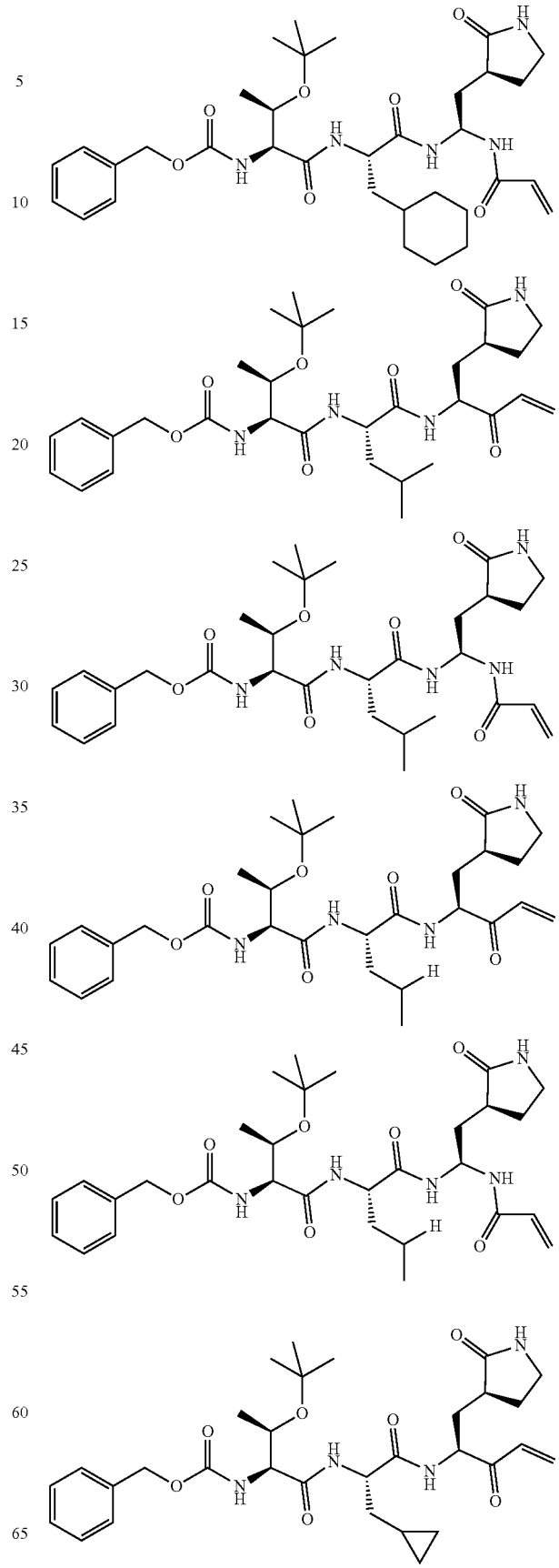

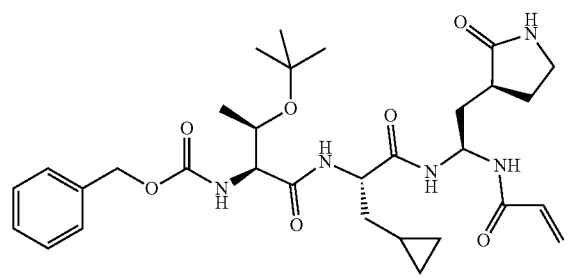
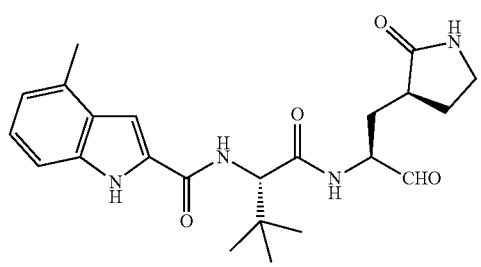
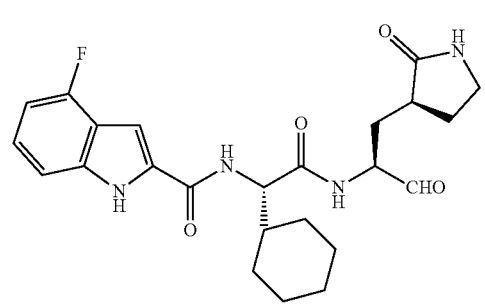
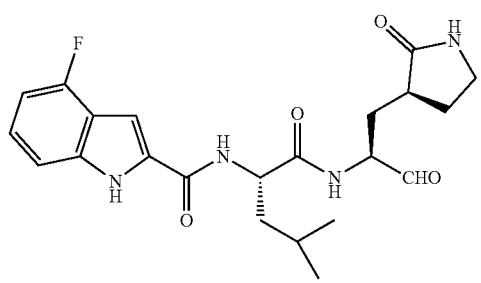
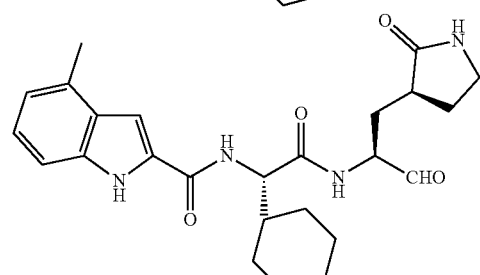
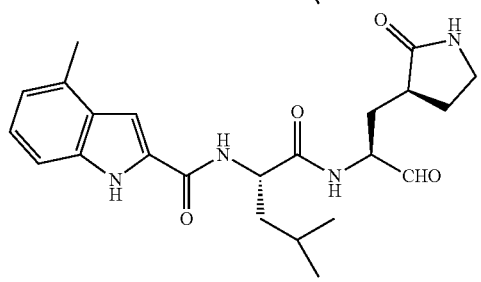
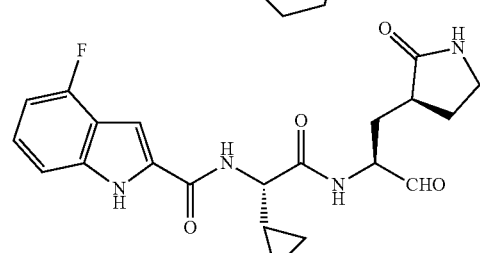
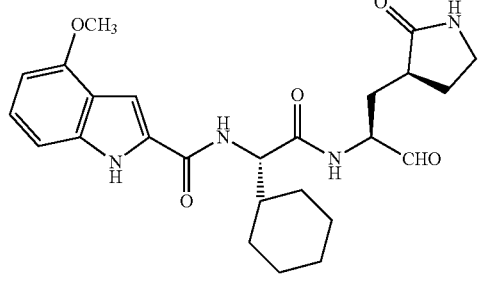
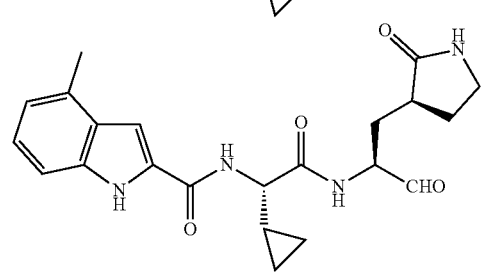
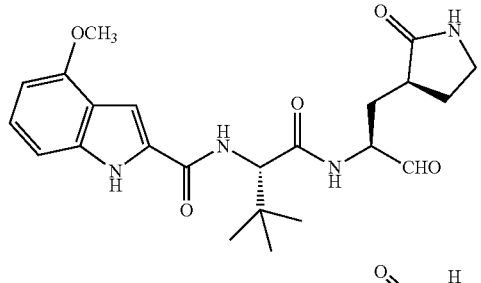
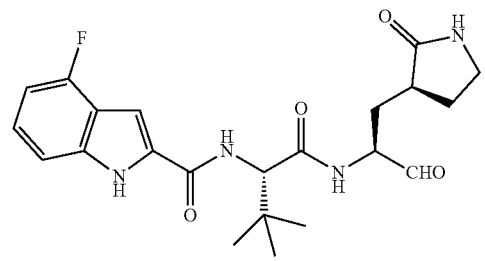
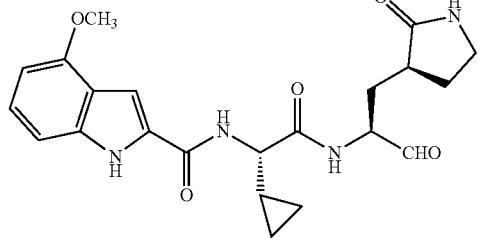

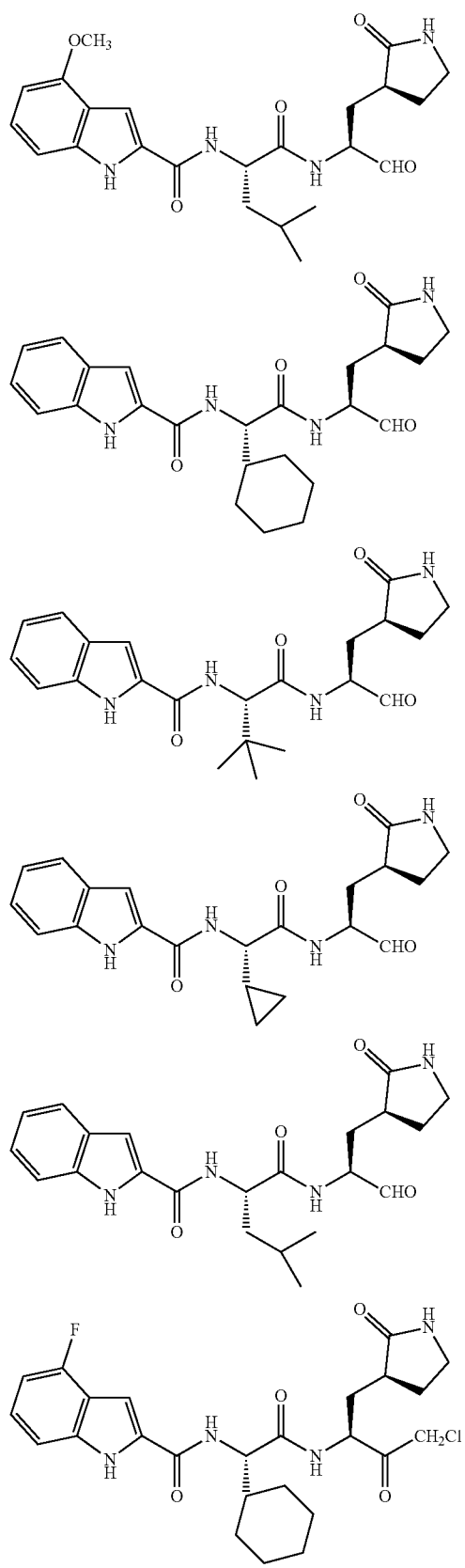
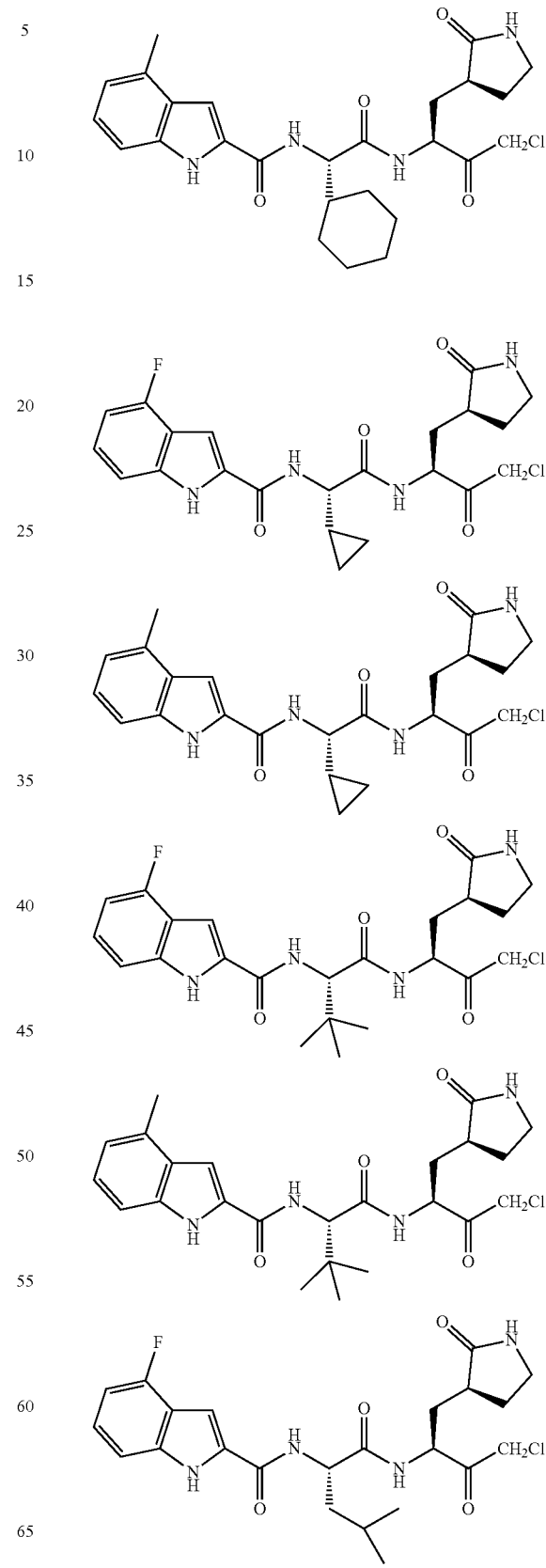

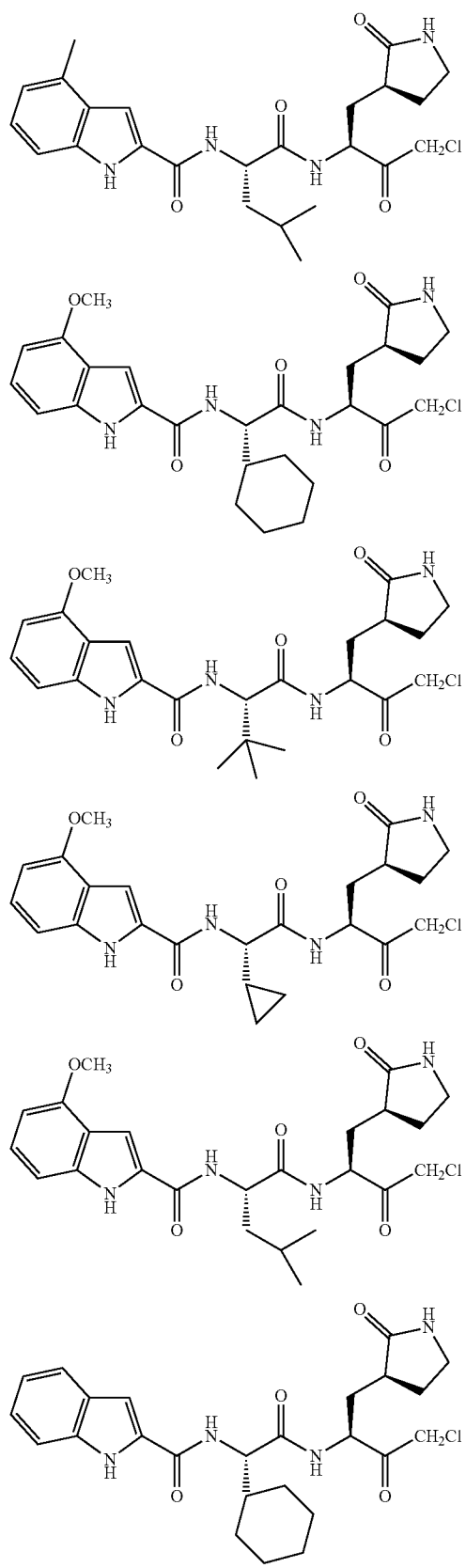
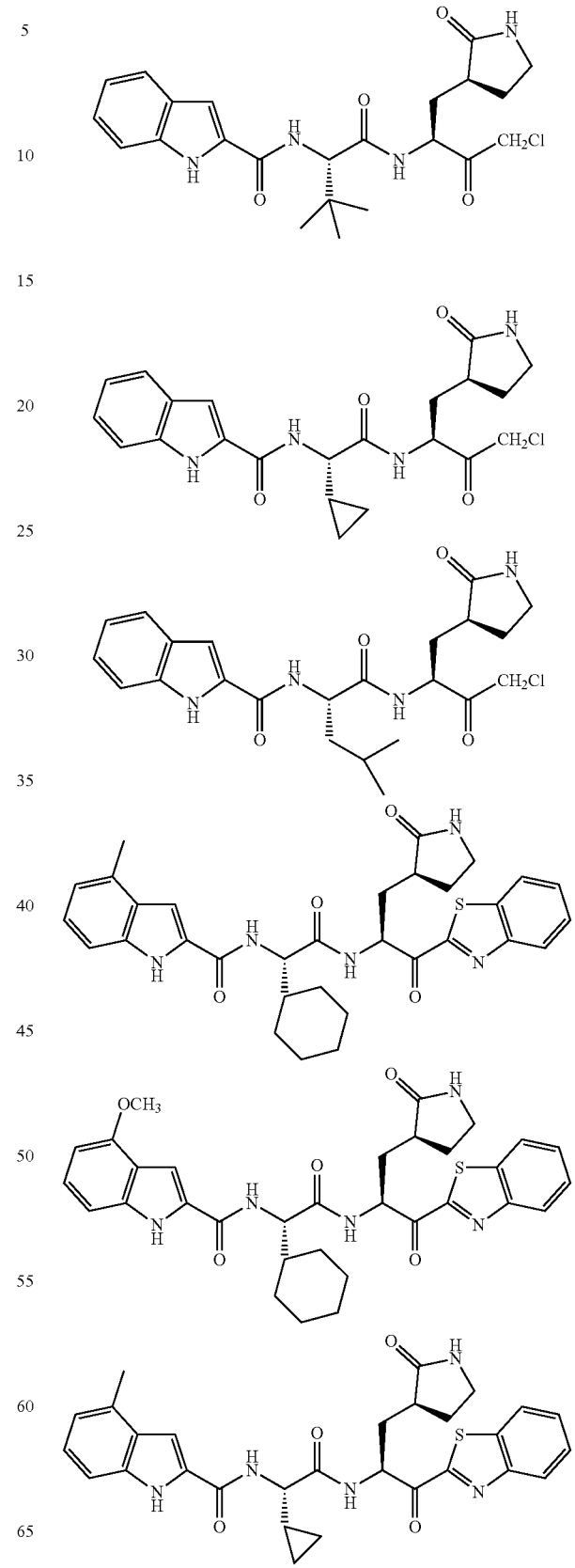

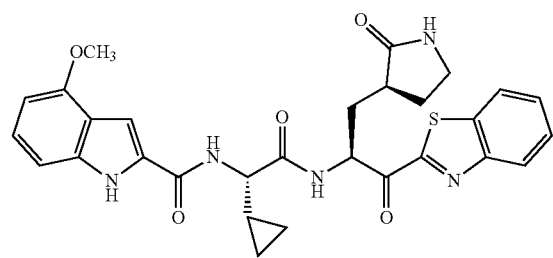
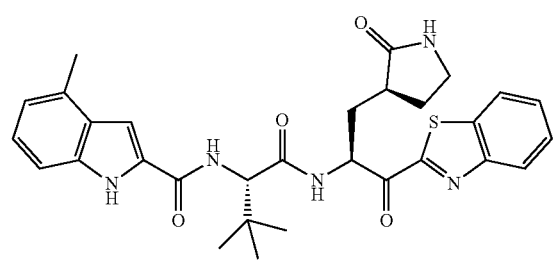
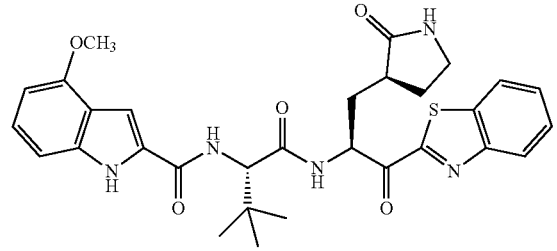
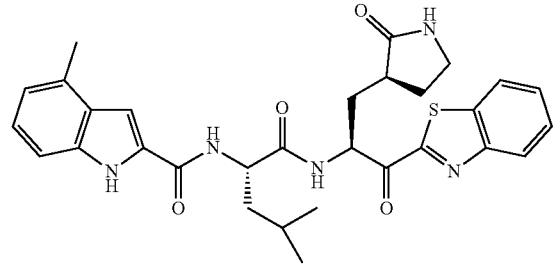
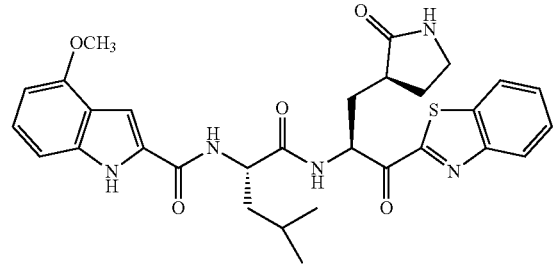
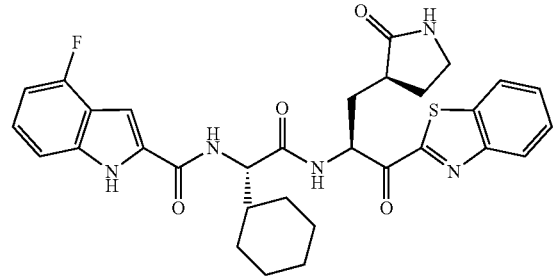
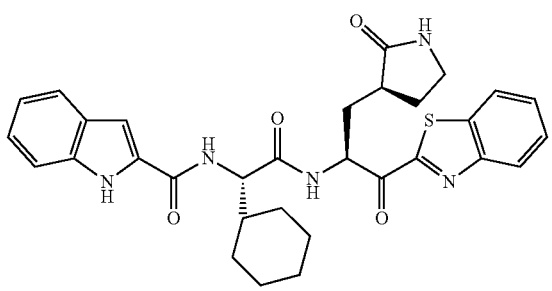
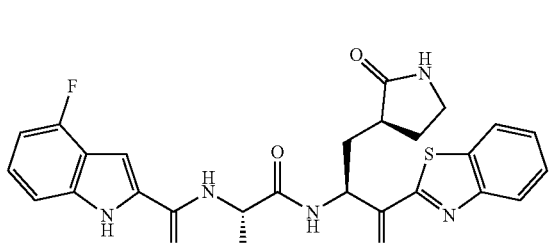
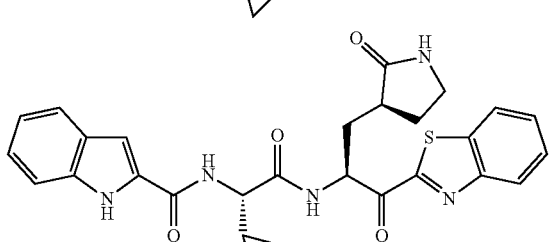
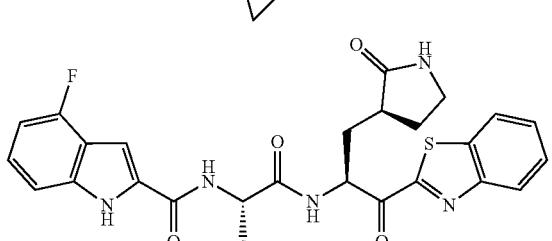
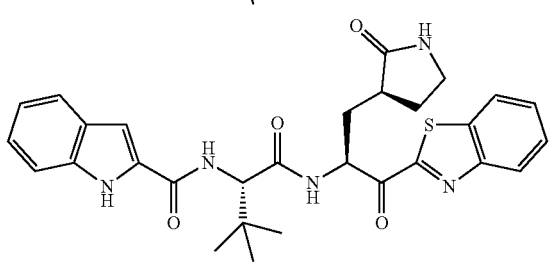
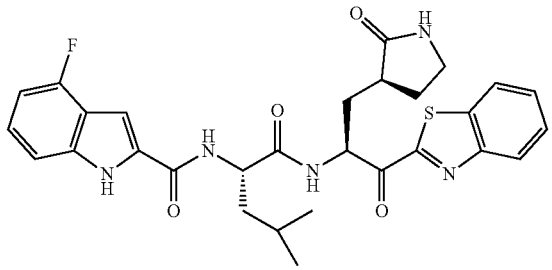

45
-continued
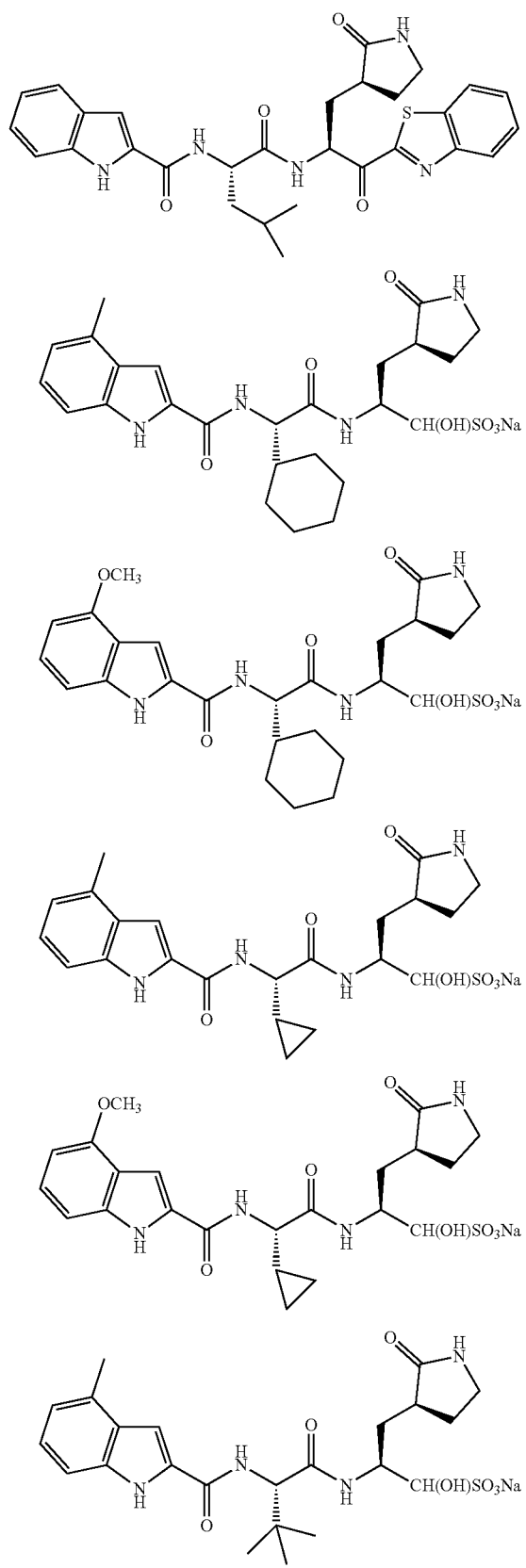
46
-continued
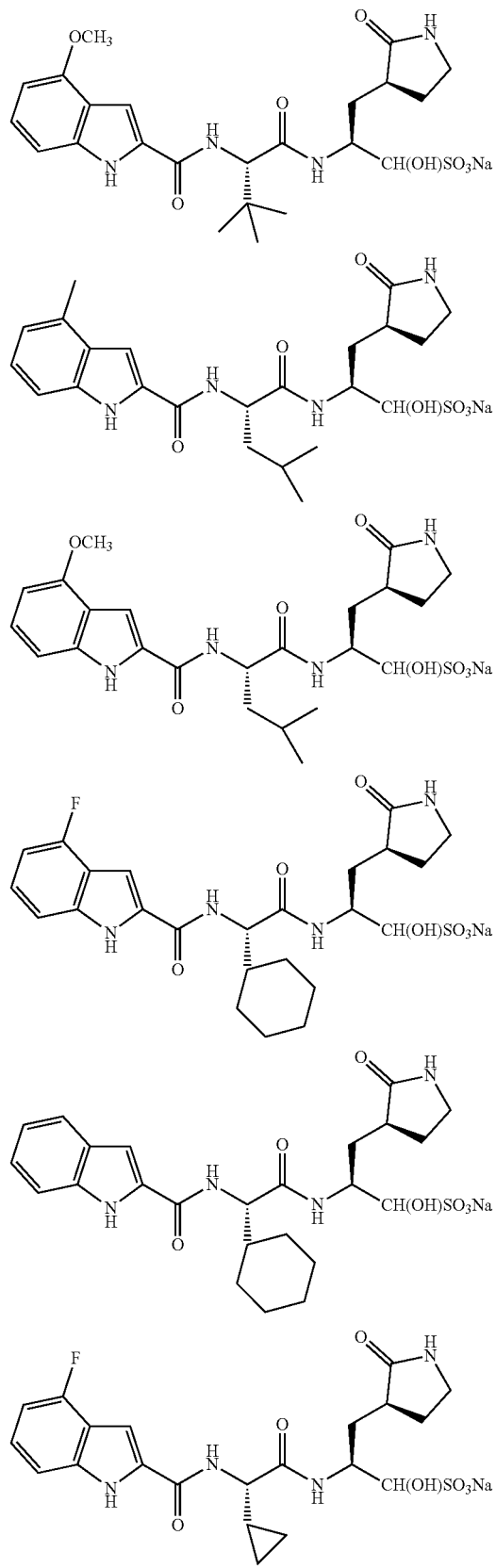

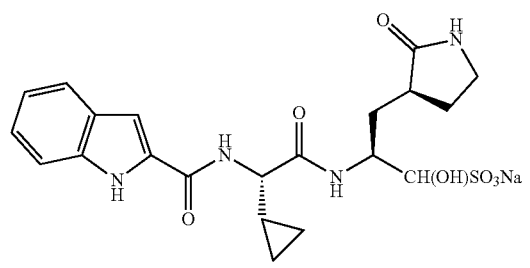
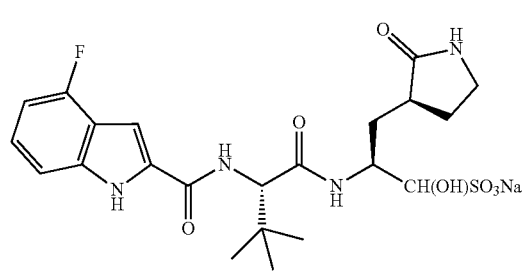
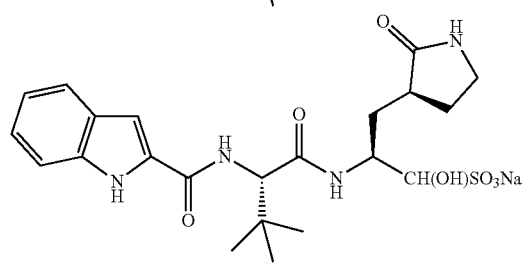
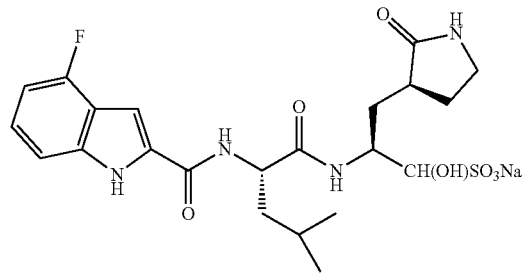
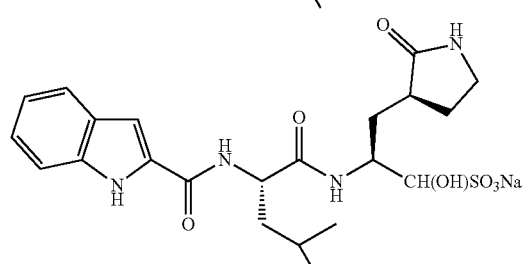
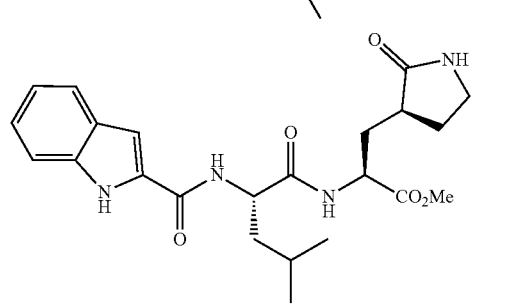
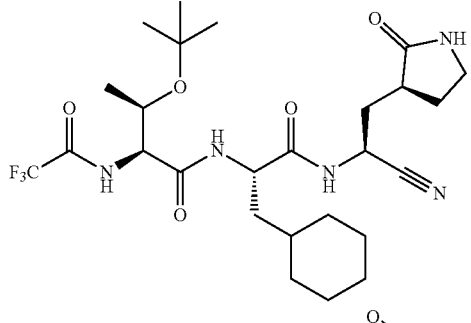
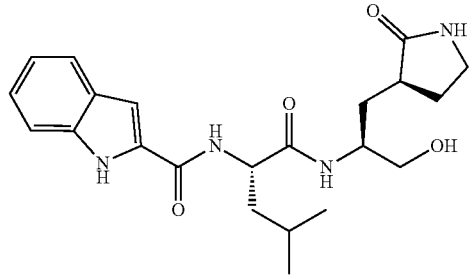
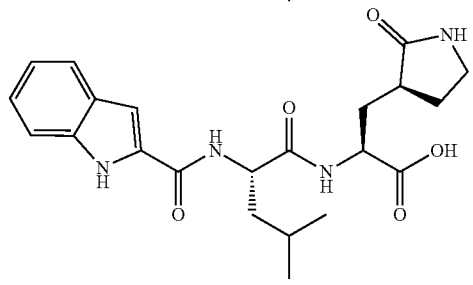
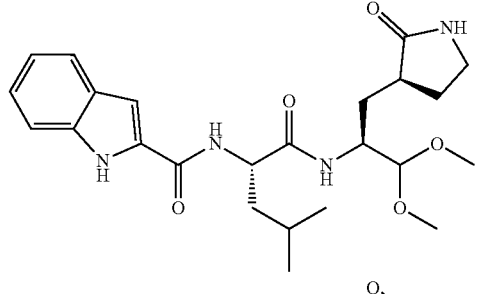
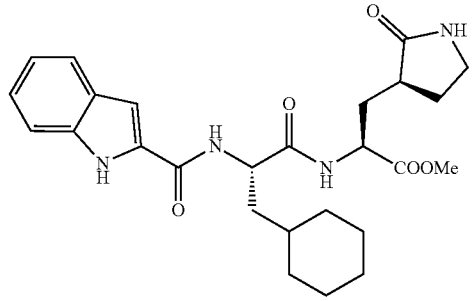
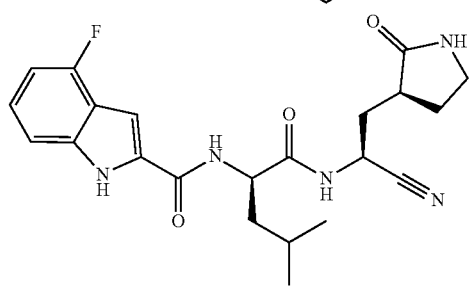

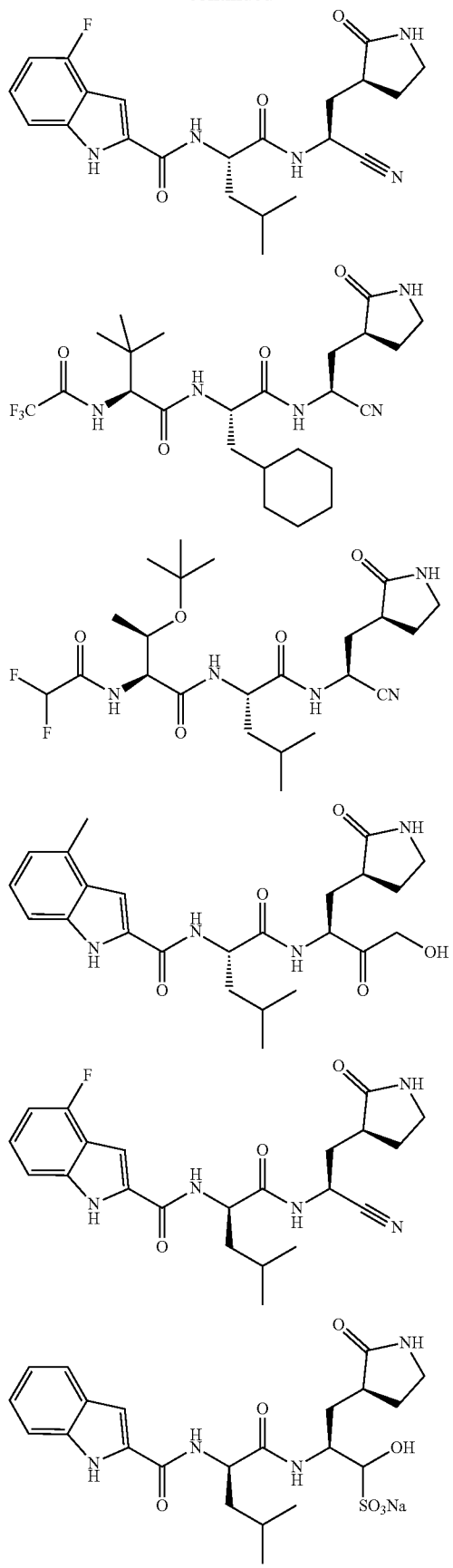
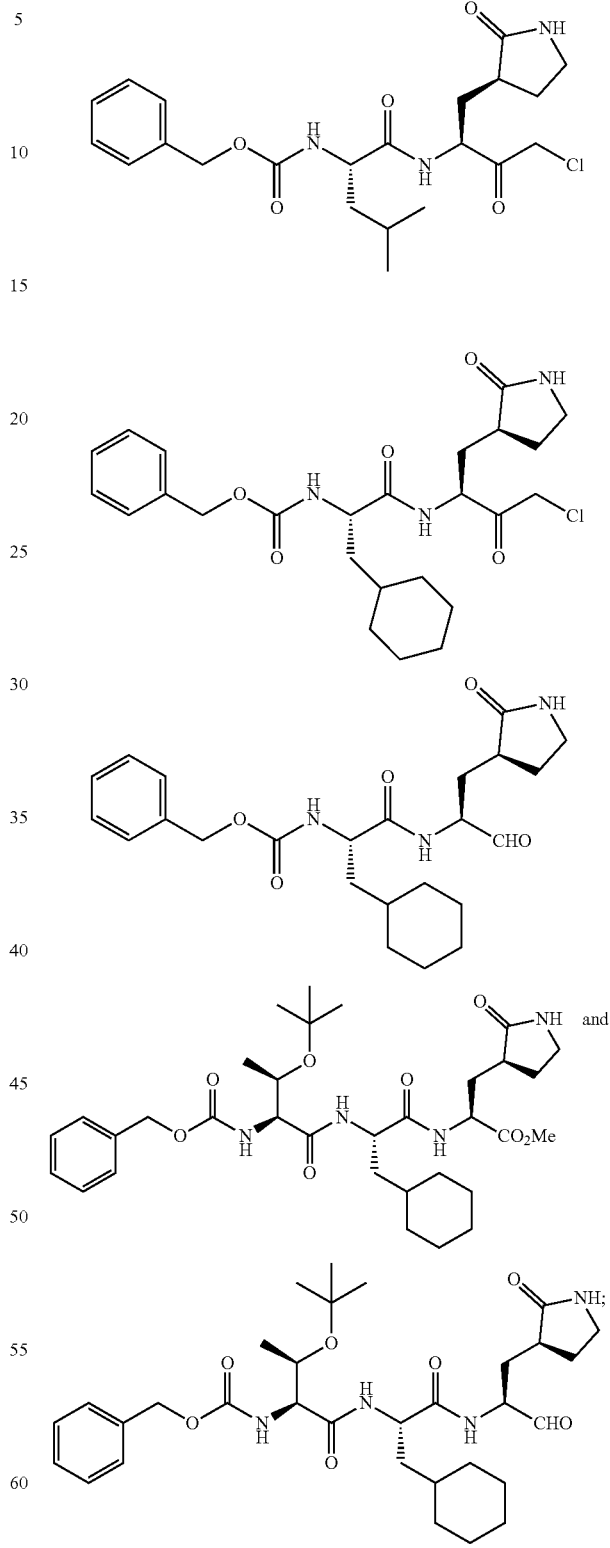
and tautomers, mixtures of two or more tautomers, and isotopic variants thereof; and pharmaceutically acceptable salts, solvates, hydrates, and prodrugs thereof.

In an aspect, provided herein is a compound of Formula (II):

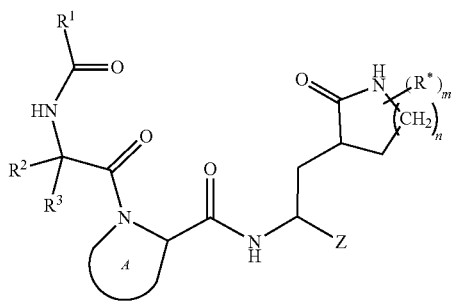

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

Ring A is a 5-9 atom cycloalkyl that is optionally substituted with up to three groups selected from $C_{1-3}$ alkyl, $C_{1-6}$ alkoxy, $C_{1-3}$ haloalkyl, and $C_{1-3}$ haloalkoxy;

Z is selected from —$CO_2$—$C_{1-3}$ alkyl, —CHO, —$CH_2CN$, —C(=O)—CH=$CH_2$, —$CH_2$—C(=O)CH=$CH_2$, —C(=O)—$C_{1-3}$ haloalkyl, —NH—C(=O)—CH=$CH_2$, —C(=O)$CH_2$OH,

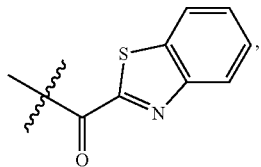 [SMILES: *C(=O)c1nc2ccccc2s1]

and —CH(OH)$SO_3^-$ (and an associated cation, such as $Na^+$);

or Z can be —CN provided $R^2$ is not t-butyl when n is 1;

$R^1$ is H, 3-7 membered cycloalkyl, $C_{1-4}$alkoxy, or $C_{1-4}$ alkyl, wherein the 3-7 membered cycloalkyl, $C_{1-4}$alkoxy and $C_{1-4}$ alkyl are optionally substituted with one to three groups independently selected from halo, CN, $C_{3-6}$ cycloalkyl, $C_{1-3}$ alkoxy, $C_{1-3}$ haloalkyl, and $C_{1-3}$haloalkoxy; or $R^1$ is 5-10 membered heteroaryl containing one or two heteroatoms selected from N, O and S as ring members, and wherein the 5-10 membered heteroaryl is optionally substituted with one to three groups independently selected from halo, CN, $C_{1-3}$ alkyl, $C_{1-3}$ alkoxy, $C_{1-3}$ haloalkyl, and $C_{1-3}$ haloalkoxy;

$R^2$ is selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy;

$R^3$ is H or $C_{1-4}$ alkyl;

each $R^*$ is independently selected from $C_{1-3}$ alkyl, $C_{1-3}$ alkoxy, $C_{1-3}$ haloalkyl, CN, halo, and —OH;

m is an integer from 0 to 2; and n is an integer from 0 to 4.

In embodiments, Ring A is a 5-membered ring that can optionally be fused to a cyclopropyl ring, forming a bicyclic ring system that is an unsubstituted 3-azabicyclo[3.1.0]hexane ring. In embodiments, Ring A is a 5-membered ring that can optionally be fused to a cyclopropyl ring, forming a bicyclic ring system that is a 3-azabicyclo[3.1.0]hexane ring, substituted with one group selected from $C_{1-3}$ alkyl, $C_{1-6}$ alkoxy, $C_{1-3}$ haloalkyl, and $C_{1-3}$ haloalkoxy. In embodiments, Ring A is a 5-membered ring that can optionally be fused to a cyclopropyl ring, forming a bicyclic ring system that is a 3-azabicyclo[3.1.0]hexane ring, substituted with two groups independently selected from $C_{1-3}$ alkyl, $C_{1-6}$ alkoxy, $C_{1-3}$ haloalkyl, and $C_{1-3}$ haloalkoxy. In embodiments, Ring A is a 5-membered ring that can optionally be fused to a cyclopropyl ring, forming a bicyclic ring system that is a 3-azabicyclo[3.1.0]hexane ring, substituted with three groups independently selected from $C_{1-3}$ alkyl, $C_{1-6}$ alkoxy, $C_{1-3}$ haloalkyl, and $C_{1-3}$ haloalkoxy.

In embodiments, Ring A is a 5-membered ring that can optionally be fused to a cyclopropyl ring, forming a bicyclic ring system that is a 3-azabicyclo[3.1.0]hexane ring substituted with two methyl groups forming a 6,6-dimethyl-3-azabicyclo[3.1.0]hexane ring.

In embodiments, Z is selected from —$CO_2CH_3$, —CHO, —$CH_2CN$, —C(=O)—CH=$CH_2$, —$CH_2$—C(=O)—CH=$CH_2$, —C(=O)—$C_{1-3}$ haloalkyl, —NH—C(=O)—CH=$CH_2$, —C(=O)$CH_2$OH,

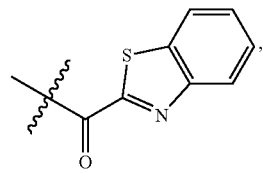 [SMILES: *C(=O)c1nc2ccccc2s1]

and —CH(OH)$SO_3^-$ (and an associated cation, such as $Na^+$). In embodiments, Z is —CN provided $R^2$ is not t-butyl when n is 1. In embodiments, Z is —CN, —$CO_2CH_3$, —$CH_2CN$, NHC(=O)CH=$CH_2$, —C(=O)$CH_2$OH, —CHO, —CH(OH)$SO_3^-$ (and an associated cation, such as $Na^+$), or —C(=O)—$CH_2$X, and wherein X is F, Cl, Br, or I.

In embodiments, Z is —$CO_2CH_3$. In embodiments, Z is —CHO. In embodiments, Z is —$CH_2CN$. In embodiments, Z is —C(=O)—CH=$CH_2$. In embodiments, Z is —$CH_2$—C(=O)—CH=$CH_2$. In embodiments, Z is —C(=O)—$C_{1-3}$ haloalkyl. In embodiments, Z is —NH—C(=O)—CH=$CH_2$. In embodiments, Z is —C(=O)$CH_2$OH. In embodiments, Z is

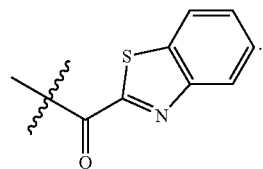 [SMILES: *C(=O)c1nc2ccccc2s1]

In embodiments, Z is —CH(OH)$SO_3^-$ (and an associated cation, such as $Na^+$). In embodiments, Z is —C(=O)—$CH_2$X where X is F, Cl, Br or I. In embodiments, Z is —C(=O)—$CH_2$F. In embodiments, Z is —C(=O)—$CH_2$Cl. In embodiments, Z is —C(=O)—$CH_2$Br. In embodiments, Z is —C(=O)—$CH_2$I.

In embodiments, $R^1$ is an indolyl, optionally substituted with one, two, or three groups independently selected from halo, CN, $C_{1-3}$ alkyl, $C_{1-3}$ alkoxy, $C_{1-3}$ haloalkyl, and $C_{1-3}$ haloalkoxy. In embodiments, $R^1$ is unsubstituted indolyl. In embodiments, $R^1$ is indolyl substituted with one group selected from halo, CN, $C_{1-3}$ alkyl, $C_{1-3}$ alkoxy, $C_{1-3}$ haloalkyl, and $C_{1-3}$ haloalkoxy. In embodiments, $R^1$ is indolyl substituted with two groups independently selected from halo, CN, $C_{1-3}$ alkyl, $C_{1-3}$ alkoxy, $C_{1-3}$ haloalkyl, and $C_{1-3}$ haloalkoxy. In embodiments, $R^1$ is indolyl substituted with three groups independently selected from halo, CN, $C_{1-3}$ alkyl, $C_{1-3}$ alkoxy, $C_{1-3}$ haloalkyl, and $C_{1-3}$ haloalkoxy. In embodiments, $R^1$ is indolyl substituted with one group selected from halo, $C_{1-3}$ alkyl, and $C_{1-3}$ alkoxy. In embodiments, $R^1$ is indolyl substituted with two groups independently selected from halo, $C_{1-3}$ alkyl, and $C_{1-3}$ alkoxy. In embodiments, $R^1$ is indolyl substituted with three groups independently selected from halo, $C_{1-3}$ alkyl, and $C_{1-3}$ alkoxy. In embodiments, $R^1$ is indolyl substituted with one group selected from fluoro, methyl, and methoxy. In embodiments, $R^1$ is indolyl substituted with two groups independently selected from fluoro, methyl, and methoxy. In embodiments, $R^1$ is indolyl substituted with three groups independently selected from fluoro, methyl, and methoxy.

In embodiments, $R^1$ is 5-10 membered heteroaryl containing one or two heteroatoms selected from N, O and S as ring members, where each 5-10 membered heteroaryl is optionally substituted with one, two or three groups independently selected from halo, CN, $C_{1-3}$ alkyl, $C_{1-3}$ alkoxy, $C_{1-3}$ haloalkyl, and $C_{1-3}$ haloalkoxy.

In embodiments, $R^1$ is unsubstituted 5-10 membered heteroaryl containing one or two heteroatoms selected from N, O and S as ring members. In embodiments, $R^1$ is unsubstituted 5-10 membered heteroaryl containing one heteroatom selected from N, O and S as ring member. In embodiments, $R^1$ is unsubstituted 5-10 membered heteroaryl containing two heteroatoms selected from N, O and S as ring members. In embodiments, $R^1$ is unsubstituted 5-10 membered heteroaryl containing one heteroatom N as ring member. In embodiments, $R^1$ is unsubstituted 5-10 membered heteroaryl containing one heteroatom O as ring member. In embodiments, $R^1$ is unsubstituted 5-10 membered heteroaryl containing one heteroatom S as ring member.

In embodiments, $R^1$ is a 5-10 membered heteroaryl containing one or two heteroatoms selected from N, O and S as ring members, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one or two heteroatoms selected from N, O and S as ring members, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one or two heteroatoms selected from N, O and S as ring members, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom selected from N, O and S as ring member, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, O and S as ring member, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, O and S as ring member, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom N, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom N, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom O, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom O, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from O, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom S, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom S, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from S, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 3-7 membered cycloalkyl optionally substituted with one to three groups independently selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is unsubstituted 3-7 membered cycloalkyl. In embodiments, $R^1$ is unsubstituted cyclopropyl. In embodiments, $R^1$ is unsubstituted cyclobutyl. In embodiments, $R^1$ is unsubstituted cyclopentyl. In embodiments, $R^1$ is unsubstituted cyclohexyl. In embodiments, $R^1$ is unsubstituted cycloheptyl. In embodiments, $R^1$ is 3-7 membered cycloalkyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopropyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclobutyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopentyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclohexyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is 3-7 membered cycloalkyl substituted with two groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopropyl substituted with two group selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is cyclobutyl substituted with two groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopentyl substituted with two groups selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is cyclohexyl substituted with two groups selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is 3-7 membered cycloalkyl substituted with three groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopropyl substituted with three group selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclobutyl substituted with three groups selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is cyclopentyl substituted with three groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclohexyl substituted with three groups selected independently from halo, CN, $C_{3-6}$ cycloalkyl, $C_{1-3}$ alkoxy, $C_{1-3}$ haloalkyl, and $C_{1-3}$ haloalkoxy.

In embodiments, $R^1$ is $C_{1-4}$alkoxy or $C_{1-4}$ alkyl optionally substituted with one to three groups independently selected from halo, CN, $C_{3-6}$ cycloalkyl, $C_{1-3}$ alkoxy, $C_{1-3}$ haloalkyl, and $C_{1-3}$haloalkoxy. In embodiments, $R^1$ is $C_{1-4}$alkoxy or $C_{1-4}$ alkyl optionally substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is $C_{1-4}$alkoxy or $C_{1-4}$ alkyl optionally substituted with two groups independently selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is $C_{1-4}$alkoxy or $C_{1-4}$ alkyl optionally substituted with three groups independently selected from halo, CN, $C_{3-6}$ cycloalkyl, $C_{1-3}$ alkoxy, $C_{1-3}$ haloalkyl, and $C_{1-3}$ haloalkoxy.

In embodiments, $R^1$ is unsubstituted $C_{1-4}$alkoxy or $C_{1-4}$ alkyl. In embodiments, $R^1$ is unsubstituted $C_{1-4}$alkoxy. In embodiments, $R^1$ is unsubstituted $C_{1-4}$alkyl. In embodiments, $R^1$ is methoxy, ethoxy, propoxy, isopropoxy, butoxy, isobutoxy, or t-butoxy. In embodiments, $R^1$ is methyl, ethyl, propyl, isopropyl, butyl, isobutyl, or t-butyl. In embodiments, $R^1$ is $C_{1-4}$alkoxy or $C_{1-4}$ alkyl substituted with one group selected from fluoro, chloro, bromo, and iodo. In embodiments, $R^1$ is $C_{1-4}$alkoxy or $C_{1-4}$ alkyl substituted with two groups selected independently from fluoro, chloro, bromo, and iodo. In embodiments, $R^1$ is $C_{1-4}$alkoxy or $C_{1-4}$ alkyl substituted with three groups selected independently from fluoro, chloro, bromo, and iodo.

In embodiments, $R^1$ is trifluoromethyl, difluoromethyl, cyclopropyl, isopropyl, t-butyl, t-butoxy; or $R^1$ is indolyl optionally substituted with one or two groups independently selected from fluoro, methyl and methoxy. In embodiments, $R^1$ is trifluoromethyl, difluoromethyl, cyclopropyl, isopropyl, t-butyl, or t-butoxy. In embodiments, $R^1$ is trifluoromethyl. In embodiments, $R^1$ is difluoromethyl. In embodiments, $R^1$ is cyclopropyl. In embodiments, $R^1$ is isopropyl. In embodiments, $R^1$ is t-butyl. In embodiments, $R^1$ is t-butoxy. In embodiments, $R^1$ is unsubstituted indolyl. In embodiments, $R^1$ is indolyl optionally substituted with one group selected from fluoro, methyl and methoxy. In embodiments, $R^1$ is indolyl optionally substituted with two groups independently selected from fluoro, methyl and methoxy. In embodiments, $R^1$ is indolyl optionally substituted with three groups independently selected from fluoro, methyl and methoxy.

In embodiments, $R^2$ is selected from unsubstituted $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl. In embodiments, $R^2$ is unsubstituted $C_{1-6}$ alkyl. In embodiments, $R^2$ is unsubstituted 3-7 membered cycloalkyl. In embodiments, $R^2$ is unsubstituted (3-7 membered cycloalkyl)-$C_{1-3}$ alkyl. In embodiments, $R^2$ is unsubstituted $C_{1-3}$ alkyl-(3-7 membered cycloalkyl). In embodiments, $R^2$ is methyl, ethyl, propyl, isopropyl, butyl, isobutyl, t-butyl, pentyl, isopentyl, t-pentyl, or hexyl. In embodiments, $R^2$ is isopropylmethyl, isobutylmethyl, isobutylethyl, or isopentylmethyl. In embodiments, $R^2$ is cyclopropyl, cyclobutyl, cyclopentyl, cyclohexyl, or cycloheptyl. In embodiments, $R^2$ is cyclopropylmethyl, cyclopropylethyl, cyclopentylmethyl, cyclopentylethyl, cyclohexylmethyl, or cyclohexylethyl. In embodiments, $R^2$ is methyl. In embodiments, $R^2$ is ethyl. In embodiments, $R^2$ is propyl. In embodiments, $R^2$ is butyl. In embodiments, $R^2$ is isopropyl. In embodiments, $R^2$ is isobutyl. In embodiments, $R^2$ is t-butyl. In embodiments, $R^2$ is pentyl. In embodiments, $R^2$ is isopentyl. In embodiments, $R^2$ is t-pentyl. In embodiments, $R^2$ is hexyl. In embodiments, $R^2$ is isopropylmethyl. In embodiments, $R^2$ is isobutylmethyl. In embodiments, $R^2$ is isobutylethyl. In embodiments, $R^2$ is isopentylmethyl. In embodiments, $R^2$ is cyclopropyl. In embodiments, $R^2$ is cyclobutyl. In embodiments, $R^2$ is cyclopentyl. In embodiments, $R^2$ is cyclohexyl. In embodiments, $R^2$ is cycloheptyl. In embodiments, $R^2$ is cyclopropylmethyl. In embodiments, $R^2$ is cyclopropylethyl. In embodiments, $R^2$ is cyclopentylmethyl. In embodiments, $R^2$ is cyclopentylethyl. In embodiments, $R^2$ is cyclohexylmethyl. In embodiments, $R^2$ is cyclohexylethyl.

In embodiments, $R^2$ is selected from ethyl, isopropyl, isobutyl, butyl, isopropylmethyl, cyclopropyl, cyclohexyl, and cyclobutyl. In embodiments, $R^2$ is t-butyl, isopropylmethyl, or cyclopropyl.

In embodiments, $R^2$ is $C_{1-6}$ alkyl, 3-7 membered cycloalkyl, $C_{1-3}$ alkyl-(3-7 membered cycloalkyl), or (3-7 membered cycloalkyl)-$C_{1-3}$ alkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl, 3-7 membered cycloalkyl, $C_{1-3}$ alkyl-(3-7 membered cycloalkyl), or (3-7 membered cycloalkyl)-$C_{1-3}$ alkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl, 3-7 membered cycloalkyl, $C_{1-3}$ alkyl-(3-7 membered cycloalkyl), or (3-7 membered cycloalkyl)-$C_{1-3}$ alkyl substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is 3-7 membered cycloalkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-3}$ alkyl-(3-7 membered cycloalkyl) substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is (3-7 membered cycloalkyl)-$C_{1-3}$ alkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is 3-7 membered cycloalkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-3}$ alkyl-(3-7 membered cycloalkyl) substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is (3-7 membered cycloalkyl)-$C_{1-3}$ alkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is 3-7 membered cycloalkyl substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-3}$ alkyl-(3-7 membered cycloalkyl) substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is (3-7 membered cycloalkyl)-$C_{1-3}$ alkyl substituted with three groups independently selected from halo, CN, $C_{1-3}$ alkyl, $C_{1-6}$ alkoxy, $C_{1-3}$ haloalkyl, and $C_{1-3}$ haloalkoxy.

In embodiments, $R^3$ is H, methyl, ethyl, propyl, isopropyl, butyl, isobutyl, or t-butyl. In embodiments, $R^3$ is H. In embodiments, $R^3$ is methyl. In embodiments, $R^3$ is ethyl. In embodiments, $R^3$ is propyl. In embodiments, $R^3$ is isopropyl. In embodiments, $R^3$ is butyl. In embodiments, $R^3$ is isobutyl. In embodiments, $R^3$ is t-butyl.

In embodiments, R* is independently selected from chloro, fluoro, bromo, iodo, methyl, ethyl, propyl, methoxy, ethoxy, propoxy, CN, —OH, trifluoromethyl, difluoromethyl, fluoromethyl, trifluoroethyl, difluoroethyl, fluoroethyl, trichloromethyl, dichloromethyl, chloromethyl, trichloroethyl, dichloroethyl, and chloroethyl. In embodiments, R* is independently chloro. In embodiments, R* is independently fluoro. In embodiments, R* is independently bromo. In embodiments, R* is independently iodo. In embodiments, R* is independently methyl. In embodiments, R* is independently ethyl. In embodiments, R* is independently propyl. In embodiments, R* is independently methoxy. In embodiments, R* is independently ethoxy. In embodiments, R* is independently propoxy. In embodiments, R* is independently CN. In embodiments, R* is independently —OH. In embodiments, R* is independently trifluoromethyl. In embodiments, R* is independently trifluoroethyl. In embodiments, R* is independently difluoromethyl. In embodiments, R* is independently difluoroethyl. In embodiments, R* is independently fluoromethyl. In embodiments, R* is independently fluoroethyl. In embodiments, R* is independently trichloromethyl. In embodiments, R* is independently trichloroethyl. In embodiments, R* is independently dichloromethyl. In embodiments, R* is independently dichloroethyl. In embodiments, R* is independently chloromethyl. In embodiments, R* is independently chloroethyl.

In embodiments, m is 0, 1, or 2. In embodiments, m is 0. In embodiments, m is 1. In embodiments, m is 2.

In embodiments, n is 0, 1, 2, 3, or 4. In embodiments, n is 1 or 2. In embodiments, n is 0. In embodiments, n is 1. In embodiments, n is 2. In embodiments, n is 3. In embodiments, n is 4.

In embodiments, provided herein is a compound of Formula (IIA):

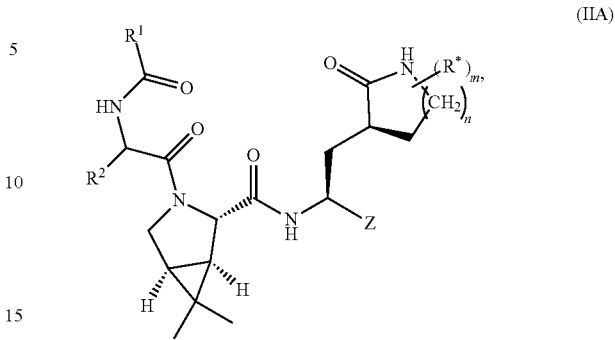

(IIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, R*, m, and n are as described herein, including in embodiments.

In embodiments, provided herein is a compound of Formula (IIA1):

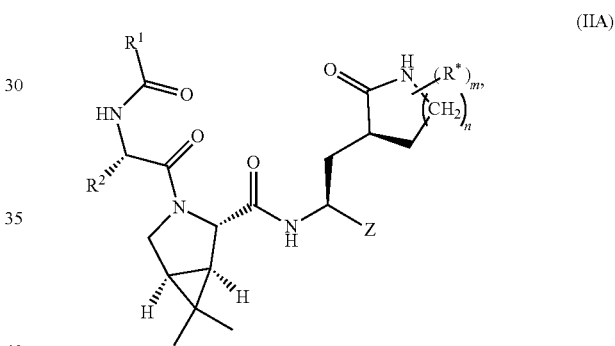

(IIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, R*, m, and n are as described herein, including in embodiments.

In embodiments, provided herein is a compound of Formula (IIB):

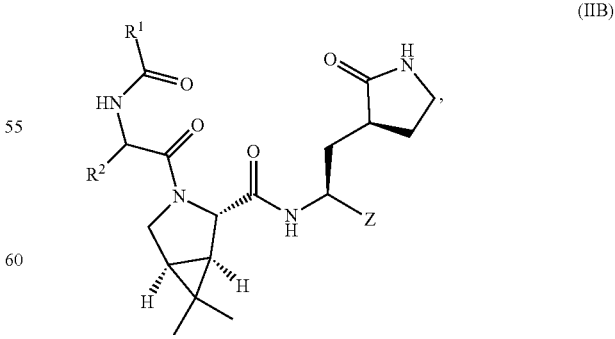

(IIB)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, and Z are as described herein, including in embodiments.

In embodiments, provided herein is a compound of Formula (IIB1):

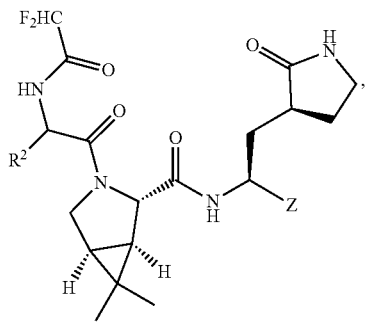

(IIB1)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIB1A):

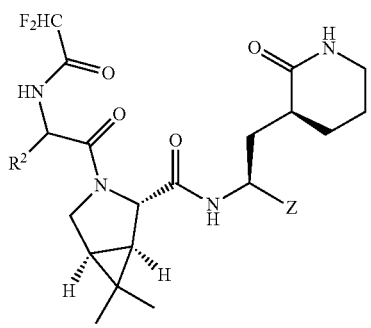

(IIB1A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIB2):


(IIB2)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIB2A):

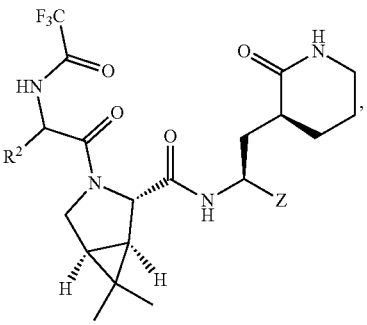

(IIB2A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIB3):

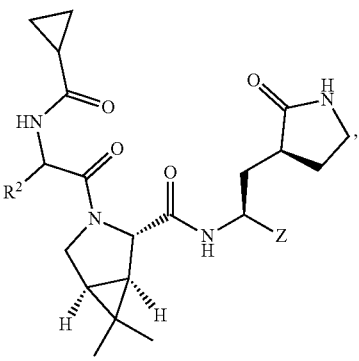

(IIB3)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIB4):

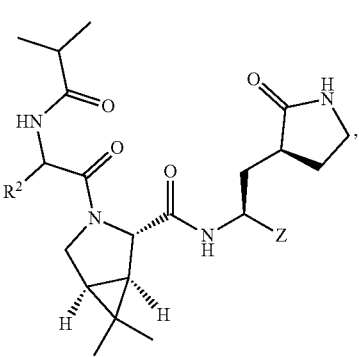

(IIB4)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIB5):

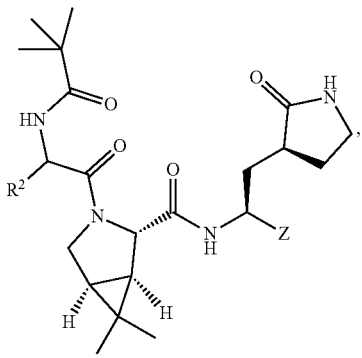

(IIB5)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIC):

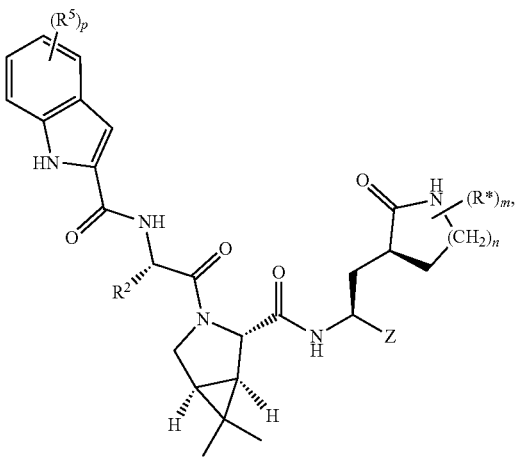

(IIC)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^5$ is independently selected from hydrogen, halo, —CN, $C_{1-3}$ alkyl, $C_{1-3}$ alkoxy, $C_{1-3}$ haloalkyl, and $C_{1-3}$ haloalkoxy; p is an integer from 0 to 4; and $R^2$, Z, R*, m, and n are as described herein, including in embodiments.

In embodiments, $R^5$ is independently selected from hydrogen, halo, $C_{1-3}$ alkyl, and $C_{1-3}$ alkoxy. In embodiments, $R^5$ is independently selected from hydrogen, halo, —CN, methyl, ethyl, propyl, methoxy, ethoxy, propoxy, trifluoromethyl, trichloromethyl, tribromomethyl, triiodomethyl, difluoromethyl, dichloromethyl, dibromomethyl, diiodomethyl, fluoromethyl, chloromethyl, bromomethyl, iodomethyl, trifluoethyl, trifluoropropyl, trichloroethyl, and tribromoethyl. In embodiments, $R^5$ is independently selected from hydrogen, —CN, fluoro, chloro, bromo, iodo, methyl, ethyl, propyl, methoxy, ethoxy, propoxy, trifluoromethyl, trichloromethyl, tribromomethyl, trifluoroethyl, trichloroethyl, and tribromoethyl. In embodiments, $R^5$ is independently selected from hydrogen, fluoro, methyl and methoxy.

In embodiments, p is 0. In embodiments, p is 1. In embodiments, p is 2. In embodiments, p is 3. In embodiments, p is 4.

In embodiments, provided herein is a compound of Formula (IID):

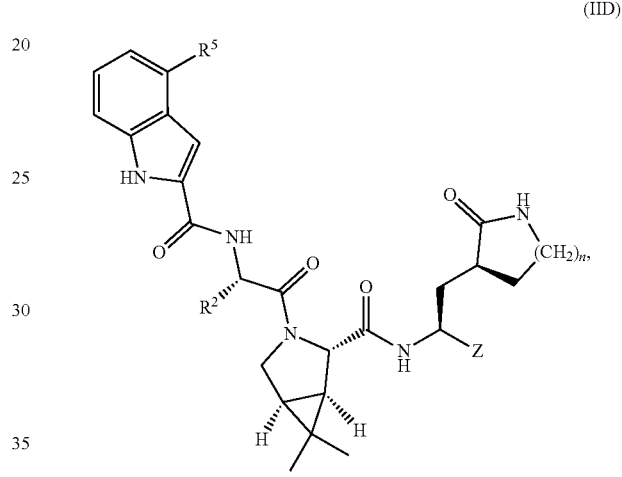

(IID)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, $R^5$, n and Z, are as described herein, including in embodiments.

In embodiments, provided herein is a compound of Formula (IID1):

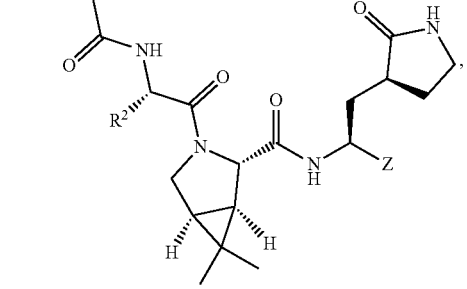

(IID1)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, $R^5$, and Z, are as described herein, including in embodiments.

In embodiments, provided herein is a compound of Formula (IID1A):

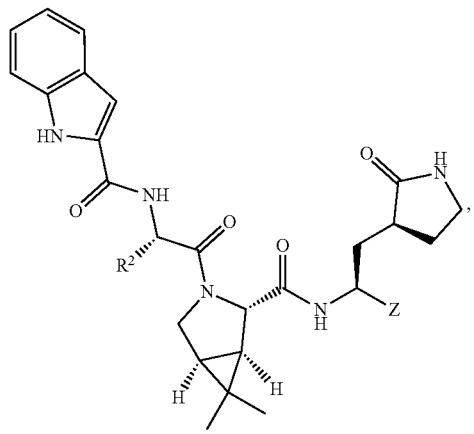

(IID1A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IID2):

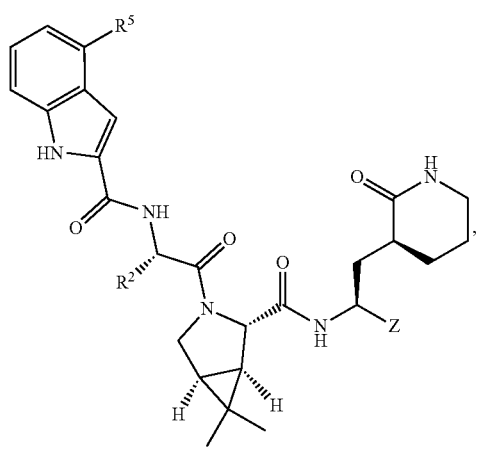

(IID2)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, $R^5$, and Z, are as described herein, including in embodiments.

In embodiments, provided herein is a compound of Formula (IID2A):

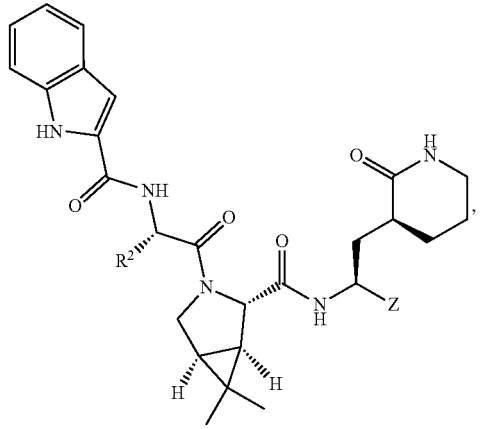

(IID2A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein are compounds selected from:

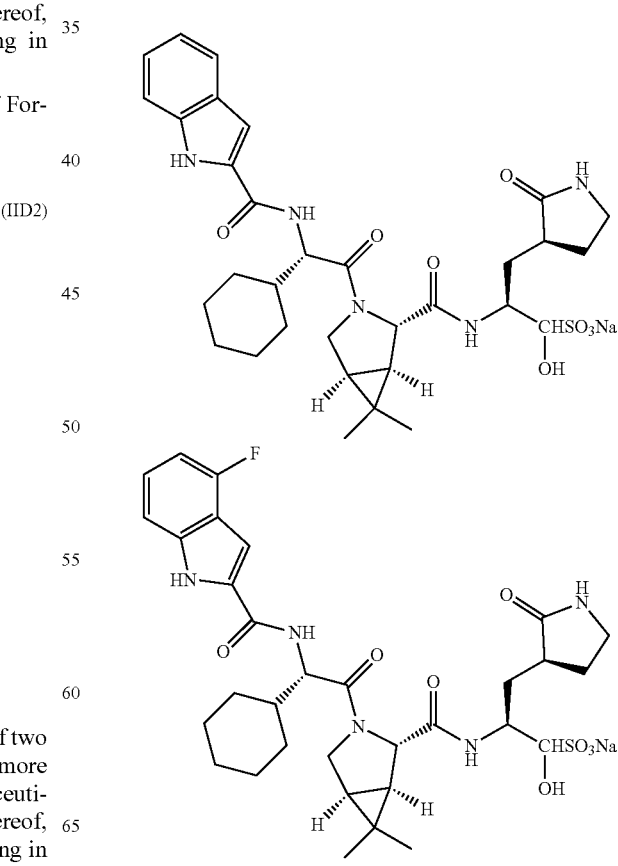

-continued
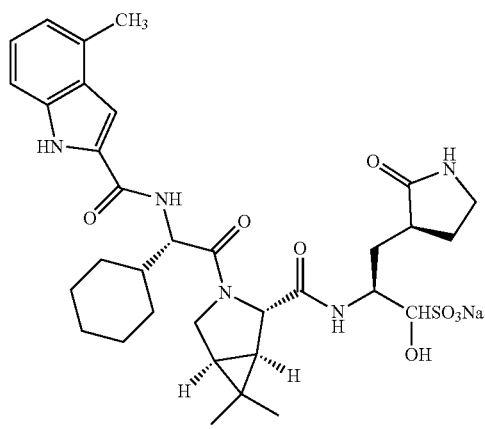
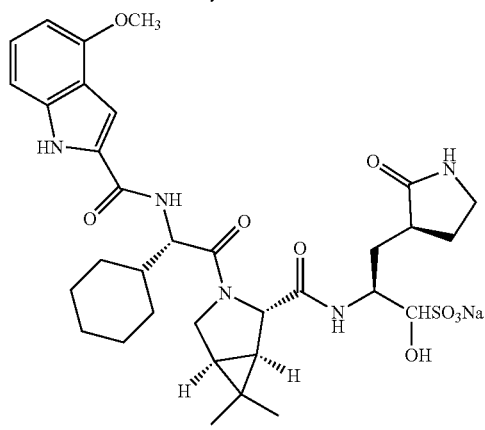
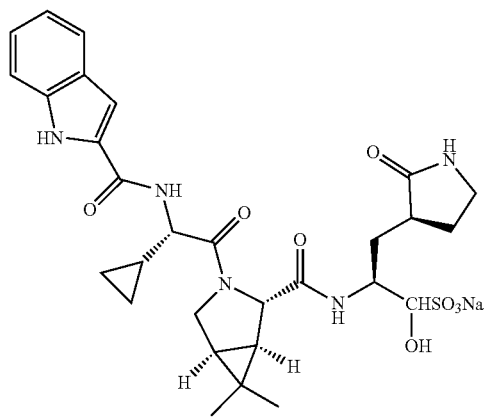
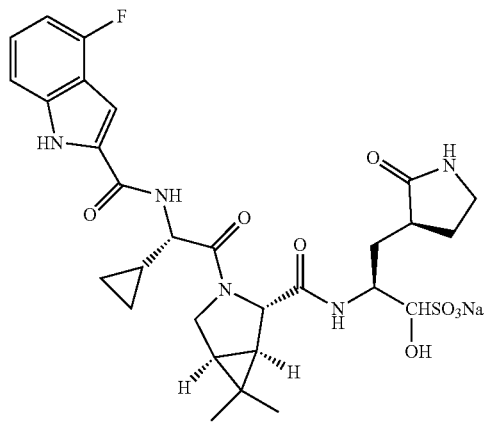
-continued
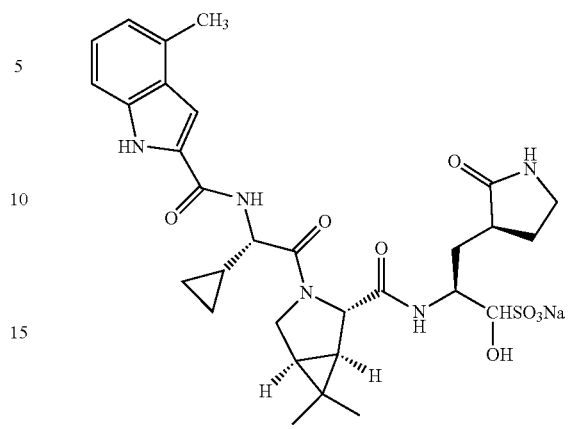
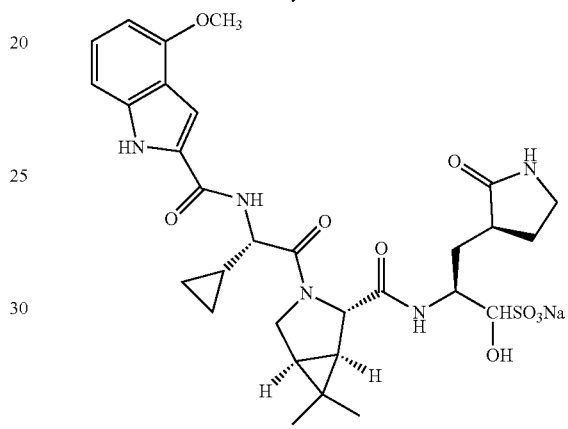
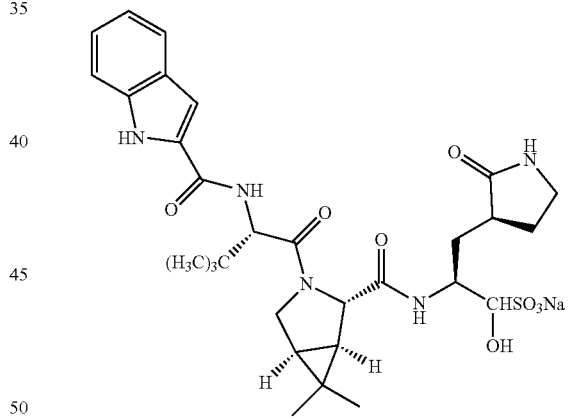
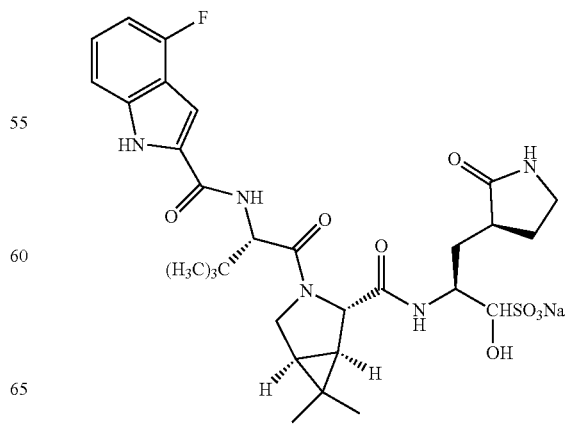

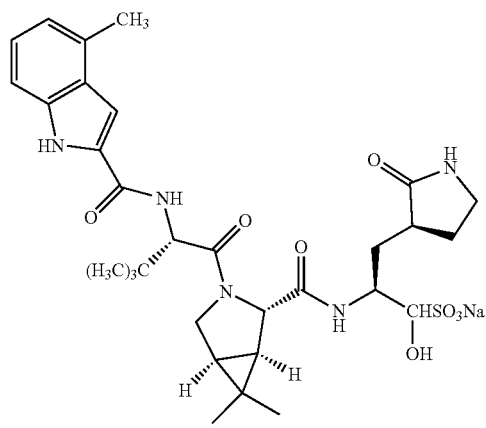
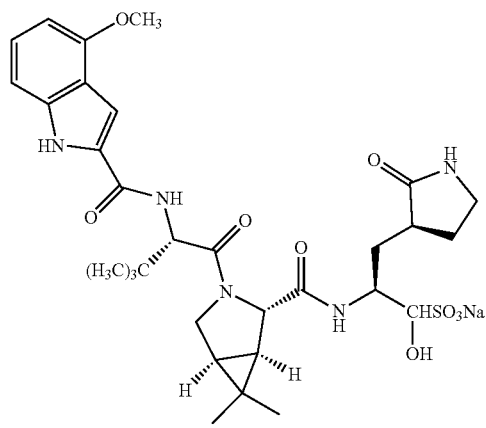
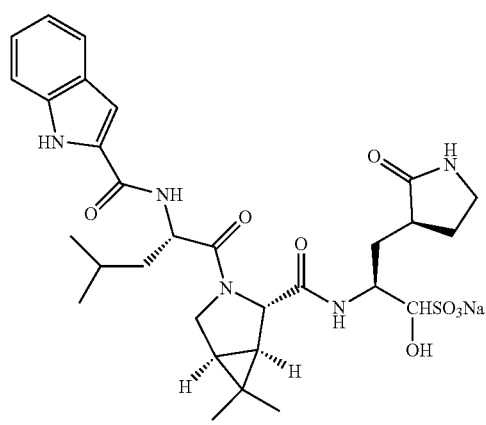
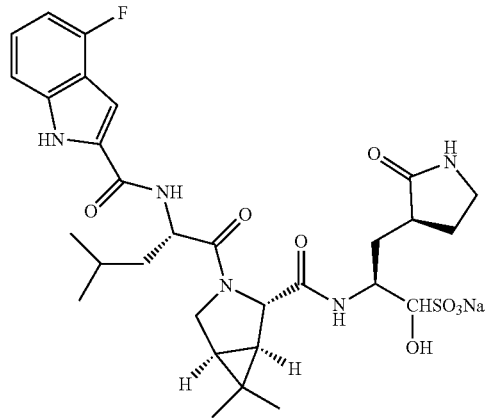
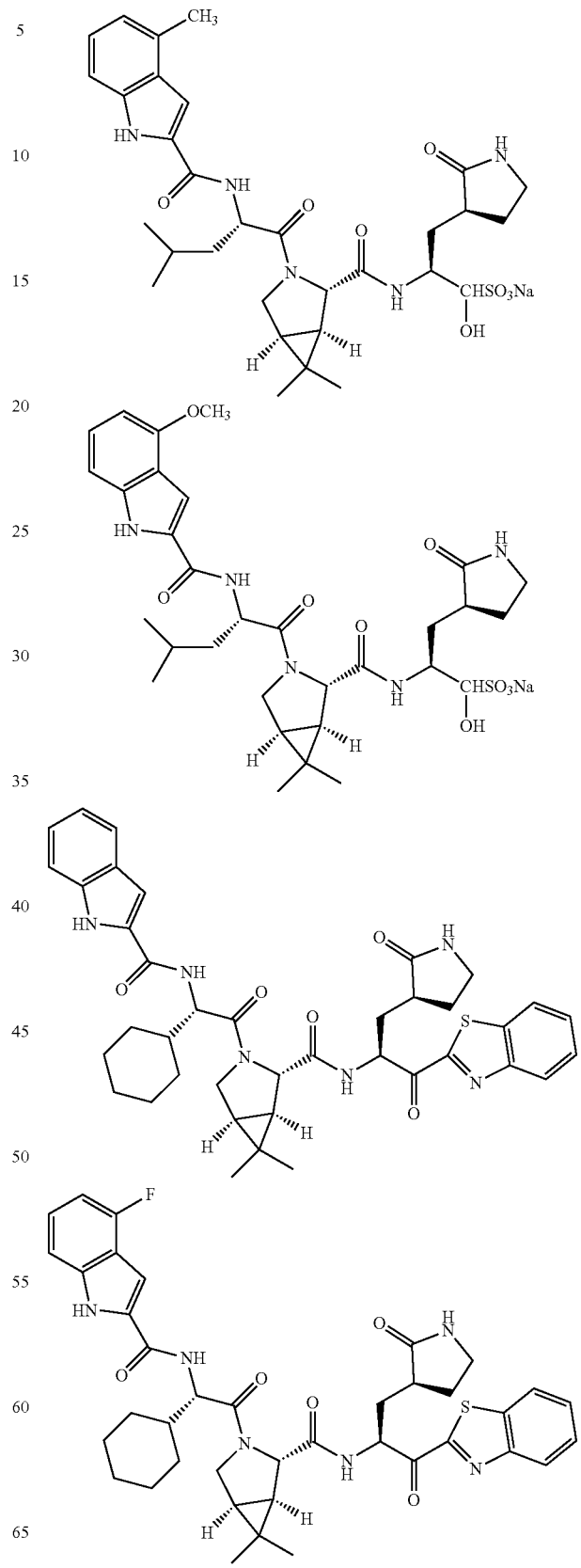

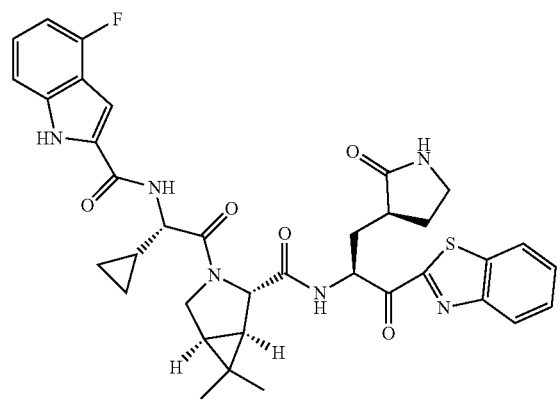
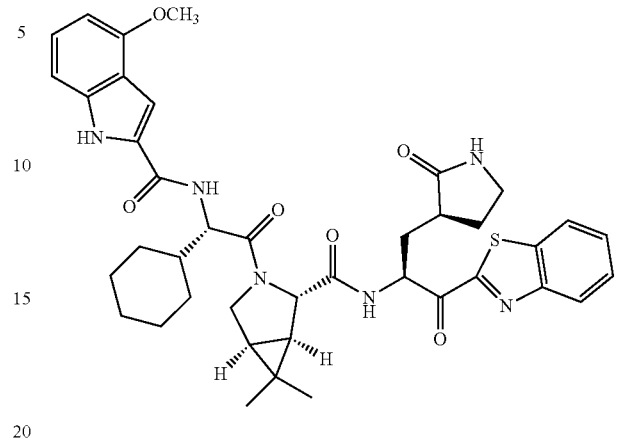
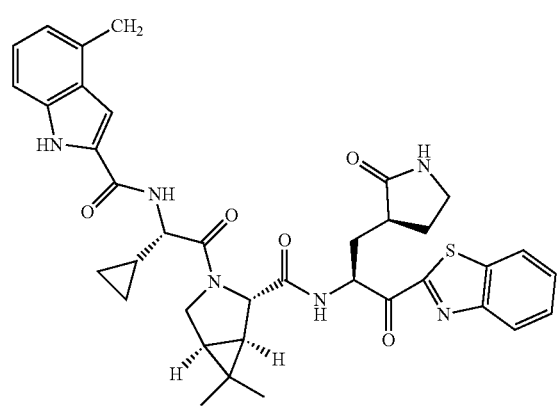
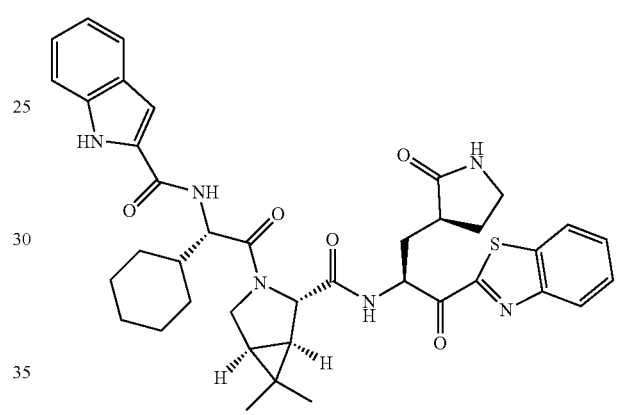
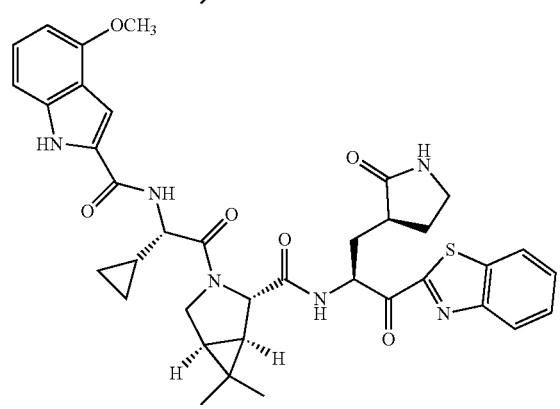
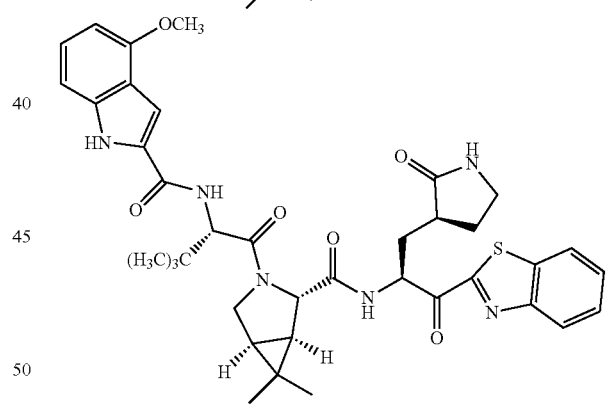
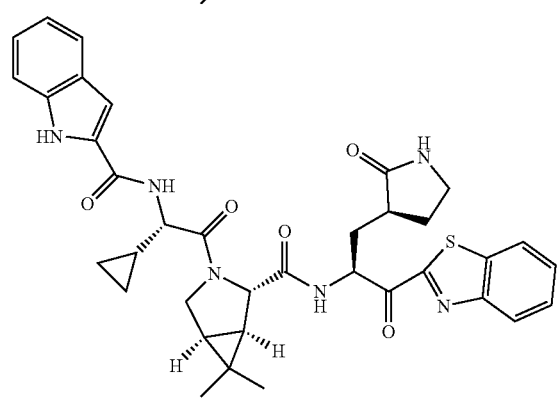
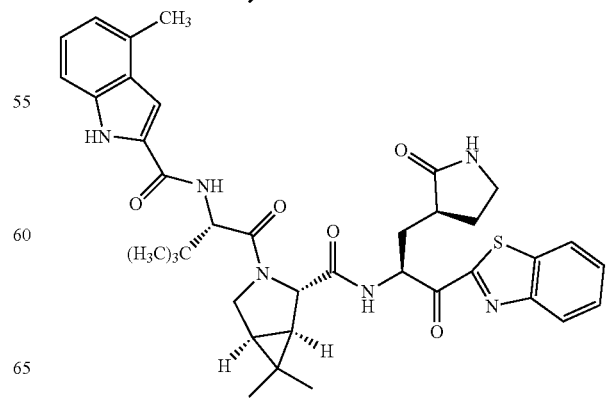

71
-continued
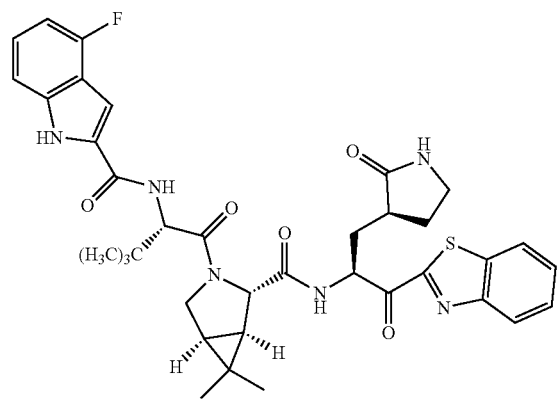
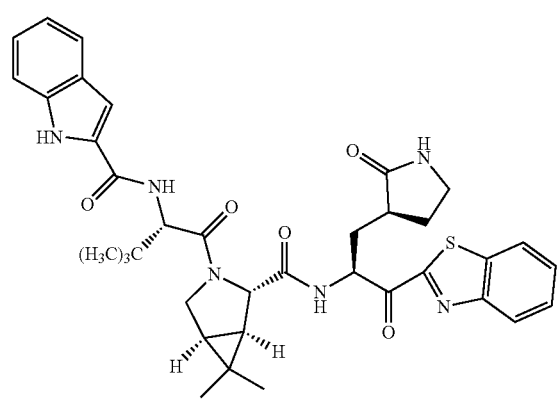
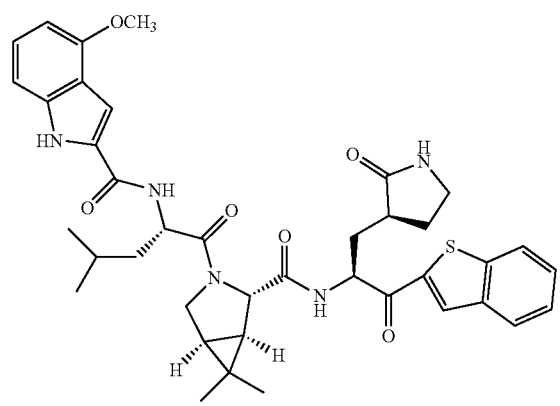
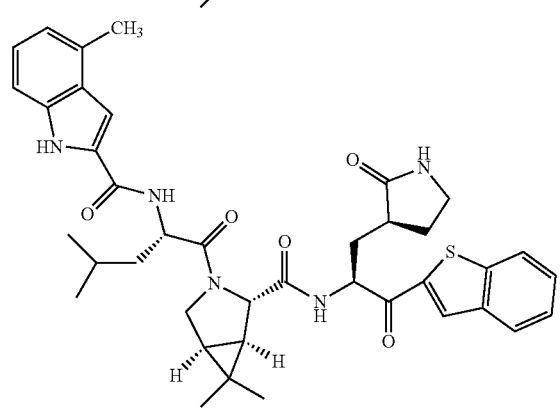
72
-continued
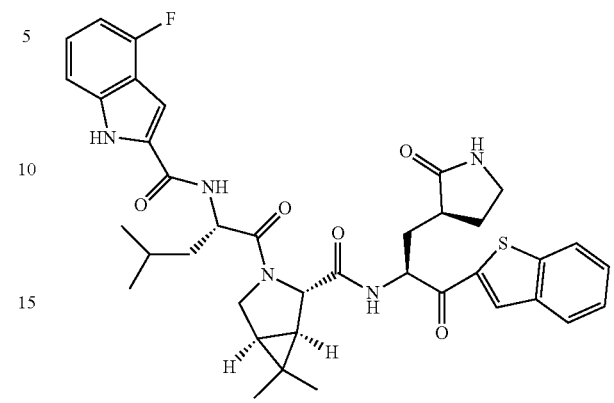
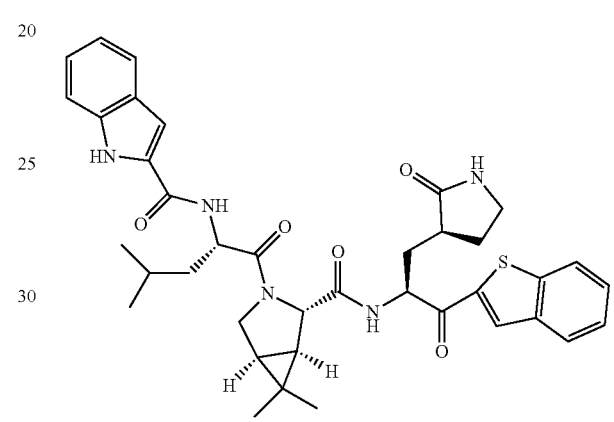
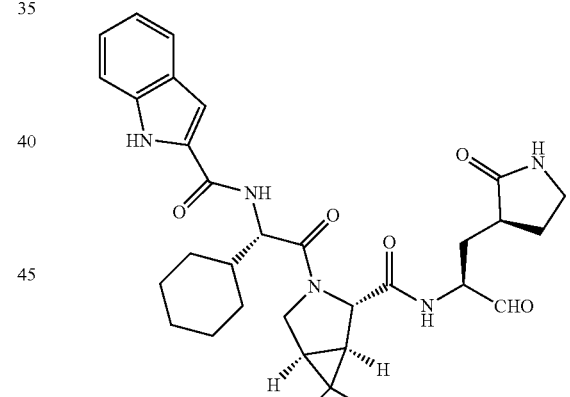
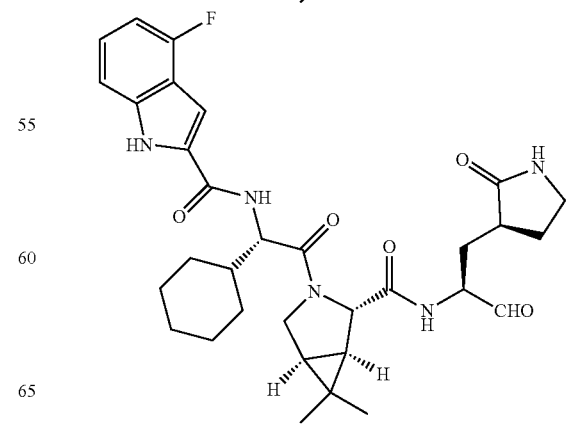

73
-continued
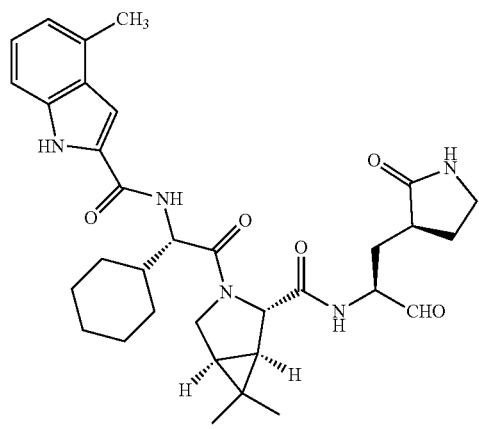
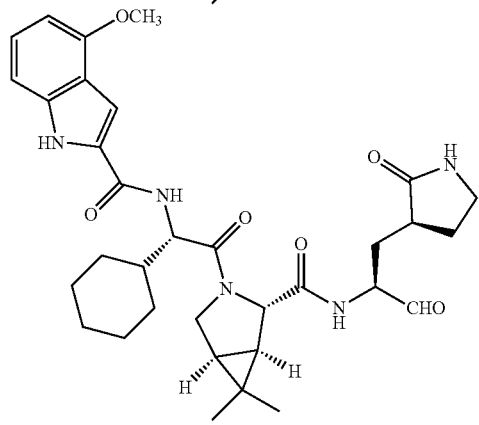
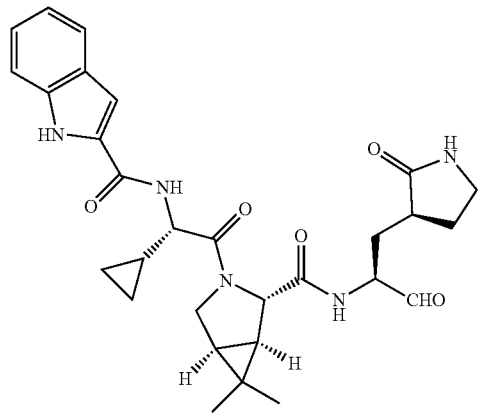
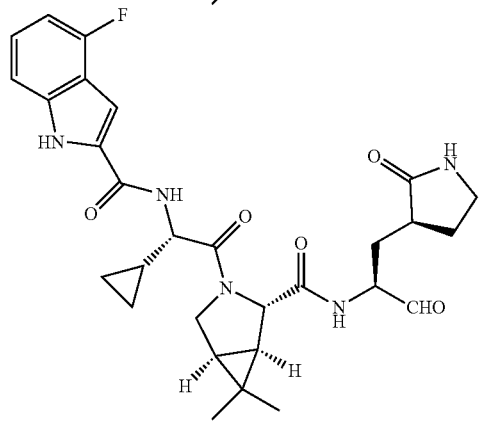
74
-continued
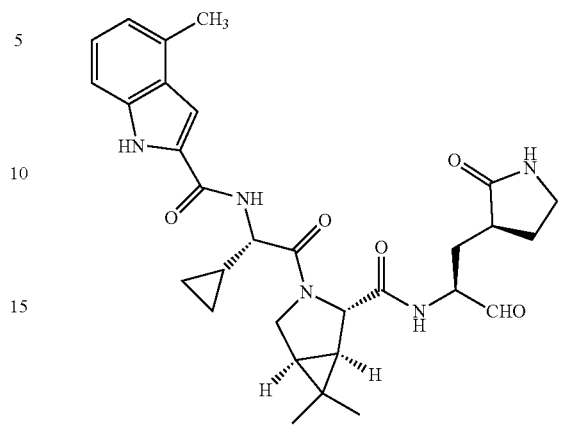
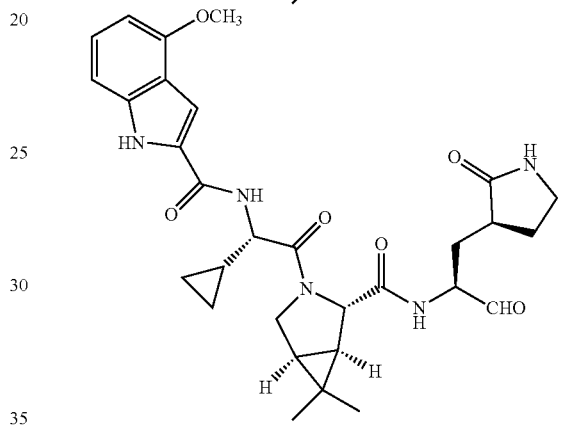
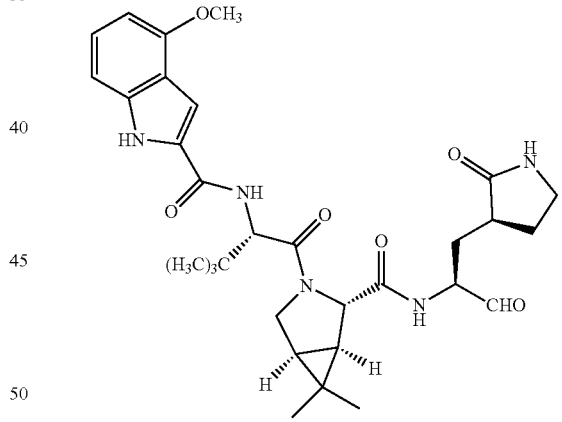
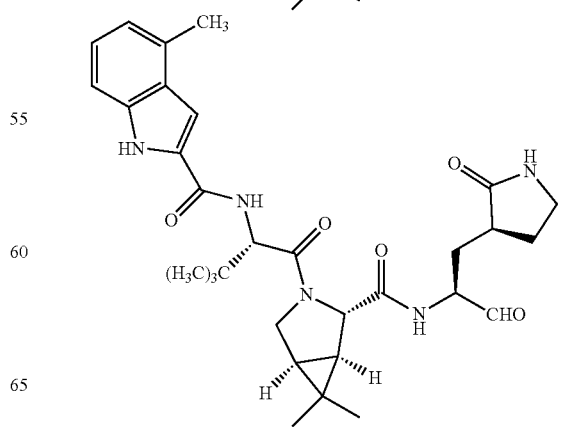

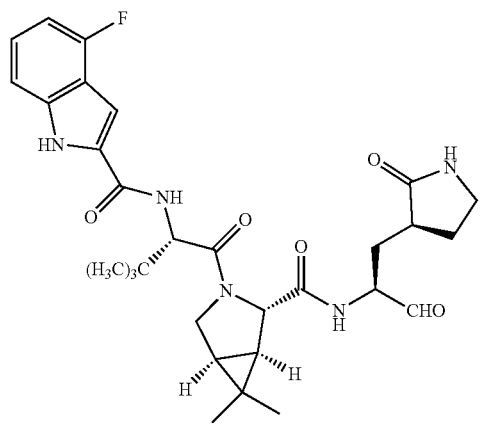
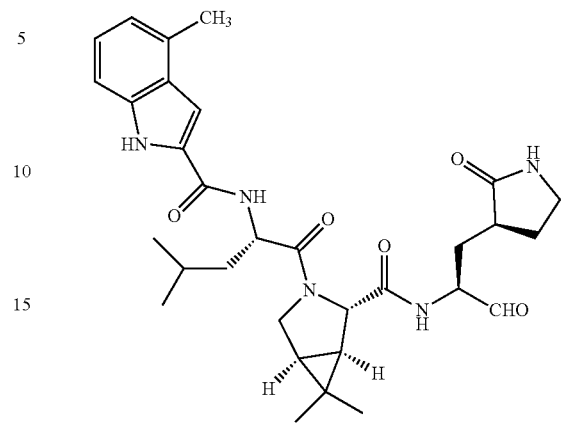
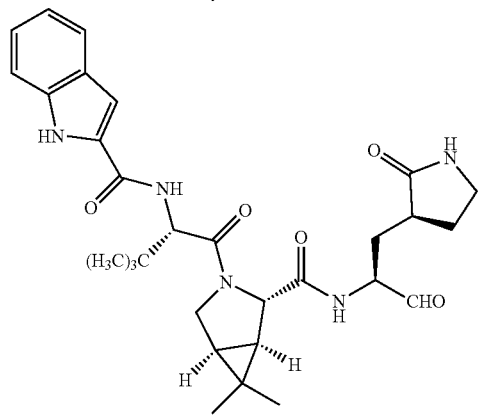
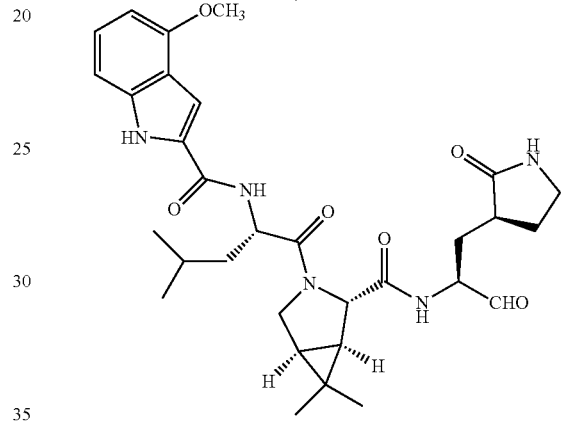
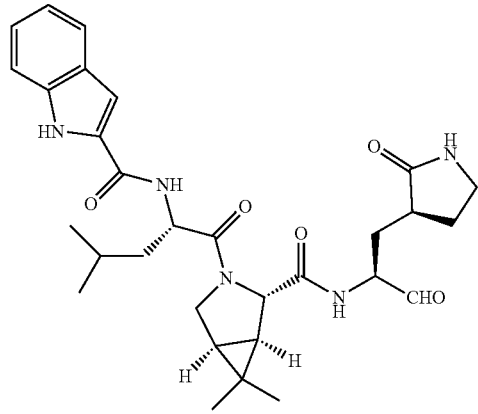
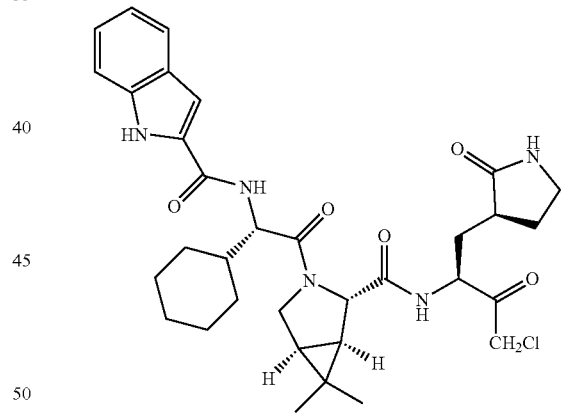
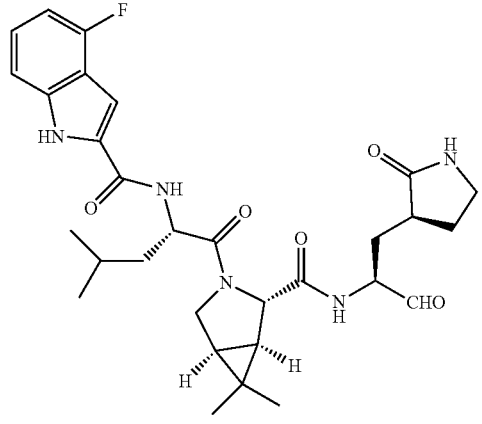
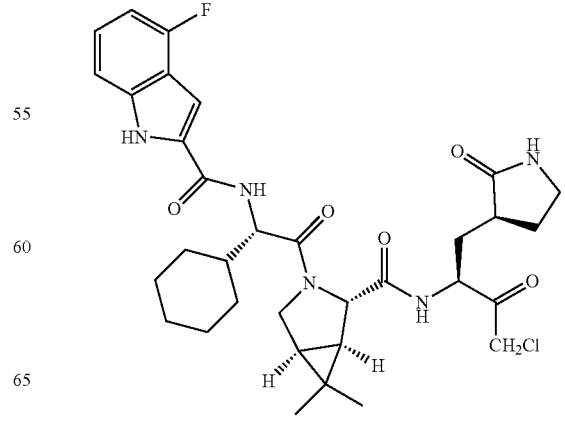

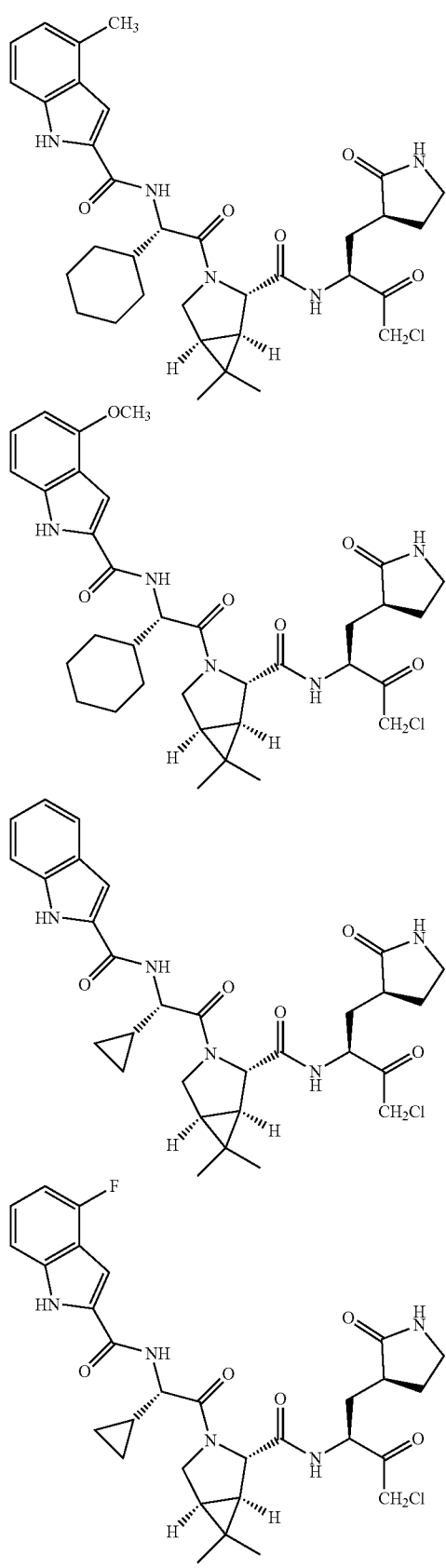
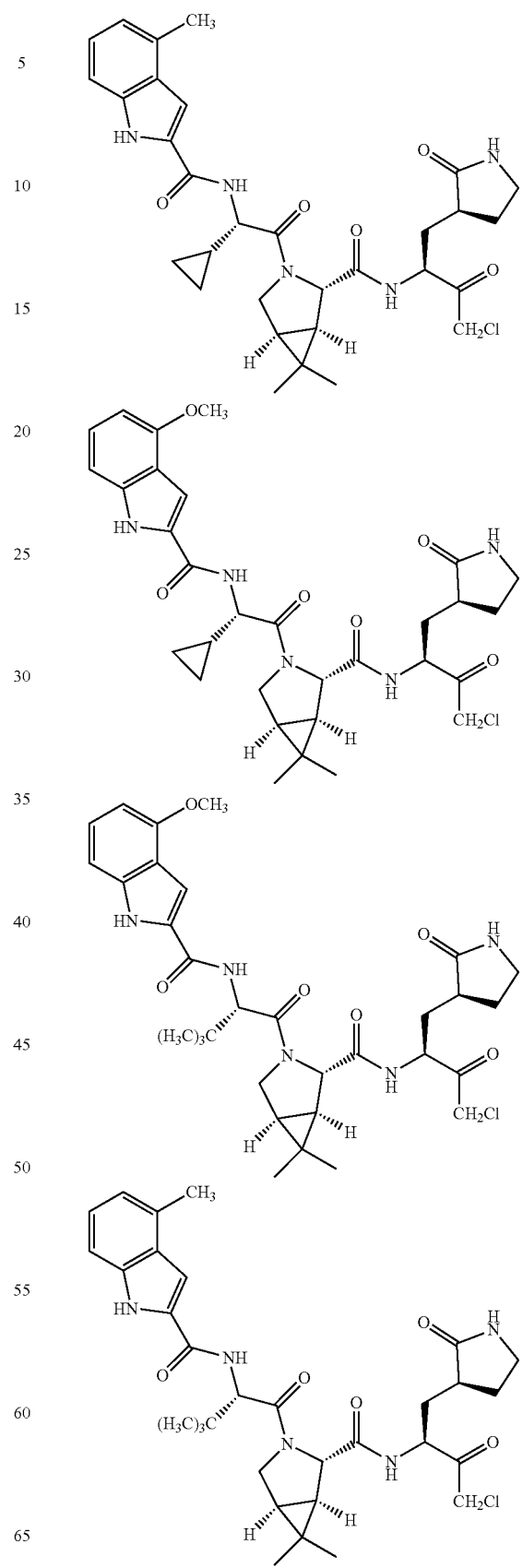

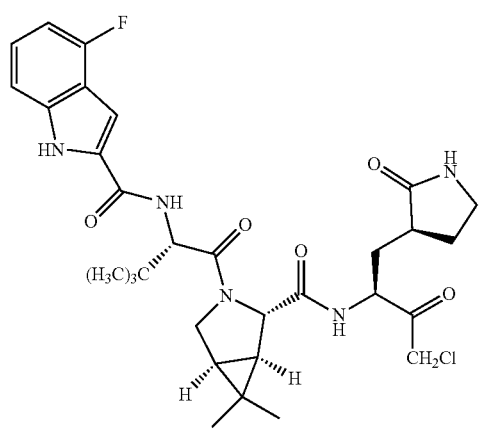
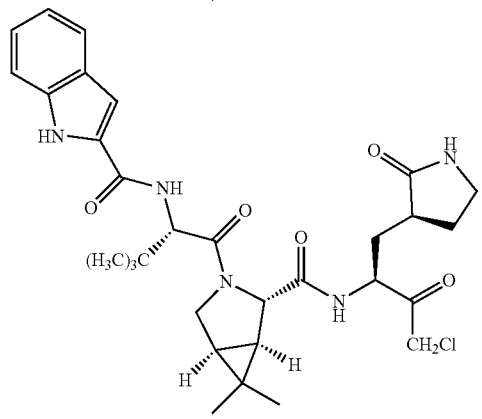
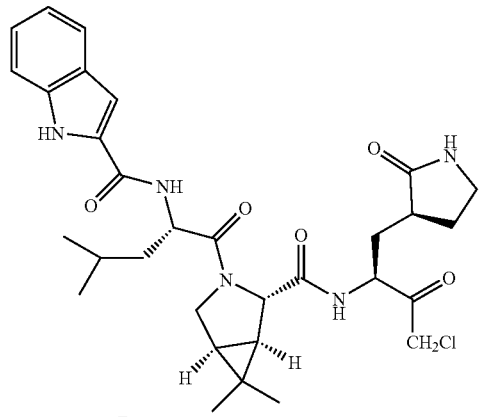
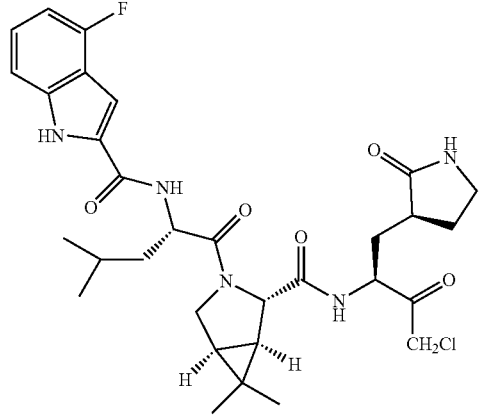
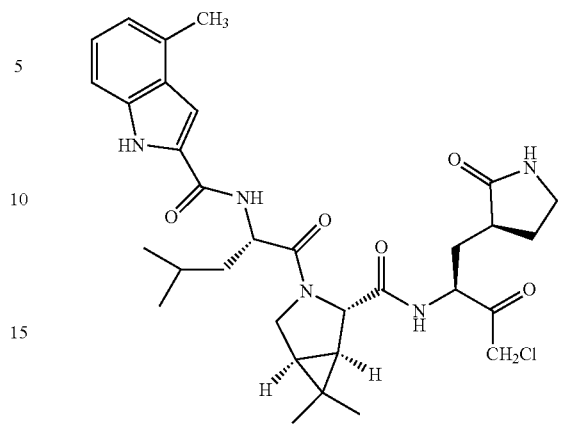
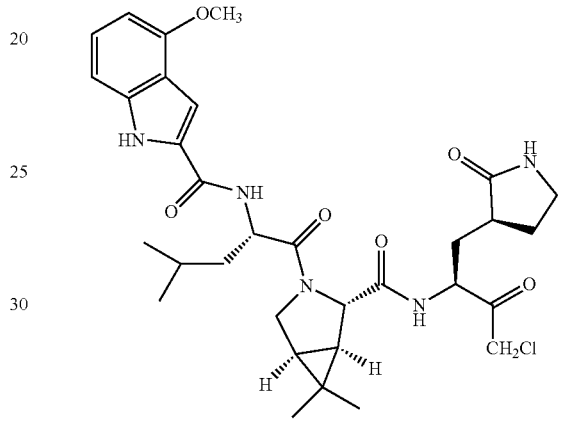
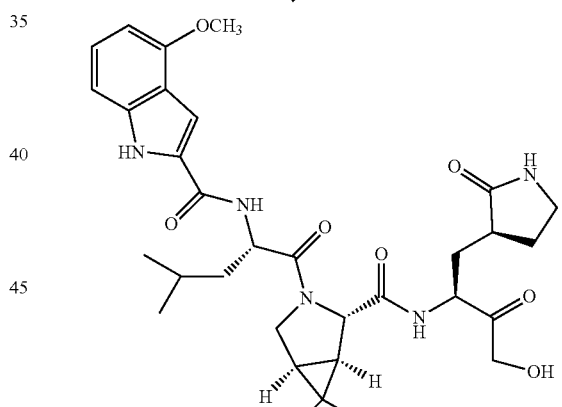
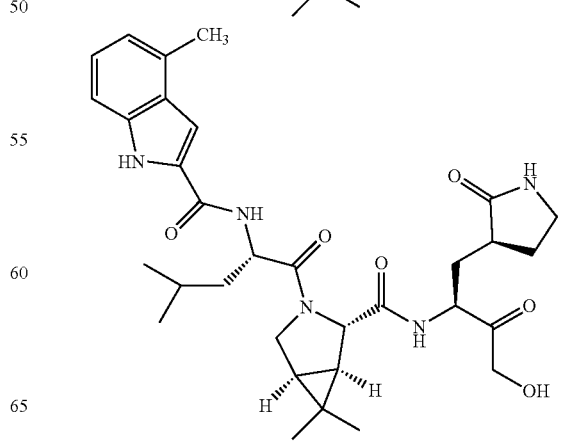

81
-continued
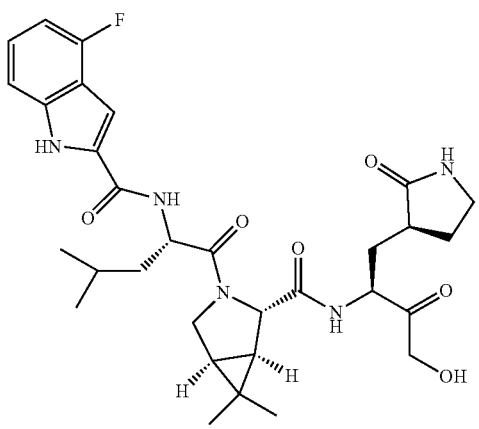
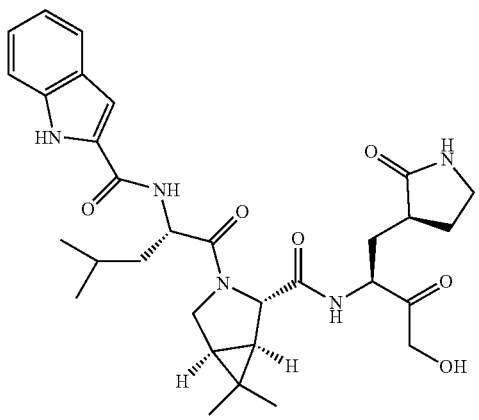
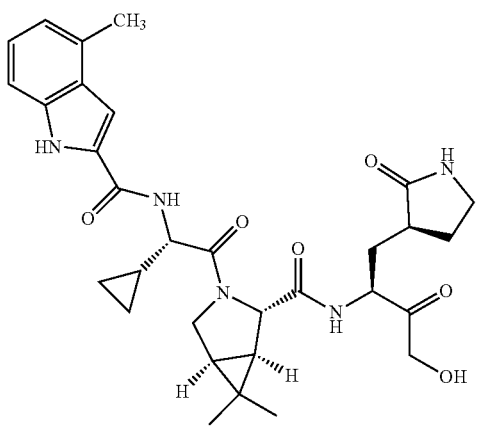
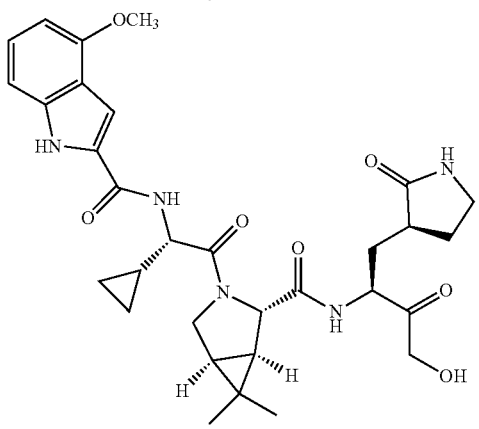
82
-continued
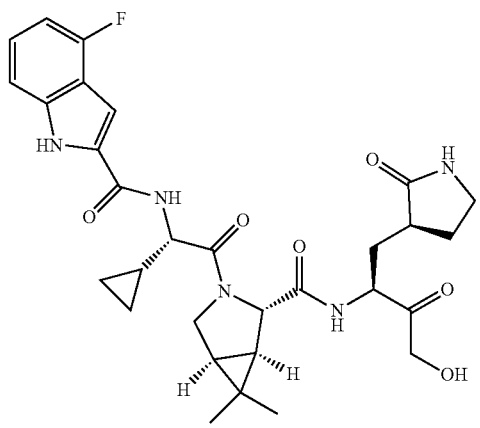
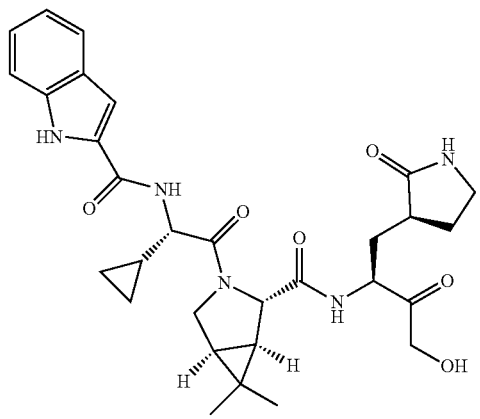
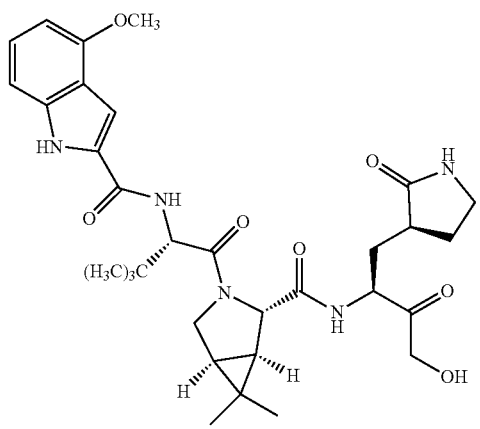
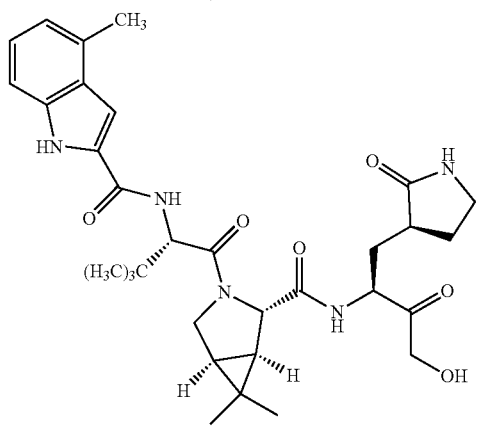

83
-continued
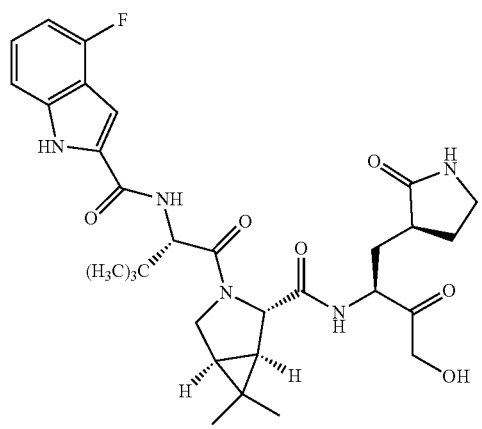
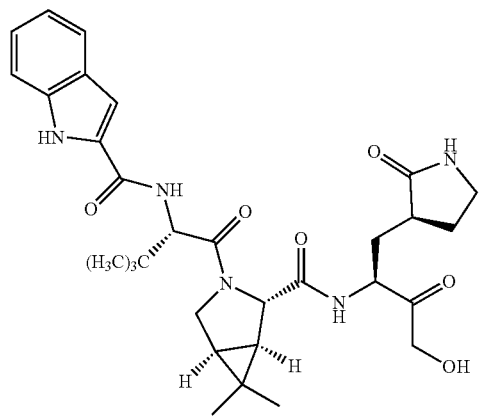
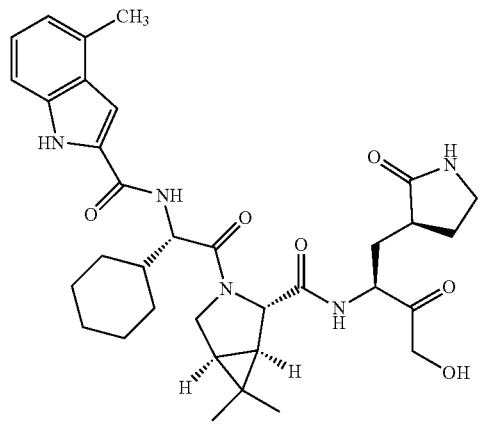
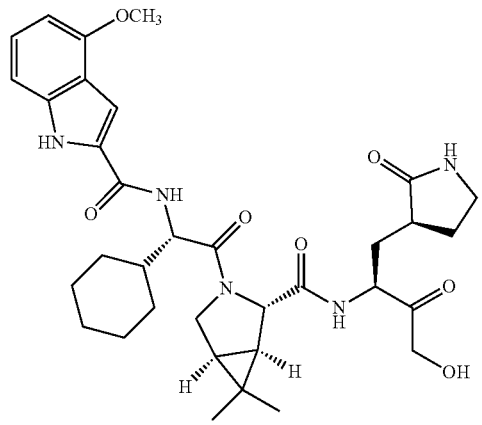
84
-continued

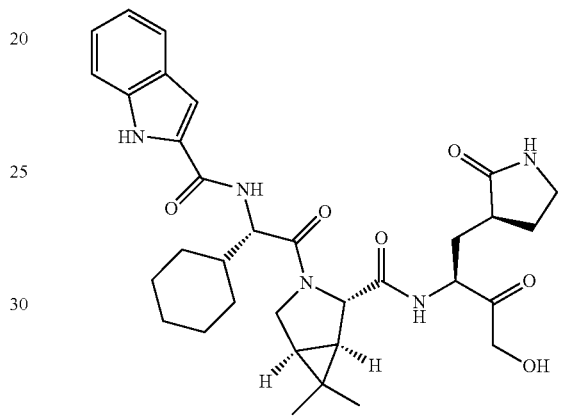
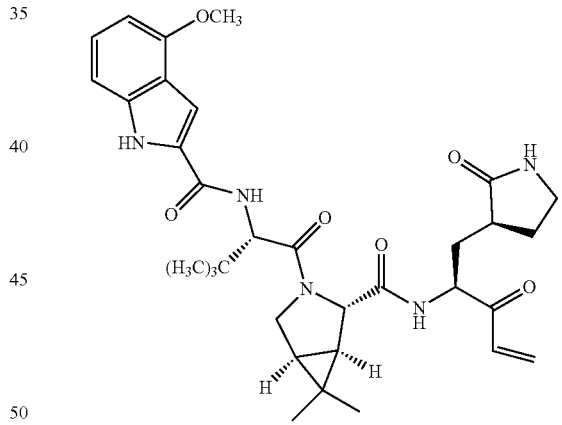
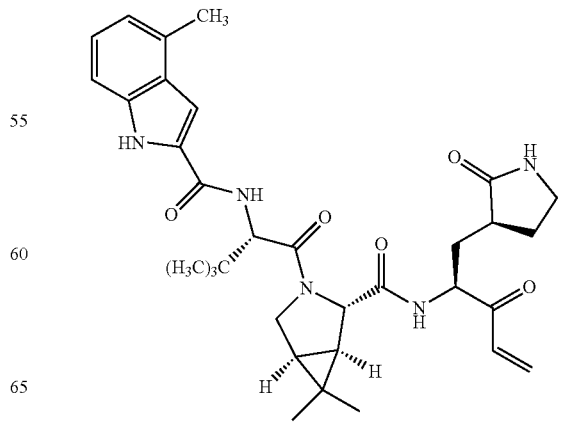

85
-continued
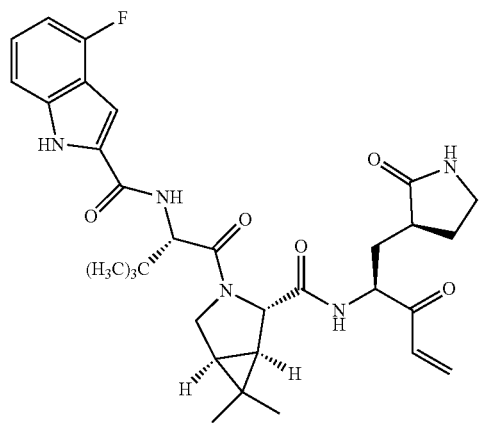
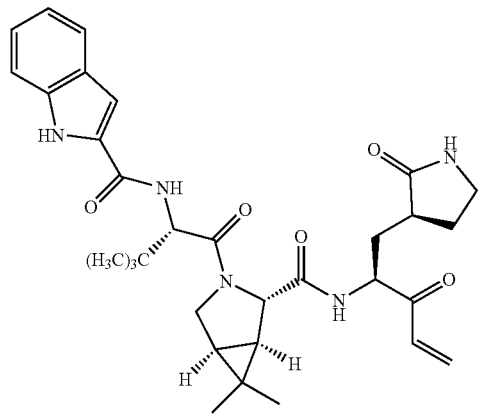
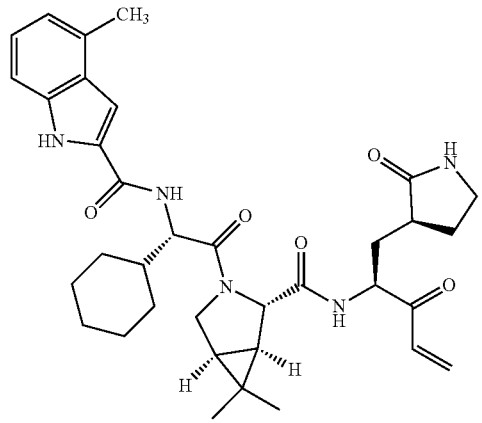
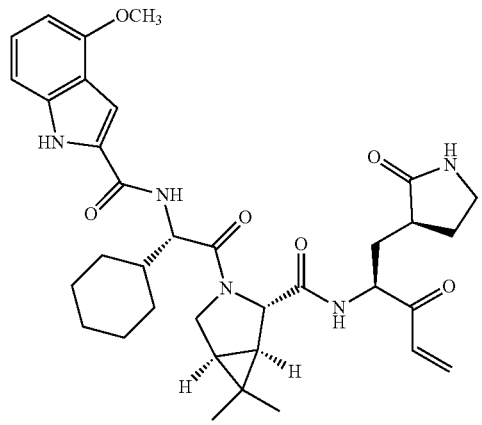
86
-continued
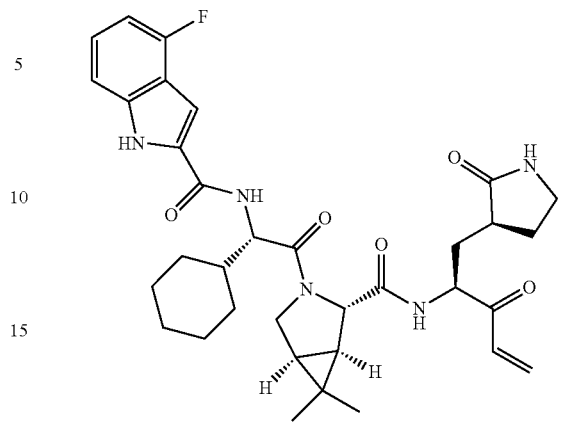
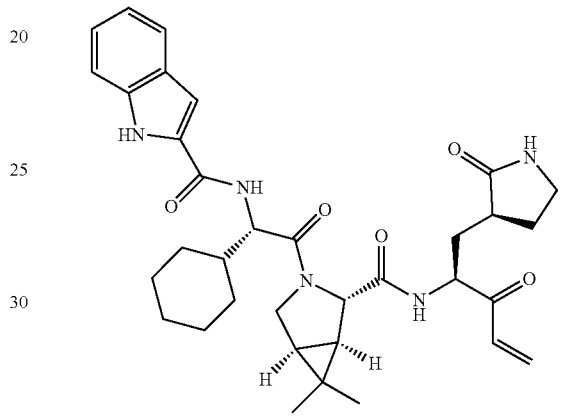
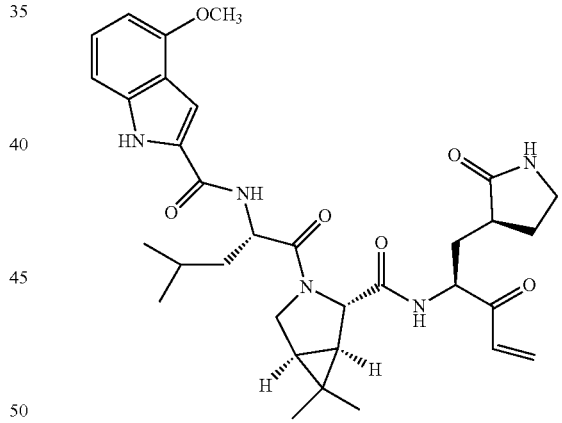
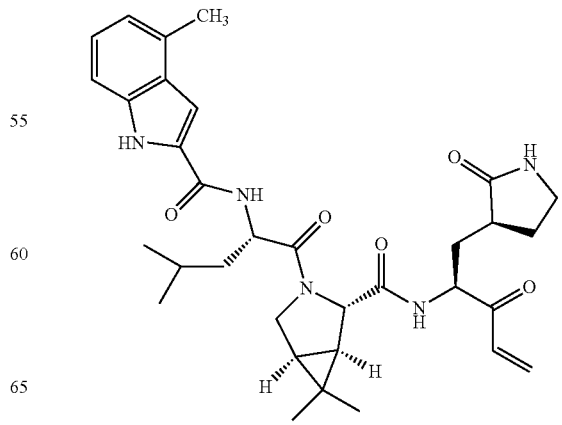

-continued
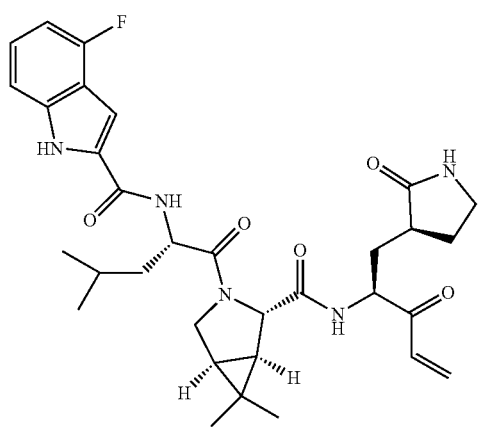
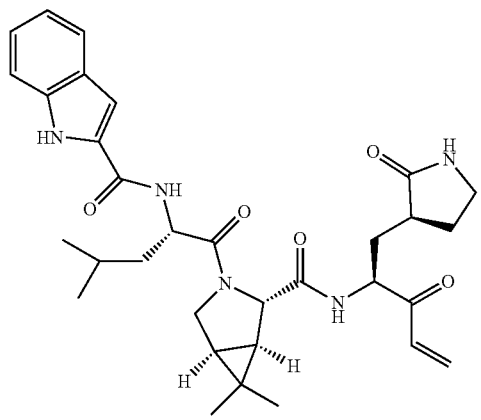
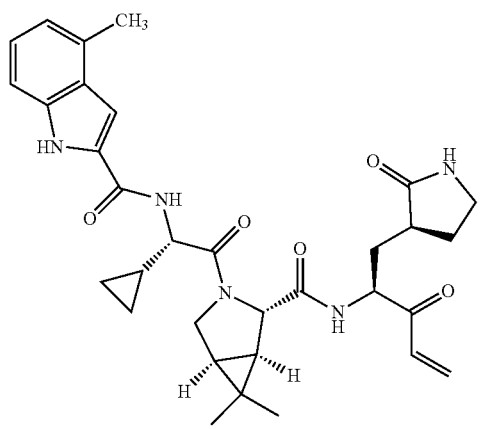
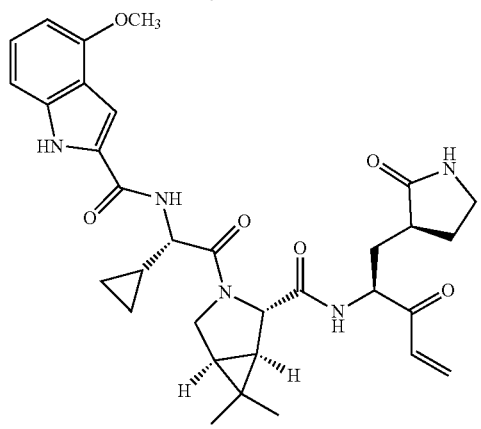
-continued
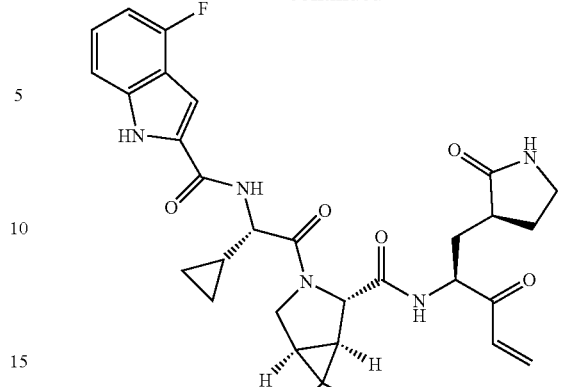
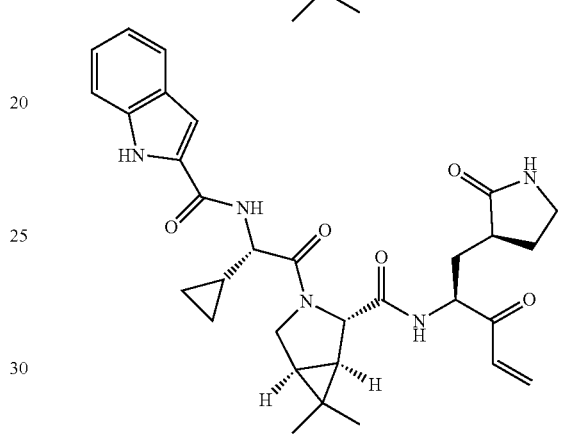
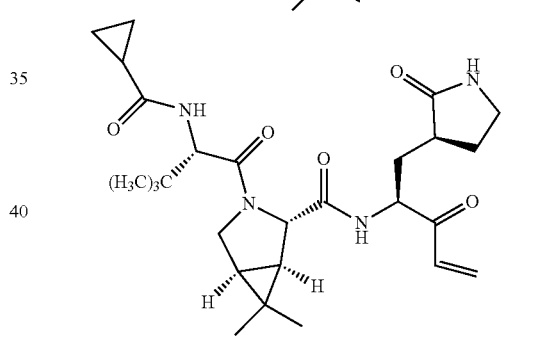
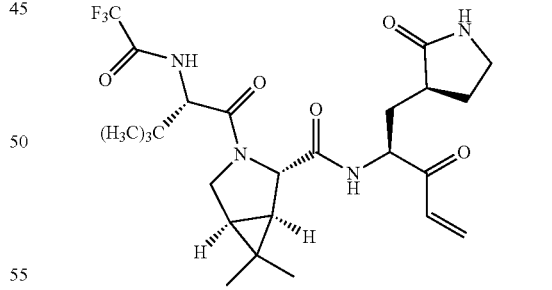
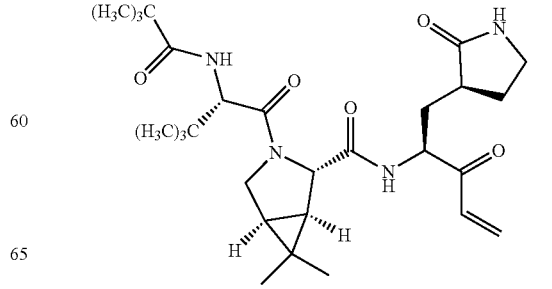

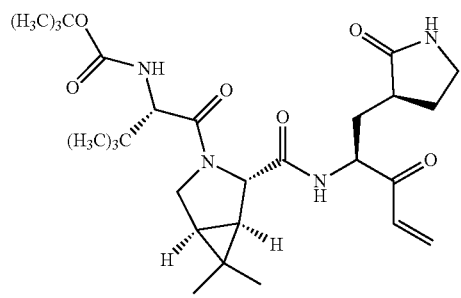
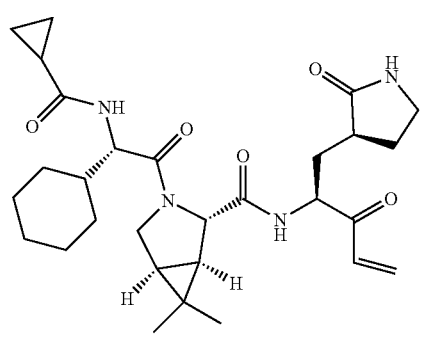
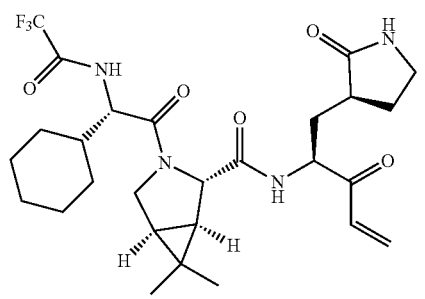
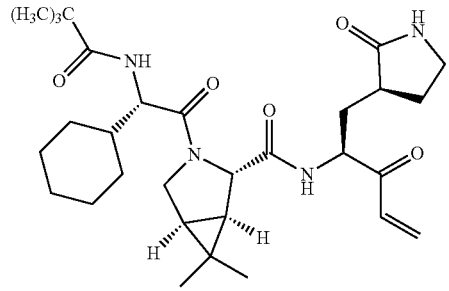
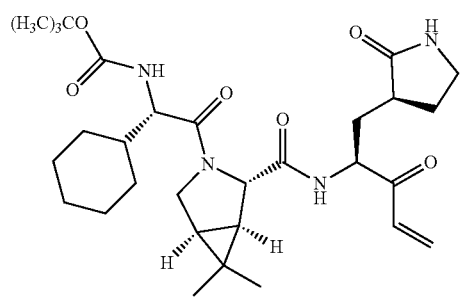
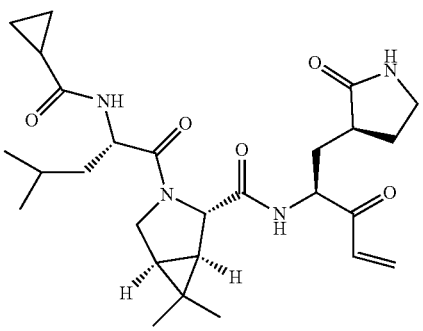
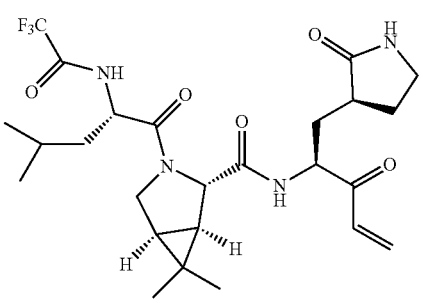
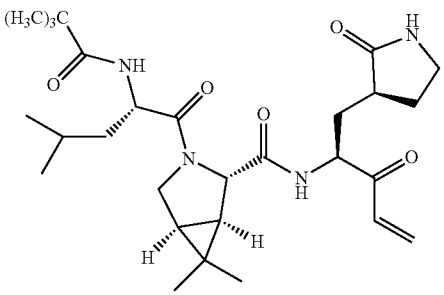
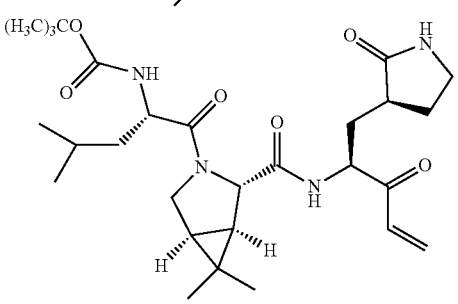
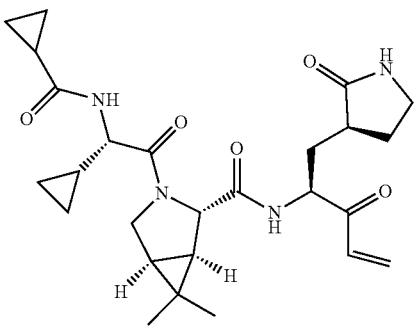

91
-continued
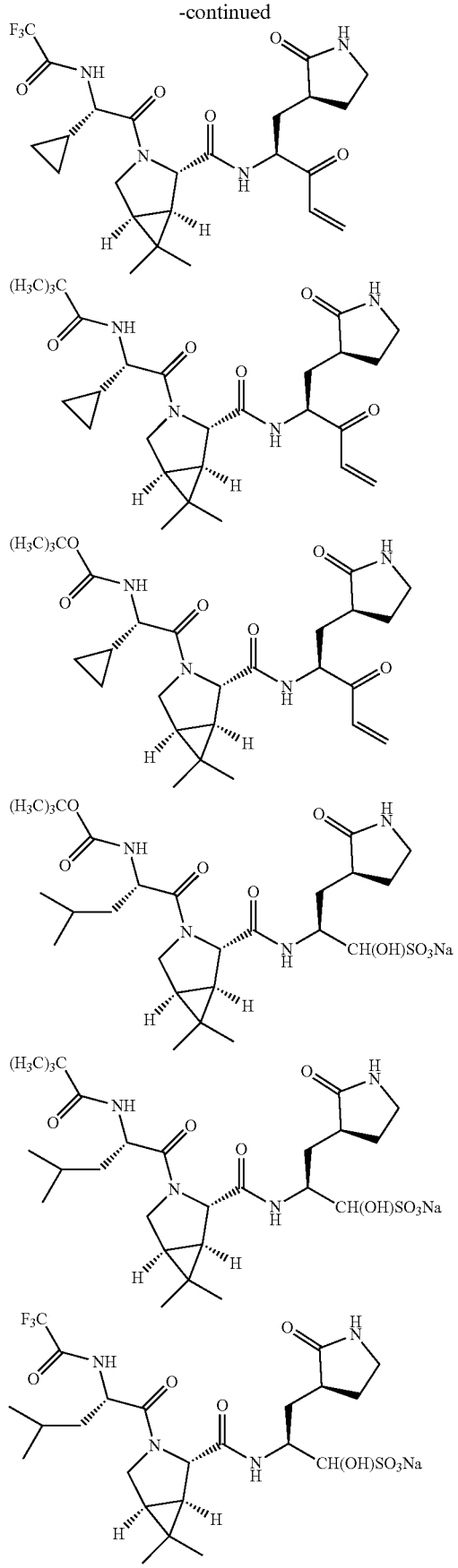
92
-continued
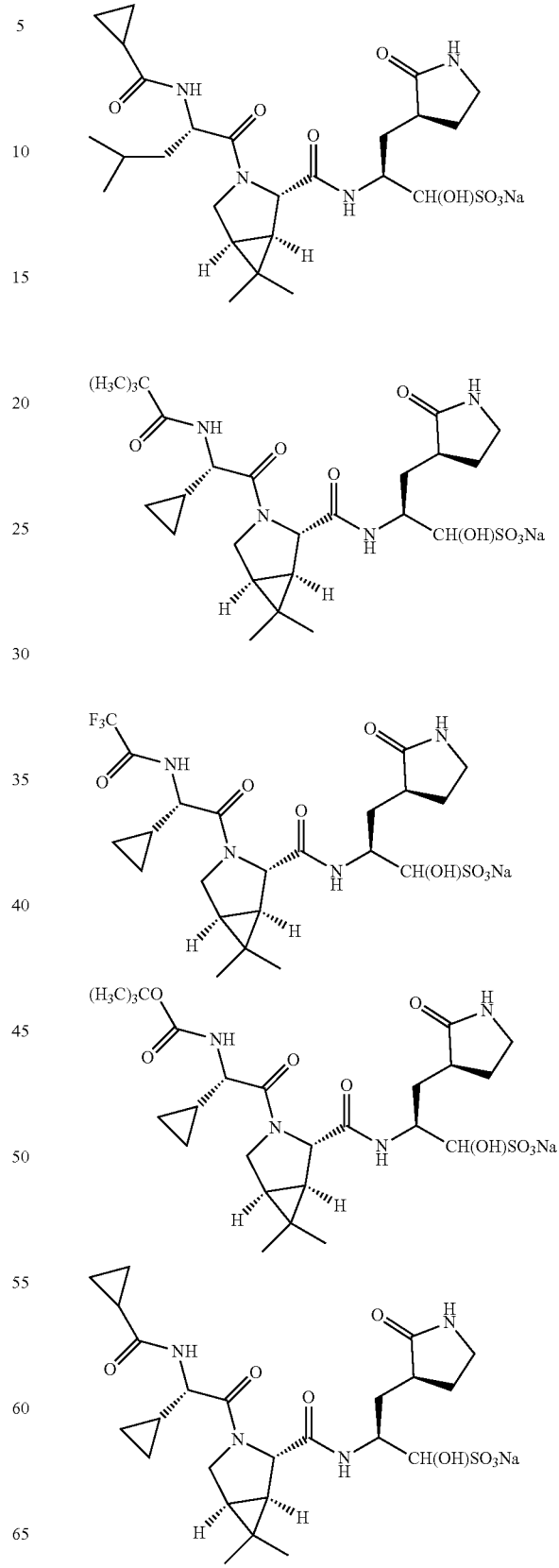

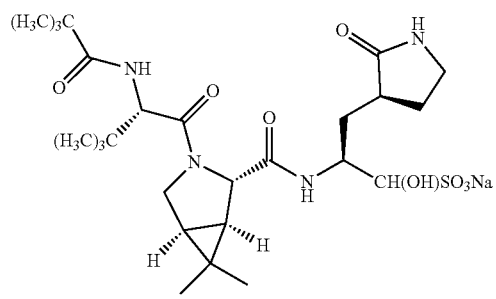
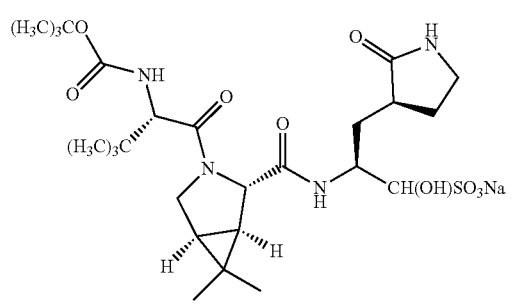
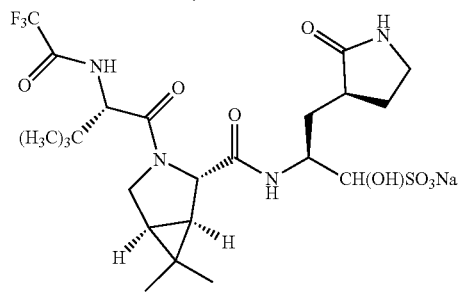
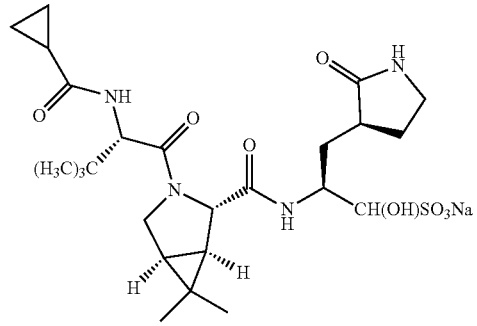
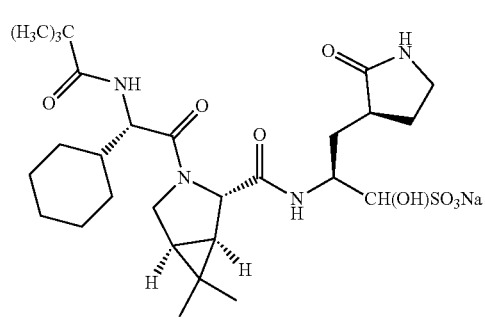
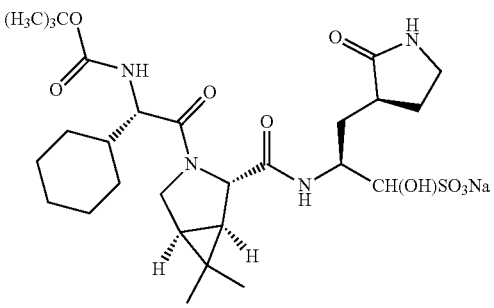
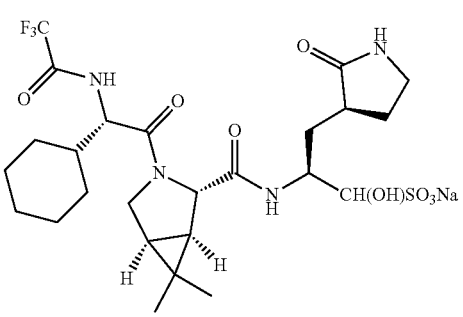
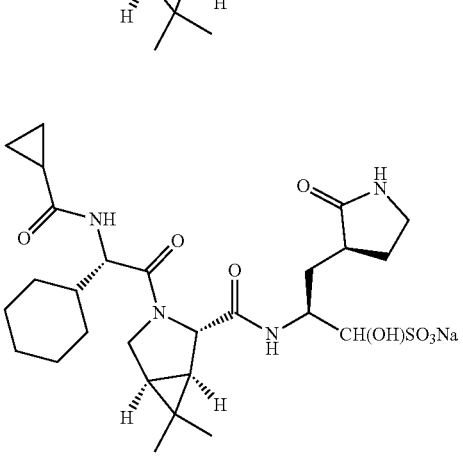
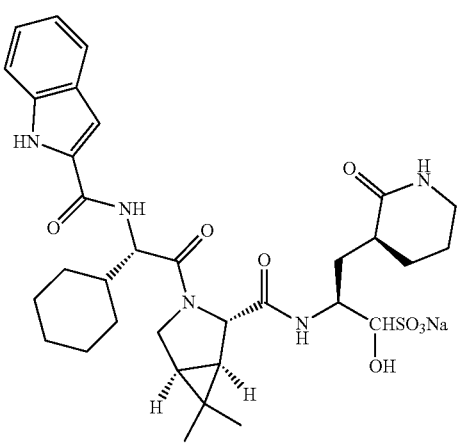

95
-continued
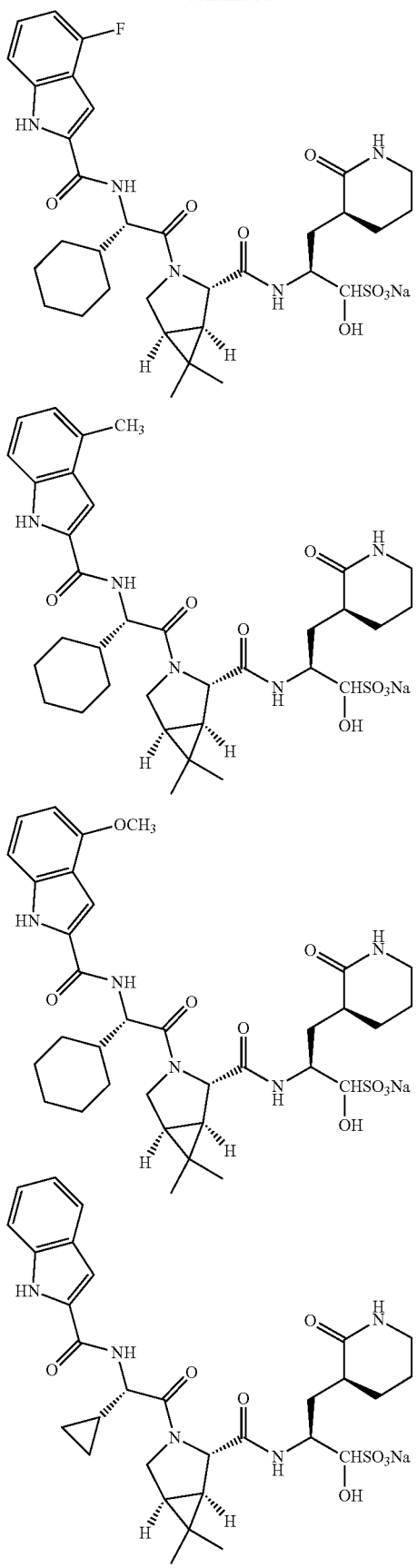
96
-continued
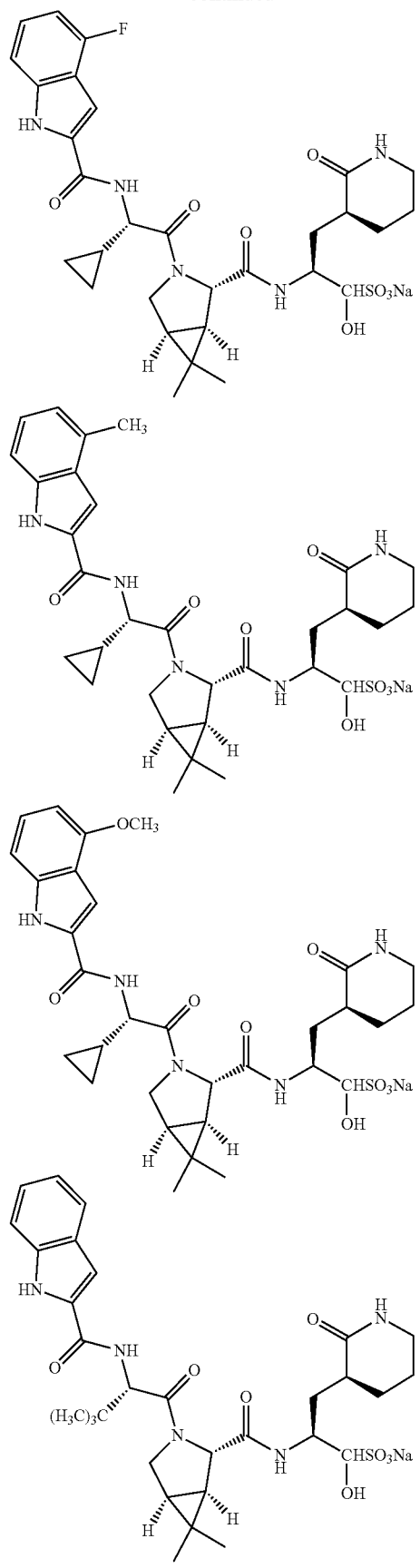

97
-continued
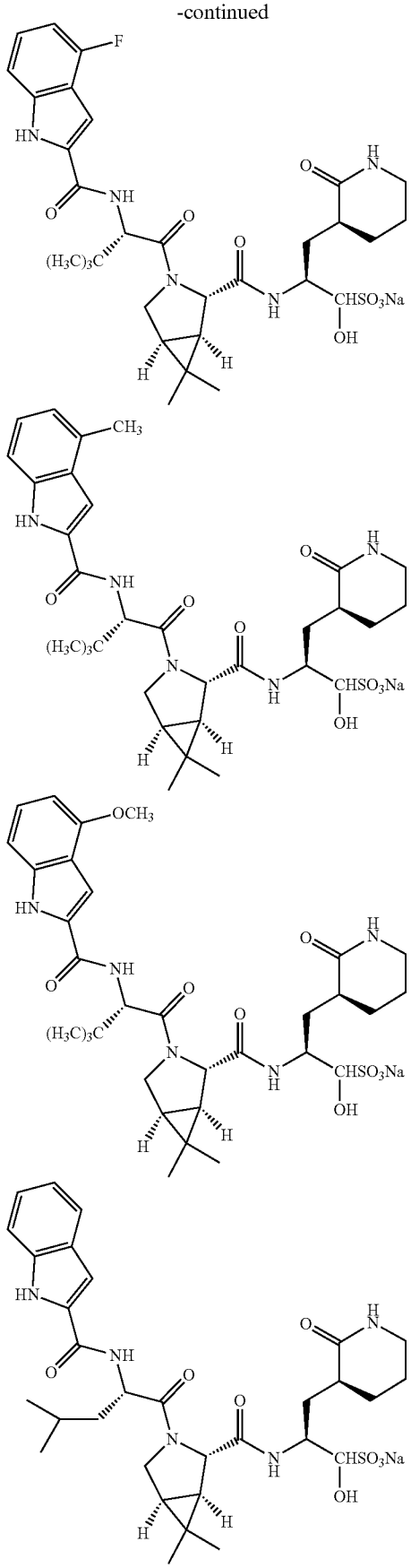
98
-continued
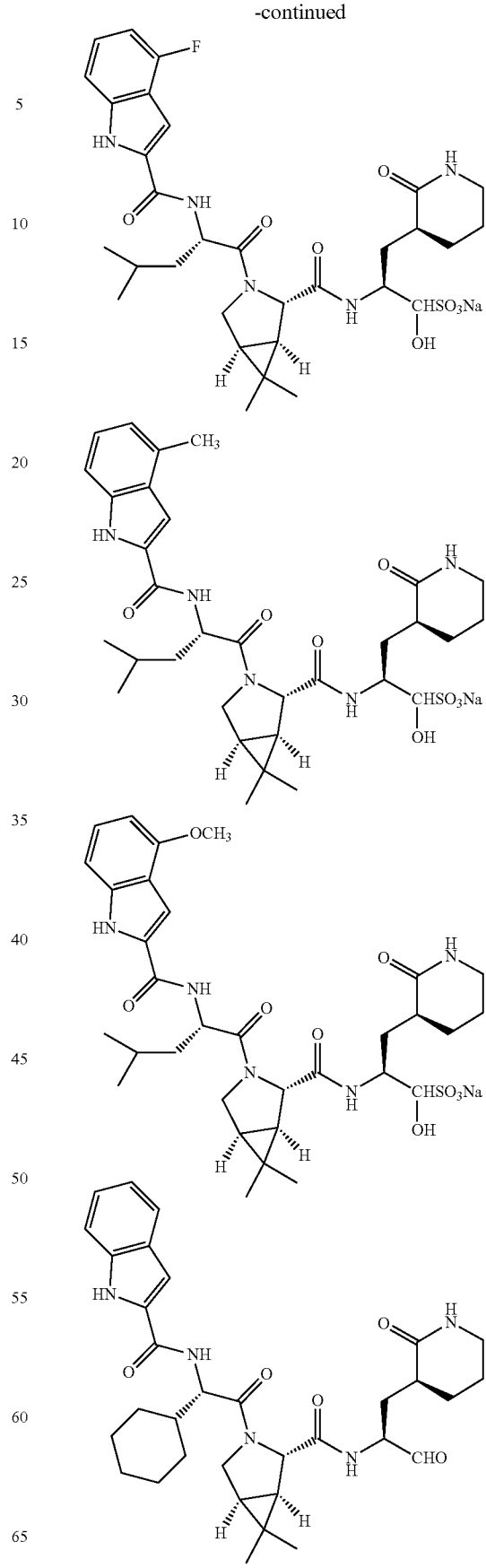

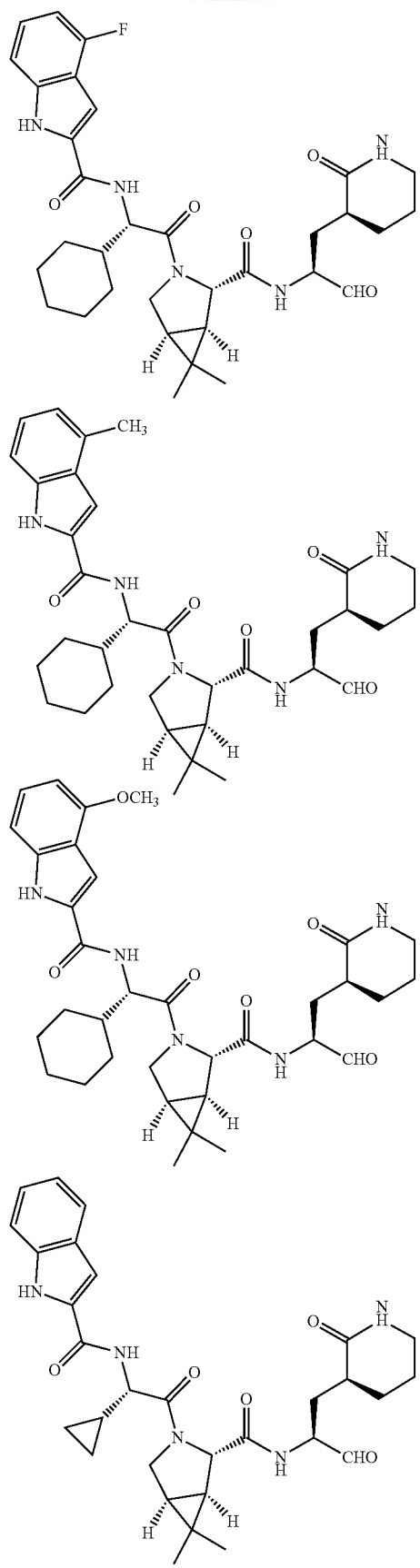
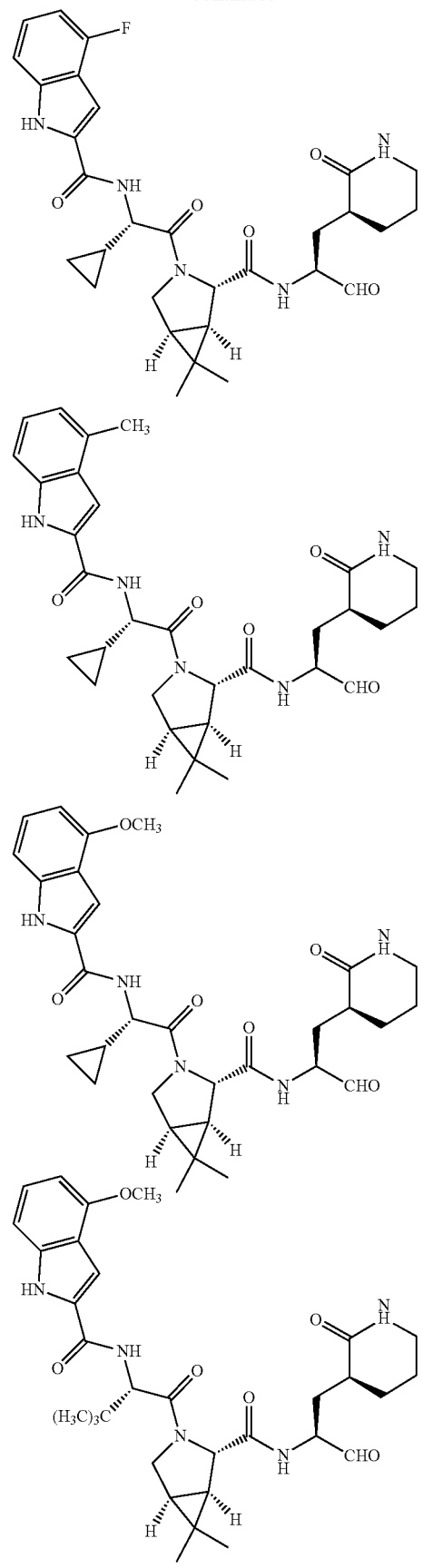

101
-continued
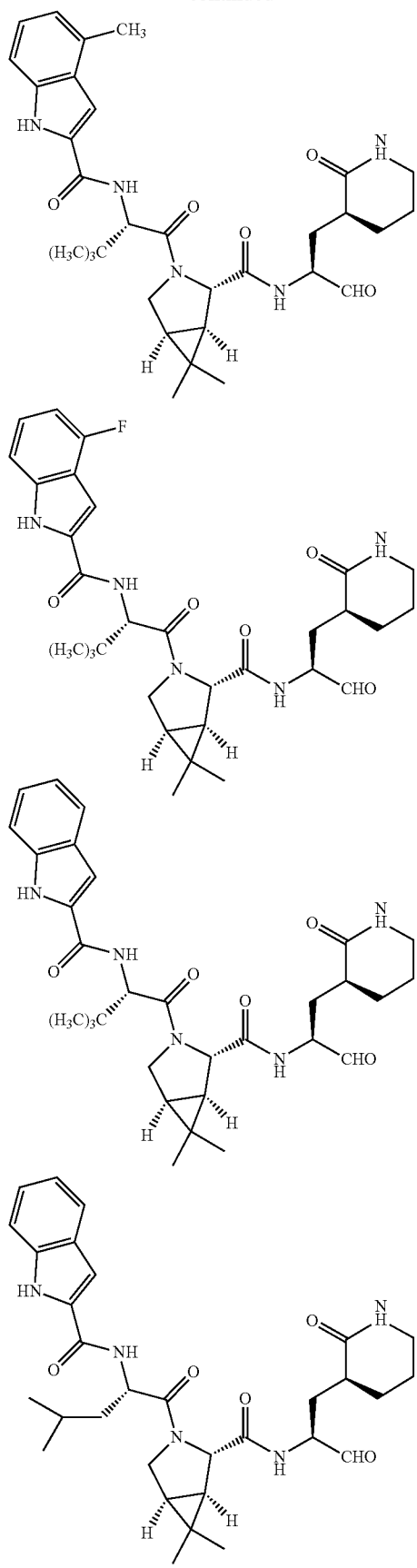
102
-continued
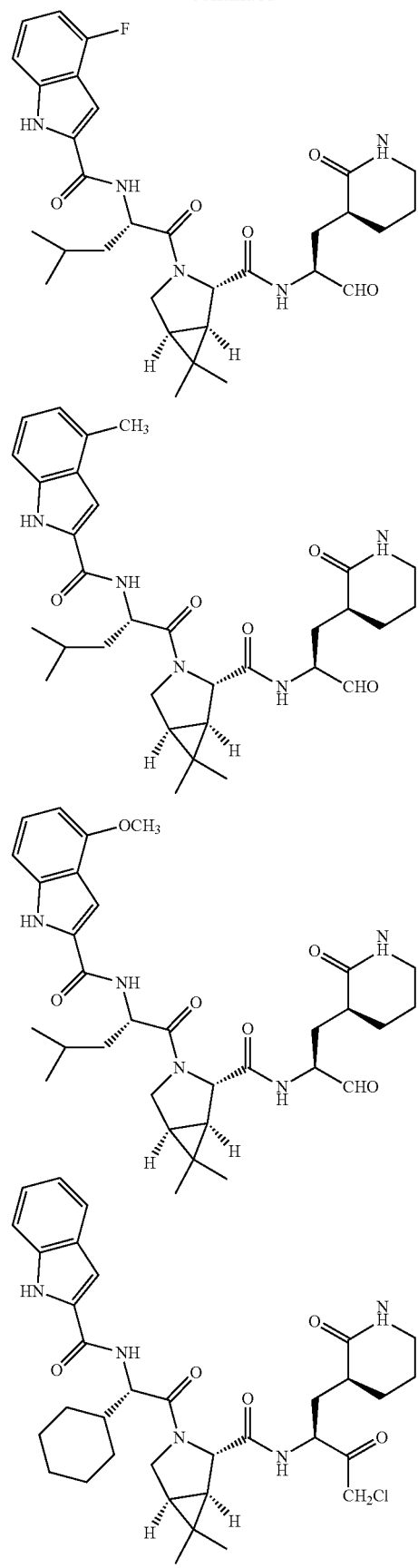

103
-continued
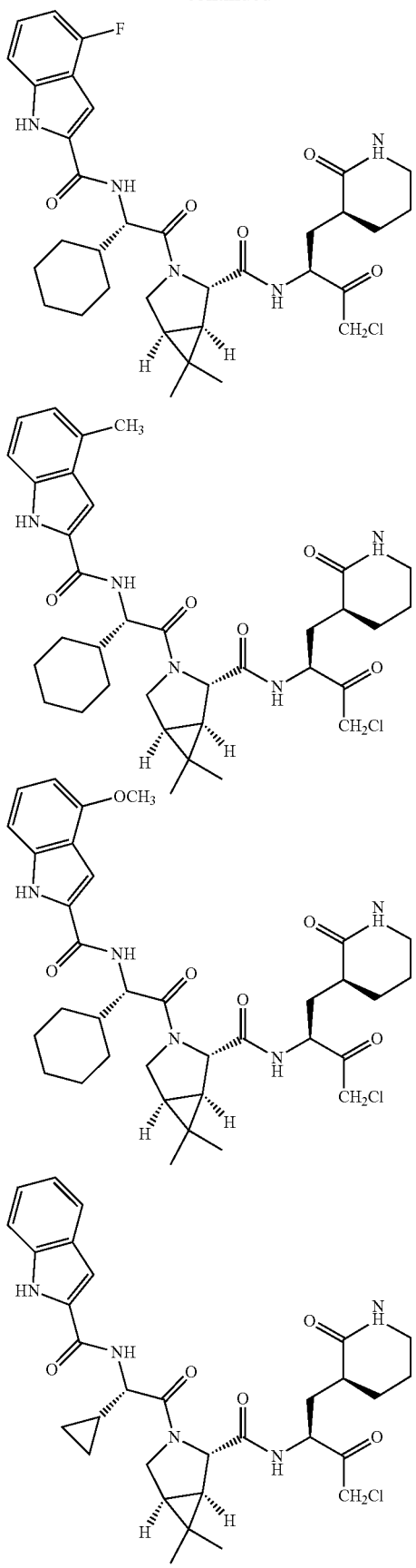
104
-continued
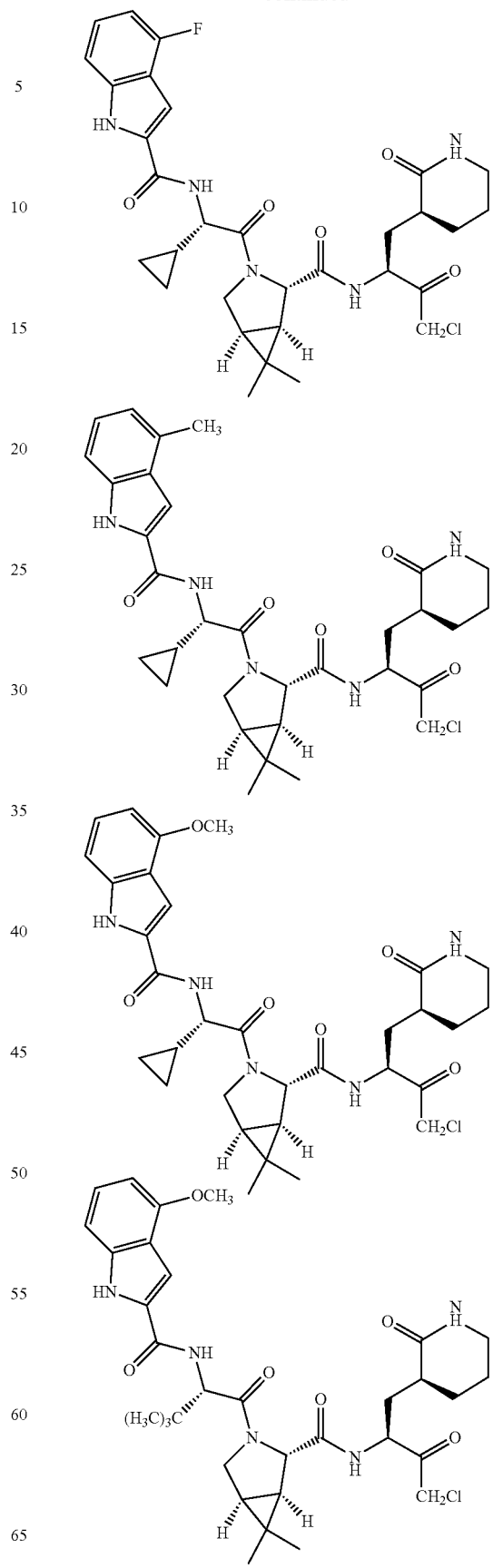

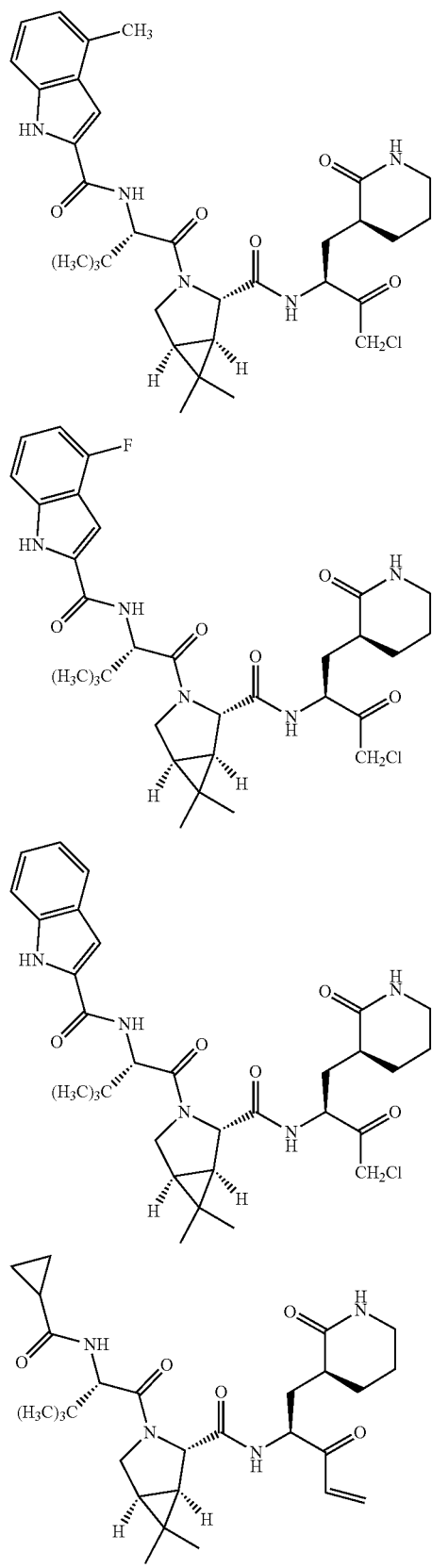
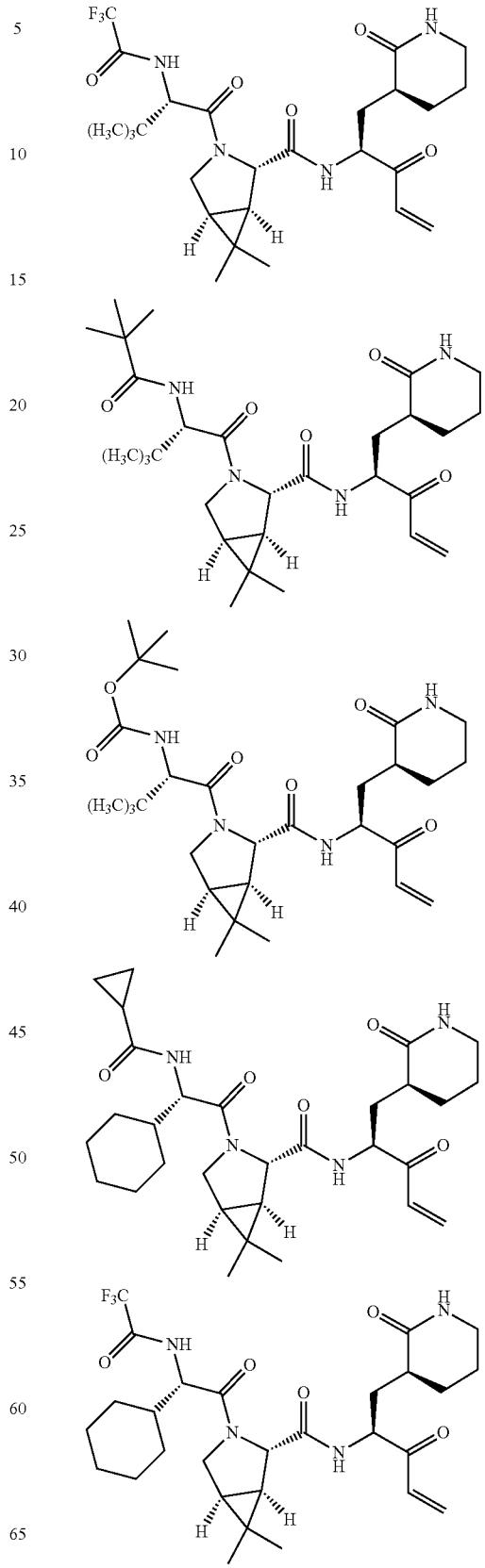

107
-continued
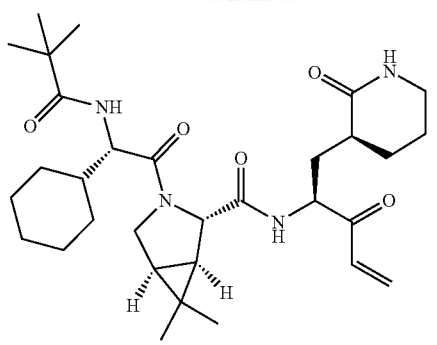
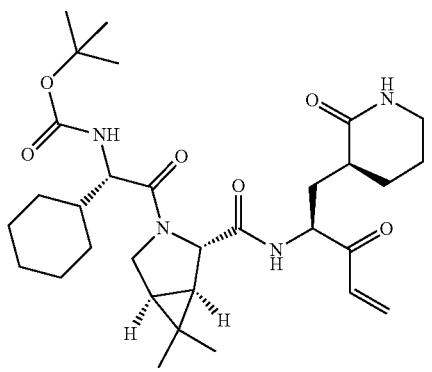
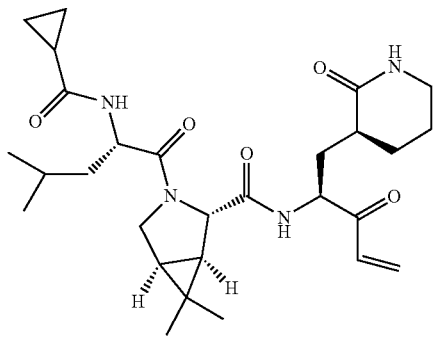
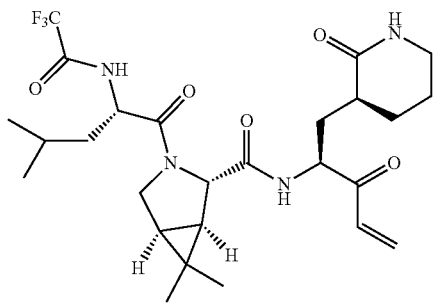
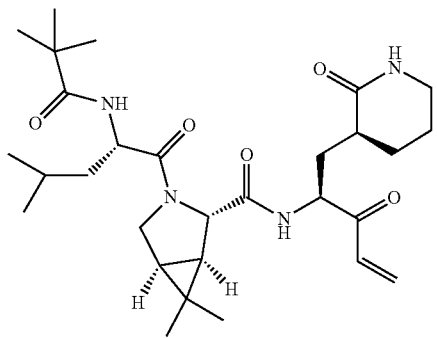
108
-continued
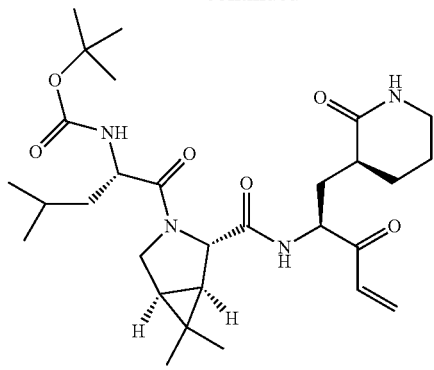
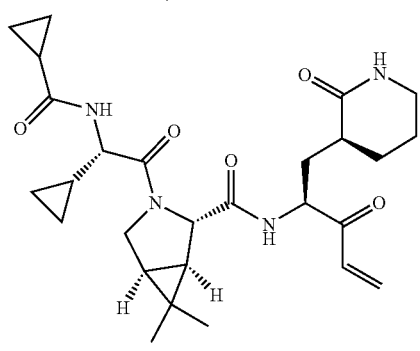
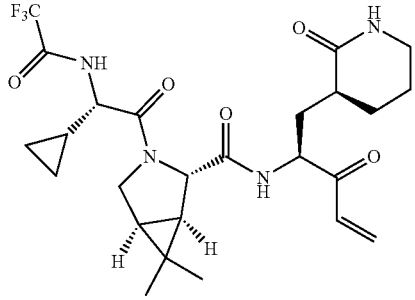
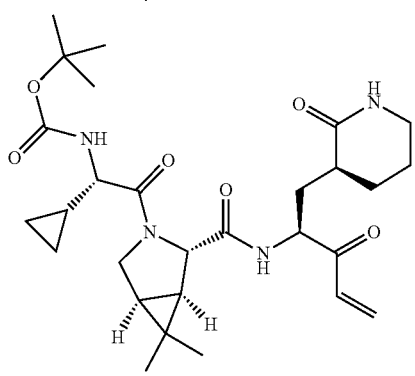
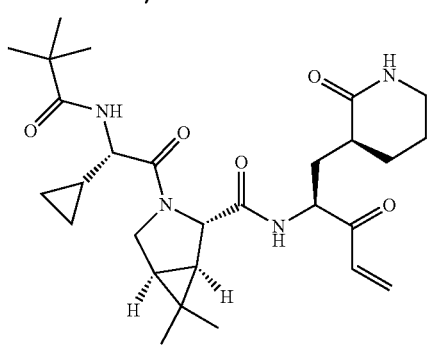

109
-continued
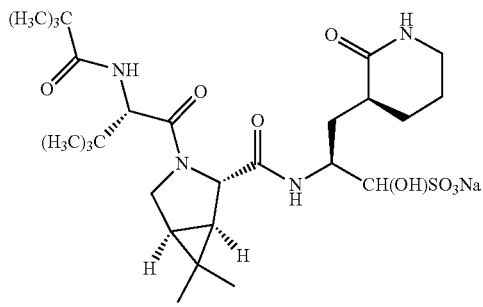
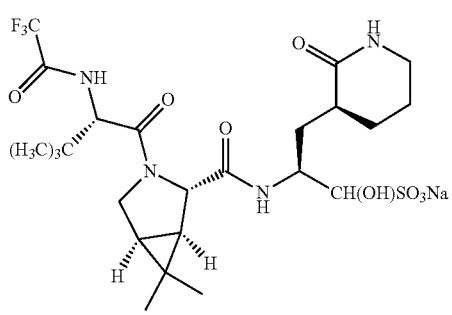
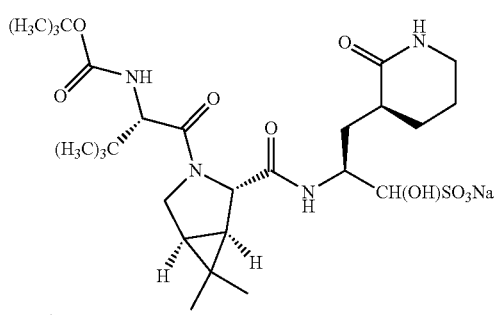
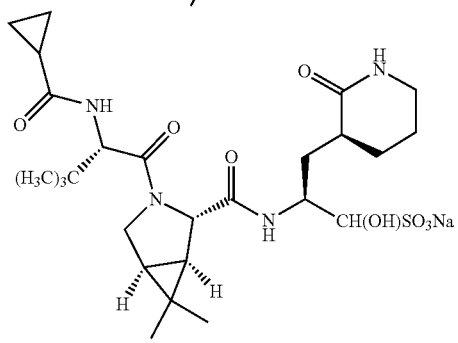
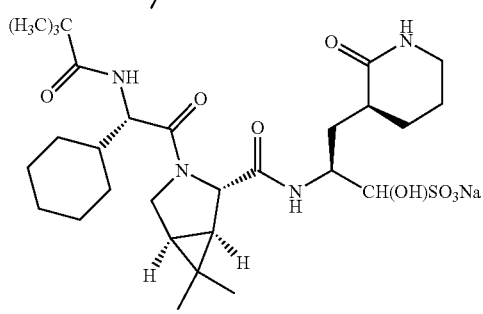
110
-continued
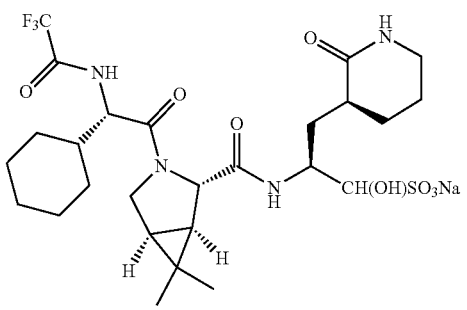
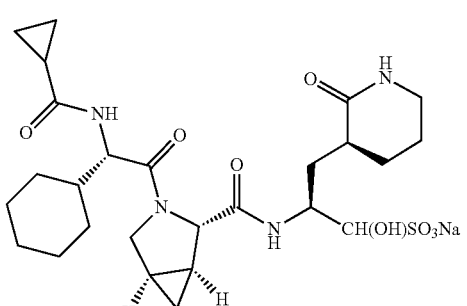

111
-continued
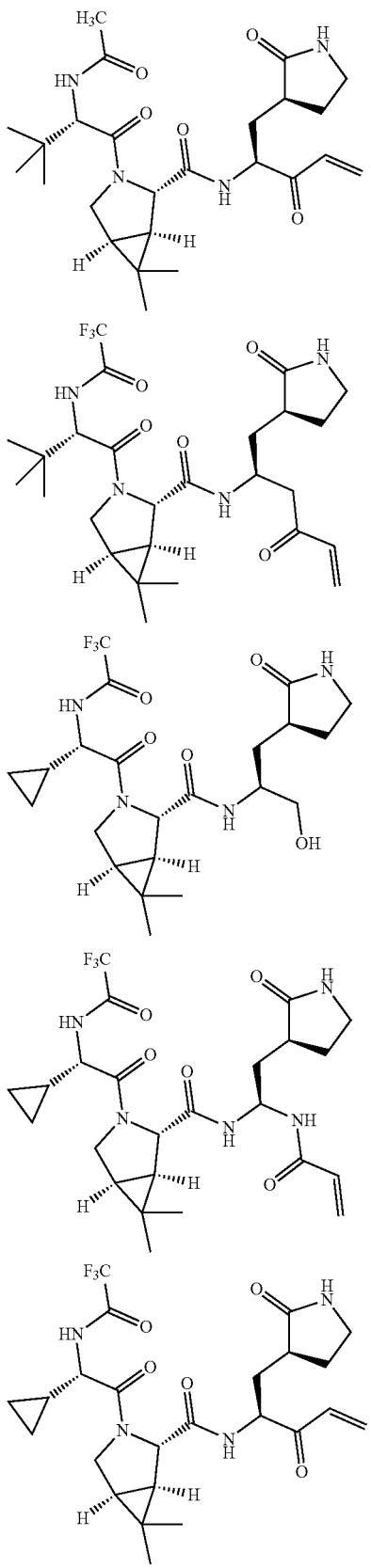
112
-continued
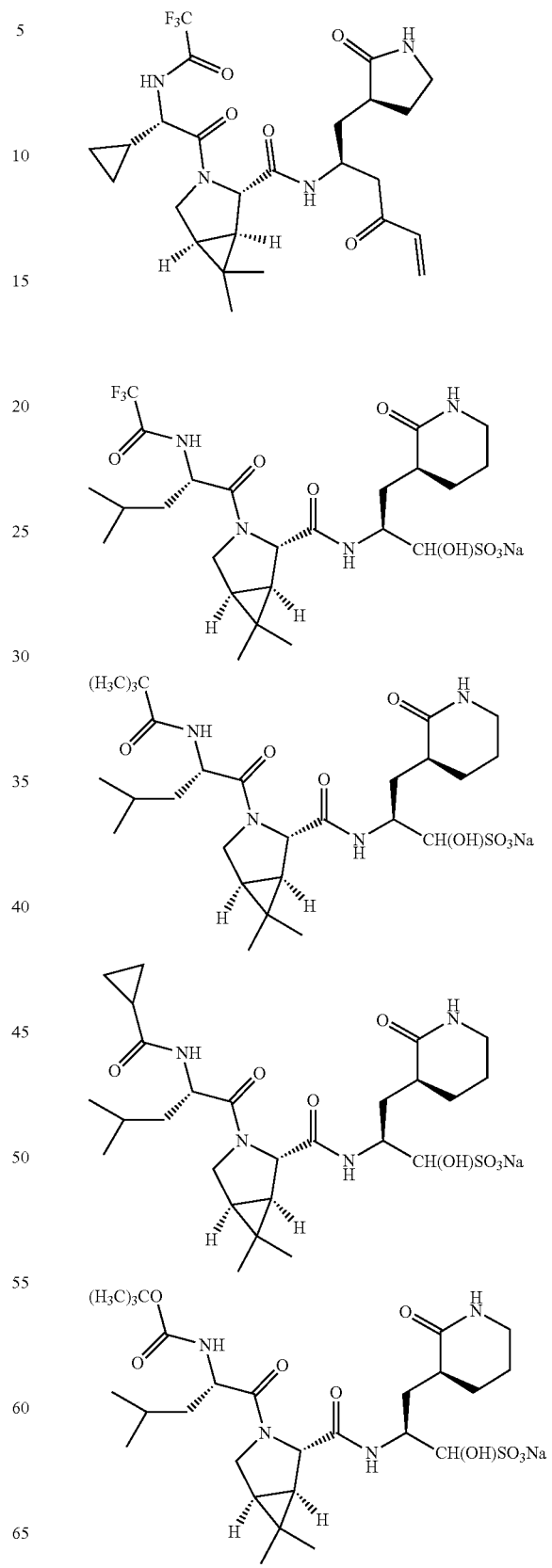

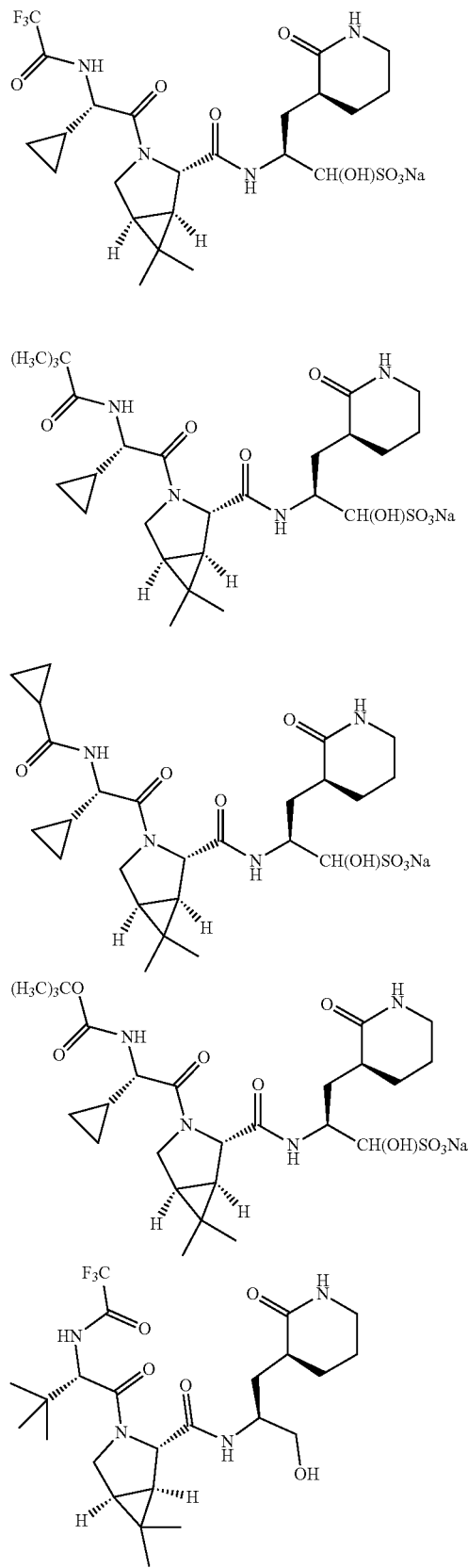

115
-continued
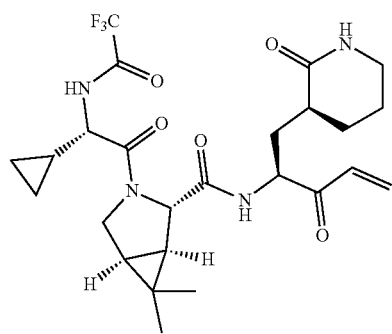
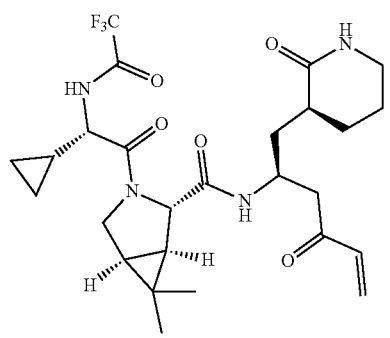
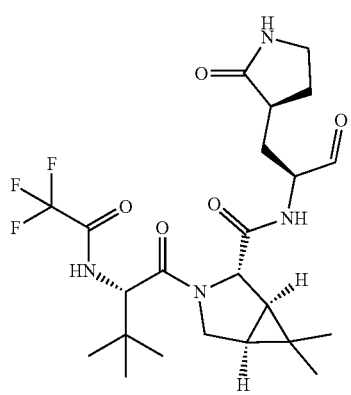
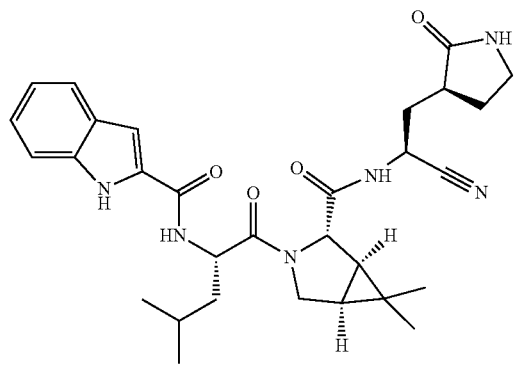
116
-continued
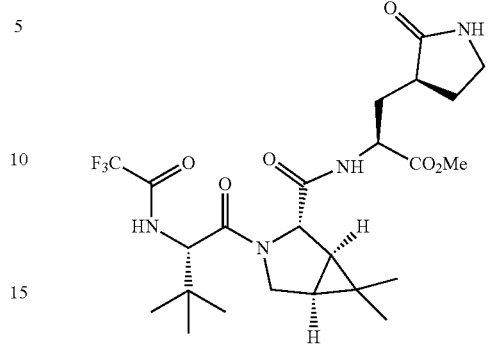
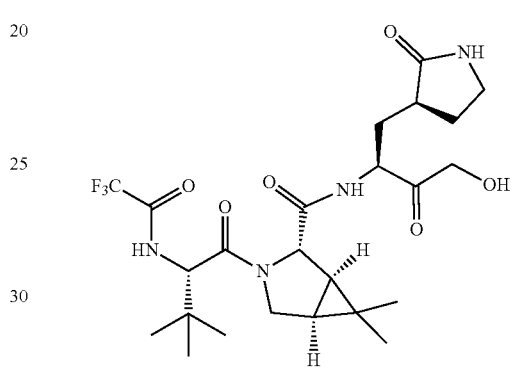

117
-continued
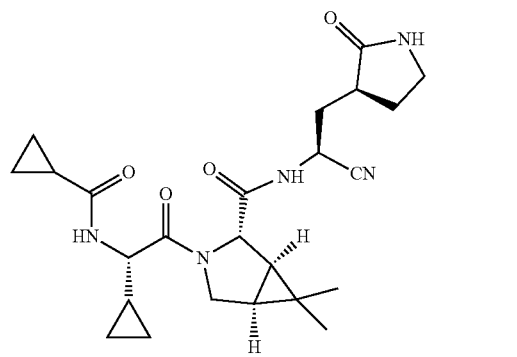
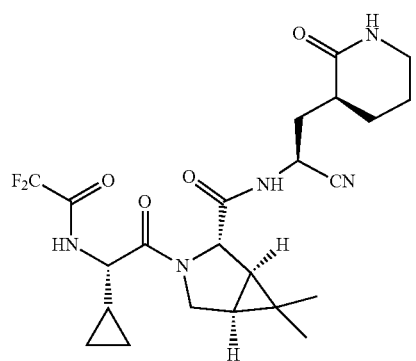
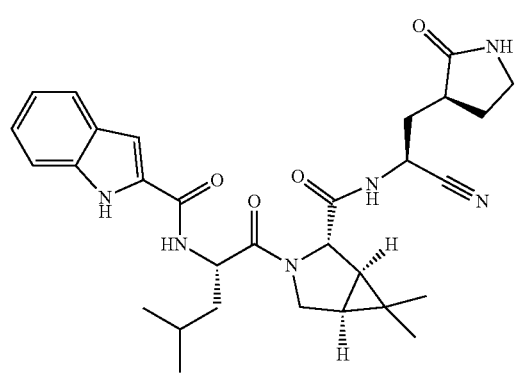
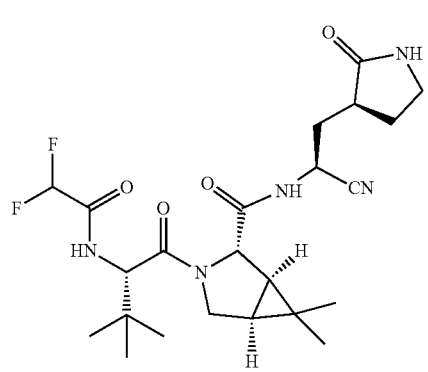
118
-continued
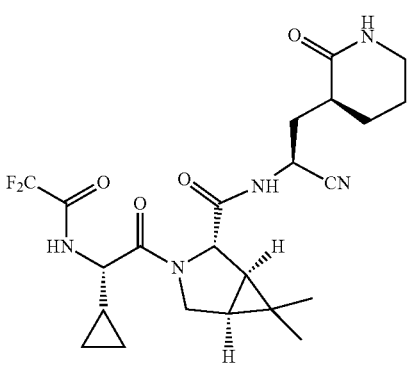
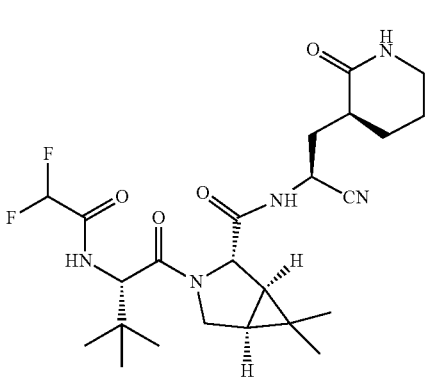
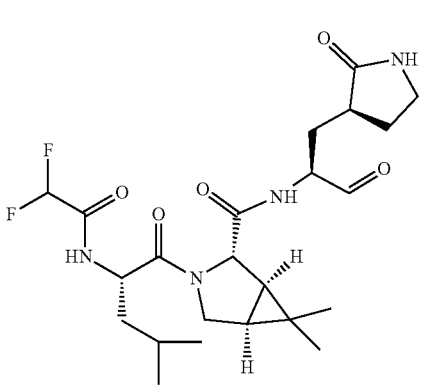
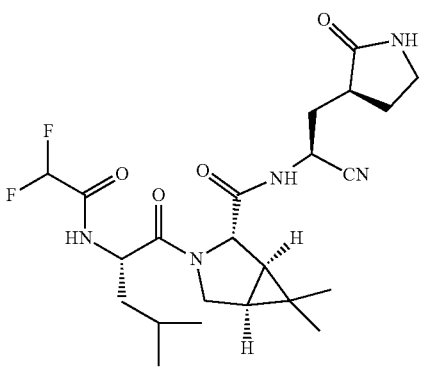

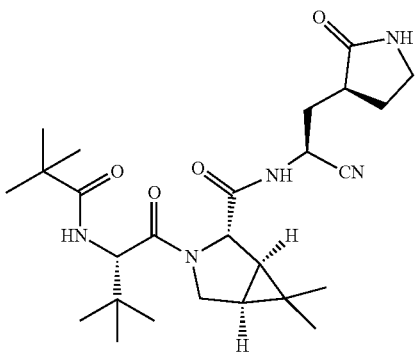

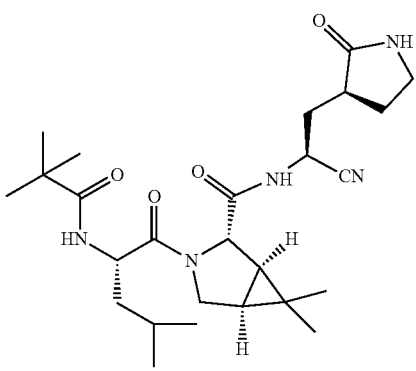

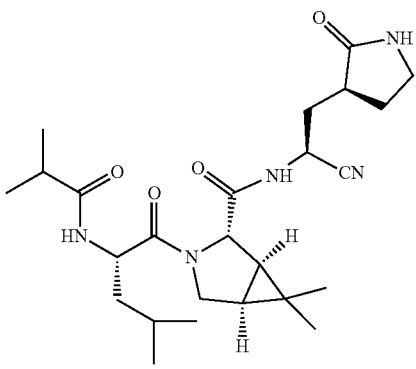

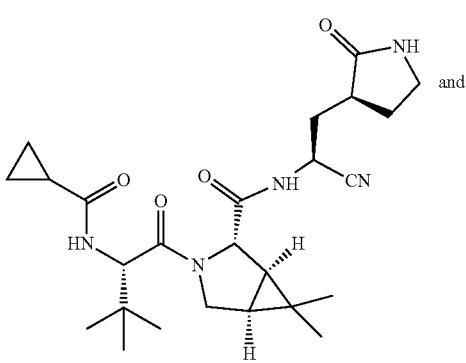

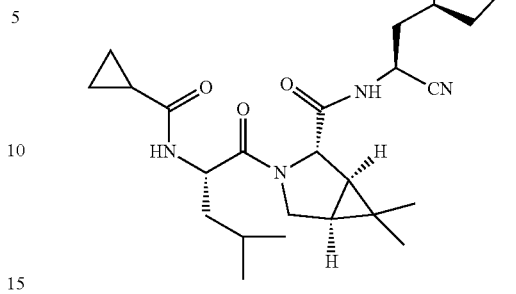

and tautomers, mixtures of two or more tautomers, and isotopic variants thereof; and pharmaceutically acceptable salts, solvates, hydrates, and prodrugs thereof.

In an aspect, provided herein is a compound of Formula (III):

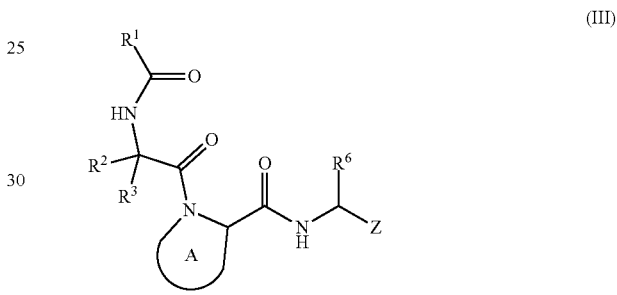

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

Ring A is a 5-9 atom cycloalkyl that is optionally substituted with up to three groups selected from $C_{1-3}$ alkyl, $C_{1-6}$ alkoxy, $C_{1-3}$ haloalkyl, and $C_{1-3}$ haloalkoxy;

Z is selected from —$CO_2$—$C_{1-3}$alkyl, —CHO, —CN, —$CH_2CN$, —C(=O)—CH=$CH_2$, —$CH_2$—C(=O)—CH=$CH_2$, —C(=O)—$C_{1-3}$ haloalkyl, —NH—C(=O)—CH=$CH_2$, —C(=O)$CH_2OH$,

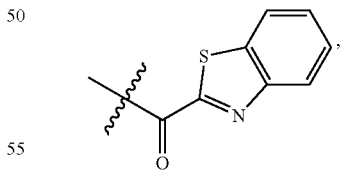

and —$CH(OH)SO_3^-$ (and an associated cation, such as $Na^+$);

$R^1$ is H, 3-7 membered cycloalkyl, $C_{1-4}$alkoxy, or $C_{1-4}$ alkyl, wherein the 3-7 membered cycloalkyl, $C_{1-4}$alkoxy and $C_{1-4}$ alkyl are optionally substituted with one to three groups independently selected from halo, CN, $C_{3-6}$ cycloalkyl, $C_{1-3}$ alkoxy, $C_{1-3}$ haloalkyl, and $C_{1-3}$haloalkoxy; or $R^1$ is 5-10 membered heteroaryl containing one or two heteroatoms selected from N, O and S as ring members, and wherein the 5-10 membered heteroaryl is optionally substituted with one to three groups independently selected from halo, CN, $C_{1-3}$ alkyl, $C_{1-3}$ alkoxy, $C_{1-3}$ haloalkyl, and $C_{1-3}$ haloalkoxy;

$R^2$ is selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy;

$R^3$ is H or $C_{1-4}$ alkyl; and $R^6$ is hydrogen, halo, $C_{1-6}$ alkyl, $C_{1-6}$ alkoxy, $C_{1-3}$ haloalkyl, or $C_{1-3}$ haloalkoxy.

In embodiments, Ring A is a 5-membered ring that can optionally be fused to a cyclopropyl ring, forming a bicyclic ring system that is an unsubstituted 3-azabicyclo[3.1.0]hexane ring. In embodiments, Ring A is a 5-membered ring that can optionally be fused to a cyclopropyl ring, forming a bicyclic ring system that is a 3-azabicyclo[3.1.0]hexane ring, substituted with one group selected from $C_{1-3}$ alkyl, $C_{1-6}$ alkoxy, $C_{1-3}$ haloalkyl, and $C_{1-3}$ haloalkoxy. In embodiments, Ring A is a 5-membered ring that can optionally be fused to a cyclopropyl ring, forming a bicyclic ring system that is a 3-azabicyclo[3.1.0]hexane ring, substituted with two groups independently selected from $C_{1-3}$ alkyl, $C_{1-6}$ alkoxy, $C_{1-3}$ haloalkyl, and $C_{1-3}$ haloalkoxy. In embodiments, Ring A is a 5-membered ring that can optionally be fused to a cyclopropyl ring, forming a bicyclic ring system that is a 3-azabicyclo[3.1.0]hexane ring, substituted with three groups independently selected from $C_{1-3}$ alkyl, $C_{1-6}$ alkoxy, $C_{1-3}$ haloalkyl, and $C_{1-3}$ haloalkoxy.

In embodiments, Ring A is a 5-membered ring that can optionally be fused to a cyclopropyl ring, forming a bicyclic ring system that is a 3-azabicyclo[3.1.0]hexane ring substituted with two methyl groups forming a 6,6-dimethyl-3-azabicyclo[3.1.0]hexane ring.

In embodiments, Z is selected from —$CO_2CH_3$, —CHO, —CN, —$CH_2CN$, —C(=O)—CH=$CH_2$, —$CH_2$—C(=O)—CH=$CH_2$, —C(=O)—$C_{1-3}$ haloalkyl, —NH—C(=O)—CH=$CH_2$, —C(=O)$CH_2$OH,

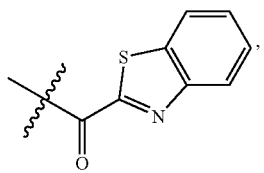 [SMILES: *C(=O)c1nc2ccccc2s1]

and —CH(OH)$SO_3^-$ (and an associated cation, such as Na$^+$). In embodiments, Z is selected from —$CO_2CH_3$, —CHO, —CN, —C(=O)—$C_{1-3}$ haloalkyl, —NH—C(=O)—CH=$CH_2$, and —CH(OH)$SO_3^-$ (and an associated cation, such as Na$^+$). In embodiments, Z is selected from —$CO_2CH_3$, —CHO, —CN, —NH—C(=O)—CH=$CH_2$, —CH(OH)$SO_3^-$ (and an associated cation, such as Na$^+$) and —C(=O)—$CH_2$X, where X is F, Cl, Br or I.

In embodiments, Z is —$CO_2CH_3$. In embodiments, Z is —CHO. In embodiments, Z is —CN. In embodiments, Z is —$CH_2CN$. In embodiments, Z is —C(=O)—CH=$CH_2$. In embodiments, Z is —$CH_2$—C(=O)—CH=$CH_2$. In embodiments, Z is —C(=O)—$C_{1-3}$ haloalkyl. In embodiments, Z is —NH—C(=O)—CH=$CH_2$. In embodiments, Z is —C(=O)$CH_2$OH. In embodiments, Z is

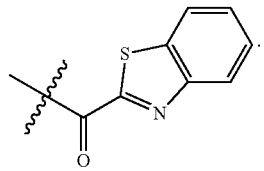 [SMILES: *C(=O)c1nc2ccccc2s1]

In embodiments, Z is —CH(OH)$SO_3$— (and an associated cation, such as Na$^+$). In embodiments, Z is —C(=O)—$CH_2$X where X is F, Cl, Br or I. In embodiments, Z is —C(=O)—$CH_2$F. In embodiments, Z is —C(=O)—$CH_2$Cl. In embodiments, Z is —C(=O)—$CH_2$Br. In embodiments, Z is —C(=O)—$CH_2$I.

In embodiments, $R^1$ is an indolyl, optionally substituted with one, two, or three groups independently selected from halo, CN, $C_{1-3}$ alkyl, $C_{1-3}$ alkoxy, $C_{1-3}$ haloalkyl, and $C_{1-3}$ haloalkoxy. In embodiments, $R^1$ is unsubstituted indolyl. In embodiments, $R^1$ is indolyl substituted with one group selected from halo, CN, $C_{1-3}$ alkyl, $C_{1-3}$ alkoxy, $C_{1-3}$ haloalkyl, and $C_{1-3}$ haloalkoxy. In embodiments, $R^1$ is indolyl substituted with two groups independently selected from halo, CN, $C_{1-3}$ alkyl, $C_{1-3}$ alkoxy, $C_{1-3}$ haloalkyl, and $C_{1-3}$ haloalkoxy. In embodiments, $R^1$ is indolyl substituted with three groups independently selected from halo, CN, $C_{1-3}$ alkyl, $C_{1-3}$ alkoxy, $C_{1-3}$ haloalkyl, and $C_{1-3}$ haloalkoxy. In embodiments, $R^1$ is indolyl substituted with one group selected from halo, $C_{1-3}$ alkyl, and $C_{1-3}$ alkoxy. In embodiments, $R^1$ is indolyl substituted with two groups independently selected from halo, $C_{1-3}$ alkyl, and $C_{1-3}$ alkoxy. In embodiments, $R^1$ is indolyl substituted with three groups independently selected from halo, $C_{1-3}$ alkyl, and $C_{1-3}$ alkoxy. In embodiments, $R^1$ is indolyl substituted with one group selected from fluoro, methyl, and methoxy. In embodiments, $R^1$ is indolyl substituted with two groups independently selected from fluoro, methyl, and methoxy. In embodiments, $R^1$ is indolyl substituted with three groups independently selected from fluoro, methyl, and methoxy.

In embodiments, $R^1$ is 5-10 membered heteroaryl containing one or two heteroatoms selected from N, O and S as ring members, where each 5-10 membered heteroaryl is optionally substituted with one, two or three groups independently selected from halo, CN, $C_{1-3}$ alkyl, $C_{1-3}$ alkoxy, $C_{1-3}$ haloalkyl, and $C_{1-3}$ haloalkoxy.

In embodiments, $R^1$ is unsubstituted 5-10 membered heteroaryl containing one or two heteroatoms selected from N, O and S as ring members. In embodiments, $R^1$ is unsubstituted 5-10 membered heteroaryl containing one heteroatom selected from N, O and S as ring member. In embodiments, $R^1$ is unsubstituted 5-10 membered heteroaryl containing two heteroatoms selected from N, O and S as ring members. In embodiments, $R^1$ is unsubstituted 5-10 membered heteroaryl containing one heteroatom N as ring member. In embodiments, $R^1$ is unsubstituted 5-10 membered heteroaryl containing one heteroatom O as ring member. In embodiments, $R^1$ is unsubstituted 5-10 membered heteroaryl containing one heteroatom S as ring member.

In embodiments, $R^1$ is a 5-10 membered heteroaryl containing one or two heteroatoms selected from N, O and S as ring members, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one or two heteroatoms selected from N, O and S as ring members, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one or two heteroatoms selected from N, O and S as ring members, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom selected from N, O and S as ring member, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, O and S as ring member, substituted with one group independently selected from halo, CN, $C_{1-3}$ alkyl, $C_{1-3}$ alkoxy, or $C_{1-3}$haloalkyl. In embodiments, $R^1$ is a 5-10 membered heteroaryl containing one heteroatom selected from N, O and S as ring member, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom N, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom N, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from N, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom O, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom O, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from O, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 5-10 membered heteroaryl containing one heteroatom S, substituted with one, two, or three groups independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom S, substituted with one group independently selected from halo, CN, $C_{1-3}$ alkyl, $C_{1-3}$ alkoxy, or $C_{1-3}$ haloalkyl. In embodiments, $R^1$ is a 5-10 membered heteroaryl containing one heteroatom selected from S, substituted with one group independently selected from fluoro, chloro, iodo, bromo, methyl, ethyl, propyl, methoxy, ethoxy, propoxy, trifluoromethyl, difluoromethyl, fluoromethyl, trichloromethyl, dichloromethyl, or chloromethyl.

In embodiments, $R^1$ is a 3-7 membered cycloalkyl optionally substituted with one to three groups independently selected from halo, CN, $C_{3-6}$ cycloalkyl, $C_{1-3}$ alkoxy, $C_{1-3}$ haloalkyl, and $C_{1-3}$haloalkoxy. In embodiments, $R^1$ is unsubstituted 3-7 membered cycloalkyl. In embodiments, $R^1$ is unsubstituted cyclopropyl. In embodiments, $R^1$ is unsubstituted cyclobutyl. In embodiments, $R^1$ is unsubstituted cyclopentyl. In embodiments, $R^1$ is unsubstituted cyclohexyl. In embodiments, $R^1$ is unsubstituted cycloheptyl. In embodiments, $R^1$ is 3-7 membered cycloalkyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopropyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclobutyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopentyl substituted with one group selected from halo, CN, $C_{3-6}$ cycloalkyl, $C_{1-3}$ alkoxy, $C_{1-3}$ haloalkyl, and $C_{1-3}$haloalkoxy. In embodiments, $R^1$ is cyclohexyl substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is 3-7 membered cycloalkyl substituted with two groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopropyl substituted with two groups selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is cyclobutyl substituted with two groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopentyl substituted with two groups selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is cyclohexyl substituted with two groups selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is 3-7 membered cycloalkyl substituted with three groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclopropyl substituted with three groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclobutyl substituted with three groups selected independently from halo, CN, $C_{3-6}$ cycloalkyl, $C_{1-3}$ alkoxy, $C_{1-3}$haloalkyl, and $C_{1-3}$ haloalkoxy. In embodiments, $R^1$ is cyclopentyl substituted with three groups selected independently from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is cyclohexyl substituted with three groups selected independently from halo, CN, $C_{3-6}$ cycloalkyl, $C_{1-3}$ alkoxy, $C_{1-3}$ haloalkyl, and $C_{1-3}$ haloalkoxy.

In embodiments, $R^1$ is $C_{1-4}$alkoxy or $C_{1-4}$ alkyl optionally substituted with one to three groups independently selected from halo, CN, $C_{3-6}$ cycloalkyl, $C_{1-3}$ alkoxy, $C_{1-3}$ haloalkyl, and $C_{1-3}$haloalkoxy. In embodiments, $R^1$ is $C_{1-4}$alkoxy or $C_{1-4}$ alkyl optionally substituted with one group selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is $C_{1-4}$alkoxy or $C_{1-4}$ alkyl optionally substituted with two groups independently selected from halo, CN, $C_{3-6}$ cycloalkyl, $C_{1-3}$ alkoxy, $C_{1-3}$ haloalkyl, and $C_{1-3}$ haloalkoxy. In embodiments, $R^1$ is $C_{1-4}$alkoxy or $C_{1-4}$ alkyl optionally substituted with three groups independently selected from halo, CN, $C_{3-6}$ cycloalkyl, $C_{1-3}$ alkoxy, $C_{1-3}$ haloalkyl, and $C_{1-3}$ haloalkoxy.

In embodiments, $R^1$ is unsubstituted $C_{1-4}$alkoxy or $C_{1-4}$ alkyl. In embodiments, $R^1$ is unsubstituted $C_{1-4}$alkoxy. In embodiments, $R^1$ is unsubstituted $C_{1-4}$alkyl. In embodiments, $R^1$ is methoxy, ethoxy, propoxy, isopropoxy, butoxy, isobutoxy, or t-butoxy. In embodiments, $R^1$ is methyl, ethyl, propyl, isopropyl, butyl, isobutyl, or t-butyl. In embodiments, $R^1$ is $C_{1-4}$alkoxy or $C_{1-4}$ alkyl substituted with one group selected from fluoro, chloro, bromo, and iodo. In embodiments, $R^1$ is $C_{1-4}$alkoxy or $C_{1-4}$ alkyl substituted with two groups selected independently from fluoro, chloro, bromo, and iodo. In embodiments, $R^1$ is $C_{1-4}$alkoxy or $C_{1-4}$ alkyl substituted with three groups selected independently from fluoro, chloro, bromo, and iodo.

In embodiments, $R^1$ is trifluoromethyl, difluoromethyl, cyclopropyl, isopropyl, t-butyl, isopropylmethyl, t-butoxy; or $R^1$ is indolyl optionally substituted with one or two groups selected from fluoro, methyl and methoxy. In embodiments, $R^1$ is trifluoromethyl or indolyl optionally substituted with one or two groups selected from fluoro, methyl and methoxy. In embodiments, $R^1$ is trifluoromethyl, difluoromethyl, cyclopropyl, isopropyl, t-butyl, or t-butoxy. In embodiments, $R^1$ is trifluoromethyl. In embodiments, $R^1$ is difluoromethyl. In embodiments, $R^1$ is cyclopropyl. In embodiments, $R^1$ is isopropyl. In embodiments, $R^1$ is t-butyl. In embodiments, $R^1$ is isopropylmethyl. In embodiments, $R^1$ is t-butoxy.

In embodiments, $R^2$ is selected from unsubstituted $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl. In embodiments, $R^2$ is unsubstituted $C_{1-6}$ alkyl. In embodiments, $R^2$ is unsubstituted 3-7 membered cycloalkyl. In embodiments, $R^2$ is unsubstituted $C_{1-3}$ alkyl-(3-7 membered cycloalkyl). In embodiments, $R^2$ is unsubstituted (3-7 membered cycloalkyl)-$C_{1-3}$ alkyl. In embodiments, $R^2$ is methyl, ethyl, propyl, isopropyl, butyl, isobutyl, t-butyl, pentyl, isopentyl, t-pentyl, or hexyl. In embodiments, $R^2$ is isopropylmethyl, isobutylmethyl, isobutylethyl, or isopentylmethyl. In embodiments, $R^2$ is cyclopropyl, cyclobutyl, cyclopentyl, cyclohexyl, or cycloheptyl. In embodiments, $R^2$ is cyclopropylmethyl, cyclopropylethyl, cyclopentylmethyl, cyclopentylethyl, cyclohexylmethyl, or cyclohexylethyl. In embodiments, $R^2$ is methyl. In embodiments, $R^2$ is ethyl. In embodiments, $R^2$ is propyl. In embodiments, $R^2$ is butyl. In embodiments, $R^2$ is isopropyl. In embodiments, $R^2$ is isobutyl. In embodiments, $R^2$ is t-butyl. In embodiments, $R^2$ is pentyl. In embodiments, $R^2$ is isopentyl. In embodiments, $R^2$ is t-pentyl. In embodiments, $R^2$ is hexyl. In embodiments, $R^2$ is isopropylmethyl. In embodiments, $R^2$ is isobutylmethyl. In embodiments, $R^2$ is isobutylethyl. In embodiments, $R^2$ is isopentylmethyl. In embodiments, $R^2$ is cyclopropyl. In embodiments, $R^2$ is cyclobutyl. In embodiments, $R^2$ is cyclopentyl. In embodiments, $R^2$ is cyclohexyl. In embodiments, $R^2$ is cycloheptyl. In embodiments, $R^2$ is cyclopropylmethyl. In embodiments, $R^2$ is cyclopropylethyl. In embodiments, $R^2$ is cyclopentylmethyl. In embodiments, $R^2$ is cyclopentylethyl. In embodiments, $R^2$ is cyclohexylmethyl. In embodiments, $R^2$ is cyclohexylethyl.

In embodiments, $R^2$ is selected from ethyl, isopropyl, isobutyl, t-butyl, isopropylmethyl, cyclopropyl, cyclohexyl, and cyclobutyl. In embodiments, $R^2$ is t-butyl, isopropylmethyl, or cyclopropyl.

In embodiments, $R^2$ is $C_{1-6}$ alkyl, 3-7 membered cycloalkyl, $C_{1-3}$ alkyl-(3-7 membered cycloalkyl), or (3-7 membered cycloalkyl)-$C_{1-3}$ alkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl, 3-7 membered cycloalkyl, $C_{1-3}$ alkyl-(3-7 membered cycloalkyl), or (3-7 membered cycloalkyl)-$C_{1-3}$ alkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl, 3-7 membered cycloalkyl, $C_{1-3}$ alkyl-(3-7 membered cycloalkyl), or (3-7 membered cycloalkyl)-$C_{1-3}$ alkyl substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is 3-7 membered cycloalkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-3}$ alkyl-(3-7 membered cycloalkyl) substituted with one group selected from halo, CN, $C_{1-3}$ alkyl, $C_{1-6}$ alkoxy, $C_{1-3}$ haloalkyl, and $C_{1-3}$haloalkoxy. In embodiments, $R^2$ is (3-7 membered cycloalkyl)-$C_{1-3}$ alkyl substituted with one group selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is 3-7 membered cycloalkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-3}$ alkyl-(3-7 membered cycloalkyl) substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is (3-7 membered cycloalkyl)-$C_{1-3}$ alkyl substituted with two groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-6}$ alkyl substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is 3-7 membered cycloalkyl substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is $C_{1-3}$ alkyl-(3-7 membered cycloalkyl) substituted with three groups independently selected from halo, CN, $C_{1-3}$ alkyl, $C_{1-6}$ alkoxy, $C_{1-3}$ haloalkyl, and $C_{1-3}$ haloalkoxy. In embodiments, $R^2$ is (3-7 membered cycloalkyl)-$C_{1-3}$ alkyl substituted with three groups independently selected from halo, CN, $C_{1-3}$ alkyl, $C_{1-6}$ alkoxy, $C_{1-3}$ haloalkyl, and $C_{1-3}$ haloalkoxy.

In embodiments, $R^3$ is H, methyl, ethyl, propyl, isopropyl, butyl, isobutyl, or t-butyl. In embodiments, $R^3$ is H. In embodiments, $R^3$ is methyl. In embodiments, $R^3$ is ethyl. In embodiments, $R^3$ is propyl. In embodiments, $R^3$ is isopropyl. In embodiments, $R^3$ is butyl. In embodiments, $R^3$ is isobutyl. In embodiments, $R^3$ is t-butyl.

In embodiments, $R^6$ is hydrogen. In embodiments, $R^6$ is halo. In embodiments, $R^6$ is $C_{1-6}$ alkyl. In embodiments, $R^6$ is $C_{1-6}$ alkoxy. In embodiments, $R^6$ is $C_{1-3}$ haloalkyl. In embodiments, $R^6$ is $C_{1-3}$ haloalkoxy.

In embodiments, $R^6$ is hydrogen, fluoro, chloro, bromo, iodo, methyl, ethyl, propyl, isopropyl, butyl, isobutyl, t-butyl, pentyl, isopentyl, t-pentyl, hexyl, methoxy, ethoxy, propoxy, butoxy, pentoxy, trifluoromethyl, trifluoroethyl, trifluoropropyl, difluoromethyl, difluoroethyl, difluoropropyl, fluoromethyl, fluoroethyl, fluoropropyl, trichloromethyl, trichloroethyl, trichloropropyl, dichloromethyl, dichloroethyl, dichloropropyl, chloromethyl, chloroethyl, chloropropyl, tribromomethyl, tribromoethyl, tribromopropyl, dibromomethyl, dibromoethyl, dibromopropyl, bromomethyl, bromoethyl, bromopropyl, triiodomethyl, triiodoethyl, triiodopropyl, diiodomethyl, diiodoethyl, diiodopropyl, iodomethyl, iodoethyl, or iodopropyl. In embodiments, $R^6$ is methyl, isopropyl, or t-butyl. In embodiments, $R^6$ is methyl. In embodiments, $R^6$ is ethyl. In embodiments, $R^6$ is propyl. In embodiments, $R^6$ is isopropyl. In embodiments, $R^6$ is butyl. In embodiments, $R^6$ is isobutyl. In embodiments, $R^6$ is t-butyl.

In embodiments, provided herein is a compound of Formula (IIIA):

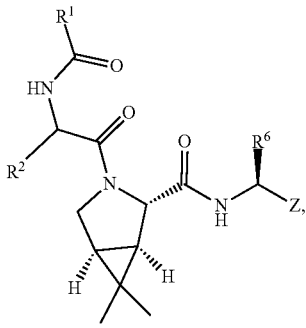

(IIIA)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, and $R^6$ are as described herein, including in embodiments.

In embodiments, provided herein is a compound of Formula (IIIB):

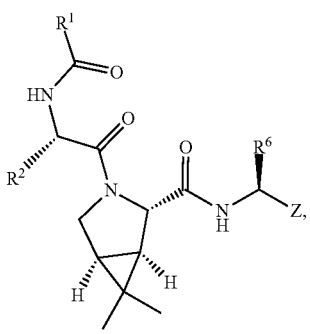

(IIIB)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^1$, $R^2$, Z, and $R^6$ are as described herein, including in embodiments.

In embodiments, provided herein is a compound of Formula (IIIC):

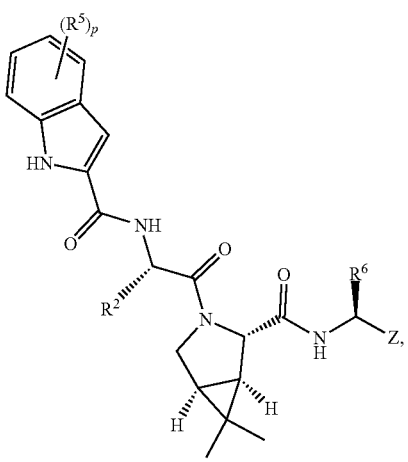

(IIIC)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^5$ is independently selected from hydrogen, halo, —CN, $C_{1-3}$ alkyl, $C_{1-3}$ alkoxy, $C_{1-3}$ haloalkyl, and $C_{1-3}$ haloalkoxy; p is an integer from 0 to 4; and $R^2$, Z, and $R^6$ are as described herein, including in embodiments.

In embodiments, $R^5$ is independently selected from hydrogen, halo, $C_{1-3}$ alkyl, and $C_{1-3}$ alkoxy. In embodiments, $R^5$ is independently selected from hydrogen, halo, —CN, methyl, ethyl, propyl, methoxy, ethoxy, propoxy, trifluoromethyl, trichloromethyl, tribromomethyl, triiodomethyl, difluoromethyl, dichloromethyl, dibromomethyl, diiodomethyl, fluoromethyl, chloromethyl, bromomethyl, iodomethyl, trifluoethyl, trifluoropropyl, trichloroethyl, and tribromoethyl. In embodiments, $R^5$ is independently selected from hydrogen, —CN, fluoro, chloro, bromo, iodo, methyl, ethyl, propyl, methoxy, ethoxy, propoxy, trifluoromethyl, trichloromethyl, tribromomethyl, trifluoroethyl, trichloroethyl, and tribromoethyl. In embodiments, $R^5$ is independently selected from hydrogen, fluoro, methyl and methoxy. In embodiments, $R^5$ is hydrogen. In embodiments, $R^5$ is fluoro. In embodiments, $R^5$ is methyl. In embodiments, $R^5$ is methoxy.

In embodiments, p is 0. In embodiments, p is 1. In embodiments, p is 2. In embodiments, p is 3. In embodiments, p is 4.

In embodiments, provided herein is a compound of Formula (IIID):

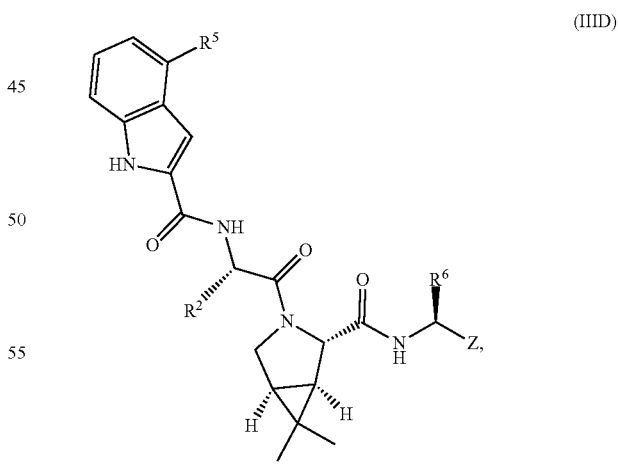

(IIID)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, $R^5$, Z, and $R^6$ are as described herein, including in embodiments.

In embodiments, provided herein is a compound of Formula (IIID1):

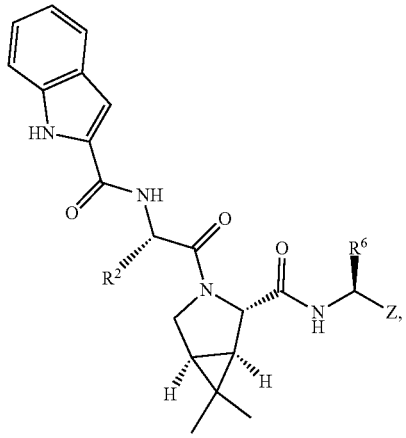

(IIID1)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, Z, and $R^6$ are as described herein, including in embodiments.

In embodiments, provided herein is a compound of Formula (IIID1A):

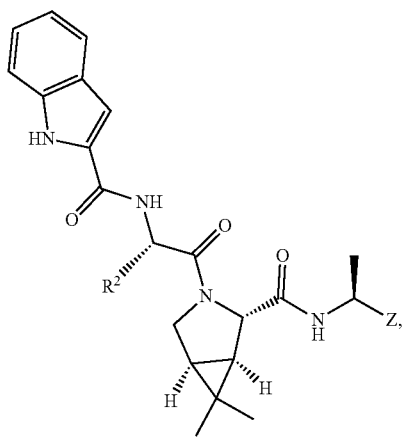

(IIID1A)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIID1B):

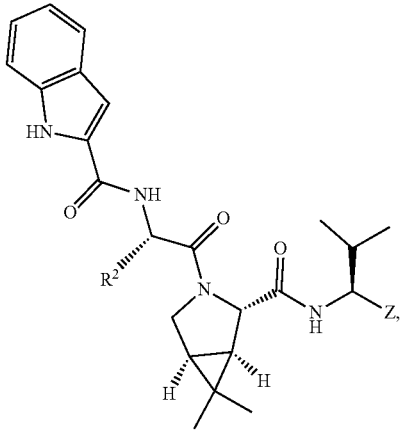

(IIID1B)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIID1C):

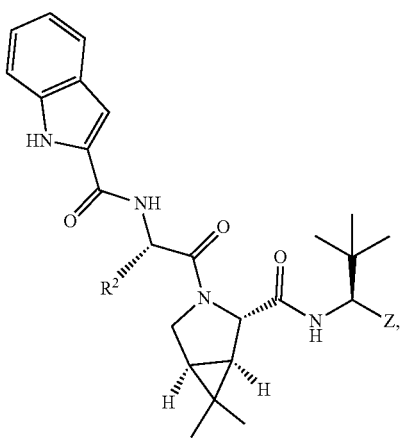

(IIID1C)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIIE):

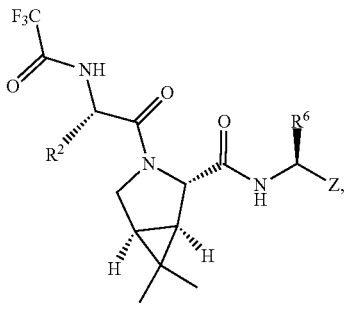

(IIIE)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$, $R^6$, and Z are as described herein, including in embodiments.

In embodiments, provided herein is a compound of Formula (IIIE1):

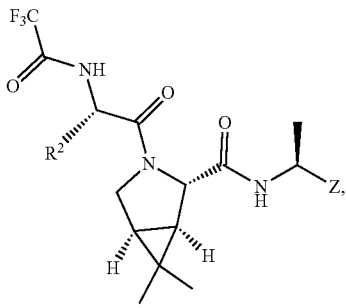

(IIIE1)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIIE2):

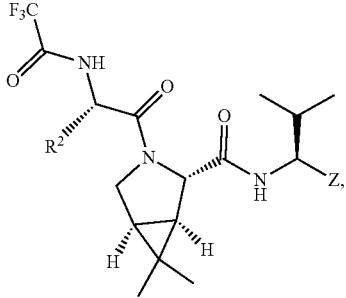

(IIIE2)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein is a compound of Formula (IIIE3):

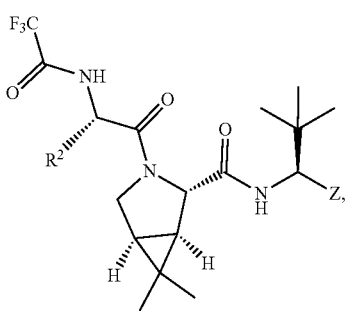

(IIIE3)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, wherein $R^2$ and Z are as described herein, including in embodiments.

In embodiments, provided herein are compounds selected from:

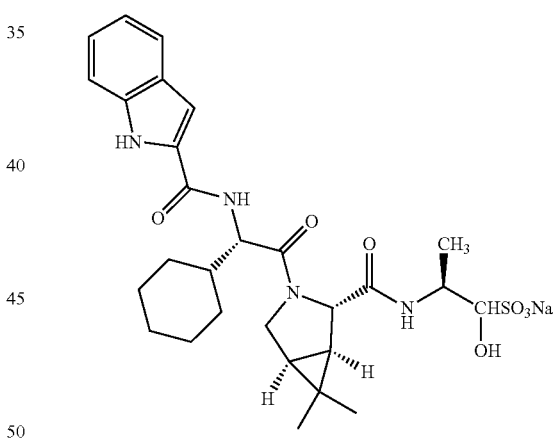

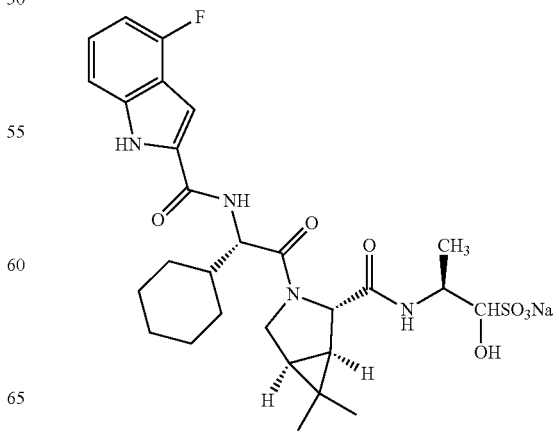

133
-continued
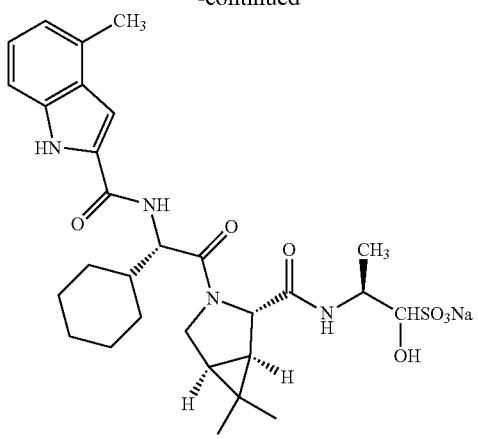
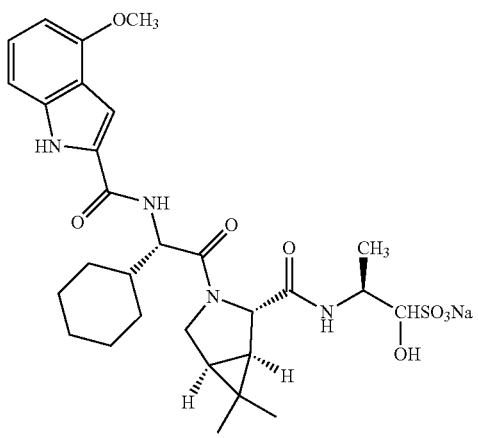
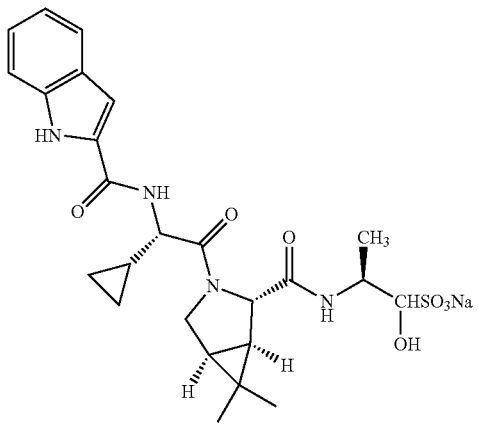
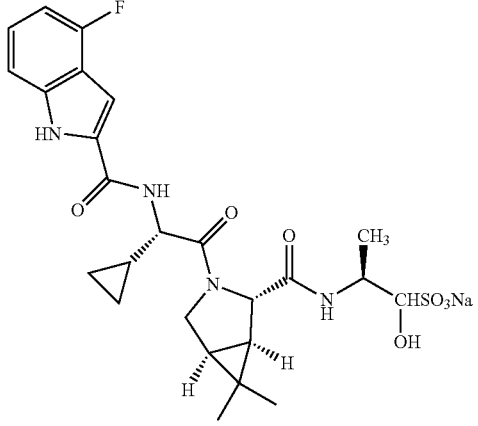
134
-continued
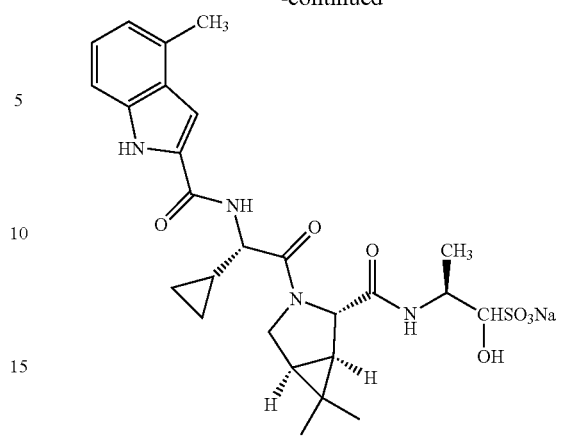
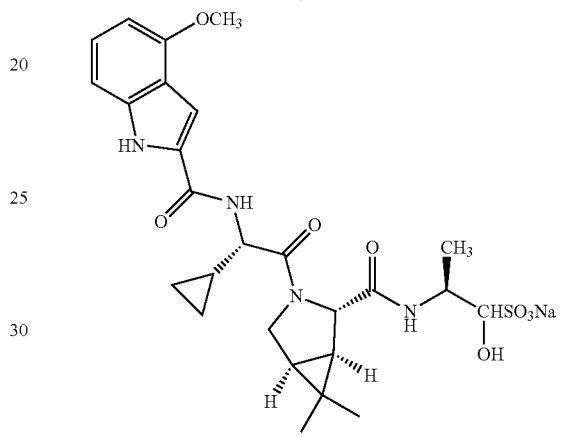
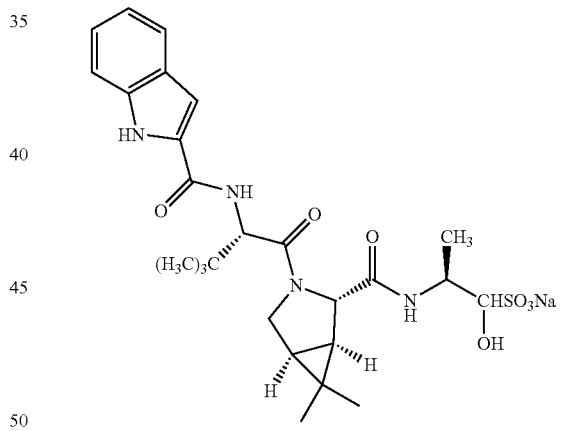
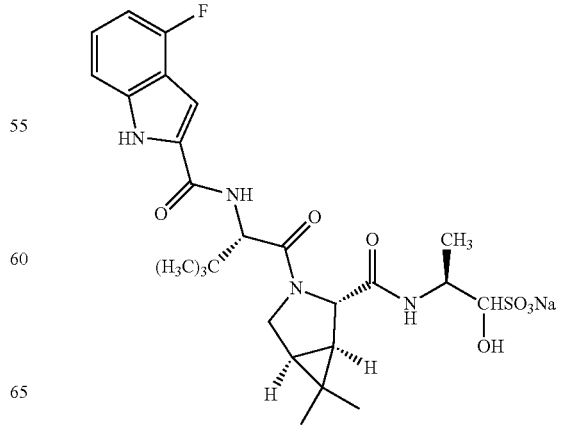

135
-continued
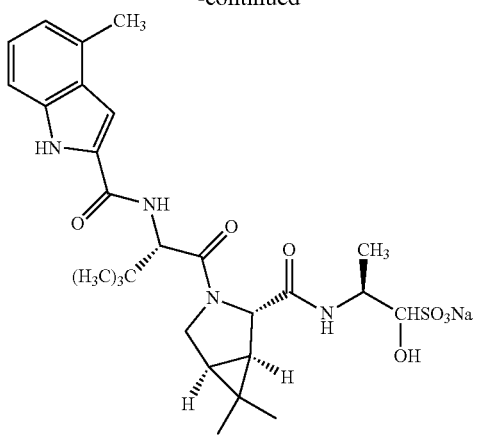
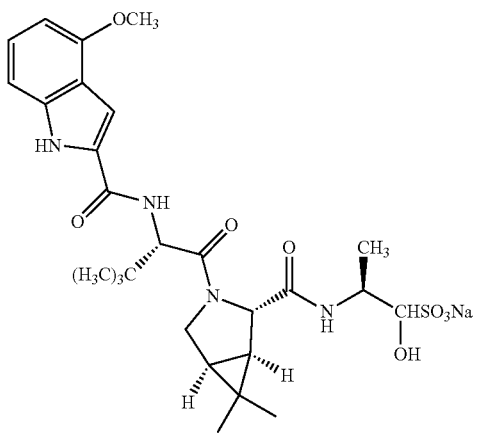
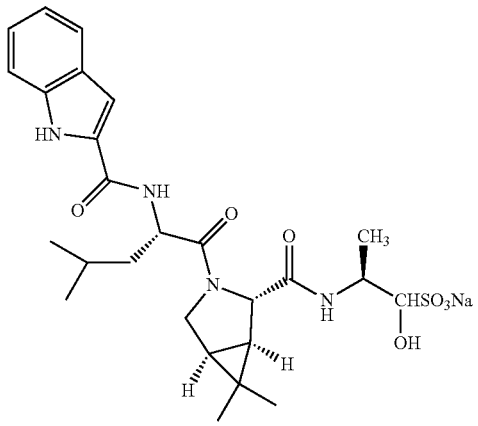
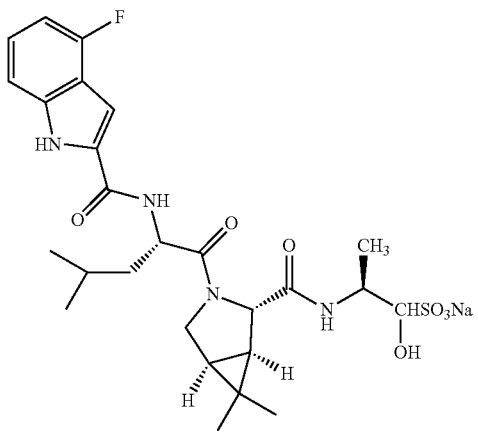
136
-continued
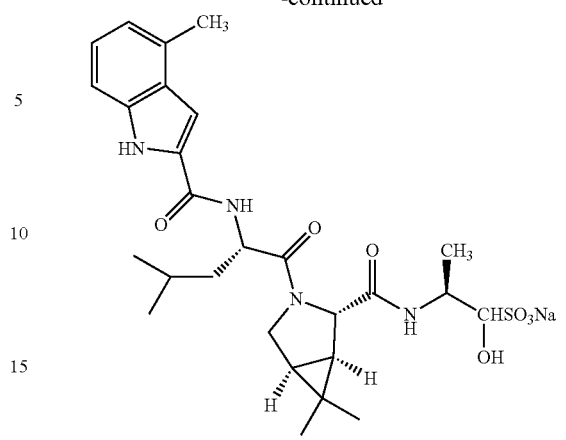
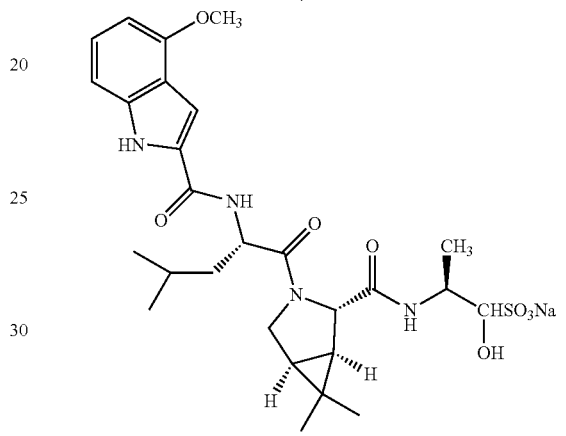
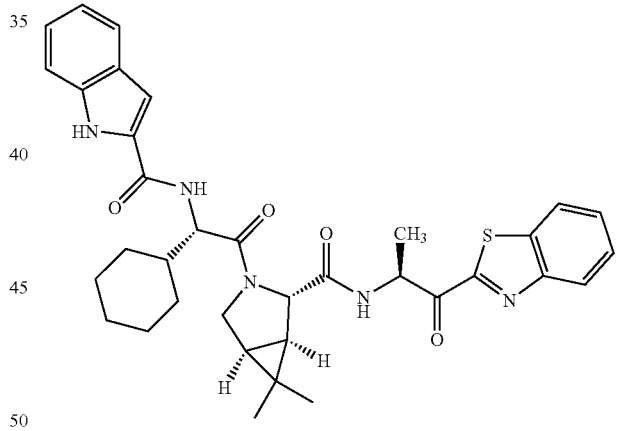
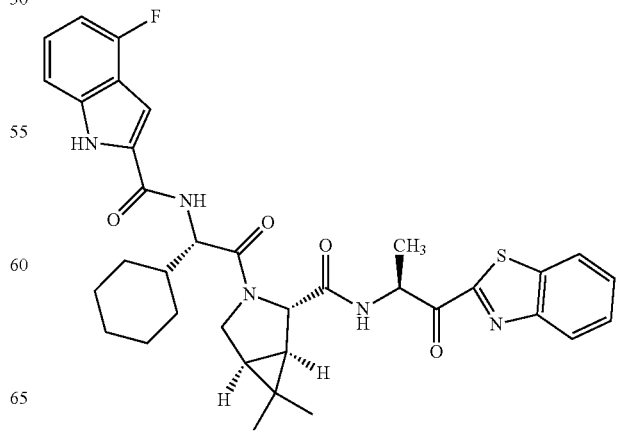

137
-continued
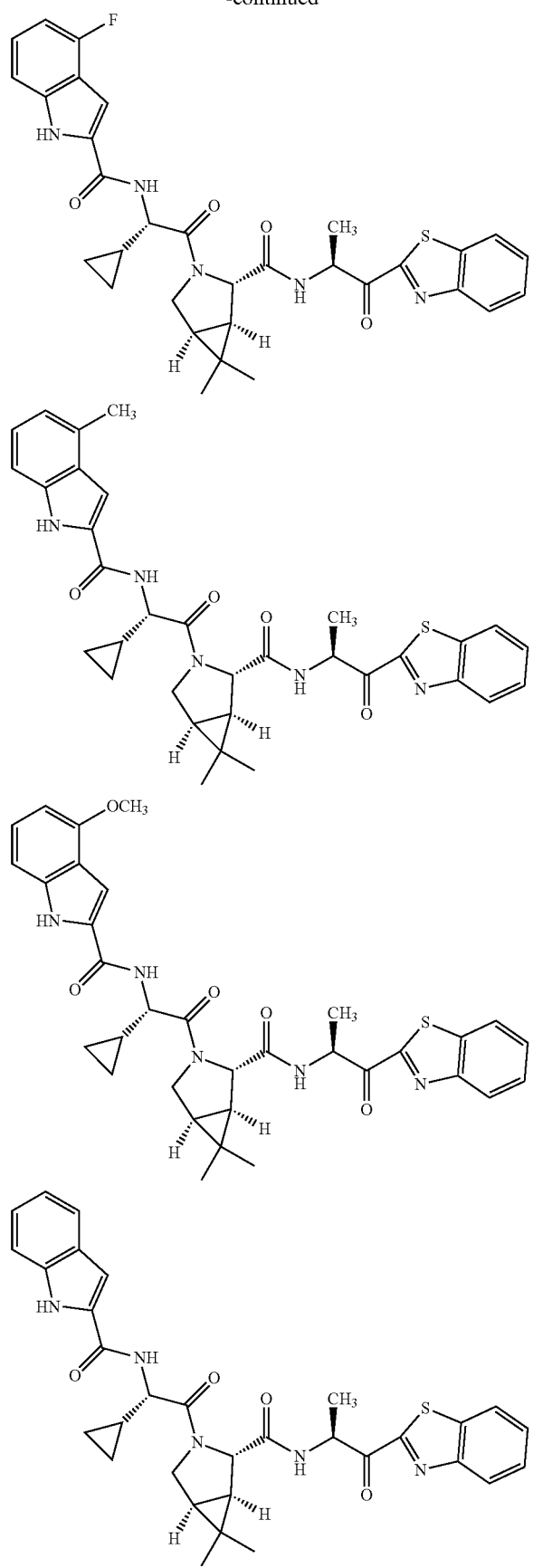
138
-continued
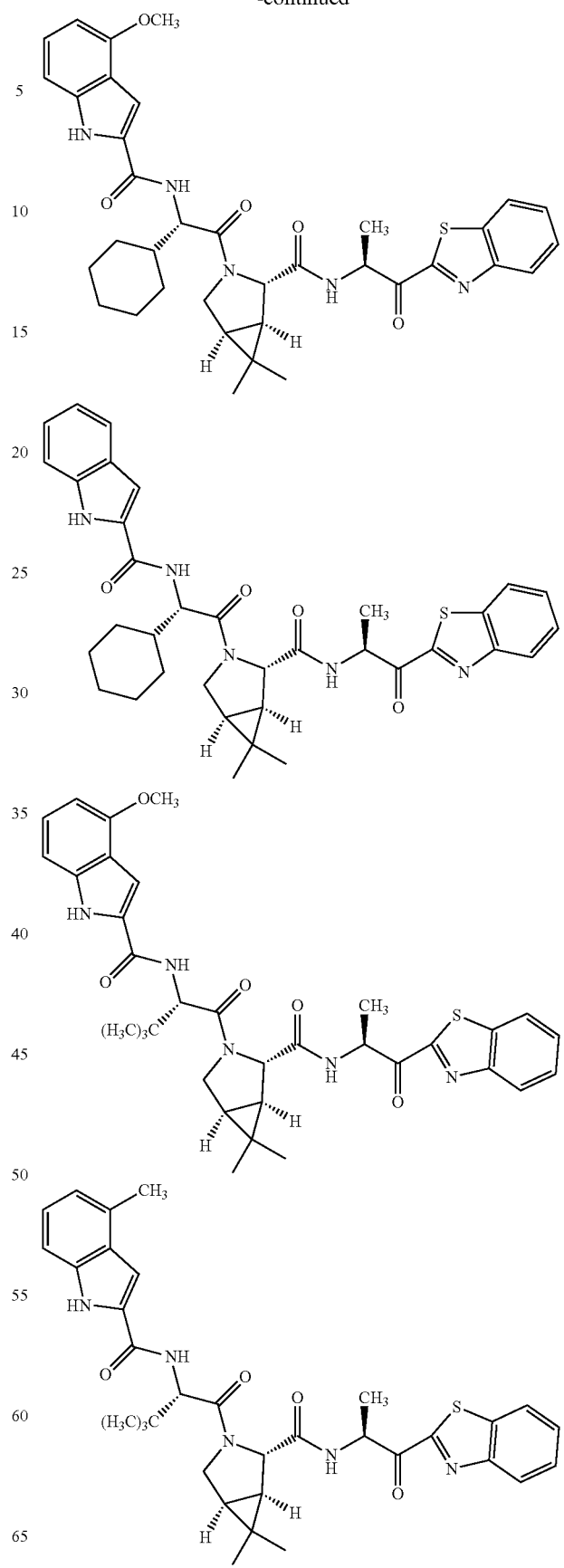

139
-continued
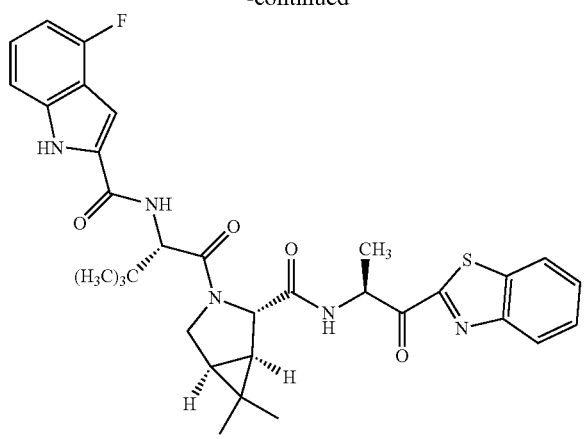
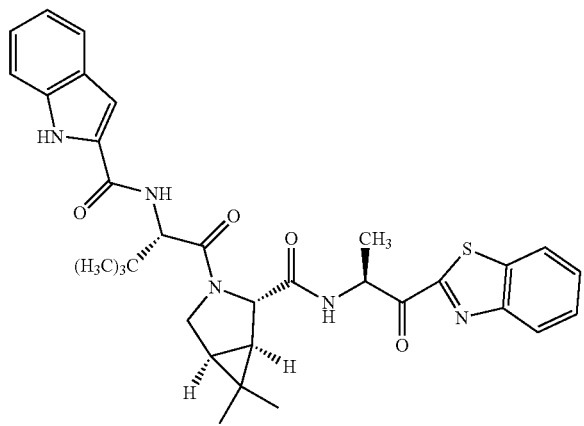
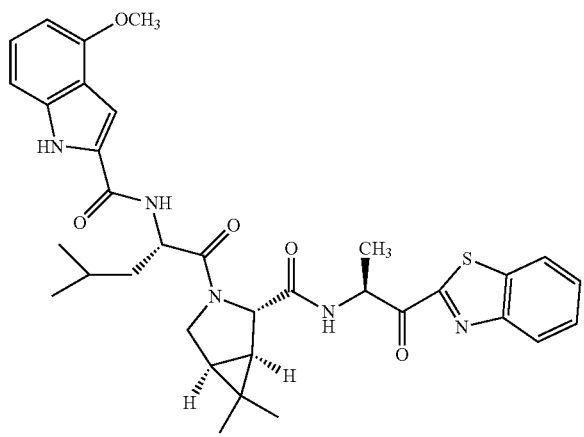
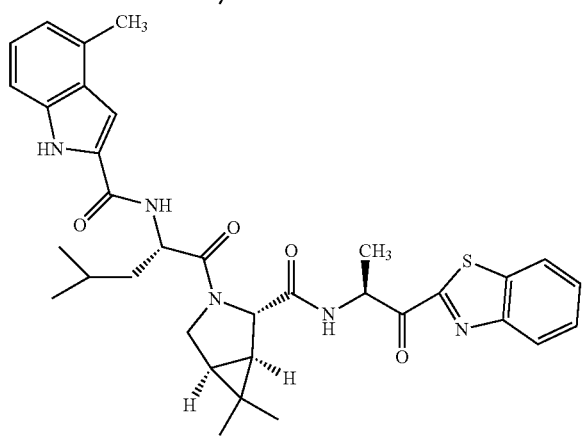
140
-continued
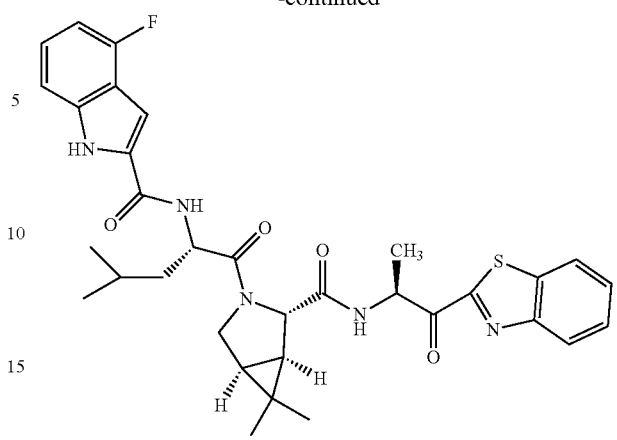
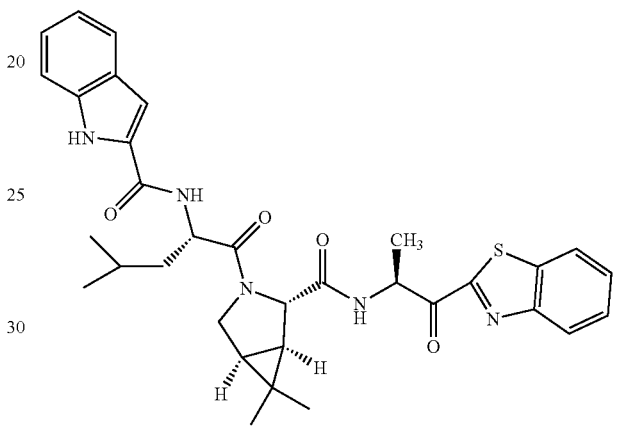
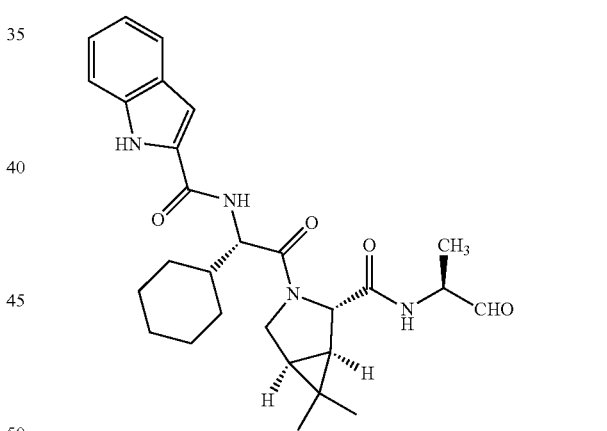
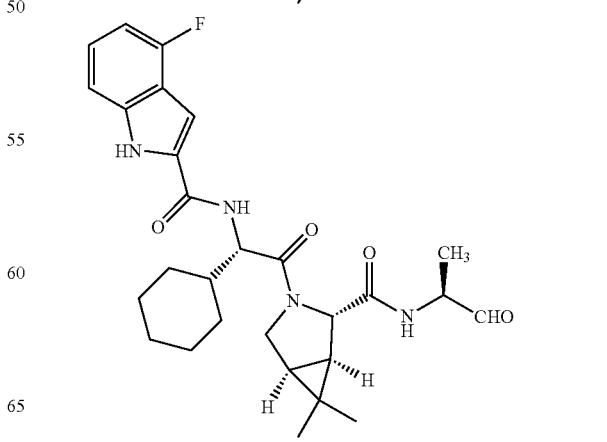

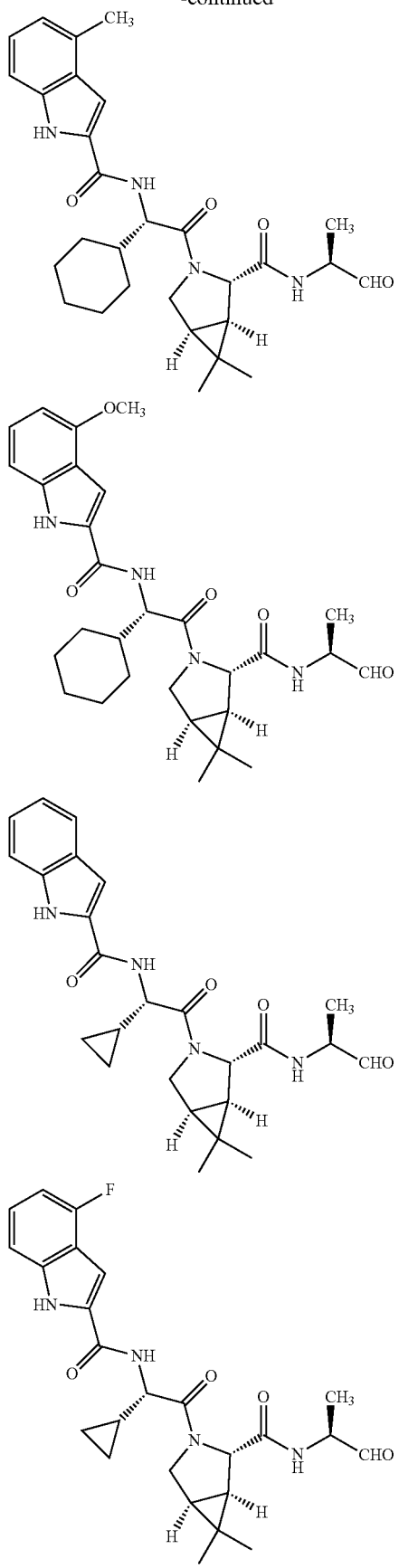
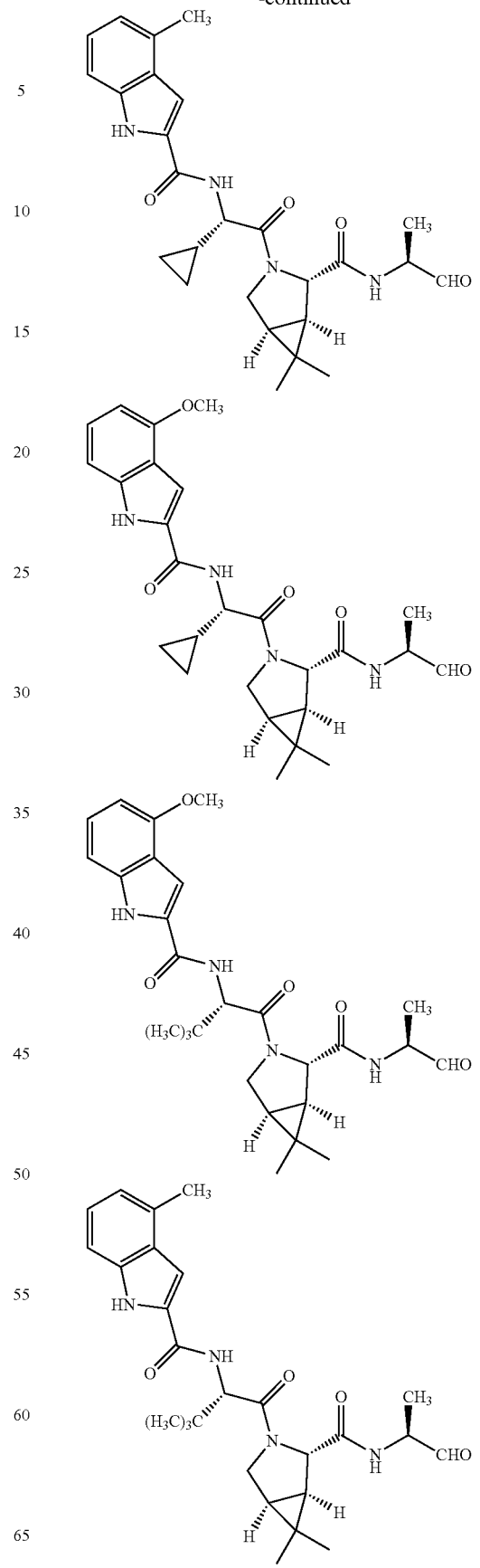

-continued
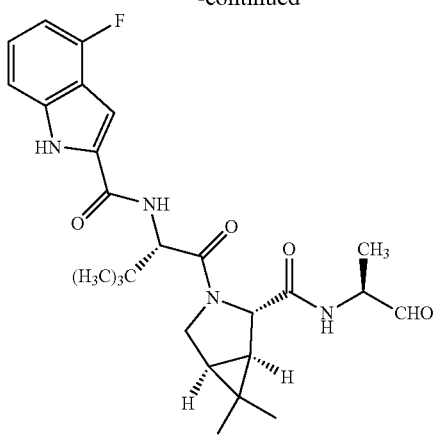
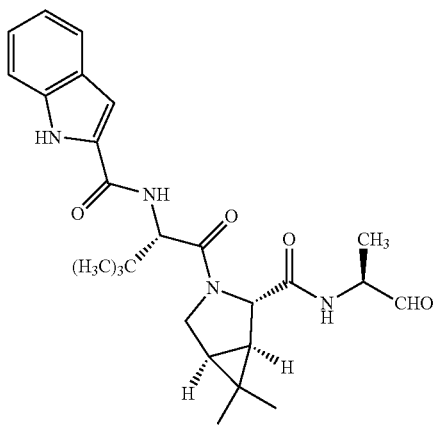
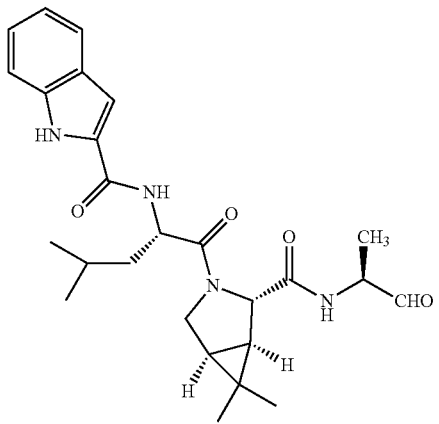
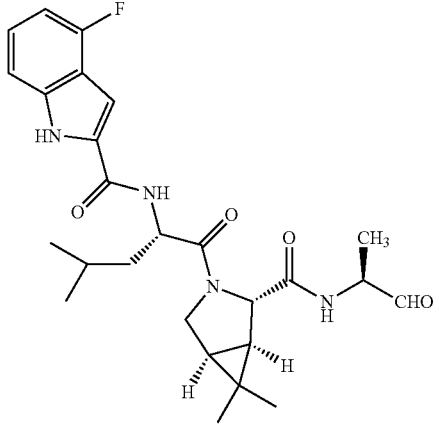
-continued
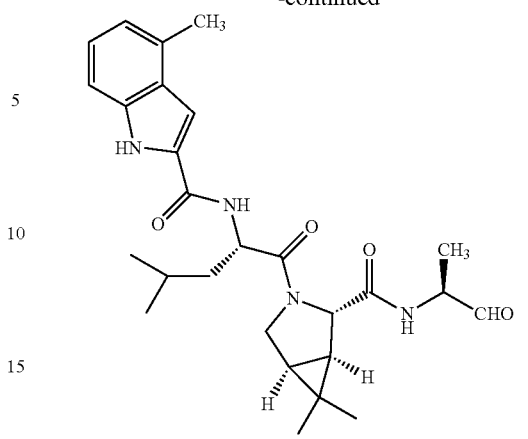
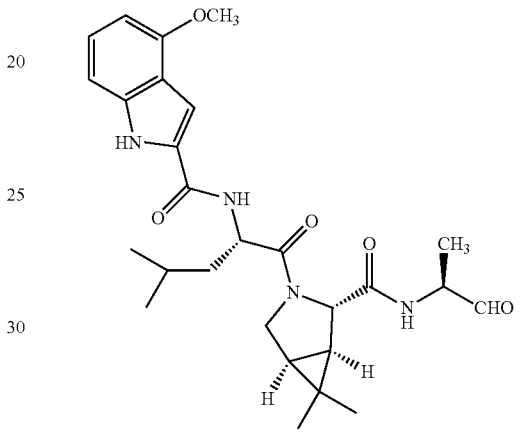
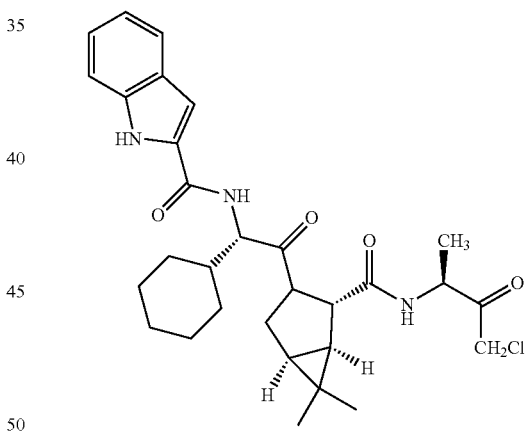
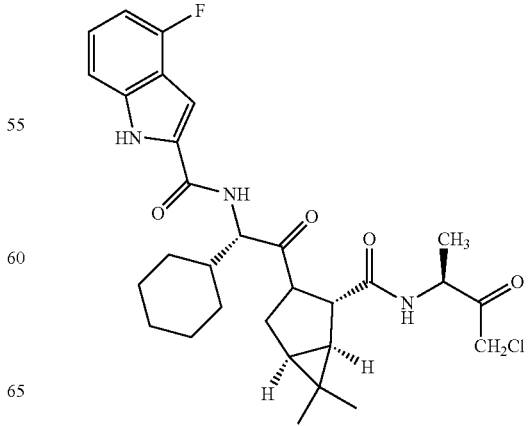

-continued
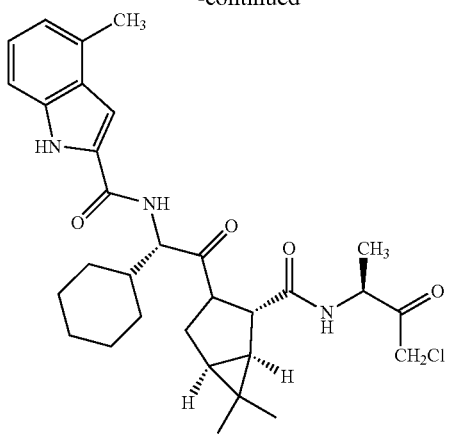
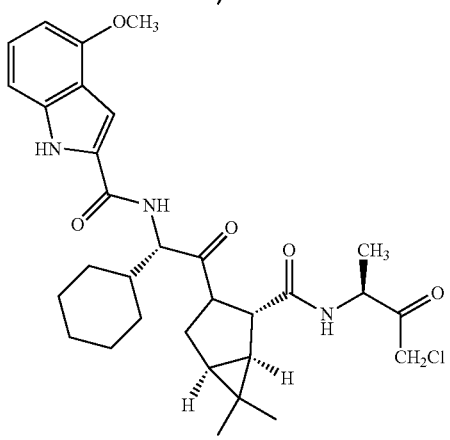
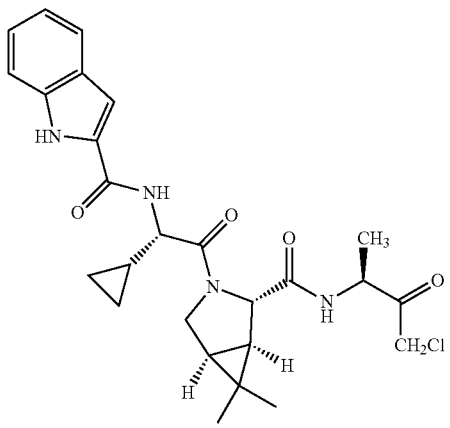
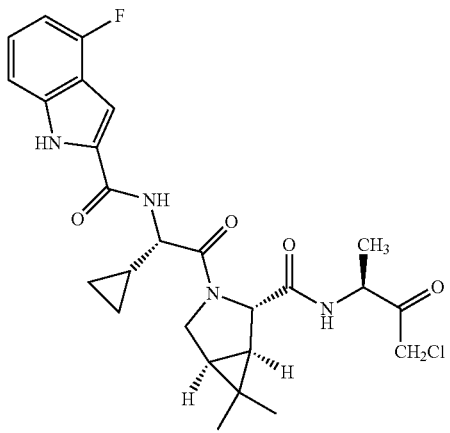
-continued
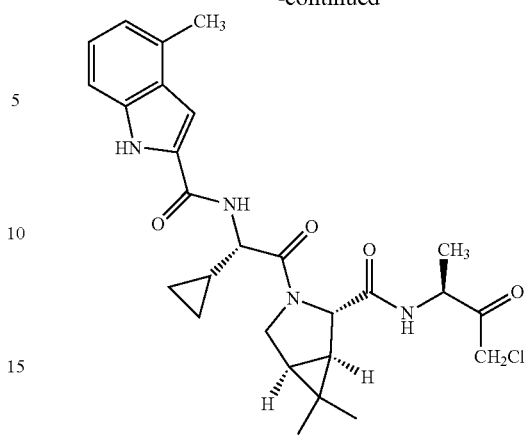
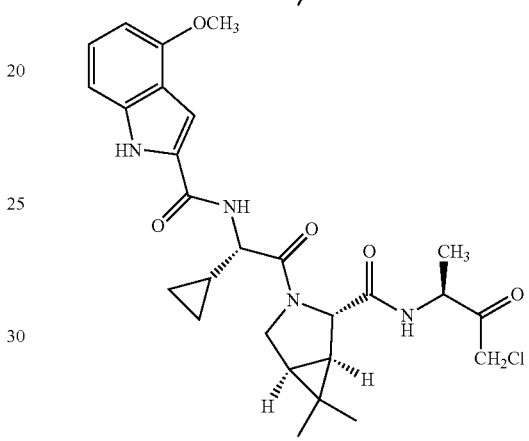
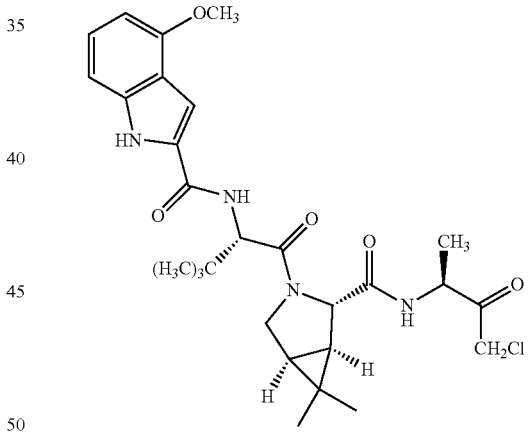
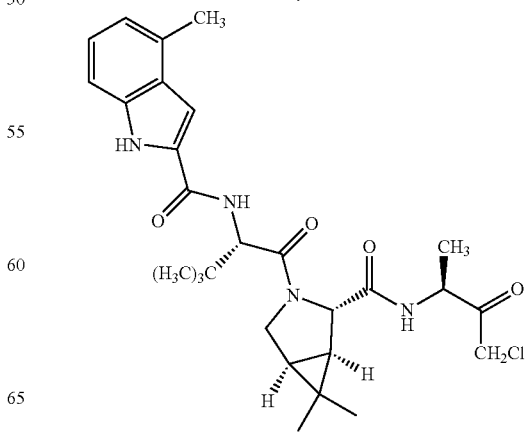

-continued
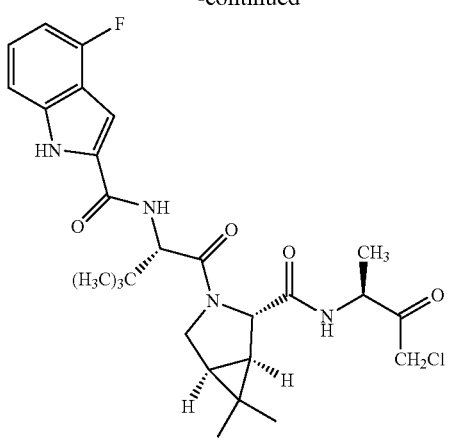
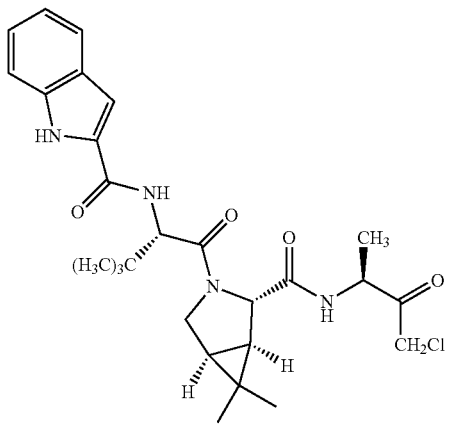
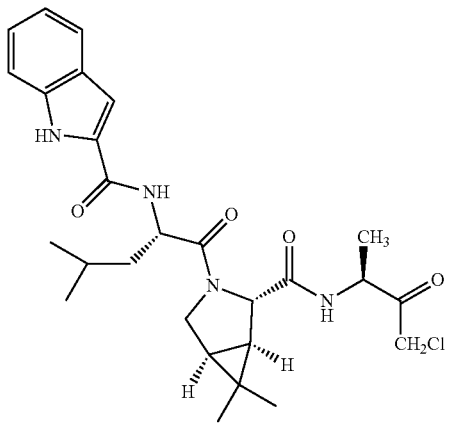
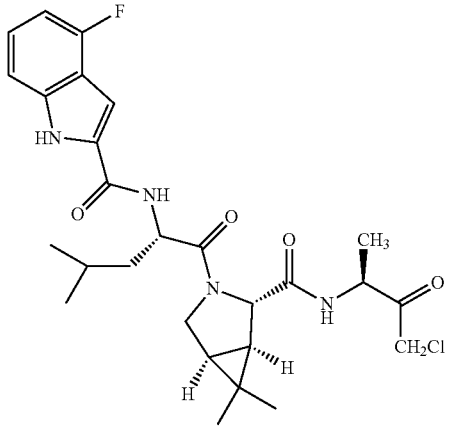
-continued
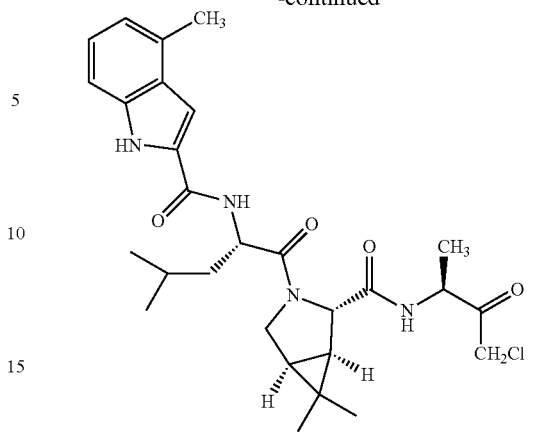
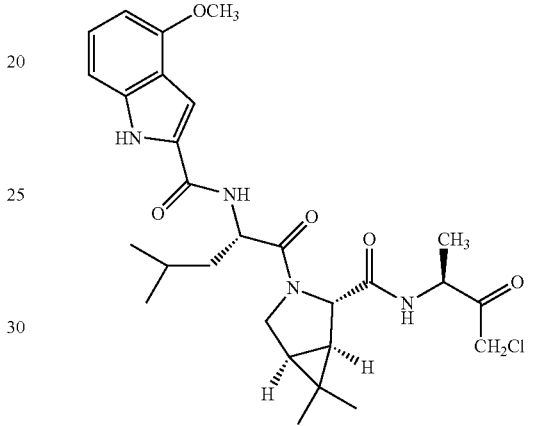
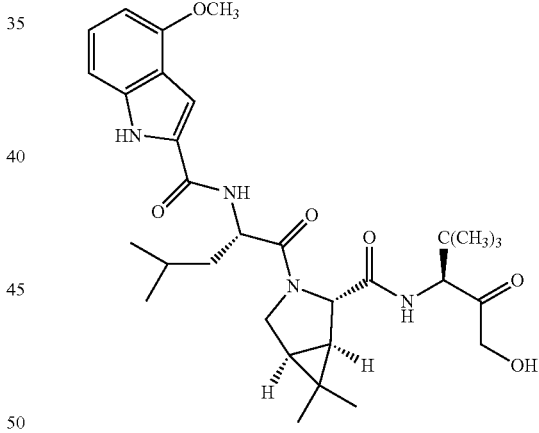
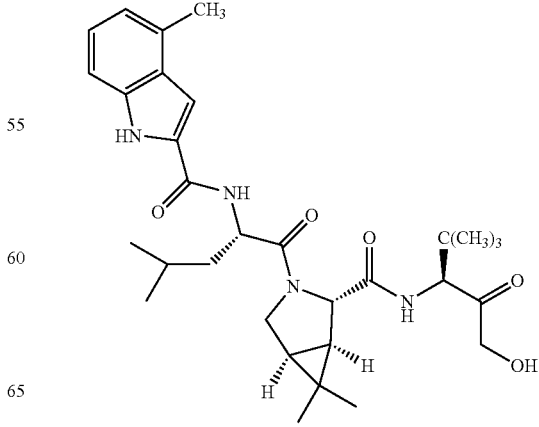

149
-continued
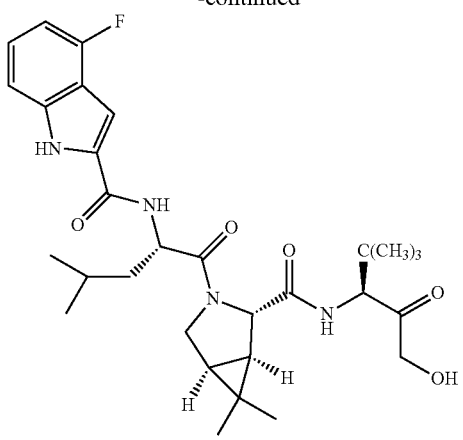
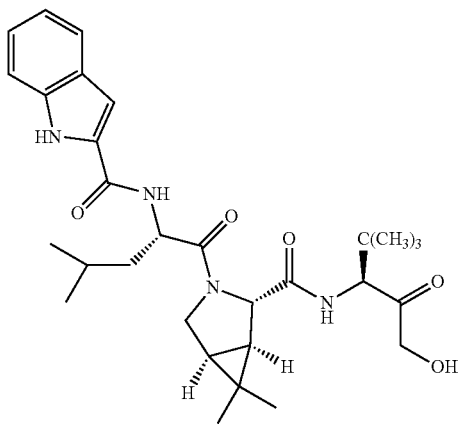
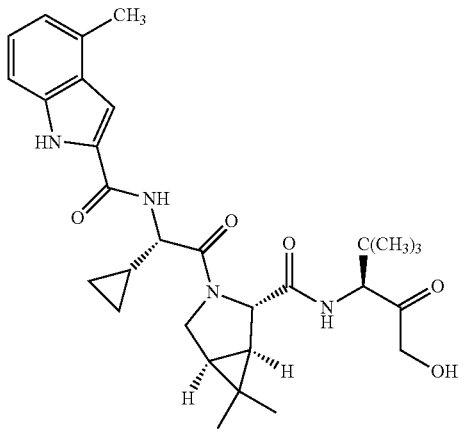
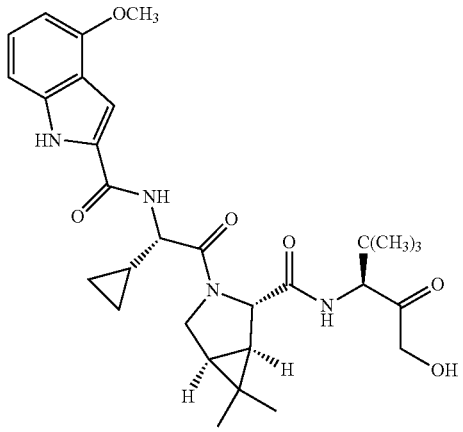
150
-continued
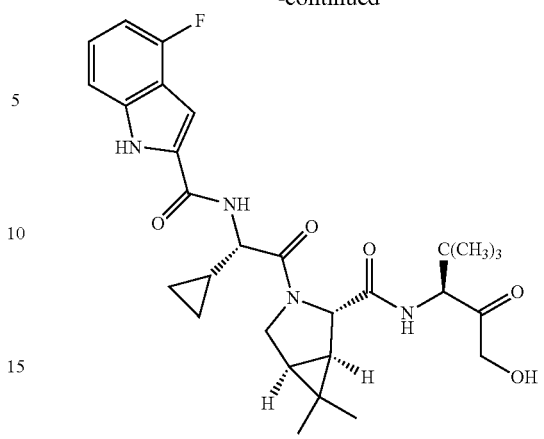
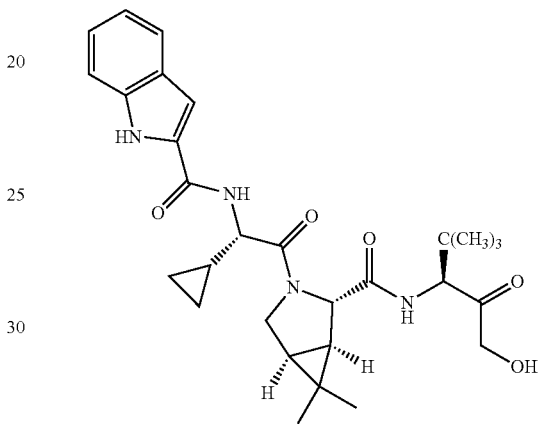
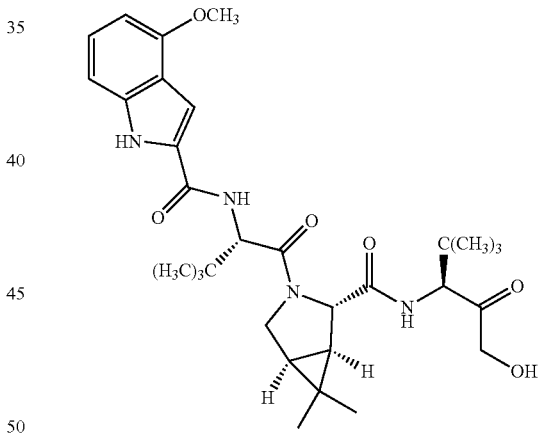
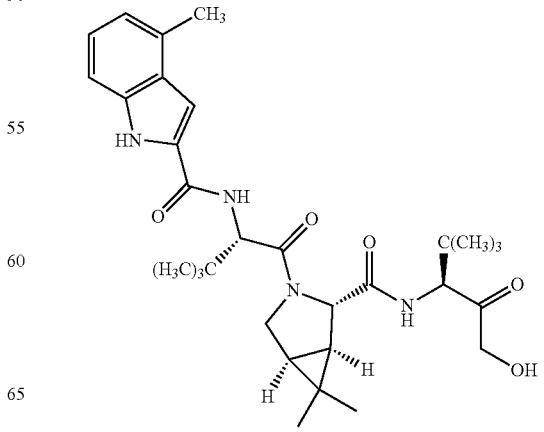

151
-continued
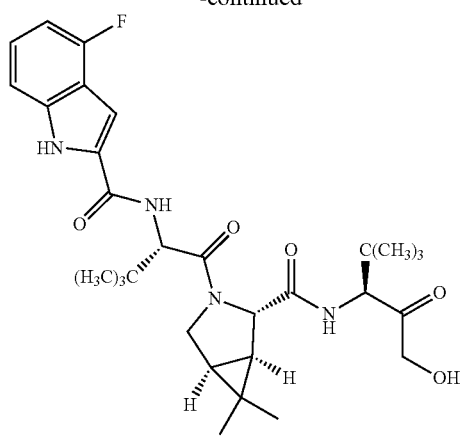
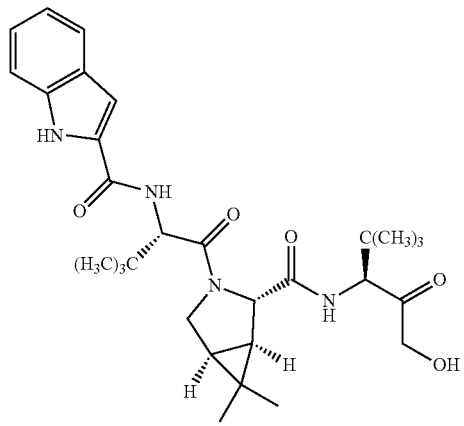
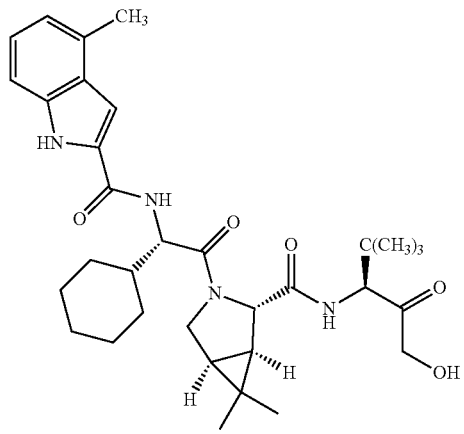
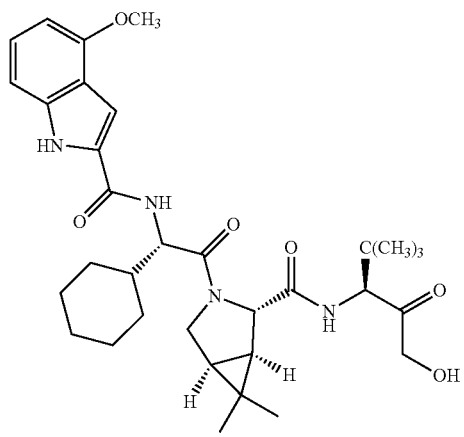
152
-continued
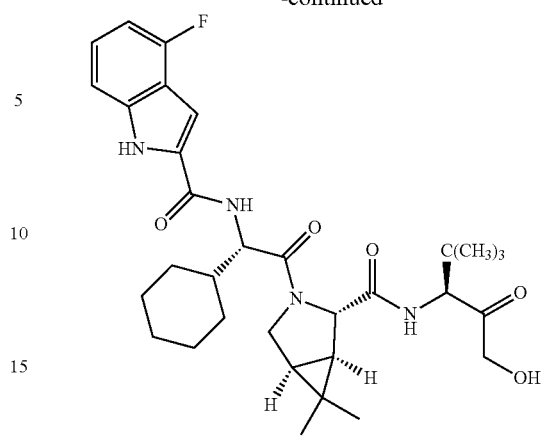
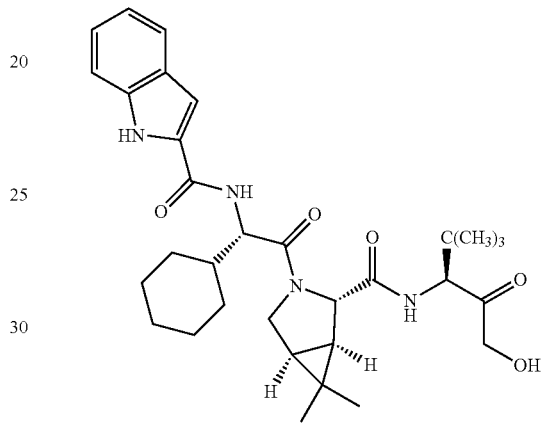
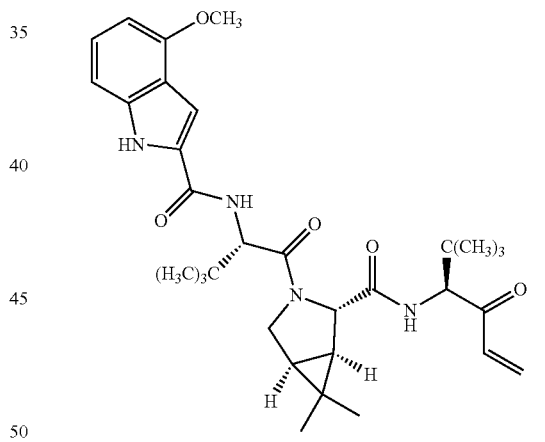
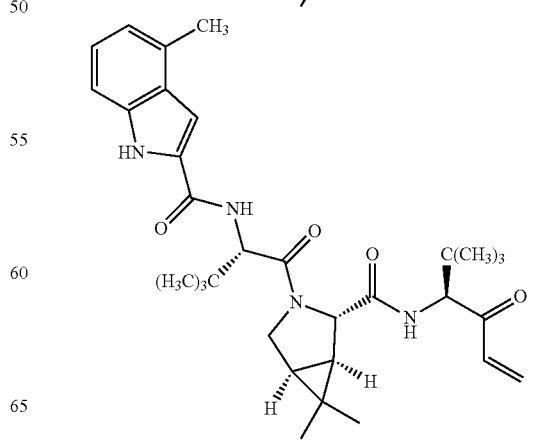

153
-continued
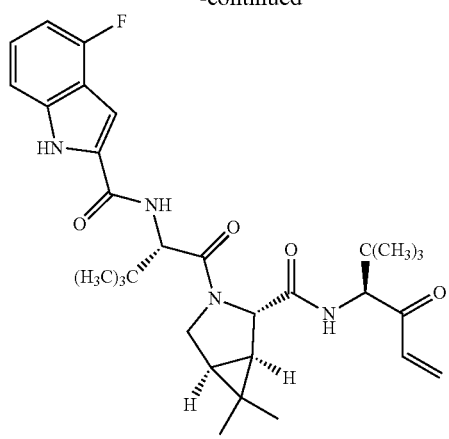
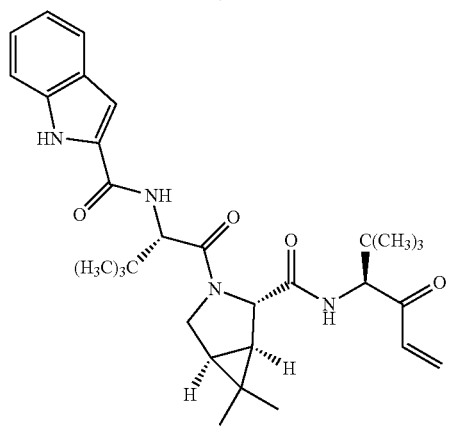
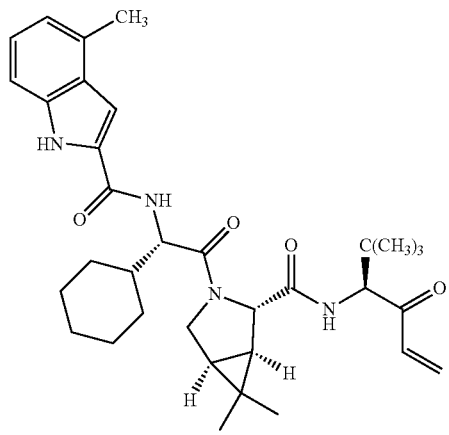
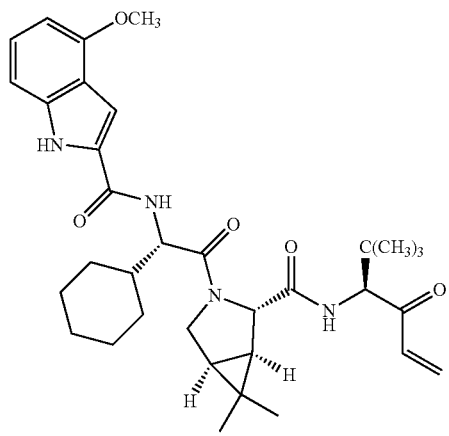
154
-continued
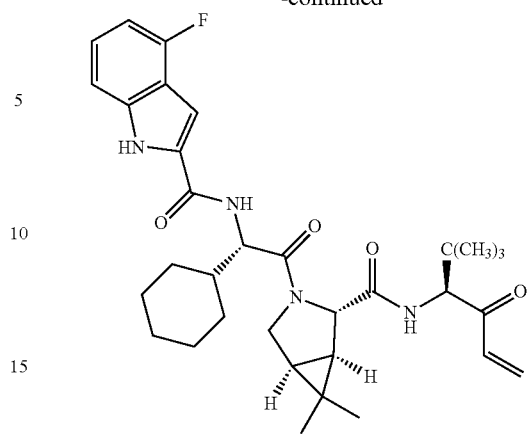
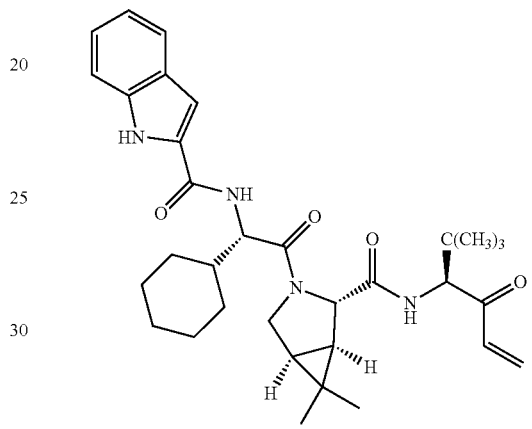
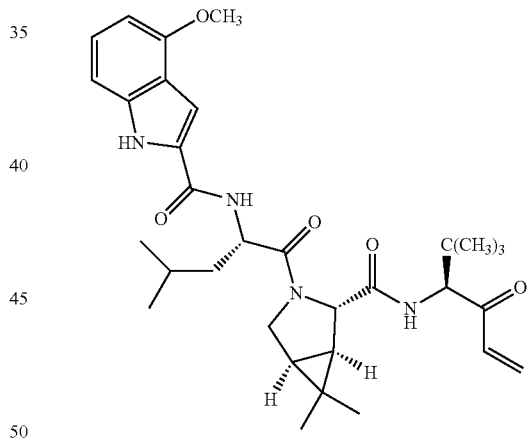
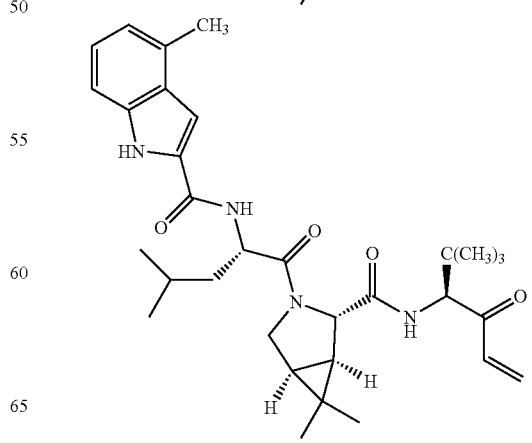

155
-continued
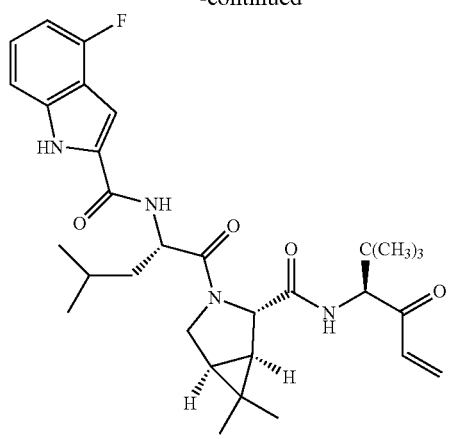
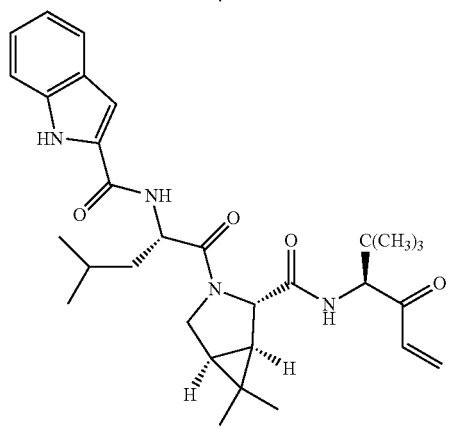
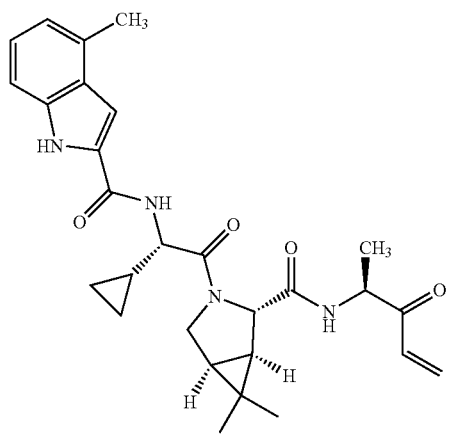
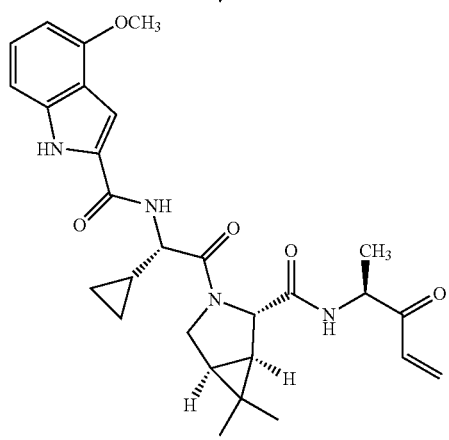
156
-continued
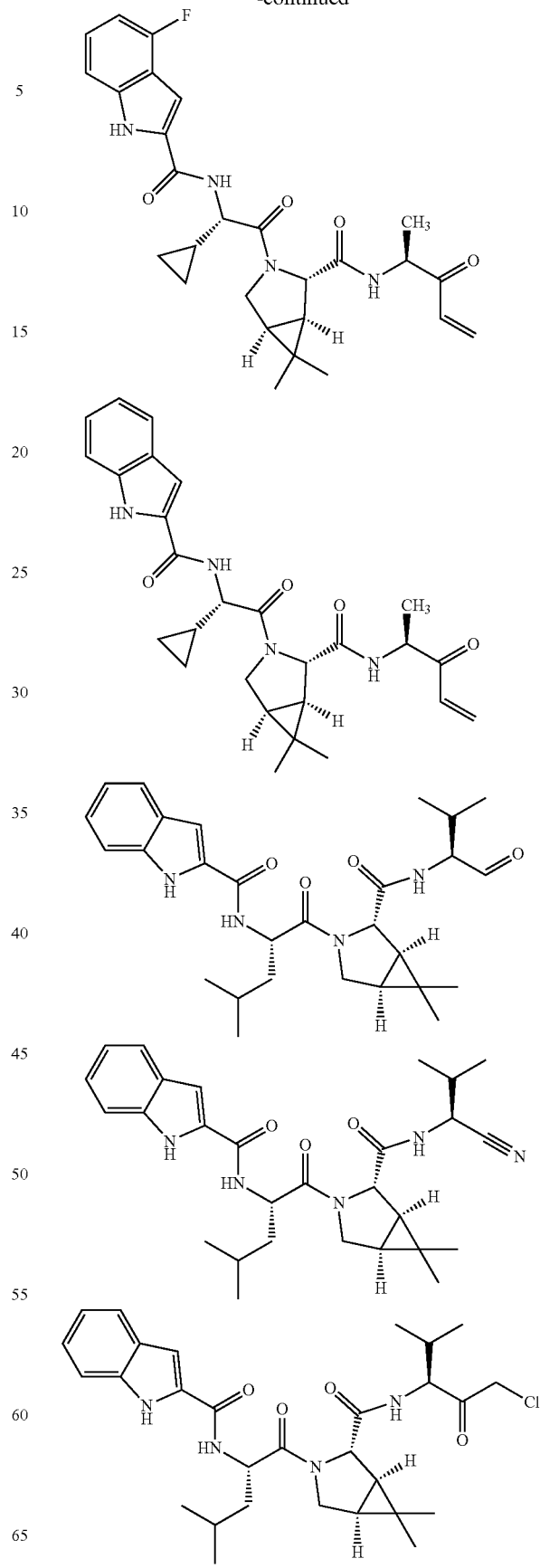

157
-continued
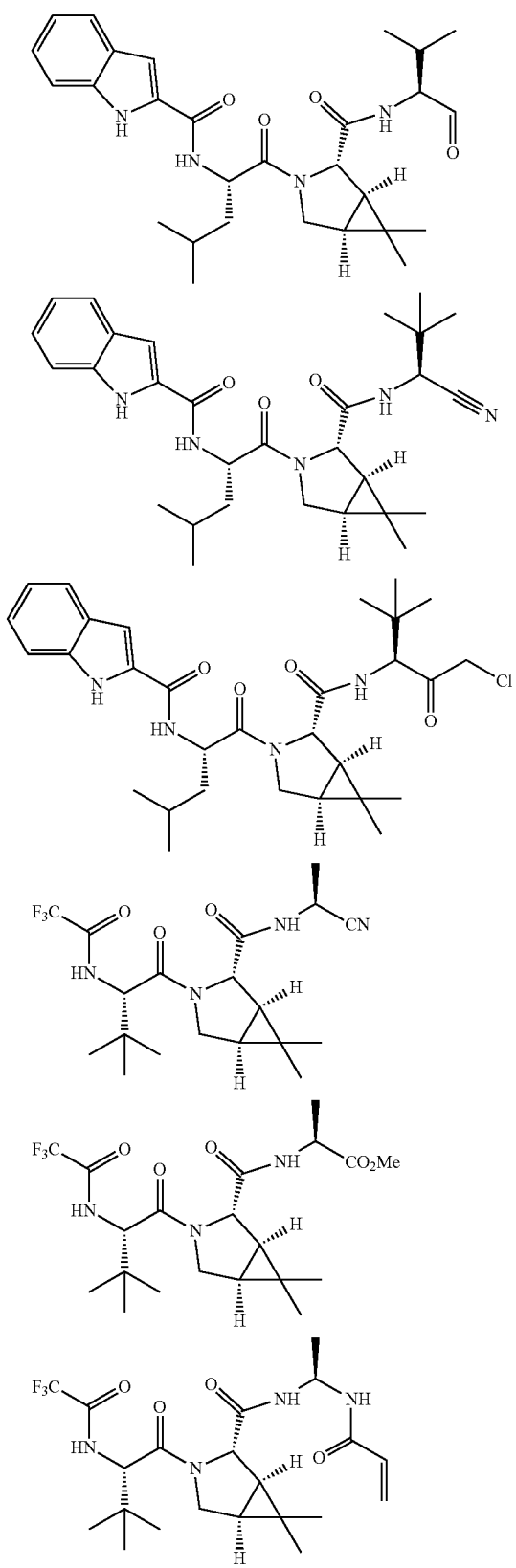
158
-continued
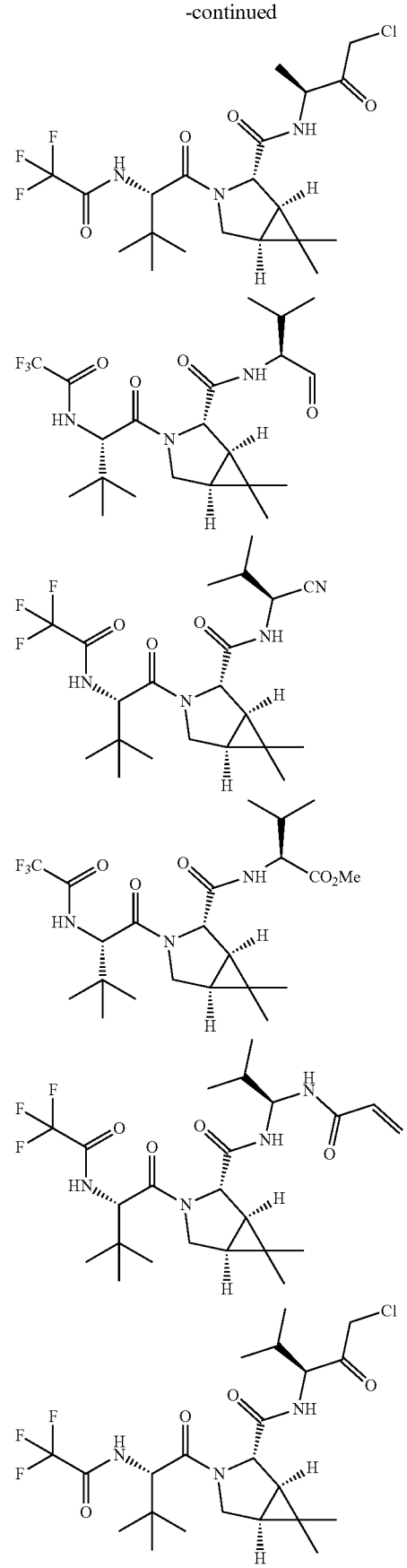

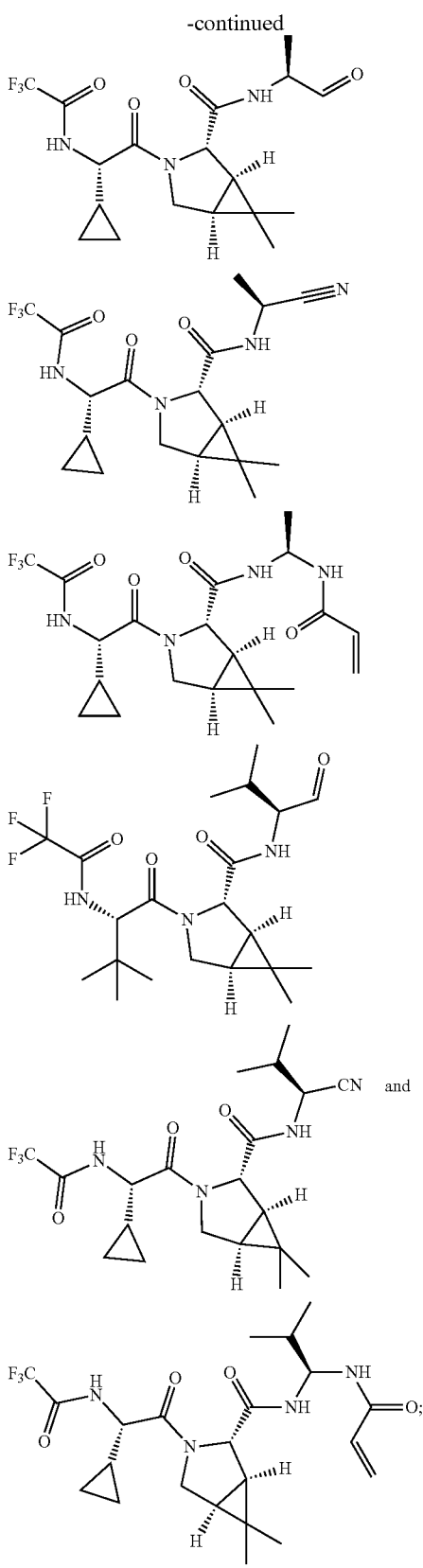

and tautomers, mixtures of two or more tautomers, and isotopic variants thereof; and pharmaceutically acceptable salts, solvates, hydrates, and prodrugs thereof.

Pharmaceutical Compositions, Combinations, and Other Related Uses

In still another aspect, the present disclosure provides for a pharmaceutical composition comprising a compound described above admixed with at least one pharmaceutically acceptable carrier or excipient.

The above-described compounds can be used for any suitable purpose. For example, the present compounds can be used in therapy and/or testing related to viral infections.

In yet another aspect, the present disclosure provides for a method for treating and/or preventing a viral infection. In embodiments, the viral infection is a coronavirus infection.

In yet another aspect, the present disclosure provides for use of compounds described above for the manufacture of a medicament and use of a compound of the invention in therapy, typically for treating a viral infection such as COVID-19.

In yet another aspect, the present disclosure provides for a combination for treating and/or preventing a viral infection in a subject, which combination comprises an effective amount of a compound described above, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and an effective amount of a second prophylactic or therapeutic agent for treating and/or preventing a viral infection.

In yet another aspect, the present disclosure provides for a method for treating and/or preventing a viral infection in a subject who has been or may be exposed to a coronavirus or enterovirus, in particular a virus that causes COVID-19.

In yet another aspect, the present disclosure provides for a method for inhibiting an activity of the main viral protease (3CL) of a coronavirus, which comprises contacting 3CL with an effective amount of a compound of the invention.

The present methods can be used for any suitable purpose. In some embodiments, the present methods can be used to treat an enteroviral or coronaviral infection such as COVID-19.

Formulations

Any suitable formulation of the compounds described herein can be prepared. See generally, Remington's Pharmaceutical Sciences, (2000) Hoover, J. E. editor, 20 th edition, Lippincott Williams and Wilkins Publishing Company, Easton, Pa., pages 780-857. A formulation is selected to be suitable for an appropriate route of administration. In some embodiments, the compound of Formula (I), (II), or (III) is formulated for oral administration; in some embodiments, the compound is formulated for parenteral administration, such as injection or infusion.

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The compounds having formula I, II, or III as described herein are generally soluble in organic solvents such as chloroform, dichloromethane, ethyl acetate, ethanol, methanol, isopropanol, acetonitrile, glycerol, N,N-dimethylformamide, N,N-dimethylacetamide, dimethylsulfoxide, etc. In one embodiment, the present invention provides formulations prepared by mixing a compound having formula I, II, or III with a pharmaceutically acceptable carrier. In one aspect, the formulation may be prepared using a method comprising: a) dissolving a described compound in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

One of ordinary skill in the art may select or modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

Drug Combinations

The methods of the embodiments comprise administering an effective amount of at least one exemplary compound of the present disclosure; optionally the compound may be administered in combination with one or more additional therapeutic agents, particularly therapeutic agents known to be useful for treating a viral infection afflicting the subject, one example of which is remdesivir.

The additional therapeutic agents may be administered in a separate pharmaceutical composition from at least one exemplary compound of the present disclosure or may be included with at least one exemplary compound of the present disclosure in a single pharmaceutical composition. The additional therapeutic agents may be administered simultaneously with, prior to, or after administration of at least one exemplary compound of the present disclosure.

Methods of Using the Exemplary Compounds and Pharmaceutical Compositions Thereof The present invention also provides pharmaceutical compositions for the treatment and/or prevention of a viral infection, comprising any compound having formula I, II, III, or any of the exemplary compounds disclosed.

To practice the method of the present invention, compounds having formula and pharmaceutical compositions thereof may be administered orally, parenterally, by inhalation, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. Suitable carriers and other pharmaceutical composition components are typically sterile.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

In addition, the compounds having formula I, II, or III, or any of the exemplary compounds disclosed herein, may be administered alone or in combination with other therapeutic agents, e.g., antiviral agents, for the treatment of viral infections such as COVID-19. Combination therapies according to the present invention comprise the administration of at least one exemplary compound of the present disclosure and at least one other therapeutic agent, such as an antiviral agent like remdesivir, in a pharmaceutical composition. The at least one exemplary compound of the present disclosure and at least one other therapeutic agent(s) may be administered as a pharmaceutical composition separately or together. The amounts of the at least one exemplary compound of the present disclosure and the at least one other therapeutic agent(s) and the relative timings of administration will be selected in order to achieve the desired combined therapeutic effect.

Biological Testing

Suitable assays and model systems for assessing therapeutic efficacy, e.g., anti-viral effectiveness, of exemplary compounds of the invention are well known in the art. "The Discovery of Ketone-Based Covalent Inhibitors of Coronavirus 3CL Proteases for the Potential Therapeutic Treatment of COVID-19," Hoffman, et al., J. Med. Chem. July 2020, pp. A-W, describes suitable SARS CoV-2 protease FRET assay to measure inhibition of the 3CL protease, and also describes suitable antiviral assays using MRC-5 cells infected with hCOV 229e coronavirus. Compounds of the invention can be tested using these or other known bioassays to select a highly potent inhibitor of 3CL and having antiviral activity in cell culture.

Methods for Making Compounds of the Invention.

Compounds of the invention are readily prepared using methods illustrated by Schemes I-X and the examples herein, in view of knowledge in the art for making related peptidomimetic compounds. See, for example, synthesis methods in Hoffman, et al., J. Med. Chem. July 2020; Science vol. 371, 1374-78 (2021); and WO2020/247665

As used herein, common organic chemistry abbreviations are defined as follows:
Ac Acetyl
ACN Acetonitrile
AcOH Acetic acid
aq. Aqueous
BOC or Boc tert-Butoxycarbonyl
CBZ Benzoxycarbonyl
DCM dichloromethane
DIEA or DIPEA Diisopropylethylamine
DMF N,N'-Dimethylformamide
DMP Dess-Martin Periodinane
DMSO Dimethyl sulfoxide
EDC or EDCI 1-Ethyl-3-(3-dimethylaminopropyl)carbodiimide
EtOAc or EA Ethyl acetate
EtOH Ethanol
Eq Equivalents
FA Formic acid
Fmoc 9-Fluorenylmethoxycarbonyl
g Gram(s)
h Hour (hours)
HATU 2-(1H-7-azabenzotriazol-1-yl)-1,1,3,3-tetramethyl uronium Hexafluorophosphate
HCl Hydrochloric acid
HOBt N-Hydroxybenzotriazole
HOPO 2-Hydroxypyridine-N-oxide
HPLC High-performance liquid chromatography
IBX 2-Iodoxybenzoic acid
IPA Isopropyl alcohol
LC/MS Liquid chromatography-mass spectrometry
LDA Lithium diisopropylamide
mg milligrams
MeOH Methanol
mL Milliliter(s)
µL/uL Microliter(s)
mol moles
mmol millimoles
µmol/umol micromoles
MS mass spectrometry
NHS or HOSu N-Hydroxysuccinimide
NMP N-Methyl-2-pyrrolidone
PE Petroleum ether
Pip piperidine
RP-HPLC reverse phase HPLC
rt room temperature
t-Bu tert-Butyl
TCFH N,N,N',N'-tetramethylchloroformamidinium hexafluorophosphate
TEA Triethylamine
Tert, t tertiary
TFA Trifluoracetic acid
TFAA Trifluoracetic anhydride
THF Tetrahydrofuran Scheme I. General methods for making aldehyde intermediates for compounds of Formula (I).

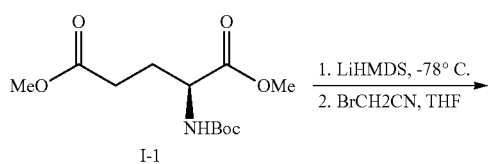

I-1

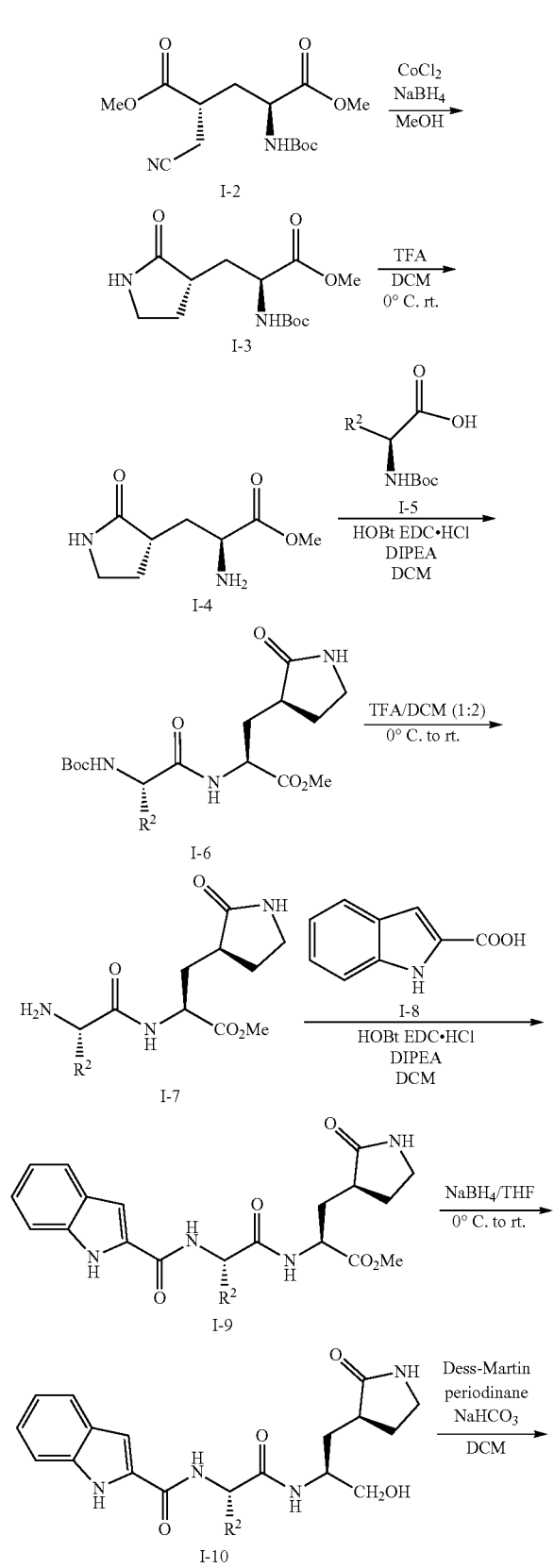
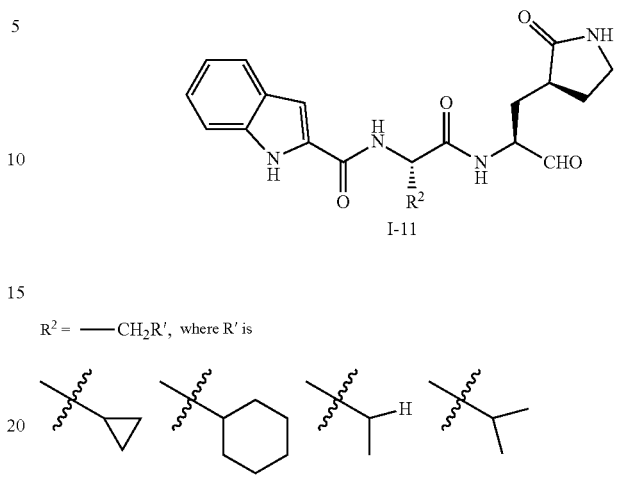
$R^2 = $ —$CH_2R'$, where $R'$ is
Scheme II. Synthesis of selected precursors.
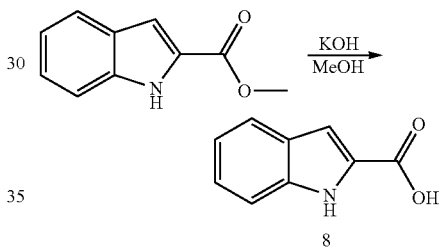
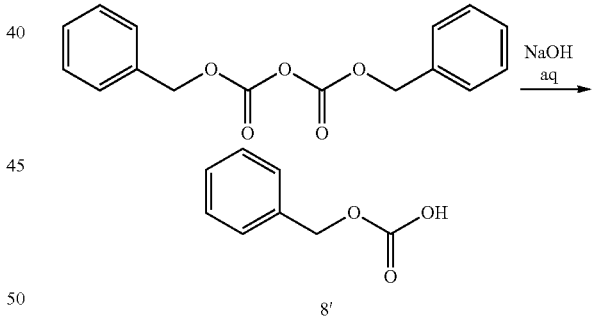
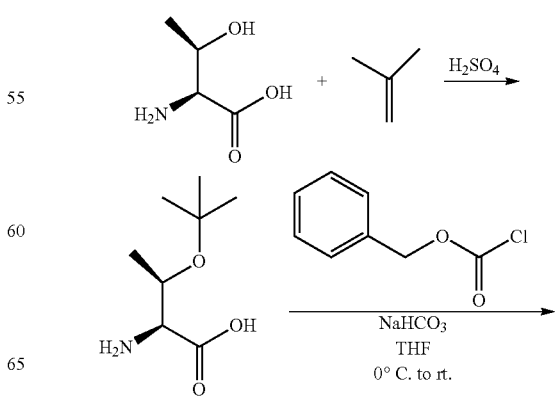

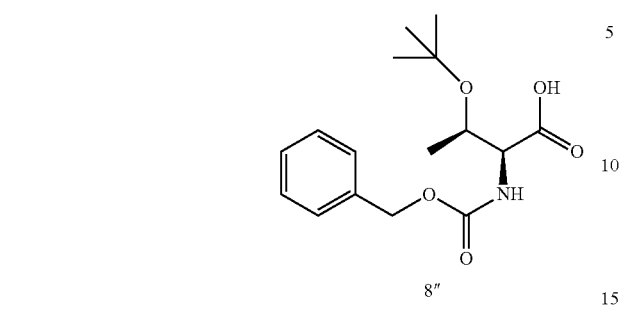
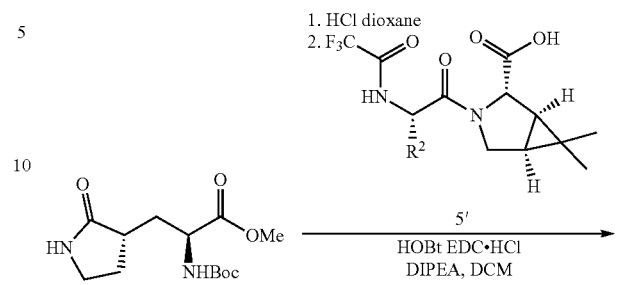
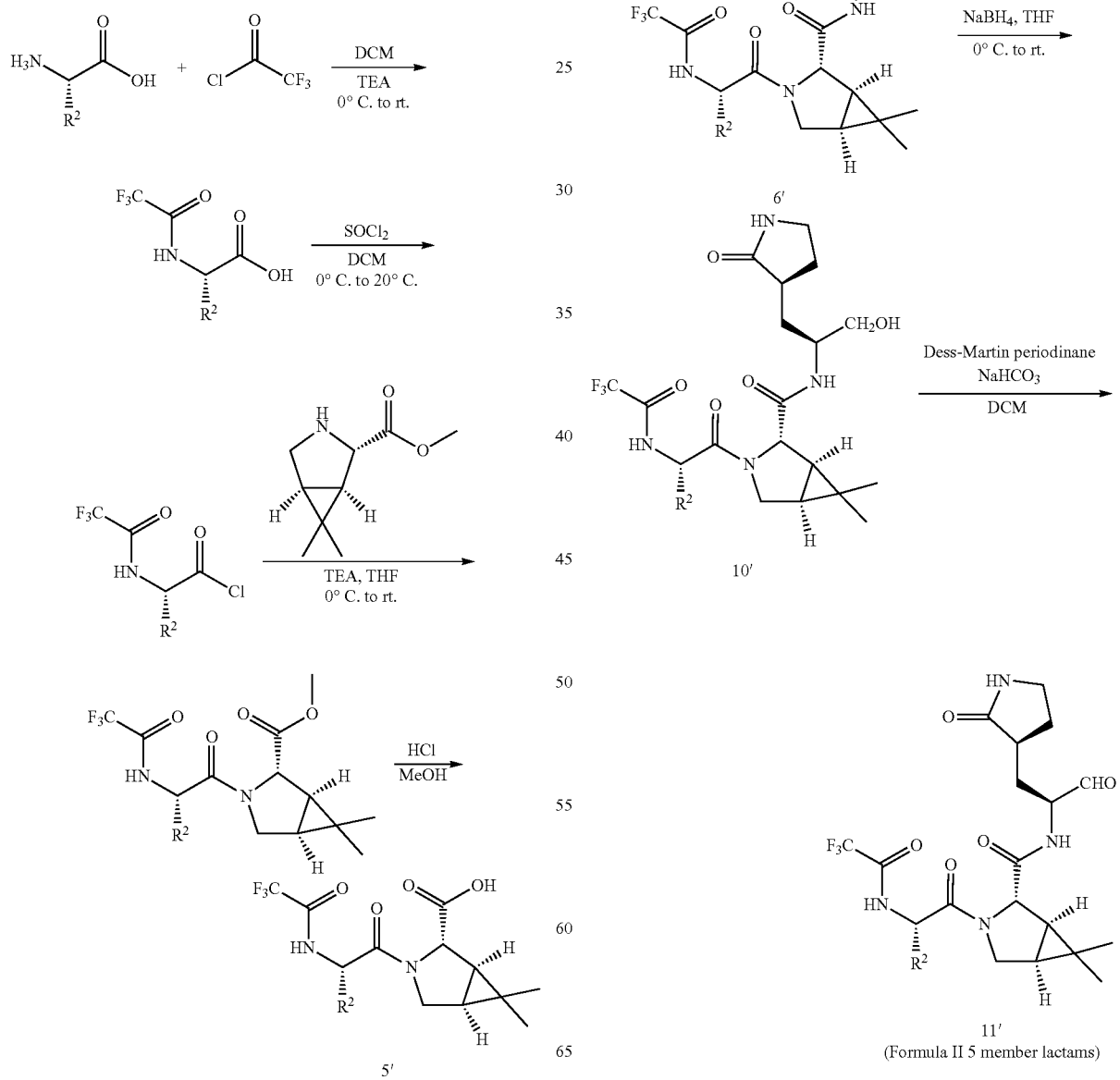

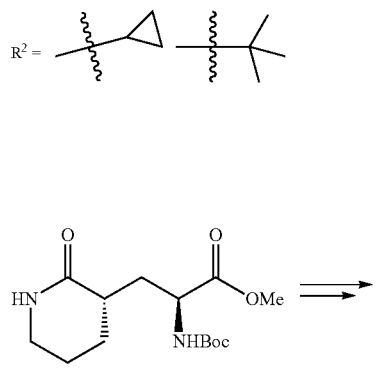
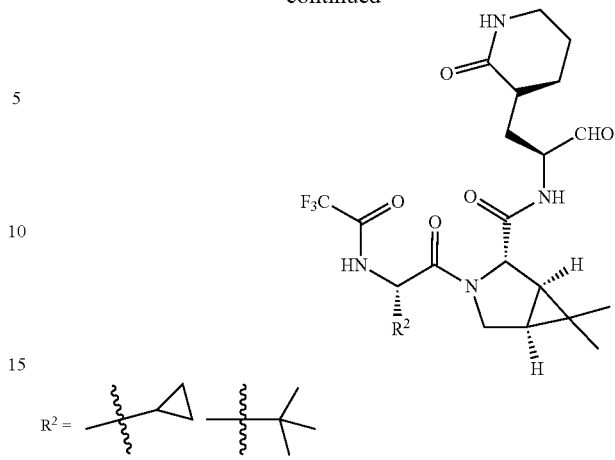
Scheme IV. Methods for introducing various groups Z into compounds of Formula I and II. General conversion of aldehyde to —CN, —CH₂CN, —C(O)CH=CH₂, —NHC(O)CH=CH₂, —CH₂C(O)CH=CH₂
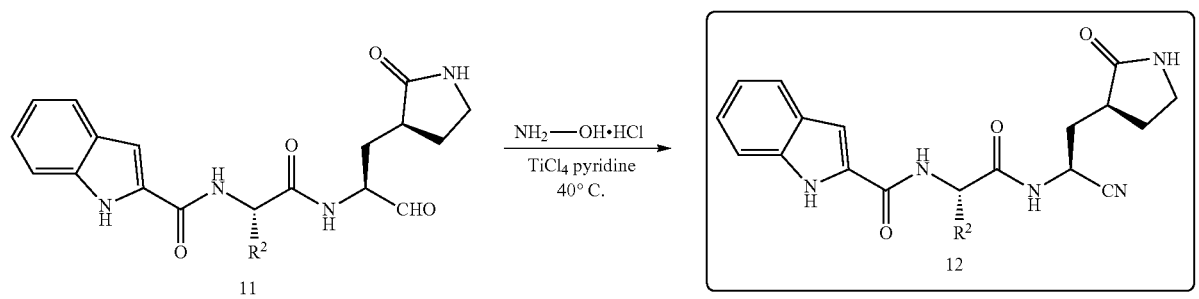
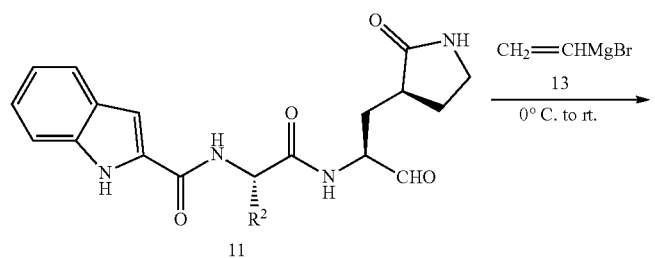
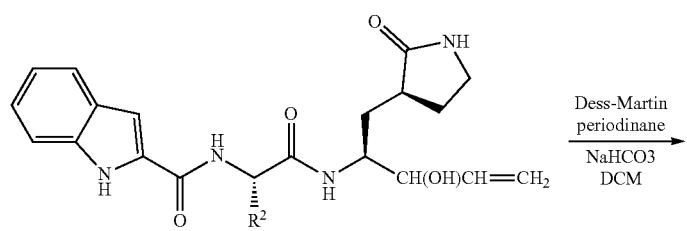

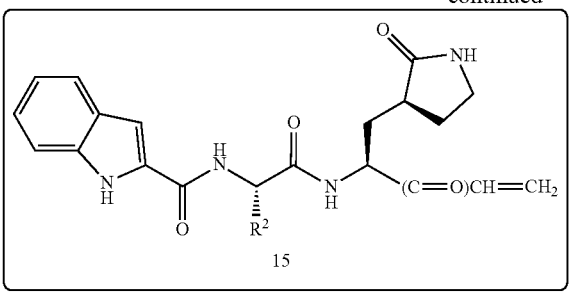
15
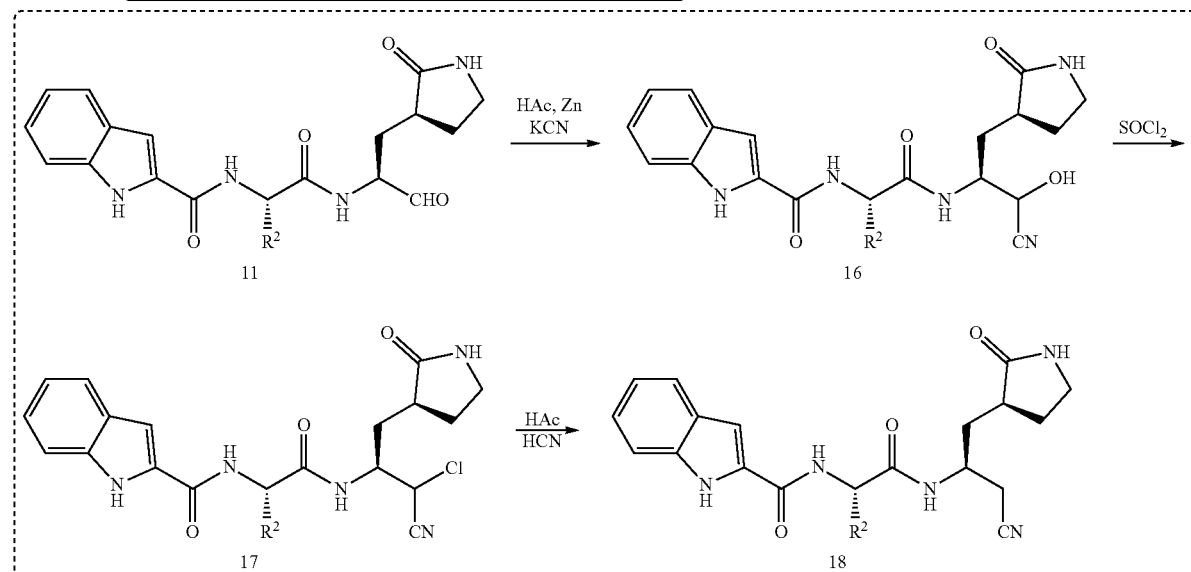
Scheme V. Additional synthesis methods for compounds of Formula (I).
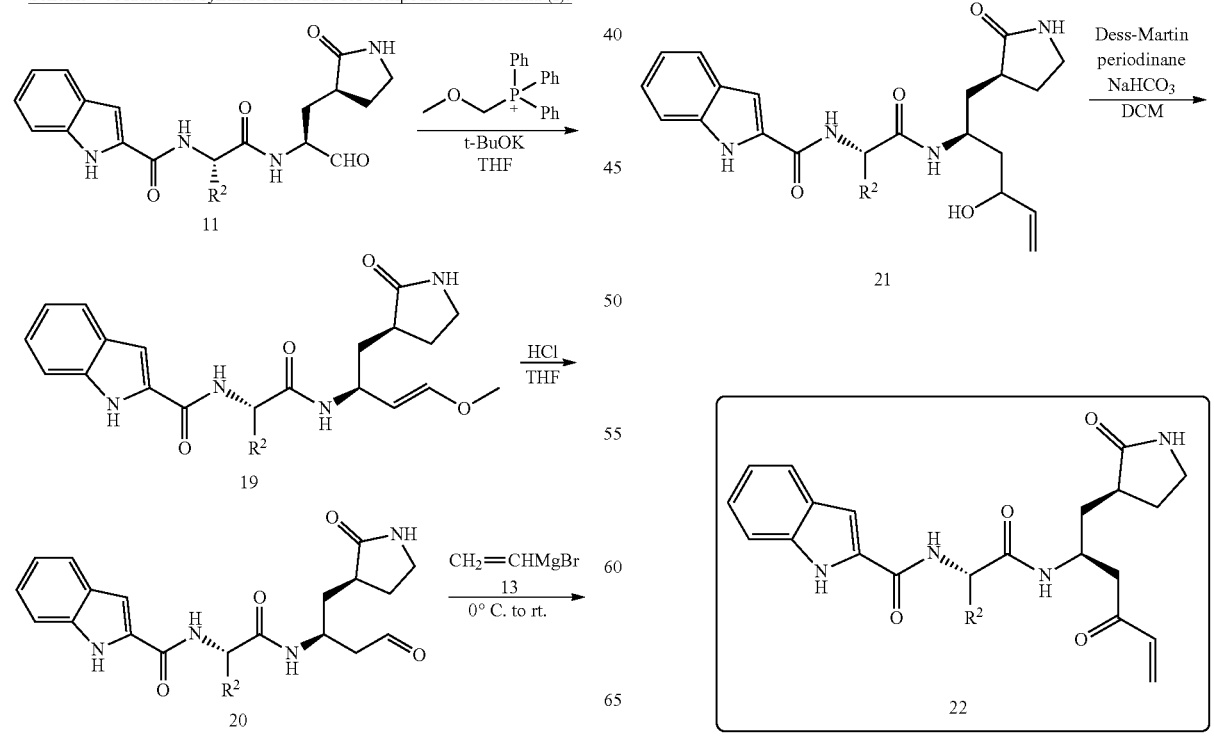

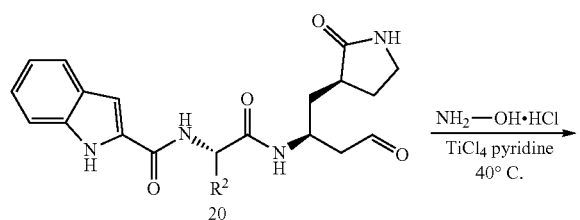
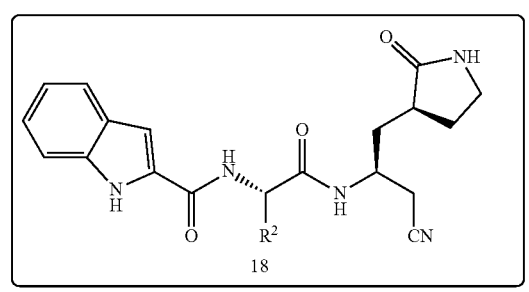
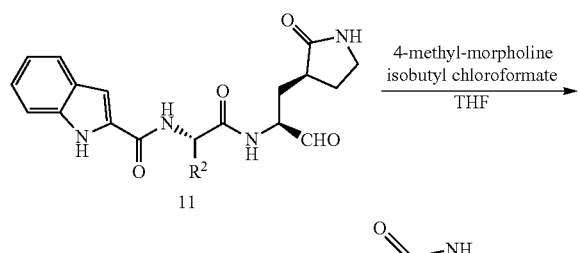
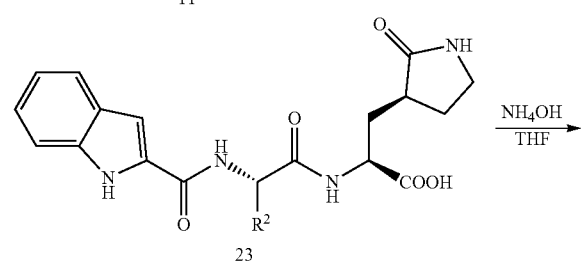
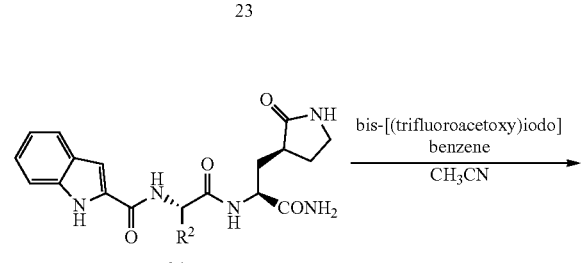
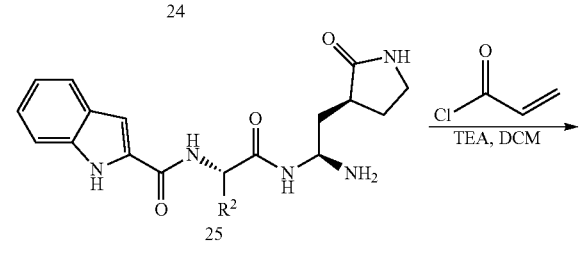
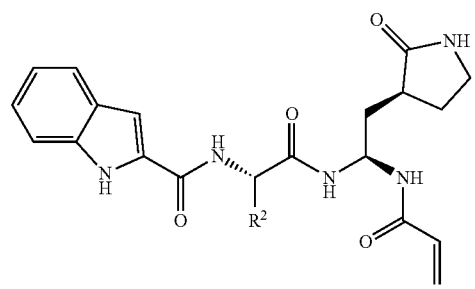
Scheme VII. Synthesis of selected compounds of Formula (I).
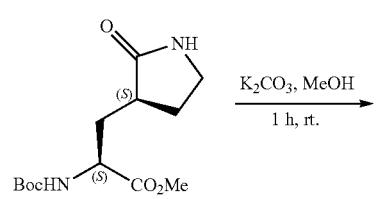
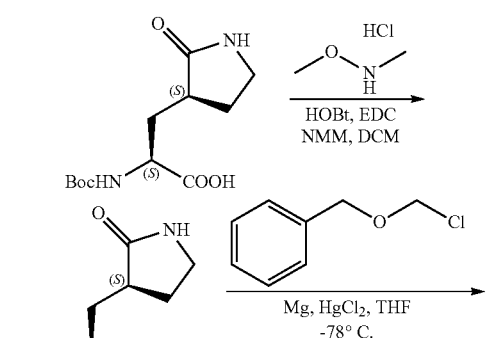
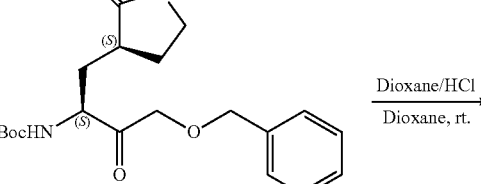
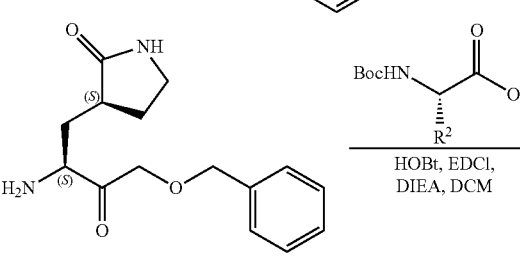

175
-continued
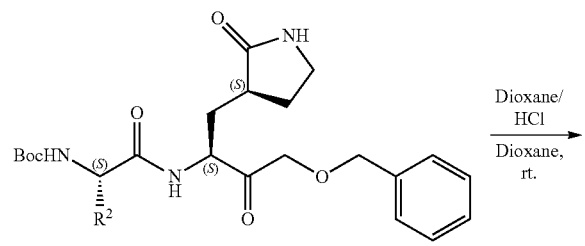
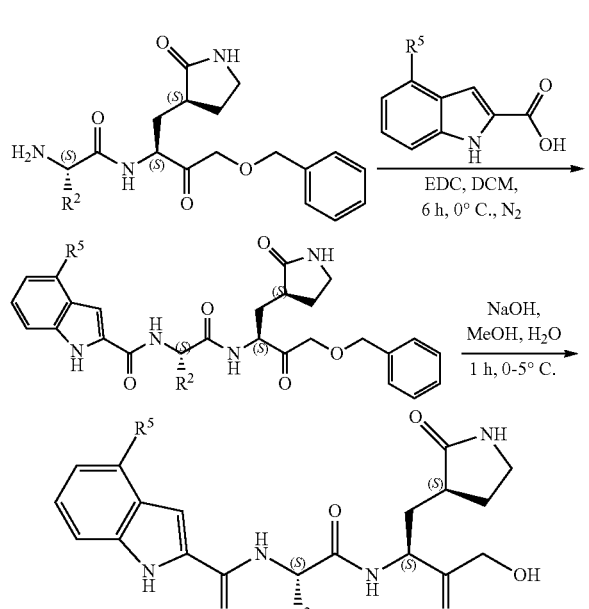
R⁵ = H, F, -CH₃, -OCH₃
R² = -CH₂CH(CH₃)₂, -C(CH₃)₃, CH₂CH₂CH₃,
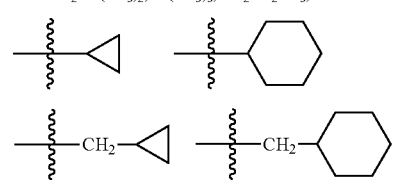
Scheme VIII. Synthesis of selected compounds of Formula (II).
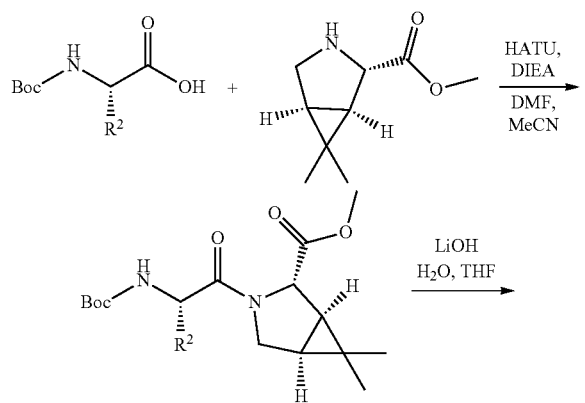
176
-continued
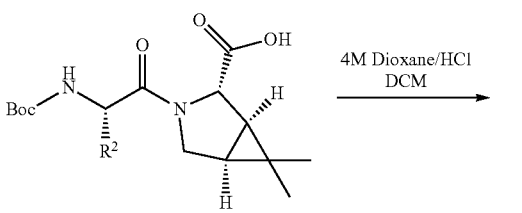
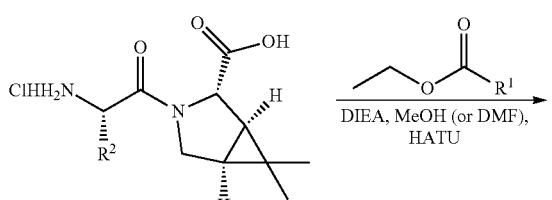
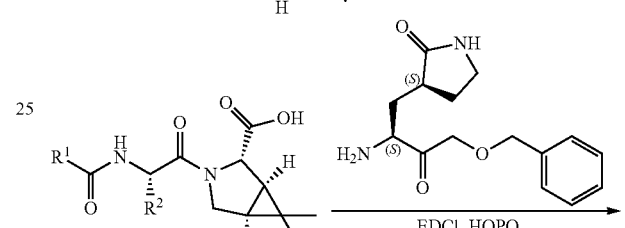
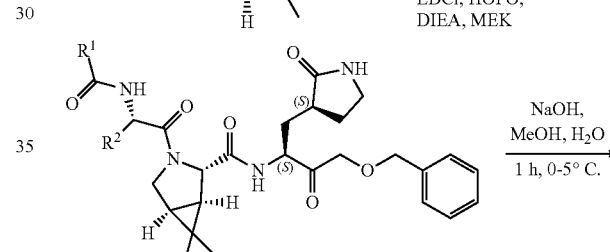
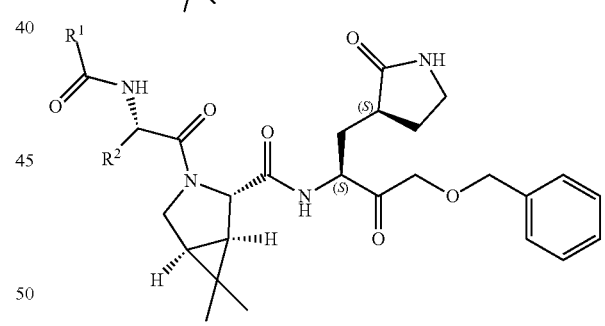
R¹ = H, CF₃, -C(CH₃)₃, -OC(CH₃)₃
R² = -CH₂CH(CH₃)₂, -C(CH₃)₃, -CH₂CH₂CH₃,
R⁵ = H, F, -CH₃, -OCH₃

Scheme IX. Synthesis of selected compounds of Formula (I), containing benzo-thiazol ketones.
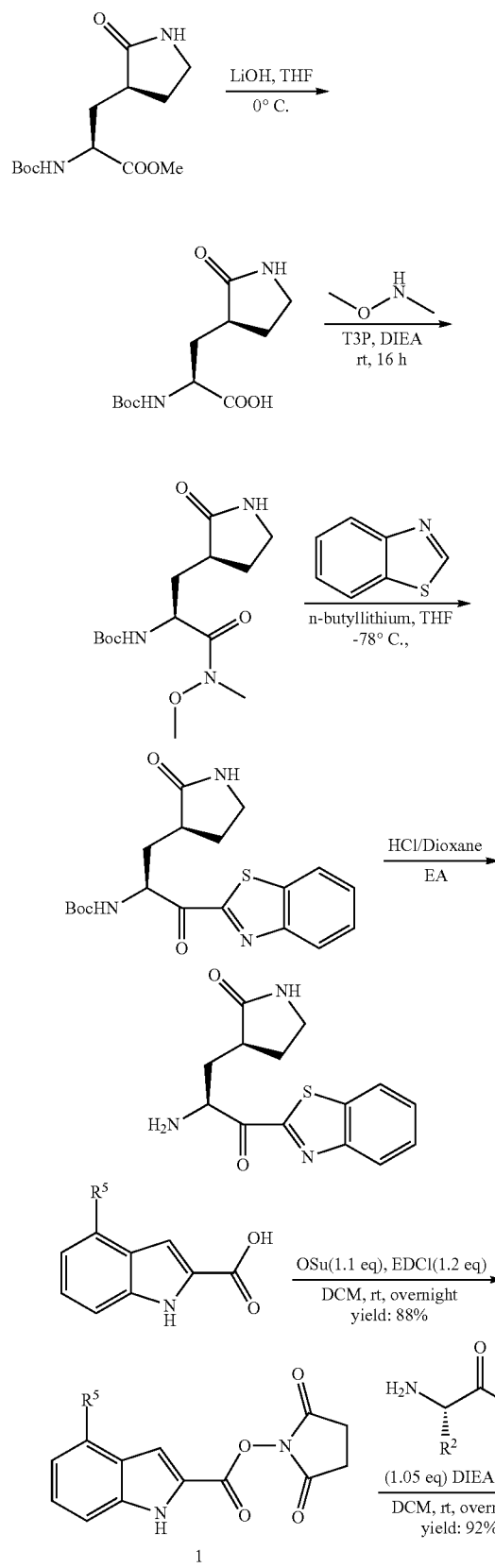
Scheme X. Synthesis of selected compounds of Formula (I). Different synthetic routes to bisulfite adduct
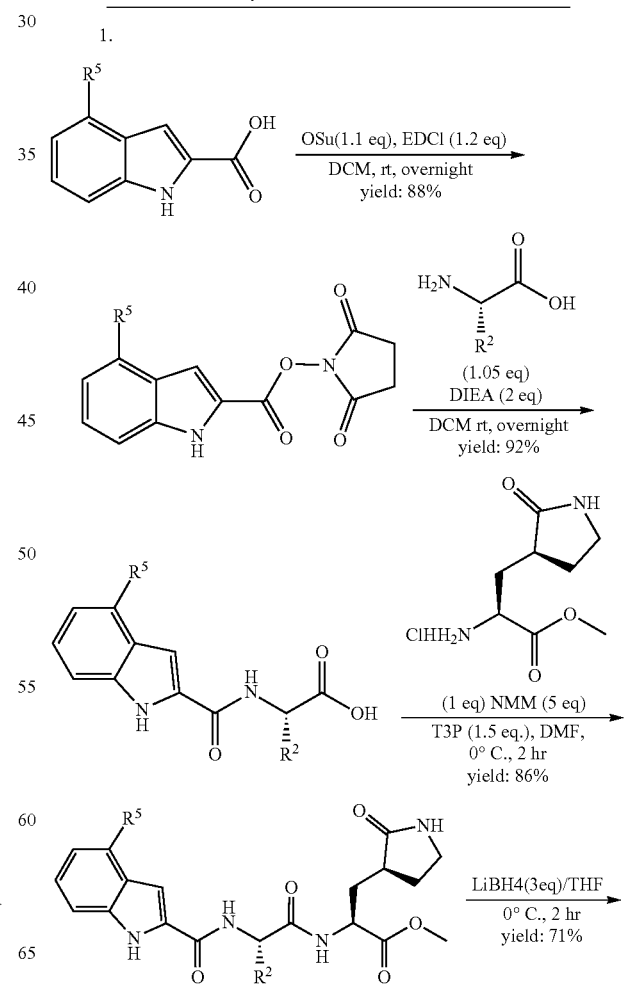

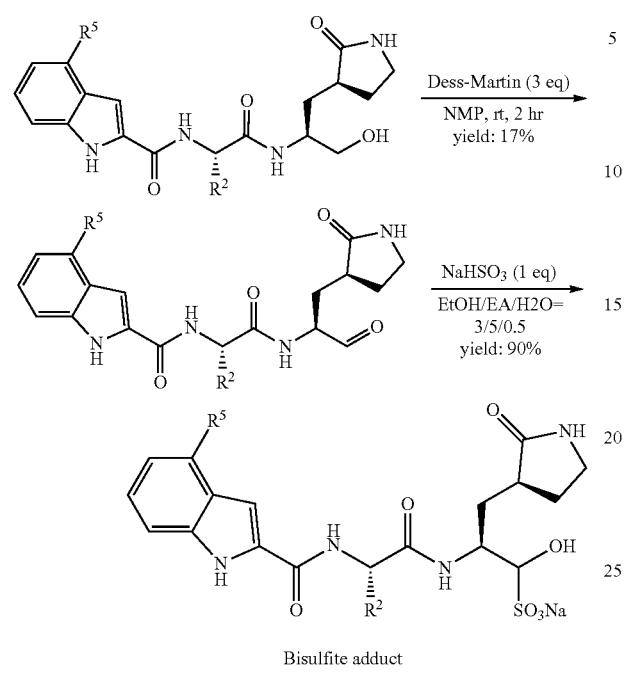
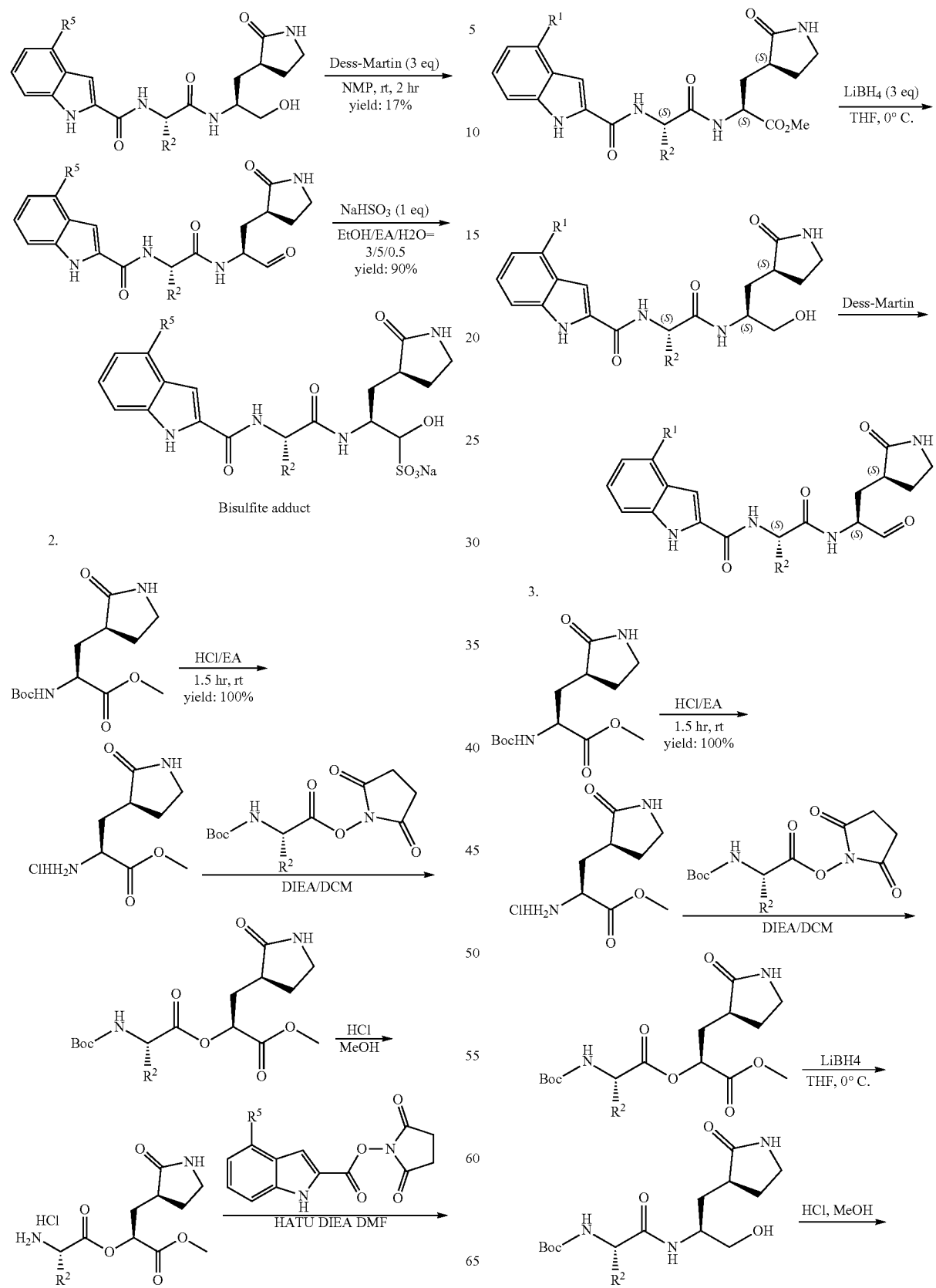
2.
3.

-continued

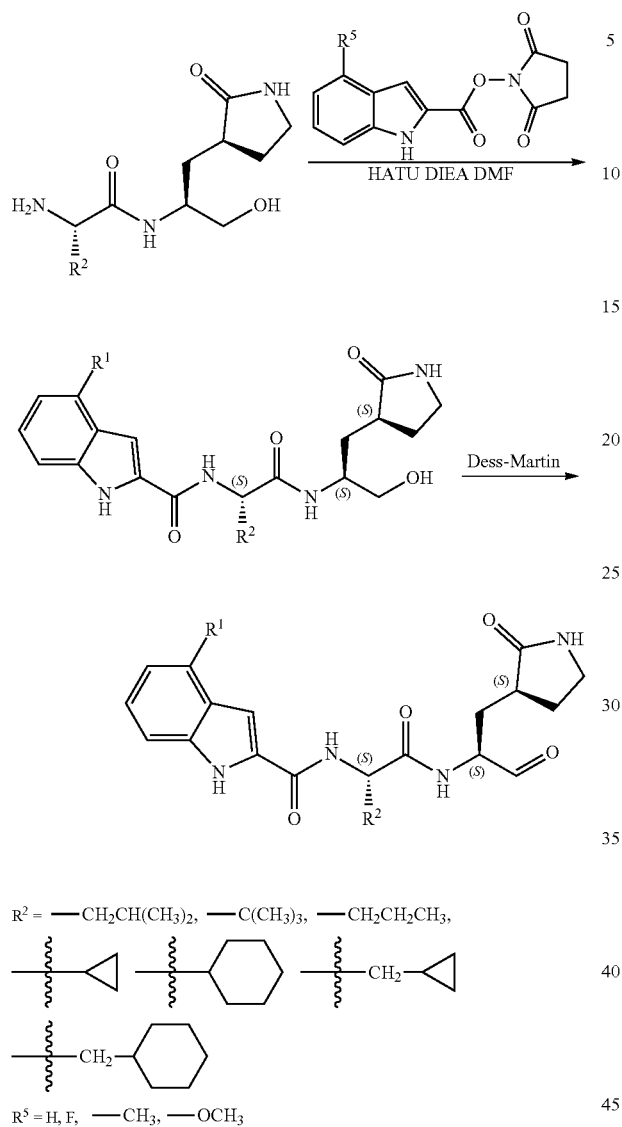

R² = —CH₂CH(CH₃)₂, —C(CH₃)₃, —CH₂CH₂CH₃,

R⁵ = H, F, —CH₃, —OCH₃

EXAMPLES

The following examples are meant to be illustrative and can be used to further understand embodiments of the present disclosure and should not be construed as limiting the scope of the present teachings in any way.

The chemical reactions described in the Examples can be readily adapted to prepare a number of other compounds of the present disclosure, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by utilizing other suitable reagents known in the art other than those described, or by making routing modifications of reaction conditions, reagents, and starting materials. Alternatively, other reactions disclosed herein or known in the art will be recognized as having applicability for preparing other compounds of the present disclosure.

SYNTHETIC EXAMPLES

Example S1: Synthesis of Compounds A-1-a, A-1-b, A-1-c and A-1-d

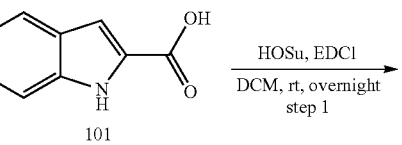

101

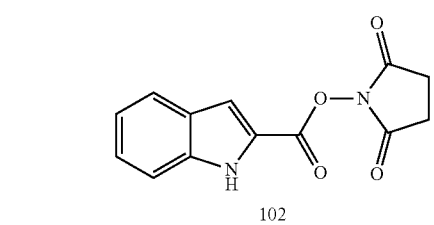

102

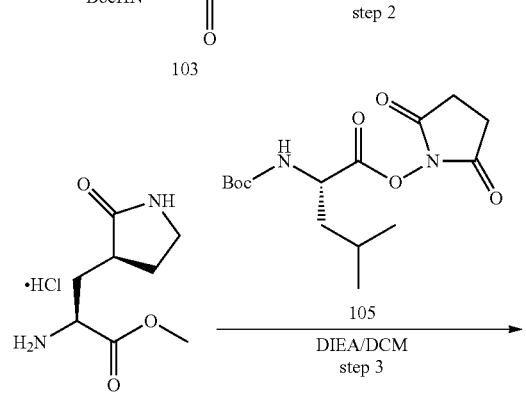

103

104

105

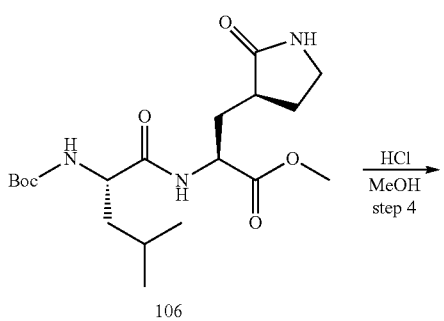

106

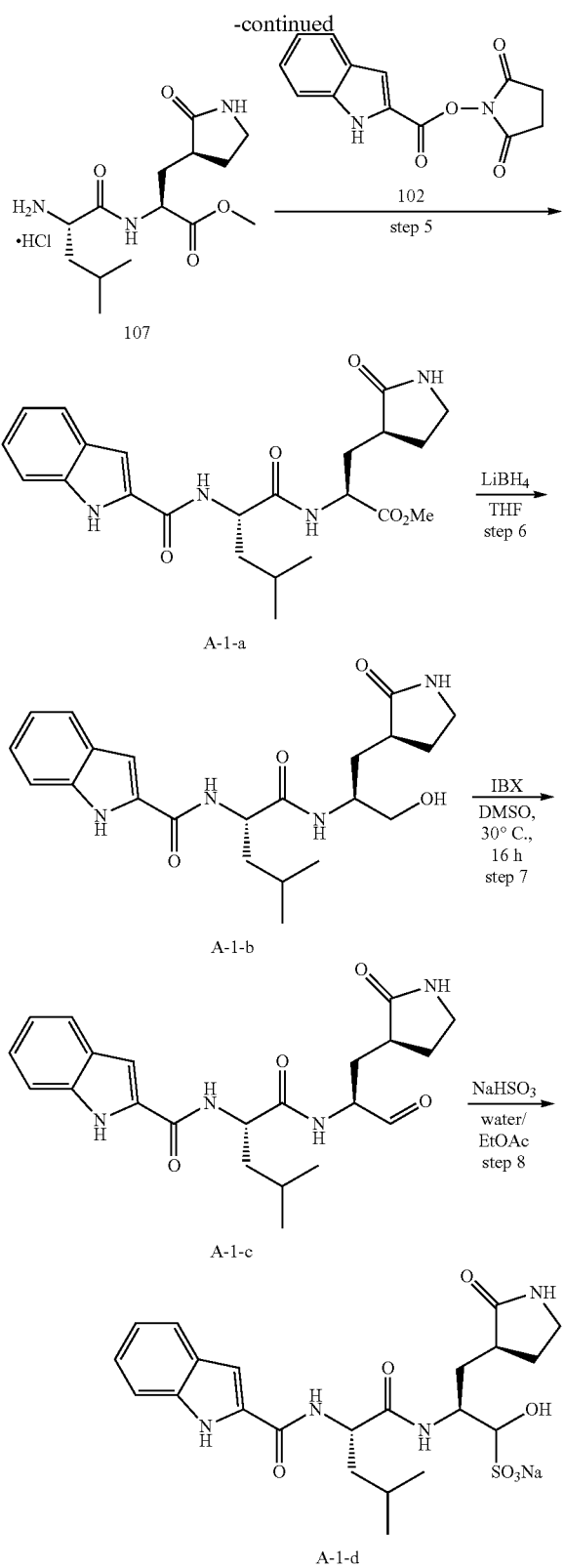

reduced pressure. The resulting solid was triturated with deionized water, and the solid was collected and dried under reduced pressure to give the compound 102 as a light-brown solid (310 g, 96%). $^1$H NMR (400 MHz, CDCl$_3$) δ 9.01 (s, 1H), 7.70 (d, J=8.2 Hz, 1H), 7.49-7.35 (m, 3H), 7.19 (t, J=7.4 Hz, 1H), 2.92 (s, 4H).

To a stirred mixture of methyl (2S)-2-{[(tert-butoxy)carbonyl]amino}-3-[(3S)-2-oxopyrrolidin-3-yl]-propanoate (compound 103) (500 g, 1748.24 mmol) in MeOH (200 mL) was added 4M HCl in 1,4-dioxane (2000 mL) at room temperature. The mixture was stirred at rt for 2 h. LCMS indicated completion of the reaction. The reaction mixture was concentrated under reduced pressure to afford methyl (2S)-2-amino-3-[(3S)-2-oxopyrrolidin-3-yl]propanoate hydrochloride salt (compound 104) (389 g, 1721 mmol, 98%) as a light-yellow solid, which was used for next step without further purification. LCMS=[M+H]$^+$: 187.1.

To a stirred mixture of methyl (2S)-2-amino-3-[(3S)-2-oxopyrrolidin-3-yl]propanoate hydrochloride (389 g, 1721 mmol) (compound 104) and DIEA (866.162 mL, 5240.94 mmol) in DCM (1800 mL) and EtOH (500 mL) was added 2,5-dioxopyrrolidin-1-yl (2R)-2-{[(tert-butoxy)carbonyl]amino}-4-methyl-pentanoate (compound 105) (573.66 g, 1746.98 mmol) at room temperature. The reaction mixture was stirred at room temperature for 2 h. LCMS indicated completion of the reaction. The reaction mixture was successively washed with water (1.0 L×2), 0.5 M HCl (1.1 L), sat. NaHCO$_3$ (1 L) and water (1 L). The organic layer was separated, dried with anhydrous Na$_2$SO$_4$, filtered and concentrated under reduced pressure to afford the compound 106 (700 g, 1752.23 mmol, >99%) as a light-yellow solid, which was used for next step without further purification. LCMS=[M+H]$^+$: 400.3. $^1$H NMR (400 MHz, DMSO-d$_6$) δ 8.32 (d, J=8.0 Hz, 1H), 7.62 (s, 1H), 6.88 (d, J=8.0 Hz, 1H), 4.40-4.28 (m, 1H), 3.94 (dd, J=15.1, 8.1 Hz, 1H), 3.74-3.52 (m, 3H), 3.15 (t, J=8.8 Hz, 1H), 3.06 (dd, J=16.4, 9.2 Hz, 1H), 2.33 (t, J=9.2 Hz, 1H), 2.14-2.00 (m, 2H), 1.68-1.51 (m, 3H), 1.42-1.34 (m, 11H), 0.87 (dd, J=11.4, 6.6 Hz, 6H).

A mixture of methyl (2S)-2-[(2S)-2-{[(tert-butoxy)carbonyl]amino}-4-methylpentanamido]-3-[(3S)-2-oxopyrrolidin-3-yl]propanoate (compound 106) (590 g, 1476.88 mmol) in HCl/dioxane (3 L) was stirred at room temperature for 2 h. LC-MS indicated completion of the reaction. The reaction mixture was concentrated under reduced pressure to give compound 107 as a yellow solid (490 g, 99%), which was used for next step without further purification. LCMS=[M+H]$^+$: 300.2.

To a stirred mixture of methyl (S)-2-((S)-2-amino-4-methylpentanamido)-3-((S)-2-oxopyrrolidin-3-yl)propanoate hydrochloride (compound 107) (418 g, 1235 mmol) and TEA (519.020 mL, 3734.03 mmol) in DMF (2500 mL) at room temperature was added 2,5-dioxopyrrolidin-1-yl 1H-indole-2-carboxylate (compound 102) (353 g, 1369.15 mmol). The reaction mixture was stirred for 1.5 h. LCMS indicated that the reaction was complete. EtOAc (6 L) was added into the reaction mixture, which was then washed with brine (6 L×6). The organic layers were combined, dried over anhydrous sodium sulfate, and concentrated down under reduced pressure. Compound A-1-a was obtained as an off-white solid (414 g. Y: 76%), which was used for next step without further purification. LCMS=[M+H]$^+$: 443.3. $^1$H NMR (400 MHz, DMSO-d$_6$) δ 11.55 (s, 1H), 8.54 (t, J=12.2 Hz, 1H), 8.40 (d, J=8.1 Hz, 1H), 7.62 (d, J=8.1 Hz, 2H), 7.43 (d, J=8.2 Hz, 1H), 7.24 (t, J=10.3 Hz, 1H), 7.18 (t, J=7.5 Hz, 1H), 7.04 (t, J=7.5 Hz, 1H), 4.65-4.50 (m, 1H), 4.44-4.28 (m, 1H), 3.72-3.55 (s, 3H), 3.19-3.06 (m, 2H), 2.36 (ddd, J=13.8, 10.3, 4.0 Hz, 1H), 2.16-2.03 (m, 2H), 1.79-1.49 (m, 5H), 0.92 (dt, J=14.4, 7.2 Hz, 6H).

To a dichloromethane (2.5 L) solution of 1H-indole-2-carboxylic acid (compound 101) (200 g, 1.24 mol) and N-hydroxy succinimide (157.1 g, 1.37 mol) was added EDCI (286 g, 1.49 mmol) at 0° C. After stirring at room temperature overnight, the solvent was removed under To a stirred solution of methyl (S)-2-((S)-2-(1H-indole-2-carboxamido)-4-methylpentanamido)-3-((S)-2-oxopyrrolidin-3-yl)propanoate (compound A-1-a) (500 g, 1131 mmol) in THF (20 L) LiBH$_4$ (74 g, 3393 mmol) was added portionwise at 0° C. The reaction mixture was stirred at 0° C. for 4 h. After reaction was completed (monitored by LCMS), the reaction mixture was quenched with sat. aqueous NH$_4$Cl until no more gas formed. The mixture was washed with brine (5 L×4), organic layer was collected, dried over anhydrous sodium sulfate, filtered, and concentrated down in vacuum. The resulting residue was purified by silica column chromatography (DCM:MeOH=15:1) to give the desired product compound A-1-b (310 g, 66%) as a white solid. LCMS=[M+H]$^+$: 415.2. $^1$H NMR (400 MHz, DMSO-d$_6$) δ 11.57 (s, 1H), 8.39 (d, J=8.2 Hz, 1H), 7.79 (d, J=9.0 Hz, 1H), 7.61 (d, J=7.9 Hz, 1H), 7.52 (s, 1H), 7.42 (d, J=8.3 Hz, 1H), 7.26 (d, J=1.4 Hz, 1H), 7.17 (t, J=7.6 Hz, 1H), 7.03 (t, J=7.5 Hz, 1H), 4.67 (t, J=5.6 Hz, 1H), 4.50 (td, J=9.7, 5.0 Hz, 1H), 3.80 (s, 1H), 3.40-3.28 (m, 1H), 3.28-3.20 (m, 1H), 3.15-2.99 (m, 2H), 2.33-2.20 (m, 1H), 2.12 (dt, J=17.8, 9.4 Hz, 1H), 1.86-1.75 (m, 1H), 1.75-1.64 (m, 2H), 1.56 (ddd, J=19.3, 9.6, 6.9 Hz, 2H), 1.45-1.35 (m, 1H), 0.91 (dd, J=15.6, 6.3 Hz, 6H).

To a stirred solution of N—((S)-1-(((S)-1-hydroxy-3-((S)-2-oxopyrrolidin-3-yl)propan-2-yl)amino)-4-methyl-1-oxopentan-2-yl)-1H-indole-2-carboxamide (compound A-1-b) (8.3 g, 20 mmol) in DMSO (60 mL) was added 2-iodoxybenzoic acid (IBX) (11.2 g, 40 mmol) at room temperature. The reaction mixture was stirred at 30° C. for 18 h, and LCMS indicated completion of the reaction. The reaction mixture was diluted with EtOAc (300 mL) and filtered. The filtrate was washed with mixture of brine and sat. aqueous NaHCO$_3$ (1:1 to 5:1, 200 mL×5). The organic layer was separated, dried over anhydrous sodium sulfate, filtered, and concentrated down at rt to afford crude product. THF (40 mL) was added, and the mixture was stirred overnight at room temperature. The resulting solid was collected and dried under vacuum to yield the desired product N—((S)-4-methyl-1-oxo-1-(((S)-1-oxo-3-((S)-2-oxopyrrolidin-3-yl)-propan-2-yl)amino)pentan-2-yl)-1H-indole-2-carboxamide (compound A-1-c) as a white solid (2.5 g, 31%). LCMS=[M+H]$^+$: 413.2. $^1$H NMR (400 MHz, CDCl$_3$) δ 9.75 (s, 1H), 9.49 (s, 1H), 8.64 (s, 1H), 7.62 (d, J=8.0 Hz, 1H), 7.40 (d, J=8.4 Hz, 1H), 7.27 (d, J=8.4 Hz, 1H), 7.14-7.05 (m, 2H), 7.01 (s, 1H), 6.34 (s, 1H), 4.90 (s, 1H), 4.34 (s, 1H), 3.27-3.22 (m, 2H), 2.43 (s, 1H), 2.30 (s, 1H), 2.01-1.96 (m, 1H), 1.94-1.91 (m, 1H) 1.88-1.65 (m, 4H), 1.00-0.98 (m, 6H).

To a stirred solution of N—((S)-4-methyl-1-oxo-1-(((S)-1-oxo-3-((S)-2-oxopyrrolidin-3-yl)propan-2-yl)amino)pentan-2-yl)-1H-indole-2-carboxamide (compound A-1-c) (31 g, 75.25 mmol) in EtOAc (300 mL) at room temperature was added a solution of NaHSO$_3$ (27.56 mg, 72.73 mmol) in water (100 mL). The reaction mixture was heated at 50° C. for 3 h. After completion of reaction (monitored by LCMS), the organic layer was separated and removed. The aqueous layer was washed with EtOAc (100 mL×5), concentrated down to remove remaining EtOAc, and then lyophilized to provide the desired product sodium (2S)-2-((S)-2-(1H-indole-2-carboxamido)-4-methylpentanamido)-1-hydroxy-3-((S)-2-oxopyrrolidin-3-yl)propane-1-sulfonate (compound A-1-d) as off-white solid (32 g, 85%). LCMS=[M−Na+2H]$^+$: 495.2. $^1$H NMR (400 MHz, DMSO-d$_6$) δ 11.57 (s, 1H), 8.45 (dd, J=20.7, 8.2 Hz, 1H), 7.72 (dd, J=48.9, 9.2 Hz, 1H), 7.62 (d, J=8.1 Hz, 1H), 7.50-7.38 (m, 2H), 7.25 (dd, J=5.1, 1.4 Hz, 1H), 7.18 (t, J=7.6 Hz, 1H), 7.04 (t, J=7.5 Hz, 1H), 5.43 (dd, J=50.7, 5.9 Hz, 1H), 4.57-4.41 (m, 1H), 4.33-4.03 (m, 1H), 4.01-3.82 (m, 1H), 3.19-2.92 (m, 2H), 2.29-2.08 (m, 2H), 2.06-1.90 (m, 1H), 1.83-1.51 (m, 5H), 1.00-0.83 (m, 6H).

Example S2: Synthesis of Compounds A-1-e and A-1-f

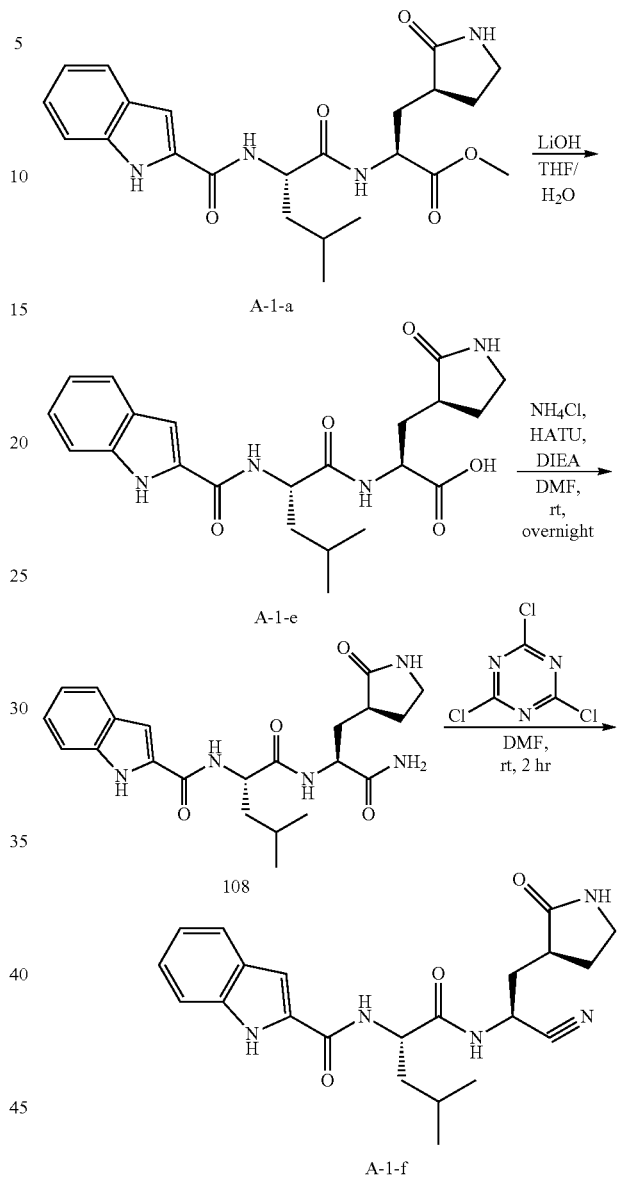

To a stirred solution of methyl (2S)-2-[(2S)-2-[(1H-indol-2-yl)formamido]-4-methylpentanamido]-3-[(3S)-2-oxopyrrolidin-3-yl]propanoate (compound A-1-a) (150 mg, 0.34 mmol) in THF (3.5 mL) and H$_2$O (3.5 mL) was added LiOH (0.01 mL, 0.68 mmol). The reaction mixture was stirred at room temperature for 1 h. After the reaction was complete (monitored by TLC), the pH of the reaction mixture was adjusted to ~3-4 with citric acid. The resulting mixture was extracted with DCM (20 mL×2) and washed with brine (5 mL). The combined organic layers were dried over anhydrous Na$_2$SO$_4$ and filtered. The solvent was removed under reduced pressure to give the compound A-1-e as an off-white solid, which was used for next step without further purification. LCMS=[M+H]$^+$: 429.1. $^1$H NMR (400 MHz, DMSO-d$_6$) δ 12.57 (s, 1H), 11.57 (s, 1H), 8.43-8.40 (m, 2H), 7.62 (d, J=8 Hz, 2H), 7.42 (d, J=8.4 Hz, 1H), 7.26 (s, 1H), 7.18 (t, J=7.6 Hz, 1H), 7.03 (t, J=7.5 Hz, 1H), 4.60-4.54 (m, 1H), 4.31-4.25 (m, 1H), 3.15-3.05 (m, 2H), 2.37-2.29 (m, 1H), 2.16-2.02 (m, 2H), 1.78-1.53 (m, 5H), 0.94-0.89 (m, 6H).

To a stirred solution of (2S)-2-[(2S)-2-[(1H-indol-2-yl)formamido]-4-methylpentanamido]-3-[(3S)-2-oxopyrrolidin-3-yl]propanoic acid (compound A-1-e) (110 mg, 0.26 mmol) in DMF (5 mL) at room temperature were added NH₄Cl (68 mg, 1.28 mmol), HATU (146 mg, 0.39 mmol) and DIEA (0.129 mL, 0.78 mmol). The reaction mixture was stirred at room temperature under N₂ for 1 h. After completion of reaction (monitored by TLC) the reaction mixture was extracted with EtOAc (50 mL×3), the organic layer was separated, washed with brine (20 mL), dried over anhydrous Na₂SO₄, and solvent was removed under reduced pressure. The resulting crude product was purified using prep-TLC (DCM:MeOH=10:1) to give compound 108 (40 mg, 0.09 mmol, 36.45%) as an off-white solid. LCMS=[M+H]⁺: 428.1. ¹H NMR (400 MHz, DMSO-d₆) δ 11.58 (s, 1H), 8.47 (d, J=8 Hz, 1H), 8.09 (d, J=8.4 Hz, 1H), 7.63-7.60 (m, 2H), 8.43 (d, J=8.4 Hz, 1H), 7.30 (s, 1H), 7.25 (d, J=1.2 Hz, 1H), 7.20-7.17 (m, 1H), 7.05-7.02 (m, 2H), 4.54-4.49 (m, 1H), 4.31-4.25 (m, 1H), 3.14-3.03 (m, 2H), 2.33-2.26 (m, 1H), 2.18-2.09 (m, 1H), 2.04-1.97 (m, 1H), 1.74-1.48 (m, 5H), 1.01-0.83 (m, 6H).

To a stirred solution of N—((S)-1-(((S)-1-amino-1-oxo-3-((S)-2-oxopyrrolidin-3-yl)propan-2-yl)amino)-4-methyl-1-oxopentan-2-yl)-1H-indole-2-carboxamide (compound 108) (30 mg, 0.070 mmol) in DMF (0.5 mL) was added 2,4,6-trichloro-1,3,5-triazine (20 mg, 0.105 mmol) at room temperature. The reaction mixture was stirred at room temperature for 2 h, and after completion (monitored by LCMS) was concentrated down. The crude material was purified by prep-HPLC to give compound A-1-f as an off-white solid (2 mg, 7%). LCMS=[M+H]⁺: 410.2. ¹H NMR (400 MHz, CDCl₃) δ 9.64 (s, 1H), 7.66 (d, J=7.6 Hz, 1H), 7.46 (d, J=8.1 Hz, 1H), 7.28-7.25 (m, 2H), 7.14 (t, J=6.9 Hz, 1H), 6.98 (d, J=9.7 Hz, 1H), 6.72 (d, J=8.2 Hz, 1H), 6.22 (d, J=8.2 Hz, 1H), 5.03-4.95 (m, 1H), 4.85-4.80 (m, 1H), 2.84-2.80 (m, 2H), 1.90-1.88 (m, 1H), 1.80-1.76 (m, 2H), 1.36-1.19 (m, 5H), 0.99 (d, J=5.8 Hz, 6H).

Example S3: Synthesis of Compound A-1-g

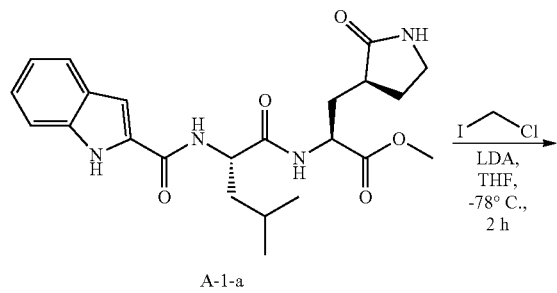

A-1-a

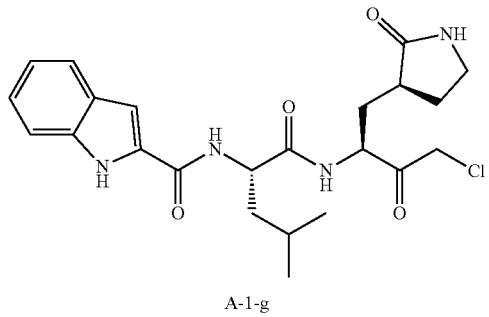

A-1-g

A solution of lithium diisopropylamide (LDA) in THF (14.124 mL, 28.25 mmol) was added dropwise to a solution of methyl (2S)-2-[(2S)-2-[(1H-indol-2-yl)formamido]-4-methylpentanamido]-3-[(3S)-2-oxopyrrolidin-3-yl]propanoate (compound A-1-a) (500 mg, 1.13 mmol) and chloroiodomethane (0.850 mL, 11.30 mmol) in THF (3 mL) under N₂ at −78° C. with stirring. The mixture was gradually warmed up to room temperature and continually stirred under N₂ for 2 h. The reaction mixture was quenched with saturated aqueous NH₄Cl and extracted with EtOAc (30 mL×3). The combined organic layers were washed with brine (30 mL×2), and solvent was removed under reduced pressure to afford the crude product, which was further purified by prep-HPLC (ACN/water (0.1% FA) to afford compound A-1-g as an off-white solid (96 mg, 0.21 mmol, 18.43%). LCMS=[M+H]⁺: 461.2. HPLC=95% ¹H NMR (400 MHz, DMSO-d₆) δ 11.59 (s, 1H), 8.65 (d, J=7.7 Hz, 1H), 8.51 (d, J=7.7 Hz, 1H), 7.67-7.59 (m, 2H), 7.43 (d, J=8.3 Hz, 1H), 7.27 (d, J=1.4 Hz, 1H), 7.22-7.14 (m, 1H), 7.03 (dd, J=11.0, 4.0 Hz, 1H), 4.61 (t, J=9.4 Hz, 2H), 4.54-4.40 (m, 2H), 3.18-3.04 (m, 2H), 2.27-2.28 (m, 1H), 2.31-2.28 (m, 1H), 2.15-2.05 (m, 1H), 1.77-1.68 (m, 2H), 1.67-1.53 (m, 3H), 0.95 (d, J=6.2 Hz, 3H), 0.90 (d, J=6.3 Hz, 3H).

Example S4: Synthesis of Compound A-1-h

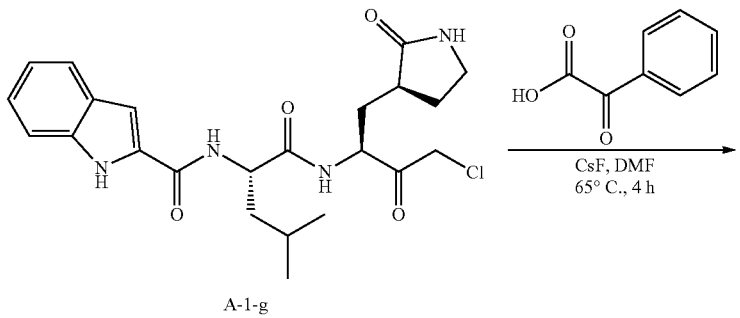

A-1-g

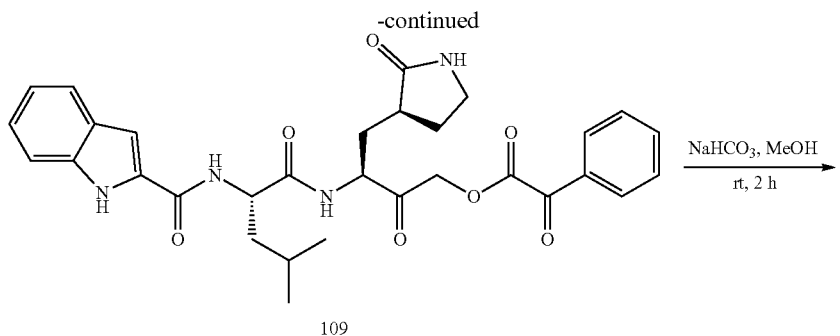

109

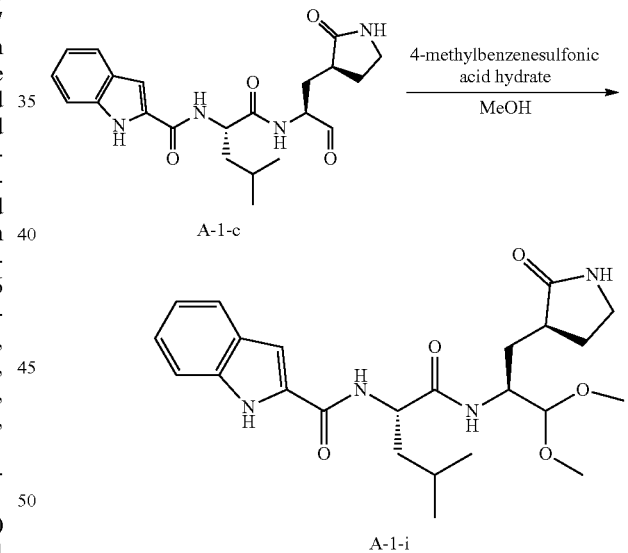

A-1-h

To a solution of (2S)—N-[(2S)-4-chloro-3-oxo-1-[(3S)-2-oxopyrrolidin-3-yl]butan-2-yl]-2-[(1H-indol-2-yl)formamido]-4-methylpentanamide (compound A-1-g) (454 mg, 0.98 mmol) and 2-oxo-2-phenyl-acetic acid (0.139 mL, 1.28 mmol) in DMF (9 mL) was added CsF (342.06 mg, 2.27 mmol). The reaction mixture was stirred at 65° C. for 2 h under $N_2$. LCMC indicated completion of the reaction. The reaction mixture was diluted with EtOAc (60 mL) and washed with brine (30 mL×2). The organic layer was dried over anhydrous $Na_2SO_4$ and concentrated down. The resulting residue was purified by reverse-phase column chromatography (ACN/water (0.1% FA) 60/40 to 70/30) to afford compound 109 (150 mg, 0.26 mmol, 26.5%) as a brown solid. LCMS=[M+H]$^+$: 575.3. $^1$H NMR (400 MHz, DMSO-$d_6$) δ 11.58 (s, 1H), 8.70 (d, J=7.9 Hz, 1H), 8.53 (d, J=7.6 Hz, 1H), 8.21-8.03 (m, 2H), 7.82 (t, J=7.4 Hz, 1H), 7.74-7.54 (m, 3H), 7.43 (d, J=8.2 Hz, 1H), 7.28 (s, 1H), 7.18 (t, J=7.6 Hz, 1H), 7.03 (t, J=7.5 Hz, 1H), 5.28 (q, J=17.1 Hz, 2H), 4.73-4.32 (m, 2H), 3.21-3.00 (m, 2H), 2.42-2.26 (m, 1H), 2.22-1.98 (m, 2H), 1.87-1.45 (m, 5H), 1.06-0.81 (m, 6H).

To a solution of (3S)-3-[(2S)-2-[(1H-indol-2-yl)formamido]-4-methylpentanamido]-2-oxo-4-[(3S)-2-oxopyrrolidin-3-yl]butyl 2-oxo-2-phenylacetate (compound 109) (210 mg, 0.37 mmol) in MeOH (8 mL) was added $NaHCO_3$ (6.14 mg, 0.07 mmol). The reaction mixture was stirred at room temperature for 2 h. LCMS indicated completion of the reaction. The reaction mixture was diluted with $H_2O$ (30 mL) and extracted with EtOAc (50 mL×3). The organic layers were combined and washed with brine (30 mL×2), dried over anhydrous $Na_2SO_4$, and concentrated down. The resulting residue was purified by prep-HPLC to afford compound A-1-h (38.79 mg, 0.09 mmol, 23.99%) as a white solid. LCMS=[M+H]$^+$: 443.2. $^1$H NMR (400 MHz, DMSO-$d_6$) δ 11.58 (s, 1H), 8.74-8.21 (m, 2H), 7.70-7.47 (m, 2H), 7.42 (d, J=8.5 Hz, 1H), 7.26 (s, 1H), 7.18 (t, J=7.2 Hz, 1H), 7.03 (t, J=7.5 Hz, 1H), 5.02 (d, J=5.9 Hz, 1H), 4.67-4.36 (m, 2H), 4.32-4.20 (m, 1H), 4.19-4.09 (m, 1H), 3.22-2.91 (m, 2H), 2.37-2.21 (m, 1H), 2.17-2.01 (m, 1H), 2.00-1.85 (m, 1H), 1.79-1.46 (m, 5H), 0.96-0.89 (m, 6H).

Example S5: Synthesis of Compound A-1-i

A mixture of N—((S)-4-methyl-1-oxo-1-(((S)-1-oxo-3-((S)-2-oxopyrrolidin-3-yl)propan-2-yl)amino)-pentan-2-yl)-1H-indole-2-carboxamide (compound A-1-c) (1 g, 2.42 mmol) and 4-methylbenzenesulfonic acid hydrate (46 mg, 0.24 mmol) in MeOH (5 mL) was stirred overnight at room temperature. The reaction mixture was concentrated down, and resulting residue was purified by prep-HPLC to give compound A-1-i (300 mg, 0.65 mmol, 27.03%) as a white solid. LCMS=[M+Na]$^+$: 482.2. $^1$H NMR (400 MHz, DMSO-$d_6$) δ 11.58 (s, 1H), 8.39 (d, J=8.0 Hz, 1H), 7.90 (d, J=9.4 Hz, 1H), 7.62 (d, J=8.0 Hz, 1H), 7.52 (s, 1H), 7.42 (d, J=8.3 Hz, 1H), 7.26 (d, J=1.4 Hz, 1H), 7.18-7.15 (m, 1H), 7.08-6.97 (m, 1H), 4.54-4.43 (m, 1H), 4.19 (d, J=5.8 Hz, 1H), 4.01-3.86 (m, 1H), 3.29 (s, 3H), 3.24 (s, 3H), 3.12-2.98

(m, 2H), 2.29-2.19 (m, 1H), 2.15-2.05 (m, 1H), 1.89-1.81 (m, 1H), 1.78-1.62 (m, 2H), 1.60-1.45 (m, 2H), 1.40-1.27 (m, 1H), 0.99-0.84 (m, 6H).

Example S6: Synthesis of Compound A-1-j

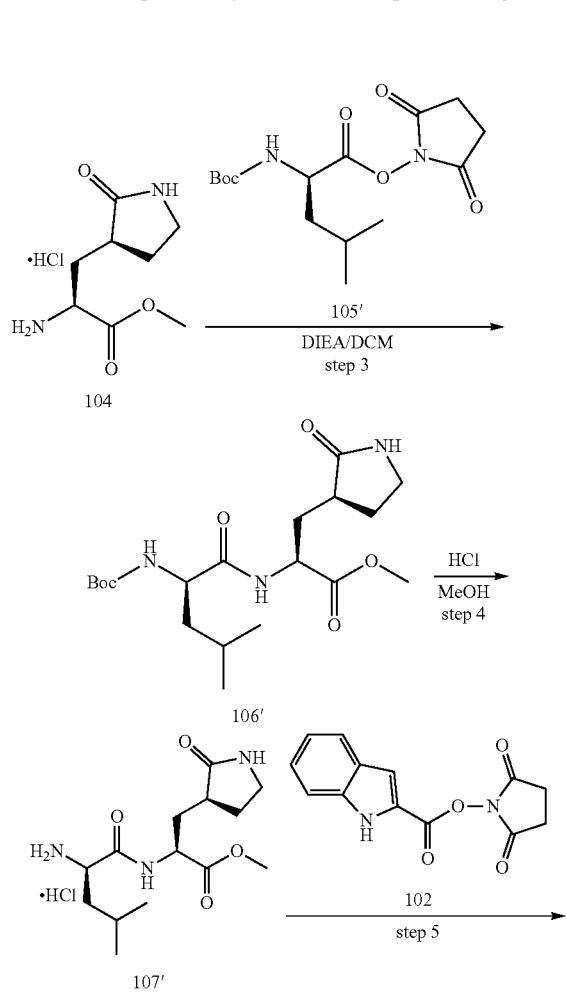

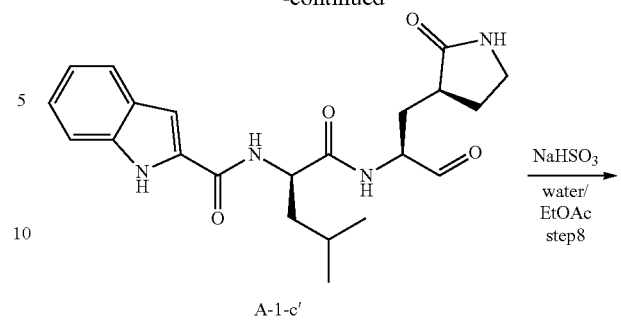

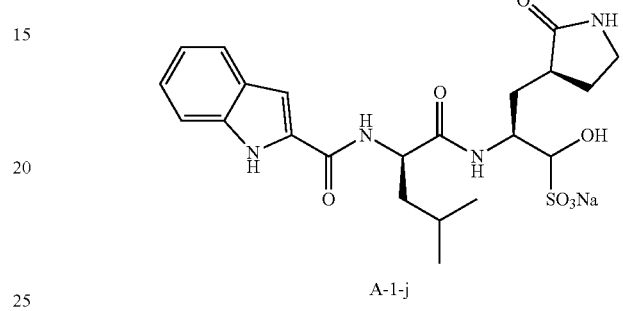

The synthesis of compound A-1-j was the same as for compound A-1-d. The water layer was washed with ethyl acetate (5 mL×5). After removing the remaining organic solvent, the residue was lyophilized to yield compound A-1-j (50 mg, 49.91%). LCMS=[M−Na+2H]$^+$: 495.2, HPLC: 81.36%. $^1$H NMR (400 MHz, DMSO) δ 11.58 (s, 1H), 8.64-8.30 (m, 1H), 7.97-7.56 (m, 2H), 7.49-7.38 (m, 2H), 7.28-7.21 (m, 1H), 7.21-7.13 (m, 1H), 7.06-6.96 (m, 1H), 5.76-5.25 (m, 1H), 4.62-4.38 (m, 1H), 4.31-3.86 (m, 2H), 3.18-3.09 (m, 1H), 3.07-2.95 (m, 1H), 2.22-1.91 (m, 3H), 1.77-1.49 (m, 5H), 0.97-0.80 (m, 6H).

Example S7: Synthesis of Compounds B-2-a, A-2-a, A-2-b, and A-2-c

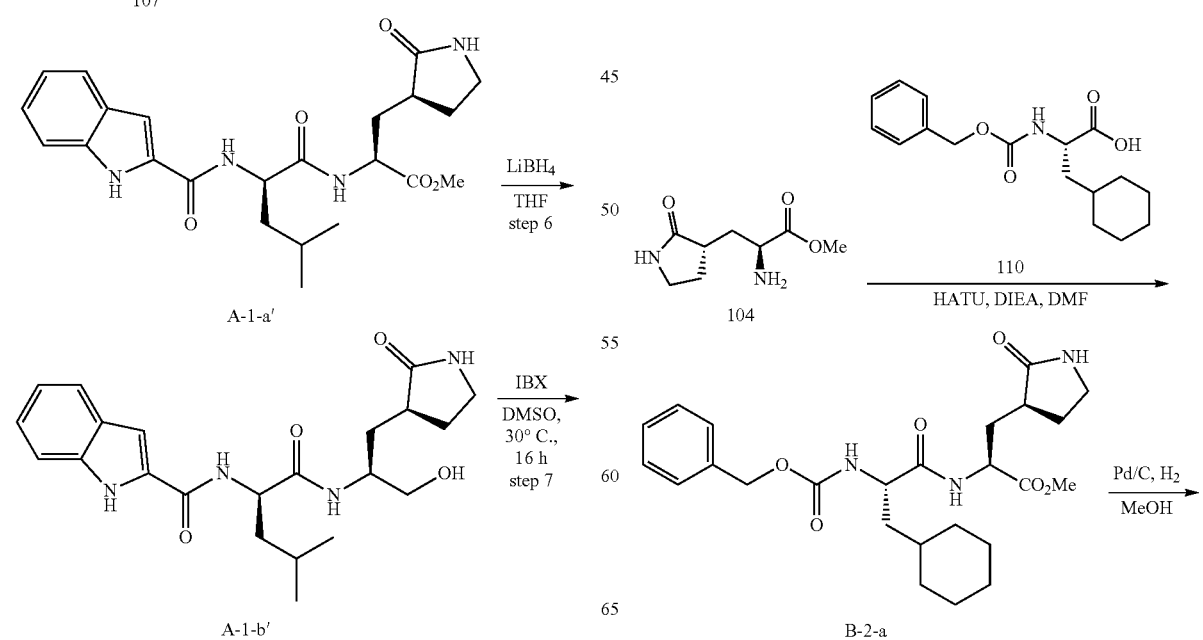

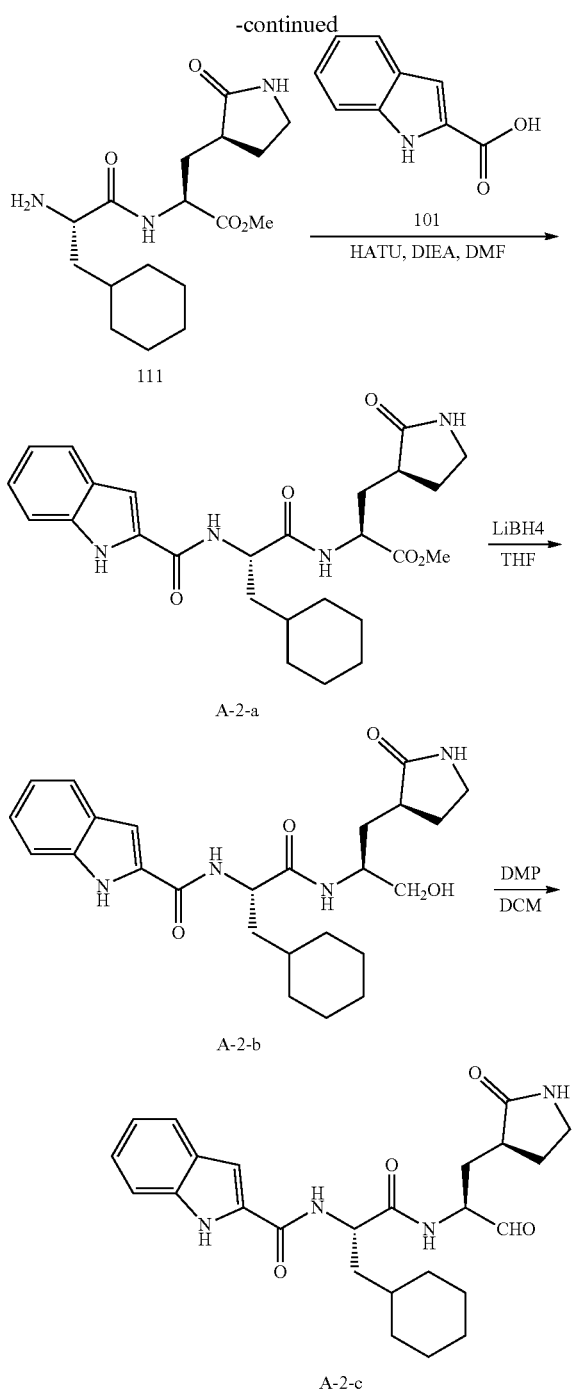

A-2-a

A-2-b

A-2-c

To a solution of compound 110 (5 g, 16.40 mmol) in anhydrous DMF (40 mL) at 0° C., HATU (5.7 g, 15.03 mmol) and DIEA (8.3 mL, 50.15 mmol) were added sequentially. The mixture was stirred at 0° C. for 15 min, then compound 104 (3.65 g, 16.40 mmol, 1.0 equiv) was added. The reaction mixture was stirred at 0° C. for 1 h. LCMS indicated completion of the reaction. The reaction mixture was diluted with EtOAc, washed with water, 1M HCl, sat. NaCl, dried over $Na_2SO_4$, and concentrated under reduced pressure. The resulting residue was purified by column chromatography (EtOAc:Hexane=1:5) to afford compound B-2-a as a white solid (5.3 g, 68.4%). LCMS=$[M+H]^+$: 474.5.

Solution of compound B-2-a (3.0 g) in MeOH (30 mL) with Pd/C (300 mg) was stirred under hydrogen atmosphere at room temperature for 3 h. LCMS indicated completion of the reaction. After the catalyst filtration, the solvent was removed under reduced pressure to afford compound 111 as an off-white solid (2.0 g). LCMS=$[M+H]^+$: 340.3

To a solution of compound 101 (0.95 g, 5.90 mmol) in anhydrous DMF (20 mL) at 0° C., HATU (3.36 g, 8.84 mmol) and DIEA (3 mL, 17.68 mmol) were added sequentially. The reaction mixture was stirred at 0° C. for 15 min. Compound 111 (2.0 g, 5.90 mmol, 1.0 equiv) was added to the solution and the reaction mixture was stirred at 0° C. for 1 h. LCMS indicated completion of the reaction. The reaction mixture was diluted with EtOAc, washed with water, 1M HCl, sat. NaCl, dried over $Na_2SO_4$, and concentrated down under reduced pressure. The resulting residue was purified by column chromatography (EtOAc:Hexane=1:5) to afford compound A-2-a as a white solid (2.7 g, 94.7%). LCMS=$[M+H]^+$: 483.5

To a stirring solution of compound A-2-a (2.7 g, 5.60 mmol) in THF (40 mL) was added $LiBH_4$ (2.0 M in THF, 8.4 mL, 16.80 mmol) portion wise at 0° C. under nitrogen atmosphere. The reaction mixture was stirred for 1 h at 0° C., and then allowed to warm up and stirred at rt for another 2 h. The reaction was quenched by adding 1.0 M HCl dropwise while cooling with an ice bath. The resulting mixture was diluted with EtOAc and $H_2O$. The organic layer was separated, and the aqueous layer was extracted with EtOAc. The combined organic layers were dried over $Na_2SO_4$, filtered, and concentrated under reduced pressure. The resulting residue was purified with column chromatography (5% MeOH in $CH_2Cl_2$ as the eluent) to give compound A-2-b as a white solid (2.0 g, 78.7%). LCMS=$[M+H]^+$: 455.4.

To a solution of A-2-b (2.0 g, 4.40 mmol) in DCM (20 mL) at 0° C. was added Dess-Martin periodinane (3.73 g, 8.80 mmol). The reaction mixture was stirred at 0° C. for 30 min, then allowed to warm up to room temperature and stirred for another 2 h. LCMS indicated completion of the reaction. The reaction was quenched at 0° C. with saturated $NaHCO_3$ solution containing 10% $Na_2S_2O_3$. The mixture was extracted with DCM. The combined organic layers were washed with brine, dried over anhydrous $Na_2SO_4$ and concentrated down under reduced pressure. The resulting residue was purified with column chromatography to afford compound A-2-c as a white solid (25 mg, 1.2%). LCMS= $[M+H]^+$: 453.6.

Example S8: Synthesis of Compounds A-3-a and A-3-b

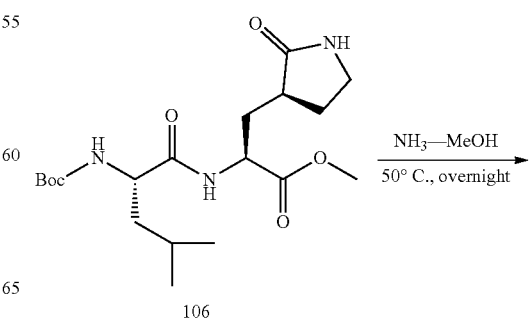

106

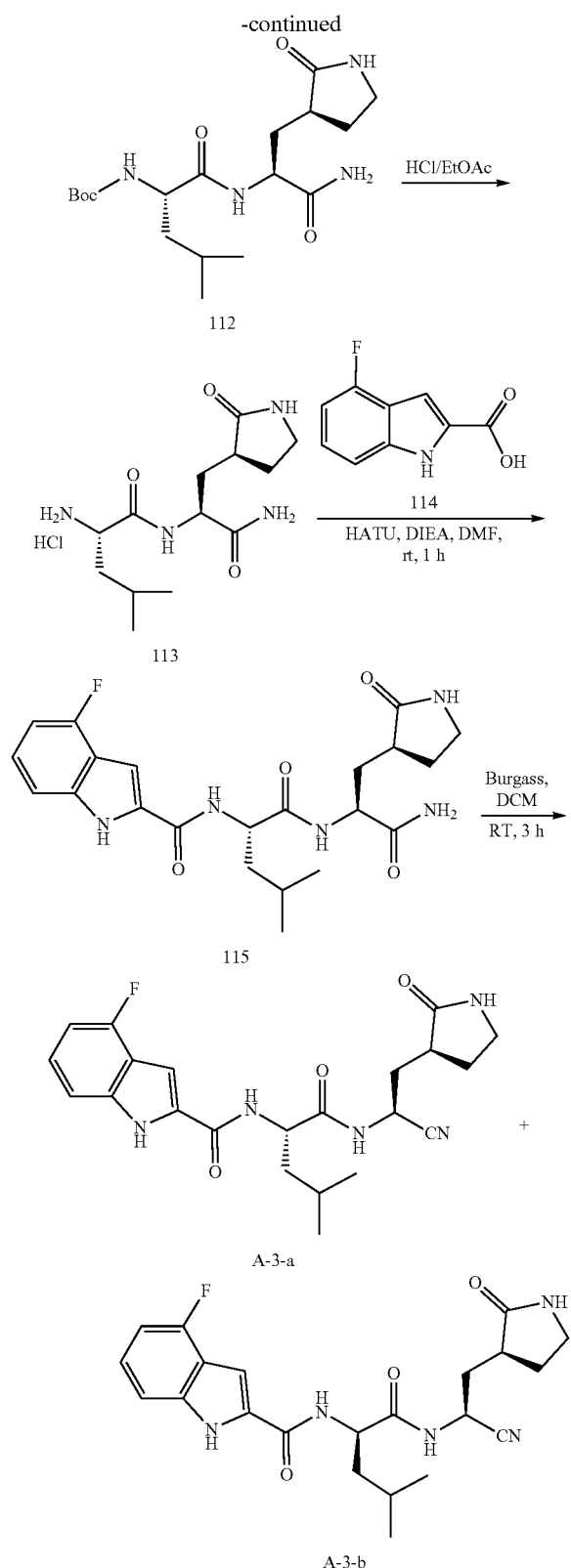

night. After completion of reaction (monitored by LCMS), the reaction mixture was concentrated down under reduced pressure to give a crude compound 112 as a white solid (10.5 g, 27.31 mmol, 109.11%), which was used for the next step without further purification. LCMS=[M+H]$^+$: 385.0. $^1$H NMR (400 MHz, DMSO-d$_6$) δ 7.83 (d, J=8.4 Hz, 1H), 7.56 (s, 1H), 7.28 (s, 1H), 7.03 (s, 1H), 6.98 (d, J=7.7 Hz, 1H), 4.33-4.22 (m, 1H), 3.96-3.86 (m, 1H), 3.22-2.99 (m, 2H), 2.32-2.09 (m, 2H), 2.05-1.95 (m, 1H), 1.72-1.56 (m, 2H), 1.54-1.46 (m, 1H), 1.45-1.32 (m, 11H), 0.91-0.76 (m, 6H).

To a solution of tert-butyl ((S)-1-(((S)-1-amino-1-oxo-3-((S)-2-oxopyrrolidin-3-yl)propan-2-yl)-amino)-4-methyl-1-oxopentan-2-yl)carbamate (compound 112) (5 g, 13.00 mmol) in EtOAc (20 mL) was added 4M HCl in EtOAc (50 mL). The reaction mixture was stirred at room temperature for 2 h. LCMS indicated completion of the reaction. The reaction mixture was concentrated down under reduced pressure to give the compound 113 (3.96 g, 12.34 mmol, 94.96%) as a white solid, which was used for next step without further purification. LCMS=[M+H]$^+$: 285.0.

To a stirred solution of 4-fluoro-1H-indole-2-carboxylic acid (compound 114) (180 mg, 1.00 mmol) in DMF (4 mL) was added (2S)-2-amino-N-[(1S)-1-carbamoyl-2-[(3S)-2-oxopyrrolidin-3-yl]ethyl]-4-methylpentan-amide hydrochloride (compound 113) (385 mg, 1.21 mmol), HATU (573 mg, 1.51 mmol) and DIEA (0.6 mL, 4.02 mmol). The reaction mixture was stirred at room temperature under N$_2$ for 1 h. LCMC indicated completion of the reaction. The reaction mixture was concentrated down under reduced pressure, and the resulting residue was purified by reverse phase column chromatography (0.5% FA/ACN) to provide compound 115 (90 mg, 0.20 mmol, 20.11%) as an off-white solid. LCMS=[M+H]$^+$: 446.0. $^1$H NMR (400 MHz, DMSO-d$_6$) δ 11.93 (s, 1H), 8.57 (d, J=7.8 Hz, 1H), 8.09 (d, J=8.3 Hz, 1H), 7.58 (s, 1H), 7.37 (s, 1H), 7.26 (d, J=8.5 Hz, 2H), 7.16 (s, 1H), 7.04 (s, 1H), 6.81 (s, 1H), 4.57-4.44 (m, 1H), 4.33-4.22 (m, 1H), 3.17-3.02 (m, 2H), 2.37-2.19 (m, 1H), 2.20-2.08 (m, 1H), 2.07-1.96 (m, 1H), 1.78-1.45 (m, 5H), 0.93 (d, J=6.1 Hz, 3H), 0.89 (d, J=6.2 Hz, 3H).

To a stirred solution of (2S)—N-[(1S)-1-carbamoyl-2-[(3S)-2-oxopyrrolidin-3-yl]ethyl]-2-[(4-fluoro-1H-indol-2-yl)formamido]-4-methylpentanamide (compound 115) (2.45 g, 5.5 mmol) in DCM (30 mL) was added Burgess reagent (2.62 g, 11 mmol). The solution was stirred at room temperature under the N$_2$ for 3 h. After the reaction was completed (monitored by LCMS), the reaction mixture was diluted with DCM and washed with water. The organic layer was separated, washed with brine, dried over sodium sulfate, and concentrated down under reduced pressure. The resulting residue was then purified by prep-HPLC to provide compound A-3-a (2S)—N-[(1S)-1-cyano-2-[(3S)-2-oxopyrrolidin-3-yl]ethyl]-2-[(4-fluoro-1H-indol-2-yl)-formamido]-4-methylpentanamide (1.08 g, 45%) as an off-white solid, and a second isomer (A-3-b) (51.6 mg, 2.2%). LCMS=[M+H]$^+$: 428.2. A-3-a $^1$H NMR (400 MHz, DMSO-d$_6$) δ 11.93 (s, 1H), 8.93 (d, J=7.9 Hz, 1H), 8.63 (d, J=7.6 Hz, 1H), 7.70 (s, 1H), 7.39 (s, 1H), 7.26 (d, J=8.3 Hz, 1H), 7.16 (dt, J=13.4, 6.7 Hz, 1H), 6.82 (dd, J=10.6, 7.7 Hz, 1H), 5.03-4.93 (m, 1H), 4.53-4.43 (m, 1H), 3.19-3.06 (m, 2H), 2.42-2.30 (m, 1H), 2.20-2.07 (m, 2H), 1.86-1.77 (m, 1H), 1.77-1.66 (m, 3H), 1.60-1.49 (m, 1H), 0.95 (d, J=6.3 Hz, 3H), 0.90 (d, J=6.3 Hz, 3H).

Second isomer (A-3-b): LCMS=[M+H]$^+$: 428.2. $^1$H NMR (400 MHz, DMSO-d$_6$) δ 11.89 (s, 1H), 8.52 (d, J=8.2 Hz, 1H), 8.43 (s, 1H), 8.10 (t, J=5.6 Hz, 1H), 7.38 (d, J=1.6 Hz, 1H), 7.26 (d, J=8.2 Hz, 1H), 7.19-7.10 (m, 1H), 6.81 (dd, J=10.6, 7.8 Hz, 1H), 4.64-4.54 (m, 1H), 4.53-4.43 (m, 1H), To a flask containing methyl (S)-2-((S)-2-((tert-butoxycarbonyl)amino)-4-methylpentanamido)-3-((S)-2-oxopyrrolidin-3-yl)propanoate (compound 106) (10 g, 25.03 mmol) was added ammonia (300 mL). The reaction mixture was placed in an autoclave reactor and stirred at 50° C. over- 3.28-3.04 (m, 2H), 2.78-2.60 (m, 1H), 2.36-2.19 (m, 1H), 2.02-1.79 (m, 2H), 1.76-1.59 (m, 2H), 1.59-1.38 (m, 2H), 0.90 (dd, J=15.8, 6.3 Hz, 6H).

Example S9: Synthesis of Compound A-3-c

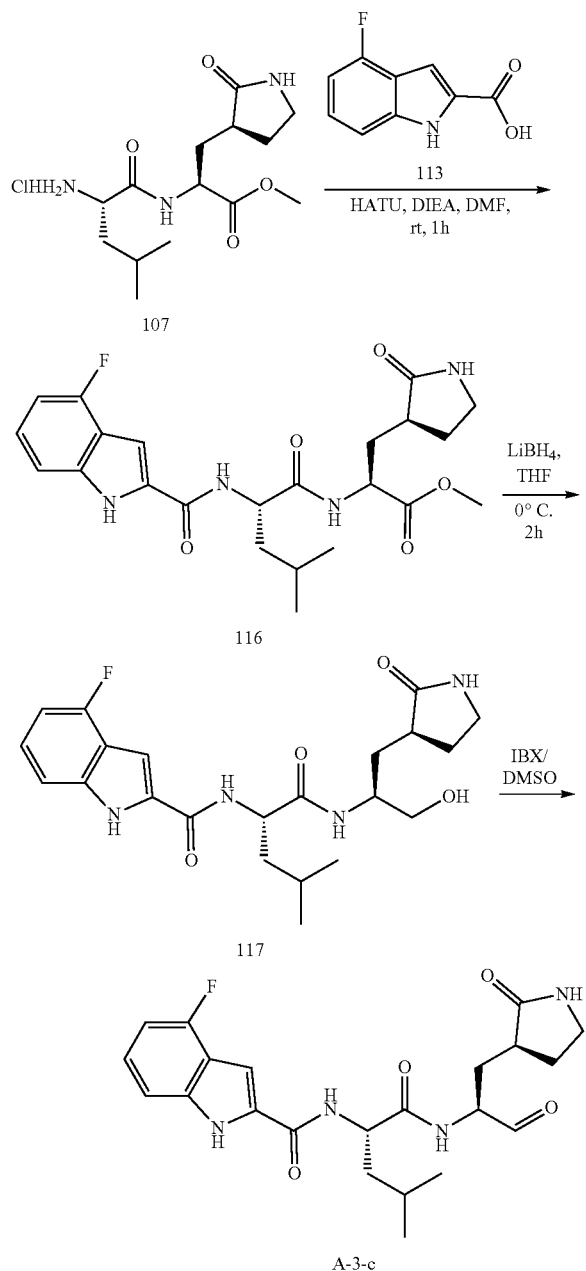

To a solution of 4-fluoro-1H-indole-2-carboxylic acid (compound 113) (2 g, 11.16 mmol) in DMF (20 mL) were added methyl 2-[(2S)-2-amino-4-methylpentanamido]-3-(2-oxopyrrolidin-3-yl) propanoate (compound 107) (3.34 g, 11.16 mmol), HATU (6.37 g, 16.75 mmol) and DIEA (7.380 mL, 44.66 mmol). The reaction mixture was stirred at rt for 1 h. LCMS indicated completion of the reaction. The reaction mixture was diluted with water and extracted with EtOAc. The organic layer was separated, washed with brine, dried over sodium sulfate, and concentrated down under reduced pressure. The resulting residue was purified by prep-HPLC to yield compound 116 (3.62 g, 7.86 mmol, 70.41%) as a yellow solid. LCMS=[M+H]$^+$: 461.0.

To a solution of methyl 2-[(2S)-2-[(4-fluoro-1H-indol-2-yl)formamido]-4-methylpentanamido]-3-(2-oxopyrrolidin-3-yl)propanoate (compound 116) (1.44 g, 3.13 mmol) (16) in THF (10 mL) was added LiBH$_4$ (0.27 g, 12.51 mmol). The reaction mixture was stirred at room temperature for 3 h. LCMS indicated completion of the reaction. The reaction was quenched with water, extracted with EtOAc. The organic phase was concentrated, and the residue was purified by column chromatography (DCM/MeOH=from 20:1 to 15:1) to yield compound 117 (1.1 g, 2.54 mmol, 81.48%) as a white solid. LCMS=[M+H]$^+$: 433.1.

To a solution of (2S)-2-[(4-fluoro-1H-indol-2-yl)formamido]-N-[1-hydroxy-3-(2-oxopyrrolidin-3-yl)propan-2-yl]-4-methylpentanamide (compound 117) (500 mg, 1.16 mmol) in DMSO (1.5 mL) were added EtOAc (3 mL) and IBX (647.45 mg, 2.31 mmol). The reaction mixture was stirred at 25° C. overnight. LCMS indicated completion of the reaction. The reaction mixture was diluted with EtOAc and then filtered. The filtrate was quenched with sat. aqueous Na$_2$S$_2$O$_3$, washed with sat. aqueous sodium bicarbonate and brine. The organic phase was separated, concentrated down under reduced pressure, and then purified by prep-HPLC to yield compound A-3-c (14 mg, 0.03 mmol, 2.80%) as a white solid. LCMS= [M+H]$^+$: 431.2, HPLC: 97.65%. $^1$H NMR (400 MHz, CDCl$_3$) δ 9.82 (s, 1H), 9.52 (s, 1H), 8.69 (d, 1H), 7.22-7.15 (m, 2H), 7.13-7.02 (m, 2H), 6.82-6.73 (m, 1H), 6.18 (s, 1H), 4.97-4.80 (m, 1H), 4.45-4.27 (m, 1H), 3.39-3.15 (m, 2H), 2.55-2.41 (m, 1H), 2.40-2.30 (m, 1H), 2.05-1.91 (m, 2H), 1.89-1.71 (m, 4H), 0.99 (d, J=3.8 Hz, 6H).

Example 510: Synthesis of Compound A-3-d

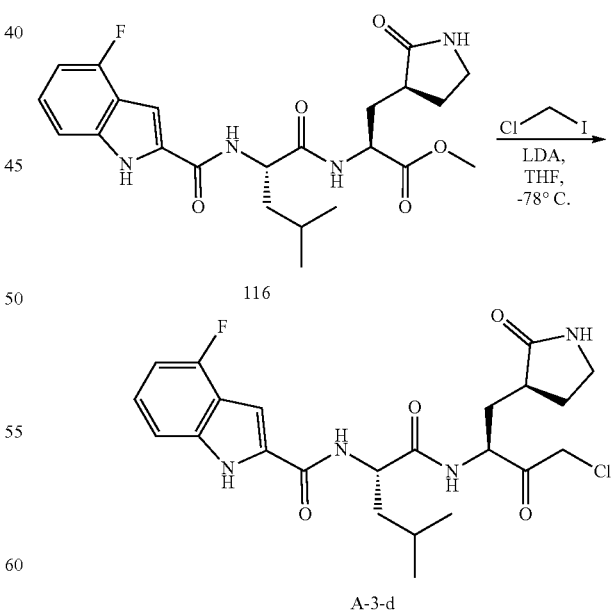

To a stirred solution of methyl (2S)-2-[(2S)-2-[(4-fluoro-1H-indol-2-yl)formamido]-4-methylpentanamido]-3-[(3S)-2-oxopyrrolidin-3-yl]propanoate (compound 116) (300 mg, 0.65 mmol) and chloroiodomethane (0.48 mL, 6.51 mmol)

in THF (10 mL) at −78° C. was added LDA (4 mL, 30.25 mmol, 2 M in THF). The reaction mixture was stirred at −78° C. under N₂ for 3 h. LCMS indicted completion of the reaction. The reaction mixture was quenched with NH₄Cl (50 ml) and extracted with EtOAc (60 ml×3). The combined organic layers were concentrated down under reduced pressure. The resulting crude material was purified by prep-HPLC to yield compound A-3-d (33.79 mg, 0.07 mmol, 10.83%) as an off-white solid. LCMS=[M+H]⁺: 479.2. ¹H NMR (400 MHz, DMSO-d₆) δ 11.94 (s, 1H), 8.69-8.57 (m, 2H), 7.65 (s, 1H), 7.39 (d, J=1.5 Hz, 1H), 7.25 (s, 1H), 7.16 (d, J=5.4 Hz, 1H), 6.81 (s, 1H), 4.59 (d, J=1.3 Hz, 2H), 4.54-4.40 (m, 2H), 3.18-3.03 (m, 2H), 2.35-2.22 (m, 1H), 2.14-1.92 (m, 2H), 1.78-1.52 (m, 5H), 0.95 (d, J=6.2 Hz, 3H), 0.90 (d, J=6.3 Hz, 3H).

Example S11: Synthesis of Compound A-3-e

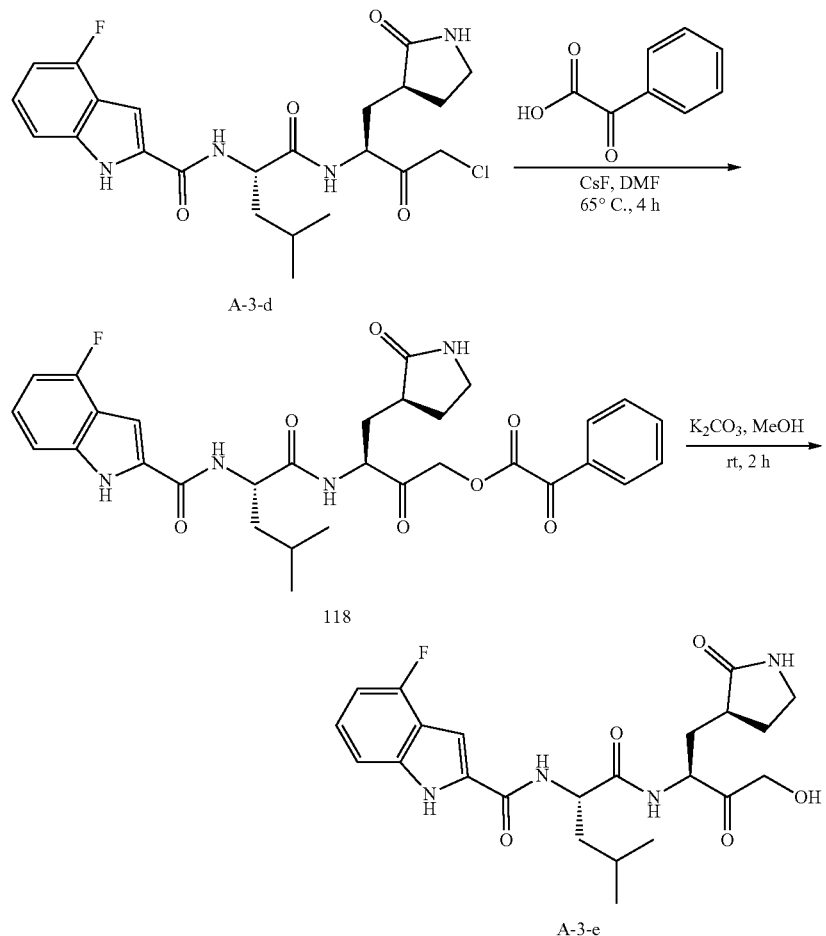

To a stirred solution of (2S)—N-[(2S)-4-chloro-3-oxo-1-[(3S)-2-oxopyrrolidin-3-yl]butan-2-yl]-2-[(4-fluoro-1H-indol-2-yl)formamido]-4-methylpentanamide (compound A-3-d) (120 mg, 0.25 mmol) in DMF (5 mL) was added 2-oxo-2-phenylacetic acid (0.035 mL, 0.33 mmol) and CsF (87.02 mg, 0.58 mmol). The reaction mixture was stirred at 65° C. under N₂ for 4 h. LCMS indicated completion of the reaction. The reaction mixture was filtered. The filtrate was concentrated down under reduced pressure. The resulting residue was purified by prep-HPLC to yield compound 118 (67 mg, 0.11 mmol, 45.12%) as a yellow solid. LCMS=[M+H]⁺: 593.0. ¹H NMR (400 MHz, DMSO-d₆) δ 11.94 (s, 1H), 8.72 (d, J=7.7 Hz, 1H), 8.64 (d, J=7.4 Hz, 1H), 8.12-8.07 (m, 2H), 7.83 (t, J=7.4 Hz, 1H), 7.70-7.62 (m, 3H), 7.41 (s, 1H), 7.27 (d, J=8.3 Hz, 1H), 7.20-7.12 (m, 1H), 6.82 (dd, J=10.5, 7.7 Hz, 1H), 5.28 (s, 2H), 4.58-4.48 (m, 2H), 3.18-3.07 (m, 2H), 2.38-2.30 (m, 1H), 2.15-2.03 (m, 2H), 1.80-1.60 (m, 5H), 0.97 (d, J=6.3 Hz, 3H), 0.92 (d, J=6.3 Hz, 3H).

To a stirred solution of (3S)-3-[(2S)-2-[(4-fluoro-1H-indol-2-yl)formamido]-4-methylpentanamido]-2-oxo-4-[(3S)-2-oxopyrrolidin-3-yl]butyl 2-oxo-2-phenylacetate (compound 118) (100 mg, 0.17 mmol) in MeOH (4 mL) was added NaHCO₃ (2 mg, 0.02 mmol). The reaction mixture was stirred at room temperature under N₂ for 2 h. After the reaction was completed (monitored by LCMS), the reaction mixture was filtered, and filtrate was concentrated down under reduced pressure. The resulting residue was purified by prep-HPLC (ACN/water (0.1% FA)) to yield compound A-3-e (2S)-2-[(4-fluoro-1H-indol-2-yl)formamido]-N-[(2S)-4-hydroxy-3-oxo-1-[(3S)-2-oxopyrrolidin-3-yl]butan-2-yl]-4-methylpentanamide (42.43 mg, 0.09 mmol, 54.60%) as an off-white solid. LCMS=[M+H]⁺: 461.2. ¹H NMR (400 MHz, DMSO) δ 11.93 (s, 1H), 8.57 (d, J=7.9 Hz, 1H), 8.50 (d, J=8.3 Hz, 1H), 7.62 (s, 1H), 7.39 (s, 1H), 7.26 (d, J=8.1 Hz, 1H), 7.19-7.11 (m, 1H), 6.85-6.77 (m, 1H), 5.06 (s, 1H), 4.57-4.40 (m, 2H), 4.30-4.09 (m, 2H), 3.16-3.05 (m, 2H), 2.34-2.29 (m, 1H), 2.13-2.05 (m, 1H), 1.99-1.88 (m, 1H), 1.78-1.58 (m, 5H), 0.95 (d, J=5.9 Hz, 3H), 0.90 (d, J=6.3 Hz, 3H).

Example S12: Synthesis of Compound A-4-a

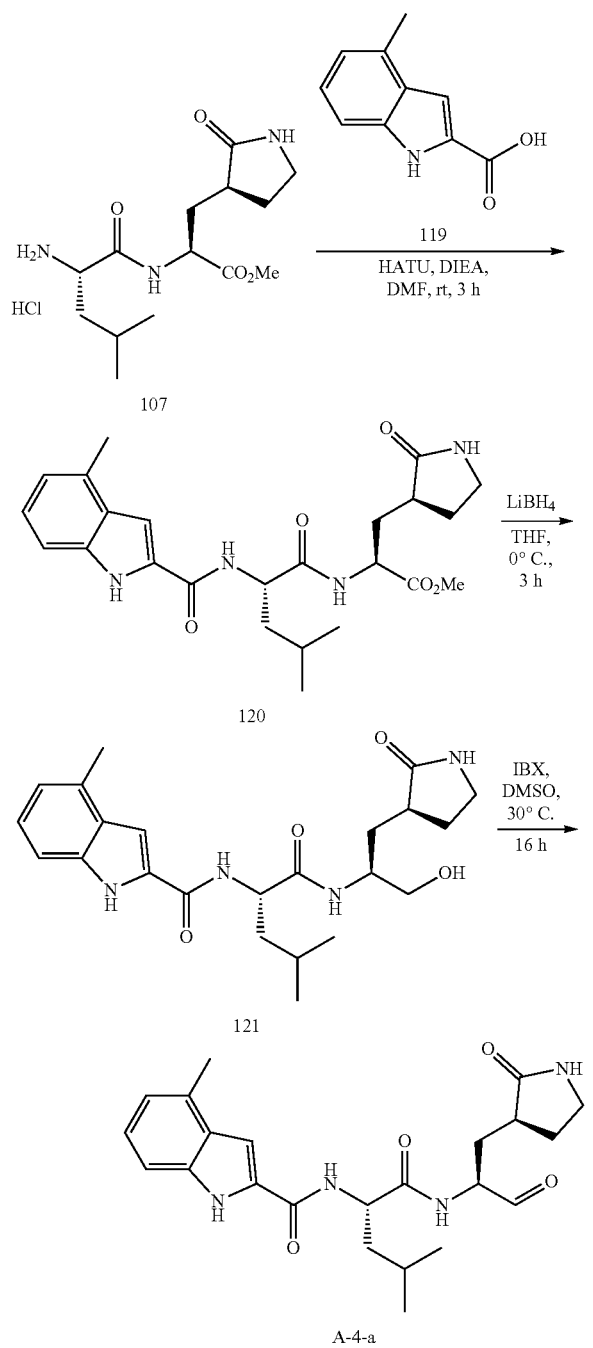

To a stirred mixture of methyl (S)-2-((S)-2-amino-4-methylpentanamido)-3-((S)-2-oxopyrrolidin-3-yl)propanoate hydrochloride (compound 107) (3.35 g, 10 mmol) and DIEA (3.87 g, 30 mmol) in DMF (20 mL) at room temperature was added 4-methyl-1H-indole-2-carboxylic acid (compound 119) (1.75 g, 10 mmol) and HATU (4.57 g, 12 mmol). The reaction mixture was stirred for 3 h. LCMS showed the reaction was complete. The reaction mixture was diluted with EtOAc and washed with brine. The organic layers were combined, dried over sodium sulfate, and concentrated down under reduced pressure. The resulting residue was purified with column chromatography (PE/EA=1:1) to yield compound 120 as an off-white solid (3 g; 65.6%). LCMS=[M+H]$^+$: 457.0.

To a stirred solution of methyl (S)-2-((S)-4-methyl-2-(4-methyl-1H-indole-2-carboxamido)-pentanamido)-3-((S)-2-oxopyrrolidin-3-yl)propanoate (1.0 g, 2.18 mmol) compound 120 in THF (30 mL) at 0° C. was added LiBH$_4$ (145 mg, 6.6 mmol). The reaction mixture was stirred at 0° C. for 3 h. After completion of reaction (monitored by LCMS), the reaction mixture was quenched with sat. aqueous NH$_4$Cl until no more gas formed. The solid was filtered. The filtrate was extracted with EtOAc (100 mL×3) and washed with water. The organic layer was dried over anhydrous Na$_2$SO$_4$ and solvent was removed under reduced pressure. The resulting residue was purified by column chromatography (DCM:MeOH=15:1) to yield compound 121 (600 mg, 64%) as a white solid. LCMS=[M+H]$^+$: 429.5. $^1$H NMR (400 MHz, DMSO-d$_6$) δ 11.59 (s, 1H), 8.43 (d, J=8.2 Hz, 1H), 7.83 (d, J=8.9 Hz, 1H), 7.57 (s, 1H), 7.38 (s, 1H), 7.30 (d, J=8.2 Hz, 1H), 7.13 (t, J=7.6 Hz, 1H), 6.89 (d, J=7.0 Hz, 1H), 4.73 (t, J=5.5 Hz, 1H), 4.61-4.47 (m, 1H), 3.87 (s, 1H), 3.37-3.26 (m, 2H), 3.22-3.04 (m, 2H), 2.56 (s, 3H), 2.38-2.12 (m, 2H), 1.88-1.81 (m, 1H), 1.78-1.70 (m, 2H), 1.64-1.53 (m, 2H), 1.49-1.37 (m, 1H), 0.97 (dd, J=16.0, 6.2 Hz, 6H).

To a stirred mixture of N—((S)-1-(((S)-1-hydroxy-3-((S)-2-oxopyrrolidin-3-yl)propan-2-yl)amino)-4-methyl-1-oxopentan-2-yl)-4-methyl-1H-indole-2-carboxamide (compound 121) (150 mg, 0.35 mmol) in DMSO (5 mL) was added IBX (196.03 mg, 0.70 mmol). The reaction mixture was stirred at 30° C. overnight. LCMS indicated completion of the reaction. The reaction mixture was concentrated down under reduced pressure and the resulting residue was purified by prep-HPLC (ACN/water (0.1% FA)) to yield compound A-4-a. LCMS=[M+H]$^+$: 427.3. $^1$H NMR (400 MHz, DMSO-d$_6$) δ 11.54 (s, 1H), 9.43 (s, 1H), 8.63-8.32 (m, 1H), 7.66-7.53 (m, 1H), 7.48 (s, 1H), 7.33 (d, J=10.7 Hz, 1H), 7.24 (d, J=8.2 Hz, 1H), 7.07 (t, J=7.7 Hz, 1H), 6.83 (d, J=7.0 Hz, 1H), 5.78-5.63 (m, 1H), 4.74-4.66 (m, 0.5H), 4.61-4.48 (m, 1H), 3.79-3.64 (m, 0.5H), 3.18-2.98 (m, 2H), 2.50 (s, 3H), 2.36-2.08 (m, 2H), 1.96-1.34 (m, 6H), 1.03-0.85 (m, 6H).

Example S13: Synthesis of Compound A-4-b

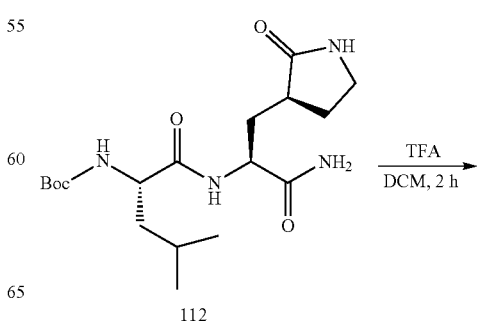

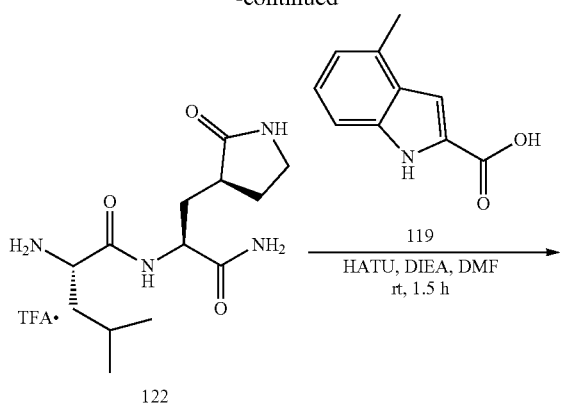

To a solution of (2S)—N-[(1S)-1-carbamoyl-2-(2-oxopyrrolidin-3-yl)ethyl]-4-methyl-2-[(4-methyl-1H-indol-2-yl)formamido]pentanamide (compound 123) (356 mg, 0.81 mmol) in DCM (6 mL) were added Burgess reagent (0.373 mL, 2.04 mmol) under 0° C. The reaction mixture was stirred at room temperature for 3 h. LCMS indicated that the reaction was complete. The reaction mixture was concentrated down under reduced pressure. The residue was purified by prep-HPLC to yield compound A-4-b (30 mg, 0.07 mmol, 8.79%) as a white solid. LCMS=[M+H]$^+$: 424.2; HPLC: 99.71%. $^1$H NMR (400 MHz, CDCl$_3$) δ 9.67 (s, 1H), 8.74 (s, 1H), 7.25-7.24 (m, 1H), 7.16 (t, J=7.5 Hz, 1H), 6.96-6.83 (m, 3H), 6.25 (s, 1H), 4.91-4.74 (m, 2H), 3.37-3.17 (m, 2H), 2.48 (s, 3H), 2.41-2.29 (m, 2H), 2.03-1.90 (m, 1H), 1.86-1.76 (m, 5H), 1.09-0.92 (m, 6H).

Example 514: Synthesis of Compound A-4-c

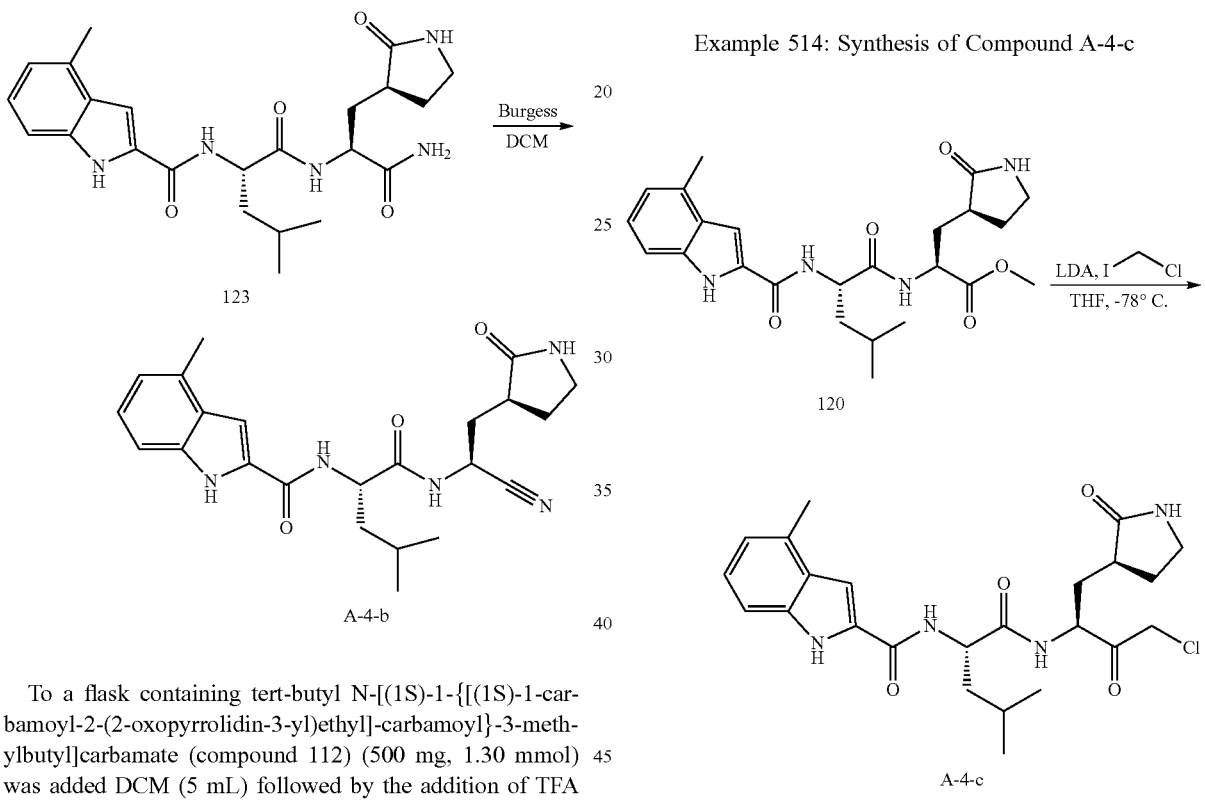

To a flask containing tert-butyl N-[(1S)-1-{[(1S)-1-carbamoyl-2-(2-oxopyrrolidin-3-yl)ethyl]-carbamoyl}-3-methylbutyl]carbamate (compound 112) (500 mg, 1.30 mmol) was added DCM (5 mL) followed by the addition of TFA (1.5 mL, 20.19 mmol). The reaction mixture was stirred at room temperature overnight. DCM was removed under reduced pressure to yield crude compound 122 (510 mg, 99%) as a yellow oil, which was used for next step without further purification. LCMS=[M+H]$^+$: 285.2.

To a solution of 4-methyl-1H-indole-2-carboxylic acid (compound 119) (175 mg, 1.00 mmol) in DMF (5 mL) were added HATU (570 mg, 1.50 mmol), DIEA (0.660 mL, 3.99 mmol) and (2S)-2-amino-N-[(1S)-1-carbamoyl-2-(2-oxopyrrolidin-3-yl)ethyl]-4-methylpentanamide TFA salt (compound 122) (crude, 510 mg, 1.30 mmol). The reaction mixture was stirred at room temperature for 3 hr. LCMS indicated completion of the reaction. The reaction mixture was diluted with water and extracted with EtOAc. The organic layer was separated, washed with brine, dried over anhydrous Na$_2$SO$_4$, and concentrated down under reduced pressure. The resulting residue was purified by prep-HPLC to yield compound 123 (356 mg, 0.81 mmol, 67.43%) as a white solid. LCMS=[M+H]$^+$: 442.1.

To a stirred mixture of methyl (2R)-2-[(2S)-4-methyl-2-[(4-methyl-1H-indol-2-yl)formamido]pentanamido]-3-[(3R)-2-oxopyrrolidin-3-yl]propanoate (compound 120) (300 mg, 0.66 mmol) and chloroiodomethane (1.16 g, 6.6 mmol) in THF (5 mL) at −78° C. was added LDA (21 mL, 7 mmol, 2 M in THF). The reaction mixture was stirred at −78° C. for 2 h, then quenched with sat. NH$_4$Cl, and extracted with EtOAc (15 mL×3). The combined organic layers were washed with brine, dried over anhydrous Na$_2$SO$_4$, filtered and concentrated under reduced pressure. The resulting residue was purified by prep-HPLC to yield compound A-4-c (28.1 mg, 0.06 mmol, 9.00%). LCMS=[M+H]$^+$: 475.3. $^1$H NMR (400 MHz, DMSO-d$_6$) δ 11.54 (s, 1H), 8.63 (d, J=7.7 Hz, 1H), 8.48 (d, J=7.6 Hz, 1H), 7.64 (s, 1H), 7.34 (s, 1H), 7.24 (d, J=8.2 Hz, 1H), 7.07 (t, J=7.7 Hz, 1H), 6.83 (d, J=7.0 Hz, 1H), 4.59 (s, 2H), 4.51-4.40 (m, 2H), 3.21-3.03 (m, 2H), 2.54 (s, 3H), 2.35-2.20 (m, 1H), 2.10 (m, 1H), 2.01-1.93 (m, 1H), 1.78-1.52 (m, 5H), 0.96-0.88 (m, 6H).

Example S15: Synthesis of Compound A-4-d

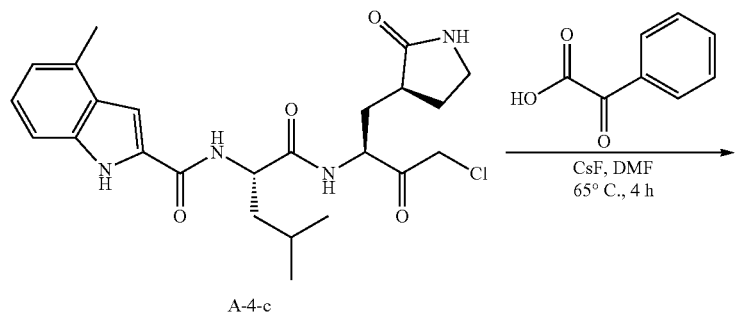

A-4-c

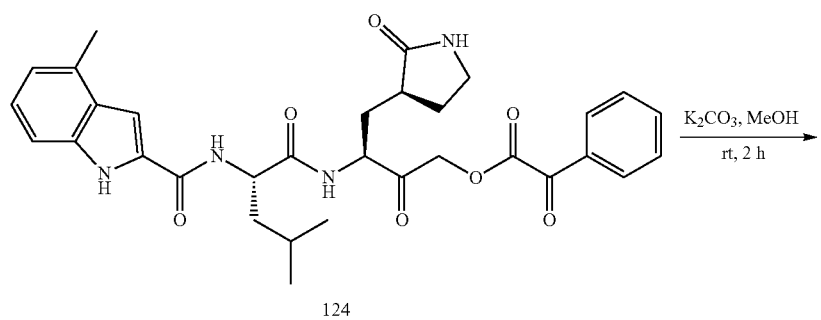

124

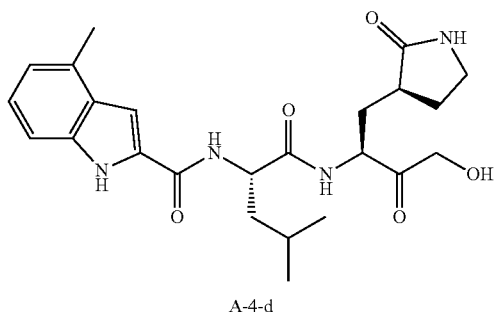

A-4-d

To a stirred solution of (2S)—N-[(2S)-4-chloro-3-oxo-1-[(3S)-2-oxopyrrolidin-3-yl]butan-2-yl]-4-methyl-2-[(4-methyl-1H-indol-2-yl)formamido]pentanamide (compound A-4-c) (200 mg, 0.42 mmol) in DMF (3 mL) was added 2-oxo-2-phenylacetic acid (0.060 mL, 0.55 mmol) and CsF (146.23 mg, 0.97 mmol). The reaction mixture was stirred at 65° C. under $N_2$ for 4 h. After the reaction was complete (monitored by LCMS), the reaction mixture was filtered. The filtrate was concentrated down under reduced pressure and resulting residue was purified by prep-HPLC to yield compound 124 (85 mg, 0.14 mmol, 34.29%) as a brown solid. LCMS=[M+H]$^+$: 589.2. $^1$H NMR (400 MHz, CDCl$_3$) δ 9.60 (s, 1H), 8.93 (d, J=5.6 Hz, 1H), 8.15 (d, J=7.3 Hz, 2H), 7.67 (t, J=7.4 Hz, 1H), 7.52 (t, J=7.8 Hz, 2H), 7.27-7.25 (m, 1H), 7.21-7.16 (m, 1H), 6.99 (s, 1H), 6.91 (d, J=7.0 Hz, 1H), 6.86 (d, J=8.0 Hz, 1H), 5.20 (d, J=16.9 Hz, 1H), 5.00 (d, J=16.9 Hz, 1H), 4.85-4.78 (m, 1H), 4.54-4.47 (m, 1H), 3.36-3.23 (m, 2H), 2.51 (s, 3H), 2.48-2.40 (m, 1H), 2.39-2.31 (m, 1H), 2.13-2.03 (m, 1H), 2.01-1.93 (m, 1H), 1.89-1.66 (m, 4H), 1.03 (d, J=4.9 Hz, 6H).

To a stirred solution of (3S)-3-[(2S)-4-methyl-2-[(4-methyl-1H-indol-2-yl)formamido]-pentanamido]-2-oxo-4-[(3S)-2-oxopyrrolidin-3-yl]butyl 2-oxo-2-phenylacetate (compound 124) (80 mg, 0.14 mmol) in MeOH (3 mL) was added NaHCO$_3$ (1.14 mg, 0.01 mmol). The reaction mixture was stirred at room temperature under the $N_2$ for 2 h. After the reaction was completed (monitored by LCMS), the reaction mixture was concentrated down under reduced pressure. The resulting residue was purified by prep-HPLC (ACN/water (0.084% NH$_4$HCO$_3$)) to yield compound A-4-d (22.97 mg, 0.05 mmol, 37.02%) as an off-white solid. LCMS=[M+H]$^+$: 457.3. $^1$H NMR (400 MHz, CDCl$_3$) δ 9.73-9.48 (m, 1H), 8.79-8.55 (m, 1H), 7.29-7.26 (m, 1H), 7.20-7.16 (m, 1H), 7.01 (d, J=7.5 Hz, 1H), 6.91 (d, J=6.9 Hz, 1H), 6.25 (br s, 1H), 4.81-4.73 (m, 1H), 4.59-4.42 (m, 2H), 4.41-4.31 (m, 1H), 3.38-3.17 (m, 2H), 2.52 (s, 3H), 2.37-2.27 (m, 1H), 2.17-1.99 (m, 6H), 1.93-1.91 (m, 1H), 1.01 (d, J=4.7 Hz, 6H).

Example S16: Synthesis of Compound A-4-e

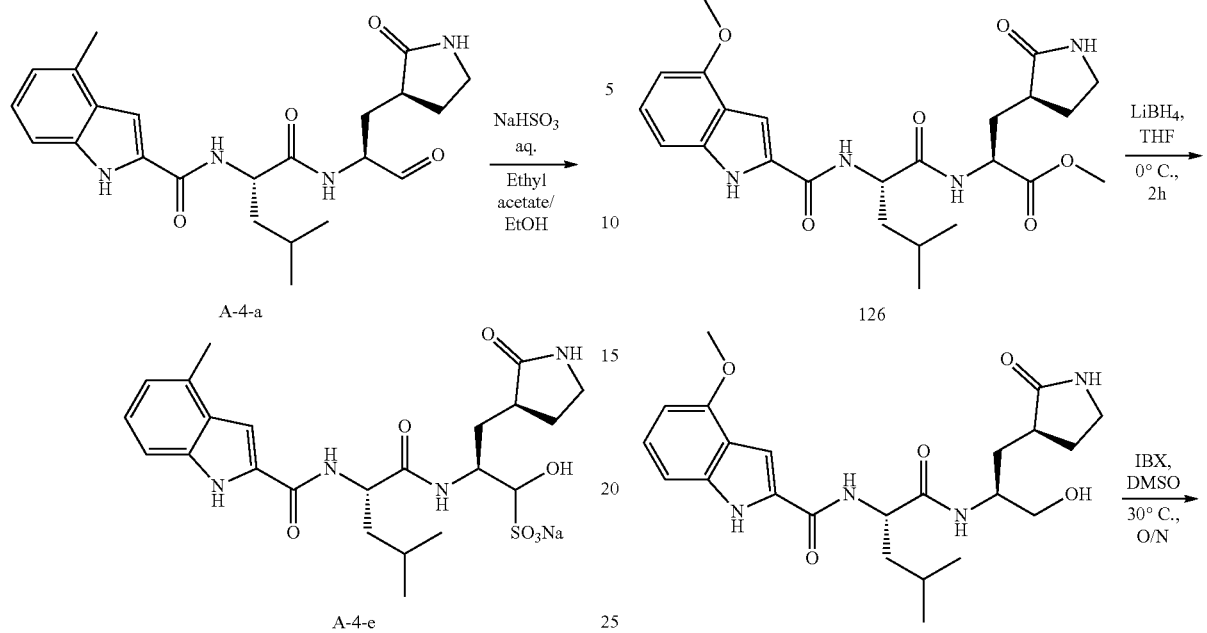

To a stirred solution of 4-methyl-N—((S)-4-methyl-1-oxo-1-(((S)-1-oxo-3-((S)-2-oxopyrrolidin-3-yl)propan-2-yl)amino)pentan-2-yl)-1H-indole-2-carboxamide (compound A-4-a) (2.0 g, 4.69 mmol) in ethyl acetate (13 mL) and EtOH (8 mL) at room temperature was added a solution of NaHSO$_3$ (0.46 mg, 4.42 mmol) in water (4.6 mL). The reaction mixture was stirred at 50° C. for 3 h. After the completion of the reaction (monitored/LCMS), the organic layer was removed. The aqueous layer was washed with ethyl acetate (100 mL×5) and concentrated down to remove remaining solvent. The residue was lyophilized to yield compound A-4-e as off-white solid (2.0 g, 80.4%). LCMS= [M−Na$^+$2H]$^+$: 509.4. $^1$H NMR (500 MHz, DMSO) δ 11.57 (d, J=5.3 Hz, 1H), 8.46 (dd, J=24.4, 8.0 Hz, 1H), 7.71 (dd, J=58.5, 9.0 Hz, 1H), 7.46 (s, 1H), 7.32 (d, J=9.6 Hz, 1H), 7.23 (d, J=7.9 Hz, 1H), 7.06 (t, J=7.5 Hz, 1H), 6.83 (d, J=6.7 Hz, 1H), 5.42 (d, J=40.7 Hz, 1H), 4.48 (d, J=32.9 Hz, 1H), 4.26 (t, J=9.8 Hz, 0.5H), 4.03 (dd, J=12.3, 5.5 Hz, 0.5H), 3.95 (s, 0.5H), 3.84 (s, 0.5H), 3.35 (s, 3H), 3.14-2.99 (m, 2H), 2.22-2.09 (m, 2H), 1.95 (dd, J=25.4, 11.7 Hz, 2H), 1.82-1.52 (m, 6H), 0.90 (d, J=18.6 Hz, 6H).

Example S17: Synthesis of Compound A-5-a

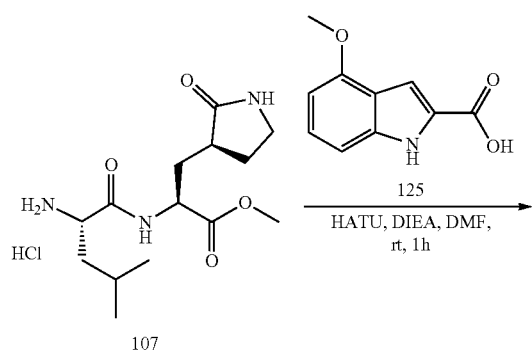

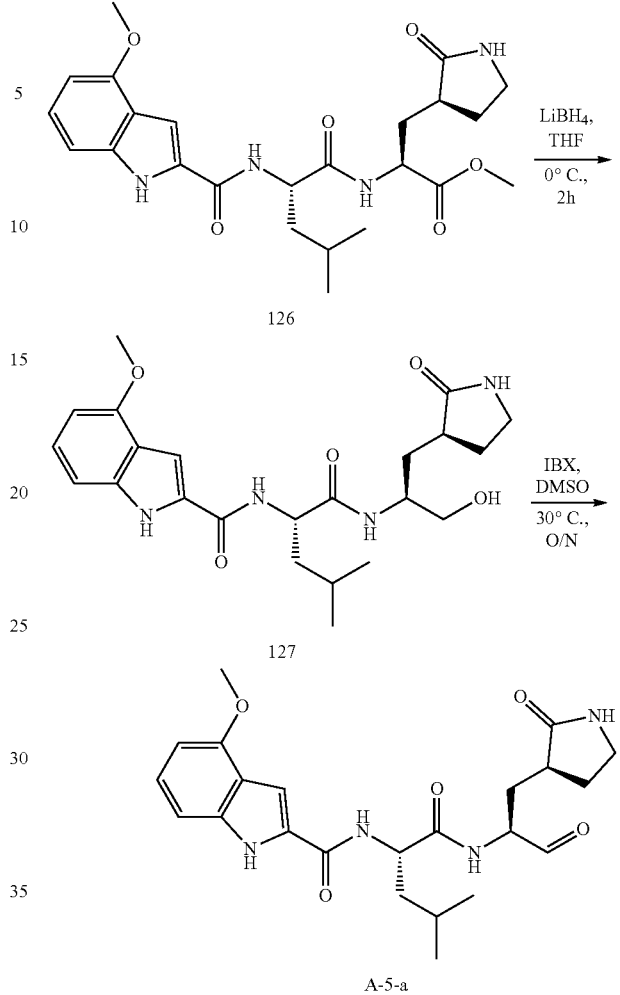

To a stirred solution of methyl (2S)-2-[(2S)-2-amino-4-methylpentanamido]-3-[(3S)-2-oxopyrrolidin-3-yl]propanoate (compound 107) (500 mg, 1.67 mmol) in DMF (10 mL) was added 4-methoxy-1H-indole-2-carboxylic acid (compound 125) (320 mg, 1.67 mmol), HATU (952 mg, 2.51 mmol) and DIEA (1.104 mL, 6.68 mmol). The reaction mixture was stirred at room temperature under N$_2$ for 1 h. LCMS indicated completion of the reaction. The reaction mixture was diluted with water and extracted with EtOAc. The organic layer was separated and concentrated down under reduced pressure. The resulting residue was purified by prep-HPLC to yield compound 126 (560 mg, 1.19 mmol, 70.96%) as an off-white solid. LCMS=[M+H]$^+$: 473.0. $^1$H NMR (400 MHz, DMSO-d$_6$) δ 11.56 (s, 1H), 8.44 (dd, J=64.4, 7.9 Hz, 2H), 7.64 (s, 1H), 7.35 (s, 1H), 7.13-6.97 (m, 2H), 6.51 (d, J=7.6 Hz, 1H), 4.59-4.30 (m, 2H), 3.88 (s, 3H), 3.62 (s, 3H), 3.20-3.02 (m, 2H), 2.41-2.27 (m, 1H), 2.18-2.02 (m, 2H), 1.77-1.49 (m, 5H), 0.96-0.86 (m, 6H).

To a stirred solution of methyl (2S)-2-[(2S)-2-[(4-methoxy-1H-indol-2-yl)-formamido]-4-methylpentanamido]-3-[(3S)-2-oxopyrrolidin-3-yl]propanoate (compound 126) (290 mg, 0.61 mmol) in THF (5 mL) under N$_2$ at 0° C. was added LiBH$_4$ (53 mg, 2.45 mmol). The reaction mixture was stirred at 0° C. for 2 h. LCMS indicated completion of the reaction. The reaction mixture was quenched with water and the solid was filtered off. The filtrate was extracted with EtOAc (60 mL×3), combined organic layers were washed with water, dried over anhydrous Na₂SO₄ and concentrated down under reduced pressure to yield crude compound 127 (230 mg, 0.52 mmol, 84.31%) as an off-white solid, which was used for next step without further purification. LCMS= [M+H]⁺: 445.0. ¹H NMR (400 MHz, DMSO-d₆) δ 11.56 (s, 1H), 8.33 (d, J=8.0 Hz, 1H), 7.73 (d, J=8.9 Hz, 1H), 7.51 (s, 1H), 7.34 (s, 1H), 7.09 (t, J=7.9 Hz, 1H), 7.00 (d, J=8.2 Hz, 1H), 6.50 (d, J=7.5 Hz, 1H), 4.66 (t, J=5.5 Hz, 1H), 4.47 (dd, J=8.7, 3.9 Hz, 1H), 3.89 (s, 3H), 3.83-3.77 (m, 1H), 3.39-3.34 (m, 1H), 3.28-3.20 (m, 1H), 3.16-2.99 (m, 2H), 2.33-2.07 (m, 2H), 1.87-1.75 (m, 1H), 1.74-1.62 (m, 2H), 1.62-1.47 (m, 2H), 1.46-1.32 (m, 1H), 0.96-0.84 (m, 6H).

To a stirred solution of (2S)—N-[(2S)-1-hydroxy-3-[(3S)-2-oxopyrrolidin-3-yl]propan-2-yl]-2-[(4-methoxy-1H-indol-2-yl)formamido]-4-methylpentanamide (compound 127) (400 mg, 1.80 mmol) in DMSO (2 mL) and EtOAc (6 mL) was added IBX (503 mg, 1.80 mmol). The reaction mixture was stirred at 30° C. for 16 h. LCMS indicated completion of the reaction. The reaction mixture was filtered, and the filtrate was diluted with EtOAc and washed with a mixture of NaCl and Na₂S₂O₃ (10:1), aqueous NaHCO₃ and brine. The organic layer was separated and concentrated down under reduced pressure. The resulting residue was purified by prep-HPLC (ACN/water (0.084% NH₄HCO₃)) to yield compound A-5-a (20.81 mg, 0.05 mmol, 2.61%) as an off-white solid. LCMS=[M+H]⁺: 443.2. ¹H NMR (400 MHz, CDCl₃) δ 9.55-9.39 (m, 2H), 8.57 (s, 1H), 7.20 (t, J=8.0 Hz, 1H), 7.13 (s, 1H), 7.02 (d, J=8.4 Hz, 1H), 6.82 (s, 1H), 6.50 (d, J=7.8 Hz, 1H), 6.12-5.94 (m, 1H), 4.89-4.81 (m, 1H), 4.38-4.30 (m, 1H), 3.94 (s, 3H), 3.39-3.19 (m, 2H), 2.57-2.42 (m, 1H), 2.40-2.25 (m, 1H), 1.99-1.91 (m, 2H), 1.85-1.77 (m, 4H), 1.00 (d, J=6.0 Hz, 6H).

Example S18: Synthesis of Compound A-5-b

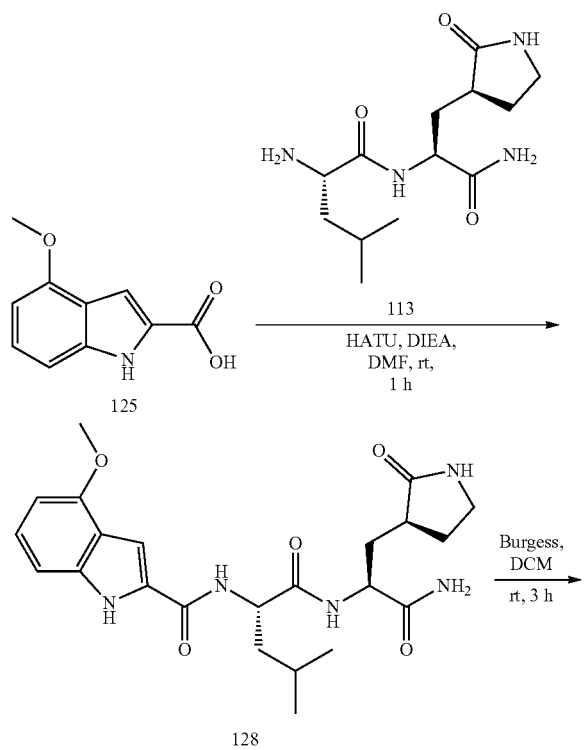

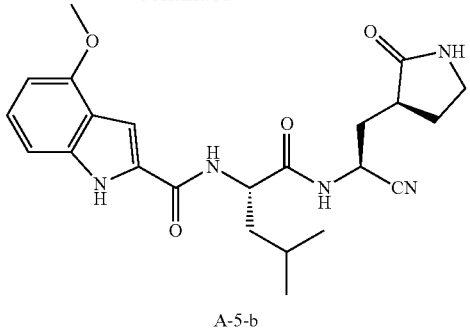

A-5-b

To a stirred solution of 4-methoxy-1H-indole-2-carboxylic acid (compound 125) (191 mg, 1.00 mmol) in DMF (5 mL) was added (2S)-2-amino-N-[(1S)-1-carbamoyl-2-[(3S)-2-oxopyrrolidin-3-yl]ethyl]-4-methylpentan-amide (compound 113) (341 mg, 1.20 mmol), HATU (570 mg, 1.50 mmol) and DIEA (0.660 mL, 4.00 mmol). The reaction mixture was stirred at room temperature under N₂ for 1 h. LCMS indicated completion of the reaction. The reaction mixture was diluted with EtOAc, organic layer was separated, washed with brine and concentrated down under reduced pressure. The resulting residue was purified by prep-HPLC (ACN/water (0.5% FA)) to yield compound 128 (200 mg, 0.44 mmol, 43.76%) as a yellow solid. LCMS= [M+H]⁺: 458.1. ¹H NMR (400 MHz, DMSO-d₆) δ 11.58 (s, 1H), 8.41 (d, J=7.9 Hz, 1H), 8.03 (d, J=8.5 Hz, 1H), 7.59 (s, 1H), 7.35 (d, J=1.7 Hz, 1H), 7.29 (s, 1H), 7.09-7.04 (m, J=19.6, 8.2 Hz, 3H), 6.51 (d, J=7.7 Hz, 1H), 4.52-4.43 (m, 1H), 4.31-4.24 (m, 1H), 3.88 (s, 3H), 3.16-2.99 (m, 2H), 2.35-2.19 (m, 1H), 2.19-2.06 (m, 1H), 2.05-1.95 (m, 1H), 1.74-1.61 (m, 3H), 1.60-1.46 (m, 2H), 0.93 (d, J=6.2 Hz, 3H), 0.88 (d, J=6.3 Hz, 3H).

To a stirred solution of (2S)—N-[(1S)-1-carbamoyl-2-[(3S)-2-oxopyrrolidin-3-yl]ethyl]-2-[(4-methoxy-1H-indol-2-yl)formamido]-4-methylpentanamide (compound 128) (100 mg, 0.22 mmol) in DCM (6 mL) was added Burgess reagent (260 mg, 0.55 mmol). The reaction mixture was stirred at room temperature under N₂ for 3 h. LCMS indicated completion of the reaction. The mixture was concentrated down under reduced pressure. The resulting residue was purified by prep-HPLC to yield compound A-5-b (26.35 mg, 0.06 mmol, 27.43%) as an off-white solid. LCMS=[M+H]⁺: 440.2. ¹H NMR (400 MHz, DMSO-d₆) δ 11.58 (s, 1H), 8.90 (d, J=8.1 Hz, 1H), 8.47 (d, J=7.7 Hz, 1H), 7.70 (s, 1H), 7.37 (d, J=1.6 Hz, 1H), 7.09 (d, J=7.9 Hz, 1H), 7.00 (d, J=8.2 Hz, 1H), 6.51 (d, J=7.6 Hz, 1H), 5.01-4.93 (m, 1H), 4.48-4.41 (m, 1H), 3.89 (s, 3H), 3.18-3.07 (m, 2H), 2.40-2.30 (m, 1H), 2.19-2.07 (m, 2H), 1.84-1.77 (m, 1H), 1.77-1.65 (m, 3H), 1.57-1.48 (m, 1H), 0.96-0.87 (m, 6H).

Example S19: Synthesis of Compound A-5-c

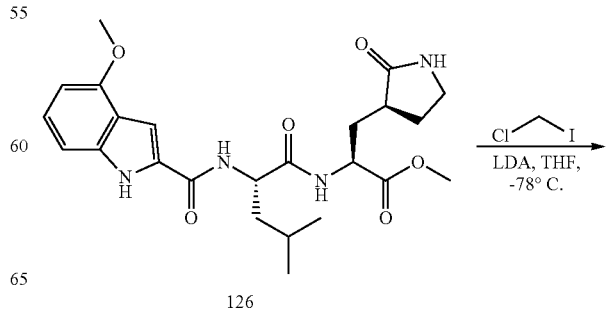

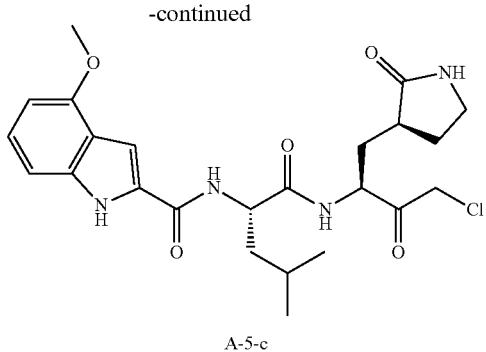

A-5-c

To a stirred solution of methyl (2S)-2-[(2S)-2-[(4-methoxy-1H-indol-2-yl)formamido]-4-methylpentanamido]-3-[(3S)-2-oxopyrrolidin-3-yl]propanoate (compound 126) (300 mg, 0.63 mmol) in THF (10 mL) under $N_2$ at −78° C. was added chloroiodomethane (0.5 mL, 6.35 mmol) and LDA (2 M in THF, 2.1 mL, 15.87 mmol). The reaction mixture was stirred at −78° C. for 2 h until LCMS indicated completion of the reaction. The mixture was quenched with sat. aq. $NH_4Cl$ and extracted with EtOAc. The organic layers were combined, dried over $Na_2SO_4$ and solvent was removed under reduced pressure. The resulting residue was purified by prep-HPLC to yield compound A-5-c (44 mg, 0.09 mmol, 14.12%) as an off-white solid. LCMS=$[M+H]^+$: 491.2. $^1$H NMR (400 MHz, DMSO-$d_6$) δ 11.57 (s, 1H), 8.60 (d, J=7.7 Hz, 1H), 8.43 (d, J=7.5 Hz, 1H), 7.63 (s, 1H), 7.36 (s, 1H), 7.09 (t, J=8.0 Hz, 1H), 7.01 (d, J=8.2 Hz, 1H), 6.51 (d, J=7.6 Hz, 1H), 4.58 (d, J=2.3 Hz, 2H), 4.49-4.42 (m, 2H), 3.88 (s, 3H), 3.18-3.04 (m, 2H), 2.34-2.22 (m, 1H), 2.17-2.04 (m, 1H), 2.03-1.92 (m, 1H), 1.77-1.65 (m, 3H), 1.64-1.52 (m, 2H), 0.94 (d, J=6.2 Hz, 3H), 0.89 (d, J=6.3 Hz, 3H).

Example S20: Synthesis of Compound A-5-d

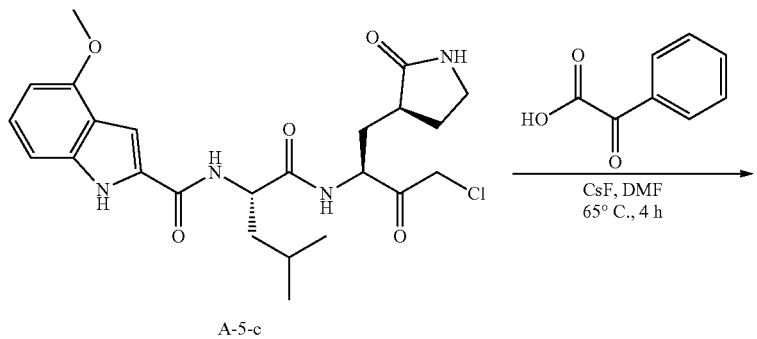

A-5-c

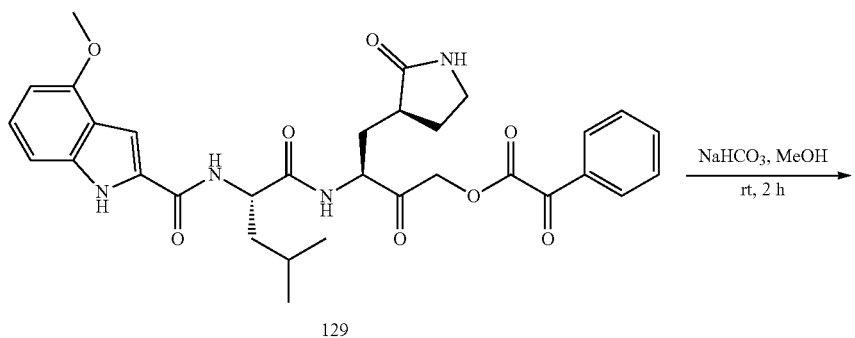

129

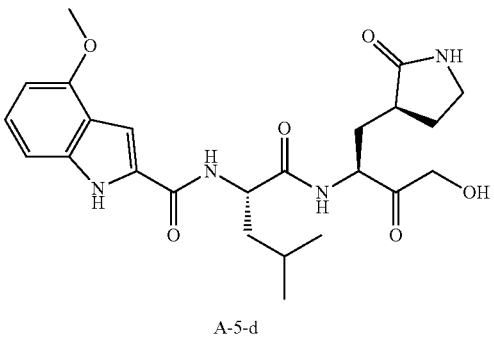

A-5-d

To a stirred solution of (2S)—N-[(2S)-4-chloro-3-oxo-1-[(3S)-2-oxopyrrolidin-3-yl]butan-2-yl]-2-[(4-methoxy-1H-indol-2-yl)formamido]-4-methylpentanamide (compound A-5-c) (200 mg, 0.41 mmol) in DMF (3 mL) was added 2-oxo-2-phenylacetic acid (0.1 mL, 0.53 mmol) and CsF (142 mg, 0.94 mmol). The reaction mixture was heated at 65° C. under N₂ for 4 h. LCMS indicated completion of the reaction. The mixture was filtered, and the filtrate was concentrated under reduced pressure. The resulting residue was purified by prep-HPLC to yield compound 129 (45 mg, 0.07 mmol, 18.27%) as a yellow solid. LCMS=[M+H]⁺: 605.1.

To a stirred solution of (3S)-3-[(2S)-2-[(4-methoxy-1H-indol-2-yl)formamido]-4-methylpentan-amido]-2-oxo-4-[(3S)-2-oxopyrrolidin-3-yl]butyl 2-oxo-2-phenylacetate (compound 129) (50 mg, 0.08 mmol) in MeOH (1 mL) was added NaHCO₃ (0.69 mg, 0.01 mmol). The reaction mixture was stirred at room temperature under N₂ for 2 h. The mixture was concentrated down under reduced pressure. The resulting residue was purified by prep-HPLC (ACN/water (0.084% NH₄HCO₃)) to yield compound A-5-d (12.79 mg, 0.03 mmol, 32.73%) as an off-white solid. LCMS=[M+H]⁺: 473.3. ¹H NMR (400 MHz, DMSO-d₆) δ 11.58 (s, 1H), 8.43 (dd, J=14.8, 8.1 Hz, 2H), 7.62 (s, 1H), 7.36 (s, 1H), 7.12-7.06 (m, 1H), 7.00 (d, J=8.3 Hz, 1H), 6.50 (d, J=7.5 Hz, 1H), 5.08 (br s, 1H), 4.53-4.40 (m, 2H), 4.31-4.19 (m, 1H), 4.17-4.10 (m, 1H), 3.88 (s, 3H), 3.17-3.03 (m, 2H), 2.35-2.24 (m, 1H), 2.20-2.04 (m, 1H), 1.98-1.88 (m, 1H), 1.76-1.47 (m, 5H), 0.97-0.86 (m, 6H).

Example S21: Synthesis of Compounds B-1-a and B-1-b

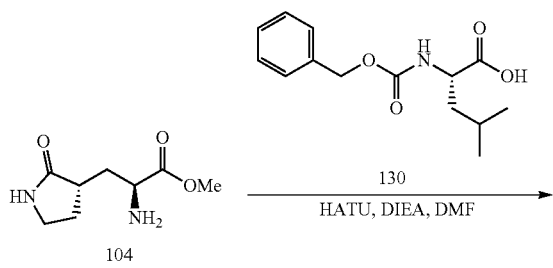

104

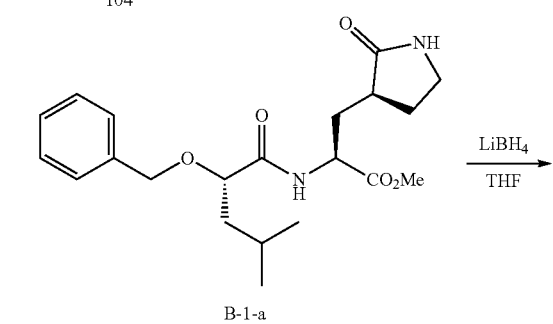

B-1-a

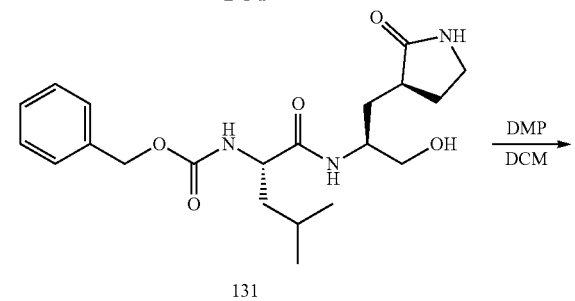

131

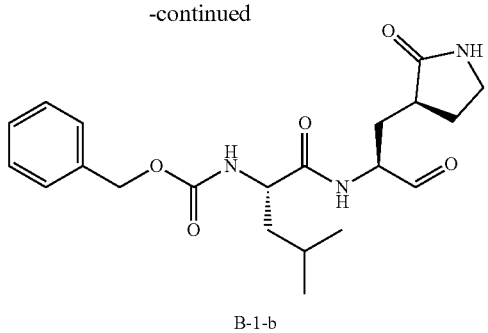

B-1-b

To a solution of compound 130 (5 g, 19.2 mmol) in anhydrous DMF (50 mL) at 0° C. was added sequentially compound 104 (5.0 g, 19.2 mmol, 1.0 equiv), HATU (11.0 g, 28.8 mmol, 1.5 equiv), and DIEA (5.0 g, 38.4 mmol, 2.0 equiv). The reaction mixture was stirred at 0-5° C. for 30 min. The mixture was diluted with EtOAc and washed with water, 1M HCl, and sat. NaCl. The combined organic layers were dried over Na₂SO₄ and concentrated down under reduced pressure. The resulting residue was purified by column chromatography (EtOAc:Hexane=1:5) to yield compound B-1-a as a white solid (5.2 g, 44.8%). LCMS=[M+H]⁺: 434.5.

To a stirred solution of compound B-1-a (2.2 g, 5.1 mmol) in THF (50 mL) was added LiBH₄ (2.0 M in THF, 12.8 mL, 25.5 mmol) portionwise at 0° C. under a nitrogen atmosphere. The reaction mixture was stirred at 0° C. for 1 h, then allowed to warm up to room temperature, and stirred for an additional 2 h. The reaction was cooled in an ice bath and quenched by dropwise addition of 1.0 M HCl. The solution was diluted with H₂O and extracted with EtOAc. The organic layers were combined, dried over Na₂SO₄, and concentrated under reduced pressure to yield a yellow oil residue, which was further purified by column chromatography (5% MeOH in DCM as the eluent) to afford compound 131 as a white solid (1.3 g, 61.9%). LCMS=[M+H]⁺: 406.5.

To a solution of compound 131 (1.3 g, 3.2 mmol) in DCM (10 mL) was added Dess-Martin periodinane (4.1 g, 9.6 mmol). The reaction mixture was stirred at room temperature for 2 h. LCMS indicated completion of the reaction. The reaction was quenched with sat. NaHCO₃ solution containing 10% Na₂S₂O₃ and extracted with DCM. The organic layers were separated, washed with brine, dried over anhydrous Na₂SO₄ and concentrated down under reduced pressure. The resulting residue was purified with flash column chromatography to yield compound B-1-b as a white solid (700 mg, 53.8%). LCMS=[M+H]⁺: 404.6.

Example S22: Synthesis of Compound B-1-c

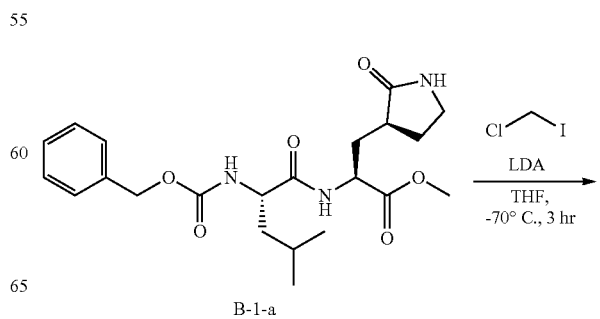

B-1-a

-continued

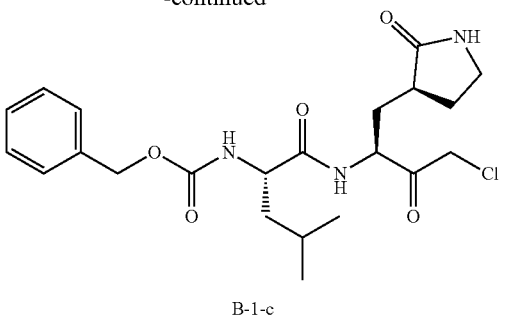

B-1-c

To a stirred solution of methyl (S)-2-((S)-2-(((benzyloxy)carbonyl)-amino)-4-methylpentanamido)-3-((S)-2-oxopyrrolidin-3-yl)propanoate (compound B-1-a) (300 mg, 0.69 mmol) and chloroiodomethane (732 mg, 4.15 mmol) in dry THF (5 mL) at −70° C. under $N_2$ atmosphere LDA was added dropwise (2 M in THF, 3.5 mL, 7 mmol). The reaction mixture was continuously stirred for 3 hr at −70° C. until LCMS indicated completion of the reaction. The reaction mixture was quenched with sat. aqueous $NH_4Cl$ (10 mL) and extracted with EtOAc (20 mL×3). The combined organic layers were washed with brine (20 mL), dried over $Na_2SO_4$, and solvent was removed under reduced pressure. The resulting residue was purified by flash chromatography (20 g SNAP silica column, 5% MeOH in DCM), and further purified by prep-HPLC to yield compound B-1-c as a white solid (8 mg, 3%). LCMS=$[M+H]^+$: 452.2. Purity=85%. $^1$H NMR (400 MHz, $CDCl_3$) δ 7.42-7.24 (m, 5H), 5.16-5.01 (m, 2H), 4.70-4.54 (m, 1H), 4.41 (s, 1H), 4.30 (s, 1H), 4.14 (t, J=7.6 Hz, 1H), 3.62-3.46 (m, 1H), 3.28-3.15 (m, 2H), 2.54-2.42 (m, 1H), 2.32 (s, 1H), 2.30-2.13 (m, 1H), 2.11-1.93 (m, 1H), 1.89-1.63 (m, 3H), 1.56 (t, J=7.3 Hz, 2H), 1.01-0.88 (m, 6H).

Example S23: Synthesis of Compound B-1-d

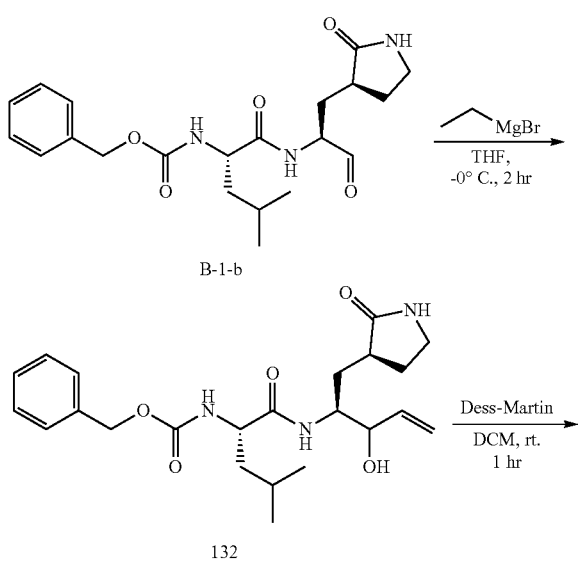

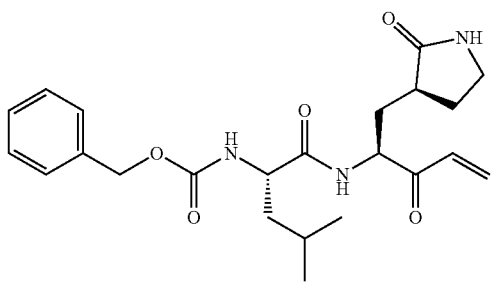

B-1-d

To a stirred solution of benzyl ((S)-4-methyl-1-oxo-1-(((S)-1-oxo-3-((S)-2-oxopyrrolidin-3-yl)propan-2-yl)amino)pentan-2-yl)carbamate (compound B-1-b) (200 mg, 0.50 mmol) in dry THF (5 mL) at 0° C. under $N_2$ atmosphere vinylmagnesium bromide (1 M in THF, 1.8 mL, 1.8 mmol) was added dropwise. The reaction mixture was stirred at 0° C. for 2 h. After completion of the reaction was indicated by LCMS, the reaction mixture was allowed to warm up to room temperature, diluted with sat. $NH_4Cl$ (aq), and extracted with EtOAc. The combined organic layers were washed with brine, dried over $Na_2SO_4$ and concentrated under reduced pressure. The resulting residue was purified by reverse phase column chromatography (C18, 40 g 20-35 um, 100 Å; mobile phase 60% ACN in water (0.1% FA aq.)) to yield compound 132 as a white solid (50 mg, 23% yield). LCMS=$[M+H]^+$: 432.1. $^1$H NMR (400 MHz, $CDCl_3$) δ 7.38-7.28 (m, 5H), 7.21 (d, J=8.3 Hz, 1H), 5.96 (s, 1H), 5.88-5.72 (m, 1H), 5.47-5.39 (m, 1H), 5.31 (t, J=14.4 Hz, 1H), 5.23-5.14 (m, 1H), 5.14-5.03 (m, 2H), 4.28-4.16 (m, 1H), 4.16-4.09 (m, 1H), 4.00 (dd, J=11.6, 7.5 Hz, 1H), 3.56 (s, 1H), 3.36-3.20 (m, 2H), 2.46-2.29 (m, 2H), 2.13-2.00 (m, 1H), 1.98-1.86 (m, 1H), 1.83-1.80 (m, 1H), 1.67-1.59 (m, 2H), 1.52-1.44 (m, 1H), 0.93 (d, J=6.2 Hz, 6H).

A mixture of benzyl ((2S)-1-(((2S)-3-hydroxy-1-((S)-2-oxopyrrolidin-3-yl)pent-4-en-2-yl)amino)-4-methyl-1-oxopentan-2-yl)carbamate compound 132 (45 mg, 0.095 mmol) and Dess-Martin periodinane (243 mg, 0.573 mmol) in DCM (10 mL) was stirred for 1 h at room temperature. After completion of the reaction was indicated by LCMS, the reaction mixture was diluted with DCM and washed with sat. $Na_2S_2O_3$ (aq), sat. $NaHCO_3$ (aq), and brine. Organic layers were collected dried over $Na_2SO_4$ and concentrated down under reduced pressure. The resulting residue was purified by prep-TLC plate (DCM:MeOH=30:1) to yield compound B-1-d as a white solid (12 mg, 27% yield). LCMS=$[M+H]^+$: 430.1. Purity=95% $^1$H NMR (400 MHz, $CDCl_3$) δ 7.84 (d, J=6.7 Hz, 1H), 7.26 (s, 5H), 6.51-6.40 (m, 1H), 6.33 (d, J=17.2 Hz, 1H), 6.25 (s, 1H), 5.77 (d, J=10.1 Hz, 1H), 5.42 (d, J=8.1 Hz, 1H), 5.03 (s, 2H), 4.72-4.54 (m, 1H), 4.30-4.07 (m, 1H), 3.22 (d, J=7.8 Hz, 2H), 2.41-2.24 (m, 2H), 2.07-1.94 (m, 1H), 1.79-1.68 (m, 2H), 1.60-1.58 (m, 2H), 1.49-1.38 (m, 1H), 0.88 (d, J=5.1 Hz, 6H).

Example S24: Synthesis of Compound B-1-e

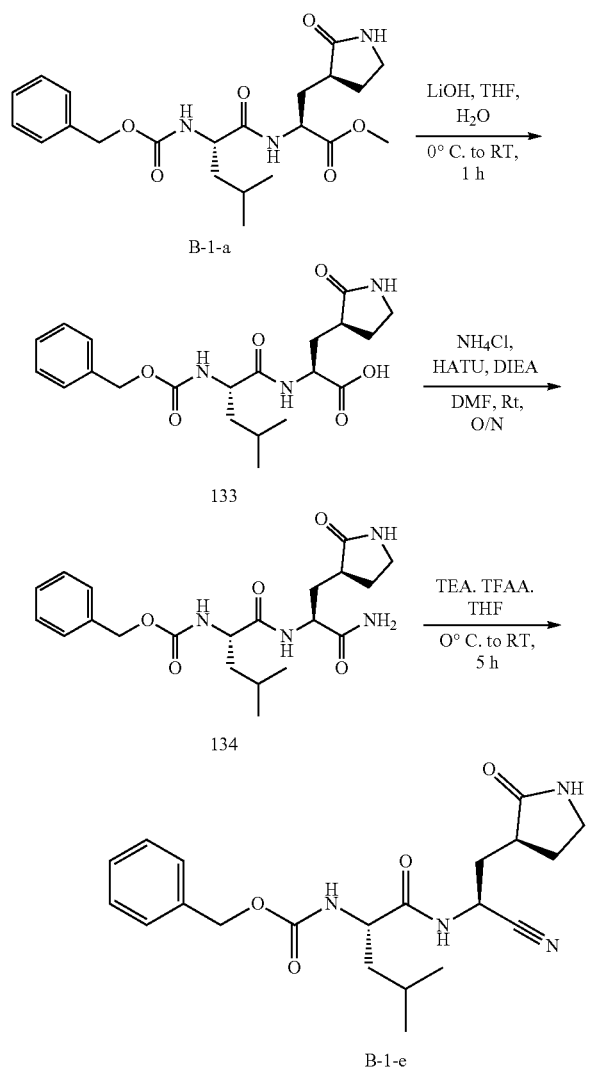

To a stirred solution of methyl (2S)-2-[(2S)-2-{[(benzyloxy)carbonyl]amino}-4-methylpentan-amido]-3-[(3S)-2-oxopyrrolidin-3-yl]propanoate (compound B-1-a) (400 mg, 0.92 mmol) in THF (10 mL) at 0° C. under $N_2$ was slowly added LiOH (44 mg, 1.85 mmol) in $H_2O$ (12 mL). The reaction mixture was stirred at room temperature for 40 min. The aqueous phase was separated, adjusted pH to ~3-4 with citric acid, and then extracted with EtOAc (50 mL×3). The combined organic layers were dried over anhydrous $Na_2SO_4$ and concentrated down under reduced pressure to yield crude compound 133 (320 mg, 0.76 mmol, 82.67%) as a yellow oil, which was directly used for next step without further purification. LCMS=[M+H]$^+$: 419.9. $^1$H NMR (400 MHz, $CDCl_3$) δ 8.04 (d, J=6.6 Hz, 1H), 7.31-7.26 (m, 5H), 6.44 (br s, 1H), 5.54 (d, J=8.2 Hz, 1H), 5.13-5.03 (m, 2H), 4.55 (br s, 1H), 4.29 (d, J=4.7 Hz, 1H), 3.40-3.28 (m, 2H), 2.55-2.46 (m, 1H), 2.35 (s, 1H), 2.24-2.11 (m, 1H), 2.06-2.03 (m, 1H), 1.99-1.78 (m, 2H), 1.57-1.47 (m, 1H), 0.94 (d, J=6.3 Hz, 6H).

To a stirred solution of (2S)-2-[(2S)-2-{[(benzyloxy)carbonyl]amino}-4-methylpentanamido]-3-[(3S)-2-oxopyrrolidin-3-yl]propanoic acid (compound 133) (320 mg, 0.76 mmol) in DMF (4 mL) was added $NH_4Cl$ (204 mg, 3.81 mmol), HATU (377 mg, 0.99 mmol) and DIEA (0.60 mL, 3.81 mmol). The reaction mixture was stirred at room temperature for 16 h. After completion of reaction (monitored by TLC), the reaction mixture was diluted with water and extracted with EtOAc (80 mL×3). The organic layers were washed with brine (40 mL), dried over anhydrous $Na_2SO_4$, and solvent was removed under reduced pressure. The resulting crude product was purified by reverse phase HPLC (ACN/water (0.1% FA)) to yield compound 134 (240 mg, 0.57 mmol, 75.18%) as a yellow solid. LCMS=[M+H]$^+$: 419.0.

To a stirred solution of benzyl N-[(1S)-1-{1[(1S)-1-carbamoyl-2-[(3S)-2-oxopyrrolidin-3-yl]ethyl]carbamoyl}-3-methylbutyl]carbamate (compound 134) (60 mg, 0.14 mmol) in THF (2 mL) at 0° C. was added TEA (0.04 mL, 0.29 mmol). The reaction mixture was stirred at 0° C. for 30 min and then TFAA (0.20 mL, 1.51 mmol) was added. The resulting mixture was continuously stirred at 0° C. for another 1 h, then allowed to warm up to room temperature and stirred for 16 h. The reaction mixture was concentrated down under reduced pressure, and the resulting crude material was purified by prep-HPLC to yield compound B-1-e (8.72 mg, 0.02 mmol, 15.19%) as an off-white solid. LCMS=[M+H]$^+$: 401.3. $^1$H NMR (400 MHz, $CDCl_3$) δ 8.36 (s, 1H), 7.33-7.30 (m, 5H), 6.21 (br s, 1H), 5.36 (br s, 1H), 5.10 (s, 2H), 4.80 (br s, 1H), 4.31 (br s, 1H), 3.35-3.33 (m, 2H), 2.38-2.33 (m, 3H), 1.94-1.90 (m, 4H), 1.53-1.50 (m, 1H), 0.95 (d, J=5.0 Hz, 6H).

Example S25: Synthesis of Compound B-1-f

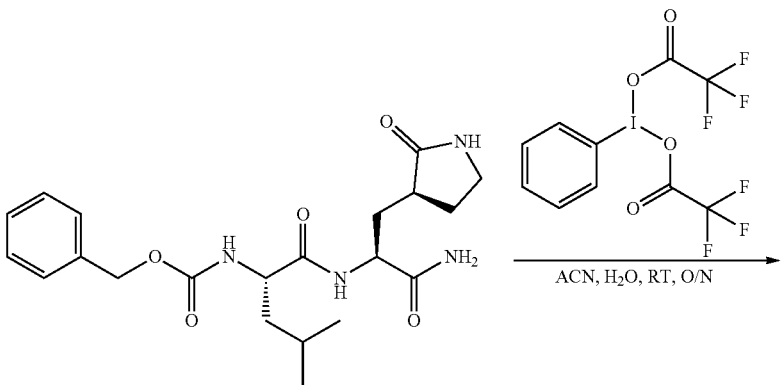

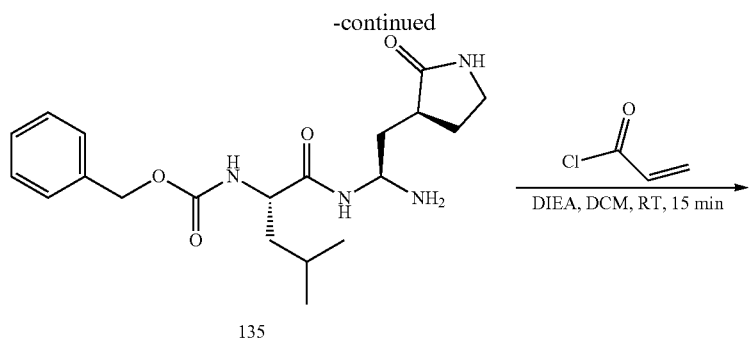

135

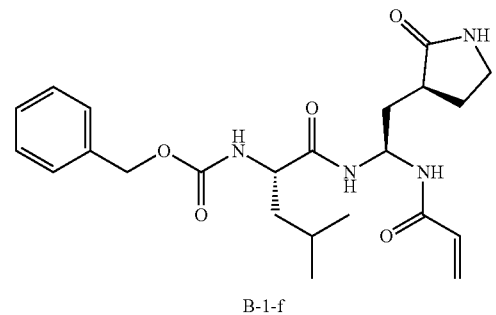

B-1-f

To a stirred solution of benzyl N-[(1S)-1-{[(1S)-1-carbamoyl-2-[(3S)-2-oxopyrrolidin-3-yl]ethyl]-carbamoyl}-3-methylbutyl]carbamate (compound 134) (90 mg, 0.22 mmol) in ACN (1 mL) and H$_2$O (1 mL) was added [bis(trifluoroacetoxy)iodo]benzene (93 mg, 0.22 mmol). The solution was stirred at room temperature under N$_2$ in darkness for 15 h. The mixture was purified by prep-HPLC (ACN/water (0.1% FA)) to yield compound 135 (45 mg, 0.12 mmol, 53.59%) as an off-white solid. LCMS=[M−NH$_2$]$^+$: 374.2.

To a stirred solution of benzyl N-[(1S)-1-{[(1S)-1-amino-2-[(3S)-2-oxopyrrolidin-3-yl]ethyl]-carbamoyl}-3-methylbutyl]carbamate (compound 135) (45 mg, 0.12 mmol) and DIEA (0.07 mL, 0.46 mmol) in DCM (1 mL) at 0° C. was slowly added prop-2-enoyl chloride (0.01 mL, 0.15 mmol). The reaction mixture was stirred at room temperature under N$_2$ for 15 min. The mixture was concentrated, and the resulting crude material was purified by prep-HPLC to yield compound B-1-f (12.78 mg, 24.95%) as an off-white solid. LCMS=[M+H]$^+$: 445.3. $^1$H NMR (400 MHz, CDCl$_3$) δ 7.90 (br s, 1H), 7.52 (br s, 1H), 7.33 (br s, 5H), 7.22 (br s, 1H), 6.28 (d, J=17.0 Hz, 1H), 5.75-5.70 (m, 3H), 5.64 (d, J=9.1 Hz, 1H), 5.09 (s, 2H), 4.18 (br s, 1H), 3.30-3.26 (m, 2H), 2.51-2.48 (m, 1H), 2.23-2.20 (m, 2H), 2.03-1.83 (m, 4H), 1.51-1.49 (m, 1H), 0.92 (d, J=5.7 Hz, 6H).

Example S26: Synthesis of Compounds B-2-a and B-2-b

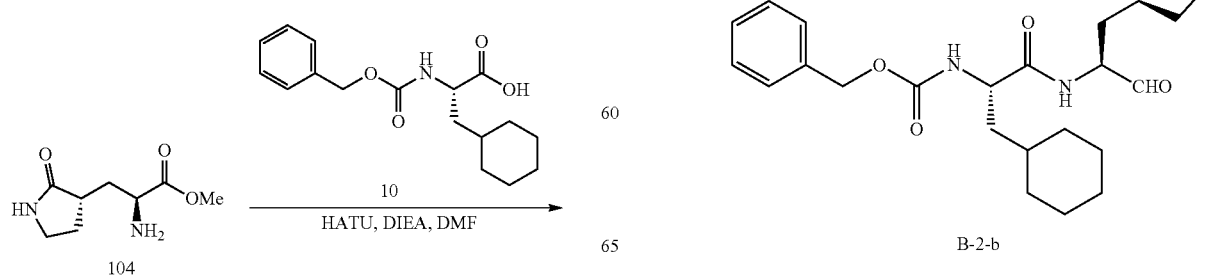

To a solution of compound 110 (5 g, 16.40 mmol) in anhydrous DMF (40 mL) at 0° C. was added sequentially HATU (5.7 g, 15.03 mmol), and DIEA (8.3 mL, 50.15 mmol). The reaction mixture was stirred at 0° C. for 15 min. Compound 104 (3.65 g, 16.40 mmol) was added, and the reaction mixture was stirred at 0° C. for another 1 h. The mixture was directly purified by a medium pressure reversed-phase column to yield compound B-2-a as a white solid (5.3 g, 68.4%). LCMS=[M+H]$^+$: 474.5.

To a stirred solution of compound B-2-a (1.85 g, 3.91 mmol) in THF (10 mL) at 0° C. under a nitrogen atmosphere LiBH$_4$ (2.0 M in THF, 5.9 mL, 11.73 mmol) was added portion-wise. The reaction mixture was stirred at 0° C. for 1 h, then allowed to warm up to room temperature and continued to stir for an another 2 h. The reaction was quenched by drop-wise addition of sat. NH$_4$Cl with cooling on an ice-bath. The reaction mixture was diluted with H$_2$O and extracted with EtOAc. The combined organic layers were dried over Na$_2$SO$_4$, filtered, and concentrated down under reduced pressure. The resulting yellow solid was further purified by medium pressure reversed-phase column to yield compound 136 as a white solid (1.6 g, 92.0%). LCMS=[M+H]$^+$: 446.3.

To a solution of compound 136 (1.6 g, 3.60 mmol) in DCM (6 mL) was added Dess-Martin periodinane (3.05 g, 7.18 mmol) at 0° C. The reaction mixture was stirred at 0° C. for 30 min, then allowed to warm up to room temperature, and continued to stir for another 2 h. The reaction was quenched with sat. NaHCO$_3$ containing 10% Na$_2$S$_2$O$_3$ at 0° C. The reaction mixture was diluted with DCM and H$_2$O and the layers were separated. The aqueous layer was extracted with DCM. The combined organic layers were washed with brine, dried with anhydrous Na$_2$SO$_4$, and concentrated under reduced pressure. The residue was purified with normal phase column chromatography to yield compound B-2-b as a pale-yellow solid (285 mg, HPLC 98%). LCMS=[M+H]$^+$: 444.6.

Example S27: Synthesis of Compound B-2-c

To a stirred solution of methyl (S)-2-((S)-2-(((benzyloxy)carbonyl)amino)-3-cyclohexylpropan-amido)-3-((S)-2-oxopyrrolidin-3-yl)propanoate (B-2-a) (270 mg, 0.57 mmol) and chloroiodomethane (402 mg, 2.28 mmol) in dry THF (5 mL) was added LDA (2 M in THF, 1.7 mL, 3.4 mmol) dropwise at −70° C. under N$_2$. The reaction mixture was stirred at −70° C. for 3 h. The reaction mixture was quenched with sat. NH$_4$Cl (aq) (10 mL), and extracted with EtOAc (10 mL×3). The combined organic layers were washed with brine, dried over anhydrous Na$_2$SO$_4$, and concentrated down under reduced pressure. The resulting crude material was purified by reverse-phase HPLC (C 18, 120 g 20-35 um, 100 Å; 65% ACN in water (0.1% FA aq.)) to yield compound B-2-c as a white solid (15 mg, 5%). LCMS=[M+H]$^+$: 492.3, Purity 93%. $^1$H NMR (400 MHz, CDCl$_3$) δ 8.47 (br s, 1H), 7.44-7.28 (m, 5H), 5.85 (br s, 1H), 5.25 (d, J=7.3 Hz, 1H), 5.12 (s, 2H), 4.79-4.50 (m, 1H), 4.28 (s, 2H), 4.25-4.10 (m, 1H), 3.42-3.28 (m, 2H), 2.48-2.40 (m, 2H), 2.06-1.93 (m, 3H), 1.90-1.76 (m, 2H), 1.71-1.63 (m, 4H), 1.53-1.44 (m, 1H), 1.43-1.30 (m, 1H), 1.29-1.09 (m, 3H), 1.03-0.84 (m, 2H).

Example S28: Synthesis of Compound B-2-d

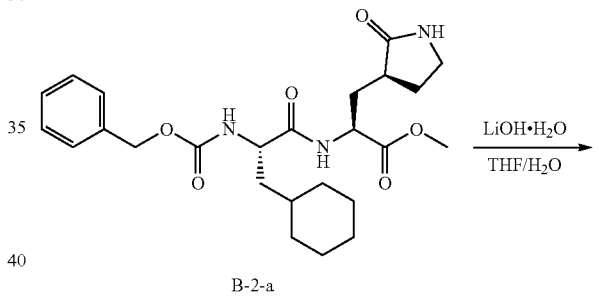

B-2-a

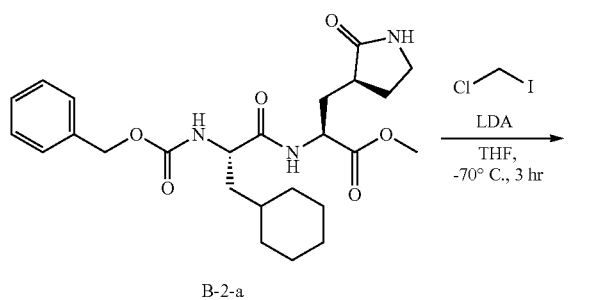

B-2-a

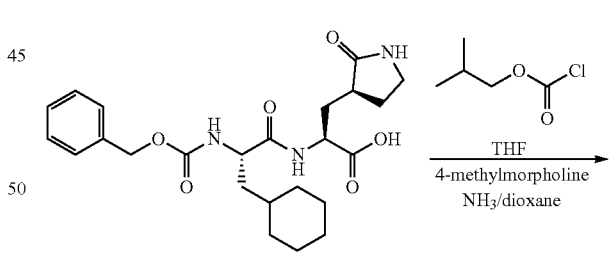

137

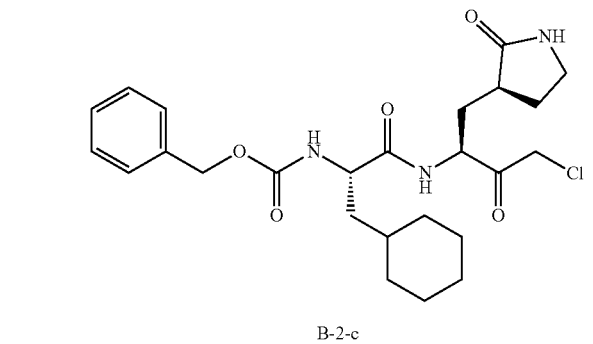

B-2-c

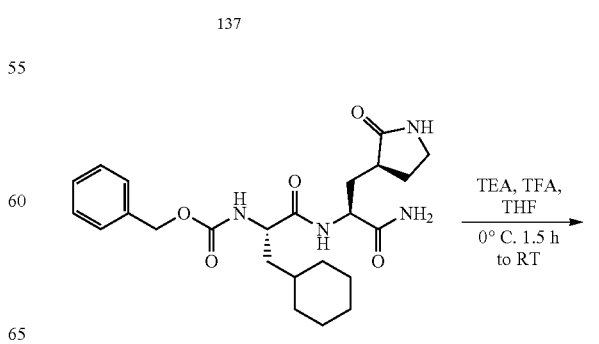

138

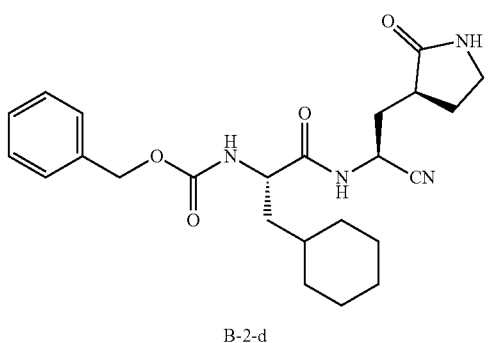

B-2-d

To a stirred solution of methyl (S)-2-((S)-2-(((benzyloxy)carbonyl)amino)-3-cyclohexylpropan-amido)-3-((S)-2-oxopyrrolidin-3-yl)propanoate (compound B-2-a) (600 mg, 1.27 mmol) in THF/water (20 mL, 1:1) was added LiOH hydrate (133 mg, 3.17 mmol) at 0° C. The reaction mixture was stirred at room temperature for 1 h. LCMS indicated completion of the reaction. The reaction mixture was concentrated down under reduced pressure. The residue was diluted with water, adjusted pH to ~3-4 with 1M HCl, and extracted with ethyl acetate. The organic layer was washed with brine, dried with anhydrous $Na_2SO_4$, and concentrated down under reduced pressure to yield compound 137 (540 mg, 92.4%) as an off-white solid. LCMS=[M+H]$^+$: 460.5. $^1$H NMR (400 MHz, CDCl$_3$) δ 7.90 (d, J=18.0 Hz, 1H), 7.37-7.28 (m, 5H), 6.64 (s, 1H), 5.59 (d, J=7.5 Hz, 1H), 5.19-5.00 (m, 2H), 4.60-4.52 (m, 1H), 4.37-4.29 (m, 1H), 3.39-3.25 (m, 2H), 2.57-2.44 (m, 1H), 2.39-2.30 (m, 1H), 2.22-2.12 (m, 1H), 2.09-2.05 (m, 1H), 1.97-1.88 (m, 1H), 1.86-1.75 (m, 2H), 1.72-1.68 (m, 1H), 1.67-1.61 (m, 3H), 1.55-1.46 (m, 1H), 1.41-1.31 (m, 1H), 1.22-1.07 (m, 3H), 0.98-0.82 (m, 2H).

To a solution of (S)-2-((S)-2-(((benzyloxy)carbonyl)amino)-3-cyclohexylpropanamido)-3-((S)-2-oxopyrrolidin-3-yl)propanoic acid (compound 137) (300 mg, 0.65 mol) in THF (5 mL) was added 4-methylmorpholine (200 mg, 0.95 mmol) and isobutyl carbonochloridate (136 mg, 0.98 mmol) at 0° C. The reaction mixture was stirred for 15 min. and NH$_3$ in dioxane (5 mL, 0.4 M) was added. The resulting mixture was stirred for 1.5 h at 0° C. under nitrogen atmosphere. LCMS indicated completion of the reaction. The reaction mixture was then quenched with water (50 mL) and extracted with ethyl acetate (50 mL×3). The combined organic layers were washed with brine (20 mL), dried over anhydrous sodium sulfate, and concentrated down under reduced pressure. The resulting residue was purified by reverse phase HPLC to yield compound 138 (250 mg, 83%) as a yellow semi solid. LCMS=[M+H]$^+$: 459.2.

To a stirred solution of benzyl ((S)-1-(((S)-1-amino-1-oxo-3-((S)-2-oxopyrrolidin-3-yl)propan-2-yl)amino)-3-cyclohexyl-1-oxopropan-2-yl)carbamate (compound 138) (100 mg, 0.22 mmol) in DCM (5 mL) was added TEA (66 mg, 0.66 mmol) and TFAA (92 mg, 0.44 mmol). The reaction mixture was stirred at room temperature under N$_2$ for 1.5 h. LCMS indicated completion of the reaction. The reaction mixture was concentrated under reduced pressure. The resulting residue was purified by prep-HPLC to yield compound B-2-d (12 mg, 47.7%) as a white solid. LCMS=[M+H]$^+$: 441.3. $^1$H NMR (400 MHz, CDCl$_3$) δ 8.29 (s, 1H), 7.41-7.30 (m, 5H), 6.24-5.72 (m, 1H), 5.38-5.16 (m, 1H), 5.16-5.06 (m, 2H), 5.00-4.75 (m, 1H), 4.37-4.19 (m, 1H), 3.53-3.24 (m, 2H), 2.97-2.76 (m, 1H), 2.56-2.23 (m, 2H), 2.06-1.97 (m, 1H), 1.92-1.85 (m, 1H), 1.83-1.74 (m, 2H), 1.74-1.67 (m, 3H), 1.64-1.58 (m, 1H), 1.55-1.44 (m, 1H), 1.37-1.29 (m, 1H), 1.25-1.08 (m, 3H), 1.02-0.80 (m, 2H).

Example S29: Synthesis of Compound B-2-e

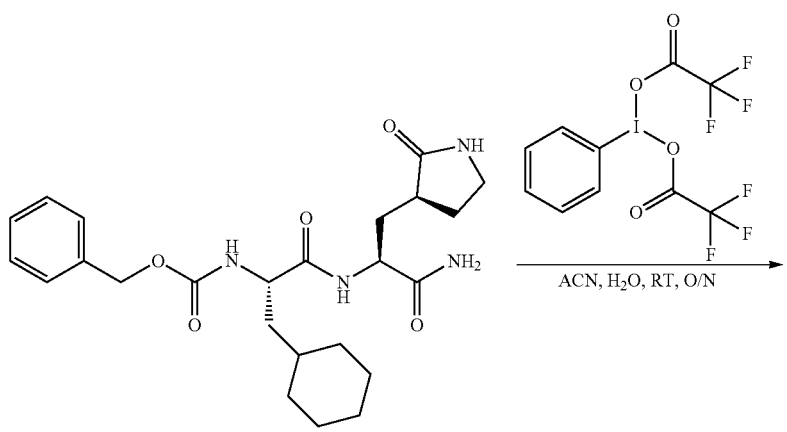

138

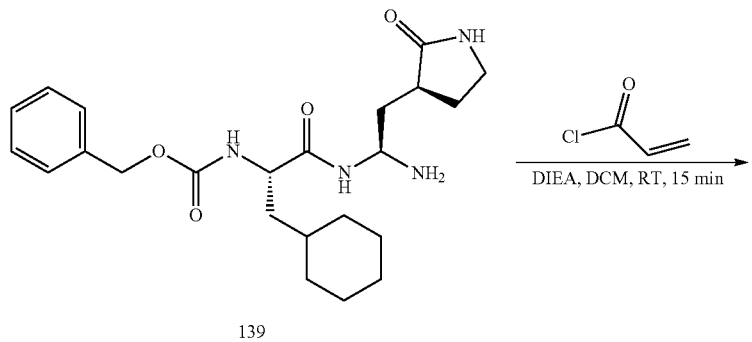

139

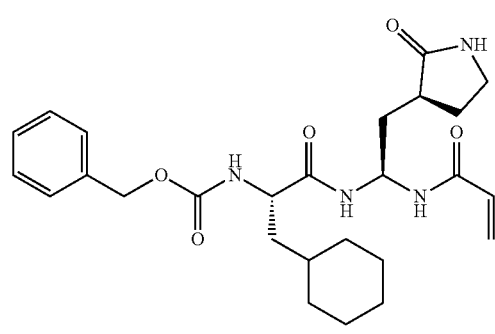

B-2-e

To a stirred solution of benzyl N-[(1S)-1-{1[(1S)-1-carbamoyl-2-[(3S)-2-oxopyrrolidin-3-yl]ethyl]-carbamoyl}-2-cyclohexylethyl]carbamate (compound 138) (140 mg, 0.31 mmol) in ACN (1 mL) and H$_2$O (1 mL) was added bis(trifluoroacetoxy)iodobenzene (132 mg, 0.31 mmol). The reaction mixture was stirred at room temperature under N$_2$ in darkness for 16 h. The mixture was directly purified by reverse phase HPLC (C18, ACN/water (0.1% FA)) to yield compound 139 (90 mg, 0.21 mmol, 68.47%) as an off-white solid. LCMS=[M+H]$^+$: 431.1.

To a stirred solution of benzyl N-[(1S)-1-{[(1S)-1-amino-2-[(3S)-2-oxopyrrolidin-3-yl]ethyl]-carbamoyl}-2-cyclohexylethyl]carbamate (compound 139)(85 mg, 0.20 mmol) and TEA (0.110 mL, 0.79 mmol) in DCM (1.5 mL) at 0° C. was slowly added prop-2-enoyl chloride (0.02 mL, 0.26 mmol). The reaction mixture was stirred at room temperature under N$_2$ for 15 min. The reaction mixture was concentrated down under reduced pressure. The resulting residue was purified by prep-HPLC to yield compound B-2-e (12.75 mg, 13.33%) as an off-white solid. LCMS=[M+H]$^+$: 485.3. $^1$H NMR (400 MHz, CDCl$_3$) δ 8.08-7.63 (m, 1H), 7.62-7.47 (m, 1H), 7.33 (s, 5H), 6.33-6.21 (m, 1H), 6.16-6.03 (m, 2H), 5.81-5.67 (m, 1H), 5.66-5.57 (m, 1H), 5.55-5.30 (m, 1H), 5.15-5.00 (m, 2H), 4.29-4.11 (m, 1H), 3.56-3.21 (m, 2H), 2.54-2.26 (m, 2H), 2.23-1.97 (m, 2H), 1.96-1.66 (m, 7H), 1.54-1.40 (m, 1H), 1.40-1.28 (m, 1H), 1.23-1.03 (m, 3H), 1.01-0.75 (m, 2H).

Example S30: Synthesis of Compounds C-1-a and C-1-b

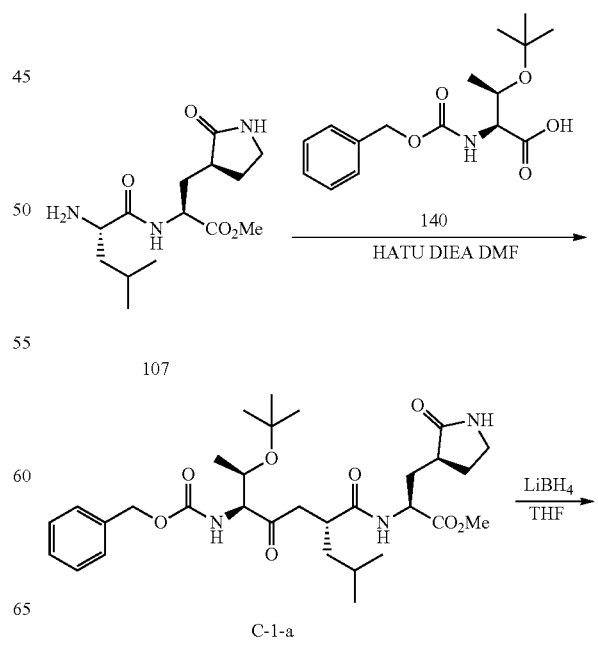

C-1-a

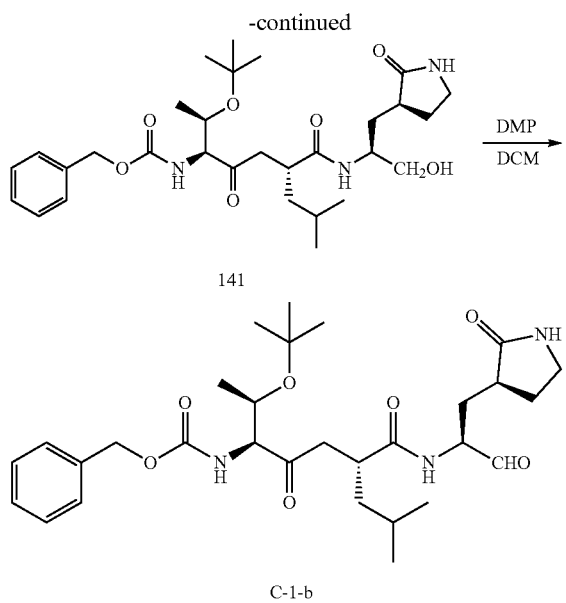

141

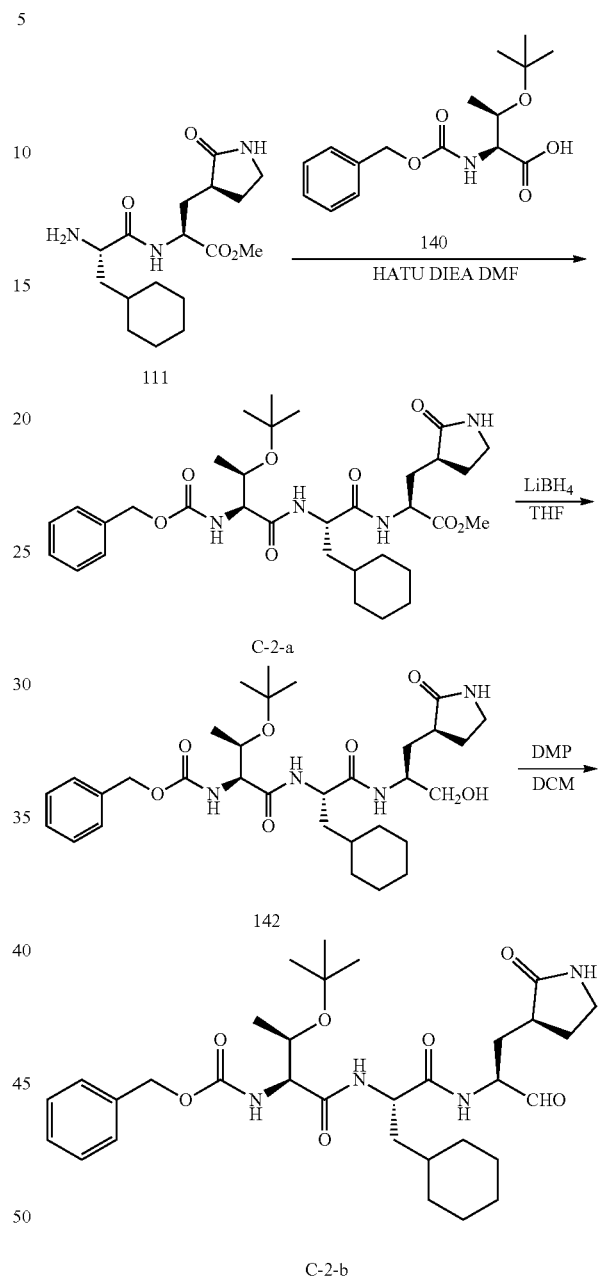

Example S31: Synthesis of Compounds C-2-a and C-2-b

To a solution of compound 107 (3 g, 10.02 mmol) in anhydrous DMF (10 mL) at 0° C. were added sequentially compound 140 (3.1 g, 10.02 mmol), HATU (5.7 g, 15.03 mmol), and DIEA (8.3 mL, 50.15 mmol). The reaction mixture was stirred at room temperature for 6 h. LCMS indicated completion of the reaction. The mixture was diluted with EtOAc and washed with water, 1M HCl, sat. NaCl, dried over $Na_2SO_4$, and concentrated down under reduced pressure. The resulting residue was purified by column chromatography (EtOAc:Hexane=1:2) to yield compound C-1-a as a white solid (3.7 g, 62.5%). LCMS=[M+H]$^+$: 591.6.

To a stirring solution of compound C-1-a (3.0 g, 5.08 mmol) in THF (30 mL) was added LiBH$_4$ (2.0 M in THF, 7.62 mL, 15.24 mmol, 3.0 equiv) in several portions at 0° C. under a nitrogen atmosphere. The reaction mixture was stirred at 0° C. for 1 h, then allowed to warm up to room temperature, and stirred for an additional 2 h. LCMS indicated completion of the reaction. The reaction was cooled in an ice bath and quenched by the dropwise addition of 1.0 M HCl. The solution was diluted with ethyl acetate and H$_2$O. The organic phase was separated, and the aqueous layer was extracted with ethyl acetate. The organic phases were combined, dried over $Na_2SO_4$, and filtered. The filtrate was concentrated down under reduced pressure to give a yellow oily residue, which was further purified by column chromatography (6% MeOH in DCM) to yield compound 141 as a white solid (2.7 g, 94.4%). LCMS=[M+H]$^+$: 563.4.

To a solution of compound 141 (2.7 g, 4.80 mmol) in DCM (20 mL) was added Dess-Martin periodinane (7.38 g, 14.40 mmol). The resulting mixture was stirred at room temperature for 12 h. LCMS indicated completion of the reaction. The reaction was quenched with sat. NaHCO$_3$ containing 10% Na$_2$S$_2$O$_3$. The organic layer was washed with saturated brine solution, dried over anhydrous Na$_2$SO$_4$ and concentrated down under reduced pressure. The resulting residue was purified with flash chromatography to yield compound C-1-b as a white solid (890 mg, 33.0%). LCMS=[M+H]$^+$: 561.7.

To a solution of compound 111 (3 g, 8.84 mmol, 1.0 equiv) in anhydrous DMF (10 mL) at 0° C., compound 140 (2.73 g, 8.84 mmol, 1.0 equiv), HATU (5.04 g, 13.26 mmol, 1.5 equiv), DIEA (7.3 mL, 44.2 mmol, 5.0 equiv) were added sequentially. The reaction mixture was stirred at room temperature for 6 h. LCMS indicated completion of the reaction. The reaction mixture was diluted with EtOAc. The organic layer was washed with water, 1M HCl, sat. NaCl, dried over Na$_2$SO$_4$, and concentrated down under reduced pressure. The resulting residue was purified by column chromatography (MeOH:DCM=1:15) to yield compound C-2-a as a white solid (4.3 g, 77.1%). LCMS=[M+H]$^+$: 631.6.

To a stirred solution of compound C-2-a (3.6 g, 5.71 mmol) in THF (36 mL), at 0° C. under nitrogen atmosphere, LiBH$_4$ (2 M in THF, 8.57 mL, 17.13 mmol) was added portion-wise. The reaction mixture was stirred at 0° C. for 1 h, then allowed to warm up to room temperature, and stirred for another 2 h. LCMS indicated completion of the reaction. The reaction mixture in an ice bath was quenched with 1.0 M HCl drop-wise and diluted with ethyl acetate and H$_2$O. The phases were separated, and the aqueous layer was extracted with ethyl acetate. The combined organic layers were combined, dried over with anhydrous Na$_2$SO$_4$, and concentrated down under reduced pressure to give a yellow oily residue, which was further purified by column chromatograph (MeOH:DCM=1:15) to yield compound 142 as a white solid (3.0 g, 87.2%). LCMS=[M+H]$^+$: 603.7.

To a solution of compound 142 (5.0 g, 8.30 mmol) in DCM (50 mL) at 0° C. Dess-Martin periodinane (10.56 g, 24.90 mmol) was added slowly. The reaction mixture was stirred at room temperature for 12 h. LCMS indicated completion of the reaction. The reaction was quenched with sat. NaHCO$_3$ containing 10% Na$_2$S$_2$O$_3$. The organic layer was washed with brine, dried over with anhydrous Na$_2$SO$_4$ and concentrated down under reduced pressure. The resulting residue was purified with flash chromatography to yield compound C-2-b as a white solid (2.3 g, 46.2%). LCMS=[M+H]$^+$: 601.7.

Example S32: Synthesis of Compound D-1-a

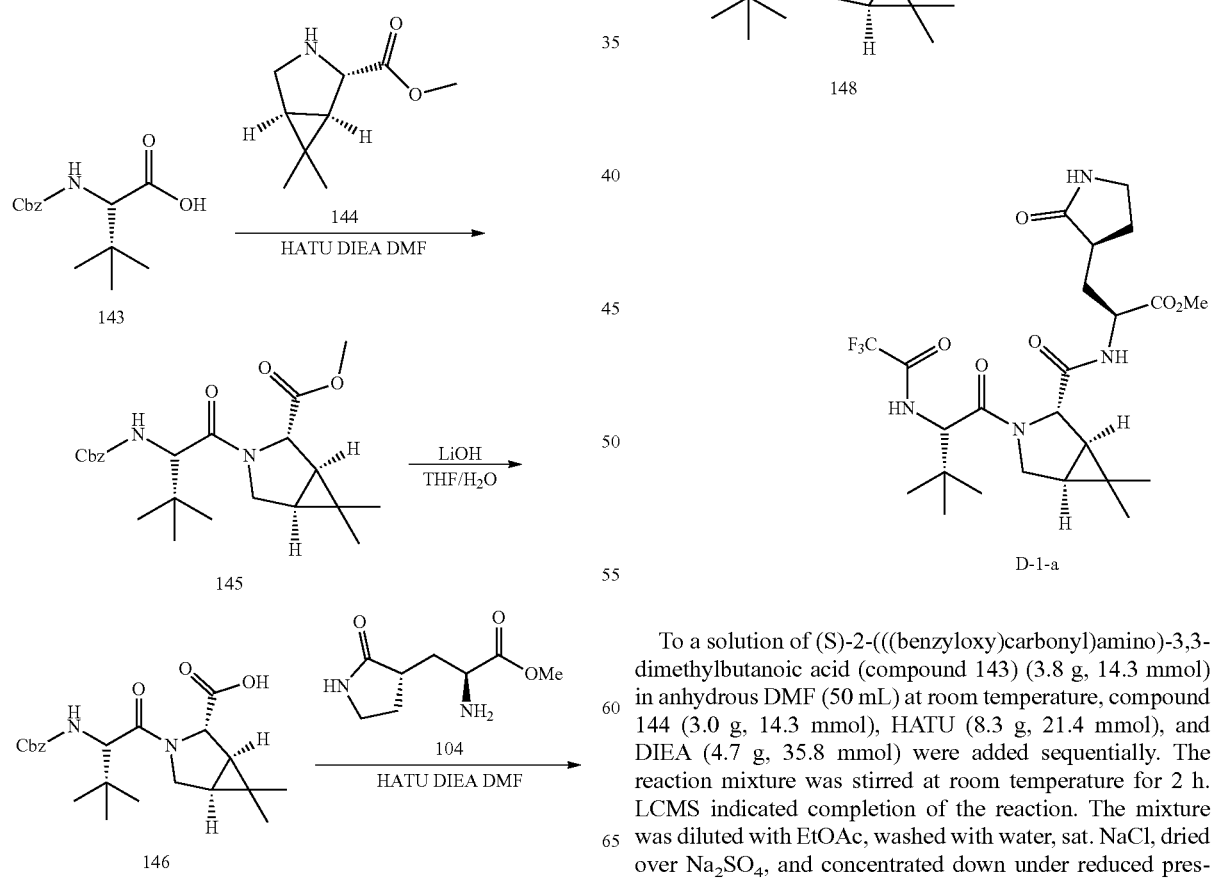

To a solution of (S)-2-(((benzyloxy)carbonyl)amino)-3,3-dimethylbutanoic acid (compound 143) (3.8 g, 14.3 mmol) in anhydrous DMF (50 mL) at room temperature, compound 144 (3.0 g, 14.3 mmol), HATU (8.3 g, 21.4 mmol), and DIEA (4.7 g, 35.8 mmol) were added sequentially. The reaction mixture was stirred at room temperature for 2 h. LCMS indicated completion of the reaction. The mixture was diluted with EtOAc, washed with water, sat. NaCl, dried over Na$_2$SO$_4$, and concentrated down under reduced pressure. The resulting residue was purified by column chromatography (EtOAc:Hexane=1:5) to yield compound 145 as a white solid (5.0 g, 83.8%). LCMS=[M+H]+: 417.4.

To a cooled to 0° C. solution of compound 145 (5 g, 12.0 mmol) in THF/H₂O (1:1) LiOH.H₂O (1.0 g, 24.0 mmol) was slowly added. The reaction mixture was stirred at room temperature for 2 h. After completion of reaction (monitored by TLC), the reaction mixture was neutralized with 1M HCl solution and then extracted with EtOAc. The combined organic layers were washed with sat. NaCl, dried over anhydrous Na₂SO₄ and concentrated down under reduced pressure to afford the crude compound 146 (1.2 g, 25%), which was directly used in the next reaction without further purification. LCMS=[M+H]+: 403.3.

To a solution of compound 146 (1.2 g, 2.98 mmol) in anhydrous DMF (15 mL) at room temperature, compound 104 (555.2 mg, 2.98 mmol), HATU (1.7 g, 4.47 mmol), and DIEA (964.1 mg, 7.45 mmol) were added sequentially. The reaction mixture was stirred at room temperature for 2 h. After completion of reaction (monitored by TLC), the mixture was diluted with EtOAc, washed with water, sat. NaCl, dried over Na₂SO₄, and concentrated down under reduced pressure. The resulting residue was purified by column chromatography (EtOAc:Hexane=1:5) to yield compound 147 (1.7 g, 99%). LCMS=[M+H]+: 571.5.

To a stirred solution of compound 147 (1.7 g, 2.98 mmol) in MeOH (20 mL) was added Pd/C (10 wt %, 170 mg) portion-wise at room temperature. The reaction mixture was stirred for 3 h under H₂ atmosphere. After completion of reaction (monitored by TLC), the mixture was filtered, and filtrate was concentrated down under reduced pressure. The resulting residue was purified by column chromatography (5% MeOH in CH₂Cl₂) to yield compound 148 as a white solid (300 mg; 23%). LCMS=[M+H]+: 527.6.

To a solution of compound 148 (300 mg, 0.69 mmol) in anhydrous DCM (15 mL) at room temperature TFAA (289 mg, 1.38 mmol) and TEA (208 mg, 2.07 mmol) were added sequentially. The reaction mixture was stirred at room temperature for 2 h. After completion of the reaction (monitored by TLC), the reaction mixture was diluted with EtOAc and washed with water, sat. NaCl, dried over anhydrous Na₂SO₄. The filtrate was concentrated down under reduced pressure. The resulting residue was purified by column chromatography (EtOAc:Hexane=1:5) to yield compound D-1-a (260 mg, 71%). LCMS=[M+H]+:533.3.

Example S33: Synthesis of Compound D-1-b

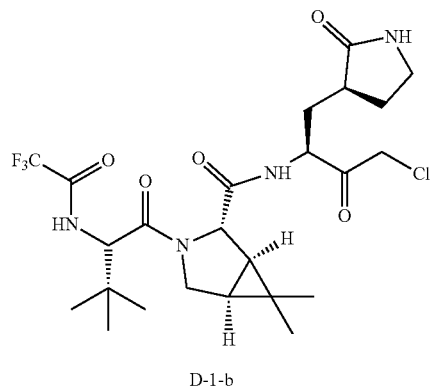

D-1-b

To a stirred solution of methyl (2S)-2-{[(1R,2S,5S)-3-[(2S)-3,3-dimethyl-2-(trifluoroacetamido)-butanoyl]-1,5-di-hydrogenio-6,6-dimethyl-3-azabicyclo[3.1.0]hexan-2-yl]formamido}-3-[(3S)-2-oxopyrrolidin-3-yl]propanoate (compound D-1-a) (300 mg, 0.56 mmol) in anhydrous THF (7 mL) under nitrogen atmosphere at −78° C. was added LDA (1.86 mL, 14.08 mmol) and chloroiodomethane (0.40 mL, 5.63 mmol). The reaction mixture was continuously stirred at −78° C. under N₂ for 1.5 h. LCMS indicated completion of the reaction. The reaction mixture was quenched with sat. NH₄Cl and extracted with ethyl acetate (20 mL×3). The combined organic layers were concentrated down under reduced pressure. The resulting residue was purified by prep-HPLC (ACN/water (0.1% FA) to yield compound D-1-b (27.76 mg, 0.05 mmol, 8.94%) as an off-white solid. LCMS=[M+H]+: 551.3. ¹H NMR (400 MHz, DMSO-d₆) δ 9.40 (d, J=8.6 Hz, 1H), 8.74 (d, J=8.1 Hz, 1H), 7.60 (s, 1H), 4.63 (s, 2H), 4.49-4.39 (m, 2H), 4.23 (s, 1H), 3.94-3.86 (m, 1H), 3.69 (d, J=10.3 Hz, 1H), 3.19-3.11 (m, 1H), 3.10-3.01 (m, 1H), 2.42-2.31 (m, 1H), 2.18-2.07 (m, 1H), 2.01-1.90 (m, 1H), 1.69-1.57 (m, 2H), 1.57-1.51 (m, 1H), 1.38 (d, J=7.7 Hz, 1H), 1.03 (s, 3H), 0.98 (s, 9H), 0.87 (s, 3H).

Example S34: Synthesis of Compound D-1-c

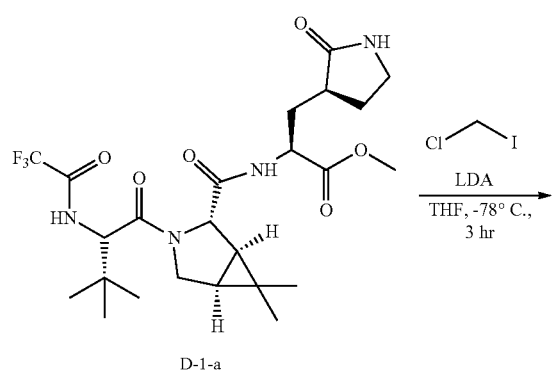

-continued

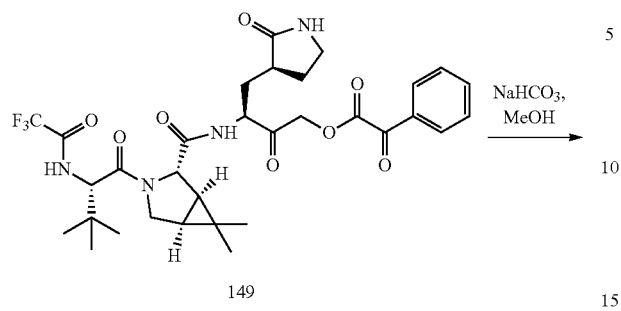

149

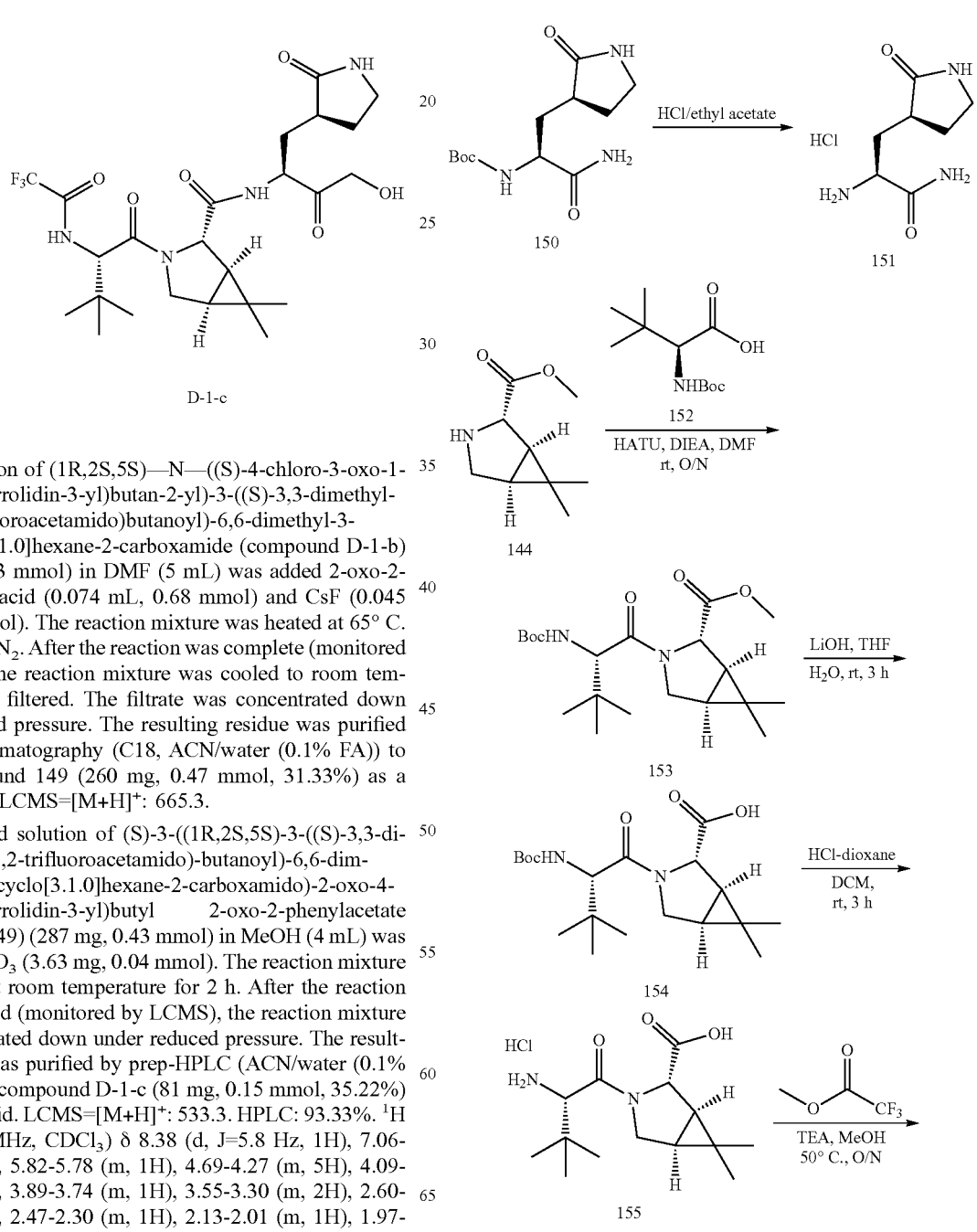

D-1-c

To a solution of (1R,2S,5S)—N—((S)-4-chloro-3-oxo-1-((S)-2-oxopyrrolidin-3-yl)butan-2-yl)-3-((S)-3,3-dimethyl-2-(2,2,2-trifluoroacetamido)butanoyl)-6,6-dimethyl-3-azabicyclo[3.1.0]hexane-2-carboxamide (compound D-1-b) (290 mg, 0.53 mmol) in DMF (5 mL) was added 2-oxo-2-phenylacetic acid (0.074 mL, 0.68 mmol) and CsF (0.045 mL, 1.22 mmol). The reaction mixture was heated at 65° C. for 2 h under $N_2$. After the reaction was complete (monitored by LCMS), the reaction mixture was cooled to room temperature, and filtered. The filtrate was concentrated down under reduced pressure. The resulting residue was purified by flash chromatography (C18, ACN/water (0.1% FA)) to yield compound 149 (260 mg, 0.47 mmol, 31.33%) as a brown solid. LCMS=[M+H]⁺: 665.3.

To a stirred solution of (S)-3-((1R,2S,5S)-3-((S)-3,3-dimethyl-2-(2,2,2-trifluoroacetamido)-butanoyl)-6,6-dimethyl-3-azabicyclo[3.1.0]hexane-2-carboxamido)-2-oxo-4-((S)-2-oxopyrrolidin-3-yl)butyl 2-oxo-2-phenylacetate (compound 149) (287 mg, 0.43 mmol) in MeOH (4 mL) was added NaHCO₃ (3.63 mg, 0.04 mmol). The reaction mixture was stirred at room temperature for 2 h. After the reaction was completed (monitored by LCMS), the reaction mixture was concentrated down under reduced pressure. The resulting residue was purified by prep-HPLC (ACN/water (0.1% FA)) to yield compound D-1-c (81 mg, 0.15 mmol, 35.22%) as a white solid. LCMS=[M+H]⁺: 533.3. HPLC: 93.33%. ¹H NMR (400 MHz, CDCl₃) δ 8.38 (d, J=5.8 Hz, 1H), 7.06-6.87 (m, 1H), 5.82-5.78 (m, 1H), 4.69-4.27 (m, 5H), 4.09-3.94 (m, 1H), 3.89-3.74 (m, 1H), 3.55-3.30 (m, 2H), 2.60-2.47 (m, 1H), 2.47-2.30 (m, 1H), 2.13-2.01 (m, 1H), 1.97-1.86 (m, 2H), 1.61-1.42 (m, 2H), 1.11-0.85 (m, 15H).

Example S35: Synthesis of Compound D-1-d

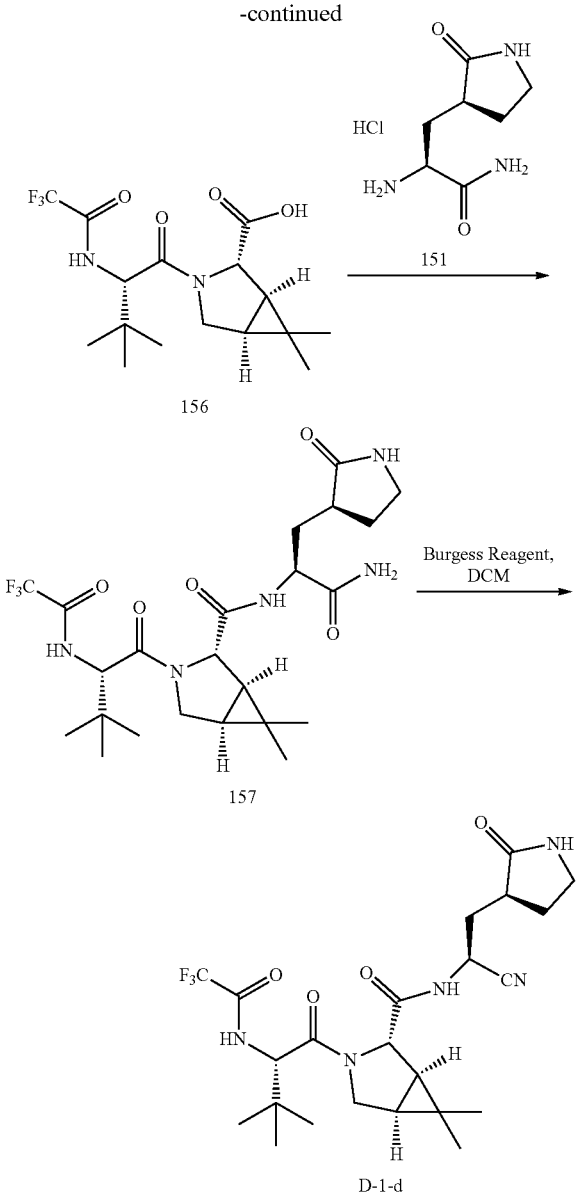

To a flask containing compound 103 (10 g, 34.93 mmol) was added 7.0 M ammonia in MeOH (300 mL). The reaction mixture was stirred at 50° C. in an autoclave reactor overnight. After completion of the reaction (monitored by LCMS), the reaction mixture was concentrated down under reduced pressure to give the crude compound 150 as a white solid (9.50 g, 35.01 mmol, 100.26%), which was directly used for next step without further purification. LCMS=[M+H]$^+$: 272.4.

To a solution of compound 150 (9.0 g, 33.17 mmol) in ethyl acetate (60 mL) was added 4.0 M HCl in ethyl acetate (50 mL). The reaction mixture was stirred at room temperature for 2 h. LCMS indicated that the reaction was complete. The reaction mixture was concentrated down under reduced pressure to yield compound 151 (7.20 g, 34.67 mmol, 104.52%) as a white solid, which was directly used in the next reaction without further purification. LCMS=[M+H]$^+$: 208.3.

To a stirred solution of (2S)-2-{[(tert-butoxy)carbonyl] amino}-3,3-dimethylbutanoic acid (compound 152) (10.16 g, 43.93 mmol) and methyl (1R,2S,5S)-1,5-dihydrogenio-6,6-dimethyl-3-azabicyclo[3.1.0]-hexane-2-carboxylate (compound 144) (8.14 g, 48.22 mmol) in DMF (10 mL) and ACN (90 mL), DIEA (19.8 mL, 119.80 mmol) and HATU (15.18 g, 39.93 mmol) were added sequentially at 0° C. The reaction mixture was stirred at room temperature under N$_2$ overnight. After completion of the reaction (monitored by LCMS), the reaction mixture was diluted with water (100 mL) and then extracted with ethyl acetate (200 mL×3). The combined organic layers were washed with brine (100 mL×3), dried over anhydrous Na$_2$SO$_4$, and concentrated down under reduced pressure to yield compound 153 (13.7 g, 35.82 mmol, 89.69%) as a yellow oil. LCMS=[M+H]$^+$: 383.1.

To a stirred solution of methyl (1R,2S,5S)-3-[(2S)-2-{[(tert-butoxy)carbonyl]amino}-3,3-dimethylbutanoyl]-1,5-dihydrogenio-6,6-dimethyl-3-azabicyclo[3.1.0]hexane-2-carboxylate (compound 153) (13.7 g, 35.82 mmol) in MeOH (60 mL) at 0° C. LiOH (1.7 g, 71.63 mmol) in H$_2$O (60 mL) was added dropwise. The reaction mixture was stirred at room temperature for 3 h under N$_2$. After completion of the reaction (monitored by LCMS), the resulting mixture was diluted with water (150 mL) and extracted with DCM (300 mL). The aqueous phase was adjusted to pH ~3-4 with 1M HCl and extracted with EtOAc (200 mL×3). The combined organic layers were dried over anhydrous Na$_2$SO$_4$ and concentrated under reduced pressure to give the crude compound 154 (7.48 g, 20.30 mmol, 56.68%) as yellow solid. LCMS=[M+H]$^+$: 369.0. $^1$H NMR (400 MHz, CDCl$_3$) δ 9.26 (s, 1H), 5.18 (d, J=9.9 Hz, 1H), 4.48 (s, 1H), 4.24 (d, J=10.2 Hz, 1H), 4.06 (d, J=10.4 Hz, 1H), 3.84 (dd, J=10.4, 5.4 Hz, 1H), 1.73-1.68 (m, 1H), 1.52-1.47 (m, 1H), 1.40 (s, 9H), 1.06 (s, 3H), 1.01 (s, 9H), 0.90 (s, 3H).

To a stirred solution of (1R,2S,5S)-3-[(2S)-2-{[(tert-butoxy)carbonyl]amino}-3,3-dimethyl-butanoyl]-1,5-dihydrogenio-6,6-dimethyl-3-azabicyclo[3.1.0]hexane-2-carboxylic acid (compound 154) (2 g, 5.43 mmol) in DCM (20 mL) at 0° C. was added 4.0 M HCl/dioxane (6.77 mL). The solution was stirred at room temperature for 3 h. After completion of the reaction (monitored by LCMS), the reaction mixture was concentrated down under reduced pressure to yield compound 155 (1.9 g, crude) as yellow solid. LCMS=[M+H]$^+$: 269.1.

To a stirred solution of (1R,2S,5S)-3-[(2S)-2-amino-3,3-dimethylbutanoyl]-1,5-dihydrogenio-6,6-dimethyl-3-azabicyclo[3.1.0]hexane-2-carboxylic acid (compound 155) (2 g, 7.45 mmol) in MeOH (20 mL) at 0° C. was added methyl 2,2,2-trifluoroacetate (3 mL, 29.81 mmol) and TEA (5.2 mL, 37.26 mmol). The reaction mixture was stirred at 50° C. overnight under N$_2$.

After completion of reaction (monitored by LCMS), the reaction mixture was concentrated down under reduced pressure. The resulting residue was diluted with water, adjusted pH to ~3-4 with 1M HCl, and extracted with ethyl acetate (100 mL×3). The combined organic layers were washed with brine, dried over anhydrous Na$_2$SO$_4$ and concentrated down under reduced pressure to give the crude compound 156 (2.2 g, 6.04 mmol, 81.02%) as an off-white solid. LCMS=[M+H]$^+$: 365.2. $^1$H NMR (400 MHz, CDCl$_3$) δ 7.43-7.27 (m, 1H), 4.57-4.51 (m, 1H), 4.40 (s, 1H), 3.89-3.84 (m, 1H), 3.79 (d, J=10.4 Hz, 1H), 1.58-1.51 (m, 1H), 1.48-1.40 (m, 1H), 1.02-0.97 (m, 12H), 0.82 (s, 3H).

To a stirred solution of (1R,2S,5S)-3-[(2S)-3,3-dimethyl-2-(trifluoroacetamido)butanoyl]-1,5-dihydrogenio-6,6-dimethyl-3-azabicyclo[3.1.0]hexane-2-carboxylic acid (compound 156) (600 mg, 1.65 mmol) and (2S)-2-amino-3-[(3S)-2-oxopyrrolidin-3-yl]propanamide (compound 151) (338 mg, 1.98 mmol) in butan-2-one (10 mL) at 0° C. was added DIEA (0.80 mL, 4.94 mmol), EDCI (410 mg, 2.14 mmol) and 2-pyridinol-1-oxide (0.20 mL, 2.14 mmol). The reaction mixture was stirred at room temperature overnight under $N_2$. After completion of the reaction (monitored by LCMS), the reaction mixture was diluted with water (200 mL) and extracted with EtOAc (200 mL×3). The combined organic layers were dried over anhydrous $Na_2SO_4$ and concentrated down under reduced pressure. The resulting residue was purified by column chromatography (C18, ACN/water (0.1% FA)) to yield compound 157 (380 mg, 0.73 mmol, 44.59%) as an off-white solid. LCMS=[M+H]$^+$: 518.5.

To a stirred solution of (2S)-2-{[(1R,2S,5S)-3-[(2S)-3,3-dimethyl-2-(trifluoroacetamido)butanoyl]-1,5-dihydrogenio-6,6-dimethyl-3-azabicyclo[3.1.0]hexan-2-yl]formamido}-3-[(3S)-2-oxopyrrolidin-3-yl]propanamide (compound 157) (330 mg, 0.64 mmol) in DCM (6 mL) was added Burgess reagent (152 mg, 0.64 mmol). The solution was stirred at room temperature under $N_2$ for 1 h. After completion of the reaction (monitored by LCMS), the reaction mixture was concentrated down under reduced pressure and the resulting residue was purified by prep-HPLC to yield compound D-1-d (111.19 mg, 0.22 mmol, 34.91%) as an off-white solid. LCMS=[M+H]$^+$: 500.3. $^1$H NMR (400 MHz, DMSO-$d_6$) δ 9.40 (d, J=8.4 Hz, 1H), 9.01 (d, J=8.5 Hz, 1H), 7.66 (s, 1H), 5.01-4.93 (m, 1H), 4.41 (d, J=8.5 Hz, 1H), 4.16 (s, 1H), 3.94-3.88 (m, 1H), 3.69 (d, J=10.5 Hz, 1H), 3.18-3.00 (m, 2H), 2.44-2.35 (m, 1H), 2.20-2.04 (m, 2H), 1.77-1.66 (m, 2H), 1.59-1.54 (m, 1H), 1.32 (d, J=7.6 Hz, 1H), 1.01 (d, J=19.1 Hz, 12H), 0.87 (s, 3H).

Example S36: Synthesis of Compound D-1-e

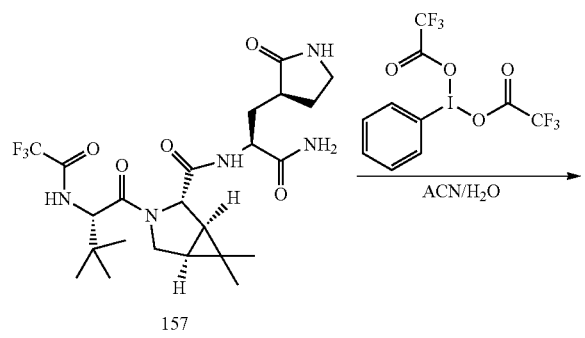

157

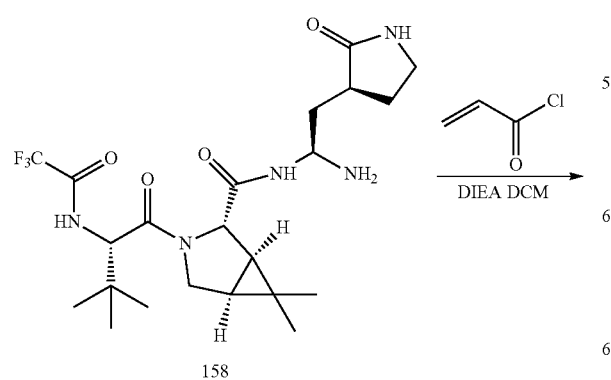

158

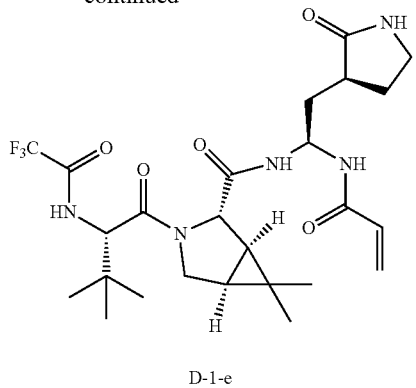

D-1-e

A solution of (1R,2S,5S)—N—((S)-1-amino-1-oxo-3-((S)-2-oxopyrrolidin-3-yl)propan-2-yl)-3-((S)-3,3-dimethyl-2-(2,2,2-trifluoroacetamido)butanoyl)-6,6-dimethyl-3-azabicyclo[3.1.0]hexane-2-carboxamide (compound 157) (150 mg, 0.29 mmol) and bis(trifluoroacetoxy)iodobenzene (125 mg, 0.29 mmol) in ACN (5 mL) and water (5 mL) was stirred at room temperature overnight. After completion of reaction (monitored by LCMS), the reaction mixture was purified by flash column chromatography (C 18, 40 g, 20-35 um, 100 Å) using eluent 50% ACN in water (0.1% FA) to yield compound 158 as a white solid (65 mg, 46%). LCMS= [M+H]$^+$: 490.2.

To a solution of (1R,2S,5S)—N—((S)-1-amino-2-((S)-2-oxopyrrolidin-3-yl)ethyl)-3-((S)-3,3-dimethyl-2-(2,2,2-trifluoroacetamido)butanoyl)-6,6-dimethyl-3-azabicyclo[3.1.0] hexane-2-carboxamide (compound 158) (60 mg, 0.12 mmol) and DIEA (63 mg, 0.49 mmol) in DCM (3 mL) at 0° C. under $N_2$ was added acryloyl chloride (15 mg, 0.16 mmol). The reaction mixture was stirred at room temperature for 15 min. After completion of the reaction (monitored by LCMS), the reaction mixture was concentrated down under reduced pressure and purified by prep-HPLC to yield compound D-1-e as a white solid (2.96 mg, 5%). LCMS= [M+H]$^+$: 544.4, Purity=94%. $^1$H NMR (400 MHz, CDCl$_3$) δ 9.94 (s, 1H), 8.23 (s, 1H), 7.67 (s, 1H), 7.13 (d, J=8.1 Hz, 1H), 6.96 (s, 1H), 6.30 (t, J=7.5 Hz, 1H), 6.15 (s, 1H), 5.98 (s, 1H), 5.79 (s, 1H), 5.72-5.51 (m, 2H), 4.56 (d, J=9.3 Hz, 1H), 4.32 (t, J=15.1 Hz, 1H), 3.93 (s, 1H), 3.82 (t, J=10.0 Hz, 1H), 3.58 (d, J=12.6 Hz, 1H), 3.48-3.34 (m, 2H), 2.89 (s, 1H), 2.65 (s, 1H), 2.56-2.47 (m, 1H), 2.41 (s, 1H), 2.23 (s, 1H), 2.09 (s, 1H), 1.60-1.46 (m, 2H), 1.07-1.00 (m, 9H), 0.85 (s, 3H).

Example S37: Synthesis of Compound D-1-f

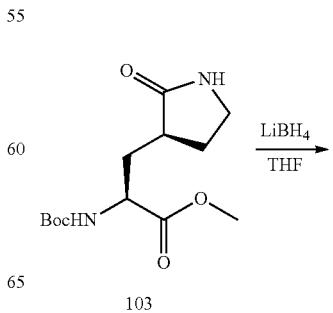

103

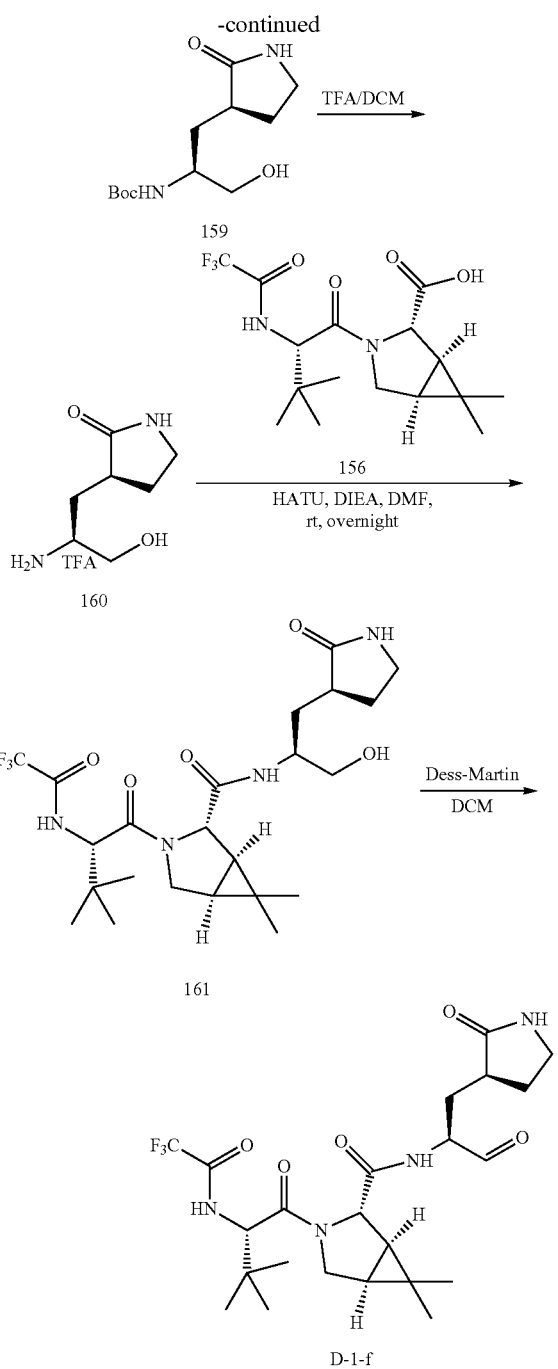

(s, 1H), 5.44 (d, J=7.1 Hz, 1H), 3.74 (d, J=5.3 Hz, 1H), 3.66-3.55 (m, 2H), 3.40-3.30 (m, 2H), 3.16 (s, 1H), 2.56-2.37 (m, 2H), 2.00-1.90 (m, 1H), 1.88-1.79 (m, 1H), 1.68-1.59 (m, 1H), 1.44 (s, 9H).

A solution of tert-butyl ((S)-1-hydroxy-3-((S)-2-oxopyrrolidin-3-yl)propan-2-yl)carbamate (compound 159) (340 mg, 12.18 mmol) and TFA (3 mL) in DCM (5 mL) was stirred at room temperature for 1 h. After completion of the reaction (monitored by LCMS), the reaction mixture was concentrated down under reduced pressure to yield compound 160 as a yellow oil (350 mg, crude), which was used in the next reaction without further purification. LCMS= [M+H]$^+$: 159.1.

To a stirred solution of (1R,2S,5S)-3-((S)-3,3-dimethyl-2-(2,2,2-trifluoroacetamido)butanoyl)-6,6-dimethyl-3-azabicyclo[3.1.0]hexane-2-carboxylic acid (compound 156) (100 mg, 0.27 mmol) in DMF (3 mL), HATU (156 mg, 0.41 mmol) and DIEA (142 mg, 1.108 mmol) were added. The reaction mixture was stirred at room temperature for 1 h, then (S)-3-((S)-2-amino-3-hydroxypropyl)pyrrolidin-2-one TFA salt (compound 160) (84 mg, 0.27 mmol) was added. The reaction mixture was stirred at room temperature overnight. After completion of the reaction (monitored by LCMS), the reaction mixture was diluted with EtOAc, washed with water, 1M HCl, sat. NaCl, dried over anhydrous Na$_2$SO$_4$, and concentrated down under reduced pressure. The resulting residue was purified by flash column chromatography (C 18, 40 g, 20-35 um, 100 Å, 60% ACN in water (0.1% FA)) to yield compound 161 as a brown solid (40 mg, 29%). LCMS=[M+H]$^+$: 505.2.

A solution of (1R,2S,5S)-3-((S)-3,3-dimethyl-2-(2,2,2-trifluoroacetamido)butanoyl)-N—((S)-1-hydroxy-3-((S)-2-oxopyrrolidin-3-yl)propan-2-yl)-6,6-dimethyl-3-azabicyclo [3.1.0]hexane-2-carboxamide (compound 161) (63 mg, 0.13 mmol) and Dess-Martin periodinane (265 mg, 0.62 mmol) in DCM (5 mL) was stirred at room temperature for 1 h. After completion of the reaction (monitored by LCMS), the reaction mixture was diluted with DCM. The organic layer was washed with sat. Na$_2$S$_2$O$_3$ (aq), sat. NaHCO$_3$ (aq), brine, dried over anhydrous Na$_2$SO$_4$, and concentrated down under reduced pressure. The resulting residue was purified by prep-HPLC to yield compound D-1-f as a white solid (10 mg, 17%). LCMS=[M+H]$^+$: 503.3. Purity=86%. $^1$H NMR (400 MHz, CDCl$_3$) δ 9.47 (d, J=6.0 Hz, 1H), 8.03 (s, 1H), 6.91 (d, J=12.7 Hz, 1H), 5.67 (s, 1H), 4.50 (d, J=9.2 Hz, 1H), 4.37 (s, 1H), 4.30 (s, 1H), 4.15 (d, J=9.0 Hz, 1H), 3.95 (dd, J=10.1, 4.9 Hz, 1H), 3.74 (d, J=10.2 Hz, 1H), 3.33 (s, 2H), 2.50 (s, 1H), 2.37 (s, 1H), 1.93 (s, 1H), 1.82 (s, 1H), 1.52-1.46 (m, 2H), 1.01 (d, J=2.8 Hz, 3H), 0.96 (d, J=6.1 Hz, 9H), 0.83 (s, 3H).

Example S38: Synthesis of Compound D-2-a

To a stirred solution of methyl (S)-2-((tert-butoxycarbonyl)amino)-3-((S)-2-oxopyrrolidin-3-yl)propanoate (compound 103) (500 mg, 1.75 mmol) in THF (10 mL) at 0° C. under N$_2$ was added LiBH$_4$ (154 mg, 6.98 mmol) portionwise. The reaction mixture was stirred at room temperature for 2 h. After completion of the reaction (monitored by LCMS), the reaction mixture was cooled to 0° C. in ice-bath, quenched with water (20 mL) and extracted with ethyl acetate (50 mL×3). The combined organic layers were washed with brine, dried over anhydrous Na$_2$SO$_4$, and concentrated down under reduced pressure to provide the crude compound 159 as a white solid (340 mg, 75%), which was used in the next reaction without further purification. LCMS=[M+H]$^+$: 259.1. $^1$H NMR (400 MHz, CDCl$_3$) δ 5.88

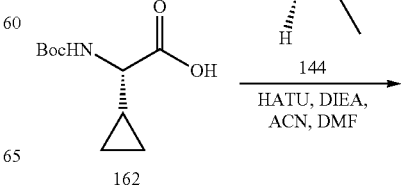

-continued

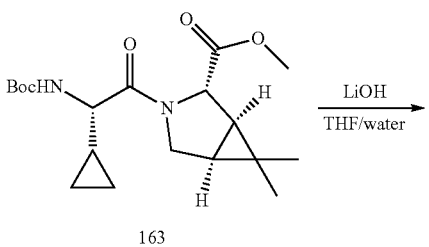

163

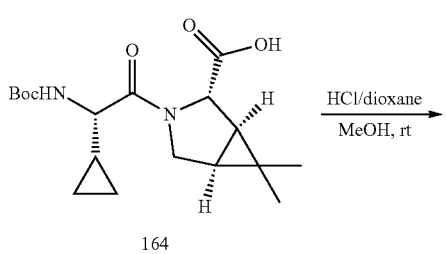

164

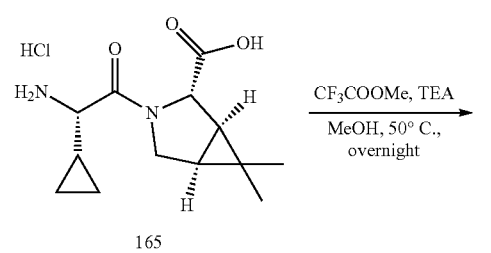

165

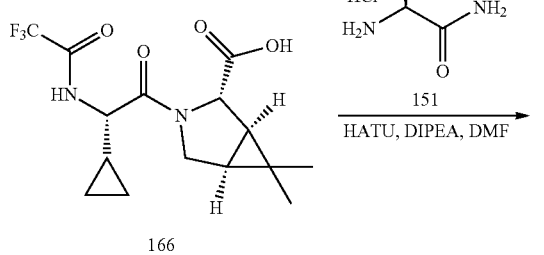

166

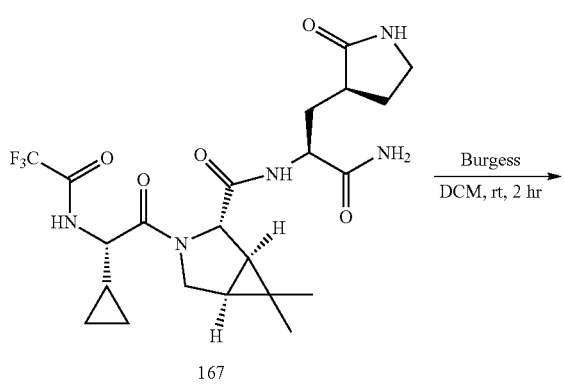

167

-continued

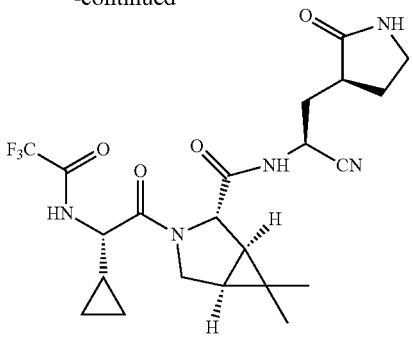

D-2-a

To a stirred solution of (S)-2-((tert-butoxycarbonyl)amino)-2-cyclopropylacetic acid (compound 162) (1.18 g, 5.5 mmol) and methyl (1R,2S,5S)-1,5-dihydrogenio-6,6-dimethyl-3-azabicyclo[3.1.0]hexane-2-carboxylate (compound 144) (1.12 g, 6.6 mmol) in DMF (4 mL) and ACN (36 mL) at 0° C., DIEA (1.42 g, 11 mmol) and HATU (2.51 g, 6.6 mmol) were added. The reaction mixture was stirred at room temperature overnight under $N_2$. After completion of the reaction (monitored by LCMS), the reaction mixture was concentrated down under reduced pressure to remove ACN, and then diluted with water (80 mL) and extracted with ethyl acetate (100 mL×3). The combined organic layers were washed with brine (100 mL×3), dried over anhydrous $Na_2SO_4$, and concentrated down under reduced pressure. The resulting residue was purified by column chromatography (C18, (ACN/water (0.1% FA)) to yield compound 163 (1.6 g, 79%) as a colourless oil. LCMS=[M+Na]$^+$: 388.9. $^1$H NMR (400 MHz, DMSO-$d_6$) δ 7.15 (d, J=7.6 Hz, 1H), 4.18 (s, 1H), 3.83 (d, J=10.4 Hz, 1H), 3.75-3.69 (m, 1H), 3.67 (d, J=2.2 Hz, 1H), 3.65 (s, 3H), 1.56-1.49 (m, 1H), 1.40 (d, J=7.5 Hz, 1H), 1.35 (d, J=2.4 Hz, 9H), 1.09-1.03 (m, 1H), 1.01 (d, J=3.7 Hz, 3H), 0.91 (s, 3H), 0.41 (d, J=8.0 Hz, 2H), 0.33 (d, J=3.2 Hz, 2H).

To a stirred solution of methyl (1R,2S,5S)-3-((S)-2-((tert-butoxycarbonyl)amino)-2-cyclopropyl-acetyl)-6,6-dimethyl-3-azabicyclo[3.1.0]hexane-2-carboxylate (compound 163) (350 mg, 0.96 mmol) in THF/water (10 mL, 1:1) at 0° C. was added LiOH (91 mg, 3.82 mmol). The reaction mixture was stirred at room temperature for 3 h. After completion of the reaction (monitored by LCMS), the reaction mixture was concentrated down under reduced pressure. The resulting residue was diluted with water, adjusted pH to ~3-4 with 1M HCl, and extracted with EtOAc (60 mL×3). The combined organic layers were washed with brine, dried over $Na_2SO_4$, and concentrated down under reduced pressure. The resulting residue was purified by column chromatography (C18, (ACN/water (0.1% FA)) to yield compound 164 (320 mg, 95%) as an off-white solid. LCMS=[M+H]$^+$: 353.2. $^1$H NMR (400 MHz, DMSO-$d_6$) δ 7.06 (d, J=6.8 Hz, 1H), 4.09 (s, 1H), 3.80 (d, J=10.4 Hz, 1H), 3.76-3.66 (m, 2H), 3.45 (d, J=5.8 Hz, 1H), 1.56-1.45 (m, 1H), 1.43-1.27 (m, 10H), 1.11-0.98 (m, 4H), 0.90 (d, J=17.6 Hz, 3H), 0.51-0.23 (m, 4H).

To a mixture of (1R,2S,5S)-3-((S)-2-((tert-butoxycarbonyl)amino)-2-cyclopropylacetyl)-6,6-dimethyl-3-azabicyclo[3.1.0]hexane-2-carboxylic acid (compound 164) (320 mg, 0.9 mmol) in DCM (5 mL) was added a solution of 4.0 M HCl in dioxane (5 mL). The reaction mixture was stirred at room temperature for 3 h. After completion of the reaction (monitored by LCMS), the reaction mixture was concentrated down under reduced pressure to provide the crude compound 165 (250 mg) as a yellow semi-solid. LCMS= [M+H]+: 253.1.

To a stirred solution of (1R,2S,5S)-3-((S)-2-amino-2-cyclopropylacetyl)-6,6-dimethyl-3-azabicyclo[3.1.0]hexane-2-carboxylic acid hydrochloride (compound 165) (250 mg, 0.87 mmol) in MeOH (10 mL) at 0° C. was added TEA (0.264 g, 2.61 mmol) and methyl-2,2,2-trifluoroacetate (0.335 g, 2.61 mmol). The reaction mixture was stirred at 50° C. overnight under N$_2$. After completion of the reaction (monitored by LCMS), the reaction mixture was concentrated down under reduced pressure. The resulting residue was diluted with water, adjusted pH to ~3-4 with 1M HCl, and extracted with ethyl acetate (50 mL×3). The combined organic layers were washed with brine, dried over anhydrous Na$_2$SO$_4$, and concentrated down under reduced pressure. The resulting residue was purified by column chromatography (C18, ACN/water (0.1% FA)) to yield compound 166 (200 mg, 65%) as an off-white solid. LCMS=[M+H]+: 349.2. $^1$H NMR (400 MHz, DMSO-d$_6$) δ 12.68 (s, 1H), 9.93 (d, J=6.0 Hz, 1H), 4.11 (s, 1H), 4.03-3.94 (m, 1H), 3.80-3.72 (m, 1H), 3.69 (d, J=10.5 Hz, 1H), 1.56-1.49 (m, 1H), 1.41 (d, J=7.6 Hz, 1H), 1.19-1.09 (m, 1H), 1.02 (d, J=3.4 Hz, 3H), 0.88 (s, 3H), 0.55-0.37 (m, 4H).

To a stirred solution of (1R,2S,5S)-3-((S)-2-cyclopropyl-2-(2,2,2-trifluoroacetamido)acetyl)-6,6-dimethyl-3-azabicyclo[3.1.0]hexane-2-carboxylic acid (compound 166) (200 mg, 0.57 mmol) and (2S)-2-amino-3-[(3S)-2-oxopyrrolidin-3-yl]propanamide (compound 151) (142 mg, 0.68 mmol) in DMF (8 mL) at 0° C. was added DIEA (220 mg, 1.71 mmol) and HATU (259 mg, 0.68 mmol). The reaction mixture was stirred at room temperature for 3 h under N$_2$. After completion of the reaction (monitored by LCMS), the reaction mixture was diluted with water (50 mL) and extracted with ethyl acetate (60 mL×3). The combined organic layers were washed with brine (40 mL×3), dried over anhydrous Na$_2$SO$_4$, and concentrated down under reduced pressure. The resulting crude product was purified by column chromatography (C18, ACN/water (0.1% FA)) to yield compound 167 (80 mg, 28%) as an off-white solid. LCMS=[M+H]+: 502.3. $^1$H NMR (400 MHz, DMSO-d$_6$) δ 9.90 (s, 1H), 8.20 (d, J=8.4 Hz, 1H), 7.58 (s, 1H), 7.23 (s, 1H), 7.03 (s, 1H), 4.30-4.20 (m, 2H), 4.08 (d, J=8.3 Hz, 1H), 3.85-3.78 (m, 1H), 3.65 (d, J=10.5 Hz, 1H), 3.19-3.02 (m, 2H), 2.40-2.29 (m, 1H), 2.20-2.09 (m, 1H), 2.02-1.85 (m, 1H), 1.72-1.60 (m, 1H), 1.59-1.45 (m, 2H), 1.38 (d, J=7.6 Hz, 1H), 1.20-1.10 (m, 1H), 1.07-0.99 (m, 3H), 0.95-0.83 (m, 3H), 0.57-0.38 (m, 4H).

To a stirred solution of (1R,2S,5S)—N—((S)-1-amino-1-oxo-3-((S)-2-oxopyrrolidin-3-yl)propan-2-yl)-3-((S)-2-cyclopropyl-2-(2,2,2-trifluoroacetamido)acetyl)-6,6-dimethyl-3-azabicyclo[3.1.0]hexane-2-carboxamide (compound 167) (80 mg, 0.16 mmol) in DCM (5 mL) was added Burgess reagent (76 mg, 0.32 mmol). The reaction mixture was stirred at room temperature for 3 h under N$_2$. After completion of the reaction (monitored by LCMS), the reaction mixture was concentrated down under reduced pressure. The resulting residue was purified by prep-HPLC to yield compound D-2-a (37 mg, 47.7%) as a white solid. LCMS=[M+H]+: 484.3. HPLC: 95.14%. $^1$H NMR (400 MHz, DMSO-d$_6$) δ 9.90 (d, J=6.5 Hz, 1H), 8.95 (d, J=8.3 Hz, 1H), 7.68 (s, 1H), 5.02-4.90 (m, 1H), 4.14 (d, J=8.2 Hz, 1H), 4.09-4.02 (m, 1H), 3.86-3.77 (m, 1H), 3.67 (d, J=10.5 Hz, 1H), 3.18-3.04 (m, 2H), 2.41-2.35 (m, 1H), 2.17-2.07 (m, 2H), 1.79-1.64 (m, 1H), 1.60-1.54 (m, 1H), 1.30 (d, J=7.5 Hz, 1H), 1.18-1.12 (m, 1H), 1.08-0.99 (m, 3H), 0.98-0.86 (m, 3H), 0.55-0.38 (m, 4H).

Example S39: Synthesis of Compound D-2-b

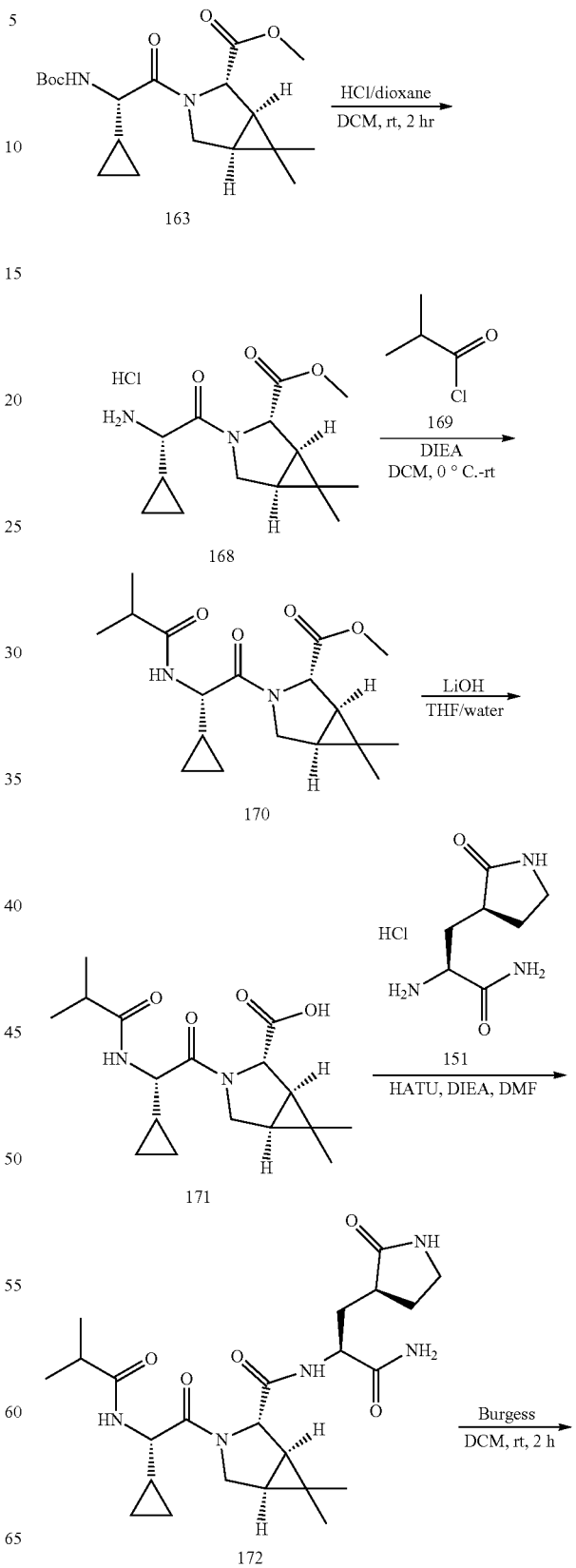

-continued

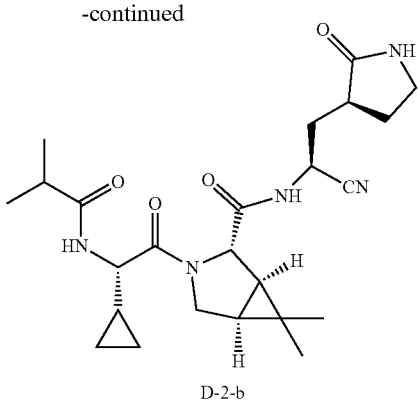

D-2-b

To a stirred solution of methyl (1R,2S,5S)-3-((S)-2-((tert-butoxycarbonyl)amino)-2-cyclopropyl-acetyl)-6,6-dimethyl-3-azabicyclo[3.1.0]hexane-2-carboxylate (compound 163) (1.2 g, 3.28 mmol) in DCM (10 mL) was added HCl in dioxane (4.0 M, 15 mL). The reaction mixture was stirred at room temperature for 2 h. After completion of the reaction (monitored by LCMS), the reaction mixture was concentrated down under reduced pressure to provide the crude compound 168 (1.1 g) as a yellow semi-solid. LCMS=[M+H]$^+$: 267.0.

To a stirred solution of methyl (1R,2S,5S)-3-((S)-2-amino-2-cyclopropylacetyl)-6,6-dimethyl-3-azabicyclo[3.1.0]hexane-2-carboxylate hydrochloride (compound 168) (293 mg, 0.97 mmol) in DCM (10 mL) at 0° C. was added DIEA (0.387 g, 3 mmol) and isobutyryl chloride (compound 169) (123 mg, 1.16 mmol). The reaction mixture was stirred at room temperature for 2 h. After completion of the reaction (monitored by LCMS), the reaction mixture was diluted with DCM, washed with brine, dried over anhydrous Na$_2$SO$_4$, and concentrated down under reduced pressure. The resulting residue was purified by column chromatography (C18, ACN/water (0.1% FA)) to yield compound 170 (200 mg, 61%) as a white solid. LCMS=[M+H]$^+$: 337.3. $^1$H NMR (400 MHz, DMSO-d$_6$) δ 8.12 (d, J=7.5 Hz, 1H), 4.16 (s, 1H), 4.05-3.91 (m, 1H), 3.74 (d, J=2.6 Hz, 2H), 3.64 (d, J=9.1 Hz, 3H), 2.48-2.39 (m, 1H), 1.57-1.50 (m, 1H), 1.40 (d, J=7.5 Hz, 1H), 1.14-1.04 (m, 1H), 1.01 (d, J=6.3 Hz, 3H), 0.99-0.91 (m, 6H), 0.87 (s, 3H), 0.47-0.36 (m, 2H), 0.35-0.23 (m, 2H).

To a stirred solution of methyl (1R,2S,5S)-3-((S)-2-cyclopropyl-2-isobutyramidoacetyl)-6,6-dimethyl-3-azabicyclo[3.1.0]hexane-2-carboxylate (compound 170) (200 mg, 0.59 mmol) in THF/water (10 mL, 2:1) was added LiOH (29 mg, 1.18 mmol). The reaction mixture was stirred for 2 h at room temperature. After completion of the reaction (monitored by LCMS), the reaction mixture was concentrated down under reduced pressure. The resulting residue was diluted with water, adjusted pH to ~3-4 with 1M HCl, and extracted with DCM (40 mL×3). The combined organic layers were concentrated down under reduced pressure, and the resulting residue was purified by column chromatography (C18, ACN/water (0.1% FA)) to yield compound 171 (170 mg, 89%) as an off-white solid. LCMS=[M+H]$^+$: 323.2. $^1$H NMR (400 MHz, DMSO-d$_6$) δ 12.73 (s, 1H), 8.09 (d, J=7.8 Hz, 1H), 4.07 (s, 1H), 4.05-3.98 (m, 1H), 3.72 (d, J=2.8 Hz, 2H), 2.48-2.39 (m, 1H), 1.55-1.44 (m, 1H), 1.38 (d, J=7.6 Hz, 1H), 1.16-1.03 (m, 1H), 1.00 (s, 3H), 0.98-0.91 (m, 6H), 0.86 (s, 3H), 0.43-0.29 (m, 4H).

To a stirred solution of (1R,2S,5S)-3-((S)-2-cyclopropyl-2-isobutyramidoacetyl)-6,6-dimethyl-3-azabicyclo[3.1.0]hexane-2-carboxylic acid (compound 171) (170 mg, 0.53 mmol) and (2S)-2-amino-3-[(3S)-2-oxopyrrolidin-3-yl]propanamide hydrochloride (compound 151) (124 mg, 0.6 mmol) in DMF (5 mL) at 0° C. were added DIEA (0.205 g, 1.59 mmol) and HATU (0.229 g, 0.6 mmol). The reaction mixture was stirred at room temperature for 1 h under N$_2$. After completion of the reaction (monitored by LCMS), the reaction mixture was diluted with water (50 mL), extracted with ethyl acetate (60 mL×3). The combined organic layers were washed with brine (40 mL×3), dried over anhydrous Na$_2$SO$_4$, and concentrated down under reduced pressure. The resulting residue was purified by column chromatography (C18, ACN/water (0.1% FA)) to yield compound 172 (150 mg, 59.5%) as an off-white solid. LCMS=[M+H]$^+$: 476.4. $^1$H NMR (400 MHz, DMSO-d$_6$) δ 8.20 (d, J=8.4 Hz, 1H), 8.10 (d, J=7.7 Hz, 1H), 7.61 (s, 1H), 7.16 (s, 1H), 7.05 (s, 1H), 4.27-4.19 (m, 1H), 4.17 (s, 1H), 4.12-4.06 (m, 1H), 3.84-3.76 (m, 1H), 3.66 (d, J=10.4 Hz, 1H), 3.18-3.05 (m, 2H), 2.47-2.41 (m, 1H), 2.40-2.28 (m, 1H), 2.25-2.10 (m, 1H), 2.01-1.85 (m, 1H), 1.73-1.51 (m, 2H), 1.51-1.42 (m, 1H), 1.39-1.32 (m, 1H), 1.13-1.04 (m, 1H), 1.04-0.99 (m, 4H), 0.98-0.90 (m, 6H), 0.87 (s, 2H), 0.47-0.22 (m, 4H).

To a stirred solution of (1R,2S,5S)—N—((S)-1-amino-1-oxo-3-((S)-2-oxopyrrolidin-3-yl)propan-2-yl)-3-((S)-2-cyclopropyl-2-isobutyramidoacetyl)-6,6-dimethyl-3-azabicyclo[3.1.0]hexane-2-carboxamide (compound 172) (150 mg, 0.31 mmol) in DCM (10 mL) was added Burgess reagent (0.147 g, 0.62 mmol). The reaction mixture was stirred at room temperature for 2 h under N$_2$. After completion of the reaction (monitored by LCMS), the reaction mixture was concentrated down under reduced pressure. The resulting residue was purified by prep-HPLC to yield compound D-2-b (50 mg, 35.2%) as a white solid. LCMS=[M+H]$^+$: 458.3, HPLC: 99.55%. $^1$H NMR (400 MHz, DMSO-d$_6$) δ 8.88 (d, J=8.2 Hz, 1H), 8.09 (d, J=7.5 Hz, 1H), 7.69 (s, 1H), 5.01-4.85 (m, 1H), 4.15-3.98 (m, 2H), 3.85-3.74 (m, 1H), 3.69 (d, J=10.3 Hz, 1H), 3.21-3.03 (m, 2H), 2.49-2.35 (m, 2H), 2.19-2.07 (m, 2H), 1.81-1.63 (m, 2H), 1.57-1.48 (m, 1H), 1.28 (d, J=7.5 Hz, 1H), 1.10-0.99 (m, 4H), 0.99-0.85 (m, 9H), 0.44-0.27 (m, 4H).

Example S40: Synthesis of Compound D-2-c

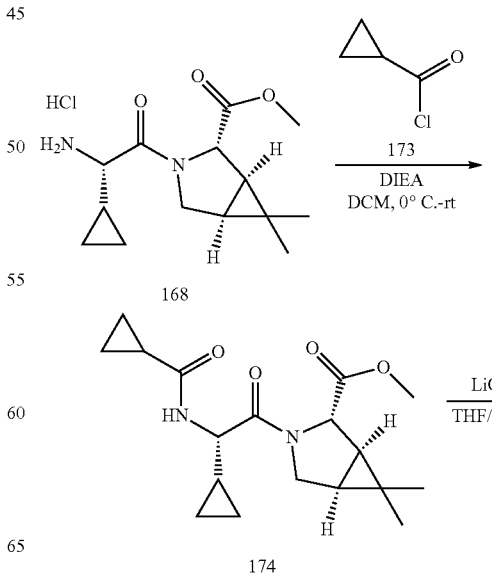

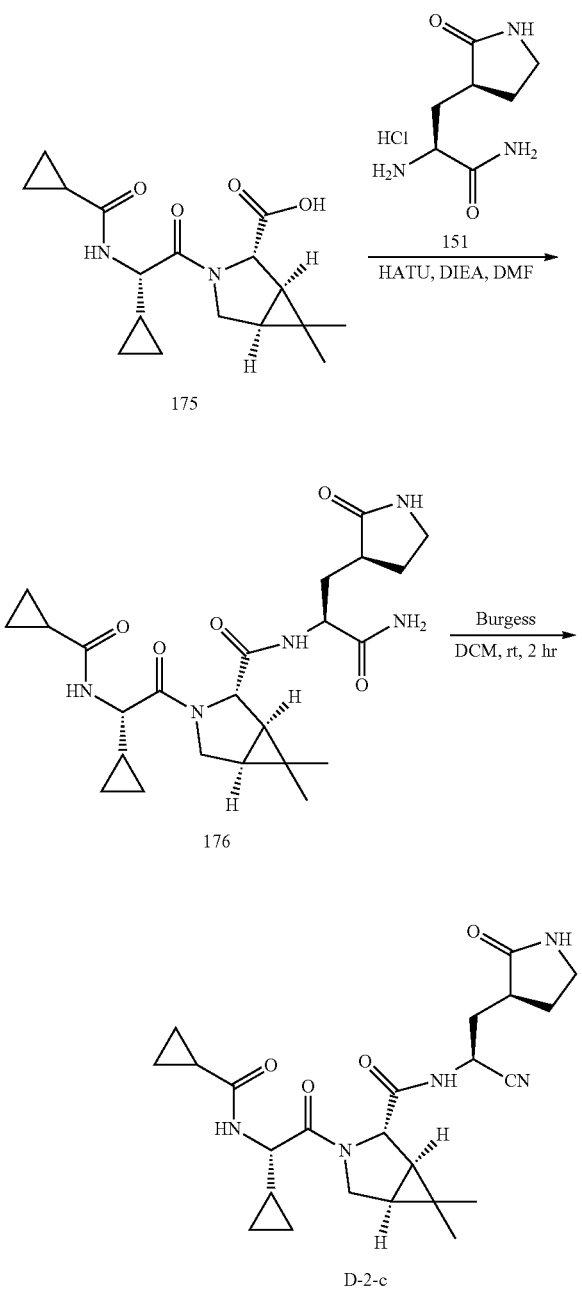

4.16 (s, 1H), 4.03-3.94 (m, 1H), 3.81-3.69 (m, 2H), 3.66 (s, 3H), 1.74-1.62 (m, 1H), 1.56-1.48 (m, 1H), 1.40 (d, J=7.5 Hz, 1H), 1.17-1.03 (m, 1H), 1.01 (d, J=7.0 Hz, 3H), 0.90 (d, J=33.8 Hz, 3H), 0.70-0.53 (m, 4H), 0.45 (d, J=8.1 Hz, 2H), 0.38-0.24 (m, 2H).

To a stirred solution of methyl (1R,2S,5S)-3-((S)-2-(cyclopropanecarboxamido)-2-cyclopropyl-acetyl)-6,6-dimethyl-3-azabicyclo[3.1.0]hexane-2-carboxylate (compound 174) (170 mg, 0.51 mmol) in THF/water (10 mL, 2:1) was added LiOH (27 mg, 1.02 mmol). The reaction mixture was stirred at room temperature for 2 h. After completion of the reaction (monitored by LCMS), the reaction mixture was concentrated down under reduced pressure. The resulting residue was diluted with water, the pH was adjusted to ~3-4 with 1M HCl and extracted with DCM (50 mL×3). The combined organic layers were concentrated down under reduced pressure, and the resulting residue was purified by column chromatography (C18, ACN/water (0.1% FA)) to yield compound 175 (150 mg, 92%) as an off-white solid. LCMS=[M+H]$^+$: 321.2. $^1$H NMR (400 MHz, DMSO-d$_6$) δ 12.71 (s, 1H), 8.44 (d, J=7.6 Hz, 1H), 4.10-4.01 (m, 2H), 3.76-3.67 (m, 2H), 1.74-1.63 (m, 1H), 1.55-1.44 (m, 1H), 1.37 (d, J=7.5 Hz, 1H), 1.15-1.05 (m, 1H), 1.01 (d, J=7.8 Hz, 3H), 0.84 (s, 3H), 0.70-0.54 (m, 4H), 0.48-0.17 (m, 4H).

To a stirred solution of (1R,2S,5S)-3-((S)-2-(cyclopropanecarboxamido)-2-cyclopropylacetyl)-6,6-dimethyl-3-azabicyclo[3.1.0]hexane-2-carboxylic acid (compound 175) (150 mg, 0.47 mmol) and (2S)-2-amino-3-[(3S)-2-oxopyrrolidin-3-yl]propanamide hydrochloride (compound 151) (124 mg, 0.6 mmol) in DMF (5 mL) at 0° C. were added DIEA (0.205 g, 1.59 mmol) and HATU (0.229 g, 0.6 mmol). The reaction mixture was stirred at room temperature for 1 h under N$_2$. After completion of the reaction (monitored by LCMS), the reaction mixture was diluted with water (50 mL) and extracted with ethyl acetate (60 mL×3). The combined organic layers were washed with brine (40 mL×3), dried over anhydrous Na$_2$SO$_4$, and concentrated down under reduced pressure. The resulting crude product was purified by reverse phase column chromatography to yield compound 176 (140 mg, 62.8%) as an off-white solid. LCMS=[M+H]$^+$: 474.4. $^1$H NMR (400 MHz, DMSO-d$_6$) δ 8.43 (d, J=7.5 Hz, 1H), 8.19 (d, J=8.5 Hz, 1H), 7.60 (s, 1H), 7.19 (s, 1H), 7.05 (s, 1H), 4.29-4.20 (m, 1H), 4.20-4.07 (m, 2H), 3.82-3.74 (m, 1H), 3.67 (d, J=10.3 Hz, 1H), 3.19-3.03 (m, 2H), 2.42-2.30 (m, 1H), 2.21-2.09 (m, 1H), 2.00-1.86 (m, 1H), 1.73-1.42 (m, 4H), 1.39-1.33 (m, 1H), 1.13-1.04 (m, 1H), 1.03-0.97 (m, 3H), 0.85 (d, J=12.2 Hz, 3H), 0.68-0.54 (m, 4H), 0.49-0.32 (m, 4H).

To a stirred solution of (1R,2S,5S)—N—((S)-1-amino-1-oxo-3-((S)-2-oxopyrrolidin-3-yl)propan-2-yl)-3-((S)-2-(cyclopropanecarboxamido)-2-cyclopropylacetyl)-6,6-dimethyl-3-azabicyclo[3.1.0]-hexane-2-carboxamide (compound 176) (140 mg, 0.29 mmol) in DCM (10 mL) was added Burgess reagent (0.143 g, 0.6 mmol). The reaction mixture was stirred at room temperature for 2 h under N$_2$. After completion of the reaction (monitored by LCMS), the mixture was concentrated down under reduced pressure. The resulting residue was purified by prep-HPLC to yield compound D-2-c (74 mg, 55.9%) as a white solid. LCMS=[M+H]$^+$: 456.3, HPLC: 95.06%. $^1$H NMR (400 MHz, DMSO-d$_6$) δ 8.94-8.85 (m, 1H), 8.41 (d, J=7.4 Hz, 1H), 7.67 (s, 1H), 5.01-4.81 (m, 1H), 4.15-3.97 (m, 2H), 3.80-3.73 (m, 1H), 3.69 (d, J=10.4 Hz, 1H), 3.21-3.04 (m, 2H), 2.45-2.35 (m, 1H), 2.21-2.08 (m, 2H), 1.80-1.63 (m, 3H), 1.56-1.49 (m, To a stirred solution of methyl (1R,2S,5S)-3-((S)-2-amino-2-cyclopropylacetyl)-6,6-dimethyl-3-azabicyclo[3.1.0]hexane-2-carboxylate hydrochloride (compound 168) (220 mg, 0.73 mmol) in DCM (10 mL) at 0° C. was added DIEA (0.387 g, 3 mmol) and cyclopropanecarbonyl chloride (compound 173) (91 mg, 0.87 mmol). The reaction mixture was stirred at room temperature for 2 h. After completion of the reaction (monitored by LCMS), the reaction mixture was diluted with DCM, washed with brine, dried over anhydrous Na$_2$SO$_4$, and concentrated down under reduced pressure. The resulting residue was purified by column chromatography (C18, ACN/water (0.1% FA)) to yield compound 174 (170 mg, 69.5%) as a white solid. LCMS=[M+H]$^+$: 335.2. $^1$H NMR (400 MHz, DMSO-d$_6$) δ 8.48 (d, J=7.3 Hz, 1H), 1H), 1.27 (d, J=7.6 Hz, 1H), 1.11-0.98 (m, 4H), 0.97-0.84 (m, 3H), 0.69-0.51 (m, 4H), 0.46-0.27 (m, 4H).

Example S41: Synthesis of Compound D-2-d

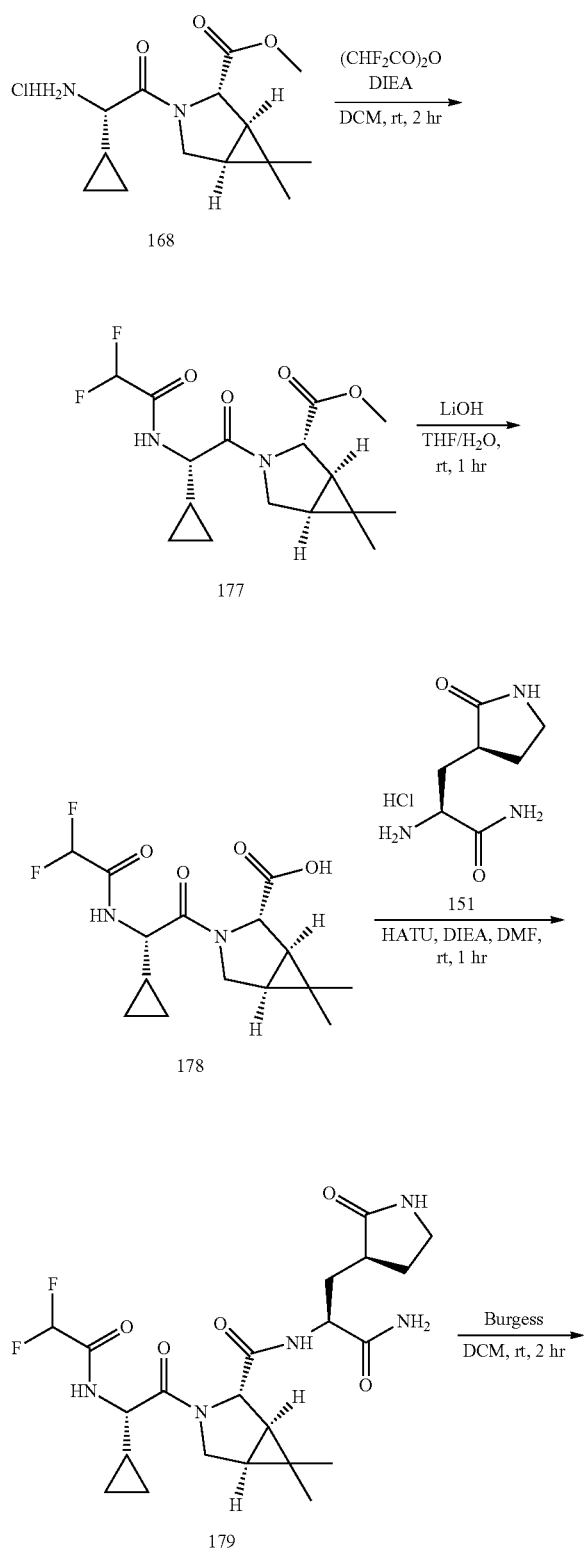

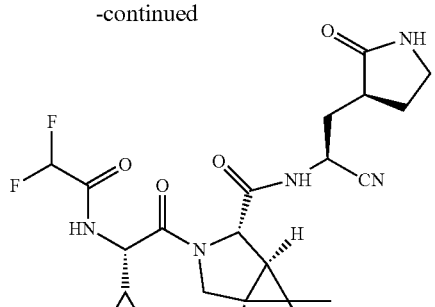

D-2-d

To a stirred solution of methyl (1R,2S,5S)-3-((S)-2-amino-2-cyclopropylacetyl)-6,6-dimethyl-3-azabicyclo[3.1.0]hexane-2-carboxylate hydrochloride (compound 168) (1.0 g, 3.31 mmol) in DCM (10 mL) at 0° C. DIEA (1.28 g, 9.93 mmol) and 2,2-difluoroacetic anhydride (0.63 g, 3.6 mmol) were added. The reaction mixture was stirred at room temperature for 2 h. After completion of the reaction (monitored by LCMS), the reaction mixture was diluted with DCM, washed with brine, dried over anhydrous $Na_2SO_4$. and concentrated down under reduced pressure. The resulting residue was purified by column chromatography (C18, ACN/water (0.1% FA)) to yield compound 177 (1.0 g, 87.5%) as a white solid. LCMS=[M+H]$^+$: 345.2. $^1$H NMR (400 MHz, DMSO-$d_6$) δ 9.25 (d, J=6.5 Hz, 1H), 6.39-6.04 (m, 1H), 4.20 (d, J=5.4 Hz, 1H), 4.10-4.02 (m, 1H), 3.83-3.72 (m, 2H), 3.70-3.62 (m, 3H), 1.62-1.53 (m, 1H), 1.48-1.39 (m, 1H), 1.19-1.11 (m, 1H), 1.03 (d, J=5.2 Hz, 3H), 0.95-0.87 (m, 3H), 0.58-0.23 (m, 4H).

To a stirred solution of methyl (1R,2S,5S)-3-((S)-2-cyclopropyl-2-(2,2-difluoroacetamido)acetyl)-6,6-dimethyl-3-azabicyclo[3.1.0]hexane-2-carboxylate (compound 177) (1.0 g, 2.9 mmol) in THF/water (10 mL, 2:1) was added LiOH (0.139 g, 5.8 mmol). The reaction mixture was stirred at room temperature for 1 h. After completion of the reaction (monitored by LCMS), the reaction mixture was concentrated down under reduced pressure. The resulting residue was diluted with water, the pH was adjusted to ~3-4 with 1M HCl and extracted with ethyl acetate (100 mL×2). The combined organic layers were concentrated down under reduced pressure, and resulting residue was purified by column chromatography (C18, ACN/water (0.1% FA)) to yield compound 178 (550 mg, 57%) as an off-white solid. LCMS=[M+H]$^+$: 331.2. $^1$H NMR (400 MHz, DMSO-$d_6$) δ 12.55 (s, 1H), 8.96 (d, J=7.0 Hz, 1H), 6.16-5.81 (m, 1H), 3.94-3.78 (m, 2H), 3.58-3.41 (m, 2H), 1.36-1.24 (m, 1H), 1.16 (d, J=7.5 Hz, 1H), 0.95-0.86 (m, 1H), 0.78 (d, J=5.3 Hz, 3H), 0.64 (s, 3H), 0.28-0.03 (m, 4H).

To a stirred solution of (1R,2S,5S)-3-((S)-2-cyclopropyl-2-(2,2-difluoroacetamido)acetyl)-6,6-dimethyl-3-azabicyclo[3.1.0]hexane-2-carboxylic acid (compound 178) (250 mg, 0.75 mmol) and (2S)-2-amino-3-[(3S)-2-oxopyrrolidin-3-yl]propanamide hydrochloride (compound 151) (187 mg, 0.91 mmol) in DMF (5 mL) at 0° C. DIEA (0.29 g, 2.25 mmol) and HATU (0.342 g, 0.9 mmol) were added. The reaction mixture was stirred at room temperature for 1 h under $N_2$. After completion of the reaction (monitored by LCMS), the reaction mixture was diluted with water (50 mL) and extracted with ethyl acetate (60 mL×3). The combined organic layers were washed with brine (40 mL×3), dried over anhydrous $Na_2SO_4$, and concentrated down under reduced pressure. The resulting residue was purified by reverse phase column chromatography to yield compound 179 (180 mg, 49.5%) as an off-white solid. LCMS=[M+H]⁺: 483.8.

To a stirred solution of (1R,2S,5S)—N—((S)-1-amino-1-oxo-3-((S)-2-oxopyrrolidin-3-yl)propan-2-yl)-3-((S)-2-cyclopropyl-2-(2,2-difluoroacetamido)acetyl)-6,6-dimethyl-3-azabicyclo[3.1.0]hexane-2-carboxamide (compound 179) (180 mg, 0.37 mmol) in DCM (10 mL) was added Burgess reagent (0.176 g, 0.74 mmol). The reaction mixture was stirred at room temperature for 2 h under N₂. After completion of the reaction (monitored by LCMS), the reaction mixture was concentrated down under reduced pressure. The resulting residue was purified by prep-HPLC to yield compound D-2-d (63 mg, 36.5%) as a white solid. LCMS=[M+H]⁺: 466.4, HPLC: 99.55%. ¹H NMR (400 MHz, DMSO-d₆) δ 9.19 (d, J=6.9 Hz, 1H), 8.95 (d, J=8.4 Hz, 1H), 7.69 (s, 1H), 6.37-6.03 (m, 1H), 5.04-4.90 (m, 1H), 4.21-4.14 (m, 1H), 4.12 (s, 1H), 3.87-3.78 (m, 1H), 3.69 (d, J=10.3 Hz, 1H), 3.18-3.04 (m, 2H), 2.44-2.34 (m, 1H), 2.18-2.07 (m, 2H), 1.81-1.63 (m, 2H), 1.59-1.53 (m, 1H), 1.30 (d, J=7.6 Hz, 1H), 1.17-1.08 (m, 1H), 1.03 (s, 3H), 0.90 (s, 3H), 0.51-0.37 (m, 4H).

Example S42: Synthesis of Compounds D-2-e and D-2-f

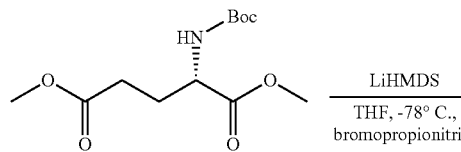

180-1

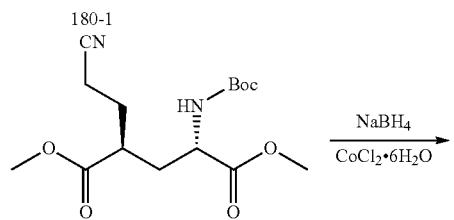

180-2

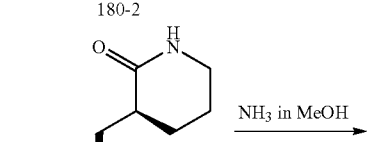

180-3

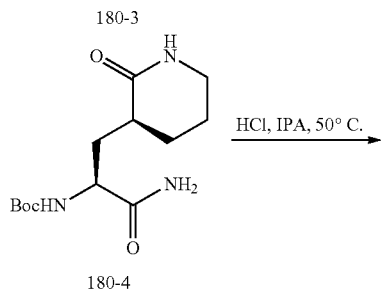

180-4

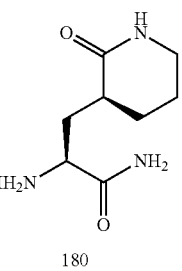

180

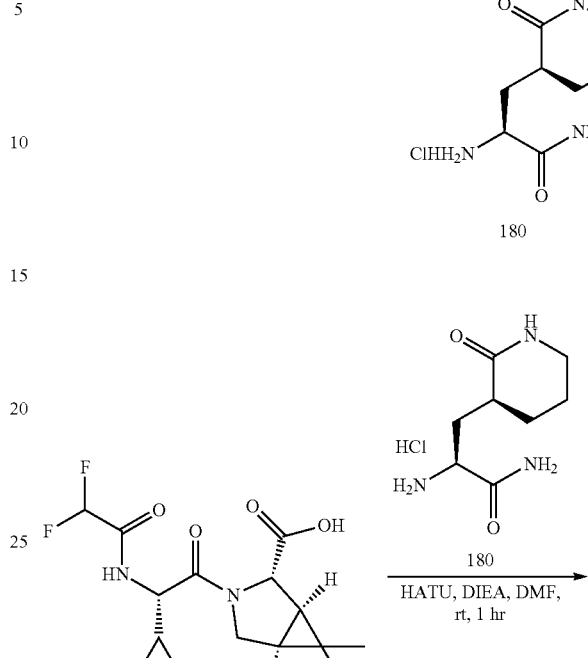

178

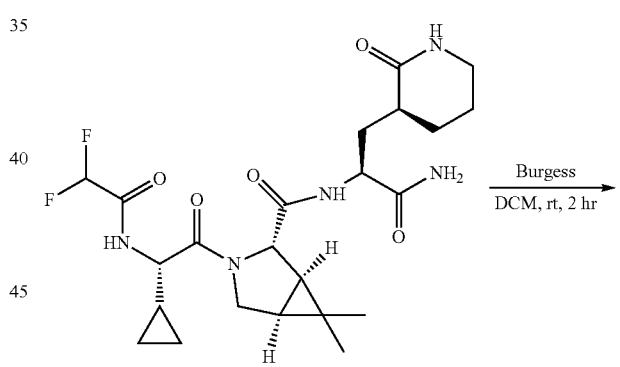

181

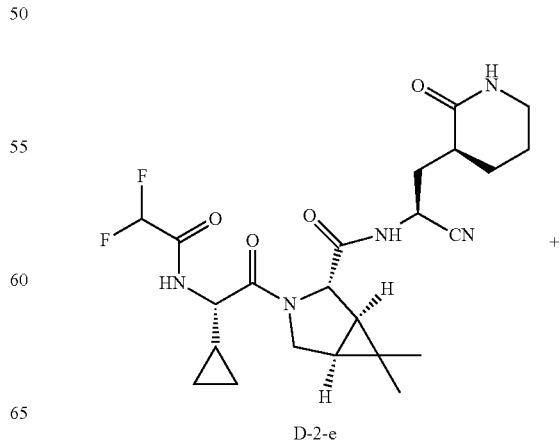

D-2-e

-continued

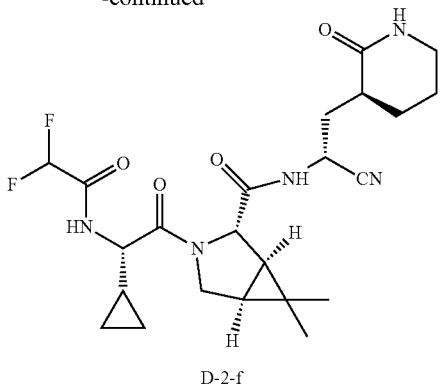

D-2-f

To a solution of dimethyl (tert-butoxycarbonyl)-L-glutamate (compound 180-1) (20 g, 72.7 mmol) in anhydrous THF (300 mL) at −78° C. under nitrogen lithium bis (trimethylsilyl)amide (145 mL, 1.0 M in THF, 145 mmol) was added dropwise. The reaction mixture was stirred at −78° C. for 30 min, and bromopropionitrile (6.8 mL, 82 mmol) was added dropwise with stirring, The reaction mixture was continuously stirred at −78° C. for 2 h. After completion of the reaction (monitored by LCMS), the reaction mixture was quenched dropwise with glacial acetic acid (10 mL). The reaction mixture was allowed to warm up to room temperature and organic solvent was removed under reduced pressure. The residue was diluted with water (200 mL) and extracted with DCM (200 mL×2). The combined organic layers were dried over anhydrous $Na_2SO_4$ and concentrated down under reduced pressure. The resulting residue was purified by flash column chromatography (PE: ethyl acetate=2:1) to yield compound 180-2 as a pale yellow oil (4.0 g, 16.7%). LCMS=$[M+H]^+$: 329.1. $^1$H NMR (400 MHz, $CDCl_3$) δ 5.05 (d, J=8.2 Hz, 1H), 4.42-4.29 (m, 1H), 3.75 (s, 3H), 3.72 (s, 3H), 2.68-2.58 (m, 1H), 2.43-2.34 (m, 2H), 2.08-1.94 (m, 4H), 1.45 (s, 9H).

To a solution of dimethyl (2S,4S)-2-((tert-butoxycarbonyl)amino)-4-(2-cyanoethyl)pentanedioate (compound 180-2) (4 g, 12.2 mmol) and cobalt chloride hexahydrate (3.2 g, 11.6 mmol) in methanol (50 mL) at 0° C. sodium borohydride (4.8 g, 126 mmol) was added portionwise. The reaction mixture was allowed to warm up to room temperature and stirred for 18 h. After completion the reaction (monitored by LCMS), the reaction mixture was quenched with sat. ammonium chloride (30 mL) and stirred for 10 min. The reaction mixture was filtered and the filtrate was concentrated down to remove the organic solvent. The resulting residue was extracted with DCM (100 mL×3). The combined organic layers were dried over anhydrous $Na_2SO_4$ and concentrated down under reduced pressure. The resulting residue was purified by column chromatography to yield compound 180-3 (1.78 g, 48.7%) as a white semi-solid. LCMS=$[M+H]^+$: 301.1. $^1$H NMR (400 MHz, DMSO-$d_6$) δ 7.56-7.31 (m, 2H), 4.12-4.02 (m, 1H), 3.61 (s, 4H), 3.14-3.06 (m, 2H), 2.21-2.07 (m, 2H), 1.92-1.83 (m, 1H), 1.82-1.71 (m, 1H), 1.67-1.53 (m, 2H), 1.43-1.35 (m, 10H).

A sealed pressure tube was charged with methyl (S)-2-((tert-butoxycarbonyl)amino)-3-((S)-2-oxopiperidin-3-yl)propanoate (compound 180-3) (1.78 g, 5.93 mmol) and 4 M ammonia in MeOH (2.8 mL). The reaction mixture was stirred at 65° C. for 16 h. After completion of the reaction (monitored by LCMS), the reaction mixture was concentrated down under reduced pressure to give the crude compound 180-4 (1.7 g), which was directly used in the next reaction without further purification. LCMS=$[M+H]^+$: 285.9.

A mixture of crude tert-butyl ((S)-1-amino-1-oxo-3-((S)-2-oxopiperidin-3-yl)propan-2-yl)carbamate (compound 180-4) (1.7 g, crude) in HCl (4.0 M in iso-propanol) (20 mL) was stirred at room temperature for 2 h. After completion of the reaction (monitored by LCMS), the reaction mixture was concentrated down under reduced pressure. The resulting residue was purified by reverse phase column chromatography to yield compound 180 (870 mg, 66% for two steps) as a white solid. LCMS=$[M+H]^+$: 186.1.

To a stirred solution of (1R,2S,5S)-3-((S)-2-cyclopropyl-2-(2,2-difluoroacetamido)acetyl)-6,6-dimethyl-3-azabicyclo[3.1.0]hexane-2-carboxylic acid (compound 178) (300 mg, 0.91 mmol) and (R)-2-amino-3-((S)-2-oxopiperidin-3-yl)propanamide hydrochloride (compound 180) (231 mg, 1.0 mmol) in DMF (5 mL) at 0° C. DIEA (0.352 g, 2.73 mmol) and HATU (0.81 g, 1.0 mmol) were added. The reaction mixture was stirred at room temperature for 1 h under $N_2$. After completion of the reaction (monitored by LCMS), the mixture was diluted with EtOAc, washed with water, 1M HCl, sat. NaCl, dried over anhydrous $Na_2SO_4$, and concentrated down under reduced pressure. The resulting residue was purified by reverse phase column chromatography to yield compound 181 (230 mg, 50.7%) as an off-white solid. LCMS=$[M+H]^+$: 498.3. $^1$H NMR (400 MHz, DMSO) δ 9.38-9.02 (m, 1H), 8.27 (d, J=8.3 Hz, 1H), 7.51-7.30 (m, 1H), 7.25-6.90 (m, 2H), 6.38-6.05 (m, 1H), 4.40-3.97 (m, 3H), 3.92-3.78 (m, 1H), 3.69-3.60 (m, 1H), 3.11 (s, 2H), 2.26-2.10 (m, 1H), 2.01-1.88 (m, 1H), 1.77-1.64 (m, 1H), 1.65-1.11 (m, 7H), 1.05-0.85 (m, 6H), 0.59-0.34 (m, 4H).

To a stirred solution of (1R,2S,5S)—N—((S)-1-amino-1-oxo-3-((S)-2-oxopiperidin-3-yl)propan-2-yl)-3-((S)-2-cyclopropyl-2-(2,2-difluoroacetamido)acetyl)-6,6-dimethyl-3-azabicyclo[3.1.0]hexane-2-carboxamide (compound 181) (230 mg, 0.46 mmol) in DCM (10 mL) was added Burgess reagent (0.22 g, 0.92 mmol). The reaction mixture was stirred at room temperature for 2 h under $N_2$. After completion of the reaction (monitored by LCMS), the reaction mixture was concentrated down under reduced pressure. The resulting residue was purified by prep-HPLC to yield two isomers; compound D-2-e (56 mg, 25.9%) and compound D-2-f (6 mg, 2.8%) as white solids. LCMS=$[M+H]^+$: 480.4. HPLC: 99.10%.

D-2-e: HPLC: 99.10%. $^1$H NMR (400 MHz, DMSO-$d_6$) δ 9.18 (d, J=7.1 Hz, 1H), 8.92 (d, J=8.0 Hz, 1H), 7.50 (s, 1H), 6.38-6.06 (m, 1H), 5.06-4.94 (m, 1H), 4.18-4.06 (m, 2H), 3.85-3.76 (m, 1H), 3.68 (d, J=10.5 Hz, 1H), 3.09 (s, 2H), 2.34-2.24 (m, 2H), 1.88 (s, 1H), 1.79-1.66 (m, 2H), 1.65-1.51 (m, 2H), 1.44-1.35 (m, 1H), 1.30-1.26 (m, 1H), 1.16-1.09 (m, 1H), 1.07-1.01 (m, 3H), 0.97-0.87 (m, 3H), 0.51-0.37 (m, 4H).

D-2-f: HPLC: 86.15%; $^1$H NMR (400 MHz, DMSO-$d_6$) δ 9.16 (d, J=7.3 Hz, 1H), 8.37 (s, 1H), 7.88 (s, 1H), 6.37-6.04 (m, 1H), 4.60-4.54 (m, 1H), 4.13 (s, 1H), 4.11-4.04 (m, 1H), 3.84-3.77 (m, 1H), 3.65 (d, J=10.5 Hz, 1H), 3.17-3.10 (m, 1H), 3.05-2.97 (m, 1H), 2.36-2.22 (m, 2H), 1.94-1.84 (m, 1H), 1.74-1.63 (m, 1H), 1.52-1.41 (m, 3H), 1.40-1.30 (m, 1H), 1.28 (d, J=7.6 Hz, 1H), 1.19-1.11 (m, 1H), 1.07-0.99 (m, 3H), 0.96-0.82 (m, 3H), 0.57-0.36 (m, 4H).

Example S43: Synthesis of Compound D-3-a

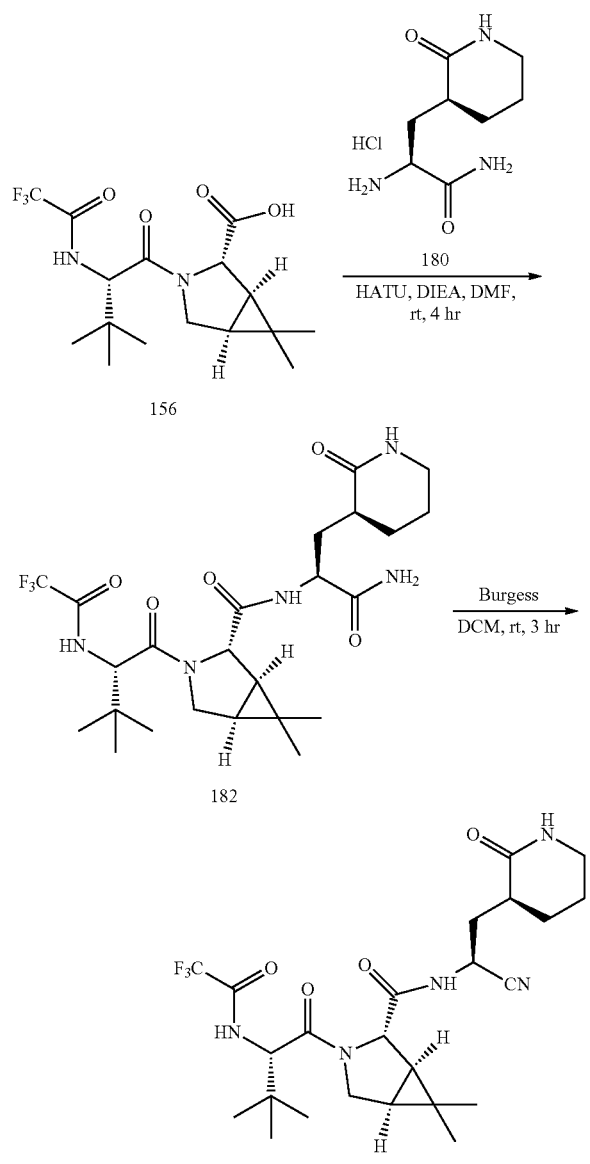

To a stirred solution of (1R,2S,5S)-3-((S)-3,3-dimethyl-2-(2,2,2-trifluoroacetamido)butanoyl)-6,6-dimethyl-3-azabicyclo[3.1.0]hexane-2-carboxylic acid (compound 156) (400 mg, 1.1 mmol) and (S)-2-amino-3-((S)-2-oxopiperidin-3-yl)propanamide hydrochloride (compound 180) (0.265 g, 1.2 mmol) in DMF (5 mL) at 0° C. DIEA (0.387 g, 3 mmol) and HATU (0.457 g, 1.2 mmol) were added. The reaction mixture was stirred at room temperature for 4 h under $N_2$. After completion of the reaction (monitored by LCMS), the reaction mixture was diluted with water (50 mL) and extracted with ethyl acetate (80 mL×3). The combined organic layers were washed with brine, dried over anhydrous $Na_2SO_4$, and concentrated down under reduced pressure. The resulting residue was purified by column chromatography (C18, ACN/water (0.1% FA)) to yield compound 182 (270 mg, 46%) as an off-white solid. LCMS=[M+H]$^+$: 532.6. $^1$H NMR (400 MHz, DMSO-d$_6$) δ 9.40 (d, J=8.6 Hz, 1H), 8.31 (d, J=8.6 Hz, 1H), 7.39 (s, 1H), 7.23 (s, 1H), 7.00 (s, 1H), 4.42 (d, J=8.6 Hz, 1H), 4.33-4.21 (m, 2H), 3.91-3.84 (m, 1H), 3.74-3.61 (m, 1H), 3.15-3.05 (m, 2H), 2.29-2.12 (m, 2H), 1.97-1.87 (m, 1H), 1.72-1.63 (m, 1H), 1.60-1.46 (m, 3H), 1.36 (d, J=7.7 Hz, 1H), 1.33-1.24 (m, 1H), 1.01 (s, 3H), 0.99 (s, 9H), 0.84 (s, 3H).

To a stirred solution of (1R,2S,5S)—N—((S)-1-amino-1-oxo-3-((S)-2-oxopiperidin-3-yl)propan-2-yl)-3-((S)-3,3-dimethyl-2-(2,2,2-trifluoroacetamido)butanoyl)-6,6-dimethyl-3-azabicyclo[3.1.0]hexane-2-carboxamide (compound 182) (300 mg, 0.56 mmol) in DCM (10 mL) was added Burgess reagent (266 mg, 1.12 mmol). The solution was stirred at room temperature for 3 h under $N_2$. After completion of the reaction (monitored by LCMS), the reaction mixture was washed with brine, dried over anhydrous $Na_2SO_4$, and concentrated down under reduced pressure. The resulting residue was purified by prep-HPLC to yield compound D-3-a (206 mg, 71%) as a white solid. LCMS= [M+H]$^+$: 514.4. $^1$H NMR (400 MHz, DMSO-d$_6$) δ 9.40 (d, J=8.3 Hz, 1H), 8.99 (d, J=8.2 Hz, 1H), 7.51 (s, 1H), 5.09-4.92 (m, 1H), 4.41 (d, J=8.3 Hz, 1H), 4.17 (s, 1H), 3.97-3.83 (m, 1H), 3.68 (d, J=10.4 Hz, 1H), 3.09 (s, 2H), 2.34-2.19 (m, 2H), 1.92-1.80 (m, 1H), 1.79-1.64 (m, 2H), 1.60-1.50 (m, 2H), 1.42-1.22 (m, 2H), 1.03 (s, 3H), 0.99 (s, 9H), 0.85 (s, 3H).

Example S44: Synthesis of Compound D-3-b

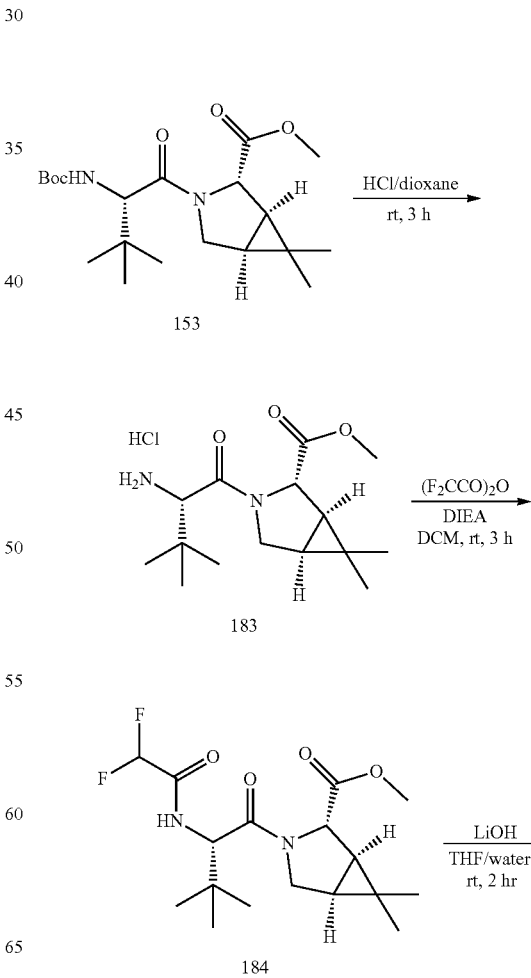

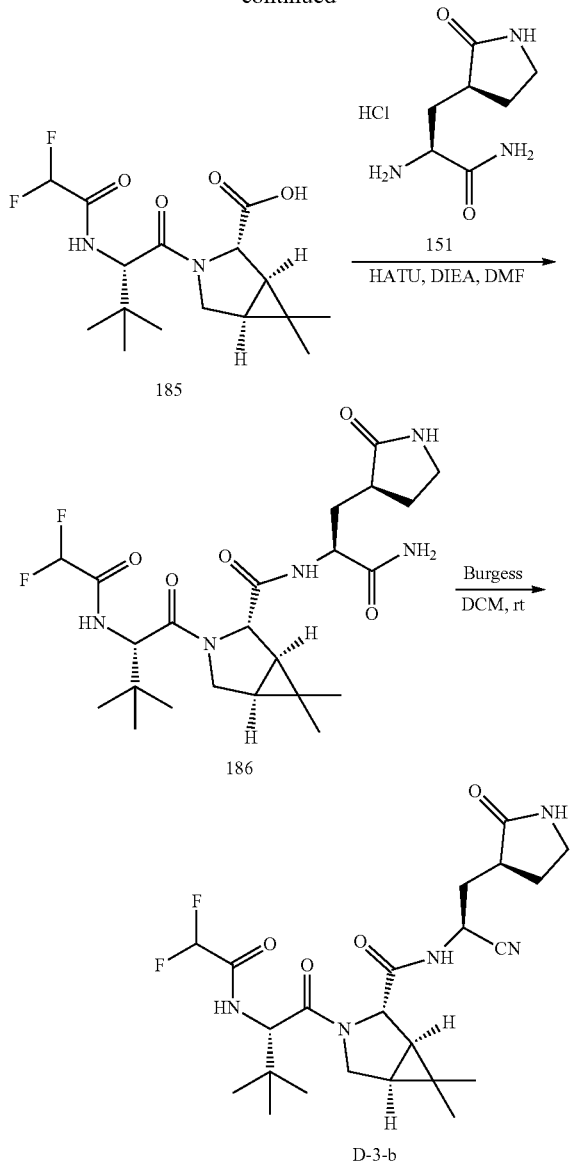

A solution of methyl (1R,2S,5S)-3-((S)-2-((tert-butoxycarbonyl)amino)-3,3-dimethylbutanoyl)-6,6-dimethyl-3-azabicyclo[3.1.0]hexane-2-carboxylate (compound 153) (10 g, 26.2 mmol) in HCl in dioxane (4M, 100 mL) was stirred at room temperature for 3 h. After completion of the reaction (monitored by LCMS), the reaction mixture was concentrated down under reduced pressure to yield the crude compound 183 (9.1 g) as a yellow semi-solid. LCMS=[M+H]⁺: 283.3.

To a stirred solution of methyl (1R,2S,5S)-3-((S)-2-amino-3,3-dimethylbutanoyl)-6,6-dimethyl-3-azabicyclo[3.1.0]hexane-2-carboxylate hydrochloride (compound 183) (9.1 g, 28.6 mmol) in DCM (100 mL) at 0° C. DIEA (11.1 g, 85.8 mmol) and 2,2-difluoroacetic anhydride (4.98 g, 28.6 mmol) were added. The reaction mixture was stirred at room temperature for 3 h. After completion of the reaction (monitored by LCMS), the reaction mixture was diluted with water (40 mL) and extracted with DCM (200 mL×3). The combined organic layers were washed with 0.5M HCl (60 mL×3) and sat. NaHCO₃ (50 mL×2), dried over anhydrous Na₂SO₄, and concentrated down under reduced pressure to yield compound 184 (9.4 g, 91%) as a yellow oil. LCMS=[M+H]⁺: 361.4. ¹H NMR (400 MHz, DMSO-d₆) δ 8.87 (d, J=8.7 Hz, 1H), 6.28 (t, J=53.7 Hz, 1H), 4.41 (d, J=8.7 Hz, 1H), 4.22 (s, 1H), 3.90-3.82 (m, 1H), 3.79 (d, J=10.5 Hz, 1H), 3.67 (s, 3H), 1.59-1.53 (m, 1H), 1.45 (d, J=7.5 Hz, 1H), 1.01 (s, 3H), 0.98 (s, 9H), 0.84 (s, 3H).

To a stirred solution of methyl (1R,2S,5S)-3-((S)-2-(2,2-difluoroacetamido)-3,3-dimethylbutanoyl)-6,6-dimethyl-3-azabicyclo[3.1.0]hexane-2-carboxylate (compound 184) (9.4 g, 26 mmol) in THF/water (100 mL, 2:1) was added LiOH (1.56 g, 65 mmol). The reaction mixture was stirred at room temperature for 2 h. After completion of the reaction (monitored by LCMS), the reaction mixture was concentrated down under reduced pressure. The resulting residue was diluted with water, the pH was adjusted to ~3-4 with 1M HCl and extracted with ethyl acetate (100 mL×3). The combined organic layers were washed with brine, dried over anhydrous Na₂SO₄, and concentrated down under reduced pressure to yield compound 185 (8.6 g, 95%) as a white solid. LCMS=[M+H]⁺: 347.1. ¹H NMR (400 MHz, DMSO) δ 12.69 (s, 1H), 8.85 (d, J=8.8 Hz, 1H), 6.28 (t, J=53.7 Hz, 1H), 4.42 (d, J=8.9 Hz, 1H), 4.14 (s, 1H), 3.91-3.70 (m, 2H), 1.58-1.47 (m, 1H), 1.43 (d, J=7.5 Hz, 1H), 1.06-0.94 (m, 12H), 0.84 (s, 3H).

To a stirred solution of (1R,2S,5S)-3-((S)-2-(2,2-difluoroacetamido)-3,3-dimethylbutanoyl)-6,6-dimethyl-3-azabicyclo[3.1.0]hexane-2-carboxylic acid (compound 185) (6.6 g, 19.0 mmol) and (2S)-2-amino-3-[(3S)-2-oxopyrrolidin-3-yl]propanamide hydrochloride (compound 151) (5.14 g, 24.7 mmol) in DMF (50 mL) at 0° C. HATU (8.67 g, 22.8 mmol) and DIEA (9.81 g, 76 mmol) were added. The reaction mixture was stirred at room temperature for 2 h. After completion of reaction (monitored by LCMS), the mixture was diluted with water (100 mL) and extracted with EtOAc (200 mL×3). The combined organic layers were washed with brine (100 mL×3), dried over anhydrous Na₂SO₄, and concentrated down under reduced pressure. The resulting residue was purified by column chromatography (C18, ACN/water (0.1% FA)) to yield compound 186 (7.0 g, 73%) as an off-white solid. LCMS=[M+H]⁺: 500.7. ¹H NMR (400 MHz, DMSO-d₆) δ 8.84 (d, J=8.8 Hz, 1H), 8.27 (d, J=8.8 Hz, 1H), 7.54 (s, 1H), 7.31 (s, 1H), 7.03 (s, 1H), 6.27 (t, J=53.8 Hz, 1H), 4.40 (d, J=8.9 Hz, 1H), 4.34-4.24 (m, 2H), 3.92-3.84 (m, 1H), 3.70 (d, J=10.4 Hz, 1H), 3.16-3.09 (m, 1H), 3.07-2.97 (m, 1H), 2.46-2.36 (m, 1H), 2.17-2.06 (m, 1H), 2.00-1.89 (m, 1H), 1.71-1.58 (m, 1H), 1.54-1.45 (m, 2H), 1.38 (d, J=7.7 Hz, 1H), 1.02 (s, 3H), 0.96 (s, 9H), 0.82 (s, 3H).

To a stirred solution of (1R,2S,5S)—N—((S)-1-amino-1-oxo-3-((S)-2-oxopyrrolidin-3-yl)propan-2-yl)-3-((S)-2-(2,2-difluoroacetamido)-3,3-dimethylbutanoyl)-6,6-dimethyl-3-azabicyclo[3.1.0]hexane-2-carboxamide (compound 186) (5.0 g, 10 mmol) in DCM (50 mL) was added Burgess reagent (4.76 g, 20 mmol). The reaction mixture was stirred at room temperature for 3 h under N₂. After completion of the reaction (monitored by LCMS), the reaction mixture was washed with brine, organic layer was separated, dried over anhydrous Na₂SO₄, and concentrated down under reduced pressure. The resulting residue was purified by flash column chromatography (DCM/MeOH=30:1) to yield compound D-3-b (3.12 g, 64.7%) as a white solid. LCMS=[M+H]⁺: 482.4. ¹H NMR (400 MHz, DMSO-d₆) δ 9.02 (d, J=8.5 Hz, 1H), 8.84 (d, J=8.6 Hz, 1H), 7.66 (s, 1H), 6.27 (t, J=53.7 Hz, 1H), 5.03-4.91 (m, 1H), 4.38 (d, J=8.7 Hz, 1H), 4.14 (s, 1H), 3.95-3.85 (m, 1H), 3.73 (d, J=10.5 Hz, 1H), 3.18-3.10 (m, 1H), 3.07-2.99 (m, 1H), 2.44-2.35 (m, 1H), 2.20-2.01 (m, 2H), 1.78-1.64 (m, 2H), 1.61-1.51 (m, 1H), 1.31 (d, J=7.6 Hz, 1H), 1.03 (s, 3H), 0.96 (s, 9H), 0.86 (s, 3H).

Example S45: Synthesis of Compound D-3-c

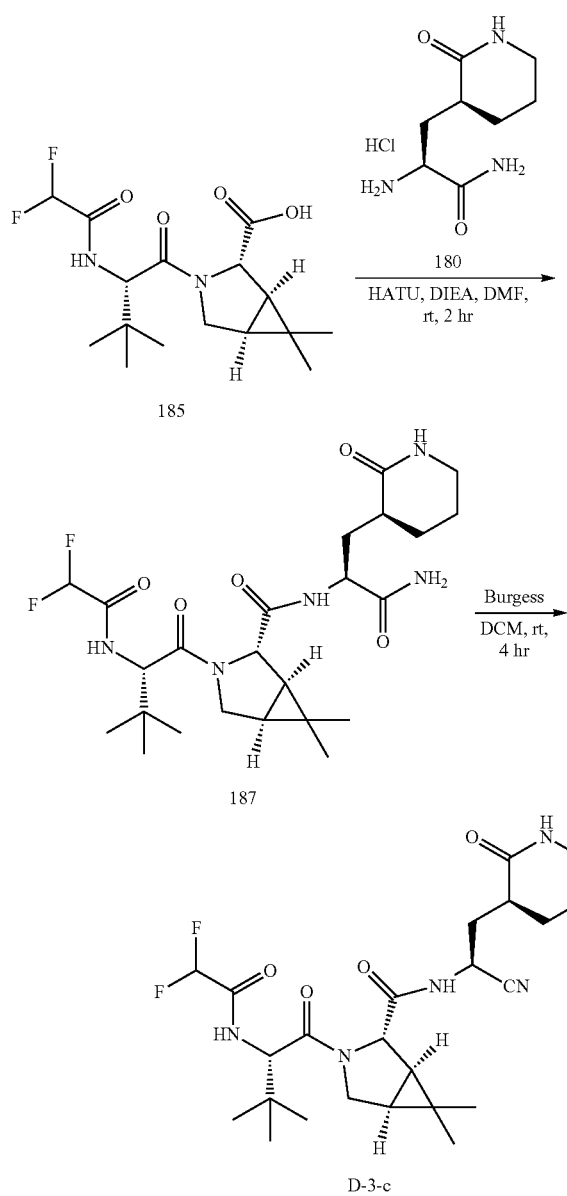

To a stirred solution of (1R,2S,5S)-3-((S)-2-(2,2-difluoroacetamido)-3,3-dimethylbutanoyl)-6,6-dimethyl-3-azabicyclo[3.1.0]hexane-2-carboxylic acid (compound 185) (346 mg, 1.0 mmol) and (S)-2-amino-3-((S)-2-oxopiperidin-3-yl)propanamide hydrochloride (compound 180) (0.265 g, 1.2 mmol) in DMF (5 mL) at 0° C. DIEA (0.387 g, 3 mmol) and HATU (0.457 g, 1.2 mmol) were added. The reaction mixture was stirred at room temperature for 2 h under $N_2$. After completion of the reaction (monitored by LCMS), the reaction mixture was diluted with water (50 mL) and extracted with ethyl acetate (80 mL×3). The combined organic layers were washed with brine, dried over anhydrous $Na_2SO_4$, and concentrated down under reduced pressure. The resulting residue was purified by column chromatography (C18, ACN/water (0.1% FA)) to yield compound 187 (300 mg, 58%) as an off-white solid. LCMS=[M+H]$^+$: 514.5. $^1$H NMR (400 MHz, DMSO-$d_6$) δ 8.83 (d, J=8.8 Hz, 1H), 8.29 (d, J=8.6 Hz, 1H), 7.39 (s, 1H), 7.24 (s, 1H), 7.00 (s, 1H), 6.28 (t, J=53.8 Hz, 1H), 4.40 (d, J=8.9 Hz, 1H), 4.33-4.22 (m, 2H), 3.94-3.83 (m, 1H), 3.70 (d, J=10.3 Hz, 1H), 3.08 (s, 2H), 2.31-2.12 (m, 2H), 1.98-1.86 (m, 1H), 1.74-1.63 (m, 1H), 1.61-1.44 (m, 3H), 1.39-1.33 (m, 1H), 1.32-1.23 (m, 1H), 1.02 (s, 3H), 0.96 (s, 9H), 0.84 (s, 3H).

To a stirred solution of (1R,2S,5S)—N—((S)-1-amino-1-oxo-3-((S)-2-oxopiperidin-3-yl)propan-2-yl)-3-((S)-2-(2,2-difluoroacetamido)-3,3-dimethylbutanoyl)-6,6-dimethyl-3-azabicyclo[3.1.0]hexane-2-carboxamide (compound 187) (300 mg, 0.58 mmol) in DCM (10 mL) was added Burgess reagent (276 mg, 1.16 mmol). The reaction mixture was stirred at room temperature for 4 h under $N_2$. After completion of the reaction (monitored by LCMS), the reaction mixture was washed with brine, organic layer was separated, dried over anhydrous $Na_2SO_4$, and concentrated down under reduced pressure. The resulting residue was purified by prep-HPLC to yield compound D-3-c (86 mg, 29.9%) as a white solid. LCMS=[M+H]$^+$: 496.4. $^1$H NMR (400 MHz, DMSO-$d_6$) δ 8.99 (d, J=8.3 Hz, 1H), 8.83 (d, J=8.7 Hz, 1H), 7.50 (s, 1H), 6.27 (t, J=53.7 Hz, 1H), 5.05-4.94 (m, 1H), 4.38 (d, J=8.8 Hz, 1H), 4.16 (s, 1H), 3.93-3.87 (m, 1H), 3.73 (d, J=10.4 Hz, 1H), 3.08 (s, 2H), 2.37-2.29 (m, 1H), 2.28-2.18 (m, 1H), 1.89-1.81 (m, 1H), 1.79-1.64 (m, 2H), 1.60-1.48 (m, 2H), 1.38 (t, J=10.2 Hz, 1H), 1.30-1.21 (m, 1H), 1.02 (s, 3H), 0.96 (s, 9H), 0.83 (s, 3H).

Example S46: Synthesis of Compound D-4-a

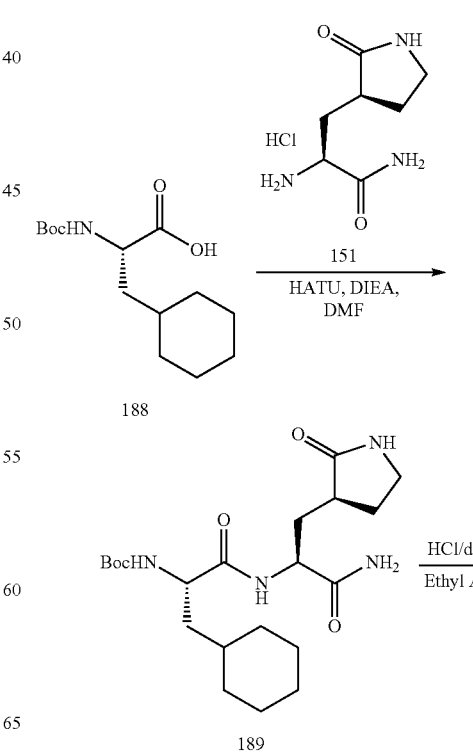

-continued

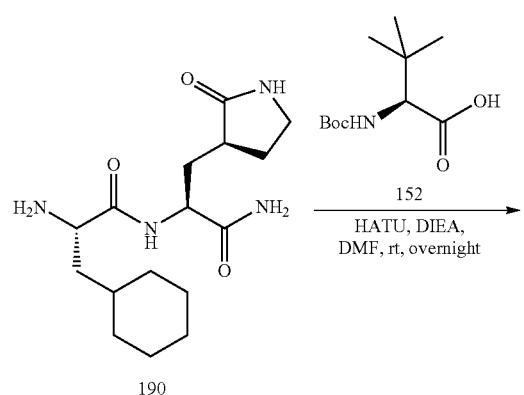

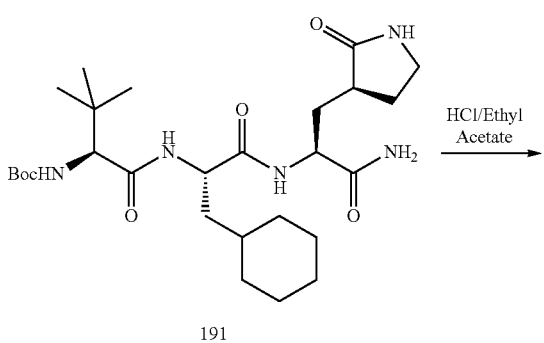

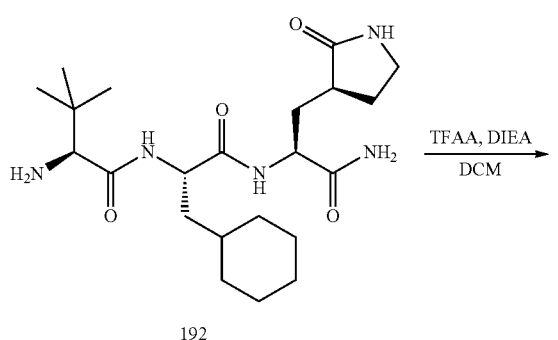

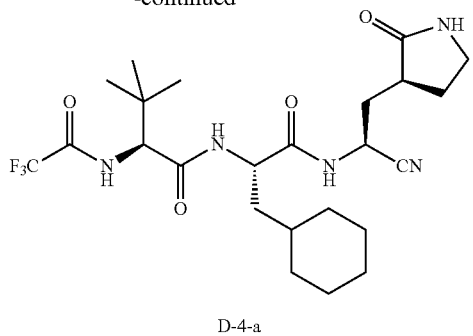

D-4-a

To a stirred solution of (S)-2-((tert-butoxycarbonyl)amino)-3-cyclohexylpropanoic acid (compound 188) (1.35 g, 5 mmol) and (S)-2-amino-3-((S)-2-oxopyrrolidin-3-yl)propanamide hydrochloride (compound 151) (1.2 g, 5.5 mmol) in DMF (20 mL) were added HATU (1.9 g, 5 mmol) and DIEA (2.58 g, 20 mmol). The reaction mixture was stirred at room temperature for 2 h. After completion of the reaction (monitored by LCMS), the reaction mixture was diluted with water and extracted with ethyl acetate (200 mL×3). The combined organic layers were concentrated down under reduced pressure. The resulting residue was purified by reverse phase column chromatography to yield compound 189 (1.8 g, 4.24 mmol, 84.80%) as a red solid. LCMS=[M+H]$^+$: 425.1. $^1$H NMR (400 MHz, CDCl$_3$) δ 8.21 (s, 1H), 7.21 (s, 1H), 5.75 (s, 1H), 5.38 (s, 1H), 5.04 (d, J=6.4 Hz, 1H), 4.49-4.37 (m, 1H), 4.12-4.02 (m, 1H), 3.43-3.32 (m, 2H), 2.49-2.34 (m, 2H), 2.15-1.97 (m, 2H), 1.96-1.84 (m, 1H), 1.78 (d, J=13.0 Hz, 1H), 1.73-1.66 (m, 3H), 1.49-1.32 (m, 12H), 1.31-1.08 (m, 4H), 1.01-0.85 (m, 2H).

To a solution of tert-butyl N-[(1S)-1-{[1-carbamoyl-2-(2-oxopyrrolidin-3-yl)ethyl]carbamoyl}-2-cyclohexylethyl]carbamate (compound 189) (400 mg, 0.94 mmol) in ethyl acetate (8 mL) was added HCl (4.0 M in EtOAc, 2 mL). The reaction mixture was stirred at 25° C. for 2 h. After completion of the reaction (monitored by LCMS), the mixture was concentrated down under reduced pressure to yield the crude compound 190 (397 mg, 1.22 mmol, 100%) as a white solid, which was used in the next reaction without further purification. LCMS=[M+H]$^+$: 325.2.

To a solution of 2-[(2S)-2-amino-3-cyclohexylpropanamido]-3-(2-oxopyrrolidin-3-yl)propenamide (compound 190) (397 mg, 1.22 mmol) in ACN (40 mL) and DMF (4 mL) at 0° C., were added 2-{[(tert-butoxy)carbonyl]amino}-3,3-dimethylbutanoic acid (compound 152) (311.33 mg, 1.35 mmol), DIEA (0.807 mL, 4.88 mmol) and HATU (695.82 mg, 1.83 mmol). The reaction mixture was stirred at room temperature for 2 h. After completion of the reaction (monitored by LCMS), the reaction mixture was diluted with water (50 mL) and extracted with ethyl acetate (60 mL×3). The combined organic layers were washed with brine (40 mL×3), dried over anhydrous Na$_2$SO$_4$, and concentrated down under reduced pressure. The resulting residue was purified by prep-HPLC (C18, ACN/water (0.1% FA)) to yield compound 191 (420 mg, 0.78 mmol, 63.83%) as a white solid. LCMS=[M+H]$^+$: 538.1.

To a stirred solution of tert-butyl N-(1-{[(1S)-1-{[1-carbamoyl-2-(2-oxopyrrolidin-3-yl)ethyl]carbamoyl}-2-cyclohexylethyl]carbamoyl}-2,2-dimethylpropyl)carbamate (compound 191) (420 mg, 0.78 mmol) in ethyl acetate (5 mL) was added HCl (4.0 M in ethyl acetate, 10 mL). The reaction mixture was stirred at room temperature for 3 h.

After completion of the reaction (monitored by LCMS), the reaction mixture was concentrated down under reduced pressure to yield compound 192 (330 mg, 0.70 mmol, 89.12%) as a white solid, which was used in the next reaction without further purification. LCMS=[M+H]⁺: 438.3.

To a solution of 2-amino-N-[(1S)-1-{[1-carbamoyl-2-(2-oxopyrrolidin-3-yl)ethyl]carbamoyl}-2-cyclohexylethyl]-3,3-dimethylbutanamide (compound 192) (330 mg, 0.75 mmol) in DCM (5 mL) DIEA (0.137 mL, 0.83 mmol) and TFAA (0.420 mL, 3.02 mmol) in DCM were added dropwise. The reaction mixture was stirred at 0° C. for 30 min. After completion of the reaction (monitored by LCMS), the reaction mixture was concentrated down under reduced pressure. The resulting residue was purified by prep-HPLC (C18, ACN/water (0.1% FA)) to yield compound 193 (90 mg, 0.17 mmol, 22.37%) as a white solid. LCMS=[M+H]⁺: 534.1.

To a solution of N-[(1S)-1-{[1-carbamoyl-2-(2-oxopyrrolidin-3-yl)ethyl]carbamoyl}-2-cyclohexylethyl]-3,3-dimethyl-2-(trifluoroacetamido)butanamide (compound 193) (90 mg, 0.17 mmol) in DCM (5 mL) was added Burgess reagent (81 mg, 0.34 mmol) at 0° C. The reaction mixture was stirred at room temperature for 1 h. After completion of the reaction (monitored by LCMS), the reaction mixture was concentrated down under reduced pressure. The resulting residue was purified by prep-HPLC to yield compound D-4-a (10 mg, 0.02 mmol, 11.50%) as a white solid. LCMS=[M+H]⁺: 516.3. HPLC: 89.75%. ¹H NMR (400 MHz, DMSO-d₆) δ 9.16 (d, J=9.3 Hz, 1H), 8.91 (d, J=8.3 Hz, 1H), 8.32 (d, J=6.8 Hz, 1H), 7.67 (s, 1H), 4.98-4.87 (m, 1H), 4.41 (d, J=9.3 Hz, 1H), 4.27-4.18 (m, 1H), 3.19-3.11 (m, 1H), 3.10-3.00 (m, 1H), 2.39-2.29 (m, 1H), 2.21-2.02 (m, 2H), 1.79-1.55 (m, 7H), 1.53-1.39 (m, 2H), 1.33-1.20 (m, 1H), 1.20-1.03 (m, 3H), 0.99-0.80 (m, 11H).

Example S47: Synthesis of Compounds E-1-a and E-1-b

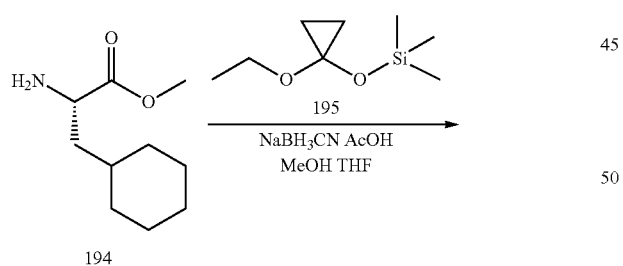

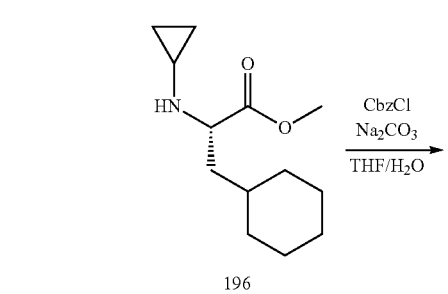

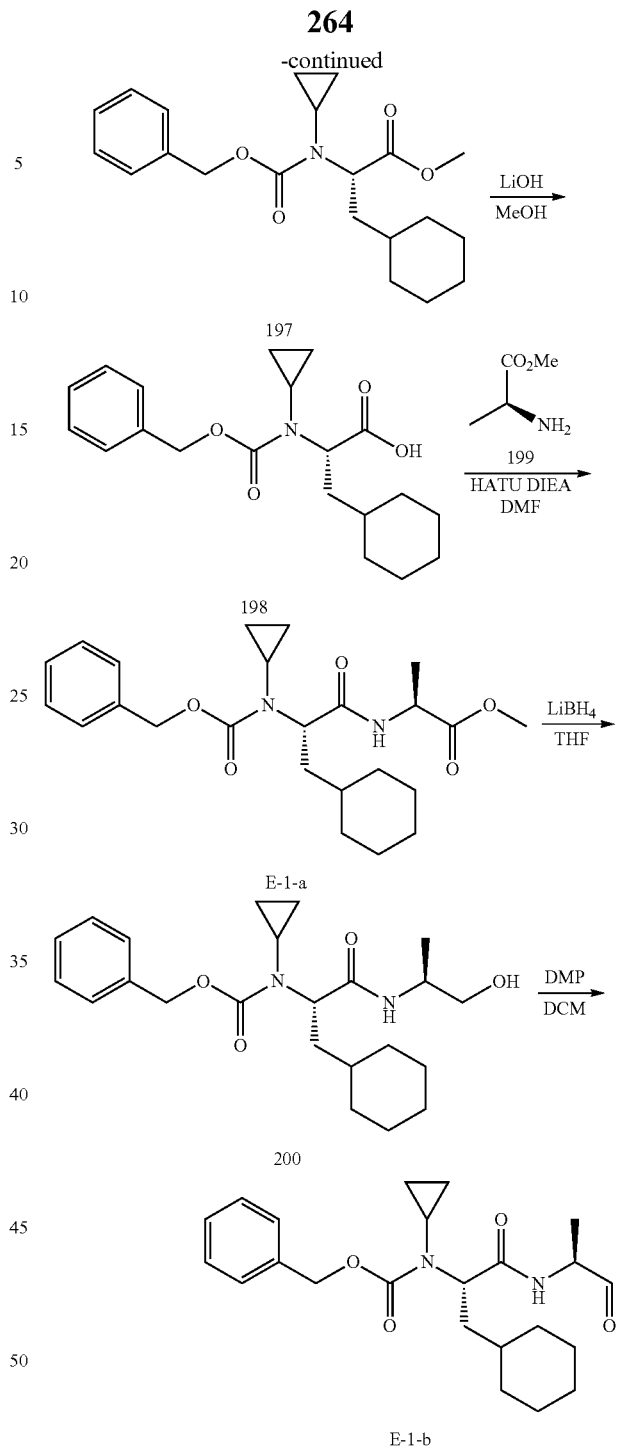

To a solution of methyl (S)-2-amino-3-cyclohexylpropanoate (compound 194) (15 g, 67.65 mmol) in MeOH/THF (75 mL/75 mL) was added compound 195 (23.59 g, 135.30 mmol), AcOH (8.13 g, 135.30 mmol) and NaBH₃CN (4.26 g, 67.65 mmol). The reaction mixture was stirred at 60° C. for 6 h. After completion of the reaction (monitored by LCMS), the reaction mixture was cooled to room temperature, concentrated down to remove the organic solvents, basified with sat. NaHCO₃ and extracted with ethyl acetate (200 mL×2). The combined organic layers were washed with brine solution (100 mL) and concentrated down under reduced pressure. The resulting residue was purified by flash column chromatography (PE/Ethyl Acetate=50:1) to yield compound 196 (5.34 g) as a colorless oil. LCMS=[M+H]+: 226.4.

To a stirred solution of compound 196 (5.34 g, 23.71 mmol) in THF/H$_2$O (50 mL, 1:1) at 5° C., Na$_2$CO$_3$ (5.03 g, 47.42 mmol) and Cbz-Cl (4.86 g, 28.46 mmol) were added dropwise. The reaction mixture was stirred at 5° C. for 30 min and warmed to room temperature and stirred for 2 h. After completion of the reaction (monitored by LCMS), the reaction mixture was quenched with water (100 mL) and extracted with ethyl acetate (100 mL×2). The combined organic layers were washed with brine (100 mL), dried over Na$_2$SO$_4$ and concentrated down under reduced pressure. The resulting residue was purified by flash column chromatography (PE/Ethyl Acetate=30:1) to afford compound 197 (6.17 g) as a colorless oil. LCMS=[M+H]+: 360.3.

To a stirred solution of compound 197 (5.17 g, 14.39 mmol) in MeOH (150 mL) was added 1M LiOH (aq) (72 mL). The reaction mixture was stirred at room temperature for 24 h. After completion of the reaction (monitored by TLC), the reaction mixture was concentrated down under reduced pressure. The resulting residue was diluted with water (25 mL), acidified with sat. citric acid and extracted with ethyl acetate (100 mL×3). The combined organic layers were washed with water (100 mL×2), brine (100 mL), dried over anhydrous Na$_2$SO$_4$, and concentrated down under reduced pressure to afford a crude compound 198 (5.17 g) as a colorless oil. LCMS=[M+H]+: 346.2.

To a solution of compound 198 (5.17 g, 14.97 mmol) in anhydrous DMF (25 mL) at 5° C. HATU (8.54 g, 22.46 mmol) and DIEA (9.67 g, 74.88 mmol) were added. The reaction mixture was stirred at 5° C. for 10 min followed by addition of compound 199 (3.14 g, 22.46 mmol). The reaction mixture was stirred at 5° C. for 30 min and 2 h at room temperature. After completion of the reaction (monitored by LCMS), the mixture was diluted with water (30 mL) and extracted with ethyl acetate (90 mL×2). The combined organic layers were washed with brine (30 mL) and concentrated down under reduced pressure. The resulting residue was purified by flash column chromatography (PE/Ethyl Acetate=10:1) to yield compound E-1-a (5.1 g) as a colorless oil. LCMS=[M+H]+: 431.4.

To a stirred solution of compound E-1-a (2.77 g, 6.44 mmol) in anhydrous THF (27 mL) at 0° C. lithium borohydride (16.1 mL, 32.2 mmol) was added dropwise. The reaction mixture was stirred at 0° C. for 3 h. After completion of the reaction (monitored by LCMS), the reaction was quenched with sat. NH$_4$Cl and extracted with ethyl acetate (200 mL×2). The combined organic layers were washed with brine (100 mL) and concentrated down under reduced pressure. The resulting residue was purified by flash column chromatography (PE/Ethyl Acetate=20:1) to afford compound 200 (1.69 g) as a colorless oil. LCMS=[M+H]+: 403.2.

To a stirred solution of compound 200 (1.69 g, 4.20 mmol) in anhydrous DCM (16 mL) at 0° C. under nitrogen atmosphere was added Dess-Martin periodinane (5.34 g, 12.60 mmol). The reaction mixture was stirred at 0° C. for 10 min and warmed to room temperature for 2 h. After the completion of the reaction (monitored by LCMS), the reaction mixture was quenched with 10% aq. sodium thiosulfate (20 mL). The organic layer was washed with 10% aq. sodium thiosulfate (20 mL), sat. sodium bicarbonate (20 mL×2), water (20 mL×2), and brine (20 mL), dried over anhydrous Na$_2$SO$_4$, and concentrated down under reduced pressure. The resulting residue was purified by flash column chromatography (DCM/MeOH=20:1) to yield compound E-1-b (320 mg) as a colorless oil. LCMS=[M+H]+: 401.44.

Example S48: Synthesis of Compound F-1-a

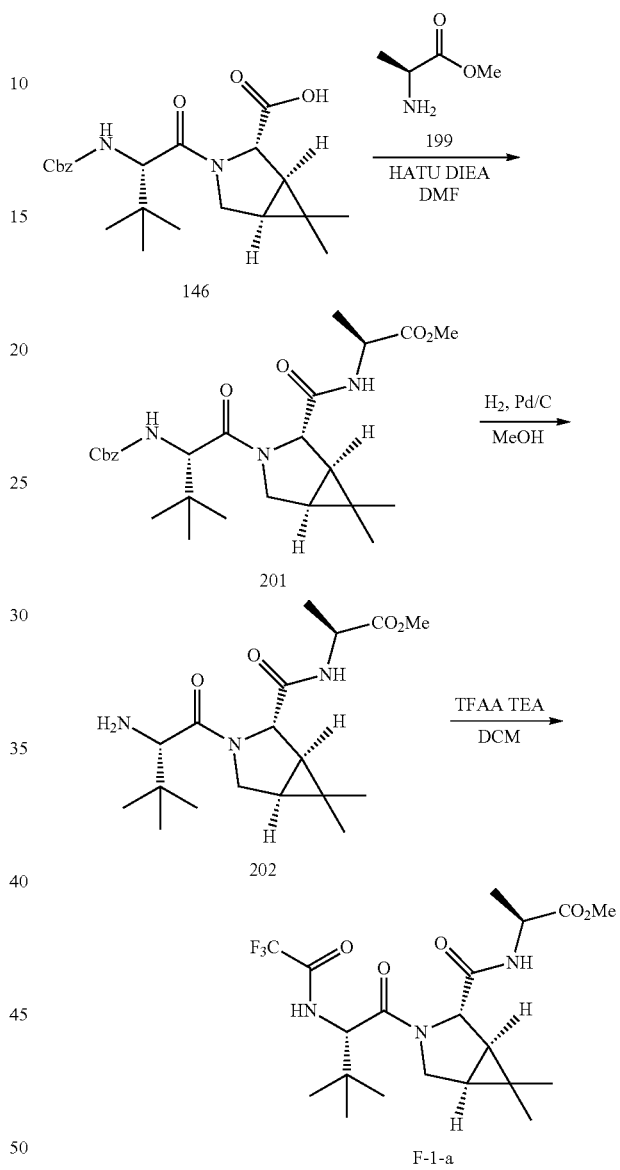

To a solution of compound 146 (1.2 g, 3.0 mmol) in anhydrous DMF (15 mL) at room temperature compound 199 (400 mg, 3.0 mmol), HATU (1.7 g, 4.5 mmol), and DIEA (1.2 g, 9.0 mmol) were added sequentially. The reaction mixture was stirred at room temperature for 1 h. The mixture was diluted with EtOAc, washed with water and sat. NaCl, organic layers were separated, dried over Na$_2$SO$_4$, and concentrated down under reduced pressure. The resulting residue was purified by flash column chromatography (EtOAc:Hexane=1:5) to yield compound 201 (1.4 g, 95.9%). LCMS=[M+H]+: 488.4.

To a stirring solution of compound 201 (1.4 g, 2.8 mmol) in MeOH (20 mL) Pd/C (10 wt. %, 140 mg) was added portion-wise and reaction mixture was stirred at room temperature under hydrogen atmosphere for 2 h. LCMS indicated completion of the reaction. The reaction mixture was filtered, the filtrate was concentrated under reduced pressure to afford the crude compound 202 (1.0 g) as a white solid. LCMS=[M+H]⁺: 354.3.

To a solution of compound 202 (1.0 g, 2.83 mmol) in anhydrous DCM (15 mL) at room temperature TFAA (300 mg, 4.25 mmol) and TEA (240 mg, 7.07 mmol) were added sequentially. The reaction mixture was stirred for 2 h, then diluted with EtOAc, washed with water and sat. NaCl, organic layers were separated, dried over anhydrous Na₂SO₄, and concentrated down under reduced pressure. The resulting residue was purified by flash column chromatography (EtOAc:Hexane=1:5) to yield compound F-1-a (800 mg, 66.7%). LCMS=[M+H]⁺: 450.4.

Example S49: Synthesis of Compound F-1-b

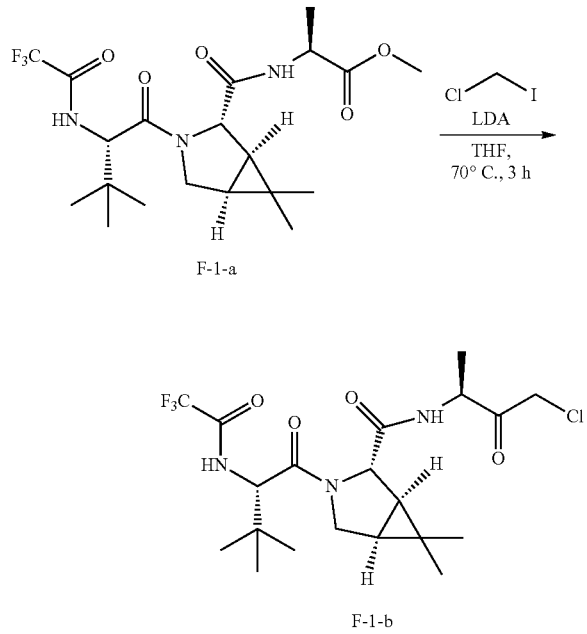

Example S50: Synthesis of Compound F-1-c

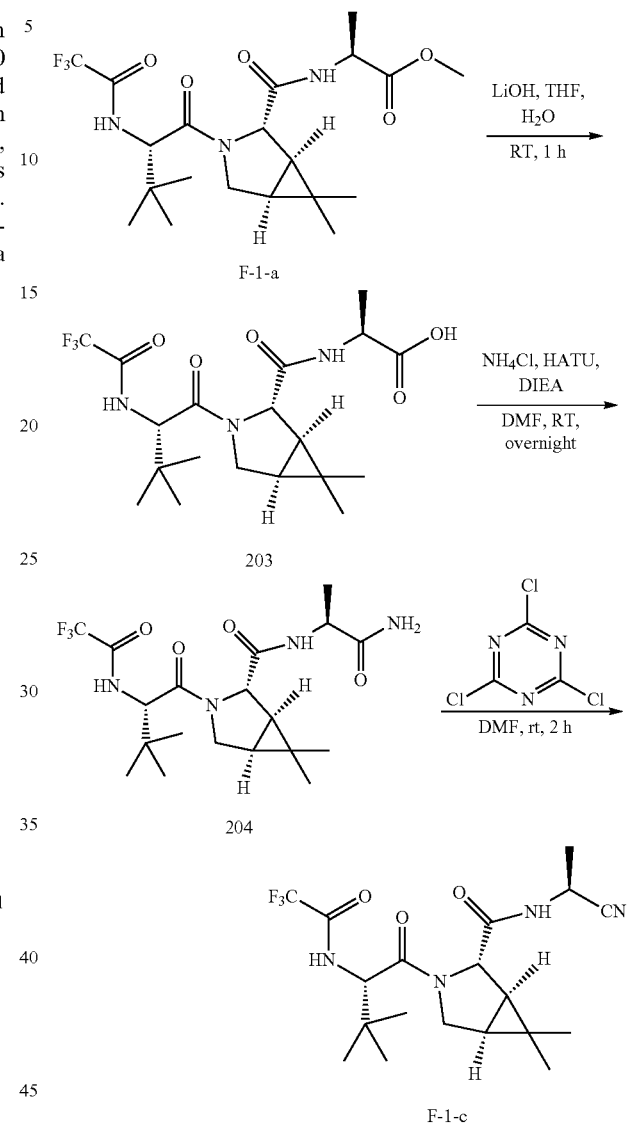

To a solution of methyl ((1R,2S,5S)-3-((S)-3,3-dimethyl-2-(2,2,2-trifluoroacetamido)butanoyl)-6,6-dimethyl-3-azabicyclo[3.1.0]hexane-2-carbonyl)-L-alaninate (compound F-1-a) (100 mg, 0.22 mmol) and chloroiodomethane (235 mg, 1.33 mmol) in dry THF (3 mL) at −70° C. under N₂ LDA (2 M in THF, 2.3 mL, 4.6 mmol) was added dropwise and the reaction mixture was stirred for 3 h at the same temperature. Then the reaction mixture was quenched with sat. NH₄Cl (aq) (10 mL) and extracted with ethyl acetate (10 mL×3). The combined organic layers were washed with brine (20 mL), dried over anhydrous Na₂SO₄, and concentrated under reduced pressure. The resulting residue was purified by prep-HPLC to yield compound F-1-b as white solid (44 mg, 43%). LCMS=[M+H]⁺: 468.2. ¹H NMR (400 MHz, CDCl₃) δ 6.89 (t, J=7.4 Hz, 2H), 4.80 (p, J=7.1 Hz, 1H), 4.56 (d, J=9.4 Hz, 1H), 4.38 (s, 1H), 4.26 (s, 2H), 3.90 (dd, J=10.4, 5.2 Hz, 1H), 3.83 (d, J=10.4 Hz, 1H), 1.62 (d, J=7.7 Hz, 1H), 1.59-1.52 (m, 1H), 1.40 (d, J=7.2 Hz, 3H), 1.06 (s, 3H), 1.03 (s, 9H), 0.86 (s, 3H).

To a solution of methyl ((1R,2S,5S)-3-((S)-3,3-dimethyl-2-(2,2,2-trifluoroacetamido)butanoyl)-6,6-dimethyl-3-azabicyclo[3.1.0]hexane-2-carbonyl)-L-alaninate (compound F-1-a) (400 mg, 0.89 mmol) in THF (5 mL) and water (5 mL) was added LiOH.H₂O (93 mg, 2.23 mmol). The reaction mixture was stirred at room temperature for 1 h. After completion of the reaction, as indicated by LCMS, the reaction mixture was adjusted to pH 3 with saturated citric acid and extracted with ethyl acetate. The organic layer was washed with brine, dried over Na₂SO₄, and concentrated down under reduced pressure to give the crude compound 203 as a white solid (350 mg, 90% yield). LCMS=[M+H]⁺: 436.1. ¹H NMR (400 MHz, CDCl₃) δ 7.35 (d, J=9.3 Hz, 1H), 7.14 (d, J=7.3 Hz, 1H), 4.63-4.56 (m, 2H), 4.44 (s, 1H), 3.93 (dd, J=10.5, 5.2 Hz, 1H), 3.87 (d, J=10.4 Hz, 1H), 3.76 (ddd, J=6.6, 4.2, 2.5 Hz, 2H), 1.88-1.84 (m, 2H), 1.67 (d, J=7.7 Hz, 1H), 1.57 (dd, J=7.7, 4.9 Hz, 1H), 1.44 (d, J=7.2 Hz, 3H), 1.06 (s, 3H), 1.03 (s, 9H), 0.85 (s, 3H).

A solution of ((1R,2S,5S)-3-((S)-3,3-dimethyl-2-(2,2,2-trifluoroacetamido)butanoyl)-6,6-dimethyl-3-azabicyclo

[3.1.0]hexane-2-carbonyl)-L-alanine (compound 203) (100 mg, 0.23 mmol), NH$_4$Cl (26 mg, 0.46 mmol), HATU (174 mg, 0.46 mmol) and DIEA (120 mg, 0.92 mmol) in DMF (2 mL) was stirred at room temperature overnight. After completion of the reaction indicated by LCMS, the reaction mixture was diluted with water and extracted with ethyl acetate. The organic layer was washed with brine, dried over anhydrous Na$_2$SO$_4$, and concentrated down under reduced pressure. The resulting residue was purified by flash chromatography (silica gel, 10 g SNAP, 65% THF in PE) to yield compound 204 as a yellow solid (90 mg, 90% yield). LCMS=[M+H]$^+$: 534.3.

To a stirred solution of (1R,2S,5S)—N—((S)-1-amino-1-oxopropan-2-yl)-3-((S)-3,3-dimethyl-2-(2,2,2-trifluoroacetamido)butanoyl)-6,6-dimethyl-3-azabicyclo[3.1.0]hexane-2-carboxamide (compound 204) (30 mg, 0.069 mmol) in DMF (0.6 mL) was added 2,4,6-trichloro-1,3,5-triazine (18 mg, 0.97 mmol) at room temperature. The reaction mixture was stirred at room temperature for 2 h. After completion of the reaction as indicated by LCMS, the reaction mixture was directly purified by prep-HPLC to yield compound F-1-c (two isomers): F-1-c-P1 as white solid (2.01 mg, 7%) and F-1-c-P2 as white solid (1.69 mg, 6%).

F-1-c-P1: LCMS=[M+H]$^+$: 417.4, purity: 59%. $^1$H NMR (400 MHz, CDCl$_3$) δ 7.35 (d, J=7.6 Hz, 0.3H), 7.05-6.97 (m, 0.6H), 6.83 (d, J=8.7 Hz, 1H), 4.95-4.78 (m, 1H), 4.63-4.49 (m, 1H), 4.44 (s, 0.3H), 4.36 (s, 0.6H), 3.93-3.78 (m, 2H), 1.79 (d, J=7.8 Hz, 0.3H), 1.71 (d, J=7.7 Hz, 0.6H), 1.55 (dd, J=10.7, 7.2 Hz, 4H), 1.08 (s, 3H), 1.05 (s, 3H), 1.02 (s, 6H), 0.85 (d, J=3.9 Hz, 3H).

F-1-c-P2: LCMS=[M+H]$^+$: 417.4, purity: 73%. $^1$H NMR (400 MHz, CDCl$_3$) δ 7.35 (d, J=8.0 Hz, 0.5H), 7.03 (d, J=7.9 Hz, 0.5H), 6.83 (d, J=8.2 Hz, 1H), 4.94-4.79 (m, 1H), 4.56 (dd, J=9.4, 5.6 Hz, 1H), 4.44 (s, 0.5H), 4.36 (s, 0.5H), 3.92-3.81 (m, 2H), 1.79 (d, J=7.8 Hz, 0.5H), 1.71 (d, J=7.7 Hz, 0.5H), 1.62-1.58 (m, 1H), 1.64-1.58 (m, 3H), 1.07 (s, 3H), 1.05 (s, 4.5H), 1.02 (s, 4.5H), 0.85 (d, J=3.7 Hz, 3H).

Example S51: Synthesis of Compound F-1-d

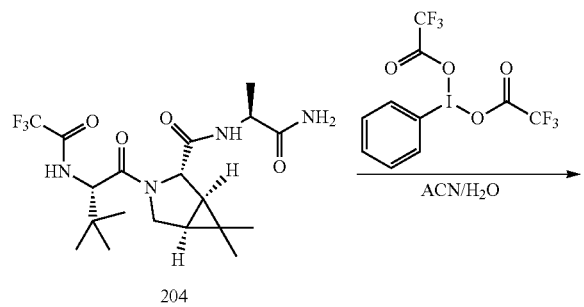

204

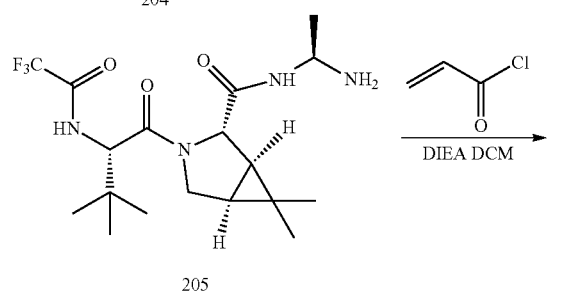

205

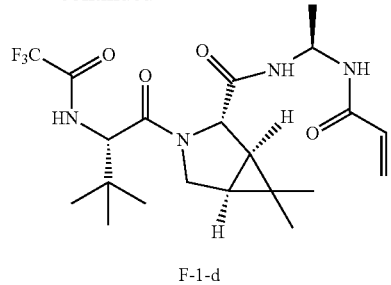

F-1-d

A solution of (1R,2S,5S)—N—((S)-1-amino-1-oxopropan-2-yl)-3-((S)-3,3-dimethyl-2-(2,2,2-trifluoro-acetamido)butanoyl)-6,6-dimethyl-3-azabicyclo[3.1.0]hexane-2-carboxamide (compound 204) (100 mg, 0.23 mmol) and phenyl-λ$^3$-iodanediyl bis(2,2,2-trifluoroacetate) (100 mg, 0.23 mmol) in acetone (3 mL) and water (3 mL) was stirred at room temperature overnight. The reaction mixture was directly purified by flash column (C 18, 40 g 20-35 um, 100 Å, 50% ACN/water (0.1% FA)) to yield compound 205 as a white solid (50 mg, 53% yield). LCMS=[M+H]$^+$: 407.2.

To a stirred solution of (1R,2S,5S)—N—((S)-1-aminoethyl)-3-((S)-3,3-dimethyl-2-(2,2,2-trifluoroacetamido)butanoyl)-6,6-dimethyl-3-azabicyclo[3.1.0]hexane-2-carboxamide (compound 205) (50 mg, 0.12 mmol) and DIEA (48 mg, 0.37 mmol) in DCM (3 mL) at 0° C. under N$_2$ was added acryloyl chloride (14 mg, 0.16 mmol). The reaction mixture was stirred at room temperature for 15 min. After completion of the reaction indicated by LCMS, the reaction mixture was concentrated and purified by prep-HPLC to yield compound F-1-d (two isomers): F-1-d-P1 as a white solid (6.50 mg, yield: 12%), F-1-d-P2 as a white solid (3.62 mg, yield: 7%).

F-1-d-P1: LCMS=[M+H]$^+$: 461.1, purity 87% $^1$H NMR (400 MHz, CDCl$_3$) δ 7.52 (s, 1H), 7.18-6.94 (m, 1H), 6.68-6.47 (m, 1H), 6.33 (d, J=16.4 Hz, 1H), 6.03 (dd, J=16.8, 10.5 Hz, 1H), 5.68 (d, 1H), 5.45-5.34 (m, 1H), 4.56 (d, J=9.5 Hz, 1H), 4.37 (s, 1H), 3.88 (s, 1H), 3.81 (d, J=10.3 Hz, 1H), 1.58 (d, 3H), 1.05 (d, J=5.4 Hz, 4H), 1.01 (s, 9H), 0.96 (s, 1H), 0.84 (s, 3H).

F-1-d-P2: LCMS=[M+H]$^+$: 461.1, purity 59%. $^1$H NMR (400 MHz, CDCl$_3$) δ 7.45 (s, 1H), 6.91 (s, 1H), 6.66 (s, 1H), 6.30 (d, J=16.4 Hz, 1H), 6.11-5.98 (m, 1H), 5.68 (d, J=9.5 Hz, 1H), 5.45 (s, 1H), 4.55 (dd, J=9.3, 3.2 Hz, 1H), 4.33 (d, J=10.6 Hz, 1H), 3.88 (d, J=10.7 Hz, 1H), 3.82 (d, J=9.9 Hz, 1H), 1.68 (d, J=4.1 Hz, 1H), 1.63-1.54 (m, 4H), 1.06 (d, J=7.9 Hz, 3H), 1.02 (t, J=5.1 Hz, 9H), 0.85 (d, J=7.9 Hz, 3H).

Example S52: Synthesis of Compound F-2-a

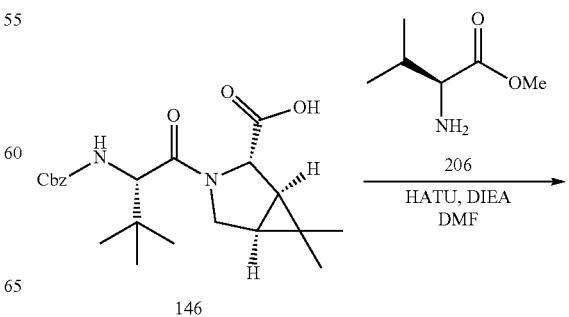

146

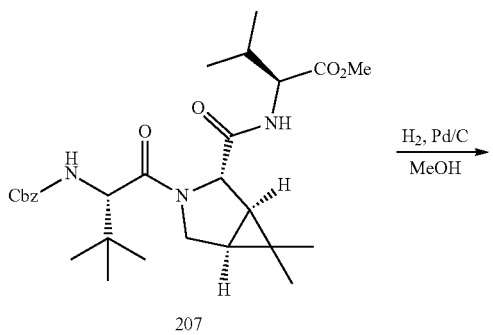

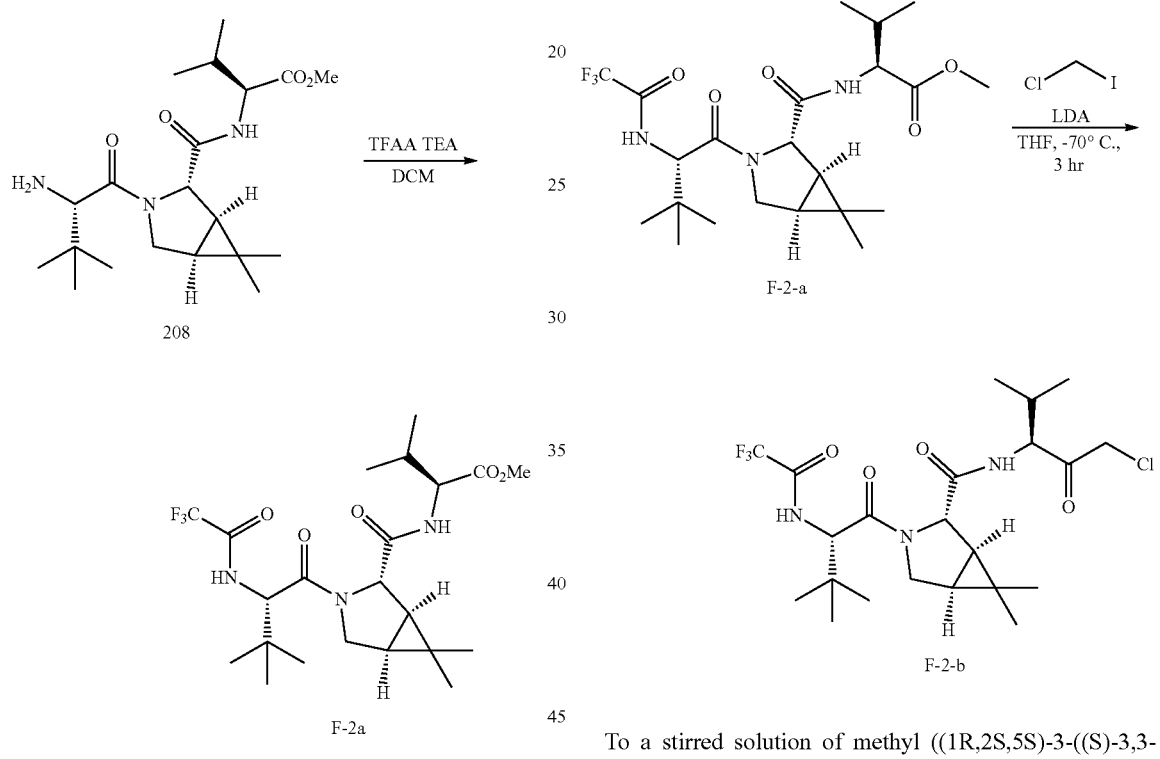

Example S53: Synthesis of Compound F-2-b

To a solution of compound 146 (1.1 g, 2.7 mmol) in anhydrous DMF (15 mL) at room temperature, compound 206 (458.6 mg, 2.7 mmol), HATU (1.56 g, 4.05 mmol), and DIEA (1.05 g, 8.1 mmol) were added sequentially. The mixture was stirred at room temperature for 2 h, then diluted with EtOAc. The organic layer was washed with water, sat. NaCl, dried over $Na_2SO_4$, and concentrated down under reduced pressure. The resulting residue was purified by flash column chromatography (EtOAc:Hexane=1:5) to yield compound 207 (600 mg, 43.2%). LCMS=[M+H]$^+$: 516.2.

To a stirring solution of compound 207 (600 mg, 1.16 mmol) in MeOH (20 mL) Pd/C (10 wt %, 60 mg) was added portion-wise. The reaction mixture was stirred under a hydrogen atmosphere at room temperature for 2 h. After completion of the reaction as indicated by LCMS, the mixture was filtered, and filtrate was concentrated down under reduced pressure to afford the crude compound 208 (500 mg) as a white solid. LCMS=[M+H]$^+$: 382.4.

To a solution of compound 208 (500 mg, 1.31 mmol) in anhydrous DCM (15 mL) at room temperature TFAA (550 mg, 2.62 mmol) and TEA (396 mg, 3.93 mmol) were added sequentially. The reaction mixture was stirred for 2 h until completion of the reaction was indicated by LCMS. The reaction mixture was diluted with EtOAc, the organic layer was washed with water, sat. NaCl, dried over $Na_2SO_4$, and concentrated down under reduced pressure. The resulting residue was purified by flash column chromatography (EtOAc:Hexane=1:5) to yield compound F-2-a (420 mg, 91%). LCMS=[M+H]$^+$: 478.3.

To a stirred solution of methyl ((1R,2S,5S)-3-((S)-3,3-dimethyl-2-(2,2,2-trifluoroacetamido)-butanoyl)-6,6-dimethyl-3-azabicyclo[3.1.0]hexane-2-carbonyl)-L-valinate compound F-2-a (100 mg, 0.21 mmol) and chloroiodomethane (222 mg, 1.26 mmol) in dry THF (3 mL) at −70° C. under $N_2$, LDA (2 M in THF, 2 mL, 4 mmol) was added dropwise. The reaction mixture was stirred at the same temperature for 3 h. After completion of the reaction as indicated by LCMS, the reaction mixture was quenched with sat aq. $NH_4Cl$ (10 mL) and extracted with ethyl acetate (10 mL×3). The combined organic layers were washed with brine (20 mL), dried over $Na_2SO_4$, and concentrated down under reduced pressure. The resulting residue was purified by prep-HPLC to yield compound F-2-b as white solid (34 mg, 33%). LCMS=[M+H]$^+$: 496.3, purity 98%. $^1$H NMR (400 MHz, CDCl$_3$) δ 6.92 (d, J=9.1 Hz, 1H), 6.72 (d, J=8.2 Hz, 1H), 4.79 (dd, J=8.3, 5.0 Hz, 1H), 4.58 (d, J=9.5 Hz, 1H), 4.38 (s, 1H), 4.25 (d, J=2.3 Hz, 2H), 3.92 (dd, J=10.3, 4.4 Hz, 1H), 3.84 (d, J=10.4 Hz, 1H), 2.28-2.17 (m, 1H), 1.81 (t, J=4.3 Hz, 1H), 1.59-1.55 (m, 3H), 1.06 (s, 3H), 1.02 (d, J=5.0 Hz, 9H), 0.89 (d, J=6.9 Hz, 3H), 0.86 (s, 3H).

Example S54: Synthesis of Compound F-2-c

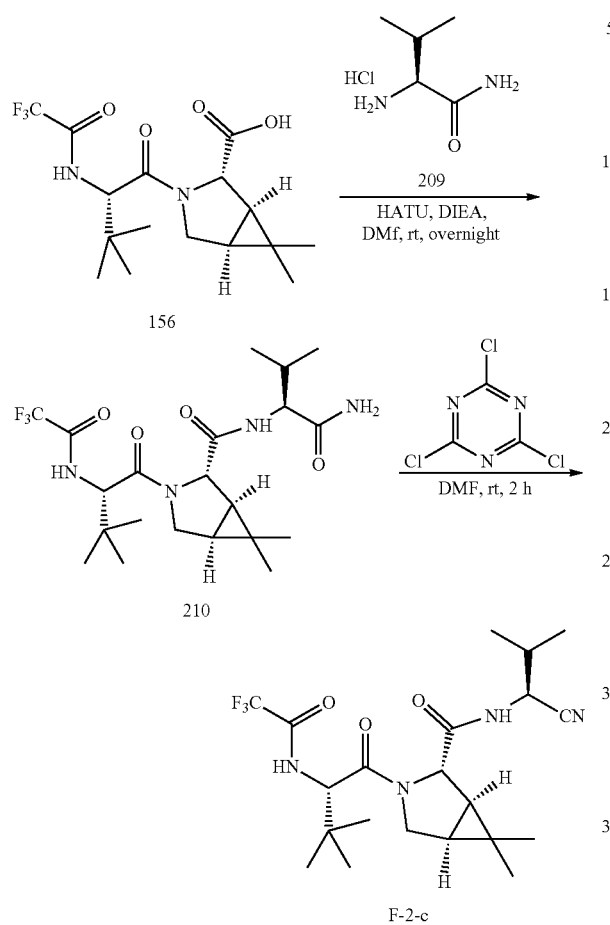

A solution of (1R,2S,5S)-3-((S)-3,3-dimethyl-2-(2,2,2-trifluoroacetamido)butanoyl)-6,6-dimethyl-3-azabicyclo[3.1.0]hexane-2-carboxylic acid (compound 156) (270 mg, 0.74 mmol), (S)-2-amino-3-methylbutanamide hydrochloride (compound 209) (170 mg, 1.11 mmol), HATU (563 mg, 1.48 mmol) and DIEA (382 mg, 2.96 mmol) in DMF (3 mL) was stirred at room temperature overnight. After completion of the reaction as indicated by LCMS, the reaction mixture was diluted with water and extracted with ethyl acetate. The combined organic layers were washed with brine, dried over $Na_2SO_4$, and concentrated down under reduced pressure. The resulting residue was purified by flash column chromatography (C 18, 120 g, 20-35 um, 100 Å, 60% ACN/water (0.1% FA)) to yield compound 210 as a yellow solid (300 mg, 87% yield). LCMS=[M+H]$^+$: 463.1.

To a stirred solution of (1R,2S,5S)—N—((S)-1-amino-3-methyl-1-oxobutan-2-yl)-3-((S)-3,3-dimethyl-2-(2,2,2-trifluoroacetamido)butanoyl)-6,6-dimethyl-3-azabicyclo[3.1.0]hexane-2-carboxamide (50 mg, 0.11 mmol) (compound 210) in DMF (1 mL) was added 2,4,6-trichloro-1,3,5-triazine (28 mg, 0.15 mmol) at room temperature. The resulting reaction mixture was stirred for 2 h, then purified directly by prep-HPLC to yield compound F-2-c as a white solid (20 mg, 41%). LCMS=[M+H]$^+$: 445.3. $^1$H NMR (400 MHz, CDCl$_3$) δ 7.02 (t, J=8.4 Hz, 1H), 6.95 (d, J=8.8 Hz, 1H), 6.90 (d, J=8.8 Hz, 0.5H), 6.73 (d, J=8.3 Hz, 0.5H), 4.79 (dd, J=9.0, 6.2 Hz, 1H), 4.70 (dd, J=9.0, 6.9 Hz, 0.5H), 4.58 (d, J=9.5 Hz, 1H), 4.44 (d, J=8.4 Hz, 0.5H), 4.35 (s, 1H), 4.31 (s, 0.5H), 4.12 (dd, J=10.3, 5.4 Hz, 0.5H), 3.92 (dd, J=10.4, 4.5 Hz, 1H), 3.86 (d, J=10.4 Hz, 1H), 3.69 (d, J=10.3 Hz, 0.5H), 2.10-1.95 (m, 1.5H), 1.68-1.54 (m, 3H), 1.11 (s, 1.5H), 1.08 (dd, J=3.3, 1.6 Hz, 8H), 1.06 (s, 5H), 1.01 (s, 9H), 0.86 (s, 3H). Note: possible mixture of two isomers.

Example S55: Synthesis of Compound F-2-d

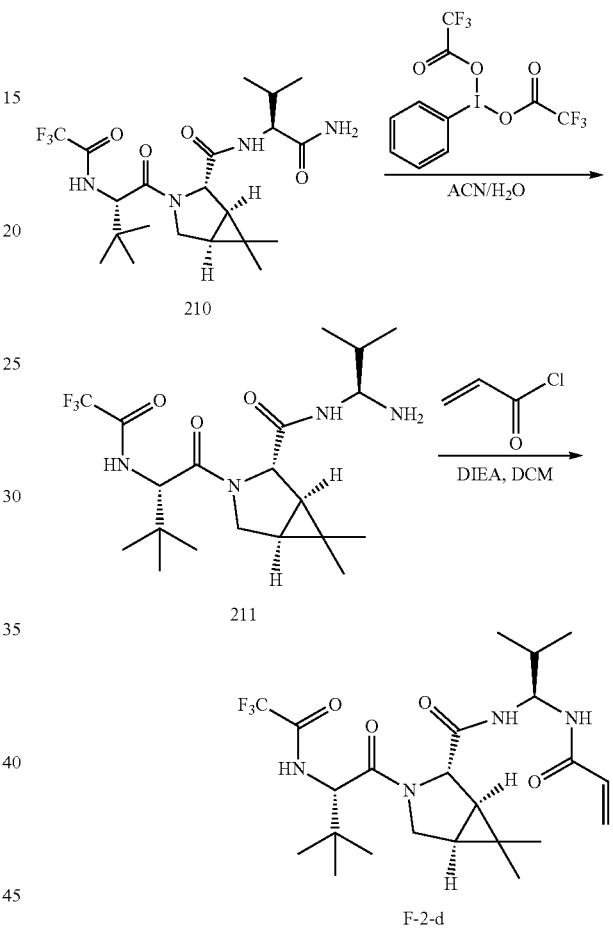

A solution of (1R,2S,5S)—N—((S)-1-amino-3-methyl-1-oxobutan-2-yl)-3-((S)-3,3-dimethyl-2-(2,2,2-trifluoroacetamido)butanoyl)-6,6-dimethyl-3-azabicyclo[3.1.0]hexane-2-carboxamide (compound 210) (200 mg, 0.43 mmol) and phenyl-λ$^3$-iodanediyl bis(2,2,2-trifluoroacetate) (200 mg, 0.43 mmol) in ACN (5 mL) and water (5 mL) was stirred at room temperature overnight. After completion of the reaction as indicated by LCMS, the reaction mixture was directly purified by flash column (C 18, 40 g, 20-35 um, 100 Å, 50% ACN/water (0.1% FA)) to yield compound 211 as a white solid (20 mg, 11%). LCMS=[2M+H]$^+$: 869.4.

To a stirred solution of (1R,2S,5S)—N—((S)-1-amino-2-methylpropyl)-3-((S)-3,3-dimethyl-2-(2,2,2-trifluoroacetamido)butanoyl)-6,6-dimethyl-3-azabicyclo[3.1.0]hexane-2-carboxamide (compound 211) (20 mg, 0.046 mmol) and DIEA (24 mg, 0.184 mmol) in DCM (1 mL) at 0° C. under $N_2$ was added acryloyl chloride (5.4 mg, 0.06 mmol). The reaction mixture was stirred at room temperature for 15 min. After completion of the reaction indicated by LCMS, the reaction mixture was concentrated down under reduced pressure. The resulting residue was purified by prep-HPLC to yield compound F-2-d as a white solid (2 mg, 9%). LCMS=[M+H]⁺: 489.3, purity 92%. ¹H NMR (400 MHz, CDCl₃) δ 7.38 (s, 1H), 6.92 (s, 1H), 6.31 (d, J=16.6 Hz, 1H), 6.10 (s, 1H), 5.70 (d, J=9.7 Hz, 1H), 4.98 (s, 1H), 4.56 (d, J=9.5 Hz, 1H), 4.35 (s, 1H), 3.90 (d, J=10.2 Hz, 1H), 3.82 (d, J=10.3 Hz, 1H), 2.41 (s, 1H), 1.53 (d, J=13.7 Hz, 2H), 1.05 (s, 3H), 1.00 (s, 9H), 0.99-0.94 (m, 6H), 0.84 (s, 3H).

Example S56: Synthesis of Compound F-2-e

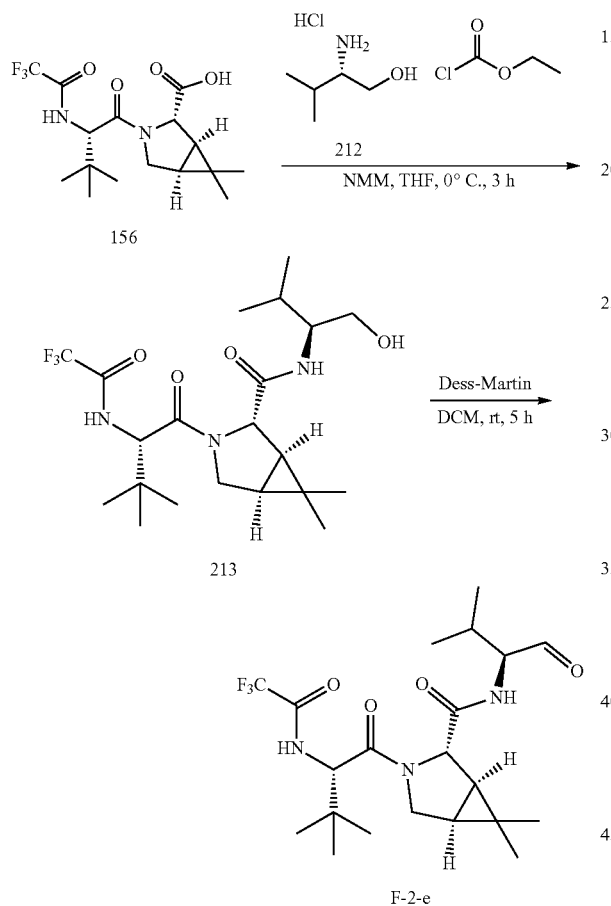

F-2-e

To a solution of (1R,2S,5S)-3-((S)-3,3-dimethyl-2-(2,2,2-trifluoroacetamido)butanoyl)-6,6-dimethyl-3-azabicyclo[3.1.0]hexane-2-carboxylic acid (compound 156) (100 mg, 274 umol) in THF (2 mL) at 0° C. 4-methylmorpholine (73 mg, 0.72 mmol) and ethyl chloroformate (62 mg, 0.57 mmol) were added. The reaction mixture was stirred for 15 min and (S)-2-amino-3-methylbutan-1-ol hydrochloride (compound 212) (60 mg, 430 umol) was added. The reaction mixture was stirred at 0° C. for 3 h under nitrogen atmosphere. After completion of the reaction indicated by LCMS, the reaction mixture was quenched with water (50 mL) and extracted with ethyl acetate (50 mL×3). The combined organic layers were washed with brine (20 mL), dried over anhydrous sodium sulfate, and concentrated under reduced pressure. The resulting residue was purified by silica gel flash column chromatography (Ethyl acetate:petroleum ether from 0:1 to 1:5) to yield compound 213 (90.0 mg, 74%) as a colorless oil. LCMS=[M+H]⁺: 450.0.

A solution of (1R,2S,5S)-3-((S)-3,3-dimethyl-2-(2,2,2-trifluoroacetamido)butanoyl)-N—((S)-1-hydroxy-3-methylbutan-2-yl)-6,6-dimethyl-3-azabicyclo[3.1.0]hexane-2-carboxamide (compound 213) (90 mg, 0.2 mmol) and Dess-Martin periodinane (254 mg, 0.6 mmol) in DCM (10 mL) was stirred at room temperature for 5 h. After completion of the reaction indicated by LCMS, the reaction mixture was diluted with DCM, washed with sat. Na₂S₂O₃ (aq), sat. NaHCO₃ (aq), and brine. Organic layer was dried over with Na₂SO₄ and concentrated down under reduced pressure. The resulting residue was purified by prep-HPLC to yield compound F-2-e as a white solid (11 mg, 12% yield). LCMS=[M+H]⁺: 448.3. ¹H NMR (400 MHz, CDCl₃) δ 9.60 (s, 1H), 7.03 (d, J=9.4 Hz, 1H), 6.85 (d, J=7.4 Hz, 2H), 4.57-4.51 (m, 2H), 4.36 (s, 1H), 3.91-3.85 (m, 1H), 3.78 (d, J=10.4 Hz, 1H), 2.29-2.21 (m, 2H), 1.18 (s, 3H), 1.03-0.84 (m, 17H), 0.79 (s, 3H).

Example S57: Synthesis of Compound F-3-a

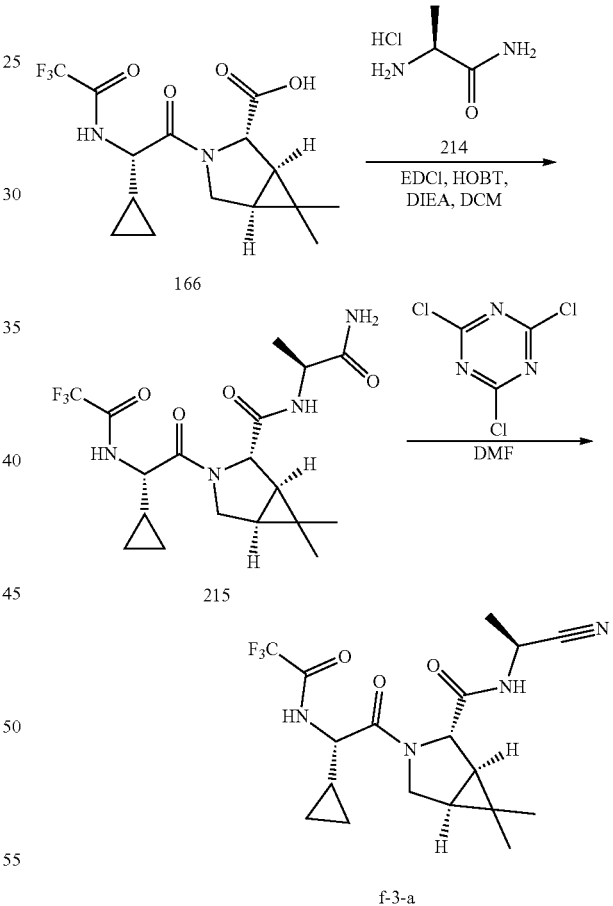

f-3-a

To a stirred solution of (1R,2S,5S)-3-[2-cyclopropyl-2-(trifluoroacetamido)acetyl]-1,5-dihydrogenio-6,6-dimethyl-3-azabicyclo[3.1.0]hexane-2-carboxylic acid (compound 166) (100 mg, 0.29 mmol) in DCM (8 mL) was added (2S)-2-aminopropanamide hydrochloride (compound 214) (30 mg, 0.34 mmol), EDCI (82 mg, 0.43 mmol), HOBT (58 mg, 0.43 mmol) and DIEA (0.2 mL, 1.15 mmol). The reaction mixture was stirred at room temperature for 1.5 h under the N₂. The reaction mixture was concentrated, and the crude material was directly purified by reverse phase column (ACN/water (0.05% FA)) to yield compound 215 (90 mg, 0.22 mmol, 74.92%) as an off-white solid. LCMS=[M+H]$^+$: 419.1.

To a stirred solution of (1R,2S,5S)—N—((S)-1-amino-1-oxopropan-2-yl)-3-((S)-2-cyclopropyl-2-(2,2,2-trifluoroacetamido)acetyl)-6,6-dimethyl-3-azabicyclo[3.1.0]hexane-2-carboxamide (compound 215) (30 mg, 0.07 mmol) in DMF (0.5 mL) was added trichloro-1,3,5-triazine (0.01 mL, 0.10 mmol). The reaction mixture was stirred at room temperature for 1.5 h under N$_2$. The reaction mixture was directly purified by prep-HPLC to yield compound F-3-a (5.24 mg, 17.74%) as an off-white solid. LCMS=[M+H]$^+$: 401.2. $^1$H NMR (400 MHz, CDCl$_3$) δ 7.10 (s, 1H), 6.96 (d, J=7.3 Hz, 1H), 4.94-4.84 (m, 1H), 4.44 (t, J=7.5 Hz, 1H), 4.33 (s, 1H), 3.91-3.85 (m, 1H), 3.73 (d, J=10.4 Hz, 1H), 1.74-1.68 (m, 1H), 1.63-1.59 (m, 2H), 1.28-1.17 (m, 1H), 1.09 (s, 4H), 1.00 (d, J=5.4 Hz, 1H), 0.92 (s, 3H), 0.65-0.58 (m, 2H), 0.52-0.43 (m, 2H).

Example S58: Synthesis of Compound F-3-b

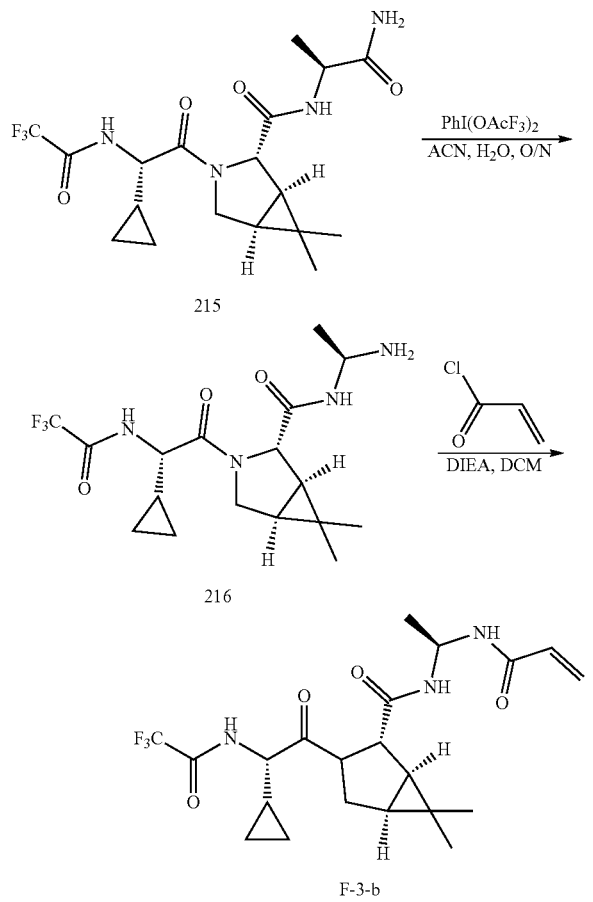

To a stirred solution of (1R,2S,5S)—N—((S)-1-amino-1-oxopropan-2-yl)-3-((S)-2-cyclopropyl-2-(2,2,2-trifluoroacetamido)acetyl)-6,6-dimethyl-3-azabicyclo[3.1.0]hexane-2-carboxamide (compound 215) (60 mg, 0.14 mmol) in ACN (1.5 mL) and H$_2$O (1.5 mL) was added bis(trifluoroacetoxy)iodobenzene (62 mg, 0.14 mmol). The reaction mixture was stirred at room temperature overnight under N$_2$ in the darkness. The mixture was directly purified by flash column (C18, ACN/water (0.05% TFA)) to yield compound 216 (40 mg, 0.10 mmol, 71.45%) as an off-white solid. LCMS= [2M+H]$^+$: 781.4.

To a stirred solution of (1R,2S,5S)—N-[(1S)-1-aminoethyl]-3-[2-cyclopropyl-2-(trifluoroacetamido)-acetyl]-1,5-dihydrogenio-6,6-dimethyl-3-azabicyclo[3.1.0]hexane-2-carboxamide (compound 216) (40 mg, 0.10 mmol) and DIEA (0.07 mL, 0.41 mmol) in DCM (1 mL) at 0° C. acryloyl chloride (0.01 mL, 0.13 mmol) was slowly added. The reaction mixture was stirred at room temperature for 15 min under N$_2$. After completion of the reaction indicated by LCMS, the reaction mixture was concentrated down under reduced pressure and the resulting residue was purified by prep-HPLC to yield compound F-3-b (2.86 mg, 5.92%) as an off-white solid. LCMS=[M+H]$^+$: 445.3. $^1$H NMR (400 MHz, DMSO-d$_6$) δ 10.09 (s, 1H), 8.22 (s, 2H), 6.19 (d, J=9.9 Hz, 1H), 6.12-6.05 (m, 1H), 5.60 (dd, J=10.1, 7.6 Hz, 2H), 5.48 (dd, J=19.6, 6.6 Hz, 1H), 4.15 (s, 1H), 4.01 (s, 1H), 3.77 (d, J=5.3 Hz, 1H), 3.62 (d, J=10.6 Hz, 1H), 1.38 (dd, J=16.1, 7.6 Hz, 2H), 1.00 (d, J=11.6 Hz, 4H), 0.93 (s, 2H), 0.80 (s, 2H), 0.55-0.40 (m, 4H).

Example S59: Synthesis of Compound F-3-c

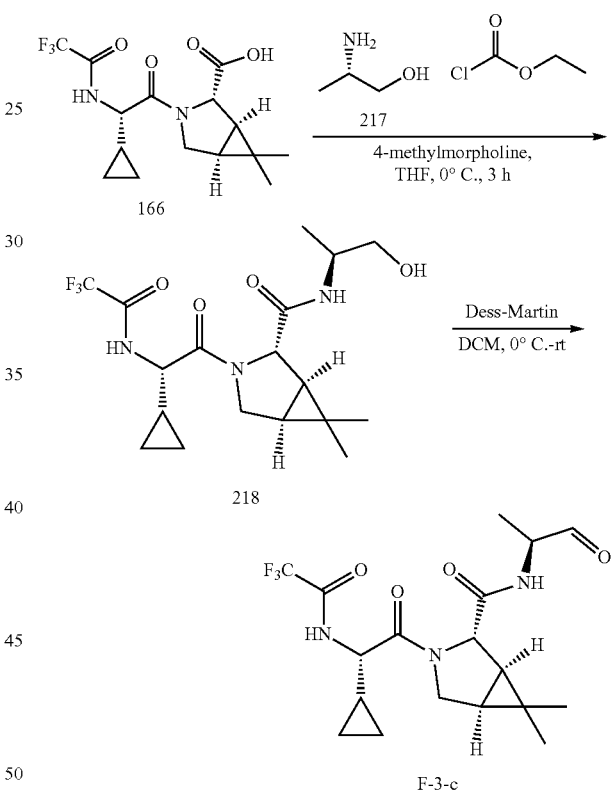

To a solution of (1R,2S,5S)-3-((S)-2-cyclopropyl-2-(2,2,2-trifluoroacetamido)acetyl)-6,6-dimethyl-3-azabicyclo [3.1.0]hexane-2-carboxylic acid (compound 166) (200 mg, 574.18 umol) in THF (2 mL) at 0° C. under nitrogen atmosphere were added 4-methylmorpholine (145.19 mg, 1.44 mmol) and ethyl chloroformate (124.62 mg, 1.15 mmol). The mixture was stirred for 15 min, and then (S)-2-aminopropan-1-ol (compound 217) (64.5 mg, 861.27 umol) was added. The resulting mixture was stirred at 0° C. for 3 h. After completion of the reaction indicated by LCMS, the reaction mixture was quenched with water (50 mL) and extracted with ethyl acetate (50 mL×3). The combined organic layers were washed with brine (20 mL), dried over anhydrous sodium sulfate, and concentrated down under reduced pressure. The resulting residue was purified by silica gel column chromatography (Ethyl acetate:petroleum ether from 0:1 to 1:5) to yield compound 218 (120.0 mg, 51.9%) as a colorless oil. LCMS=[M+H]⁺: 406.0.

A solution of (1R,2S,5S)-3-((S)-2-cyclopropyl-2-(2,2,2-trifluoroacetamido)acetyl)-N—((S)-1-hydroxypropan-2-yl)-6,6-dimethyl-3-azabicyclo[3.1.0]hexane-2-carboxamide (compound 218) (100 mg, 0.30 mmol) and Dess-Martin periodinane (636 mg, 1.5 mmol) in DCM (10 mL) was stirred at room temperature for 3 h. After completion of the reaction indicated by LCMS, the reaction mixture was diluted with DCM, washed with sat. $Na_2S_2O_3$ (aq), sat. $NaHCO_3$ (aq), and brine. Organic layer was separated, dried over $Na_2SO_4$, and concentrated down under reduced pressure. The resulting residue was purified by prep-HPLC to yield compound F-3-c as a white solid (7 mg, 5.8% yield). LCMS=[M+H]⁺: 404.2. ¹H NMR (400 MHz, $CDCl_3$) δ 9.56-9.46 (m, 1H), 7.16 (s, 1H), 7.00-6.74 (m, 1H), 4.57-4.28 (m, 2H), 4.13-4.00 (m, 1H), 3.97-3.90 (m, 1H), 3.78-3.61 (m, 1H), 1.73-1.64 (m, 1H), 1.62-1.51 (m, 1H), 1.41-1.37 (m, 1H), 1.36-1.28 (m, 3H), 1.12-1.05 (m, 3H), 1.04-0.98 (m, 3H), 0.93 (s, 1H), 0.75-0.59 (m, 2H), 0.58-0.41 (m, 2H).

Example S60: Synthesis of Compound F-4-a

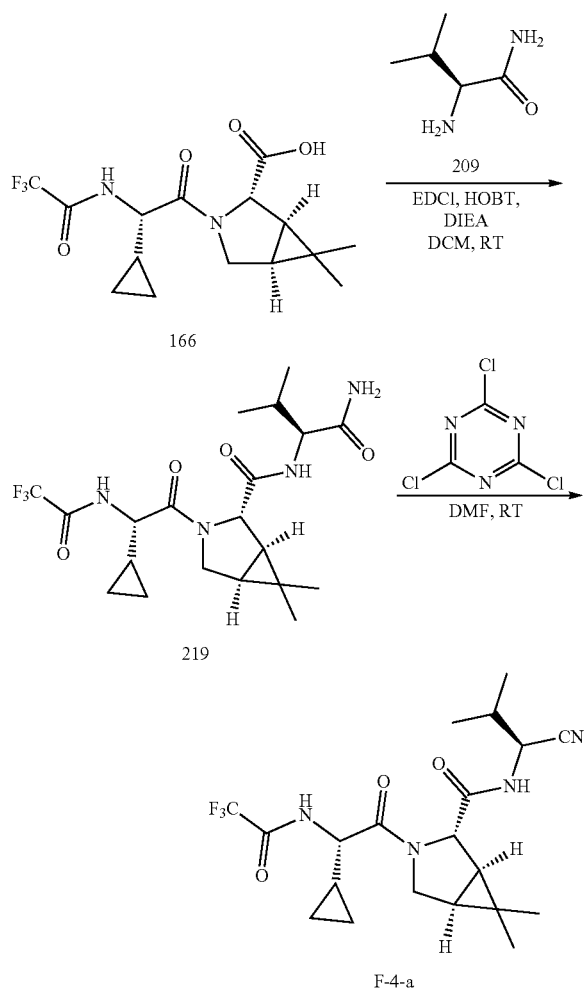

To a stirred solution of (1R,2S,5S)-3-[2-cyclopropyl-2-(trifluoroacetamido)acetyl]-1,5-dihydrogenio-6,6-dimethyl-3-azabicyclo[3.1.0]hexane-2-carboxylic acid (compound 166) (300 mg, 0.86 mmol) in DCM (5 mL) was added (2S)-2-amino-3-methylbutanamide (compound 209) (120 mg, 1.03 mmol), EDCI (247 mg, 1.29 mmol), HOBT (174 mg, 1.29 mmol) and DIEA (0.70 mL, 4.31 mmol). The reaction mixture was stirred at room temperature for 1.5 h under the $N_2$. After completion of the reaction indicated by LCMS, the reaction mixture was concentrated down under reduced pressure. The resulting residue was purified by prep-HPLC (C18, ACN/water (0.5% FA)) to yield compound 219 (209 mg, 0.47 mmol, 54.35%) as an off-white solid. LCMS=[M+H]⁺: 447.2.

To a stirred solution of (1R,2S,5S)—N—((S)-1-amino-3-methyl-1-oxobutan-2-yl)-3-((S)-2-cyclopropyl-2-(2,2,2-trifluoroacetamido)acetyl)-6,6-dimethyl-3-azabicyclo[3.1.0]hexane-2-carboxamide (compound 219) (50 mg, 0.11 mmol) in DMF (0.6 mL) was added trichloro-1,3,5-triazine (29 mg, 0.16 mmol). The reaction mixture was stirred at room temperature for 1 h under $N_2$. After completion of the reaction indicated by LCMS, the mixture was directly purified by prep-HPLC to yield compound F-4-a (as two isomers): F-4-a-P1 (13.45 mg, 28.03%) and F-4-a-P2 (6.55 mg, 12%) as off-white solid. LCMS=[M+H]⁺: 429.2.

F-4-a-P1 ¹H NMR (400 MHz, $CDCl_3$) δ 7.15 (d, J=6.8 Hz, 1H), 7.07 (d, J=8.7 Hz, 1H), 4.78 (dd, J=8.9, 6.1 Hz, 1H), 4.40-4.34 (m, 2H), 3.87 (dd, J=10.4, 5.3 Hz, 1H), 3.76 (d, J=10.4 Hz, 1H), 2.08-1.98 (m, 1H), 1.73 (s, 1H), 1.62 (dd, J=7.7, 5.2 Hz, 1H), 1.25-1.16 (m, 1H), 1.10-1.05 (m, 9H), 0.91 (s, 3H), 0.63-0.58 (m, 2H), 0.51-0.44 (m, 2H).

F-4-a-P2 δ ¹H NMR (400 MHz, $CDCl_3$) δ 7.20 (d, J=8.6 Hz, 1H), 7.05 (d, 1H), 4.66 (dd, J=8.7, 6.6 Hz, 1H), 4.41 (s, 1H), 4.09-4.03 (m, 1H), 3.96 (dd, J=10.3, 5.4 Hz, 1H), 3.67 (d, J=10.3 Hz, 1H), 2.11-1.98 (m, 1H), 1.81 (d, J=7.7 Hz, 1H), 1.54 (s, 1H), 1.22 (d, J=8.6 Hz, 1H), 1.10 (s, 3H), 1.03 (dd, J=12.0, 7.1 Hz, 9H), 0.75-0.62 (m, 2H), 0.60-0.44 (m, 2H).

Example 561: Synthesis of Compound F-4-b

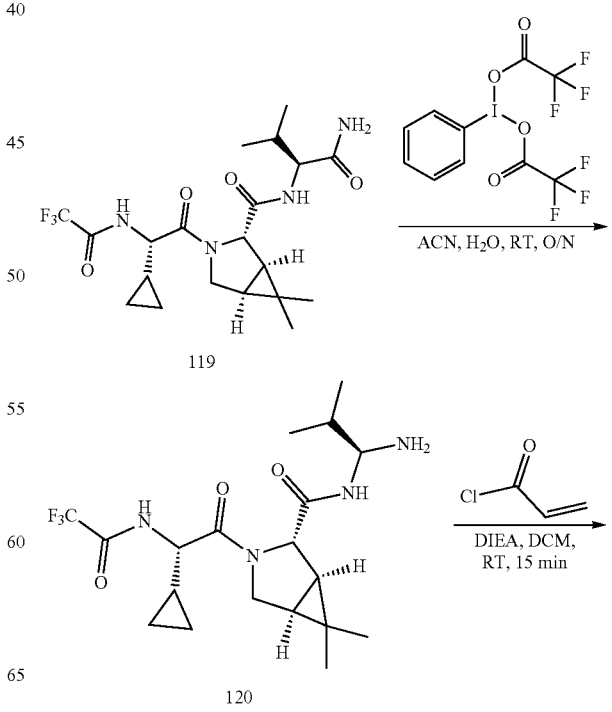

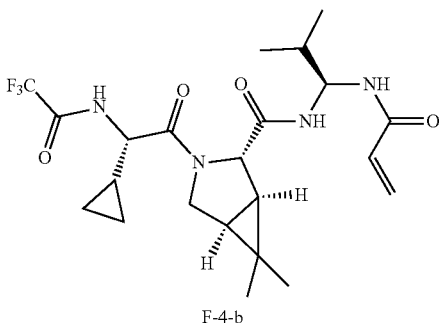

F-4-b

To a stirred solution of (1R,2S,5S)—N—((S)-1-amino-3-methyl-1-oxobutan-2-yl)-3-((S)-2-cyclopropyl-2-(2,2,2-trifluoroacetamido)acetyl)-6,6-dimethyl-3-azabicyclo[3.1.0]hexane-2-carboxamide 119 (80 mg, 0.18 mmol) in ACN (0.7 mL) and H₂O (0.7 mL) was added bis(trifluoroacetoxy)iodanebenzene (77 mg, 0.18 mmol). The reaction mixture was stirred at room temperature for 15 h in the darkness. After the completion of the reaction indicated by LCMS, the reaction mixture was directly purified by prep-HPLC to give title product 120 (55 mg, 0.13 mmol, 73.35%) as an off-white solid. LCMS=[M+H]⁺: 418.9.

To a stirred solution of (1R,2S,5S)—N-[(1S)-1-amino-2-methylpropyl]-3-[2-cyclopropyl-2-(trifluoroacetamido)acetyl]-1,5-dihydrogenio-6,6-dimethyl-3-azabicyclo[3.1.0]hexane-2-carboxamide 120 (55 mg, 0.13 mmol) and DIEA (0.02 mL, 0.13 mmol) in DCM (1.4 mL) was added slowly at 0° C. acryloyl chloride (0.01 mL, 0.13 mmol). The reaction mixture was stirred at room temperature for 15 min under N₂. After the completion of the reaction indicated by LCMS, the mixture was concentrated down under reduced pressure. The resulting residue was purified by prep-HPLC to give the title product F-4-b (4.7 mg, 7.57%) as an off-white solid. LCMS=[M+H]⁺: 473.3.

¹H NMR (400 MHz, CDCl₃) δ 7.22-7.14 (m, 1H), 6.44 (s, 1H), 6.27 (s, 1H), 6.07 (s, 1H), 5.67 (s, 1H), 5.02 (s, 1H), 4.35-4.30 (m, 1H), 3.91 (s, 1H), 3.67 (d, J=37.8 Hz, 1H), 2.17 (br s, 1H), 1.67 (s, 1H), 1.49-1.45 (m, 1H), 1.25 (br s, 1H), 1.06 (s, 3H), 0.93-0.90 (m, 9H), 0.58-0.50 (m, 4H).

Example S62: Synthesis of Compound F-4-b

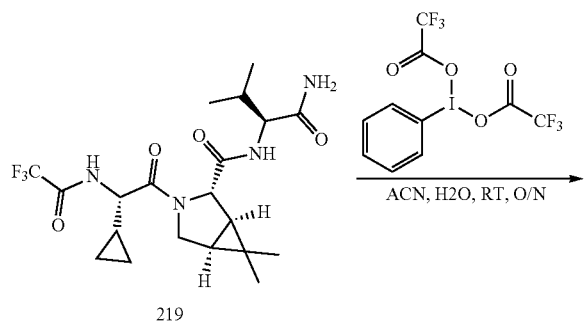

219

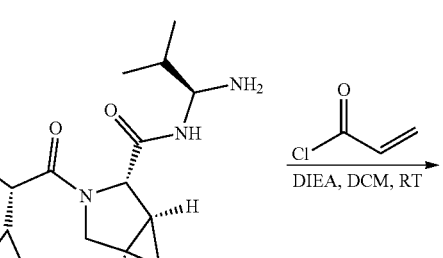

220

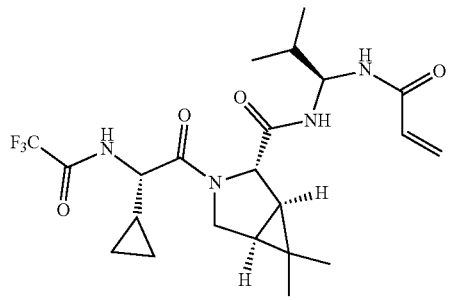

F-4-b

To a stirred solution of (1R,2S,5S)—N—((S)-1-amino-3-methyl-1-oxobutan-2-yl)-3-((S)-2-cyclopropyl-2-(2,2,2-trifluoroacetamido)acetyl)-6,6-dimethyl-3-azabicyclo[3.1.0]hexane-2-carboxamide (compound 219) (80 mg, 0.18 mmol) in ACN (0.7 mL) and H₂O (0.7 mL) was added phenyl-λ³-iodanediyl bis(2,2,2-trifluoroacetate) (77 mg, 0.18 mmol). The reaction mixture was stirred at room temperature for 15 h in the darkness. After completion of the reaction indicated by LCMS, the reaction mixture was directly purified by prep-HPLC to yield compound 220 (55 mg, 0.13 mmol, 73.35%) as an off-white solid. LCMS=[M+H]⁺: 418.9.

To a stirred solution of (1R,2S,5S)—N-[(1S)-1-amino-2-methylpropyl]-3-[2-cyclopropyl-2-(trifluoroacetamido)acetyl]-1,5-dihydrogenio-6,6-dimethyl-3-azabicyclo[3.1.0]hexane-2-carboxamide (compound 220) (55 mg, 0.13 mmol) and DIEA (0.02 mL, 0.13 mmol) in DCM (1.4 mL) at 0° C. acryloyl chloride (0.01 mL, 0.13 mmol) was added slowly. The reaction mixture was stirred at room temperature for 15 min under N₂. After completion of the reaction indicated by LCMS, the mixture was concentrated down under reduced pressure. The resulting residue was purified by prep-HPLC to yield compound F-4-b (4.7 mg, 7.57%) as an off-white solid. LCMS=[M+H]⁺: 473.3. ¹H NMR (400 MHz, CDCl₃) δ 7.22-7.14 (m, 1H), 6.44 (s, 1H), 6.27 (s, 1H), 6.07 (s, 1H), 5.67 (s, 1H), 5.02 (s, 1H), 4.35-4.30 (m, 1H), 3.91 (s, 1H), 3.67 (d, J=37.8 Hz, 1H), 2.17 (br s, 1H), 1.67 (s, 1H), 1.49-1.45 (m, 1H), 1.25 (br s, 1H), 1.06 (s, 3H), 0.93-0.90 (m, 9H), 0.58-0.50 (m, 4H).

Example S63: Synthesis of Compound F-4-c

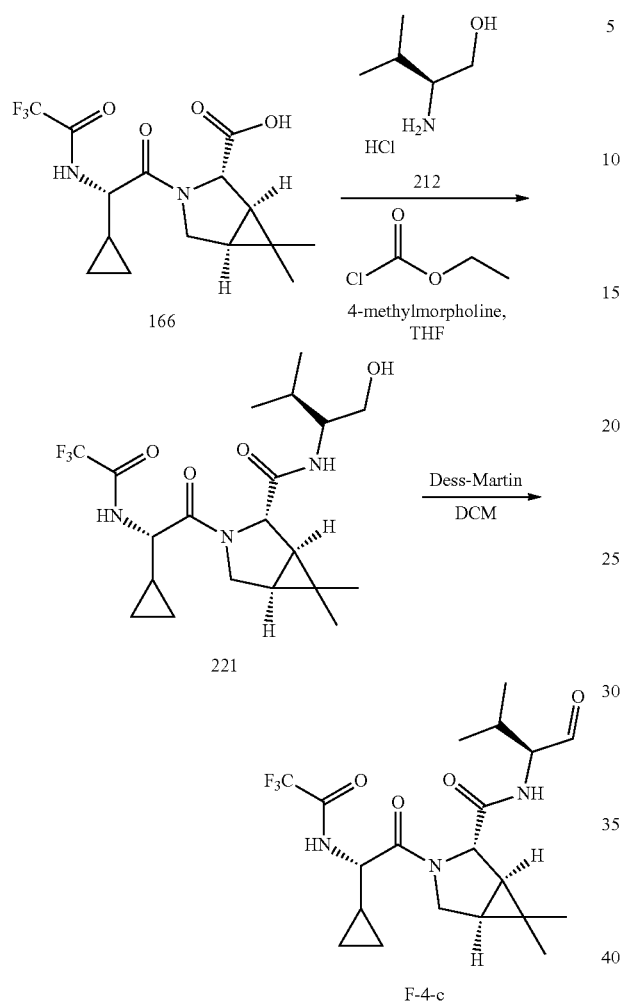

To a solution of (1R,2S,5S)-3-((S)-2-cyclopropyl-2-(2,2,2-trifluoroacetamido)acetyl)-6,6-dimethyl-3-azabicyclo[3.1.0]hexane-2-carboxylic acid (compound 166) (200 mg, 574.18 mmol) in THF (2 mL) at 0° C. 4-methylmorpholine (145.19 mg, 1.44 mmol) and ethyl chloroformate (124.62 mg, 1.15 mmol) were added. The mixture was stirred for 15 min and then (S)-2-amino-3-methylbutan-1-ol hydrochloride (compound 212) (120.25 mg, 861.27 umol) was added. The reaction mixture was stirred at 0° C. for 3 h under nitrogen atmosphere, then quenched with water (50 mL) and extracted with ethyl acetate (50 mL×3). The combined organic layers were washed with brine (20 mL), dried over anhydrous sodium sulfate and concentrated down under reduced pressure. The resulting residue was purified by silica gel flash column chromatography (Ethyl acetate:Petroleum ether from 0:1 to 1:5) to yield compound 221 (180.00 mg, 415.25 umol, 72.32%) as a colorless oil. LCMS=[M+H]$^+$: 434.0.

A solution of (1R,2S,5S)-3-((S)-2-cyclopropyl-2-(2,2,2-trifluoroacetamido)acetyl)-N—((S)-1-hydroxy-3-methylbutan-2-yl)-6,6-dimethyl-3-azabicyclo[3.1.0]hexane-2-carboxamide (compound 221) (150 mg, 0.35 mmol) and Dess-Martin periodinane (750 mg, 1.73 mmol) in DCM (10 mL) was stirred at room temperature for 1 h. After completion of the reaction indicated by LCMS, the reaction mixture was diluted with DCM, washed with sat. Na$_2$S$_2$O$_3$ (aq), sat. NaHCO$_3$ (aq), and brine. Organic layer was separated, dried over Na$_2$SO$_4$, and concentrated down under reduced pressure. The resulting residue was purified by prep-HPLC to yield compound F-4-c as a white solid (12 mg, 8% yield). LCMS=[M+H]$^+$: 432.3, purity 91%. $^1$H NMR (400 MHz, CDCl$_3$) δ 9.70-9.53 (m, 1H), 7.29-7.20 (m, 3H), 6.95-6.74 (m, 1H), 4.65-4.36 (m, 2H), 4.18 (t, J=7.7 Hz, 1H), 4.05-3.89 (m, 1H), 3.80-3.65 (m, 1H), 2.35-2.29 (m, 1H), 1.77-1.64 (m, 1H), 1.61-1.53 (m, 1H), 1.30-1.19 (m, 1H), 1.11-1.07 (m, 3H), 1.04-1.00 (m, 3H), 1.00-0.95 (m, 3H), 0.93 (d, J=4.7 Hz, 3H), 0.71-0.43 (m, 4H).

Example S64: Synthesis of Compound G-1-a

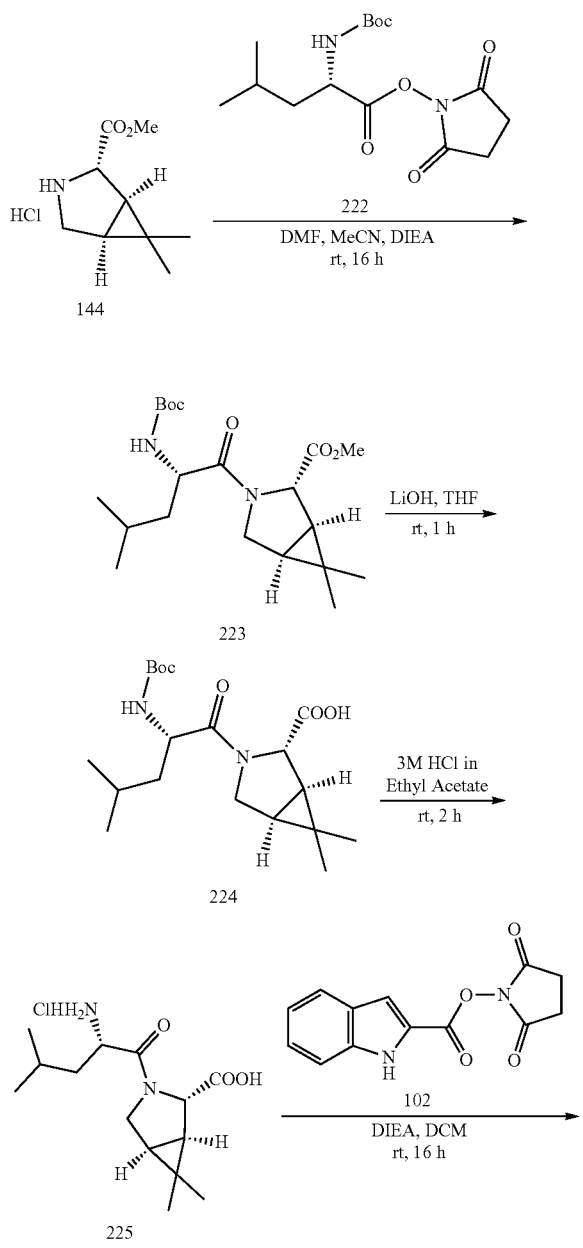

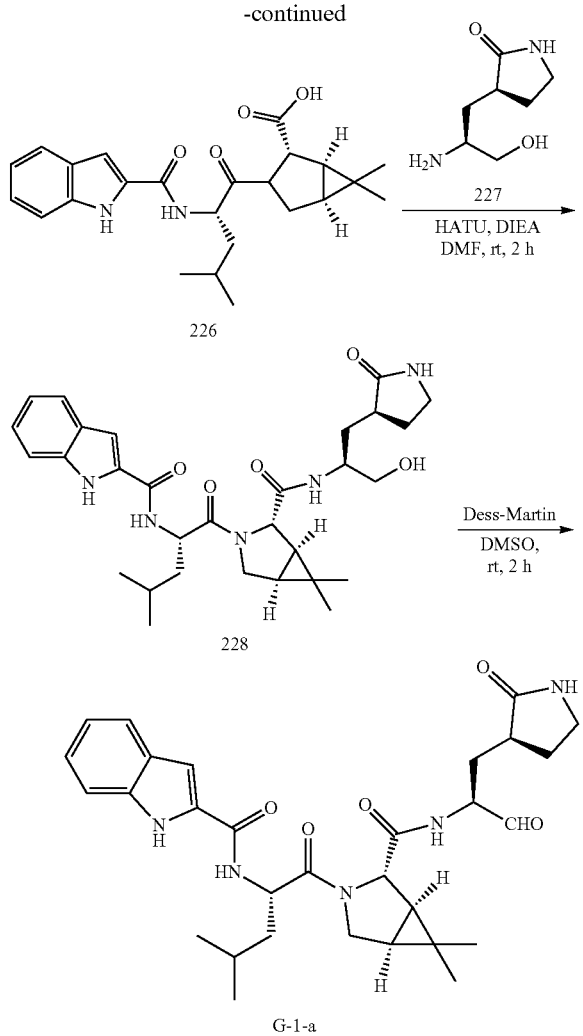

To a solution of methyl (1R,2S,5S)-1,5-dihydrogenio-6,6-dimethyl-3-azabicyclo[3.1.0]hexane-2-carboxylate hydrochloride (9.434 mL, 48.78 mmol) (compound 144) and 2,5-dioxopyrrolidin-1-yl (2S)-2-{[(tert-butoxy)carbonyl]amino}-4-methylpentanoate (compound 222) (17.62 g, 53.66 mmol) in ACN (180 mL) and DMF (20 mL) was added DIEA (24.186 mL, 146.34 mmol) at room temperature. The reaction mixture was stirred overnight and concentrated down under reduced pressure. The resulting residue was diluted with water (50 mL) and extracted with ethyl acetate (200 mL×3). The combined organic layers were washed with brine (80 mL×3), dried over anhydrous Na₂SO₄ and concentrated down under reduced pressure. The resulting residue was purified by column chromatography (C18, ACN/water (0.1% FA)=65/40 to 70/30) to yield compound 223 (11.5 g, 30.07 mmol, 61.83%) as a light-yellow solid. LCMS=[M+H]$^+$: 383.2. $^1$H NMR (400 MHz, CDCl₃) δ 5.02 (d, J=7.6 Hz, 1H), 4.42-4.29 (m, 2H), 3.87 (d, J=10.1 Hz, 1H), 3.80-3.72 (m, 1H), 3.70-3.61 (m, 3H), 1.71-1.61 (m, 1H), 1.52-1.41 (m, 2H), 1.40-1.37 (m, 2H), 1.33 (s, 9H), 0.99 (s, 3H), 0.92-0.86 (m, 9H).

To a solution of methyl (1R,2S,5S)-3-[(2S)-2-{[(tert-butoxy)carbonyl]amino}-4-methylpentanoyl]-1,5-dihydrogenio-6,6-dimethyl-3-azabicyclo[3.1.0]hexane-2-carboxylate (compound 223) (11.5 g, 30.07 mmol) in THF (70 mL) and H₂O (15 mL) was added LiOH (1.44 g, 60.13 mmol). The reaction mixture was stirred at room temperature for 1 h, and then concentrated down to remove THF. The remaining solution was adjusted to pH ~3-4 with 1M HCl, and then extracted with ethyl acetate (200 mL×3). The combined organic layers were washed with brine (80 mL×2), dried over anhydrous Na₂SO₄ and then concentrated down under reduced pressure to yield compound 224 (11 g, 29.85 mmol, 99.29%) as light-yellow solid. LCMS=[M+H]$^+$: 369.2. $^1$H NMR (400 MHz, DMSO-d₆) δ 12.57 (s, 1H), 7.03 (d, J=7.9 Hz, 1H), 4.20-4.06 (m, 2H), 3.86 (d, J=10.2 Hz, 1H), 3.75-3.64 (m, 1H), 1.69-1.47 (m, 2H), 1.41-1.36 (m, 2H), 1.34 (s, 9H), 1.09-0.78 (m, 13H).

To a solution of (1R,2S,5S)-3-[(2S)-2-{[(tert-butoxy)carbonyl]amino}-4-methylpentanoyl]-1,5-dihydrogenio-6,6-dimethyl-3-azabicyclo[3.1.0]hexane-2-carboxylic acid (compound 224) (11 g, 29.85 mmol) in DCM (5 mL) was added HCl (3M in ethyl acetate, 37.316 mL). The reaction mixture was stirred at room temperature for 2 h. The mixture was concentrated down under reduced pressure to yield compound 225 (9.1 g, yield 99%) as a white solid. LCMS=[M+H]$^+$: 269.2. $^1$H NMR (400 MHz, DMSO-d₆) δ 12.83 (s, 1H), 8.18 (br s, 3H), 4.18 (s, 1H), 4.07 (d, J=5.5 Hz, 1H), 3.80-3.63 (m, 2H), 1.64-1.41 (m, 4H), 1.14-0.78 (m, 13H).

To a solution of (1R,2S,5S)-3-(L-leucyl)-6,6-dimethyl-3-azabicyclo[3.1.0]hexane-2-carboxylic acid hydrochloride (compound 225) (9.1 g, 29.84 mmol) in EtOH (30 mL) and DCM (180 mL) was added DIEA (7.70 g, 59.67 mmol) and 2,5-dioxopyrrolidin-1-yl 1H-indole-2-carboxylate (compound 102) (8.48 g, 32.82 mmol). The reaction mixture was stirred at room temperature overnight, and then concentrated down to remove organic solvents. The remaining solution was diluted with water (50 mL) and extracted with ethyl acetate (200 mL×3). The combined organic layers were washed with brine (80 mL×2), dried over anhydrous Na₂SO₄ and concentrated down under reduced pressure. The resulting residue was purified by column chromatography (C18, ACN/water (0.1% FA)=65/35 to 73/27) to yield compound 226 (10.6 g, 25.76 mmol, 86.34%) as yellow solid. LCMS=[M+H]$^+$: 412.2. $^1$H NMR (400 MHz, DMSO) δ 12.66 (s, 1H), 11.52 (s, 1H), 8.60 (d, J=7.4 Hz, 1H), 7.60 (d, J=8.0 Hz, 1H), 7.41 (d, J=8.2 Hz, 1H), 7.26 (s, 1H), 7.17 (t, J=7.6 Hz, 1H), 7.02 (t, J=7.3 Hz, 1H), 4.70-4.60 (m, 1H), 4.14 (s, 1H), 3.90 (d, J=10.2 Hz, 1H), 3.84-3.72 (m, 1H), 1.81-1.62 (m, 2H), 1.60-1.52 (m, 1H), 1.52-1.43 (m, 1H), 1.10-0.79 (m, 13H).

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (500 mg, 1.22 mmol) and (S)-3-((S)-2-amino-3-hydroxypropyl)pyrrolidin-2-one (compound 227) (231.47 mg, 1.46 mmol) in DMF (6 mL) were added HATU (693.85 mg, 1.82 mmol) and DIEA (0.804 mL, 4.87 mmol). The reaction mixture was stirred at room temperature for 16 h. The mixture was diluted with water (20 mL) and extracted with ethyl acetate (30 mL×3). The combined organic layers were washed with brine (20 mL×3), dried over with Na₂SO₄, and concentrated down under reduced pressure to afford the crude product, which was further purified by C18 column chromatography (ACN/water (0.1% FA)) to yield compound 228 (500 mg, 0.91 mmol, 90.69%). LCMS=[M+H]$^+$: 552.4.

To a solution of N-[(2S)-1-[(1R,2S,5S)-1,5-dihydrogenio-2-{[(2S)-1-hydroxy-3-(2-oxopyrrolidin-3-yl)propan-2-yl]carbamoyl}-6,6-dimethyl-3-azabicyclo[3.1.0]hexan-3-yl]-4-methyl-1-oxopentan-2-yl]-1H-indole-2-carboxamide (compound 228) (500 mg, 0.91 mmol) in DMSO (10 mL) at 0° C. was added Dess-Martin periodinane (1.15 g, 2.72 mmol). The reaction mixture was stirred at room temperature for 2 h, and then diluted with water (30 mL) and extracted with ethyl acetate (40 mL×3). The combined organic layers were washed with brine (40 mL×3), dried over Na$_2$SO$_4$ and concentrated down under reduced pressure to afford the 1$^{st}$ crude product, which was purified by C18 column chromatography (ACN/water (0.1% FA)) to afford a 2$^{nd}$ crude product. The 2$^{nd}$ crude product was further purified by prep-HPLC (ACN/water (0.1% NH$_4$OH)) to yield compound G-1-a (26.69 mg, 0.05 mmol, 5.09%). LCMS=[M+H]$^+$: 550.4. $^1$H NMR (400 MHz, DMSO-d$_6$) δ 11.54 (s, 1H), 8.58 (dd, J=30.3, 7.5 Hz, 1H), 7.67 (d, J=9.5 Hz, 1H), 7.63-7.55 (m, 1H), 7.45 (s, 1H), 7.40 (d, J=8.4 Hz, 1H), 7.26 (s, 1H), 7.18 (dd, J=17.4, 9.5 Hz, 1H), 7.02 (t, J=7.4 Hz, 1H), 5.70 (dd, J=9.5, 6.2 Hz, 1H), 4.69-4.61 (m, 1H), 4.25-4.20 (m, 2H), 3.90 (d, J=9.9 Hz, 1H), 3.85-3.65 (m, 1H), 3.22-3.00 (m, 2H), 2.39-2.24 (m, 1H), 2.23-2.10 (m, 1H), 1.95-1.69 (m, 2H), 1.68-1.55 (m, 2H), 1.55-1.47 (m, 2H), 1.42-1.36 (m, 1H), 1.36-1.29 (m, 1H), 1.07-0.99 (m, 3H), 0.96-0.87 (m, 9H).

Example S65: Synthesis of Compounds G-1-b and G-1-c

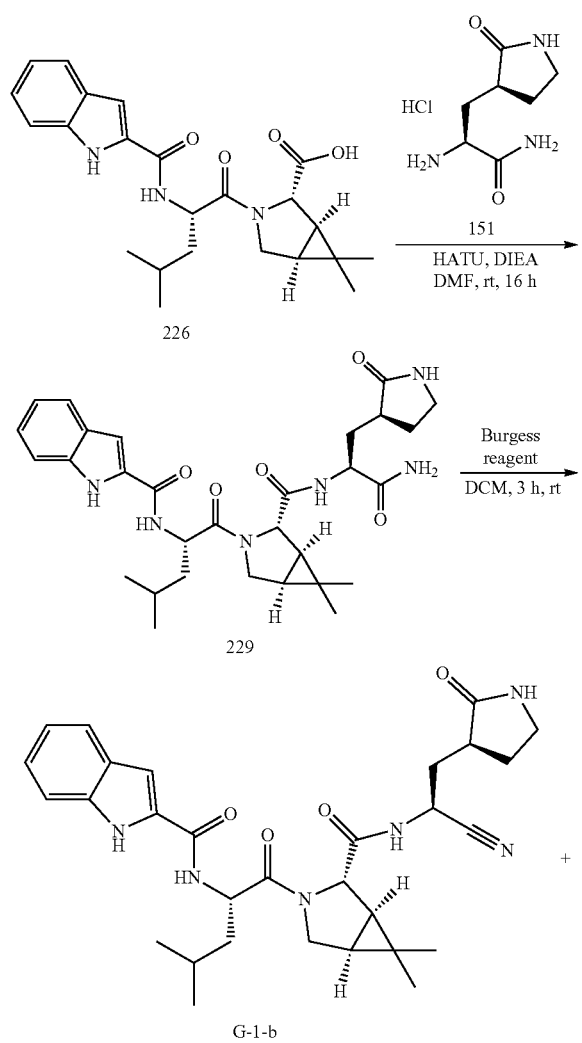

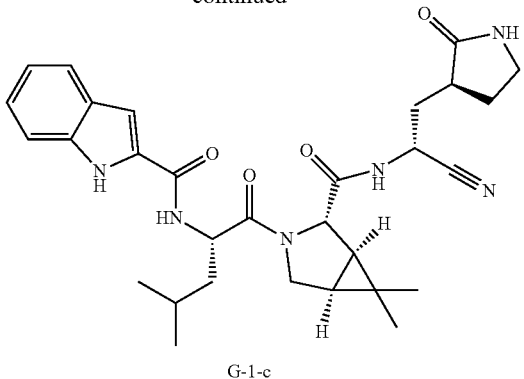

G-1-c

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (1 g, 2.43 mmol) and (2S)-2-amino-3-(2-oxopyrrolidin-3-yl)propanamide hydrochloride (compound 151) (0.76 g, 3.65 mmol) in DMF (10 mL) were added DIEA (1.606 mL, 9.72 mmol) and HATU (1.39 g, 3.65 mmol). The reaction mixture was stirred at room temperature overnight. The mixture was diluted with water (30 mL) and extracted with EtOAc (50 mL×3). The combined organic layers were washed with brine (20 mL×3), dried with Na$_2$SO$_4$ and concentrated down under reduced pressure to afford the crude product, which was purified by C18 column chromatography eluted with (ACN/water (0.1% FA)) to yield compound 229 (1.25 g, 2.21 mmol, 91.09%) as a white solid. LCMS=[M+H]$^+$: 565.4. $^1$H NMR (400 MHz, DMSO-d$_6$) δ 11.54 (s, 1H), 8.63 (d, J=7.5 Hz, 1H), 8.24 (d, J=8.3 Hz, 1H), 7.67-7.55 (m, 2H), 7.41 (d, J=8.2 Hz, 1H), 7.26 (d, J=1.4 Hz, 1H), 7.18 (dd, J=15.6, 8.5 Hz, 2H), 7.03 (dd, J=13.9, 6.7 Hz, 2H), 4.70-4.58 (m, 1H), 4.25-4.19 (m, 2H), 3.91 (s, 2H), 3.20-3.02 (m, 2H), 2.41-2.30 (m, 1H), 2.20-2.09 (m, 1H), 1.98-1.89 (m, 1H), 1.80-1.70 (m, 1H), 1.70-1.58 (m, 2H), 1.58-1.46 (m, 3H), 1.43-1.35 (m, 1H), 1.06-1.00 (m, 3H), 0.96-0.88 (m, 9H).

To a solution of N-[(2S)-1-[(1R,2S,5S)-2-{[(1S)-1-carbamoyl-2-[(3S)-2-oxopyrrolidin-3-yl]ethyl]carbamoyl}-1,5-dihydrogenio-6,6-dimethyl-3-azabicyclo[3.1.0]hexan-3-yl]-4-methyl-1-oxopentan-2-yl]-1H-indole-2-carboxamide (compound 229) (260 mg, 0.46 mmol) in DCM (8 mL) was added Burgess reagent (238 mg, 1.15 mmol). The reaction mixture was stirred at room temperature for 3 h, and then concentrated down under reduced pressure to afford a crude product, which was purified by prep-HPLC (ACN/water (0.1% FA)) to afford two products (two isomers). The first fraction gave the G-1-b product (96.35 mg, 0.18 mmol, 38.28%) and the 2$^{nd}$ fraction gave the G-1-c product (21.86 mg, 0.04 mmol, 8.68%), both were white solid. LCMS=[M+H]$^+$: 547.4.

G-1-b: $^1$H NMR (400 MHz, DMSO-d$_6$) δ 11.54 (s, 1H), 8.90 (d, J=8.1 Hz, 1H), 8.60 (d, J=7.5 Hz, 1H), 7.69 (s, 1H), 7.60 (d, J=8.0 Hz, 1H), 7.41 (d, J=8.2 Hz, 1H), 7.25 (d, J=1.4 Hz, 1H), 7.17 (t, J=7.6 Hz, 1H), 7.02 (t, J=7.4 Hz, 1H), 4.99-4.89 (m, 1H), 4.68-4.59 (m, 1H), 4.16 (s, 1H), 3.94-3.81 (m, 2H), 3.20-3.05 (m, 2H), 2.45-2.34 (m, 1H), 2.19-2.06 (m, 2H), 1.80-1.56 (m, 5H), 1.49 (ddd, J=13.4, 8.8, 4.5 Hz, 1H), 1.31 (d, J=7.6 Hz, 1H), 1.04 (s, 3H), 0.97-0.88 (m, 9H).

G-1-c: $^1$H NMR (400 MHz, DMSO-d$_6$) δ 11.54 (s, 1H), 8.57 (d, J=7.8 Hz, 1H), 8.45 (s, 1H), 7.94 (t, J=5.4 Hz, 1H), 7.60 (d, J=8.0 Hz, 1H), 7.41 (d, J=8.2 Hz, 1H), 7.25 (s, 1H), 7.17 (t, J=7.7 Hz, 1H), 7.02 (t, J=7.4 Hz, 1H), 4.71-4.62 (m, 1H), 4.58 (t, J=7.3 Hz, 1H), 4.13 (s, 1H), 3.85 (s, 2H), 3.12-3.03 (m, 1H), 2.68 (dt, J=12.4, 8.3 Hz, 1H), 2.37-2.24 (m, 1H), 2.00-1.78 (m, 2H), 1.77-1.60 (m, 2H), 1.49 (dd, J=13.5, 9.3 Hz, 3H), 1.32-1.20 (m, 2H), 1.01 (s, 3H), 0.96-0.87 (m, 9H).

Example S66: Synthesis of Compound G-1-d

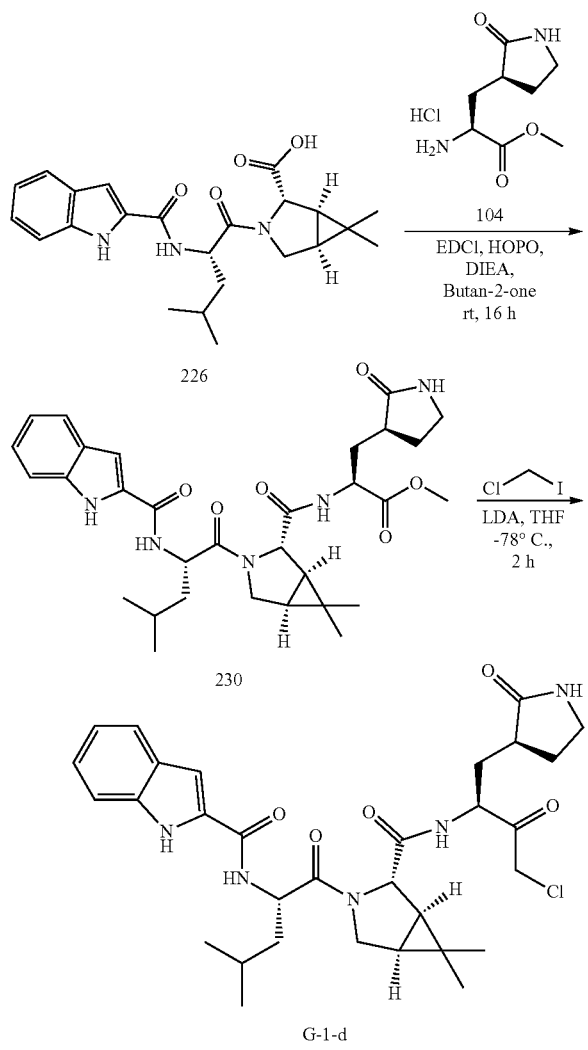

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (300 mg, 0.73 mmol), methyl (2S)-2-amino-3-(2-oxopyrrolidin-3-yl)propanoate hydrochloride (compound 104) (243.09 mg, 1.09 mmol) and HOPO (726 mg, 1.09 mmol) in butan-2-one (6 mL) was added DIEA (0.361 mL, 2.19 mmol). The reaction mixture was stirred at room temperature for 16 h. The mixture was diluted with water (20 mL) and extracted with ethyl acetate (20 mL×3). The combined organic layers were washed with brine (20 mL×3), dried over with $Na_2SO_4$, and concentrated under reduced pressure to afford the crude product, which was purified by C18 column chromatography (ACN/water (0.1% FA)) to yield compound 230 (220 mg, 0.38 mmol, 52.06%) as a white solid. LCMS=[M+H]$^+$: 580.1. $^1$H NMR (400 MHz, DMSO-$d_6$) δ 11.54 (s, 1H), 8.64-8.50 (m, 2H), 7.67-7.55 (m, 2H), 7.40 (d, J=8.0 Hz, 1H), 7.26 (s, 1H), 7.17 (t, J=7.4 Hz, 1H), 7.02 (t, J=7.2 Hz, 1H), 4.68-4.57 (m, 1H), 4.42-4.31 (m, 1H), 4.25 (s, 1H), 3.92-3.87 (m, 1H), 3.86-3.78 (m, 1H), 3.64 (s, 3H), 3.20-3.06 (m, 2H), 2.42-2.32 (m, 1H), 2.17-1.93 (m, 2H), 1.79-1.68 (m, 1H), 1.69-1.52 (m, 4H), 1.30 (d, J=7.3 Hz, 1H), 1.24 (s, 1H), 1.04 (s, 3H), 0.99-0.86 (m, 9H).

To a solution of methyl (2S)-2-{[(1R,2S,5S)-1,5-dihydrogenio-3-[(2S)-2-[(1H-indol-2-yl)formamido]-4-methylpentanoyl]-6,6-dimethyl-3-azabicyclo[3.1.0]hexan-2-yl]formamido}-3-[(3S)-2-oxopyrrolidin-3-yl]propanoate (compound 230) (170 mg, 0.29 mmol) and chloroiodomethane (0.214 mL, 2.93 mmol) in THF (6 mL) at −78° C. under $N_2$ was added LDA (2M in THF; 3.7 mL, 7.33 mmol). The reaction mixture was stirred at room temperature for 2 h. The mixture was quenched with sat. $NH_4Cl$ (aq) and extracted with ethyl acetate (30 mL×3). The combined organic layers were washed with brine (20 mL×3), dried over anhydrous $Na_2SO_4$, and concentrated down under reduced pressure to afford the crude product, which was purified by prep-HPLC (ACN/water (0.1% $NH_4OH$)) to yield compound G-1-d (25.80 mg, 0.04 mmol, 14.71%) as a white solid. LCMS=[M+H]$^+$: 598.4. $^1$H NMR (400 MHz, DMSO-$d_6$) δ 11.55 (s, 1H), 8.69 (d, J=7.6 Hz, 1H), 8.64 (d, J=7.5 Hz, 1H), 7.65 (s, 1H), 7.60 (d, J=8.0 Hz, 1H), 7.41 (d, J=8.3 Hz, 1H), 7.26 (s, 1H), 7.17 (t, J=7.5 Hz, 1H), 7.02 (t, J=7.5 Hz, 1H), 4.70-4.60 (m, 1H), 4.57 (d, J=17.3 Hz, 1H), 4.44-4.34 (m, 1H), 4.20 (s, 1H), 3.87 (s, 2H), 3.30-3.26 (m, 1H), 3.20-3.07 (m, 2H), 2.36-2.25 (m, 1H), 2.18-2.07 (m, 1H), 2.04-1.91 (m, 1H), 1.78-1.70 (m, 1H), 1.64-1.60 (m, 2H), 1.60-1.56 (m, 2H), 1.54-1.47 (m, 1H), 1.39-1.33 (m, 1H), 1.05 (d, J=13.2 Hz, 3H), 0.96-0.88 (m, 9H).

Example S67: Synthesis of Compound G-1-e

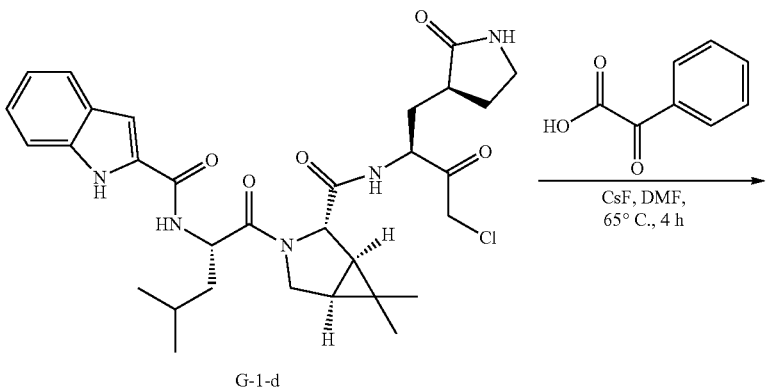

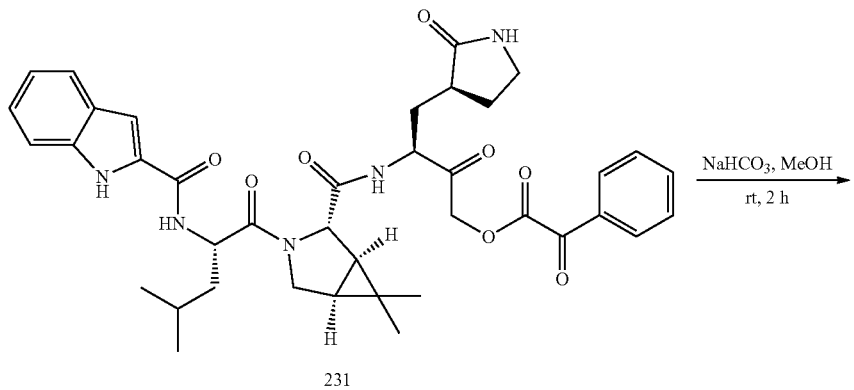

231

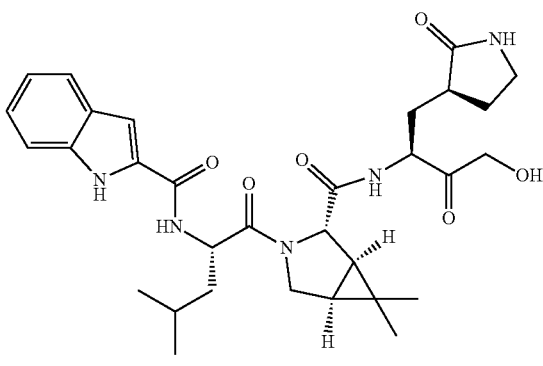

G-1-e

To a solution of N-[(2S)-1-[(1R,2S,5S)-2-{[(2S)-4-chloro-3-oxo-1-[(3S)-2-oxopyrrolidin-3-yl]butan-2-yl]carbamoyl}-1,5-dihydrogenio-6,6-dimethyl-3-azabicyclo[3.1.0]hexan-3-yl]-4-methyl-1-oxopentan-2-yl]-1H-indole-2-carboxamide (compound G-1-d) (450 mg, 0.75 mmol) and 2-oxo-2-phenylacetic acid (0.106 mL, 0.98 mmol) in DMF (20 mL) was added CsF (261.28 mg, 1.73 mmol). The reaction mixture was stirred at 65° C. for 4 h. The mixture was diluted with water (30 mL) and extracted with ethyl acetate (50 mL×3). The combined organic layers were washed with brine (40 mL×3), dried over anhydrous $Na_2SO_4$, and concentrated down under reduced pressure. The resulting residue was purified by column chromatography (C18, ACN/water (0.1% FA)=60/40 to 70/30) to yield compound 231 (340 mg, 0.48 mmol, 63.49%) as white solid. LCMS=[M+H]$^+$: 712.4. $^1$H NMR (400 MHz, DMSO-d$_6$) δ 11.52 (sz, 1H), 8.74 (d, J=7.9 Hz, 1H), 8.63 (d, J=7.5 Hz, 1H), 8.16-8.05 (m, 2H), 7.83 (t, J=7.4 Hz, 1H), 7.74-7.55 (m, 4H), 7.41 (d, J=8.2 Hz, 1H), 7.27 (d, J=1.3 Hz, 1H), 7.17 (t, J=7.7 Hz, 1H), 7.02 (t, J=7.7 Hz, 1H), 5.39-5.19 (m, 2H), 4.72-4.59 (m, 1H), 4.54-4.41 (m, 1H), 4.24 (s, 1H), 3.91 (s, 2H), 3.23-3.05 (m, 2H), 2.43-2.28 (m, 1H), 2.08-2.00 (m, 2H), 1.81-1.47 (m, 6H), 1.13-0.72 (m, 13H).

To a solution of (3S)-3-{[(1R,2S,5S)-1,5-dihydrogenio-3-[(2S)-2-[(1H-indol-2-yl)formamido]-4-methylpentanoyl]-6,6-dimethyl-3-azabicyclo[3.1.0]hexan-2-yl]formamido}-2-oxo-4-[(3S)-2-oxopyrrolidin-3-yl]butyl 2-oxo-2-phenylacetate (compound 231) (310 mg, 0.44 mmol) in MeOH (8 mL) was added NaHCO$_3$ (7.32 mg, 0.09 mmol).

The reaction mixture was stirred at room temperature for 2 h under $N_2$. The mixture was diluted with water (30 mL) and extracted with ethyl acetate (50 mL×3). The combined organic layers were concentrated down under reduced pressure. The resulting residue was purified by prep-HPLC to yield compound G-1-e (100.10 mg, 0.17 mmol, 39.65%) as a white solid. LCMS=[M+H]$^+$: 580.3. $^1$H NMR (400 MHz, DMSO-d$_6$) δ 11.54 (s, 1H), 8.61 (d, J=8.0 Hz, 1H), 8.48 (d, J=8.0 Hz, 1H), 7.59-7.61 (m, 2H), 7.41 (d, J=8.0 Hz, 1H), 7.25-7.27 (m, 1H), 7.15-7.20 (m, 1H), 7.00-7.04 (m, 1H), 5.04 (t, J=4.0 Hz, 1H), 4.64-4.67 (m, 1H), 4.41-4.46 (m, 1H), 4.14-4.31 (m, 3H), 3.83-3.91 (m, 2H), 3.07-3.19 (m, 2H), 2.32-2.37 (m, 1H), 2.09-2.15 (m, 1H), 1.86-1.93 (m, 1H), 1.51-1.74 (m, 6H), 0.90-1.07 (m, 13H).

Example S68: Synthesis of Compound G-2-a

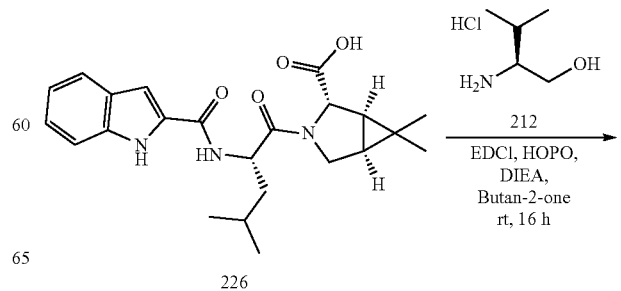

226

1H), 4.70-4.60 (m, 1H), 4.38 (s, 1H), 4.13-4.05 (m, 1H), 3.88-3.76 (m, 2H), 2.23-2.15 (m, 1H), 1.78-1.61 (m, 2H), 1.57-1.52 (m, 1H), 1.48-1.33 (m, 2H), 1.08-0.76 (m, 18H).

Example S69: Synthesis of Compound G-2-b

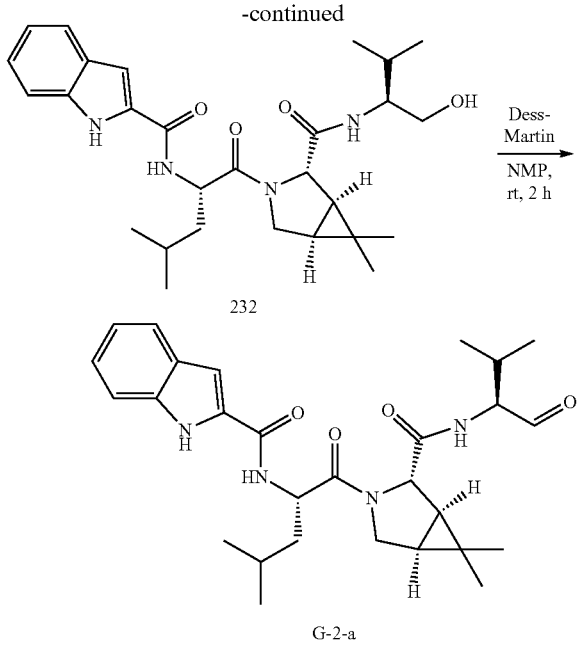

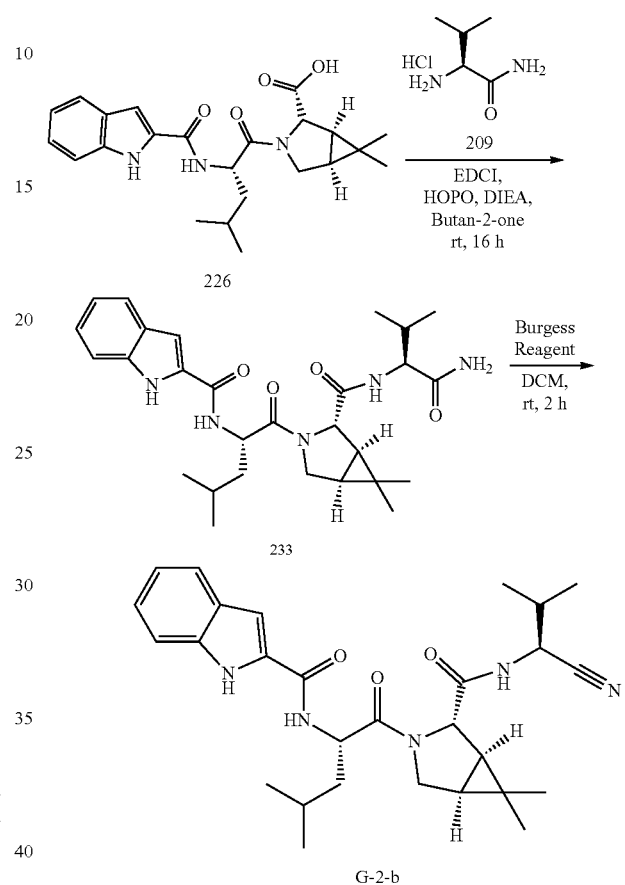

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (250 mg, 0.61 mmol), (2S)-2-amino-3-methylbutan-1-ol (compound 212) (0.082 mL, 0.73 mmol), EDCI (174.70 mg, 0.91 mmol) and HOPO (101.25 mg, 0.91 mmol) in butan-2-one (10 mL) was added DIEA (0.301 mL, 1.82 mmol) at room temperature. The reaction mixture was stirred for 16 h at room temperature. The mixture was diluted with water (30 mL) and extracted with ethyl acetate (40 mL×3). The combined organic layers were washed with brine (30 mL×3), dried over Na$_2$SO$_4$, and concentrated down under reduced pressure to afford a crude product, which was purified by C18 column chromatography (ACN/water (0.1% FA)) to yield compound 232 (240 mg, 0.48 mmol, 79.54%) as a white solid. LCMS=[M+H]$^+$: 497.4. $^1$H NMR (400 MHz, DMSO-d$_6$) δ 11.62 (s, 1H), 8.60 (d, J=7.7 Hz, 1H), 7.60 (d, J=8.5 Hz, 2H), 7.41 (d, J=8.1 Hz, 1H), 7.25 (s, 1H), 7.17 (t, J=7.5 Hz, 1H), 7.02 (t, J=7.4 Hz, 1H), 4.57-4.49 (m, 1H), 4.27 (s, 1H), 3.90-3.74 (m, 1H), 3.59-3.49 (m, 1H), 3.40-3.36 (m, 2H), 1.82-1.64 (m, 3H), 1.56-1.39 (m, 3H), 1.06-0.77 (m, 18H).

To a solution of N-[(2S)-1-[(1R,2S,5S)-1,5-dihydrogenio-2-{[(2S)-1-hydroxy-3-methylbutan-2-yl]carbamoyl}-6,6-dimethyl-3-azabicyclo[3.1.0]hexan-3-yl]-4-methyl-1-oxopentan-2-yl]-1H-indole-2-carboxamide (compound 232) (240 mg, 0.48 mmol) in NMP (8 mL) at 0° C. was added Dess-Martin periodinane (407 mg, 0.96 mmol). The mixture was stirred at room temperature for 2 h. The mixture was diluted with water (30 mL) and extracted with ethyl acetate (40 mL×3). The combined organic layers were washed with brine (30 mL×3), dried with anhydrous Na$_2$SO$_4$, and concentrated down under reduced pressure to afford a crude product, which was purified by C18 column chromatography (ACN/water (0.1% FA)) to yield compound G-2-a (75 mg, 0.15 mmol, 31.38%) as a white solid. LCMS=[M+H]$^+$: 495.3. $^1$H NMR (400 MHz, DMSO-d$_6$) δ 11.56 (s, 1H), 9.49 (d, J=0.5 Hz, 1H), 8.56 (t, J=8.1 Hz, 1H), 8.31 (d, J=7.8 Hz, 1H), 7.60 (d, J=8.0 Hz, 1H), 7.41 (d, J=8.3 Hz, 1H), 7.26 (d, J=1.3 Hz, 1H), 7.16 (d, J=8.0 Hz, 1H), 7.02 (t, J=7.5 Hz, To a mixture of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (250 mg, 0.61 mmol), (S)-2-amino-3-methylbutanamide hydrochloride (compound 209) (24.02 mg, 0.16 mmol), EDCI (174.70 mg, 0.91 mmol) and HOPO (101.25 mg, 0.91 mmol) in DMF (10 mL) was added DIEA (0.301 mL, 1.82 mmol). The mixture was stirred at room temperature overnight. The mixture was diluted with water (30 mL) and extracted with ethyl acetate (40 mL×3). The combined organic layers were washed with brine (40 mL×3), dried with Na$_2$SO$_4$, and concentrated down under reduced pressure to afford a crude product which was purified by C18 column chromatography eluted with (ACN/water (0.1% FA)) to yield compound 233 (220 mg, 0.43 mmol, 71.05%). LCMS=[M+H]$^+$: 510.4. $^1$H NMR (400 MHz, DMSO-d$_6$) δ 11.53 (d, J=11.8 Hz, 1H), 8.56 (d, J=7.6 Hz, 1H), 7.83 (d, J=8.9 Hz, 1H), 7.60 (d, J=8.0 Hz, 1H), 7.41 (d, J=8.2 Hz, 1H), 7.33 (s, 1H), 7.25 (s, 1H), 7.17 (t, J=7.5 Hz, 1H), 7.05-6.98 (m, 2H), 4.70-4.61 (m, 1H), 4.37 (s, 1H), 4.12-4.09 (m, 1H), 3.88-3.84 (m, 1H), 3.82-3.77 (m, 1H), 2.04-1.91 (m, 1H), 1.78-1.63 (m, 2H), 1.55-1.44 (m, 2H), 1.38-1.32 (m, 1H), 1.03 (s, 3H), 0.96-0.90 (m, 9H), 0.88-0.82 (m, 6H).

To a solution of N-[(2S)-1-[(1R,2S,5S)-2-{[(1S)-1-carbamoyl-2-methylpropyl]carbamoyl}-1,5-dihydrogenio-6,6-dimethyl-3-azabicyclo[3.1.0]hexan-3-yl]-4-methyl-1-oxopentan-2-yl]-1H-indole-2-carboxamide (compound 233) (200 mg, 0.39 mmol) in DCM (10 mL) was added Burgess reagent (233.79 mg, 0.98 mmol). The reaction mixture was stirred at room temperature for 2 h. The mixture was concentrated down under reduced pressure to afford a crude product, which was purified by C18 column chromatography (ACN/water (0.1% FA)) to yield compound G-2-b (41 mg, 0.08 mmol, 21.25%). LCMS=[M+H]$^+$: 549.4, HPLC: 96%. $^1$H NMR (400 MHz, DMSO-d$_6$) δ 11.56 (s, 1H), 8.83 (d, J=8.2 Hz, 1H), 8.57 (d, J=7.6 Hz, 1H), 7.60 (d, J=8.0 Hz, 1H), 7.41 (d, J=8.2 Hz, 1H), 7.25 (s, 1H), 7.17 (t, J=7.5 Hz, 1H), 7.02 (t, J=7.4 Hz, 1H), 4.68-4.59 (m, 2H), 4.26 (s, 1H), 3.89-3.80 (m, 2H), 1.99 (dq, J=13.8, 6.9 Hz, 1H), 1.78-1.69 (m, 1H), 1.69-1.62 (m, 1H), 1.61-1.56 (m, 1H), 1.50-1.41 (m, 1H), 1.29 (d, J=7.5 Hz, 1H), 1.06-1.03 (m, 3H), 1.03-0.99 (m, 3H), 0.98-0.90 (m, 12H).

Example S70: Synthesis of Compound G-2-c

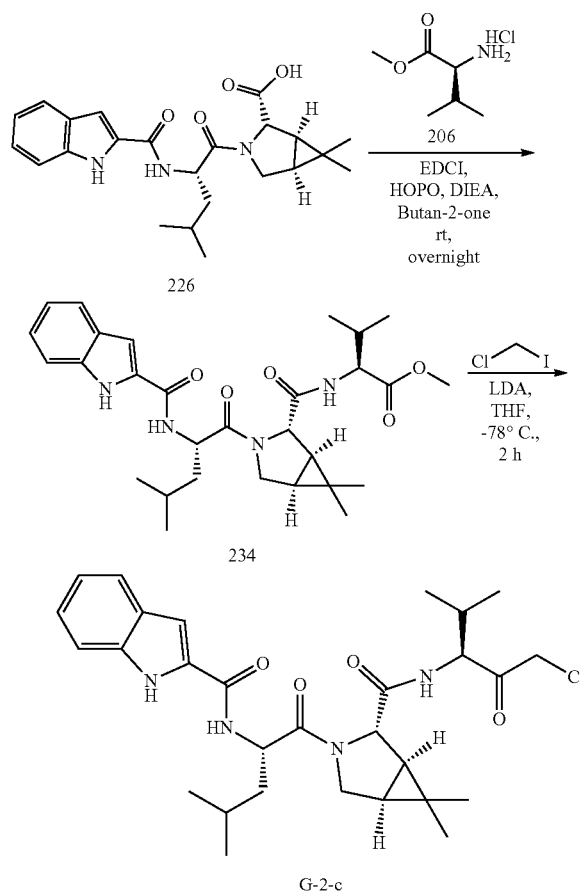

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (800 mg, 1.94 mmol) and methyl (2S)-2-amino-3-methylbutanoate hydrochloride (compound 206) (0.436 mL, 2.53 mmol) in butan-2-one (35 mL) was added 2-Pyridinol-1-Oxide (0.292 mL, 2.92 mmol), DIEA (0.321 mL, 1.94 mmol) and EDCI (931.71 mg, 4.86 mmol) at 0° C. The reaction mixture was stirred overnight at room temperature. The mixture was diluted with water (50 mL) and extracted with ethyl acetate (60 mL×3). The combined organic layers were washed with brine (40 mL×2), dried over anhydrous Na$_2$SO$_4$, and concentrated under reduced pressure. The resulting residue was purified by column chromatography (C18, ACN/water (0.1% FA)=65/35 to 70/30) to yield compound 234 (630 mg, 1.20 mmol, 61.77%) as a light-yellow solid. LCMS=[M+H]$^+$: 525.4. $^1$H NMR (400 MHz, DMSO-d$_6$) δ 11.55 (s, 1H), 8.55 (d, J=7.7 Hz, 1H), 8.32 (d, J=8.2 Hz, 1H), 7.60 (d, J=8.0 Hz, 1H), 7.40 (d, J=8.2 Hz, 1H), 7.25 (d, J=1.4 Hz, 1H), 7.17 (t, J=7.2 Hz, 1H), 7.02 (t, J=7.4 Hz, 1H), 4.71-4.57 (m, 1H), 4.39 (s, 1H), 4.18 (dd, J=8.1, 6.2 Hz, 1H), 3.88-3.82 (m, 1H), 3.82-3.74 (m, 1H), 3.70 (s, 3H), 2.11-1.96 (m, 1H), 1.80-1.59 (m, 2H), 1.57-1.48 (m, 1H), 1.43-1.40 (m, 1H), 1.30 (d, J=7.6 Hz, 1H), 1.12-0.70 (m, 18H).

To a solution of methyl (2S)-2-{[(1R,2S,5S)-1,5-dihydrogenio-3-[(2S)-2-[(1H-indol-2-yl)formamido]-4-methylpentanoyl]-6,6-dimethyl-3-azabicyclo[3.1.0]hexan-2-yl]formamido}-3-methylbutanoate (compound 234) (530 mg, 1.01 mmol) in THF (20 mL) at −78° C. under N$_2$ was added chloroiodomethane (0.736 mL, 10.10 mmol) and LDA (2M in THF; 12.627 mL). The reaction mixture was stirred at −78° C. for 2 h, and then allowed to warm up to room temperature. The reaction was diluted with sat. NH$_4$Cl (30 mL) and extracted with ethyl acetate (50 mL×3). The combined organic layers were washed with brine (50 mL×3), dried over anhydrous Na$_2$SO$_4$, and concentrated down under reduced pressure. The resulting residue was purified by prep-HPLC to yield compound G-2-c (65.29 mg, 0.12 mmol, 11.90%) as white solid. LCMS=[M+H]$^+$: 543.3. $^1$H NMR (400 MHz, DMSO-d$_6$) δ 11.53 (d, J=18.6 Hz, 1H), 8.58 (d, J=7.7 Hz, 1H), 8.39 (d, J=8.0 Hz, 1H), 7.60 (d, J=8.0 Hz, 1H), 7.40 (d, J=8.2 Hz, 1H), 7.25 (s, 1H), 7.17 (t, J=7.6 Hz, 1H), 7.02 (t, J=7.4 Hz, 1H), 4.71-4.51 (m, 3H), 4.40-4.26 (m, 2H), 3.92-3.71 (m, 2H), 2.24-2.11 (m, 1H), 1.78-1.61 (m, 2H), 1.59-1.52 (m, 1H), 1.51-1.39 (m, 1H), 1.34 (d, J=7.6 Hz, 1H), 1.13-0.72 (m, 18H).

Example S71: Synthesis of Compound G-3-a

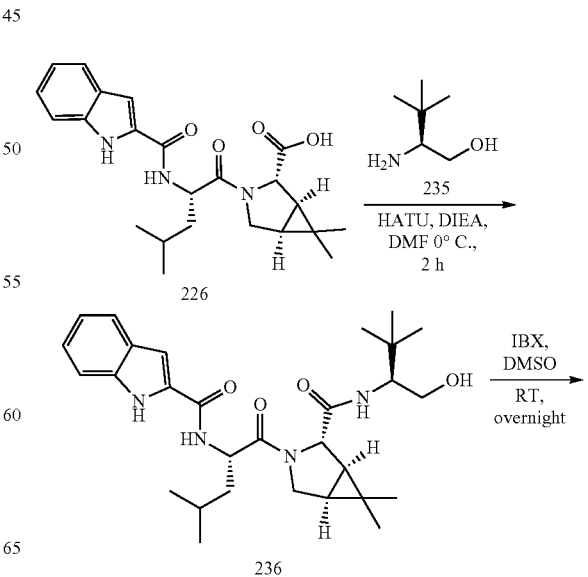

Example S72: Synthesis of Compound G-3-b

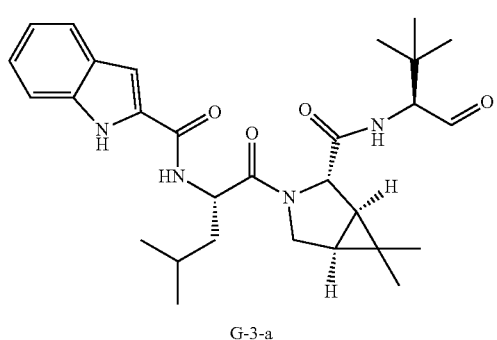

G-3-a

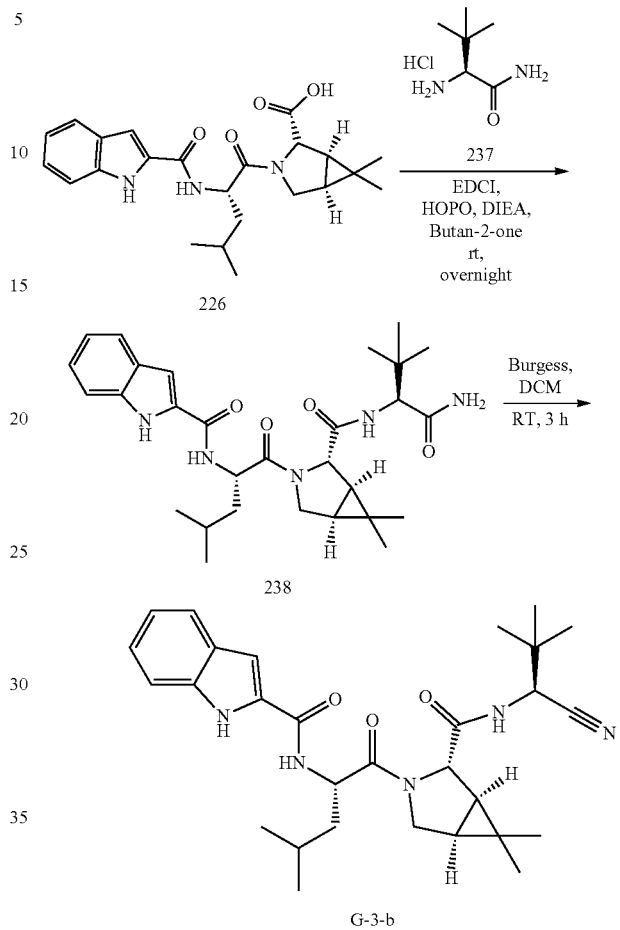

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (700 mg, 1.7 mmol), (S)-2-amino-3,3-dimethylbutan-1-ol (compound 235) (234 mg, 2.0 mmol) in DMF at 0° C. (15 mL) was added DIEA (438 mg, 3.4 mmol) and HATU (762 mg, 2.0 mmol). The reaction mixture was stirred at room temperature for 2 h. The mixture was diluted with water (30 mL) and extracted with ethyl acetate (40 mL×3). The combined organic layers were washed with brine (30 mL×3), dried over $Na_2SO_4$, and concentrated down under reduced pressure to afford a crude product, which was purified by C18 column chromatography (ACN/water (0.1% FA)) to yield compound 236 (650 mg, 74.5%) as a white solid. LCMS=[M+H]$^+$: 511.3. $^1$H NMR (400 MHz, DMSO-d$_6$) δ 11.55 (s, 1H), 8.57 (d, J=7.6 Hz, 1H), 7.60 (d, J=7.7 Hz, 2H), 7.40 (d, J=8.2 Hz, 1H), 7.25 (s, 1H), 7.17 (t, J=7.6 Hz, 1H), 7.02 (t, J=7.5 Hz, 1H), 4.70-4.59 (m, 1H), 4.39-4.33 (m, 1H), 4.31 (s, 1H), 3.89-3.75 (m, 2H), 3.63-3.50 (m, 2H), 1.80-1.61 (m, 2H), 1.56-1.38 (m, 3H), 1.04 (s, 3H), 0.96 (s, 3H), 0.95-0.89 (m, 6H), 0.84 (s, 9H).

To a solution of N—((S)-1-((1R,2S,5S)-2-(((S)-1-hydroxy-3,3-dimethylbutan-2-yl)carbamoyl)-6,6-dimethyl-3-azabicyclo[3.1.0]hexan-3-yl)-4-methyl-1-oxopentan-2-yl)-1H-indole-2-carboxamide (compound 236) (550 mg, 1.08 mmol) in DMSO (8 mL) was added IBX (907 mg, 3.24 mmol) at 0° C. The reaction mixture was stirred at room temperature overnight. The mixture was diluted with water (100 mL). The solid was filtered and the filter cake was washed with ethyl acetate. The combined organic layers were washed with sat. $Na_2S_2O_3$, sat. $NaHCO_3$ and brine, dried with anhydrous $Na_2SO_4$, and then concentrated down under reduced pressure to afford a crude product, which was purified by C18 column chromatography (ACN/water (0.1% FA)) to yield compound G-3-a (293 mg, 53.3%) as a white solid. LCMS=[M+H]$^+$: 509.4. $^1$H NMR (400 MHz, CDCl$_3$) δ 9.81 (s, 1H), 9.17 (s, 1H), 7.63 (d, J=7.9 Hz, 1H), 7.41 (d, J=8.3 Hz, 1H), 7.33-7.28 (m, 1H), 7.16-7.08 (m, 1H), 7.05-6.94 (m, 2H), 6.92 (s, 1H), 5.07-4.83 (m, 1H), 4.55-4.50 (m, 1H), 4.48 (s, 1H), 4.02-3.96 (m, 1H), 3.92-3.85 (m, 1H), 1.77-1.70 (m, 1H), 1.69-1.53 (m, 4H), 1.11-1.05 (m, 11H), 1.05-0.93 (m, 10H).

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (500 mg, 1.22 mmol) and (2S)-2-amino-3,3-dimethylbutanamide hydrochloride (compound 237) (189.83 mg, 1.46 mmol) in butan-2-one (3 mL) at 0° C. was added 2-Pyridinol-1-Oxide (0.182 mL, 1.82 mmol), DIEA (0.201 mL, 1.22 mmol) and EDCI (349.39 mg, 1.82 mmol). The reaction mixture was stirred at room temperature overnight. The mixture was diluted with water (30 mL) and extracted with ethyl acetate (50 mL×3). The combined organic layers were washed with brine (30 mL×2), dried over anhydrous $Na_2SO_4$, and concentrated down under reduced pressure. The resulting residue was purified by column chromatography (C18, ACN/water (0.1% FA=60/40 to 70/30) to yield compound 238 (300 mg, 0.57 mmol, 47.15%) as brown solid. LCMS=[M+H]$^+$: 524.2.

To a solution of N-[(2S)-1-[(1R,2S,5S)-2-{[(1S)-1-carbamoyl-2,2-dimethylpropyl]carbamoyl}-1,5-dihydrogenio-6,6-dimethyl-3-azabicyclo[3.1.0]hexan-3-yl]-4-methyl-1-oxopentan-2-yl]-1H-indole-2-carboxamide (compound 238) (500 mg, 0.95 mmol) in DCM (15 mL) was added Burgess reagent (568.10 mg, 2.39 mmol). The reaction mixture was stirred at room temperature for 3 h. The mixture was diluted with sat. $NaHCO_3$ (20 mL) and extracted with DCM (50 mL×3). The combined organic layers were washed with brine (30 mL×2), dried over anhydrous Na₂SO₄, and concentrated down under reduced pressure. The resulting residue was purified by prep-HPLC to yield compound G-3-b (265.54 mg, 0.53 mmol, 55.00%) as a white solid. LCMS=[M+H]⁺: 506.2. ¹H NMR (400 MHz, DMSO-d₆) δ 11.54 (s, 1H), 8.87 (d, J=9.2 Hz, 1H), 8.57 (d, J=7.6 Hz, 1H), 7.60 (d, J=8.0 Hz, 1H), 7.40 (d, J=8.2 Hz, 1H), 7.24 (d, J=1.5 Hz, 1H), 7.17 (t, J=7.6 Hz, 1H), 7.02 (t, J=7.5 Hz, 1H), 4.75 (d, J=9.1 Hz, 1H), 4.66-4.54 (m, 1H), 4.33 (s, 1H), 3.94-3.74 (m, 2H), 1.79-1.53 (m, 3H), 1.50-1.36 (m, 1H), 1.31 (d, J=7.6 Hz, 1H), 1.12-0.81 (m, 21H).

Example S73: Synthesis of Compound G-3-c

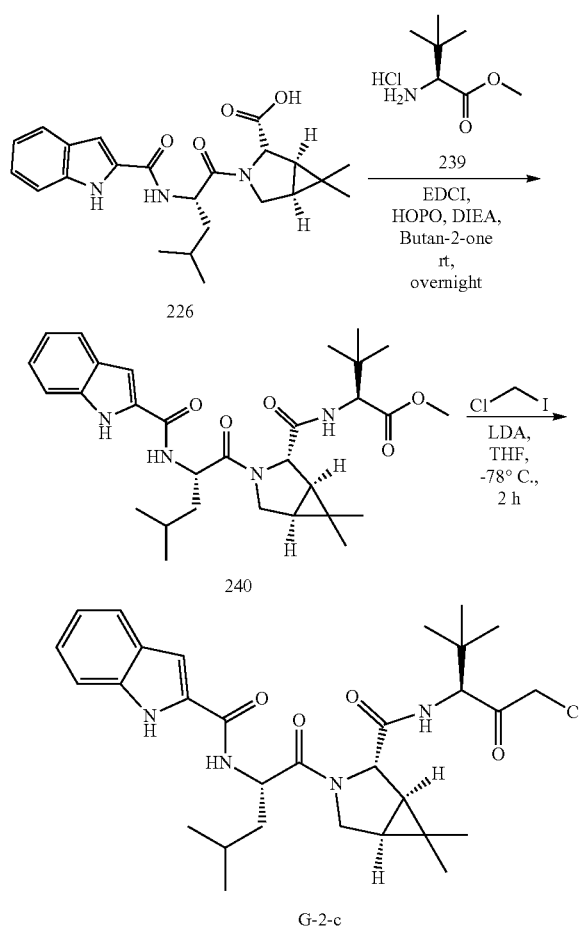

To a solution of (1R,2S,5S)-1,5-dihydrogenio-3-[(2S)-2-[(1H-indol-2-yl)formamido]-4-methylpentanoyl]-6,6-dimethyl-3-azabicyclo[3.1.0]hexane-2-carboxylic acid (compound 226) (800 mg, 1.94 mmol) and methyl (2S)-2-amino-3,3-dimethylbutanoate hydrochloride (compound 239) (366.97 mg, 2.53 mmol) in butan-2-one (20 mL) at 0° C. was added 2-Pyridinol-1-Oxide (0.292 mL, 2.92 mmol), DIEA (1.606 mL, 9.72 mmol) and EDCI (931.71 mg, 4.86 mmol). The reaction mixture was stirred at room temperature overnight. The mixture was concentrated to remove organic solvent. The remaining solution was diluted with water (30 mL) and extracted with ethyl acetate (50 mL×3). The combined organic layers were washed with brine (30 mL×2), dried over with anhydrous Na₂SO₄, and concentrated down under reduced pressure. The resulting residue was purified by column chromatography (C18, ACN/water (0.1% FA)=65/35 to 70/30) to yield compound 240 (500 mg, 0.93 mmol, 47.74%) as brown solid. LCMS=[M+H]⁺: 539.3. ¹H NMR (400 MHz, DMSO-d₆) δ 11.55 (s, 1H), 8.55 (d, J=7.6 Hz, 1H), 8.27 (d, J=8.9 Hz, 1H), 7.60 (d, J=7.9 Hz, 1H), 7.40 (d, J=8.2 Hz, 1H), 7.25 (s, 1H), 7.17 (t, J=7.4 Hz, 1H), 7.02 (t, J=7.4 Hz, 1H), 4.63 (t, J=7.1 Hz, 1H), 4.46 (s, 1H), 4.18 (d, J=8.7 Hz, 1H), 3.92-3.72 (m, 2H), 3.64 (d, J=3.5 Hz, 3H), 1.81-1.59 (m, 2H), 1.56-1.49 (m, 1H), 1.46-1.34 (m, 1H), 1.25 (d, J=8.1 Hz, 1H), 1.11-1.00 (m, 3H), 1.00-0.82 (m, 18H).

To a solution of methyl (2S)-2-{[(1R,2S,5S)-1,5-dihydrogenio-3-[(2S)-2-[(1H-indol-2-yl)formamido]-4-methylpentanoyl]-6,6-dimethyl-3-azabicyclo[3.1.0]hexan-2-yl]formamido}-3,3-dimethylbutanoate (compound 240) (390 mg, 0.72 mmol) in anhydrous THF (20 mL) at −78° C. under N₂ was added chloroiodomethane (0.528 mL, 7.24 mmol) and LDA (2M in THF; 9.050 mL). The reaction mixture was stirred at −78° C. for 2 h, and then allowed to warm up to room temperature. The mixture was diluted with NH₄Cl (30 mL) and extracted with ethyl acetate (50 mL×3). The combined organic layers were washed with brine (50 mL×3), dried over anhydrous Na₂SO₄, and concentrated down under reduced pressure. The resulting residue was purified by prep-HPLC to yield compound G-3-c (34.89 mg, 0.06 mmol, 8.65%) as white solid. LCMS=[M+H]⁺: 557.3. ¹H NMR (400 MHz, DMSO) δ 11.56 (s, 1H), 8.57 (d, J=7.5 Hz, 1H), 8.39 (d, J=7.9 Hz, 1H), 7.60 (d, J=8.0 Hz, 1H), 7.40 (d, J=8.1 Hz, 1H), 7.25 (s, 1H), 7.17 (t, J=7.6 Hz, 1H), 7.02 (t, J=7.4 Hz, 1H), 4.67-4.60 (m, 1H), 4.59-4.47 (m, 2H), 4.40 (s, 1H), 4.31 (d, J=7.8 Hz, 1H), 3.89-3.82 (m, 1H), 3.82-3.75 (m, 1H), 1.79-1.59 (m, 2H), 1.58-1.50 (m, 1H), 1.47-1.37 (m, 1H), 1.32 (d, J=7.6 Hz, 1H), 1.06-0.85 (m, 21H).

Example S74: Synthesis of Compound H-1-a

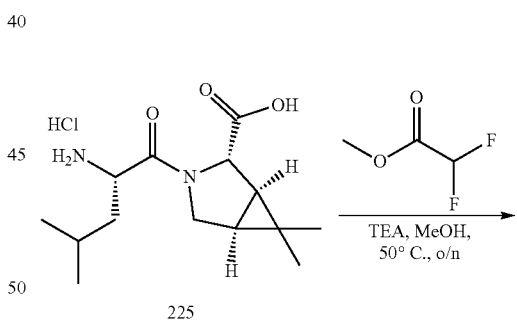

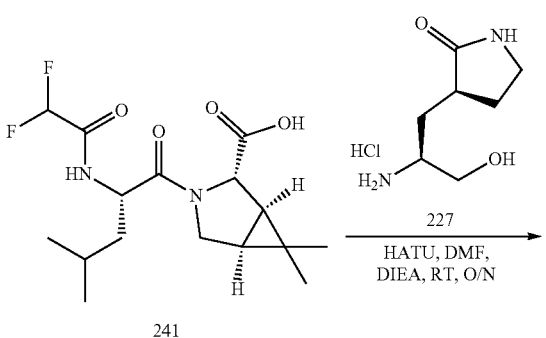

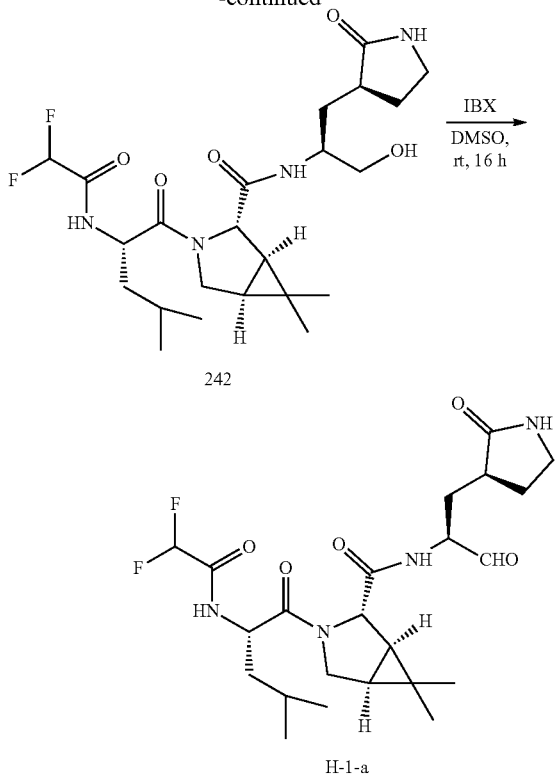

242

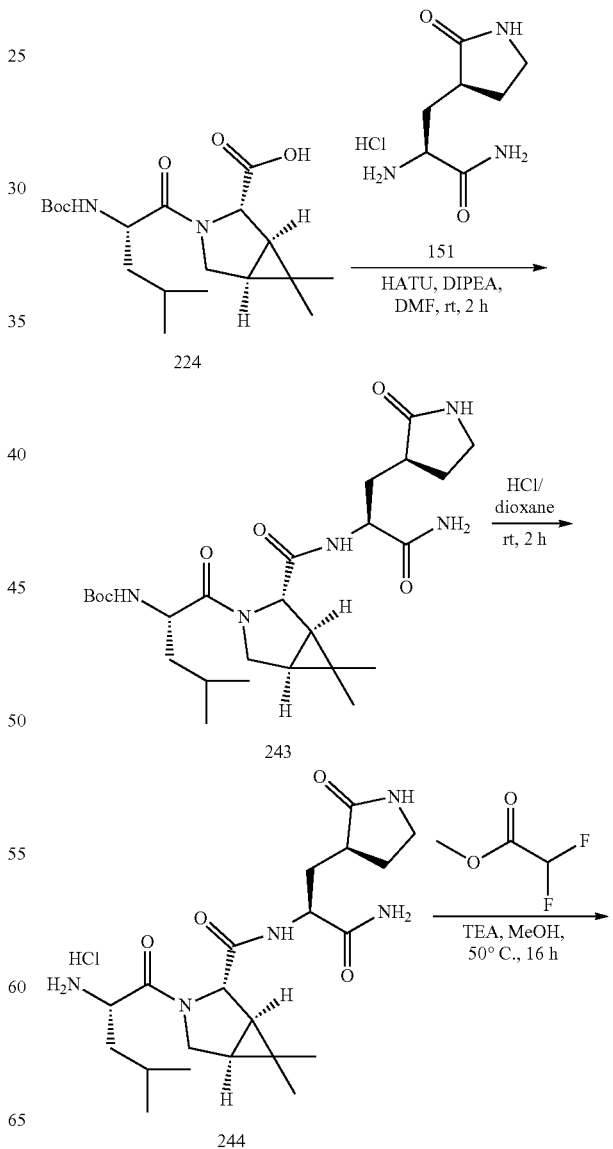

H-1-a

To a stirred solution of (1R,2S,5S)-3-(L-leucyl)-6,6-dimethyl-3-azabicyclo[3.1.0]hexane-2-carboxylic acid hydrochloride (compound 225) (850 mg, 2.8 mmol) in MeOH (10 mL) at 0° C. was added methyl 2,2-difluoroacetate (1.23 g, 11.2 mmol) and TEA (1.41 g, 14 mmol). The reaction mixture was stirred at 50° C. overnight under $N_2$. LCMS indicated completion of the reaction. The mixture was concentrated down under reduced pressure. The residue was diluted with water and pH was adjusted to ~3-4 with 1M HCl (aq), then product was extracted with ethyl acetate (100 mL×3). The combined organic layers were washed with brine, dried over $Na_2SO_4$, filtered and concentrated down under reduced pressure. The resulting residue was purified by reverse phase HPLC to yield compound 241 (519 mg, 54%) as an off-white solid. LCMS=[M+H]$^+$: 347.2.

To a solution of (1R,2S,5S)-3-((2,2-difluoroacetyl)-L-leucyl)-6,6-dimethyl-3-azabicyclo[3.1.0]hexane-2-carboxylic acid (compound 241) (500 mg, 1.44 mmol), (S)-3-((S)-2-amino-3-hydroxypropyl)pyrrolidin-2-one hydrochloride (compound 227) (419 mg, 2.16 mmol) in DMF (10 mL) at 0° C. was added DIEA (438 mg, 3.4 mmol) and HATU (762 mg, 2.0 mmol). The reaction mixture was stirred at room temperature for 16 h. LCMS indicated completion of the reaction. The mixture was diluted with water (30 mL) and extracted with ethyl acetate (40 mL×3). The combined organic layers were washed with brine (30 mL×3), dried with anhydrous $Na_2SO_4$, and concentrated under reduced pressure. The resulting residue was purified by C18 column chromatography (ACN/water (0.1% FA)) to yield compound 242 (600 mg, 85.7%) as a white solid. LCMS=[M+H]$^+$: 487.0.

To a solution of (1R,2S,5S)-3-((2,2-difluoroacetyl)-L-leucyl)-N—((S)-1-hydroxy-3-((S)-2-oxopyrrolidin-3-yl)propan-2-yl)-6,6-dimethyl-3-azabicyclo[3.1.0]hexane-2-carboxamide (compound 242) (486 mg, 1.0 mmol) in DMSO (8 mL) at 0° C. was added IBX (540 mg, 3.0 mmol). The reaction mixture was stirred at room temperature overnight. The mixture was diluted with ethyl acetate (100 mL), filtered and the filter cake was washed through with ethyl acetate. The combined organic layers were washed with sat. $Na_2S_2O_3$, sat. $NaHCO_3$ and brine, dried over with anhydrous $Na_2SO_4$ and concentrated down under reduced pressure. The resulting residue was purified by C18 column chromatography (ACN/water (0.1% FA)) to yield compound H-1-a (140 mg, 28.8%) as a white solid. LCMS=[M+H]$^+$: 485.2. $^1$H NMR (400 MHz, CDCl$_3$) δ 9.44 (s, 1H), 8.25 (d, J=5.5 Hz, 1H), 6.96-6.87 (m, 1H), 5.98-5.58 (m, 2H), 4.72-4.47 (m, 1H), 4.35-4.10 (m, 2H), 3.90-3.57 (m, 2H), 3.36-3.21 (m, 2H), 2.66-2.44 (m, 1H), 2.42-2.30 (m, 1H), 1.95-1.78 (m, 3H), 1.58-1.50 (m, 5H), 1.01 (s, 3H), 0.96-0.83 (m, 9H).

Example S75: Synthesis of Compound H-1-b

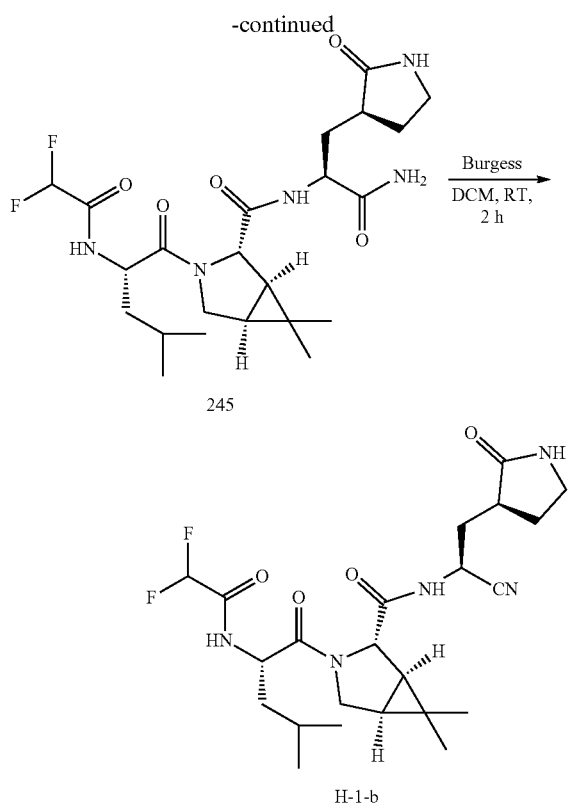

245

H-1-b

To a stirred solution of (1R,2S,5S)-3-((tert-butoxycarbonyl)-L-leucyl)-6,6-dimethyl-3-azabicyclo[3.1.0]hexane-2-carboxylic acid (compound 224) (500 mg, 1.37 mmol) and (S)-2-amino-3-((S)-2-oxopyrrolidin-3-yl)propanamide hydrochloride (compound 151) (310 mg, 1.49 mmol) in DMF (5 mL) at 0° C. under $N_2$ was added DIEA (0.87 mL, 5.43 mmol) and HATU (774 mg, 2.03 mmol). The reaction mixture was stirred at room temperature for 2 h under $N_2$. After completion of the reaction indicated by LCMS, the reaction mixture was diluted with water (80 mL) and extracted with ethyl acetate (80 mL×3). The combined organic layers were washed with brine (80 mL×2), dried over with anhydrous $Na_2SO_4$, filtered and concentrated down under reduced pressure. The resulting residue was purified by flash column chromatography (C18, ACN/water (0.1% FA) to yield 243 (370 mg, 52.3%) as a colourless oil. LCMS=[M+H]$^+$: 522.3.

To a mixture of tert-butyl ((S)-1-((1R,2S,5S)-2-(((S)-1-amino-1-oxo-3-((S)-2-oxopyrrolidin-3-yl)propan-2-yl)carbamoyl)-6,6-dimethyl-3-azabicyclo[3.1.0]hexan-3-yl)-4-methyl-1-oxopentan-2-yl)carbamate (compound 243) (370 mg, 0.71 mmol) in DCM (5 mL) was added HCl (4M in dioxane, 5 mL), the reaction mixture was stirred at room temperature for 3 h. The mixture was concentrated down under reduced pressure to yield the crude compound 244 (330 mg) as a yellow semi-solid. LCMS=[M+H]$^+$: 422.4.

To a solution of 2-{[(1R,2S,5S)-3-[(2R)-2-amino-4-methylpentanoyl]-1,5-dihydrogenio-6,6-dimethyl-3-azabicyclo[3.1.0]hexan-2-yl]formamido}-3-(2-oxopyrrolidin-3-yl)propenamide (compound 244) (250 mg, 0.59 mmol) in MeOH (3 mL) 0° C. was added triethylamine (1.237 mL, 8.90 mmol) and methyl 2,2-difluoroacetate (0.622 mL, 7.12 mmol). The reaction mixture was stirred at 50° C. overnight. After completion of the reaction indicated by LCMS, the reaction mixture was concentrated down under reduced pressure. The resulting residue was diluted with water, pH was adjusted to pH ~5 with 1M HCl (aq), and then reaction mixture was extracted with ethyl acetate (40 mL×3). The combined organic layers were dried over sodium sulfate and filtered. The filtrate was concentrated down under reduced pressure to give the crude compound 245 (160 mg, 0.32 mmol, 54.00%) as a white solid. LCMS=[M+H]$^+$: 500.0. $^1$H NMR (400 MHz, CDCl$_3$) δ 8.75 (d, J=4.9 Hz, 1H), 8.28 (br s, 1H), 7.11 (br s, 1H), 6.64 (s, 1H), 6.01 (s, 1H), 5.87 (t, 1H), 4.81-4.74 (m, 1H), 4.34-4.25 (m, 1H), 4.24 (s, 1H), 4.18-4.12 (m, 1H), 3.93 (d, J=10.3 Hz, 1H), 3.41-3.35 (m, 2H), 2.48-2.41 (m, 2H), 2.22-2.15 (m, 1H), 1.93-1.87 (m, 1H), 1.84-1.74 (m, 2H), 1.73-1.70 (m, 1H), 1.60-1.55 (m, 1H), 1.51-1.48 (m, 2H), 1.07-1.03 (m, 3H), 0.99-0.93 (m, 6H), 0.90 (d, J=6.2 Hz, 3H).

To a solution of 2-{[(1R,2S,5S)-3-[(2R)-2-(2,2-difluoroacetamido)-4-methylpentanoyl]-1,5-dihydrogenio-6,6-dimethyl-3-azabicyclo[3.1.0]hexan-2-yl]formamido}-3-(2-oxopyrrolidin-3-yl)propanamide (140 mg, 0.28 mmol) (compound 245) in DCM (5 mL) was added Burgess reagent (0.102 mL, 0.56 mmol). The reaction mixture was stirred at room temperature for 2 h. After completion of the reaction indicated by LCMS, the reaction mixture was concentrated down under reduced pressure. The resulting residue was purified by prep-HPLC (C18, ACN/water (0.1% FA)) to give the crude compound H-1-b (75 mg, 0.16 mmol, 55.58%) as a white solid. LCMS=[M+H]$^+$: 482.2. HPLC: 97.20%. $^1$H NMR (400 MHz, DMSO-d$_6$) δ 9.12 (d, J=7.4 Hz, 1H), 8.93 (d, J=8.1 Hz, 1H), 7.69 (s, 1H), 6.33-6.03 (m, 1H), 4.99-4.87 (m, 1H), 4.47-4.40 (m, 1H), 4.14 (s, 1H), 3.85-3.70 (m, 2H), 3.20-3.04 (m, 2H), 2.43-2.31 (m, 1H), 2.16-2.04 (m, 2H), 1.79-1.65 (m, 2H), 1.64-1.53 (m, 2H), 1.53-1.40 (m, 2H), 1.31 (d, J=7.6 Hz, 1H), 1.04 (d, J=8.4 Hz, 3H), 0.93-0.83 (m, 9H).

Example S76: Synthesis of Compound H-1-c

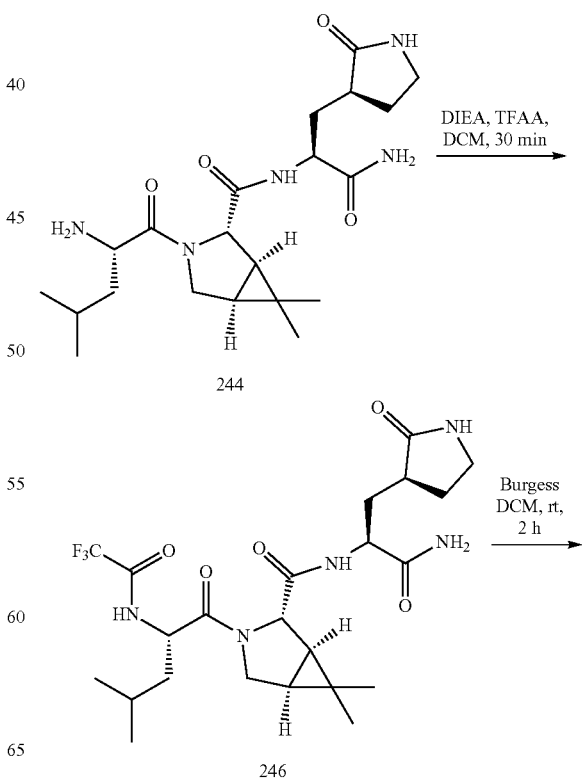

244

246

Example S77: Synthesis of Compound H-1-d

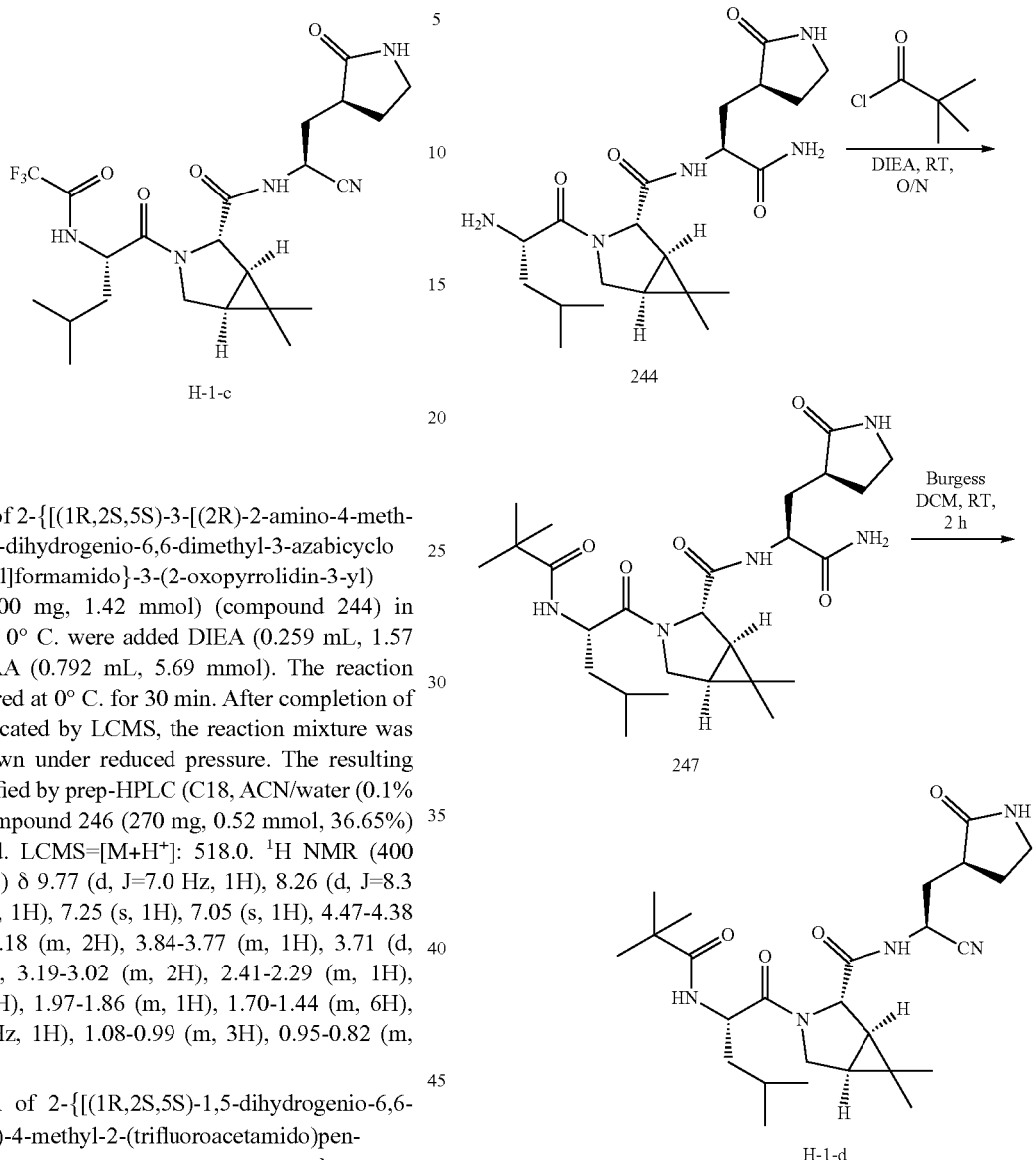

To a solution of 2-{[(1R,2S,5S)-3-[(2R)-2-amino-4-methylpentanoyl]-1,5-dihydrogenio-6,6-dimethyl-3-azabicyclo[3.1.0]hexan-2-yl]formamido}-3-(2-oxopyrrolidin-3-yl)propanamide (600 mg, 1.42 mmol) (compound 244) in DCM (5 mL) at 0° C. were added DIEA (0.259 mL, 1.57 mmol) and TFAA (0.792 mL, 5.69 mmol). The reaction mixture was stirred at 0° C. for 30 min. After completion of the reaction indicated by LCMS, the reaction mixture was concentrated down under reduced pressure. The resulting residue was purified by prep-HPLC (C18, ACN/water (0.1% FA)) to yield compound 246 (270 mg, 0.52 mmol, 36.65%) as a white solid. LCMS=[M+H$^+$]: 518.0. $^1$H NMR (400 MHz, DMSO-d$_6$) δ 9.77 (d, J=7.0 Hz, 1H), 8.26 (d, J=8.3 Hz, 1H), 7.61 (s, 1H), 7.25 (s, 1H), 7.05 (s, 1H), 4.47-4.38 (m, 1H), 4.27-4.18 (m, 2H), 3.84-3.77 (m, 1H), 3.71 (d, J=10.1 Hz, 1H), 3.19-3.02 (m, 2H), 2.41-2.29 (m, 1H), 2.17-2.07 (m, 1H), 1.97-1.86 (m, 1H), 1.70-1.44 (m, 6H), 1.40 (d, J=7.6 Hz, 1H), 1.08-0.99 (m, 3H), 0.95-0.82 (m, 9H).

To a solution of 2-{[(1R,2S,5S)-1,5-dihydrogenio-6,6-dimethyl-3-[(2R)-4-methyl-2-(trifluoroacetamido)pentanoyl]-3-azabicyclo[3.1.0]hexan-2-yl]formamido}-3-(2-oxopyrrolidin-3-yl)propanamide (compound 246) (260 mg, 0.50 mmol) in DCM (3 mL) was added Burgess reagent (0.184 mL, 1.00 mmol) and the mixture was stirred at room temperature for 2 h. After completion of the reaction indicated by LCMS, the reaction mixture was concentrated down under reduced pressure. The resulting residue was purified directly by prep-HPLC (C18, ACN/water (0.1% FA)) to yield compound H-1-c (71 mg, 0.14 mmol, 28.29%) as a white solid. LCMS=[M+H]$^+$: 500.3. HPLC: 95.20%. $^1$H NMR (400 MHz, DMSO-d$_6$) δ 9.74 (s, 1H), 8.94 (d, J=8.1 Hz, 1H), 7.69 (s, 1H), 4.98-4.88 (m, 1H), 4.41 (s, 1H), 4.16 (d, J=8.4 Hz, 1H), 3.85-3.77 (m, 1H), 3.72 (d, J=10.2 Hz, 1H), 3.21-3.06 (m, 2H), 2.42-2.31 (m, 1H), 2.16-2.06 (m, 2H), 1.81-1.56 (m, 5H), 1.51-1.41 (m, 1H), 1.32 (d, J=7.5 Hz, 1H), 1.05 (d, J=6.7 Hz, 3H), 0.96-0.82 (m, 9H).

To a solution of 2-{[(1R,2S,5S)-3-[(2R)-2-amino-4-methylpentanoyl]-1,5-dihydrogenio-6,6-dimethyl-3-azabicyclo[3.1.0]hexan-2-yl]formamido}-3-(2-oxopyrrolidin-3-yl)propanamide (compound 244) (250 mg, 0.59 mmol) in DCM (5 mL) at 0° C. DIEA (0.390 mL, 2.36 mmol) and 2,2-dimethylpropanoyl chloride (0.088 mL, 0.71 mmol) in DCM (1 mL) were added dropwise. The reaction mixture was stirred at 0° C. for 30 min. After completion of the reaction indicated by LCMS, the reaction mixture was concentrated down under reduced pressure. The resulting residue was purified by prep-HPLC (C18, ACN/water (0.1% FA)) to yield compound 247 (190 mg, 0.38 mmol, 63.33%) as a white solid. LCMS=[M+H]$^+$: 506.3. $^1$H NMR (400 MHz, DMSO-d$_6$) δ 8.21 (d, J=8.3 Hz, 1H), 7.60 (s, 1H), 7.51 (d, J=8.0 Hz, 1H), 7.20 (s, 1H), 7.04 (s, 1H), 4.51-4.43 (m, 1H), 4.28-4.17 (m, 2H), 3.78 (br s, 2H), 3.16-3.04 (m, 2H), 2.41-2.29 (m, 1H), 2.18-2.07 (m, 1H), 1.98-1.84 (m, 1H), 1.67-1.51 (m, 3H), 1.50-1.43 (m, 3H), 1.36 (d, J=7.6 Hz, 1H), 1.06 (d, 9H), 1.01 (s, 3H), 0.89-0.86 (m, 6H), 0.83 (d, J=6.5 Hz, 3H).

To a solution of N-[(2R)-1-[(1R,2S,5S)-2-{[1-carbamoyl-2-(2-oxopyrrolidin-3-yl)ethyl]carbamoyl}-1,5-dihydrogenio-6,6-dimethyl-3-azabicyclo[3.1.0]hexan-3-yl]-4-methyl-1-oxopentan-2-yl]-2,2-dimethylpropanamide (compound 247) (180 mg, 0.36 mmol) in DCM (2 mL) was added Burgess reagent (0.130 mL, 0.71 mmol). The reaction mixture was stirred at room temperature for 2 h. After completion of the reaction indicated by LCMS, the reaction mixture was concentrated down under reduced pressure. The resulting residue was purified by prep-HPLC (C18, ACN/water (0.1% FA)) to yield compound H-1-d (31 mg, 0.06 mmol, 17.86%) as a white solid. LCMS=[M+H]⁺: 488.3. HPLC: 98.77%. ¹H NMR (400 MHz, DMSO-d₆) δ 8.87 (d, J=8.1 Hz, 1H), 7.69 (s, 1H), 7.51 (d, J=7.9 Hz, 1H), 4.97-4.85 (m, 1H), 4.48-4.41 (m, 1H), 4.11 (s, 1H), 3.78 (d, J=2.6 Hz, 2H), 3.21-3.04 (m, 2H), 2.45-2.29 (m, 1H), 2.21-2.02 (m, 2H), 1.80-1.65 (m, 2H), 1.61-1.51 (m, 2H), 1.50-1.38 (m, 2H), 1.28 (d, J=7.6 Hz, 1H), 1.06 (d, J=2.8 Hz, 9H), 1.02 (s, 3H), 0.91-0.86 (m, 6H), 0.84 (d, J=6.5 Hz, 3H).

Example S78: Synthesis of Compound H-1-e

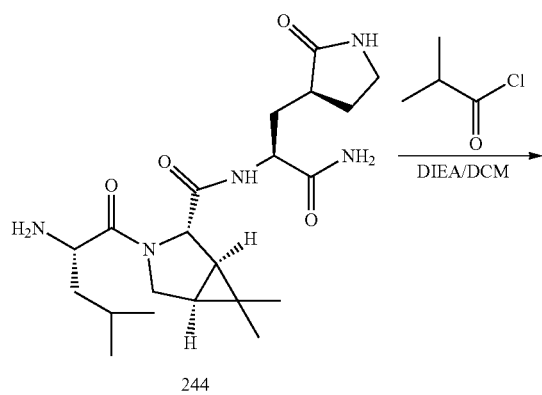

244

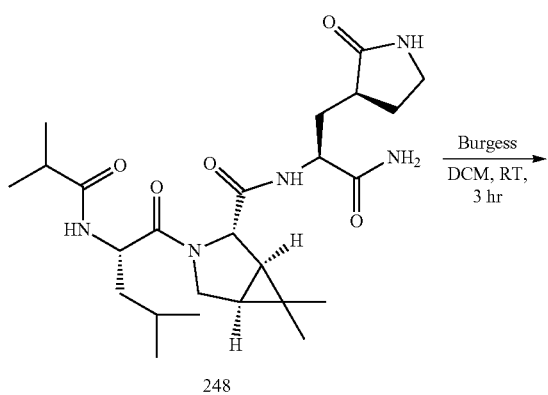

248

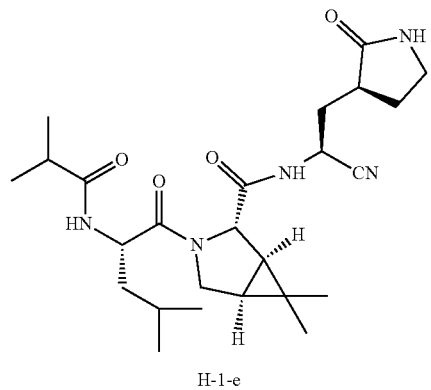

H-1-e

To a solution of 2-{[(1R,2S,5S)-3-[(2R)-2-amino-4-methylpentanoyl]-1,5-dihydrogenio-6,6-dimethyl-3-azabicyclo[3.1.0]hexan-2-yl]formamido}-3-(2-oxopyrrolidin-3-yl)propenamide (compound 244) (700 mg, 1.53 mmol) in DCM (5 mL) at 0° C. triethylamine (0.850 mL, 6.11 mmol) and 2-methylpropanoyl chloride (0.192 mL, 1.83 mmol) in DCM (1 mL) were added dropwise. The reaction mixture was stirred at 0° C. for 15 min. After completion of the reaction indicated by LCMS, the reaction mixture was concentrated down under reduced pressure. The resulting residue was purified by prep-HPLC (C18, ACN/water (0.1% FA)) to yield compound 248 (481 mg, 0.98 mmol, 64.01%) as a white solid. LCMS=[M+H]⁺: 492.4. ¹H NMR (400 MHz, DMSO-d₆) 8.22 (d, J=8.4 Hz, 1H), 8.00 (d, J=8.0 Hz, 1H), 7.61 (s, 1H), 7.22 (s, 1H), 7.04 (s, 1H), 4.49-4.42 (m, 1H), 4.24-4.19 (m, 2H), 3.80 (br s, 2H), 3.16-3.06 (m, 2H), 2.43-2.34 (m, 2H), 2.18-2.07 (m, 1H), 1.97-1.87 (m, 1H), 1.66-1.53 (m, 3H), 1.50-1.43 (m, 2H), 1.40-1.34 (m, 2H), 1.02 (s, 3H), 0.97-0.87 (m, 12H), 0.84 (d, J=6.5 Hz, 3H).

To a solution of N-[(2R)-1-[(1R,2S,5S)-2-{[1-carbamoyl-2-(2-oxopyrrolidin-3-yl)ethyl]carbamoyl}-1,5-dihydrogenio-6,6-dimethyl-3-azabicyclo[3.1.0]hexan-3-yl]-4-methyl-1-oxopentan-2-yl]-2-methylpropanamide (compound 248) (481 mg, 0.98 mmol) in DCM (3 mL) at 0° C. was added Burgess reagent (0.358 mL, 1.96 mmol). The reaction mixture was stirred at room temperature for 3 h. After completion of the reaction indicated by LCMS, the reaction mixture was concentrated down under reduced pressure. The resulting residue was purified by prep-HPLC to yield compound H-1-e (97 mg, 0.20 mmol, 20.93%) as a white solid. LCMS=[M+H]⁺: 474.3. HPLC: 94.79%. ¹H NMR (400 MHz, DMSO-d₆) δ 8.88 (d, J=8.2 Hz, 1H), 7.98 (d, J=8.0 Hz, 1H), 7.68 (s, 1H), 4.99-4.86 (m, 1H), 4.47-4.33 (m, 1H), 4.12 (br s, 1H), 3.88-3.73 (m, 2H), 3.21-3.03 (m, 2H), 2.43-2.32 (m, 2H), 2.20-2.02 (m, 2H), 1.79-1.65 (m, 2H), 1.64-1.52 (m, 2H), 1.46-1.35 (m, 2H), 1.28 (d, J=7.6 Hz, 1H), 1.02 (s, 3H), 0.98-0.87 (m, 12H), 0.84 (d, J=6.5 Hz, 3H).

Example S79: Synthesis of Compound H-1-f

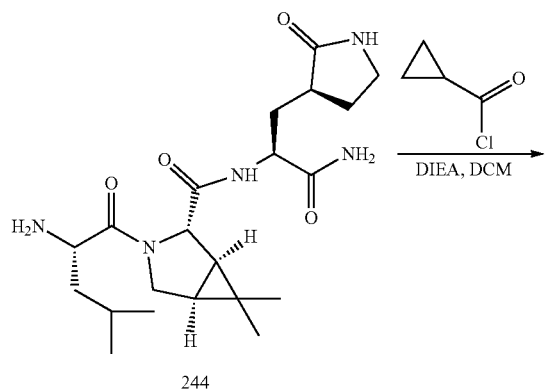

244

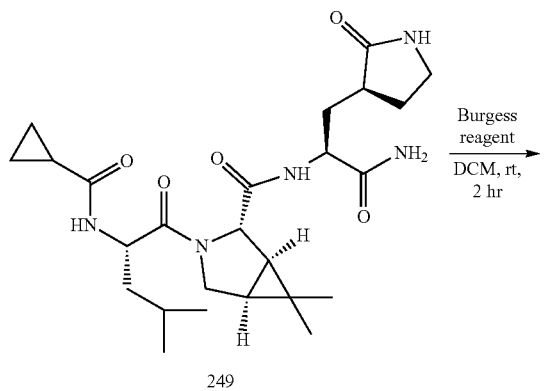

249

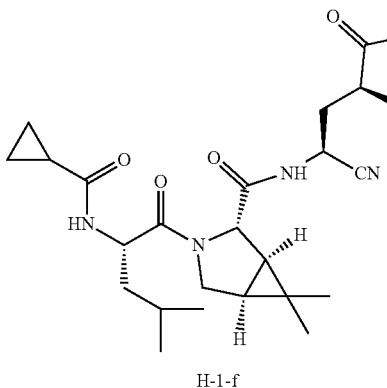

H-1-f

To a solution of 2-{[(1R,2S,5S)-3-[(2S)-2-amino-4-methylpentanoyl]-1,5-dihydrogenio-6,6-dimethyl-3-azabicyclo[3.1.0]hexan-2-yl]formamido}-3-(2-oxopyrrolidin-3-yl)propanamide (compound 244) (360 mg, 0.85 mmol) in DCM (10 mL) at 0° C. was added DIEA (0.565 mL, 3.42 mmol) followed by dropwise addition of cyclopropanecarbonyl chloride (0.093 mL, 1.02 mmol) in DCM (1 mL). The reaction mixture was stirred at 0° C. for 15 min. After completion of the reaction indicated by LCMS, the reaction mixture was concentrated down under reduced pressure. The resulting residue was purified by prep-HPLC to yield compound 249 (160 mg, 0.33 mmol, 38.26%) as a white solid. LCMS=[M+H]$^+$: 490.1. $^1$H NMR (400 MHz, DMSO-d$_6$) δ 8.31 (d, J=7.9 Hz, 1H), 8.20 (d, J=8.4 Hz, 1H), 7.59 (s, 1H), 7.19 (s, 1H), 7.03 (s, 1H), 4.47-4.42 (m, 1H), 4.27-4.22 (m, 2H), 3.80-3.74 (m, 2H), 3.16-3.08 (m, 2H), 2.43-2.31 (m, 1H), 2.18-2.05 (m, 1H), 1.97-1.84 (m, 1H), 1.84-1.73 (m, 1H), 1.68-1.39 (m, 6H), 1.36 (d, J=7.6 Hz, 1H), 1.01 (s, 3H), 0.94-0.79 (m, 9H), 0.70-0.52 (m, 4H).

To a solution of N-[(2S)-1-[(1R,2S,5S)-2-{[1-carbamoyl-2-(2-oxopyrrolidin-3-yl)ethyl]carbamoyl}-1,5-dihydrogenio-6,6-dimethyl-3-azabicyclo[3.1.0]hexan-3-yl]-4-methyl-1-oxopentan-2-yl]cyclopropanecarboxamide (compound 249) (160 mg, 0.33 mmol) in DCM (5 mL) was added Burgess reagent (0.120 mL, 0.65 mmol). The mixture was stirred at room temperature for 2 h. After completion of the reaction indicated by LCMS, the reaction mixture was concentrated down under reduced pressure. The resulting residue was purified by prep-HPLC (C18, ACN/water (0.1% FA)) to yield compound H-1-f (48 mg, 0.10 mmol, 31.15%) as a white solid. LCMS=[M+H]$^+$: 472.3. HPLC: 93.33%. $^1$H NMR (400 MHz, DMSO-d$_6$) δ 8.89 (d, J=8.2 Hz, 1H), 8.32 (d, J=7.8 Hz, 1H), 7.69 (s, 1H), 5.00-4.88 (m, 1H), 4.45-4.35 (m, 1H), 4.11 (s, 1H), 3.84-3.69 (m, 2H), 3.23-2.99 (m, 2H), 2.44-2.33 (m, 1H), 2.19-2.01 (m, 2H), 1.77-1.51 (m, 5H), 1.44-1.35 (m, 2H), 1.28 (d, J=7.6 Hz, 1H), 1.02 (s, 3H), 0.92-0.82 (m, 9H), 0.68-0.52 (m, 4H).

Example S80: Synthesis of Compound H-2-a

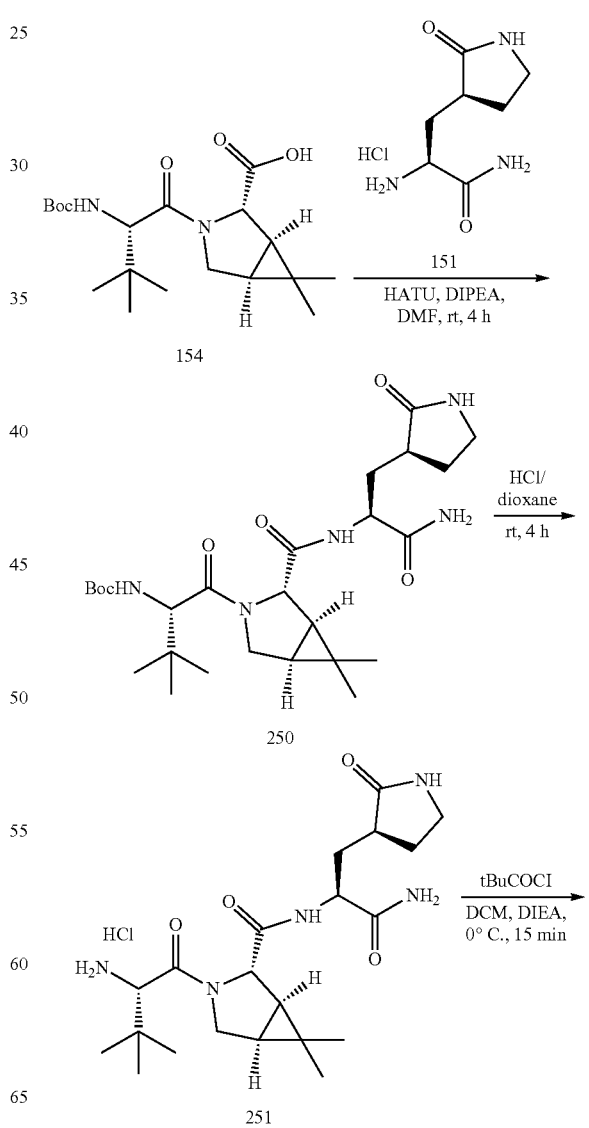

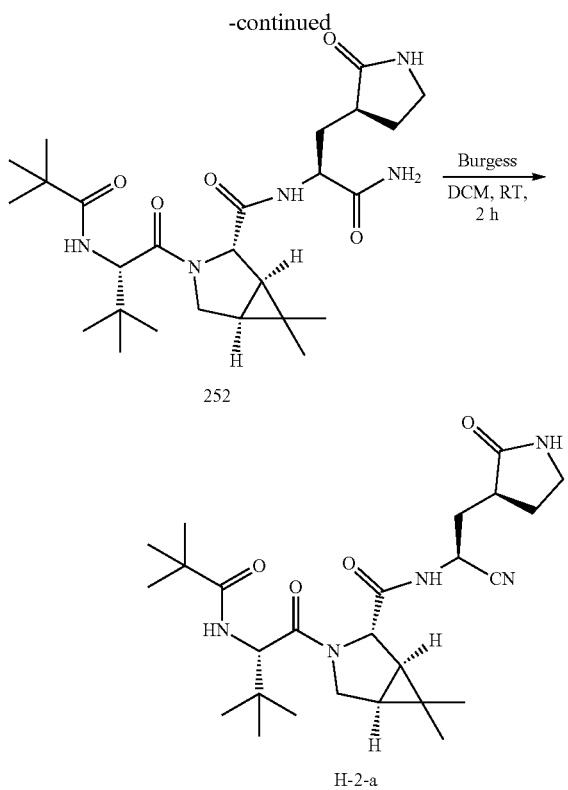

252

H-2-a

To a stirred solution of (1R,2S,5S)-3-((S)-2-((tert-butoxycarbonyl)amino)-3,3-dimethylbutanoyl)-6,6-dimethyl-3-azabicyclo[3.1.0]hexane-2-carboxylic acid (compound 154) (800 mg, 2.17 mmol) and (S)-2-amino-3-((S)-2-oxopyrrolidin-3-yl)propanamide hydrochloride (compound 151) (539 mg, 2.60 mmol) in DMF (10 mL) at 0° C. was added HATU (991 mg, 2.6 mmol) and DIEA (0.839 g, 6.51 mmol). The reaction mixture was stirred at room temperature for 4 h. After completion of the reaction indicated by LCMS, the reaction mixture was diluted with water (80 mL) and extracted with ethyl acetate (100 mL×2). The combined organic layers were washed with brine (80 mL×2), dried over anhydrous Na$_2$SO$_4$, filtered and concentrated down under reduced pressure. The resulting residue was purified by column chromatography (C18, 35%-40% ACN/water (0.1% FA)) to yield compound 250 (500 mg, 44%) as an off-white solid. LCMS=[M+H]$^+$: 522.1. $^1$H NMR (400 MHz, CDCl$_3$) δ 8.19 (d, J=5.8 Hz, 1H), 7.19 (s, 1H), 6.02 (s, 1H), 5.61 (s, 1H), 5.11 (d, J=10.3 Hz, 1H), 4.49-4.39 (m, 1H), 4.28-4.21 (m, 2H), 4.17-4.06 (m, 1H), 4.03-3.96 (m, 1H), 3.42-3.33 (m, 2H), 2.54-2.38 (m, 2H), 2.15-2.08 (m, 1H), 2.00-1.85 (m, 2H), 1.46 (d, J=7.1 Hz, 2H), 1.40 (s, 9H), 1.11-0.95 (m, 12H), 0.89 (s, 3H).

A solution of tert-butyl ((S)-1-((1R,2S,5S)-2-(((S)-1-amino-1-oxo-3-((S)-2-oxopyrrolidin-3-yl)propan-2-yl)carbamoyl)-6,6-dimethyl-3-azabicyclo[3.1.0]hexan-3-yl)-3,3-dimethyl-1-oxobutan-2-yl)carbamate (compound 250) (500 mg, 0.96 mmol) in HCl (4M in dioxane, 10 mL) was stirred at room temperature for 4 h. The mixture was concentrated down under reduced pressure to yield the crude compound 251 (450 mg) as a yellow semi-solid. LCMS=[M+H]$^+$: 422.0.

To a stirred solution of (1R,2S,5S)—N—((S)-1-amino-1-oxo-3-((S)-2-oxopyrrolidin-3-yl)propan-2-yl)-3-((S)-2-amino-3,3-dimethylbutanoyl)-6,6-dimethyl-3-azabicyclo[3.1.0]hexane-2-carboxamide hydrochloride (compound 251) (450 mg, 0.96 mmol) in DCM (100 mL) at 0° C. was added DIEA (0.37 g, 2.88 mmol) and pivaloyl chloride (0.115 g, 0.96 mmol). The mixture was stirred at 0° C. for 15 min. LCMS indicated completion of the reaction. The reaction mixture was diluted with water (40 mL) and extracted with DCM (100 mL). The organic phase was separated, dried over anhydrous Na$_2$SO$_4$, and concentrated under reduced pressure. The resulting residue was purified by reverse phase HPLC to yield compound 252 (400 mg, yield: 82%) as a yellow oil. LCMS=[M+H]$^+$: 506.3. $^1$H NMR (400 MHz, CDCl$_3$) δ 8.31 (d, J=5.4 Hz, 1H), 7.23 (s, 1H), 6.10 (d, J=9.7 Hz, 1H), 5.73 (s, 1H), 5.33 (s, 1H), 4.69-4.59 (m, 1H), 4.48-4.36 (m, 1H), 4.23 (s, 1H), 4.18-4.11 (m, 1H), 4.00-3.92 (m, 1H), 3.42-3.31 (m, 2H), 2.56-2.36 (m, 2H), 2.18-2.07 (m, 1H), 2.01-1.84 (m, 2H), 1.70-1.68 (m, 2H), 1.17 (s, 9H), 1.01-0.98 (m, 12H), 0.83 (s, 3H).

To a stirred solution of (1R,2S,5S)—N—((S)-1-amino-1-oxo-3-((S)-2-oxopyrrolidin-3-yl)propan-2-yl)-3-((S)-3,3-dimethyl-2-pivalamidobutanoyl)-6,6-dimethyl-3-azabicyclo[3.1.0]hexane-2-carboxamide (compound 252) (250 mg, 0.49 mmol) in DCM (0 mL) was added Burgess reagent (238 mg, 1.0 mmol). The reaction mixture was stirred at room temperature under N$_2$ for 2 h. The reaction mixture was concentrated down under reduced pressure. The resulting residue was purified by prep-HPLC to yield compound H-2-a (48 mg, 20.1%) as a white solid. LCMS=[M+H]$^+$: 488.3. $^1$H NMR (400 MHz, DMSO-d$_6$) δ 8.95 (d, J=8.7 Hz, 1H), 7.67 (s, 1H), 6.87 (d, J=9.2 Hz, 1H), 5.03-4.89 (m, 1H), 4.44 (d, J=9.3 Hz, 1H), 4.12 (s, 1H), 3.92-3.80 (m, 1H), 3.73 (d, J=10.5 Hz, 1H), 3.15 (t, J=9.4 Hz, 1H), 3.08-2.97 (m, 1H), 2.44-2.36 (m, 1H), 2.18-2.02 (m, 2H), 1.79-1.63 (m, 2H), 1.57-1.48 (m, 1H), 1.29 (d, J=7.6 Hz, 1H), 1.08 (s, 9H), 1.02 (s, 3H), 0.92 (s, 9H), 0.81 (s, 3H).

Example 581: Synthesis of Compound H-2-b

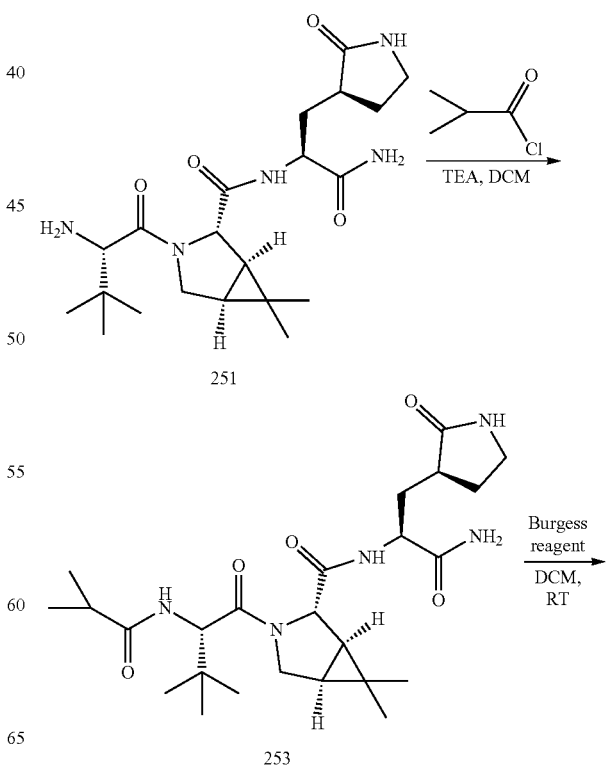

251

253

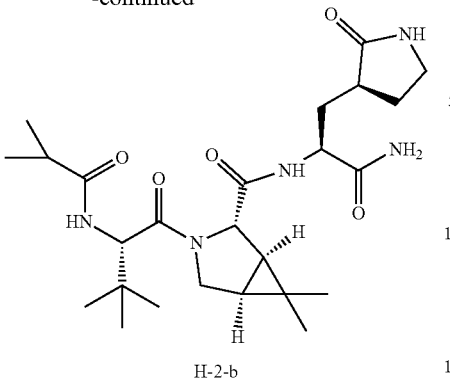

H-2-b

To a stirred mixture of (1R,2S,5S)—N—((S)-1-amino-1-oxo-3-((S)-2-oxopyrrolidin-3-yl)propan-2-yl)-3-((S)-2-amino-3,3-dimethylbutanoyl)-6,6-dimethyl-3-azabicyclo[3.1.0]hexane-2-carboxamide (compound 251) (458 mg, 1.00 mmol) and TEA (416.992 μL, 3.00 mmol) in DCM (5 ml) at 0° C. was added isobutyryl chloride. The reaction mixture was stirred for 0.5 h. The reaction mixture was concentrated down under reduced pressure. The resulting residue was purified by reverse phase column chromatography (ACN/water (0.1% FA), 0% to 100%, 40 min) to yield compound 253 (300 mg, 0.61 mmol, 61.02%). LCMS=[M+H]⁺: 492.3.

To a mixture of (1R,2S,5S)—N—((S)-1-amino-1-oxo-3-((S)-2-oxopyrrolidin-3-yl)propan-2-yl)-3-((S)-2-isobutyramido-3,3-dimethylbutanoyl)-6,6-dimethyl-3-azabicyclo[3.1.0]hexane-2-carboxamide (compound 253) (286.00 mg, 0.58 mmol) in DCM (5 mL) at 0° C. was added Burgess reagent (168.00 mg, 0.02 mmol). The reaction mixture was stirred at room temperature overnight. LCMS indicated completion of the reaction. The reaction mixture was concentrated down under reduced pressure. The resulting residue was purified by prep-HPLC to yield compound H-2-b (20.00 mg, 0.03 mmol, 8.74%) as a white solid. LCMS=[M+H]⁺: 474.1. ¹H NMR (400 MHz, DMSO-d₆) δ 8.95 (d, J=8.6 Hz, 1H), 7.76 (d, J=9.2 Hz, 1H), 7.65 (s, 1H), 5.01-4.90 (m, 1H), 4.39 (d, J=9.2 Hz, 1H), 4.09 (s, 1H), 3.92-3.73 (m, 2H), 3.21-3.11 (m, 1H), 3.09-2.97 (m, 1H), 2.58-2.55 (m, 1H), 2.45-2.40 (m, 1H), 2.20-2.14 (m, 1H), 2.12 (s, 1H), 1.76-1.63 (m, 2H), 1.56-1.49 (m, 1H), 1.28 (d, J=7.6 Hz, 1H), 1.02 (s, 3H), 0.96 (d, J=6.8 Hz, 3H), 0.92 (s, 9H), 0.89 (d, J=6.8 Hz, 3H), 0.82 (s, 3H).

Example S82: Synthesis of Compound H-2-c

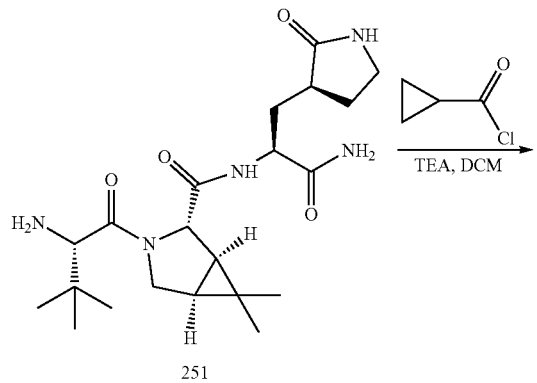

251

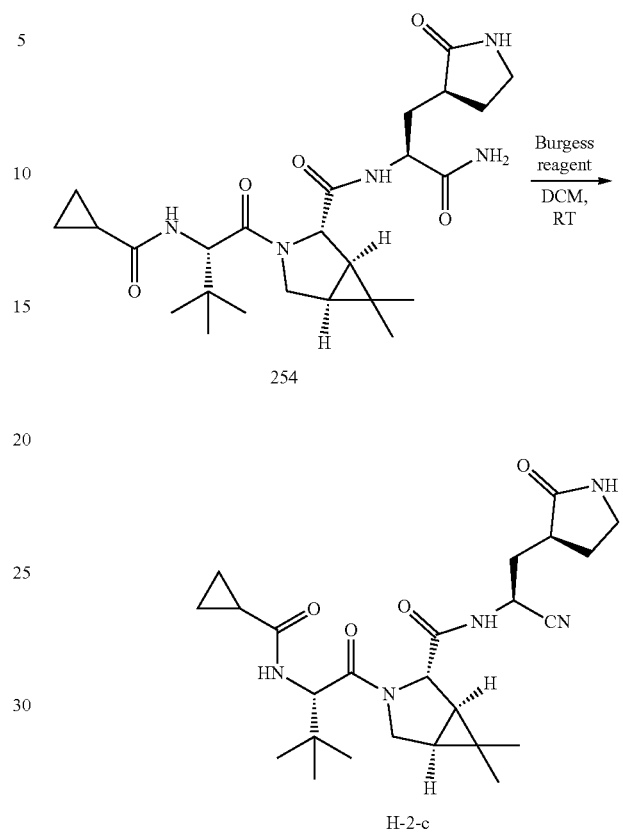

To a stirred mixture of (1R,2S,5S)—N—((S)-1-amino-1-oxo-3-((S)-2-oxopyrrolidin-3-yl)propan-2-yl)-3-((S)-2-amino-3,3-dimethylbutanoyl)-6,6-dimethyl-3-azabicyclo[3.1.0]hexane-2-carboxamide (compound 251) (458 mg, 1.00 mmol) and TEA (416.992 μL, 3.00 mmol) in DCM (5 mL) at 0° C. was added cyclopropanecarbonyl chloride (99.995 μL, 1.10 mmol). The reaction mixture was stirred at 0° C. for 0.5 h. The reaction mixture was concentrated down under reduced pressure. The resulting residue was purified by C18 column chromatography (ACN/water (0.1% FA), 0% to 100%, 40 min) to yield compound 254 (200 mg, 0.41 mmol, 40.85%) as a yellow solid. LCMS=[M+H]⁺: 490.3.

To a mixture of (1R,2S,5S)—N—((S)-1-amino-1-oxo-3-((S)-2-oxopyrrolidin-3-yl)propan-2-yl)-3-((S)-2-(cyclopropanecarboxamido)-3,3-dimethylbutanoyl)-6,6-dimethyl-3-azabicyclo[3.1.0]hexane-2-carboxamide (compound 254) (190 mg, 0.39 mmol) in DCM (5 mL) at 0° C. was added Burgess reagent (4.608 μL, 0.02 mmol). The reaction mixture was stirred at room temperature overnight. The reaction mixture was concentrated down under reduced pressure. The resulting residue was purified by prep-HPLC to yield compound H-2-c as a white solid. LCMS=[M+H]⁺: 472.3. ¹H NMR (400 MHz, DMSO-d₆) δ 8.96 (d, J=8.6 Hz, 1H), 8.08 (d, J=8.9 Hz, 1H), 7.64 (s, 1H), 5.02-4.89 (m, 1H), 4.36 (d, J=9.0 Hz, 1H), 4.12 (s, 1H), 3.93-3.76 (m, 2H), 3.19-3.11 (m, 1H), 3.10-3.00 (m, 1H), 2.20-2.06 (m, 2H), 1.87-1.78 (m, 1H), 1.77-1.66 (m, 2H), 1.54-1.48 (m, 1H), 1.27 (d, J=7.6 Hz, 1H), 1.24 (s, 1H), 1.01 (s, 3H), 0.94 (s, 9H), 0.82 (s, 3H), 0.65 (s, 1H), 0.64-0.57 (m, 2H), 0.56-0.50 (m, 1H).

Example S83: Synthesis of Compound H-3-a

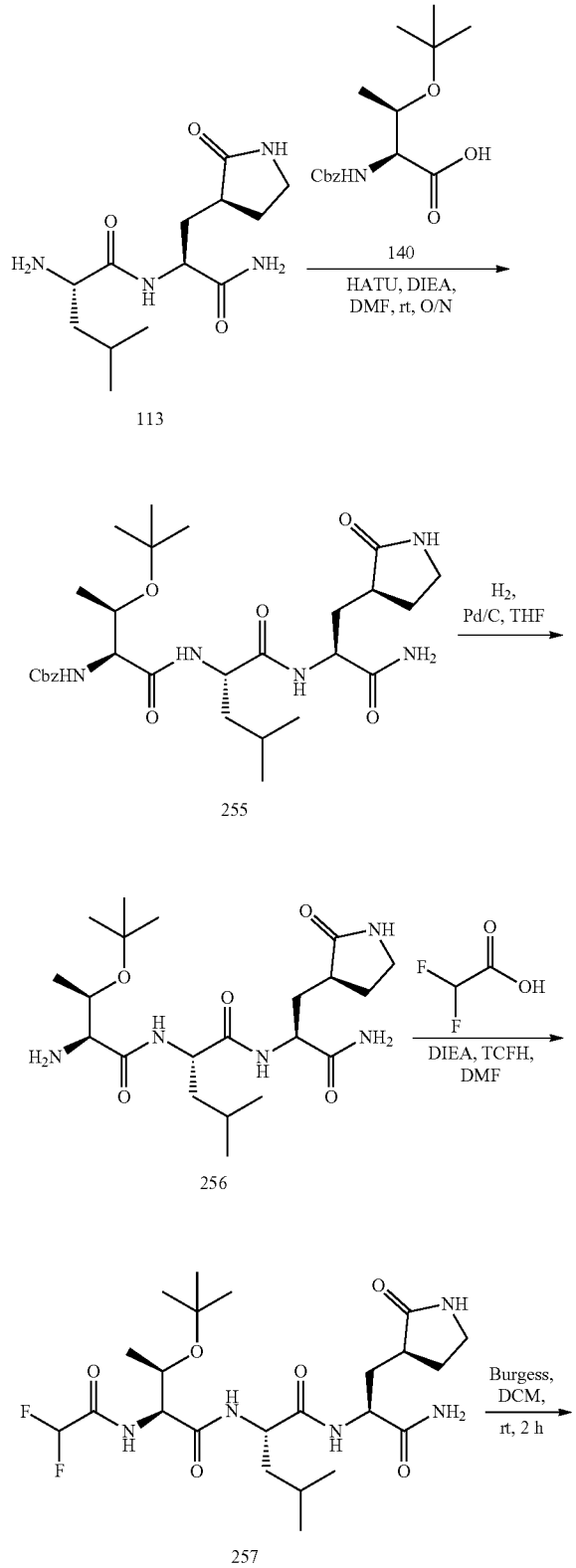

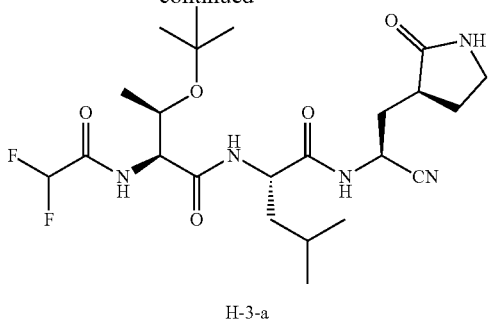

H-3-a

To a solution of (2S)-2-amino-N-[1-carbamoyl-2-(2-oxopyrrolidin-3-yl)ethyl]-4-methylpentanamide (compound 113) (364 mg, 1.28 mmol) in DMF (2 mL) at 0° C. were added 2-{[(benzyloxy)carbonyl]amino}-3-(tert-butoxy)butanoic acid (compound 140) (475.20 mg, 1.54 mmol), DIEA (0.846 mL, 5.12 mmol) and HATU (730.08 mg, 1.92 mmol). The reaction mixture was stirred at room temperature overnight. LCMS indicated completion of the reaction. The mixture was directly purified by column chromatography (C18, ACN/water (0.1% FA)) to yield compound 255 (480 mg, 0.83 mmol, 65.13%) as a white solid. LCMS=[M+H]$^+$: 576.1.

To a solution of benzyl N-[2-(tert-butoxy)-1-{1[(1S)-1-{[1-carbamoyl-2-(2-oxopyrrolidin-3-yl)ethyl]carbamoyl}-3-methylbutyl]carbamoyl}propyl]carbamate (compound 255) (450 mg, 0.78 mmol) in THF (10 mL) were added Pd/C (10%, 0.044 mL, 0.42 mmol). The reaction mixture was stirred at room temperature overnight under hydrogen atmosphere. After completion of the reaction indicated by LCMS, the mixture was filtered, and filtrate was concentrated down under reduced pressure to yield compound 256 (325 mg, 0.74 mmol, 94.16%) as a white solid. LCMS=[M+H]$^+$: 442.1. $^1$H NMR (400 MHz, DMSO-$d_6$) δ 8.12 (d, J=8.4 Hz, 1H), 7.98 (s, 1H), 7.61 (s, 1H), 7.22 (s, 1H), 7.01 (s, 1H), 4.30-4.20 (m, 2H), 3.89-3.85 (m, 1H), 3.16-3.05 (m, 2H), 2.96 (d, J=3.8 Hz, 1H), 2.22-2.17 (m, 1H), 2.13-2.08 (m, 1H), 1.98-1.94 (m, 1H), 1.66-1.58 (m, 2H), 1.50-1.44 (m, 3H), 1.10-1.06 (m, 12H), 0.90-0.85 (m, 6H).

To a solution of N,N,N',N'-tetramethylchloroformamidinium hexafluorophosphate (TCFH) (207.63 mg, 0.74 mmol) in DMF (3 mL) were added DIEA (0.487 mL, 2.94 mmol) and 2,2-difluoroacetic acid (0.046 mL, 0.74 mmol) at 0° C. The mixture was stirred for 1 h at 0° C. and a solution of (2S)-2-[amino-3-(tert-butoxy)butanamido]-N-[1-carbamoyl-2-(2-oxopyrrolidin-3-yl)ethyl]-4-methylpentanamide (compound 256) (325 mg, 0.74 mmol) in DMF (3 mL) was added. The reaction mixture was stirred at room temperature for 1 h, then concentrated under reduced pressure and purified by column chromatography (C18, ACN/water (0.1% FA)) to yield compound 257 (170 mg, 0.33 mmol, 44.21%) as a white solid. LCMS=[M+H]$^+$: 520.3. $^1$H NMR (400 MHz, DMSO-$d_6$) δ 8.52 (d, J=8.7 Hz, 1H), 8.19-8.05 (m, 2H), 7.61 (s, 1H), 7.27 (s, 1H), 7.01 (s, 1H), 6.53-6.18 (m, 1H), 4.41-4.29 (m, 2H), 4.27-4.20 (m, 1H), 3.93-3.85 (m, 1H), 3.17-3.02 (m, 2H), 2.25-2.07 (m, 2H), 2.02-1.93 (m, 1H), 1.72-1.55 (m, 2H), 1.52-1.42 (m, 3H), 1.12 (d, J=11.8 Hz, 9H), 1.03 (d, J=6.2 Hz, 3H), 0.90-0.84 (m, 6H).

To a solution of (2S)-2-[3-(tert-butoxy)-2-(2,2-difluoroacetamido)butanamido]-N-[1-carbamoyl-2-(2-oxopyrrolidin-3-yl)ethyl]-4-methylpentanamide (compound 257) (170 mg, 0.33 mmol) in DCM (10 mL) was added Burgess reagent (0.120 mL, 0.65 mmol). The reaction mixture was stirred at room temperature for 3 h and then was concentrated down under reduced pressure. The resulting residue was purified by prep-HPLC to yield compound H-3-a (100 mg, 0.20 mmol, 60.94%) as a white solid. LCMS=[M+Na]$^+$: 524.3, HPLC: 99.28%. $^1$H NMR (400 MHz, DMSO) δ 8.92 (d, J=7.9 Hz, 1H), 8.59-8.45 (m, 1H), 8.24 (d, J=7.8 Hz, 1H), 7.72 (s, 1H), 6.51-6.18 (m, 1H), 4.98-4.87 (m, 1H), 4.41-4.33 (m, 1H), 4.33-4.25 (m, 1H), 3.97-3.82 (m, 1H), 3.22-3.04 (m, 2H), 2.38-2.24 (m, 1H), 2.20-2.02 (m, 2H), 1.84-1.65 (m, 2H), 1.64-1.53 (m, 1H), 1.53-1.40 (m, 2H), 1.10 (s, 9H), 1.03 (d, J=6.2 Hz, 3H), 0.91 (d, J=6.5 Hz, 3H), 0.87 (d, J=6.4 Hz, 3H).

Example B1: Wild Type SARS-CoV-2 M$^{pro}$ Inhibition Assay

M$^{pro}$ activity was measured according to the manufacturer's protocol (BPS Biosciences, cat #78042-2) in 384-well plates. The included recombinant un-tagged M$^{pro}$ (referred to as 3CL protease in the kit) was tested for ability to cleave a FRET peptide substrate (DABCYL-KTSAVLQSG-FRKME-EDANS) to generate a fluorescent product (SG-FRKME-EDANS) over time. The final volume is 25 ml in indicated assay buffer, with final M$^{pro}$ and substrate concentrations as 17 nM and 40 uM respectively. Fluorescent intensities were monitored once every 5 minutes after adding substrate into the rest of reaction mixture. Enzyme activity was represented using the initial linear slope of the kinetic curve.

Compounds were first serially diluted in DMSO as 1000× working stock, then diluted in assay buffer before adding to reaction mixture following manufacture's protocol. 100 mM GC376 was used as 100% inhibition control. For no inhibition control, no compound was added. Blank wells contained buffer, substrate but no M$^{pro}$. Final 0.1% DMSO was included as vehicle no inhibition control.

GraphPad Prism nonlinear regression model of log(inhibitor) vs. response Variable slope (four parameters) was used to calculate IC$_{50}$ values based on activity %. Activity % was calculated as follows: activity %=(Sample−Average blank)/(DMSO−Average blank) %.

Summary of IC$_{50}$ Values (nM) of the protease inhibitors are presented in Table 1.

TABLE 1

IC$_{50}$ values of novel protease inhibitors - inhibition of SARS-CoV-2M$^{pro}$ activity.

| Compound # | SARS-CoV-2M$^{pro}$ inhibition IC$_{50}$ (nM) |
|---|---|
| A-1-c | 2.74 |
| A-1-d | 2.8 |
| A-1-f | ND |
| A-1-g | 46.98 |
| A-1-h | 10.18 |
| A-1-i | >10000 |
| A-1-j | >2000 |
| A-2-a | ND |
| A-2-c | ND |
| A-3-a | 46.39 |
| A-3-b | inactive |
| A-3-c | 1.95 |
| A-3-d | 335 |
| A-3-e | 5.11 |
| A-4-a | 2.39 |
| A-4-b | 172.5 |
| A-4-c | 1120 |
| A-4-d | 4.13 |
| A-4-e | 2.41 |
| A-5-a | 3.18 |

TABLE 1-continued

IC$_{50}$ values of novel protease inhibitors - inhibition of SARS-CoV-2M$^{pro}$ activity.

| Compound # | SARS-CoV-2M$^{pro}$ inhibition IC$_{50}$ (nM) |
|---|---|
| A-5-b | 84.25 |
| A-5-c | 358.9 |
| A-5-d | 2.94 |
| B-1-a | ND |
| B-1-b | ND |
| B-1-c | ND |
| B-1-d | ND |
| B-1-e | ND |
| B-1-f | ND |
| B-2-a | ND |
| B-2-b | ND |
| B-2-c | ND |
| B-2-d | ND |
| B-2-e | ND |
| C-1-a | ND |
| C-1-b | 1.3 |
| C-2-a | ND |
| C-2-b | 3.4 |
| D-1-c | 1.59 |
| D-1-d | 6.3 |
| D-1-e | ND |
| D-1-f | 1.08 |
| D-2-a | 23.97 |
| D-2-b | 42.54 |
| D-2-c | 69.73 |
| D-2-d | 58.71 |
| D-2-e | 7.02 |
| D-2-f | >5000 |
| D-3-a | 5.83 |
| D-3-b | 2.16 |
| D-3-c | 4.79 |
| D-4-a | 21.27 |
| E-1-a | ND |
| E-1-b | ND |
| F-1-a | ND |
| F-1-b | ND |
| F-1-c | ND |
| F-1-d | ND |
| F-2-a | ND |
| F-2-b | ND |
| F-2-c | ND |
| F-2-d | ND |
| F-2-e | ND |
| F-3-a | ND |
| F-3-b | ND |
| F-3-c | ND |
| F-4-a | ND |
| F-4-b | ND |
| F-4-c | ND |
| G-1-a | 9.57 |
| G-1-b | 377.2 |
| G-1-d | 967.5 |
| G-1-e | 57.85 |
| G-2-a | >2000 |
| G-2-b | >10000 |
| G-2-c | >2000 |
| G-3-a | >10000 |
| G-3-b | >10000 |
| G-3-c | >10000 |
| G-1-c | 963.5 |
| H-1-a | 6.35 |
| H-1-b | 7.53 |
| H-1-c | 36.7 |
| H-1-d | 39.65 |
| H-1-e | 43.26 |
| H-1-f | 28.6 |
| H-2-a | 40.73 |
| H-2-b | 6.6 |
| H-2-c | 6.1 |
| H-3-a | 8.1 |

Example B2: SARS-CoV-2 Omicron M$^{pro}$ Inhibition Assay

M$^{pro}$ activity was measured according to the manufacturer's protocol (BPS Biosciences, cat #78350-2) in 384-well plates. The included recombinant un-tagged Omicron M$^{pro}$ (referred as 3CL protease in the kit) was tested for ability to cleave a FRET peptide substrate (DABCYL-KTSAVLQSG-FRKME-EDANS) to generate a fluorescent product (SG-FRKME-EDANS) over time. The final volume was 25 ml in indicated assay buffer, with final M$^{pro}$ and substrate concentrations as 34 nM and 40 uM respectively. Fluorescent intensities were monitored once every 5 minutes after adding substrate into the rest of reaction mixture. Enzyme activity was represented using the initial linear slope of the kinetic curve.

Compounds were first serially diluted in DMSO as 1000× working stock, then diluted in assay buffer before adding to reaction mixture following manufacture's protocol. 100 uM GC376 was used as 100% inhibition control. For no inhibition control, no compound was added. Blank wells contained buffer, substrate but no M$^{pro}$. Final 0.1% DMSO was included as vehicle no inhibition control.

To calculate IC$_{50}$ values, activity % was derived as following: activity %=(Sample−Average blank)/(DMSO−Average blank) %. GraphPad Prism nonlinear regression model of log(inhibitor) vs. response—Variable slope (four parameters) was used to calculate IC$_{50}$ values based on activity %.

Summary of IC$_{50}$ Values (nM) of the protease inhibitors are presented in Table 2.

TABLE 2

IC$_{50}$ values of novel protease inhibitors - inhibition of SARS-CoV-2 Omicron M$^{pro}$ activity.

| Compound ID# | SARS-CoV-2 Omicron M$^{pro}$ inhibition IC$_{50}$ (nM) |
|---|---|
| A-1-c | 14.27 |
| A-1-d | 13.35 |
| A-3-a | 49.92 |
| A-3-c | 11.49 |
| C-2-b | 23.94 |
| D-1-c | 5.93 |
| D-3-b | 4.3 |
| D-4-a | 72.8 |
| H-1-b | 4.94 |

Example B3: Anti-Viral In Vitro PRNT Assay in Vero E6 Cells

Vero E6 cells grown in 96 well plates were infected with 1000 pfu SARS-CoV-2 for one hour. An overlay containing 1% methylcellulose was added and plates were incubated for 3 days. Staining was performed by discarding the supernatant, fixing the cells for 30 minutes and staining with crystal violet. Plaques were counted and a reduction of plaques was calculated relative to untreated wells (Ranawaka, P. et al. (2020) Eurosurveill. 25(16), published online).

To calculate the EC$_{50}$ from dose responses, a non-linear regression program in Prism (4 parameters variable slope) was used. EC$_{90}$ was calculated using a Prism non-linear regression—Find ECanything program.

Summary of EC$_{50}$ Values (nM) of novel protease inhibitors in Vero E6 Cells is presented in Table 3.

TABLE 3

EC$_{50}$ Values (nM) of novel protease inhibitors in Vero E6 Cells

| Compound ID# | anti-SARS-CoV2 (PRNT) in Vero E6 EC$_{50}$ (μM) |
|---|---|
| A-1-a | inactive |
| A-1-c | EC$_{50}$ = 0.30 |
| A-1-d | EC$_{50}$ = 1.06 |
| A-1-f | inactive |
| A-1-g | EC$_{50}$ = 18.19 |
| A-1-h | Inactive |
| A-2-a | inactive |
| A-2-c | EC$_{50}$ = 0.64 |
| A-3-a | EC$_{50}$ = 5.18 |
| A-3-c | EC$_{50}$ = 0.31 |
| A-4-a | EC$_{50}$ = 1.13 |
| A-4-d | EC$_{50}$ = 2.06 |
| A-5-a | EC$_{50}$ = 1.52 |
| A-5-b | inactive |
| A-5-d | EC$_{50}$ = 3.5 |
| B-1-a | inactive |
| B-1-b | EC$_{50}$ = 1.13 |
| B-1-c | EC$_{50}$ = 2.29 |
| B-1-d | inactive |
| B-1-e | EC$_{50}$ = 10.49 |
| B-1-f | inactive |
| B-2-a | inactive |
| B-2-b | EC$_{50}$ = 3.24 |
| B-2-d | EC$_{50}$ = 32.80 |
| B-2-e | inactive |
| C-1-a | inactive |
| C-1-b | EC$_{50}$ = 1.02 |
| C-2-a | inactive |
| C-2-b | EC$_{50}$ = 0.73 |
| D-1-a | inactive |
| D-1-c | EC$_{50}$ = 0.61 |
| D-1-e | inactive |
| D-1-f | EC$_{50}$ = 7.59 |
| D-3-a | EC$_{50}$ = 1.27 |
| D-3-b | EC$_{50}$ = 3.57 |
| E-1-a | inactive |
| E-1-b | inactive |
| F-1-a | inactive |
| F-1-b | inactive |
| F-1-c | inactive |
| F-1-d | inactive |
| F-2-a | inactive |
| F-2-b | EC$_{50}$ = 0.42 |
| F-2-c | inactive |
| F-2-d | inactive |
| F-3-a | inactive |
| F-3-b | inactive |
| F-3-c | inactive |
| F-4-a | inactive |
| F-4-b | inactive |
| F-4-c | EC$_{50}$ = 18.15 |
| G-1-a | EC$_{50}$ = 25.09 |
| H-1-a | inactive |
| H-1-d | Inactive |
| H-1-f | Inactive |
| H-2-a | Inactive |
| H-2-c | EC$_{50}$ = 3.36 |
| H-3-a | EC$_{50}$ = 2.19 |

Example B4: FRNT Assay in Vero E6 or A549-hACE2 Cells

Vero E6 or A549-hACE2 cells grown in 96 well plates were infected with 500 pfu SARS-CoV-2 for one hour. An overlay containing 1% methylcellulose was added and plates were incubated for 24 hours. Staining was performed by discarding the supernatant, fixing the cells for 30 minutes and staining with anti SARS-CoV-2 nucleocapsid protein, followed with Alexa Fluor 488 conjugated goat anti-mouse JgG secondary antibody. Virus foci were counted using florescence microscope, and a reduction of foci were calculated relative to untreated wells (Vanderheiden, A. et al. (2020) Curr. Protoc. Immunol. 131:e116).

To calculate the $EC_{50}$ from dose responses, a non-linear regression program in Prism (4 parameters variable slope) was used. $EC_{90}$ was calculated using a Prism non-linear regression—Find ECanything program.

Example B5: Virus Release Assay Using EpiAirway

EpiAirway (Mattek cat #Air-100) were grown on transwell inserts placed in 12 well Holey top plates (HNG-TOP-12) with culture medium (AIR-100-MM) added to the basolateral side, and apical side exposed to a humidified 5% $CO_2$ environment at 37° C. SARS-CoV-2 Omicron stock solutions were added to apical side to infect EpiAirway at a MOI of approximately 0.1. Compound treatment was performed at the basolateral side, with compound refreshed very other day. After 3 and 5 days, viruses released into the apical compartment were harvested.

The viral titers were measured by pfu on Vero E6-TM-PRSS2-T2A-ACE2 cells grown in 24 well plate. Each log 10 dilution of the virus was inoculated onto the plate. The plate was then incubated at 36° C. for 1 hour before adding an overlay with 1% methylcellulose. After 3 days incubation, the cell monolayer was fixed by 4% PFA and stained with Crystal Violet. Virus plaques were counted and final virus titer from the working virus stock was calculated.

Summary of $EC_{50}$ and $EC_{90}$ Values (nM) of A-1-d in Vero E6 and A549-hACE2 Cells is presented in Table 4.

TABLE 4

$EC_{50}$ Values (nM) of A-1-d in Vero E6 and A549-hACE2 Cells

| Compound ID# | Omicron (Vero E6, FRNT) | Omicron (A549-hACE2, FRNT) | Omicron (EpiAirway, virus release) |
|---|---|---|---|
| A-1-d | $EC_{50}$ = 0.36 µM<br>$EC_{90}$ = 0.41 µM | $EC_{50}$ = 0.13 µM<br>$EC_{90}$ = 0.28 µM | $EC_{50}$ &<br>$EC_{90}$: 12-41 nM |

Example B6: Liver Microsomal Stability Assay

Metabolic stability of novel protease inhibitors was determined via liver microsomal stability assay. Human, mouse, SD rat, beagle dog or monkey liver microsomes were incubated with the test compound for 5 to 60 minutes at 37° C., and then the remaining parent compound was quantified by LC-MS/MS. Percentage of the test compound remaining, half-life ($t_{1/2}$), in vitro intrinsic clearance ($CL_{int,\,in\,vitro}$), in vivo intrinsic clearance ($CL_{int,\,in\,vivo}$), hepatic clearance ($CL_h$) and extraction ratio (ER) were calculated.

Procedure: The assay was done as described in Baranczewski, P. et al. (2006) Pharmacological Reports 58:453-472; Pearson, P. and Wienkers, L. (2008) Handbook of Drug Metabolism, $2^{nd}$ Edition. CRC Pres, P.478; and Venkatesh, P. et al. (2007) Biol. Pharm. Bull. 30:1021-2024. 0.625 mg/mL liver microsomes solution was prepared by mixing 2325 µL 100 mM of K-phosphate buffer (pH 7.4) containing 2.5 mM of $MgCl_2$, 1.25 mM of EDTA, and 75 µL microsomes (20 mg/mL) in a vial for each species.

1.25 µM compound or positive control was prepared in 0.625 mg/mL liver microsomes mixture as follows: 995 µL 0.625 mg/mL liver microsomes solution, 5 µL compound or positive control working solution (250 µM) were mixed in a vial for each test compound. Positive control compound: (±) Verapamil hydrochloride (Cat No.: V4629; Lot No.: MKBV4993V; Source: Sigma)

40 µL aliquots of the liver microsome/test compound mixture were dispensed into 96-well plate in triplicate and pre-warmed the mixture for 5 minutes at 37° C. Then, 10 µL of 5 mM NADPH solution was added to each well to initiate the reaction, and gently mixed. The samples were incubated at 37° C. with gentle shaking. (Final concentrations: compound=1 µM; liver microsomes protein=0.5 mg/mL; $MgCl_2$=2 mM; EDTA=1 mM; ACN=0.1%; DMSO=0.05%).

After incubation for designated times, 200 µL of ACN containing 1% FA and internal standard (A-1-a synthesized in house or Tolbutamide purchased from Sigma used as internal standard) (50 ng/mL) was added to precipitate proteins and stop the reaction, and mixed well.

For 0-min samples, 200 µL of ACN containing internal standard was added to 40 µL of liver microsome/test compound mixture, followed by addition of 5 mM NADPH, and mixed gently.

For negative control: 40 µL of liver microsome/test compound mixture was incubated at 37° C. with gentle shaking for 60 minutes, followed by addition of 200 µL ACN containing 1% FA and internal standard and 10 µL of 5 mM NADPH, mixed gently.

All samples were centrifuged at 4° C. for 20 minutes at 4,000 rpm. Then, 100 µL of the supernatant from each sample was transferred to a new 96-well plate and 100 µL of ultrapure water containing 1% FA was added to each well, and mixed gently. Samples were analyzed by LC-MS/MS.

Data Analysis: Peak area ratio (Peak Area of test compound/Peak Area of internal standard) was used to represent the concentration of compound in each sample. The remaining percentage (% Remaining) at appointed time points was calculated versus the concentration of compound at 0 min. The Ln value of the remaining percentage was linearly fitted against the incubation time.

The half-life and clearance were calculated using the following equations:

Determined percent of the remaining test compound:

$$\% \text{ remaining} = [\text{area at } t_x/\text{average areas at } t_0] \times 100 \quad (1)$$

$$\% \text{ metabolized} = [100 - \% \text{ remaining}] \quad (2)$$

Calculated the half-life ($t_{1/2}$) using the slope (k) of the log-linear regression from the concentration of remaining parent compound versus time (min) relationship:

$$t_{1/2} \text{ (min)} = -\ln 2/k. \quad (3)$$

$Cl_{int,\,in\,vitro}$ (mL/min/mg)

$$Cl_{int,in\,vitro} = k/c, (c\text{:Liver microsome concentration in the incubation system}) \quad (4)$$

Calculated the predicted intrinsic clearance ($CL_{int,\,in\,vivo}$, mL/min/kg) (Baranczewski, P. (2006) Pharmacol. Rep. 58:453-472):

$$CL_{int,in\,vivo} = (0.693/t_{1/2}) \times (1/(\text{microsomal protein concentration } (0.5 \text{ mg/mL})) \times \text{Scaling Factor} \quad (5)$$

Hepatic Clearance (CLh)

$$CL_h = Cl_{int,in\,vivo} * \text{Hepatic Blood Flow (mL/min/kg)}/(\text{Hepatic Blood Flow (mL/min/kg)} + Cl_{int,in\,vivo}) \quad (6)$$

Extraction ratio (ER):

$$ER = CL_{int,in\,vivo}/(Qh + CL_{int,in\,vivo}) * 100, Qh\text{:liver blood flow} \quad (7)$$

Summary of Liver Microsomal Stability of human, mouse, SD rat, Beagle dog and monkey is presented in Table 5.

TABLE 5

Liver Microsomal Stability (ER, 1 uM)

| Compound ID# | Human | Mouse | SD rat | Beagle dog | Monkey |
|---|---|---|---|---|---|
| A-1-c | 0.12, 0.45(0.1 uM)* | 0.04 | 0.05 | 0.09 | 0.14 |
| A-1-d | 0.08 | 0.10 | 0.12 | 0.04 | N/A |
| A-1-e | 0.00 | 0.09 | −0.02 | 0.02 | N/A |
| A-1-f | N/A | N/A | N/A | N/A | N/A |
| A-1-g | 0.80 | 0.53 | 0.77 | 0.71 | 0.68 |
| A-1-h | 0.07 | 0.23 | 0.13 | 0.03 | N/A |
| A-1-j | 0.02 | 0.01 | 0.16 | −0.04 | N/A |
| A-3-a | 0.02 | 0.07 | 0.21 | 0.03 | 0.27 |
| A-3-b | 0.18 | 0.37 | 0.37 | 0.06 | N/A |
| A-3-c | 0.18 | 0.14 | 0.14 | −0.02 | N/A |
| A-3-d | 0.84 | 0.58 | 0.77 | 0.78 | 0.72 |
| A-3-e | 0.11 | 0.23 | 0.17 | 0.05 | N/A |
| A-4-a | 0.21 | 0.13 | 0.06 | 0.22 | 0.098 |
| A-4-b | 0.02 | 0.47 | 0.20 | 0.06 | 0.43 |
| A-4-c | 0.67 | 0.81 | 0.70 | 0.72 | 0.69 |
| A-4-d | 0.18 | 0.44 | 0.19 | 0.08 | N/A |
| A-4-e | N/A | N/A | N/A | N/A | N/A |
| A-5-a | 0.10 | 0.19 | 0.11 | 0.05 | N/A |
| A-5-b | 0.08 | 0.11 | 0.22 | 0.12 | 0.47 |
| A-5-c | 0.89 | 0.84 | 0.74 | 0.80 | 0.79 |
| A-5-d | 0.09 | 0.38 | 0.11 | 0.07 | N/A |
| A-3-b | 0.18 | 0.37 | 0.37 | 0.06 | N/A |
| B-1-e | 0.24 | 0.00 | 0.48 | 0.37 | 0.11 |
| B-1-f | −0.19 | 0.07 | 0.13 | 0.04 | 0.04 |
| B-2-e | 0.73 | 0.43 | 0.19 | 0.47 | 0.70 |
| C-1-b | 0.66 | 0.45 | 0.23 | 0.48 | 0.51 |
| C-2-b | 0.66 | 0.48 | 0.29 | 0.48 | 0.43 |
| D-1-c | 0.04 | 0.18 | 0.04 | −0.06 | N/A |
| D-1-d | 0.15, 0.60(0.1 uM)* | 0.08 | stable | 0.04 | 0.28 |
| D-1-e | −0.05 | −0.04 | 0.04 | −0.04 | −0.10 |
| D-1-f | 0.093, 0.22(0.1 uM)* | −0.02 | −0.02 | 0.01 | 0.13 |
| D-2-a | 0.05 | 0.13 | 0.03 | −0.04 | N/A |
| D-2-b | 0.08 | 0.10 | 0.00 | 0.06 | N/A |
| D-2-d | 0.03 | 0.18 | 0.05 | 0.05 | N/A |
| D-2-e | 0.09 | 0.17 | 0.04 | −0.03 | N/A |
| D-2-f | 0.09 | 0.07 | 0.01 | 0.05 | N/A |
| D-3-a | 0.38 | 0.66 | 0.09 | 0.16 | N/A |
| D-3-b | 0.01 | 0.26 | 0.02 | −0.01 | N/A |
| D-4-a | 0.46 | 0.72 | 0.29 | 0.21 | N/A |
| F-1-b | 0.48 | 0.38 | 0.53 | 0.46 | 0.44 |
| F-2-b | 0.81 | 0.50 | 0.65 | 0.55 | 0.57 |
| F-3-c | −0.35 | −0.05 | 0.02 | −0.04 | −0.03 |
| F-4-a | 0.07 | 0.03 | 0.20 | 0.08 | 0.07 |
| G-1-a | 0.28 | 0.00 | 0.16 | 0.09 | 0.33 |
| G-1-b | 0.38 | 0.16 | 0.33 | 0.33 | 0.51 |
| G-1-d | 0.83 | 0.59 | 0.78 | 0.81 | 0.92 |
| G-1-e | 0.17 | 0.25 | 0.07 | 0.07 | N/A |
| G-2-a | 0.54 | 0.16 | 0.53 | 0.56 | 0.48 |
| G-2-b | 0.51 | 0.22 | 0.33 | 0.53 | 0.52 |
| G-2-c | 0.85 | 0.92 | 0.79 | 0.84 | N/A |
| G-3-a | 0.70 | 0.78 | 0.54 | 0.62 | N/A |
| G-3-b | 0.28 | 0.55 | 0.20 | 0.32 | N/A |
| G-1-c | 0.67 | 0.27 | 0.30 | 0.30 | 0.58 |
| H-1-a | 0.08 | 0.24 | 0.05 | 0.10 | N/A |
| H-1-b | 0.09 | 0.35 | 0.06 | 0.05 | N/A |
| H-1-c | 0.15 | 0.44 | 0.06 | 0.02 | N/A |
| H-1-d | 0.26 | 0.63 | 0.09 | 0.16 | N/A |
| H-1-e | 0.05 | 0.31 | 0.06 | 0.05 | N/A |
| H-1-f | 0.03 | 0.27 | 0.04 | 0.01 | N/A |
| H-2-a | 0.53 | 0.83 | 0.15 | 0.52 | N/A |
| H-2-b | 0.18 | 0.37 | 0.37 | 0.06 | N/A |
| H-2-c | 0.02 | 0.32 | 0.01 | 0.01 | N/A |
| H-3-a | 0.35 | 0.68 | 0.21 | 0.06 | N/A |

ER was determined for compounds at 1 uM concentration.
*ER determined at 0.1 uM concentration.

Example B7: Mouse Oral PK Study

Pharmacokinetics of test compounds was evaluated following an oral administration of a single dose (at 40 mg/kg) to female Balb/c mice.

Procedure: Test compounds were administered to Balb/c mice (n=3 per sex per time point) by a single oral gavage. The target dose level for oral administration was 40 mg/kg. Blood samples were collected at pre-dose, and at 0.083, 0.25, 0.50, 1, 2, 4, 6, 8, and 12 hours post-dose. Concentrations of test compound were determined by an LC-MS/MS. Non-compartmental Pharmacokinetic parameters of test compounds were analyzed using Phoenix WinNonlin 8.3.

Preparation of Dosing Formulation: test compounds were dissolved in:

$PEG$400 (polyethylene glycol 400):$D5W$(5% dextrose in water)=40:60($v/v$).

Animal Dosing: All animals were fasted overnight through approximately 4 hours post-dose. Tap water was provided to mice ad Libitum. The mice were dosed orally at 10.0 ml/kg. The formulation volume of the test compound administered to each animal was calculated based on the body weight measured on the day of dosing.

Sample Collection and Analysis: Approximately 0.20 mL of blood was collected via orbital sinus vein puncture into EDTA-K2 tubes. Plasma samples were harvested by centrifugation and stored at −80° C. until analysis. The analytical method for test compound involved protein precipitation by adding acetonitrile containing 1% FA and internal standard (A-1-a synthesized in house or Tolbutamide purchased from Sigma), and final analysis by LC-MS/MS. A standard curve was prepared using mouse plasma for the test compound. The calibration curve was linear over a concentration range of 1.0 to 1000 ng/mL. The general acceptance criteria for each analytical batch were that at least 75% of the calibration standards had to be within ±15% of their nominal concentrations (±20% at the lower limit of quantification).

Pharmacokinetic and Statistic Analysis: The reported plasma concentrations of test compounds were used to determine pharmacokinetic parameters, using a non-compartmental model for data analysis (Phoenix WinNonlin 8.3). The common pharmacokinetic parameters were calculated, whenever possible, from the plasma concentration-versus-time data. Nominal doses and sampling times were used, except where deviations were noted. Concentration values below the lower limit of quantitation (<2.0 ng/mL) would be labelled as 0 ng/mL before Tmax and BQL after Tmax. BQL after Tmax would not participate in calculation of PK parameters. F %

Summary of mouse oral pharmacokinetics study is presented in Table 6.

TABLE 6

Mouse Oral Pharmacokinetics

Mouse oral PK (female, 40 mg/kg)

| Compound ID# | $AUC_{0-t}$ (h · ng/mL) | $t_{1/2}$ (h) | $T_{max}$ (h) | $C_{max}$ (ng/mL) | F % (bioavailability) |
|---|---|---|---|---|---|
| A-1-c | 2166 | 1.07 | 3 | 734 | 8.0 |
| A-1-d | 2619 | 0.893 | 0.5 | 1610 | N/A |
| A-3-a | 15451 | 0.976 | 1 | 8050 | N/A |
| A-3-e | 261 | 1.25 | 0.25 | 131 | N/A |
| A-4-a | 0.77 | 1 | 231 | NA | N/A |
| A-4-d | 120 | 2.14 | 4 | 52 | N/A |
| A-4-e | N/A | N/A | N/A | N/A | N/A |
| C-1-b | 128.4 | 0.704 | 2 | 46.1 | 2.9 |
| C-2-b | 665.2 | 0.876 | 0.25 | 496 | 5.0 |
| D-1-c | 1359 | 2.9 | 0.5 | 410 | N/A |
| D-1-d | 4571 | 0.76 | 0.25 | 3420 | N/A |
| D-1-f | 1402 | 1.37 | 1 | 839 | N/A |
| D-3-a | 5590 | 0.706 | 0.25 | 7070 | N/A |
| D-3-b | 3768 | 1.86 | 1 | 1190 | 20.2 |
| G-1-a | 36.1 | 0.92 | 1 | 13.3 | N/A |
| G-3-b | 383.7 | 0.773 | 2 | 169 | N/A |
| H-1-b | 304 | 2.39 | 0.5 | 193 | N/A |
| H-1-f | 72.0 | 1.43 | 1.0 | 32.1 | N/A |

Example B38: Dog Oral PK Study

Pharmacokinetics of test compounds was evaluated following an oral administration of a single dose (at 40 mg/kg) to female Beagle dogs.

Procedure: Test compounds were orally administered to beagle dogs (single dose). The target dose level for oral administration was 40 mg/kg. Blood samples were collected at pre-dose, and at 0.083, 0.25, 0.50, 1, 2, 4, 6, 8, and 24 hours post-dose. Concentrations of test compound were determined by an LC-MS/MS. Non-compartmental Pharmacokinetic parameters of test compounds were analyzed using Phoenix WinNonlin 8.3.

Preparation of Dosing Formulation: test compounds were dissolved in:

PEG400 (polyethylene glycol 400):D5W (5% dextrose in water)=40:60(v/v).

Animal Dosing: All animals were fasted ~17-19 h prior to dosing and fed approximately 4 hours after dosing. Tap water was provided to mice ad Libitum. The dogs were dosed at 10.0 ml/kg. The formulation volume of the test compound administered to each animal was calculated based on the body weight measured on the day of dosing.

Sample Collection and Analysis: Approximately 1 mL of blood was collected by jugular vein puncture into tubes containing EDTA-K2 anticoagulant. Plasma samples were harvested by centrifugation (2000 g for 10 minutes at 4° C. within 2 hours after collection) and stored at −80° C. until analysis. The analytical method for test compound involved protein precipitation by adding acetonitrile containing 1% FA and internal standard (A-1-a synthesized in house or Tolbutamide purchased from Sigma), and final analysis by LC-MS/MS. A standard curve was prepared using dog plasma for the test article. The calibration curve was linear over a concentration range of 1.0 to 1000 ng/mL. The general acceptance criteria for each analytical batch were that at least 75% of the calibration standards had to be within ±15% of their nominal concentrations (±20% at the lower limit of quantification).

Pharmacokinetic and Statistic Analysis: The reported plasma concentrations of test compounds were used to determine pharmacokinetic parameters, using a non-compartmental model for data analysis (Phoenix WinNonlin 8.3). The common pharmacokinetic parameters were calculated, whenever possible, from the plasma concentration-versus-time data. Nominal doses and sampling times were used, except where deviations were noted. Concentration values below the lower limit of quantitation (<2.0 ng/mL) would be labelled as 0 ng/mL before Tmax and BQL after Tmax. BQL after Tmax would not participate in calculation of PK parameters.

Summary of dog oral pharmacokinetics study is presented in Table 7.

TABLE 7

Dog Oral Pharmacokinetics

Dog oral PK (female, 40 mpk)

| Compound ID# | $AUC_{0-t}$ (h · ng/mL) | $t_{1/2}$ (h) | $T_{max}$ (h) | $C_{max}$ (ng/mL) | F % (bioavailability) |
|---|---|---|---|---|---|
| A-1-c | 36685 | 4.84 | 0.833 | 13833 | 31 |
| A-1-d | 95900 | 2.73 | 2 (2-3) | 27800 | >83 |

Example B9: Monkey Oral PK Study

Pharmacokinetics of test compounds is evaluated following an oral administration of a single dose (at 84 mg/kg) or a single intravenous administration at 2.5 mg/kg to female cynomolgus monkeys.

Procedure: Test compounds are orally administered to female cynomolgus monkeys (single dose). The target dose level for oral administration is 84 mg/kg. Blood samples will be collected at pre-dose, and at 0.25, 0.50, 1, 2, 4, 6, 8, and 24 hours post-dose. The target dose level for intravenous administration is 2.5 mg/kg. Blood samples will be collected at pre-dose, and at 0.083, 0.25, 0.50, 1, 2, 4, 6, 8, and 24 hours post-dose. Concentrations of test compound are determined by an LC-MS/MS. Non-compartmental Pharmacokinetic parameters of test compounds is analyzed using Phoenix WinNonlin 8.3.

Preparation of Dosing Formulation: test compounds are dissolved in:

Oral Dose (vehicle 1):1.7% (Poloxamer 124)+2.6% PEG400+2.8% (Labrasol ALF)+92.9% D5W (5% dextrose in water)=w:w:w:w IV Dose (vehicle 2): 25% PEG400+75% D5W (5% dextrose injection).

Oral Dose preparation: weigh an appropriate amount (corrected by the correction factor) of the test compound, measure an appropriate volume of vehicle 1, and then mix well with ultrasound or stirring to obtain the dosing formulation for oral dosing groups with the corresponding concentrations of 8.4 mg/mL. The dosing formulation should be freshly prepared for use, stored at room temperature, and protected from light.

IV Dose preparation: weigh an appropriate amount (corrected by the correction factor) of the test compound, measure an appropriate volume of PEG400, and then mix to clear with ultrasound or stirring, measure an appropriate volume of D5W to designated volume, and then mix to clear with ultrasound or stirring, then filter into a sterile container with a 0.22 μm membrane in a biological safety cabinet, to obtain the dosing formulation for IV group with the corresponding concentration of 2.5 mg/mL. The dosing formulation should be freshly prepared for use, stored at room temperature, and protected from light.

Animal Dosing: All animals are fasted ~10-14 h prior to dosing and fed approximately 4 hours after dosing. Tap water is provided to monkeys ad Libitum. The monkeys are dosed at 10.0 ml/kg for oral dosing and at 1.0 ml/kg for IV dosing. The formulation volume of the test compound administered to each animal is calculated based on the body weight measured on the day of dosing.

Sample Collection and Analysis: Approximately 1 mL of blood is collected by femoral vein puncture into tubes containing EDTA-K2 anticoagulant. Plasma samples are harvested by centrifugation (2000 g for 10 minutes at 4° C. within 2 hours after collection) and stored at −80° C. until analysis. The analytical method for test compound involves protein precipitation by adding acetonitrile containing 1% FA and internal standard (A-1-a synthesized in house or Tolbutamide purchased from Sigma), and final analysis by LC-MS/MS. A standard curve is prepared using monkey plasma for the test article. The calibration curve is linear over a concentration range of 2.0 to 2000 ng/mL. The general acceptance criteria for each analytical batch is that at least 75% of the calibration standards are within ±15% of their nominal concentrations (±20% at the lower limit of quantification).

Pharmacokinetic and Statistic Analysis: The reported plasma concentrations of test compounds are used to determine pharmacokinetic parameters, using a non-compartmental model for data analysis (Phoenix WinNonlin 8.3). The common pharmacokinetic parameters are calculated, whenever possible, from the plasma concentration-versus-time data. Nominal doses and sampling times are used, except where deviations are noted. Concentration values below the lower limit of quantitation (<2.0 ng/mL) will be labelled as 0 ng/mL before Tmax and BQL after Tmax. BQL after Tmax would not participate in calculation of PK parameters.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The invention claimed is:

1. A compound of Formula (I):

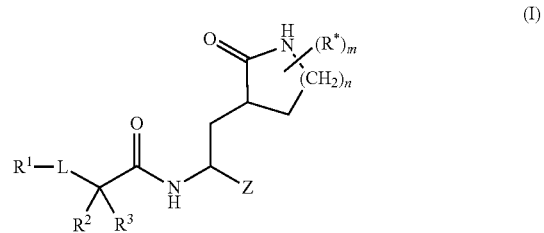

or an enantiomer, a mixture of enantiomers, a mixture of two or more diastereomers, a tautomer, a mixture of two or more tautomers, or an isotopic variant thereof, or a pharmaceutically acceptable salt, solvate or hydrate thereof; wherein:

Z is selected from —$CH_2CN$, —C(=O)—CH=$CH_2$, and —CH(OH)$SO_3^-$ (and an associated cation, optionally wherein the associated cation is $Na^+$);

L is —C(=O)—NH—;

$R^1$ is

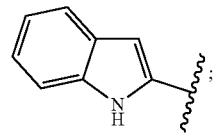 [SMILES: *c1cc2ccccc2[nH]1]

$R^2$ is selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy;

$R^3$ is H or $C_{1-4}$ alkyl;

each R* is independently selected from $C_{1-3}$ alkyl, $C_{1-3}$ alkoxy, $C_{1-3}$ haloalkyl, CN, halo, and —OH;

m is an integer from 0 to 2; and n is an integer from 0 to 4.

2. The compound of claim 1, which is:

a compound of Formula (IE):

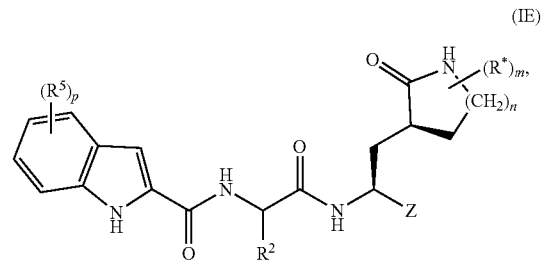

or an enantiomer, a mixture of enantiomers, a mixture of two or more diastereomers, a tautomer, a mixture of two or more tautomers, or an isotopic variant thereof; or a pharmaceutically acceptable salt, solvate or hydrate thereof; wherein:
p is 0; or
a compound of Formula (IF):

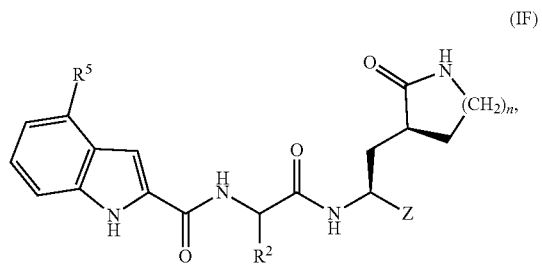

or an enantiomer, a mixture of enantiomers, a mixture of two or more diastereomers, a tautomer, a mixture of two or more tautomers, or an isotopic variant thereof, or a pharmaceutically acceptable salt, solvate or hydrate thereof; wherein:
$R^5$ is hydrogen.

3. The compound of claim 1, which is a compound of Formula (IG):

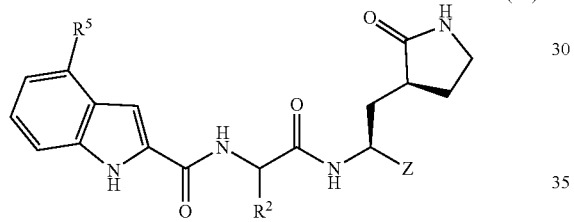

or an enantiomer, a mixture of enantiomers, a mixture of two or more diastereomers, a tautomer, a mixture of two or more tautomers, or an isotopic variant thereof; or a pharmaceutically acceptable salt, solvate or hydrate thereof;
wherein $R^5$ is hydrogen.

4. A compound of Formula (IG2):

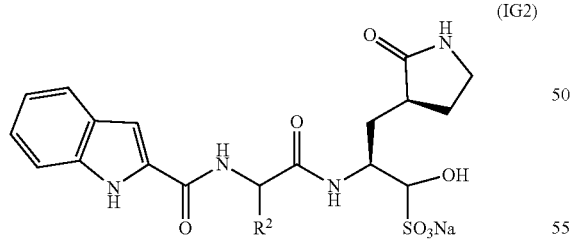

or an enantiomer, a mixture of enantiomers, a mixture of two or more diastereomers, a tautomer, a mixture of two or more tautomers, or an isotopic variant thereof; or a pharmaceutically acceptable salt, solvate or hydrate thereof;
wherein $R^2$ is selected from $C_{1-6}$ alkyl, 3-7 membered cycloalkyl, $C_{1-3}$ alkyl-(3-7 membered cycloalkyl), and (3-7 membered cycloalkyl)-$C_{1-3}$ alkyl, each of which is optionally substituted with up to three groups selected from halo, CN, $C_{1-3}$ alkyl, $C_{1-6}$ alkoxy, $C_{1-3}$ haloalkyl, and $C_{1-3}$ haloalkoxy.

5. The compound of claim 1, wherein $R^2$ is $C_{1-4}$ alkyl, 3-7 membered cycloalkyl, $C_{1-2}$ alkyl-($C_{3-6}$ cycloalkyl) or ($C_{3-6}$ cycloalkyl)$C_{1-2}$ alkyl optionally substituted with $C_{1-6}$ alkoxy.

6. The compound of claim 5, wherein $R^2$ is methyl, ethyl, propyl, isopropyl, t-butyl, isobutyl, isopropylmethyl, 1-methyl-t-butoxyethyl, cyclopropyl, cyclohexyl, cyclopropylmethyl, or cyclohexylmethyl.

7. The compound of claim 4, wherein $R^2$ is t-butyl, isopropylmethyl, cyclohexylmethyl or 1-methyl-t-butoxyethyl.

8. The compound of claim 1, wherein n is 1, 2 or 3.

9. The compound of claim 1, wherein Z is —C(═O) CH═CH$_2$.

10. The compound of claim 1, wherein Z is —CH(OH) SO$_3^-$ and an associated cation, which is optionally Na$^+$.

11. The compound of claim 1, which is selected from:

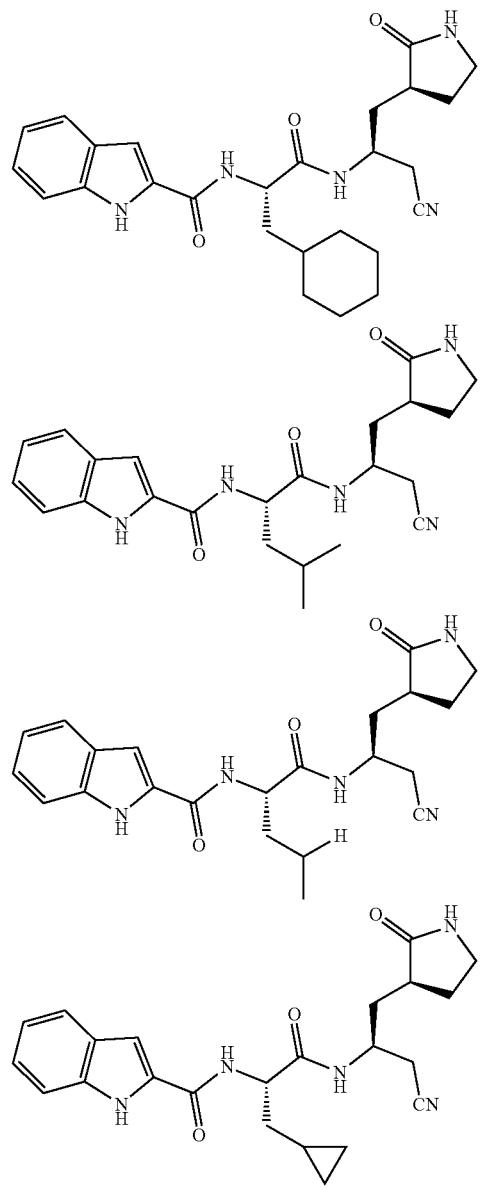

331
-continued
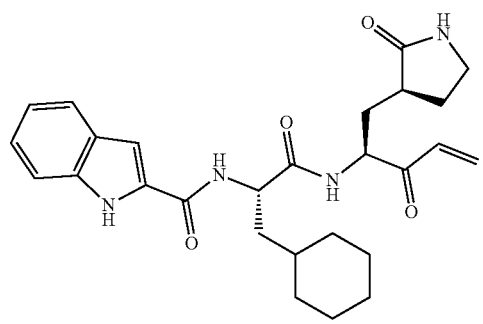
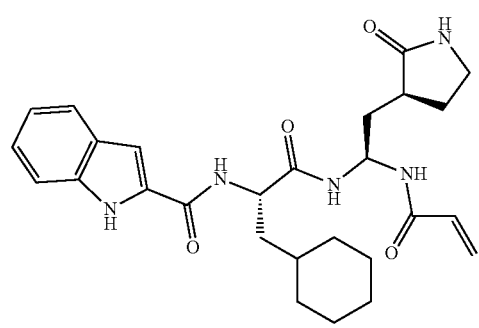
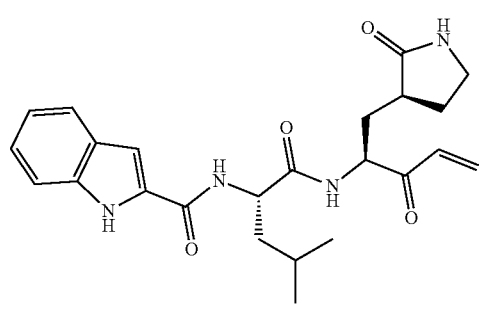
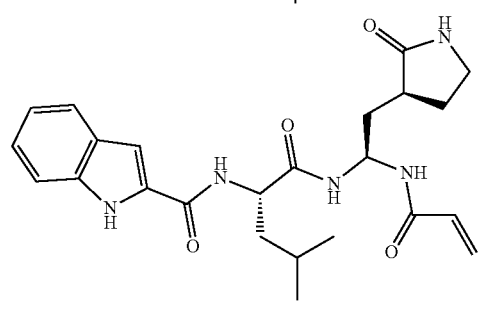
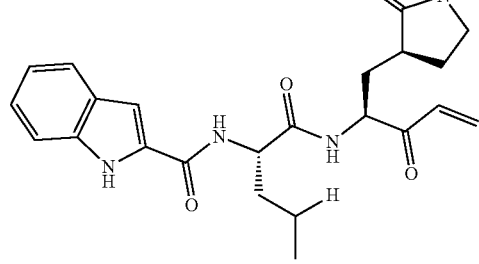
332
-continued
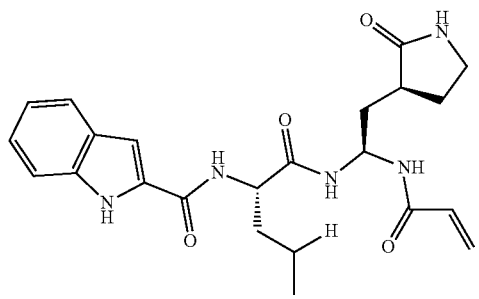
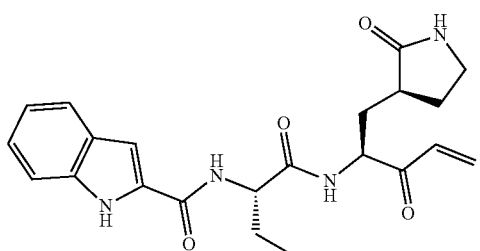
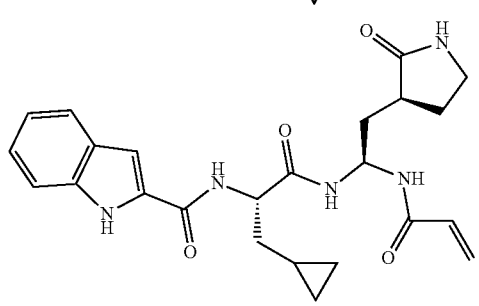
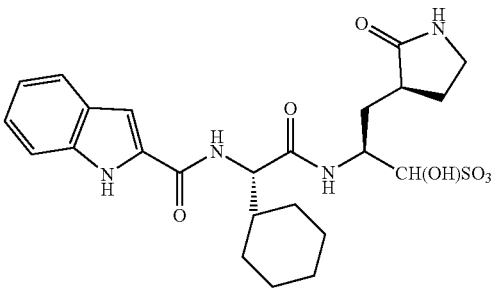
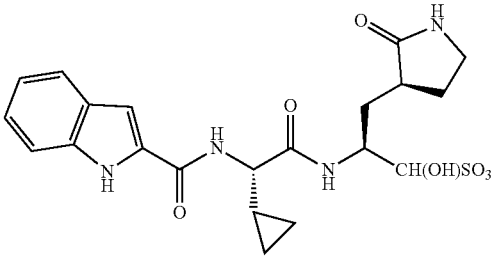
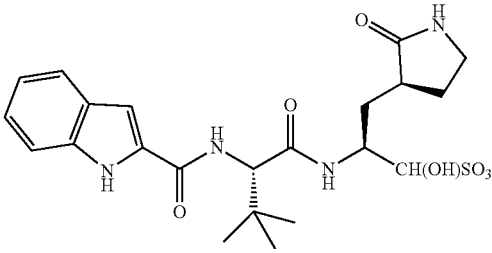

-continued

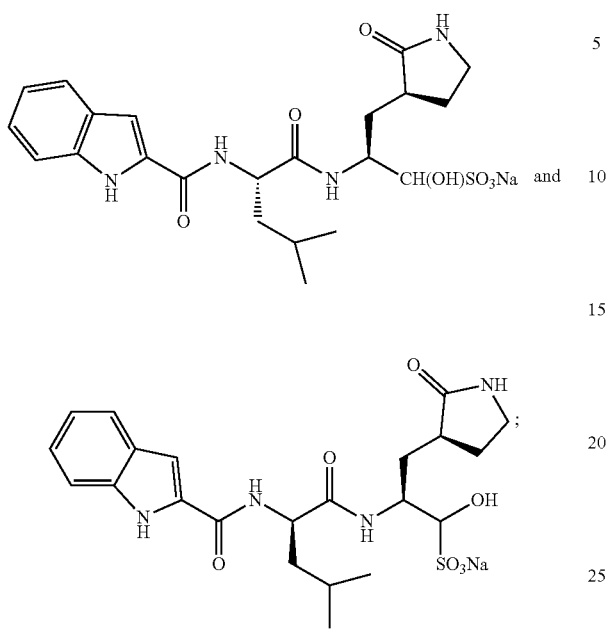

and tautomers, mixtures of two or more tautomers, and isotopic variants thereof; and pharmaceutically acceptable salts, solvates or hydrate thereof.

12. The compound of claim 1, which is selected from:

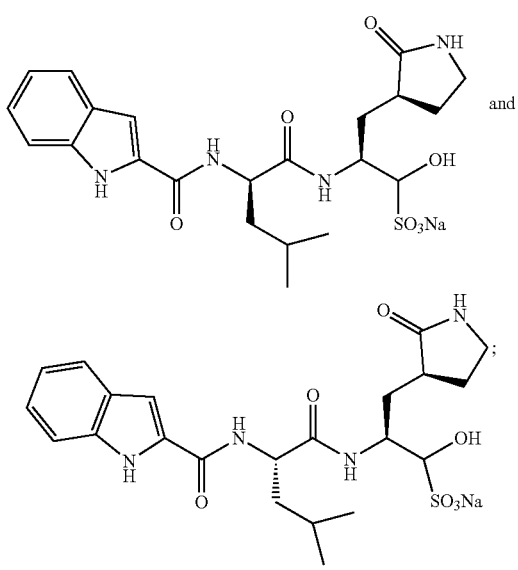

and tautomers, mixtures of two or more tautomers, and isotopic variants thereof; and pharmaceutically acceptable salts, solvates or hydrate thereof.

13. A pharmaceutical composition comprising a compound of claim and at least one pharmaceutically acceptable excipient.

14. The pharmaceutical composition of claim 13, further comprising a second therapeutic agent.

15. The compound of claim 1, which is selected from:

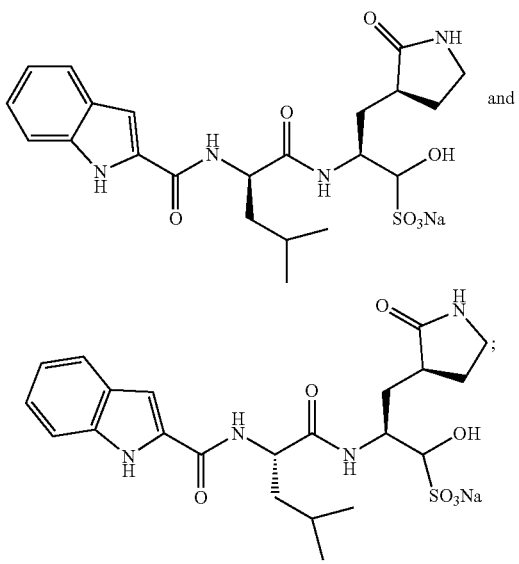

and pharmaceutically acceptable salts, solvates, and hydrates thereof.

16. The compound of claim 1, which is selected from:

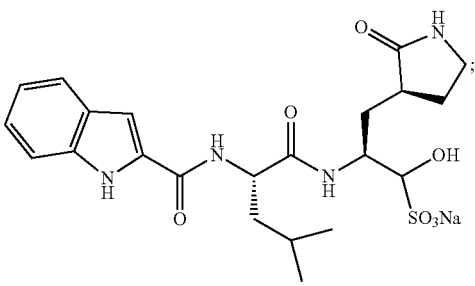

and tautomers, mixtures of two or more tautomers, and isotopic variants thereof; and pharmaceutically acceptable salts, solvates or hydrate thereof.

17. The compound of claim 1, which is selected from:

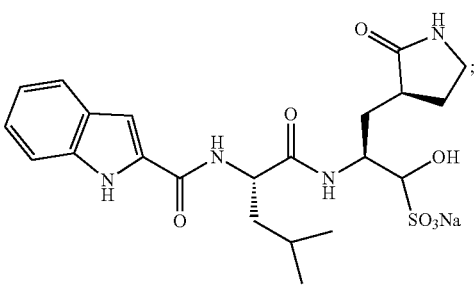

and pharmaceutically acceptable salts, solvates, and hydrates thereof.

18. A pharmaceutical composition comprising the compound of claim 17.

* * * * *